(12) United States Patent
Lerchen et al.

(10) Patent No.: US 10,973,923 B2
(45) Date of Patent: Apr. 13, 2021

(54) SITE SPECIFIC HOMOGENEOUS WITH KSP INHIBITORS

(71) Applicant: BAYER PHARMA AKTIENGESELLSCHAFT, Berlin (DE)

(72) Inventors: Hans-Georg Lerchen, Leverkusen (DE); Yolanda Cancho Grande, Leverkusen (DE); Beatrix Stelte-Ludwig, Wülfrath (DE); Anette Sommer, Berlin (DE); Christoph Mahlert, Wuppertal (DE); Anne-Sophie Rebstock, Champagne au Mont d'Or (FR); Simone Greven, Dormagen (DE); Nils Griebenow, Dormagen (DE); Jan Tebbe, Cologne (DE); Oliver Kensch, Pulheim (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 306 days.

(21) Appl. No.: 15/739,130

(22) PCT Filed: Jun. 20, 2016

(86) PCT No.: PCT/EP2016/064120
§ 371 (c)(1),
(2) Date: Dec. 21, 2017

(87) PCT Pub. No.: WO2016/207090
PCT Pub. Date: Dec. 29, 2016

(65) Prior Publication Data
US 2019/0262463 A1    Aug. 29, 2019

(30) Foreign Application Priority Data

Jun. 23, 2015  (EP) .................................. 15173488
Mar. 16, 2016  (EP) .................................. 16160780

(51) Int. Cl.
*A61K 47/68* (2017.01)
*C07K 16/30* (2006.01)

(52) U.S. Cl.
CPC ...... *A61K 47/6803* (2017.08); *A61K 47/6849* (2017.08); *A61K 47/6851* (2017.08);
(Continued)

(58) Field of Classification Search
None
See application file for complete search history.

(56) References Cited

U.S. PATENT DOCUMENTS 10,022,453 B2   7/2018  Lerchen
10,485,880 B2  11/2019  Lerchen
(Continued)

FOREIGN PATENT DOCUMENTS

CA   2990411 A1  12/2016
CA   3018630 A1   9/2017
(Continued)

OTHER PUBLICATIONS

Panowksi, et al., (2014) Site-specific antibody drug conjugates for cancer therapy. mAbs. 6. 34-45 (Year: 2014).*
(Continued)

*Primary Examiner* — Karl J Puttlitz
(74) *Attorney, Agent, or Firm* — Wilson Sonsini Goodrich & Rosati

(57) ABSTRACT

The invention relates to site specific homogeneous binder drug conjugates of kinesin spindle protein inhibitors, to active metabolites of these conjugates, to processes for preparing these conjugates, to the use of these conjugates for the treatment and/or prophylaxis of diseases and to the use of these conjugates for preparing medicaments for treatment and/or prevention of diseases, in particular hyperproliferative and/or angiogenic disorders such as, for example,
(Continued)

```
              34        40         50          60         68
Human     APCSRGSSWSADLDKCMDCASCRARPHSDFCLGCA
Rat       APCSSGSSWSADLDKCMDCASCRARPHSDFCLGCA
Mac       APCSHGSSWSADLDKCMDCASCRARPHSDFCLGCS
Pig       TPCSRGSSWSADLDKCMDCASCRARPHSDFCLGCA
Mouse     SPCSSGSSWSADLDKCMDCASCRARPHSDFCLGCA
Dog       TPCTRGSSWSADLDKCMDCASCRARPHSDFCLGCT
              ^         ^
``` cancer diseases. Such treatments can be carried out as monotherapy or else in combination with other medicaments or further therapeutic measures.

37 Claims, 8 Drawing Sheets

Specification includes a Sequence Listing.

(52) U.S. Cl.
CPC ...... *A61K 47/6855* (2017.08); *A61K 47/6857* (2017.08); *A61K 47/6863* (2017.08); *A61K 47/6865* (2017.08); *C07K 16/30* (2013.01)

(56) References Cited

U.S. PATENT DOCUMENTS

| 2014/0322247 | A1* | 10/2014 | Barsanti | C07D 233/64 424/178.1 |
|---|---|---|---|---|
| 2016/0346402 | A1 | 12/2016 | Lerchen | |
| 2018/0015176 | A1 | 1/2018 | Lerchen | |
| 2018/0169256 | A1 | 6/2018 | Lerchen | |
| 2018/0185510 | A1 | 7/2018 | Lerchen | |
| 2018/0318437 | A1 | 11/2018 | Lerchen | |
| 2018/0318438 | A1 | 11/2018 | Lerchen | |
| 2019/0077752 | A1 | 3/2019 | Lerchen | |
| 2019/0328897 | A1 | 10/2019 | Lerchen | |
| 2019/0330357 | A1 | 10/2019 | Lerchen | |
| 2019/0351066 | A1 | 11/2019 | Lerchen | |
| 2019/0365916 | A1 | 12/2019 | Lerchen | |

FOREIGN PATENT DOCUMENTS

| WO | WO2006002236 A1 | 1/2006 |
|---|---|---|
| WO | WO2006044825 A2 | 4/2006 |
| WO | 2009020933 | * 2/2009 |
| WO | WO2009020933 A2 | 2/2009 |
| WO | WO2009023265 A1 | 2/2009 |
| WO | 2009140177 | * 11/2009 |
| WO | WO2009140177 A2 | 8/2010 |
| WO | WO2014093640 A1 | 6/2014 |
| WO | WO2014151030 A1 | 9/2014 |
| WO | WO2015054659 A1 | 4/2015 |
| WO | WO2015096982 A1 | 7/2015 |
| WO | WO2015138615 A2 | 9/2015 |
| WO | WO2015189143 A1 | 12/2015 |
| WO | WO2016020791 A1 | 2/2016 |
| WO | WO2016096610 A1 | 6/2016 |
| WO | WO2016207089 A1 | 12/2016 |
| WO | WO2016207094 A1 | 12/2016 |
| WO | WO2016207098 A1 | 12/2016 |
| WO | WO2016207103 A1 | 12/2016 |
| WO | WO2016207104 A1 | 12/2016 |
| WO | WO2017162663 A1 | 9/2017 |
| WO | WO2017216028 A1 | 12/2017 |
| WO | WO2018114578 A1 | 6/2018 |
| WO | WO2018114798 A1 | 6/2018 |
| WO | WO2018114804 A1 | 6/2018 |

OTHER PUBLICATIONS

Sochaj et al., Biotechnology Advances 33 (2015) 775-784 (Year: 2015).*

International Search Report dated Jan. 17, 2017, for PCT Application No. PCT/EP2016/064120, filed on Jun. 20, 2016, ten pages.

Liu, F. et al. (2007). "Pharmacophore identification of KSP inhibitors," Bioorganic & Medicinal Chemistry Letters 17: 722-726.

Luo, X, et al. (2012). "3D-QSAR Studies of Dihydropyrazole and Dihydropyrrole Derivatives as Inhibitors of Human Mitotic Kinesin Eg5 Based on Molecular Docking," Molecules 17(12):2015-2029.

U.S. Appl. No. 15/739,471, filed Feb. 22, 2019, for Lerchen et al. (U.S. Patent Application is not submitted herewith pursuant to the waiver of 37 C.F.R § 1.98(a)(2)(iii) issued by the Office on Sep. 21, 2004.).

Zhou H. et al. (2011). "Development and Characterization of a Potent Immunoconjugate Targeting the Fn14 Receptor on Solid Tumor Cells," Mol Cancer Therapeutics 10(7):276-1288.

Zhou H. et al. (2012). "The TWEAK Receptor Fn14 is a Novel Therapeutic Target in Melanoma: Immunotoxins Targeting Fn14 Receptor for Malignant Melanoma Treatment," J. Invest Dermatol. 133(4):1052-1062.

* cited by examiner

```
        34     40         50         60        68
Human   APCSRGSSWSADLDKCMDCASCRARPHSDFCLGCA
Rat     APCSSGSSWSADLDKCMDCASCRARPHSDFCLGCA
Mac     APCSHGSSWSADLDKCMDCASCRARPHSDFCLGCS
Pig     TPCSRGSSWSADLDKCMDCASCRARPHSDFCLGCA
Mouse   SPCSSGSSWSADLDKCMDCASCRARPHSDFCLGCA
Dog     TPCSRGSSWSADLDKCMDCASCRARPHSDFCLGCT
             ^         ^
```

*FIG. 1*

SITE SPECIFIC HOMOGENEOUS WITH KSP INHIBITORS

CROSS REFERENCE TO RELATED APPLICATIONS

This application is the national stage of International Application No. PCT/EP2016/064120, filed internationally on Jun. 20, 2016, which claims the benefit of European Application Nos. 16160780.9, filed Mar. 16, 2016 and 15173488.6, filed Jun. 23, 2015.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052019300seqlist.txt, date recorded: Dec. 18, 2017, size: 405 KB).

Introduction and State of the Art

The invention relates to site specific homogeneous binder drug conjugates of kinesin spindle protein inhibitors, to active metabolites of these conjugates, to processes for preparing these conjugates, to the use of these conjugates for the treatment and/or prophylaxis of diseases and to the use of these conjugates for preparing medicaments for treatment and/or prevention of diseases, in particular hyperproliferative and/or angiogenic disorders such as, for example, cancer diseases. Such treatments can be carried out as monotherapy or else in combination with other medicaments or further therapeutic measures.

Cancer diseases are the consequence of uncontrolled cell growth of the most diverse tissues. In many cases, the new cells penetrate into existing tissue (invasive growth), or they metastase into remote organs. Cancer diseases occur in the most diverse organs and often have tissue-specific courses of the disease. The term cancer as a generic term therefore describes a large group of defined diseases of various organs, tissue and cell types.

Tumours in early stages can possibly be removed by surgical and radiotherapy measures. Metastased tumours as a rule can only be treated palliatively by chemotherapeutics. The aim here is to achieve the optimum combination of an improvement in the quality of life and prolonging of life.

Conjugates of binder proteins with one or more active compound molecules are known, in particular in the form of antibody drug conjugates (ADCs) in which an internalising antibody directed against a tumour-associated antigen is covalently attached via a linker to a cytotoxic agent. Following introduction of the ADCs into the tumour cell and subsequent dissociation of the conjugate, either the cytotoxic agent itself or a cytotoxic metabolite formed therefrom is released within the tumour cell and can unfold its action therein directly and selectively. In this manner, in contrast to conventional chemotherapy, damage to normal tissue is contained in significantly narrower limits [see, for example, J. M. Lambert, Curr. Opin. Pharmacol. 5, 543-549 (2005); A. M. Wu and P. D. Senter, Nat. Biotechnol. 23, 1137-1146 (2005); P. D. Senter, Curr. Opin. Chem. Biol. 13, 235-244 (2009); L. Ducry and B. Stump, Bioconjugate Chem. 21, 5-13 (2010)]. Thus, WO2012/171020 describes ADCs in which a plurality of toxophor molecules are attached via a polymeric linker to an antibody. As possible toxophors, WO2012/171020 mentions, among others, the substances SB 743921, SB 715992 (Ispinesib), MK-0371, AZD8477, AZ3146 and ARRY-520.

The substances mentioned last are kinesin spindle protein inhibitors. Kinesin spindle protein (KSP, also known as Eg5, HsEg5, KNSL1 or KIF11) is a kinesin-like motorprotein which is essential for the bipolar mitotic spindle to function. Inhibition of KSP leads to mitotic arrest and, over a relatively long term, to apoptosis (Tao et al., Cancer Cell 2005 Jul. 8(1), 39-59). After the discovery of the first cell-penetrating KSP inhibitor, Monastrol, KSP inhibitors have established themselves as a class of novel chemotherapeutics (Mayer et al., Science 286: 971-974, 1999), and they are subject of a number of patent applications (e.g. WO2006/044825; WO2006/002236; WO2005/051922; WO2006/060737; WO03/060064; WO03/040979; and WO03/049527). However, since KSP unfolds its action only during a relatively short period of time during the mitosis phase, KSP inhibitors have to be present in a sufficiently high concentration during these initial phases.

Antibody conjugation methods typically include chemical reaction of lysines or cysteines with activated esters or maleimide functionality respectively. However, these reactions are difficult to control with regard to site-specificity and stoechiometry, which leads to heterogeneous products (Wang et al., Protein Sci. 14, 2436-2446 (2005); Hamblett et al., Clin. Cancer Res. 10, 7063-7070 (2004); Sun et al., Bioconjug. Chem. 16, 1282-1290 (2005); Willner et al., Bioconjug. Chem. 4, 521-527 (1993)). Consequently, heterogeneous ADCs may contain both unconjugated and overloaded antibodies. Unconjugated antibodies compete with drug-loaded species for antigen binding that can diminish the activity of ADC therapeutics. On the other hand, a high degree of the antibody modification may result in antibody aggregation, increased toxicity, decreased stability and shorter half-life of ADCs in the circulation (Sochaj et al., Biotechnology Advances, 33, 775-784 (2015)). It has been reported that heterogeneity of ADC species can influence its pharmacokinetics (PK), in vivo performance and safety profiles (Jackson et al., PLoS One 9, e83865 (2014); Junutula et al., Nat. Biotechnol. 26, 925-932 (2008); Strop et al., Chem. Biol. 20, 161-167 (2013); Boswell et al., Bioconjugate Chem. 22, 1994-2004 (2011)). In addition, batch to batch consistency in ADC production is challenging and requires diligent manufacturing capabilities. Therefore regulatory requirements may change in the future for the approval of new ADCs.

Site specific conjugation, in which a known number of linker-drugs are consistently conjugated to defined sites, is one way to overcome these challenges. Heterogeneity is minimized and ADC properties are more predictable, with consistent conjugate production from batch to batch. Drug-to-antibody ratio (DAR) is precisely controlled and can be tailored to various linker-drugs. There are various methods described in literature for site specific conjugation (Agarwal et al., Bioconjug. Chem. 26, 176-192 (2015); Cal et al., Angew. Chem. Int. Ed. Engl. 53, 10585-10587 (2014); Behrens et al., MAbs 6, 46-53 (2014); Panowski et al., MAbs 6, 34-45 (2014)). Methods for site specific conjugation include, in particular, enzymatic methods, e.g using transglutaminases (TGases), glycyltransferases or formylglycine generating enzyme (Sochaj et al., Biotechnology Advances, 33, 775-784 2015).

In WO2014/198817 anti-TWEAKR antibodies and in WO2015/189143 aglycosylated anti-TWEAKR antibodies are described that can used in antibody drug conjugates (ADCs).

Further, in WO2015/096982 antibody drug conjugates (ADCs) are described with kinesin spindel Protein (KSP). Especially this application describes ADCs with a TWEAKR antibody.

The present invention provides new site specific homogeneous binder conjugates of kinesin spindle protein inhibitors where the kinesin spindle protein inhibitors are conjugated to glutamine side chains of the binder and lacking the described disadvantages of randomly coupled binder drug conjugates.

More specifically the present invention provides new site specific homogeneous binder conjugates of kinesin spindle protein inhibitors where the kinesin spindle protein inhibitors are conjugated to glutamine side chains of the binder and lacking the described disadvantages of randomly coupled binder drug conjugates using transglutaminases (TGases).

SUMMARY OF THE INVENTION

Against this background it is an object of the present invention to provide substances which, after administration at a relatively low concentration, unfold apoptotic action and may therefore be of benefit for cancer therapy.

To achieve this object, the invention provides site specific homogenous conjugates of a binder or derivatives thereof with one or more active compound molecules, the active compound molecule being one or more kinesin spindle protein inhibitor (KSP inhibitor) or a prodrug thereof, attached to the binder via a linker L. The binder is preferably a binder protein or peptide, particularly preferably a human, humanized or chimeric monoclonal antibody or an antigen-binding fragment thereof, in particular an anti-TWEAKR antibody or an antigen-binding fragment thereof or an anti-EGFR antibody or an antigen-binding fragment thereof. Particular preference is given to an anti-TWEAKR antibody which binds specifically to amino acid D in position 47 (D47) of TWEAKR (SEQ ID NO: 169), in particular the anti-TWEAKR antibody TPP-2090, or the anti-Her2 antibody trastuzumab. If the binder is an antibody it comprises an acceptor glutamine, preferentially in the constant region. Such acceptor glutamines can be introduced by mutations of suitable positions into glutamine (e.g. mutation N297Q, Kabat EU numbering) or by generation of deglycosylated or aglycosylated antibodies (e.g. by enzymatic deglycosylation by PNGase F or by mutation of N297X, Kabat EU numbering). In that later case of a deglycosylated or an aglycosylated antibody the glutamine Q295 (Kabat EU numbering) becomes an acceptor glutamine. Highly preferred is an antibody comprising a mutation N297A or N297Q (Kabat EU numbering). Therefore in general, antibodies described here also include aglycosylated variants of these antibodies generated either by deglycosylation by PNGase F or by mutation of N297 (Kabat numbering system of antibodies, see Kabat et al., Sequences of Proteins of Immunological Interest, 5th Ed. Public Health Service, National Institutes of Health, Bethesda, Md. (1991)) of the heavy chain to any amino acid. Furthermore antibodies described here also include variants of the described antibodies being engineered to contain one or more acceptor glutamine residues for transglutaminase (TGase) catalyzed reactions.

One way for this attachment are literature-described approaches dealing with a site specific conjugation of binders using transglutaminase. Transglutaminases (TGase) including bacterial transglutaminase (BTG) (EC 2.3.2.13) are a family of enzymes that catalyze the formation of a covalent bond between the γ-carbonyl amide group of glutamines and the primary amine of lysines. Since some TGases also accept substrates other than lysine as the amine donor, they have been used to modify proteins including antibodies at suitable acceptor glutamine residues (Jeger et al., *Angewandte Chemie Int. Ed. Engl* 49, 9995-9997 (2010); Josten et al., *J. Immunol. Methods* 240, 47-54 (2000); Mindt et al., *Bioconjugate Chem.* 19, 271-278 (2008); Dennler et al., in *Antibody Drug Conjuagtes* (Ducry, L., Ed.), pp 205-215, Humana Press. (2013)). On the one hand transglutaminases were used for coupling of drugs to antibodies bearing genetically artificial glutamine tags being transglutaminse acceptor glutamines introduced by genetically engineering (Strop et al., *Chem. Biol.* 20, 161-167 (2013)). On the other hand it was reported that the conserved glutamine Q295 (Kabat numbering system of IgGs) located in the constant domain of the heavy chain is the sole γ-carbonyl amide donor for bacterial transglutaminase (EC 2.3.2.13) within the backbone of a aglycosylated IgG1, whereas no acceptor glutamine is present in the backbone in IgG1 being glycosylated at position N297 (kabat numbering) of the heavy chain (Jeger et al., *Angewandte Chemie Int. Ed. Engl* 49, 9995-9997 (2010)). In summary, the bacterial transglutaminase can be used for the conjugation of an amine group of the linker/drug to an acceptor glutamine residue of the antibody. Such acceptor glutamines can be introduced by engineering of the antibody by mutations or by generation of aglycosylated antibodies. Such aglycosylated antibodies can be generated by deglycosylation using N-glycosidase F (PNGaseF) or by mutation of the N297 (Kabat numbering) of the glycosylation site of the heavy chain to any other amino acid. Enzymatic conjugation of such aglycosylated antibodies was described for aglycosylated antibody variants bearing the mutations N297D, N297Q (Jeger et al., *Angewandte Chemie Int. Ed. Engl* 49, 9995-9997 (2010)), or N297S (see patent applications WO2013092998A1 and WO2013092983A2). Enzymatic conjugation using transglutaminase of such aglycosylated antibodies provides ADCs with DAR of 2 in general, in which both heavy chains are functionalized site specifically at position Q295 (Kabat numbering). The mutation N297Q of the antibody provides 1 additional site for conjugation at each heavy chain leading for example to ADCS with DAR of 4, in which both heavy chains are functionalized site-specifically at position Q295 and Q297 (Kabat numbering). Antibody variants bearing the mutations Q295N and N297Q provide one acceptor glutamine residue at position Q297 (Simone Jeger, Site specific conjugation of tumour targeting antibodies using transglutaminase, Dissertation at ETH Zurich (2009)). There are several examples in literature describing site specific conjugation of aglycosylated antibodies via transglutaminase (e.g. Dennler et al., *Bioconjugate Chemistry* 19, 569-578 (2014); Lhospice et al., *Molecular Pharmaceutics* 12, 1863-1871 (2015)). The strategy using transglutaminase catalyzed conjugation of aglycosylated antibodies is summarized in FIG. 8.

The inventors have found a way to attach the binder to the KSP inhibitor in a site specific homogenous manner in order to achieve the object mentioned above. Furthermore they demonstrated that transglutaminase could efficiently catalyse conjugation to aglycosylated antibody variants bearing the mutation N297A (Kabat numbering).

The invention provides site specific homogeneous conjugates of a binder or derivative thereof with one or more active compound molecules, the active compound molecule being a kinesin spindle protein inhibitor (KSP inhibitor) attached to the binder via a linker L and the linker L being conjugated to a specific site at the binder, preferably a glutamine side chain of the binder.

More specifically the invention provides site specific homogeneous conjugates of a binder or derivative thereof with one or more active compound molecules, the active compound molecule being a kinesin spindle protein inhibitor (KSP inhibitor) attached to the binder via a linker L and the linker L being conjugated to a glutamine side chain of the binder using transglutaminases (TGases).

The conjugate according to the invention can be represented by the general formula

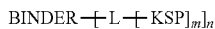

BINDER─[L─[KSP]$_m$]$_n$ where BINDER represents the binder, preferably an antibody, L represents the linker, KSP represents the KSP inhibitor, m represents a number from 1 to 5, preferably 1, and n represents 2 to 10, preferably 2 to 4, and also preferably 2 or 4. Here, m is the number of KSP inhibitors per linker and n the number of KSP inhibitor/linker conjugates per BINDER. The sum of all KSP present in the conjugate is thus the product of m and n. The binder is preferably a binder peptide or protein such as, for example, an antibody. If the binder is an antibody it comprises an acceptor glutamine, preferentially in the constant region. Such acceptor glutamines can be introduced by mutations of suitable positions into glutamine (e.g. mutation N297Q, Kabat EU numbering) or by generation of deglycosylated or aglycosylated antibodies (e.g. by enzymatic deglycosylation by PNGase F or by mutation of N297X, Kabat EU numbering). In that later case of a deglycosylated or an aglycosylated antibody the glutamine Q295 (Kabat EU numbering) becomes an acceptor glutamine. Highly preferred is an antibody comprising a mutation N297A or N297Q (Kabat EU numbering). Furthermore, the linker is attached to glutamine residues of the binder peptide or protein or derivative thereof. Particular preference is given to binding to glutamine residues of an antibody.

According to the invention, the kinesin spindle protein inhibitors may have the substructure I(sub) below:

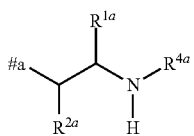

I(sub)

where a represents a bond to the remainder of the molecule;
$R^{1a}$ represents —H, -MOD, or —(CH$_2$)$_{0-3}$Z,
  where -MOD is represented as defined infra,
  where Z represents —H, halogen, —OY$^3$, —SY$^3$, —NHY$^3$, —C(=O)—NY$^1$Y$^2$ or —C(=O)—OY$^3$,
  where Y$^1$ and Y$^2$ independently of one another represent —H, —NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z',
  where Y$^3$ represents H or —(CH$_2$)$_{0-3}$Z',
  where Z' represents —H, —SO$_3$H, —NH$_2$, —COOH, —NH—C(=O)—CH$_2$—CH$_2$—CH(NH$_2$)COOH or —(C=O—NH—CHY$^4$)$_{1-3}$COOH,
  where W represents —H or —OH,
  where Y$^4$ represents linear or branched C$_{1-6}$-alkyl which is optionally substituted by —NHC(=O)—NH$_2$, or represents aryl or benzyl which are optionally substituted by —NH$_2$;
$R^{2a}$ represents —H, —C(=O)—CHY$^4$—NHY$^5$ or —(CH$_2$)$_{0-3}$Z,
  where Z represents —H, —OY$^3$, —SY$^3$, —NHY$^3$, —C(=O)—NY$^1$Y$^2$ or —C(=O)—OY$^3$,
  where Y$^1$ and Y$^2$ independently of one another represent —H, —NH$_2$ or —(CH$_2$)$_{0-3}$Z',
  where Y$^3$ represents —H or —(CH$_2$)$_{0-3}$Z',
  where Z' represents —H, —SO$_3$H, —NH$_2$ or —COOH;
  where Y$^4$ represents linear or branched C$_{1-6}$-alkyl which is optionally substituted by —NH—C(=O)—NH$_2$, or represents aryl or benzyl which are optionally substituted by —NH$_2$,
  where Y$^5$ represents —H or —C(=O)—CHY$^6$—NH$_2$,
  where Y$^6$ represents linear or branched C$_{1-6}$-alkyl;
$R^{4a}$ represents H, —C(=O)—CHY$^4$—NHY$^5$ or —(CH$_2$)$_{0-3}$Z,
  where Z represents —H, —OY$^3$, —SY$^3$, —NHY$^3$, —C(=O)—NY$^1$Y$^2$ or —C(=O)—OY$^3$,
  where Y$^1$ and Y$^2$ independently of one another represent —H, —NH$_2$ or —(CH$_2$)$_{0-3}$Z',
  where Y$^3$ represents —H or —(CH$_2$)$_{0-3}$Z',
  where Z' represents —H, —SO$_3$H, —NH$_2$ or —COOH;
  where Y$^4$ represents linear or branched C$_{1-6}$-alkyl which is optionally substituted by —NHC(=O)—NH$_2$, or represents aryl or benzyl which are optionally substituted by —NH$_2$,
  where Y$^5$ represents —H or —C(=O)—CHY$^6$—NH$_2$,
  where Y$^6$ represents linear or branched C$_{1-6}$-alkyl,
or
$R^{4a}$ represents a group of $R^{21}$—(C=O)$_{(0-1)}$-(P3)$_{(0-2)}$-P2-NH—CH(CH$_2$C(=O)—NH$_2$)—C(=O)— or the cathepsin cleavable group or a group $R^{21}$—(C=O)$_{(0-1)}$-(P3)$_{(0-2)}$-P2-,
  where $R^{21}$ represents C$_{1-10}$-alkyl-, C$_{5-10}$-aryl- or C$_{6-10}$-aralkyl-, C$_{5-10}$-heteroalkyl-, C$_{1-10}$-alkyl-O—C$_{6-10}$-aryl-, C$_{5-10}$-heterocycloalkyl-, heteroaryl-, heteroaryl-alkyl-, C$_{1-10}$-alkoxy-, C$_{6-10}$-aryloxy- or C$_{6-10}$-aralkoxy-, C$_{5-10}$-heteroalkoxy-, C$_{1-10}$-alkyl-O—C$_{6-10}$-aryloxy-, C$_{5-10}$-heterocycloalkoxy group, which may be substituted one or more times with —NH$_2$, —NH-alkyl, —N(alkyl)$_2$, —NH—C(=O)-alkyl, —N(alkyl)-C(=O)-alkyl, —SO$_3$H, —SO$_2$NH$_2$, —SO$_2$—N(alkyl)$_2$, —COOH, —C(=O)—NH$_2$, —C(=O)—N(alkyl)$_2$, or —OH; or which represents —H or a group —(O)$_x$—(CH$_2$CH$_2$O)$_y$—R$^{22}$,
  where x is 0 or 1,
  where v is a number from 1 to 10,
  where $R^{22}$ represents —H, -alkyl (preferably C$_{1-12}$-alkyl), —CH$_2$—COOH, —CH$_2$—CH$_2$—COOH, or —CH$_2$—CH$_2$—NH$_2$);
  where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;
  where P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the corresponding N-alkyl amino acids, preferably N-methyl amino acids; or $R^{2a}$ and $R^{4a}$ together represent (with formation of a pyrrolidine ring) —CH$_2$—CHR$^{10}$— or —CHR$^{10}$—CH$_2$—,
  where R$^{10}$ represents —H, halogen (preferably —F or —Cl), —NH$_2$, —COOH, —SO$_3$H, —SHC$_{1-4}$-alkyl, Halo-C$_{1-4}$-alkyl, C$_{1-4}$-alkoxy, hydroxy substituted C$_{1-4}$-alkyl, —C(=O)—O—(C$_{1-4}$-alkyl) or —OH.

According to the invention, the kinesin spindle protein inhibitor may be attached to the binder via a linker by substitution of a hydrogen atom at R$^{1a}$, R$^{2a}$, R$^{4a}$ or R$^{10}$.

The KSP inhibitor which is attached to this binder (or the KSP inhibitors, since frequently more than one KSP inhibitor is attached to the binder), is preferably a compound of the formula (Ia) below:

Formula (Ia):

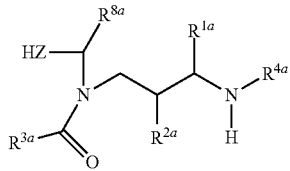

(Ia)

where
R$^{1a}$ represents —H, -MOD or —(CH$_2$)$_{0-3}$Z,
  where -MOD is represented as defined infra,
  where Z represents —H, halogen, —OY$^3$, —SY$^3$, —NHY$^3$, —C(O)—NY$^1$Y$^2$ or —C(O)—OY$^3$,
  where Y$^1$ and Y$^2$ independently of one another represent —H, —NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z',
  Y$^3$ represents —H or —(CH$_2$)$_{0-3}$Z',
  where Z' represents —H, —SO$_3$H, —NH$_2$, —COOH, —NH—C(=O)—CH$_2$—CH$_2$—CH(NH$_2$)COOH or —(C(=O)—NH—CHY$^4$)$_{1-3}$COOH,
  where W represents —H or —OH,
  where Y$^4$ represents linear or branched C$_{1-6}$-alkyl which is optionally substituted by —NHC(=O)—NH$_2$, or represents aryl or benzyl which are optionally substituted by —NH$_2$;
R$^{2a}$ represents —H, -MOD, —C(=O)—CHY$^4$—NHY$^5$ or —(CH$_2$)$_{0-3}$Z,
  where -MOD is represented as defined infra,
  where Z represents —H, —OY$^3$, —SY$^3$, —NHY$^3$, —C(=O)—NY$^1$Y$^2$ or —C(=O)—OY$^3$,
  where Y$^1$ and Y$^2$ independently of one another represent —H, —NH$_2$ or —(CH$_2$)$_{0-3}$Z',
  where Y$^3$ represents —H or —(CH$_2$)$_{0-3}$Z',
  where Z' represents —H, —SO$_3$H, —NH$_2$ or —COOH;
  where Y$^4$ represents linear or branched C$_{1-6}$-alkyl which is optionally substituted by —NH—C(=O)—NH$_2$, or represents aryl or benzyl which are optionally substituted by —NH$_2$,
  where Y$^5$ represents —H or —C(=O)—CHY$^6$—NH$_2$,
  where Y$^6$ represents linear or branched C$_{1-6}$-alkyl;
R$^{4a}$ represents —H, —C(=O)—CHY$^4$—NHY$^5$ or —(CH$_2$)$_{0-3}$Z,
  where Z represents —H, —OY$^3$, —SY$^3$, —NHY$^3$, —C(=O)—NY$^1$Y$^2$ or —C(=O)—OY$^3$,
  where Y$^1$ and Y$^2$ independently of one another represent —H, —NH$_2$ or —(CH$_2$)$_{0-3}$Z',
  where Y$^3$ represents —H or —(CH$_2$)$_{0-3}$Z',
  where Z' represents —H, —SO$_3$H, —NH$_2$ or —COOH;
  where Y$^4$ represents linear or branched C$_{1-6}$-alkyl which is optionally substituted by —NH—C(=O)—NH$_2$, or represents aryl or benzyl which are optionally substituted by —NH$_2$, and
  where Y$^5$ represents —H or —C(=O)—CHY$^6$—NH$_2$,
  where Y$^6$ represents linear or branched C$_{1-6}$-alkyl,
or
R$^{4a}$ represents a group of
  R$^{21}$—(C=O)$_{(0-1)}$-(P3)$_{(0-2)}$-P2-NH—CH(CH$_2$C(=O)—NH$_2$)—C(=O)—, or
  R$^{21}$—(C=O)$_{(0-1)}$-(P3)$_{(0-2)}$-P2-NH—CH(CH$_2$COOH)—C(=O)—, or the cathepsin cleavable group or formula R$^{21}$—(C=O)$_{(0-1)}$-(P3)$_{(0-2)}$-P2-,
  where R$^{21}$ represents C$_{1-10}$-alkyl-, C$_{5-10}$-aryl- or C$_{6-10}$-aralkyl-, C$_{5-10}$-heteroalkyl-, C$_{1-10}$-alkyl-O—C$_{6-10}$-aryl-, C$_{5-10}$-heterocycloalkyl-, heteroaryl-, heteroaryl-alkyl-, C$_{1-10}$-alkoxy-, C$_{6-10}$-aryloxy- or C$_{6-10}$-aralkoxy-, C$_{5-10}$-heteroalkoxy-, C$_{1-10}$-alkyl-O—C$_{6-10}$-aryloxy-, C$_{5-10}$-heterocycloalkoxy group (which may be substituted one or more times with —NH$_2$, —NH-alkyl, —N(alkyl)$_2$, —NH—C(=O)-alkyl, —N(alkyl)-C(=O)-alkyl, —SO$_3$H, —S(=O)$_2$NH$_2$, —S(=O)$_2$—N(alkyl)$_2$, —COOH, —C(=O)—NH$_2$, —C(=O)—N(alkyl)$_2$, or —OH), —H or a group —(O)$_x$—(CH$_2$CH$_2$O)$_y$—R$^{22}$,
  where x is 0 or 1 and
  where v is a number from 1 to 20,
  where R$^{22}$ represents —H, -alkyl (preferably C$_{1-12}$-alkyl), —CH$_2$—COOH, —CH$_2$—CH$_2$—COOH, or —CH$_2$—CH$_2$—NH$_2$);
  where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;
  where P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the corresponding N-alkyl amino acids, preferably N-methyl amino acids;
or
R$^{2a}$ and R$^{4a}$ together represent (with formation of a pyrrolidine ring) —CH$_2$—CHR$^{10}$— or —CHR$^{10}$—CH$_2$—,
  where R$^{10}$ represents —H, halogen (preferably —F or —Cl), —NH$_2$, —COOH, —SO$_3$H, —SH, C$_{1-4}$-alkyl, halo-C$_{1-4}$-alkyl, C$_{1-4}$-alkoxy, hydroxy substituted C$_{1-4}$-alkyl, —C(=O)—O—(C$_{1-4}$-alkyl) or —OH;
R$^{3a}$ represents -MOD or an optionally substituted alkyl, cycloalkyl, aryl, heteroaryl, heteroalkyl or heterocycloalkyl group, preferably a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—C(=O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)$_n$-alkyl groups, 1-3 —S(=O)$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups,
  where Z represents —H, halogen, —OY$^3$, —SY$^3$, —NHY$^3$, —C(=O)—NY$^1$Y$^2$ or —C(=O)—OY$^3$,
  where -MOD is represented as defined infra, where n is 0, 1 or 2,
where $Y^1$ and $Y^2$ independently of one another represent —H, —$NH_2$ or —$(CH_2)_{0-3}Z'$,
where $Y^3$ represents —H, —$(CH_2)_{0-3}$—CH(NHC(=O)—$CH_3$)$Z'$, —$(CH_2)_{0-3}$—CH($NH_2$)$Z'$ or —$(CH_2)_{0-3}Z'$,
where $Z'$ represents —H, —$SO_3H$, —$NH_2$ or —COOH
$R^{8a}$ represents $C_{1-10}$-alkyl or —$(CH_2)_{0-2}$—($HZ^2$),
where $HZ^2$ represents a 4- to 7-membered heterocycle having up to two heteroatoms selected from the group consisting of N, O and S;
HZ represents a mono- or bicyclic heterocycle which may be substituted by one or more substituents selected from the group consisting of halogen, $C_{1-10}$-alkyl groups, $C_{6-10}$-aryl groups and $C_{6-10}$-aralkyl groups which may optionally be substituted by halogen;
-MOD as defined supra represents —($NR^{10}$)n-(G1)o-G2-G3,
where $R^{10}$ represents —H; halogen or $C_1$-$C_3$-alkyl;
where G1 represents —NHC(=O)—, —C(=O)—NH— or

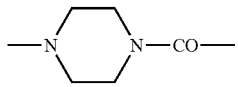

(where, if G1 represents —NHC(=O)— or

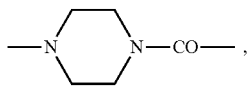

$R^{10}$ does not represent $NH_2$);
n is 0 or 1;
o is 0 or 1;
G2 represents a linear and/or branched hydrocarbon group which has 1 to 10 carbon atoms and which may be interrupted once or more than once by one or more of the groups
—O—, —S—, —S(=O)—, —S(=O)$_2$—, —$NR^y$—, —$NR^yC$(=O)—, —C(=O)—$NR^y$—, —$NR^yNR^y$—, —S(=O)$_2$—NRyNRy-, —C(=O)—$NR^yNR^y$—, —C(=O)—, —$CR^x$=N—O—,
and where the hydrocarbon group including any side chains may be substituted by —NHC(=O)—$NH_2$, —COOH, —OH, —$NH_2$, —NH—$CNNH_2$, sulphonamide, sulphone, sulphoxide or sulphonic acid,
where $R^y$ represents H, phenyl, $C_1$-$C_{10}$-alkyl, $C_2$-$C_{10}$-alkenyl or $C_2$-$C_{10}$-alkynyl, each of which may be substituted by —NHC(=O)—$NH_2$, —COOH, —OH, —$NH_2$, NH—$CNNH_2$, sulphonamide, sulphone, sulphoxide or sulphonic acid,
where $R^x$ represents —H, $C_1$-$C_3$-alkyl or phenyl),
where G3 represents —H or —COOH,
where-MOD preferably has at least one group —COOH;
and where the kinesin spindle protein inhibitor is attached to the linker by substitution of a hydrogen atom at $R^{1a}$, $R^{2a}$, $R^{3a}$, $R^{4a}$, $R^{8a}$ or $R^{10}$ or optionally via one of the substituents of HZ, in particular via $R^{1a}$, $R^{2a}$, $R^{3a}$, $R^{4a}$ or $R^{10}$ and the salts, solvates, salts of the solvates, and epimers thereof.

KSP-L- in the above shown formula has preferably the following formula (IIa):

Formula (IIa)

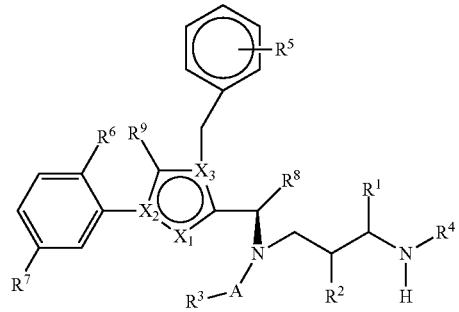

(IIa)

where
$X_1$ represents N, $X_2$ represents N and $X_3$ represents C; or
$X_1$ represents N, $X_2$ represents C and $X_3$ represents N; or
$X_1$ represents CH or CF, $X_2$ represents C and $X_3$ represents N; or
$X_1$ represents NH, $X_2$ represents C and $X_3$ represents C; or
$X_1$ represents CH, $X_2$ represents N and $X_3$ represents C
(with $X_1$ representing CH, $X_2$ representing C and $X_3$ representing N being preferred);
$R^1$ represents H, -L-#1, -MOD or —$(CH_2)_{0-3}Z$,
where -L-#1 represents the linker and #1 represents the bond to the binder or derivative thereof.
where -MOD is represented as defined infra,
where Z represents —H, halogen, —$OY^3$, —$SY^3$, —$NHY^3$, —C(=O)—$NY^1Y^2$ or —C(=O)—$OY^3$,
where $Y^1$ and $Y^2$ independently of one another represent —H, —$NH_2$, —($CH_2CH_2O$)$_{0-3}$—$(CH_2)_{0-3}Z'$ (e.g. —$(CH_2)_{0-3}Z'$) or —CH($CH_2W$)$Z'$,
where $Y^3$ represents —H or —$(CH_2)_{0-3}Z'$,
where $Z'$ represents —H, —$NH_2$, —$SO_3H$, —COOH, —NH—C(=O)—$CH_2$—$CH_2$—CH($NH_2$)COOH or —(C(=O)—NH—$CHY^4$)$_{1-3}$COOH,
where W represents —H or —OH,
where $Y^4$ represents linear or branched $C_{1-6}$-alkyl which is optionally substituted by —NHC(=O)—$NH_2$, or represents aryl or benzyl which are optionally substituted by —$NH_2$;
$R^2$ represents -L-#1, H, -MOD, —C(=O)—$CHY^4$—$NHY^5$ or —$(CH_2)_{0-3}Z$,
where -L-#1 represents the linker and #1 represents the bond to the binder or derivative thereof,
where -MOD is represented as defined infra,
where Z represents —H, halogen, —$OY^3$, —$SY^3$, $NHY^3$, —C(=O)—$NY^1Y^2$ or —C(=O)—$OY^3$,
where $Y^1$ and $Y^2$ independently of one another represent —H, —$NH_2$ or —$(CH_2)_{0-3}Z'$, and
where $Y^3$ represents —H or —$(CH_2)_{0-3}Z'$,
where $Z'$ represents —H, —$SO_3H$, —$NH_2$ or —COOH;
where $Y^4$ represents linear or branched $C_{1-6}$-alkyl which is optionally substituted by —NHC(=O)—

NH$_2$, or represents aryl or benzyl which are optionally substituted by —NH$_2$, where Y$^5$ represents —H or —C(=O)—CHY$^6$—NH$_2$, where Y$^6$ represents linear or branched C$_{1-6}$-alkyl;

R$^4$ represents -L-#1, —H, —C(=O)—CHY$^4$—NHY$^5$ or —(CH$_2$)$_{0-3}$Z, where -L-#1 represents the linker and #1 represents the bond to the binder or derivative thereof, where Z represents —H, —OY$^3$, —SY$^3$, —NHY$^3$, —C(=O)—NY$^1$Y$^2$ or —C(=O)—OY$^3$, where Y$^1$ and Y$^2$ independently of one another represent —H, —NH$_2$ or —(CH$_2$)$_{0-3}$Z', where Y$^3$ represents —H or —(CH$_2$)$_{0-3}$Z', where Z' represents —H, —SO$_3$H, —NH$_2$ or —COOH;

where Y$^4$ represents linear or branched C$_{1-6}$-alkyl which is optionally substituted by —NHC(=O)—NH$_2$, or represents aryl or benzyl which are optionally substituted by —NH$_2$, and where Y$^5$ represents —H or —C(=O)—CHY$^6$—NH$_2$, where Y$^6$ represents linear or branched C$_{1-6}$-alkyl, or R$^4$ represents a group of R$^{21}$—(C=O)$_{(0-1)}$-(P3)$_{(0-2)}$-P2-NH—CH(CH$_2$C(=O)—NH$_2$)—C(=O)— or R$^{21}$—(C=O)$_{(0-1)}$-(P3)$_{(0-2)}$-P2-NH—CH(CH$_2$COOH)—C(=O)— or the cathepsin cleavable group R$^{21}$—(C=O)$_{(0-1)}$-(P3)$_{(1-2)}$-P2-, where R$^{21}$ represents H, C$_{1-10}$-alkyl-, C$_{5-10}$-aryl- or C$_{6-10}$-aralkyl-, C$_{5-10}$-heteroalkyl-, C$_{1-10}$-alkyl-O—C$_{6-10}$-aryl-, C$_{1-10}$-heterocycloalkyl-, heteroaryl-, heteroaryl-alkyl-, C$_{1-10}$-alkoxy-, C$_{6-10}$-aryloxy- or C$_{6-10}$-aralkoxy-, C$_{5-10}$-heteroalkoxy-, C$_{1-10}$-alkyl-O—C$_{6-10}$-aryloxy-, C$_{1-10}$-heterocycloalkoxy group (which may be substituted one or more times with —NH$_2$, —NH-alkyl, —N(alkyl)$_2$, —NH—C(=O)-alkyl, N(alkyl)-C(=O)-alkyl, —SO$_3$H, —SO$_2$NH$_2$, —S(=O)$_2$—N(alkyl)$_2$, —COOH, —C(=O)—NH$_2$, —C(=O)—N(alkyl)$_2$, or —OH), —H or a group —(O)$_x$—(CH$_2$CH$_2$O)$_v$—R$^{22}$, where x is 0 or 1 and where v is a number from 1 to 20, where R$^{22}$ represents —H, -alkyl (preferably C$_{1-12}$-alkyl), —CH$_2$—COOH, —CH$_2$—CH$_2$—COOH, or —CH$_2$—CH$_2$—NH$_2$);

where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

where P3 is an amino acid independently selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the corresponding N-alkyl amino acids, preferably N-methyl amino acids; in case there is more than one amino acid P3, P3 may have the same or different amino acids, as defined above;

or

R$^2$ and R$^4$ together (with formation of a pyrrolidine ring) represent —CH$_2$—CHR$^{10}$— or —CHR$^{10}$—CH$_2$—, where R$^{10}$ represents L-#1, —H, —NH$_2$, —SO$_3$H, —COOH, —SH or —OH, and wherein the hydrogen atom of the secondary amino group in the pyrrolidine ring may be replaced by R$^{21}$—C(=O)-P3$_{(0-2)}$-P2-NH—CH(CH$_2$C(=O)—NH$_2$)—C(=O)-SIG-;

where L-#1 represents the linker and #1 represents the bond to the binder or derivative thereof, where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

where P3 is an amino acid independently selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the corresponding N-alkyl amino acids, preferably N-methyl amino acids;

where -SIG is a self-immolative group, which, upon cleavage of the —C(=O)-SIG bond provides the free secondary amine;

A represents —C(=O)—, —S(=O)—, —S(=O)$_2$—, —S(=O)$_2$—NH— or —C(=N—NH$_2$)—;

R$^3$ represents -L-#1, -MOD or an optionally substituted alkyl, cycloalkyl, aryl, heteroaryl, heteroalkyl, heterocycloalkyl group, preferably -L-#1 or a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3 —OH groups, 1-3 halogen atoms, 1-3 halogenated alkyl groups (each having 1-3 halogen atoms), 1-3 —O-alkyl groups, 1-3 —SH groups, 1-3 —S-alkyl groups, 1-3 —O—C(=O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)$_n$-alkyl groups, 1-3 —S(=O)$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups, where -L-#1 represents the linker and #1 represents the bond to the binder or derivative thereof, where -MOD is represented as defined infra, where n represents 0, 1 or 2, where Z represents —H, halogen, —OY$^3$, —SY$^3$, —NHY$^3$, —C(=O)—NY$^1$Y$^2$ or —C(=O)—OY$^3$, where Y$^1$ and Y$^2$ independently of one another represent —H, —NH$_2$ or —(CH$_2$)$_{0-3}$Z' and where Y$^3$ represents —H, —(CH$_2$)$_{0-3}$—CH(NHC(=O)—CH$_3$)Z', —(CH$_2$)$_{0-3}$—CH(NH$_2$)Z' or —(CH$_2$)$_{0-3}$Z', where where Z' represents —H, —SO$_3$H, —NH$_2$ or —COOH R$^5$ represents -L-#1, —H, —NH$_2$, —NO$_2$, halogen (in particular —F, —Cl, —Br), —CN, —CF$_3$, —OCF$_3$, —CH$_2$F, —CH$_2$F, —SH or —(CH$_2$)$_{0-3}$Z, where -L-#1, represents the linker and #1 represents the bond to the binder or derivative thereof, where Z represents —H, —OY$^3$, —SY$^3$, halogen, —NHY$^3$, —C(O)—NY$^1$Y$^2$ or —C(O)—OY$^3$, where Y$^1$ and Y$^2$ independently of one another represent —H, —NH$_2$ or —(CH$_2$)$_{0-3}$Z', where Y$^3$ represents —H or —(CH$_2$)$_{0-3}$Z', where Z' represents —H, —SO$_3$H, —NH$_2$ or —COOH;

R$^6$ and R$^7$ independently of one another represent —H, cyano, (optionally fluorinated) C$_{1-10}$-alkyl, (optionally fluorinated) C$_{2-10}$-alkenyl, (optionally fluorinated) $C_{2-10}$-alkynyl, hydroxy, $-NO_2$, $-NH_2$, $-COOH$ or halogen (in particular $-F$, $-Cl$, $-Br$), $R^8$ represents (optionally fluorinated) $C_{1-10}$-alkyl, (optionally fluorinated) $C_{2-10}$-alkenyl, (optionally fluorinated) $C_{2-10}$-alkynyl, (optionally fluorinated) $C_{4-10}$-cycloalkyl or $-(CH_2)_{0-2}-(HZ^2)$, where $HZ^2$ represents a 4- to 7-membered heterocycle having up to two heteroatoms selected from the group consisting of N, O and S, where each of these groups may be substituted by $-OH$, $-COOH$ or $-NH_2$ or -L-#1;

where -L-#1 represents the linker and #1 represents the bond to the binder or derivative thereof, and where -MOD as defined supra represents $-(NR^{10})$ n-(G1)o-G2-G3, where $R^{10}$ represents H or $C_1$-$C_3$-alkyl;

where G1 represents $-NH-C(=O)-$, $-C(=O)-NH-$ or

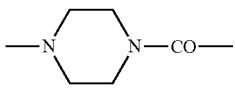

(where, if G1 represents $-NHC(=O)-$ or

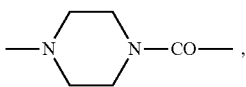

$R^{10}$ does not represent $-NH_2$);

where n is 0 or 1;

where o is 0 or 1;

where G2 represents a linear and/or branched hydrocarbon group which has 1 to 10 carbon atoms and which may be interrupted once or more than once by one or more of the groups $-O-$, $-S-$, $-S(=O)-$, $-S(=O)_2-$, $-NR^y-$, $-NR^yC(=O)-$, $-C(=O)-NR-$, $-NR^yNR^y-$, $-S(=O)_2-NR_yNR_y-$, $-C(=O)-NR^yNR^y-$, $-C(=O)-$, $-CR^x=N-O-$, and where the hydrocarbon chain including any side chains may be substituted by $-NH-C(=O)-NH_2$, $-COOH$, $-OH$, $-NH_2$, NH$-CNNH_2$, sulphonamide, sulphone, sulphoxide or sulphonic acid, where $R^y$ represents $-H$, phenyl, $C_1$-$C_{10}$-alkyl, $C_2$-$C_{10}$-alkenyl or $C_2$-$C_{10}$-alkynyl, each of which may be substituted by $-NH-C(=O)-NH_2$, $-COOH$, $-OH$, $-NH_2$, NH$-CNNH_2$, sulphonamide, sulphone, sulphoxide or sulphonic acid, where $R^x$ represents $-H$, $C_1$-$C_3$-alkyl or phenyl, where G3 represents $-H$ or $-COOH$, and where -MOD preferably has at least one $-COOH$ group;

and the salts, solvates, salts of the solvates, and epimers thereof.

The conjugates according to the invention can have chemically labile linkers, enzymatically labile linkers or stable linkers. Particular preference is given to stable linkers and linkers which can be cleaved by legumain or cathepsin.

The invention furthermore provides processes for preparing the site specific homogeneous conjugates according to the invention, and also precursors and intermediates for the preparation.

The preparation of the conjugates according to the invention regularly comprises the following steps:

(i) Preparation of a linker precursor which optionally carries protective groups and has a reactive group which is capable of coupling to the binder;

(ii) Conjugation of the linker precursor to the derivative, which optionally carries protective groups, of a low-molecular weight KSP inhibitor (preferably a KSP inhibitor having the substructure I(sub), particularly preferably of formula (Ia) and in particular of formula (IIa), where in these formulae there is as yet no bond to a linker), giving a reactive KSP inhibitor/linker conjugate which optionally carries protective groups;

(iii) Removal of any protective groups present in the KSP inhibitor/linker conjugate and (iv) Site specific conjugation of the binder to the KSP inhibitor/linker conjugate, preferably using transglutaminase, giving the binder/KSP inhibitor site specific homogenous conjugate according to the invention.

Attachment of the reactive group may also take place after the construction of an optionally protected KSP inhibitor/linker precursor conjugate.

As illustrated above, conjugation of the linker precursor to a low-molecular weight KSP inhibitor may take place by substitution of a hydrogen atom at $R^{1a}$, $R^{2a}$, $R^{4a}$ or $R^{10}$ in substructur I(sub), $R^{1a}$, $R^{2a}$, $R^{3a}$, $R^{4a}$, $R^{8a}$ or $R^{10}$ in formula (Ia), or $R^1$, $R^2$, $R^3$, $R^4$, $R^5$, $R^8$ or $R^{10}$ in formula (IIa) by the linker. In the synthesis steps prior to the conjugation, any functional groups present may also be present in protected form. Prior to the conjugation step, these protective groups are removed by known methods of peptide chemistry. Conjugation can take place chemically by various routes, as shown in an exemplary manner in Schemes 2 to 6 in the examples. In particular, it is optionally possible to modify the low-molecular weight KSP inhibitor for conjugation to the linker, for example by introduction of protective groups or leaving groups to facilitate substitution.

In particular, the invention provides low-molecular weight KSP inhibitors conjugated to a binder. These r binder conjugates have the following general formula (IIIa):

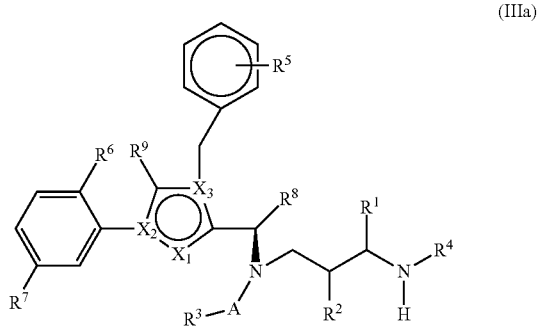

(IIIa)

where $X_1$ represents N, $X_2$ represents N and $X_3$ represents C; or $X_1$ represents N, $X_2$ represents C and $X_3$ represents N; or $X_1$ represents CH or CF, $X_2$ represents C and $X_3$ represents N; or $X_1$ represents NH, $X_2$ represents C and $X_3$ represents C; or $X_1$ represents CH, $X_2$ represents N and $X_3$ represents C (with $X_1$ representing CH, $X_2$ representing C and $X_3$ representing N being preferred);

$R^1$ represents $-H$, -L-BINDER, -MOD or $-(CH_2)_{0-3}Z$, where Z represents —H, —NHY$^3$, —OY$^3$, —SY$^3$, halogen, —C(=O)—NY$^1$Y$^2$ or —C(=O)—OY$^3$, where Y$^1$ and Y$^2$ independently of one another represent —H, —NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z', and where Y$^3$ represents H or —(CH$_2$)$_{0-3}$Z', where Z' represents —H, —NH$_2$, —SO$_3$H, —COOH, —NH—C(=O)—CH$_2$—CH$_2$—CH(NH$_2$)COOH or —(C(=O)—NH—CHY$^4$)$_{1-3}$COOH, where W represents —H or —OH, where Y$^4$ represents linear or branched C$_{1-6}$-alkyl which is optionally substituted by —NH—(C=O)—NH$_2$, or represents aryl or benzyl which are optionally substituted by —NH$_2$;

R$^2$ represents -L-BINDER, H, -MOD, —C(=O)—CHY$^4$—NHY$^5$ or —(CH$_2$)$_{0-3}$Z, or R$^2$ and R$^4$ together (with formation of a pyrrolidine ring) represent —CH$_2$—CHR$^{10}$— or —CHR$^{10}$—CH$_2$—, where R$^{10}$ represents L-#1, —H, —NH$_2$, —SO$_3$H, —COOH, —SH, or —OH;

where Z represents —H, halogen, —OY$^3$, —SY$^3$, —NHY$^3$, —C(=O)—NY$^1$Y$^2$ or —C(=O)—OY$^3$, where Y$^1$ and Y$^2$ independently of one another represent —H, —NH$_2$ or —(CH$_2$)$_{0-3}$Z', where Y$^3$ represents —H or —(CH$_2$)$_{0-3}$Z', where Z' represents —H, —SO$_3$H, —NH$_2$ or —COOH;

where Y$^4$ represents linear or branched C$_{1-6}$-alkyl which is optionally substituted by —NH—C(=O)—NH$_2$, or represents aryl or benzyl which are optionally substituted by —NH$_2$, where Y$^5$ represents —H or —C(=O)—CHY$^6$—NH$_2$, where Y$^6$ represents linear or branched C$_{1-6}$-alkyl;

R$^4$ represents -L-BINDER, —H, —C(O)—CHY$^4$—NHY$^5$ or —(CH$_2$)$_{0-3}$Z, where Z represents —H, —OY$^3$, —SY$^3$, —NHY$^3$, —C(=O)—NY$^1$Y$^2$ or —C(=O)—OY$^3$, where Y$^1$ and Y$^2$ independently of one another represent —H, —NH$_2$ or —(CH$_2$)$_{0-3}$Z', where Y$^3$ represents —H or —(CH$_2$)$_{0-3}$Z', where Z' represents —H, —SO$_3$H, —NH$_2$ or —COOH;

where Y$^4$ represents linear or branched C$_{1-6}$-alkyl which is optionally substituted by —NH—C(=O)—NH$_2$, or represents aryl or benzyl which are optionally substituted by —NH$_2$, where Y$^5$ represents —H or —C(=O)—CHY$^6$—NH$_2$, where Y$^6$ represents linear or branched C$_{1-6}$-alkyl, or R$^4$ represents a group of R$^{21}$—(C=O)$_{(0-1)}$-(P3)$_{(0-2)}$-P2-NH—CH(CH$_2$C(=O)—NH$_2$)—C(=O)—, or R$^{21}$—(C=O)$_{(0-1)}$-(P3)$_{(0-2)}$-P2-NH—CH(CH$_2$COOH)—C(=O)—, or the cathepsin cleavable group or formula R$^{21}$—(C=O)$_{(0-1)}$-(P3)$_{(1-2)}$-P2-, where R$^{21}$ represents —H, C$_{1-10}$-alkyl-, C$_{5-10}$-aryl- or C$_{6-10}$-aralkyl-, C$_{5-10}$-heteroalkyl-, C$_{1-10}$-alkyl-O—C$_{6-10}$-aryl-, C$_{5-10}$-heterocycloalkyl-, heteroaryl-, heteroaryl-alkyl-, C$_{1-10}$-alkoxy-, C$_{6-10}$-aryloxy- or C$_{6-10}$-aralkoxy-, C$_{5-10}$-heteroalkoxy-, C$_{1-10}$-alkyl-O—C$_{6-10}$-aryloxy-, C$_{5-10}$-heterocycloalkoxy group, which may be substituted one or more times with —NH$_2$, —NH-alkyl, —N(alkyl)$_2$, —NH—C(=O)-alkyl, —N(alkyl)-C(=O)-alkyl, —SO$_3$H, —SO$_2$NH$_2$, —S(=O)$_2$—N(alkyl)$_2$, —COOH, —C(=O)—NH$_2$, —C(=O)—N(alkyl)$_2$, or —OH, or is —H or a group —O$_x$—(CH$_2$CH$_2$O)$_y$—R$^{22}$, where x is 0 or 1, where v is a number from 1 to 20, and where R$^{22}$ represents —H, -alkyl (preferably C1-12-alkyl), —CH$_2$—COOH, —CH$_2$—CH$_2$—COOH, or —CH$_2$—CH$_2$—NH$_2$;

where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

where P3 is an amino acid independently selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the corresponding N-alkyl amino acids, preferably N-methyl amino acids;

or

R$^2$ and R$^4$ together (with formation of a pyrrolidine ring) represent —CH$_2$—CHR$^{10}$— or —CHR$^{10}$—CH$_2$—, where R$^{10}$ represents L-#1, —H, —NH$_2$, —SO$_3$H, —COOH, —SH, halogen C$_{1-4}$ Alkyl, C$_{1-4}$ Haloalkyl, C$_{1-4}$ Alkoxy, Hydroxyl-substituted C$_{1-4}$ Alkyl, COO(C$_{1-4}$ Alkyl) or —OH; and wherein the hydrogen atom of the secondary amino group in the pyrrolidine ring may be replaced by R$^{21}$—C(=O) P3$_{(0-2)}$-P2-NH—CH(CH$_2$C(=O)NH$_2$)—C(=O)-SIG-;

where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

where P3 is an amino acid independently selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the corresponding N-alkyl amino acids, preferably N-methyl amino acids;

where -SIG is a self-immolative group, which, upon cleavage of the —C(=O)-SIG bond provides the free secondary amine;

A represents —C(=O)—, —S(=O)—, —S(=O)$_2$—, —S(=O)$_2$—NH— or —C(=N—NH$_2$)—;

R$^3$ represents -L-BINDER, -MOD or an optionally substituted alkyl, cycloalkyl, aryl, heteroaryl, heteroalkyl, heterocycloalkyl group, preferably -L-BINDER, or a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3 —OH groups, 1-3 halogen atoms, 1-3 halogenated alkyl groups (each having 1-3 halogen atoms), 1-3 —O-alkyl groups, 1-3 —SH groups, 1-3 —S-alkyl groups, 1-3 —O—C(=O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)$_n$-alkyl groups, 1-3 —S(=O)$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups, where n is 0, 1 or 2, where Z represents —H, halogen, —OY$^3$, —SY$^3$, —NHY$^3$, —C(=O)—NY$^1$Y$^2$ or —C(=O)—OY$^3$, where Y$^1$ and Y$^2$ independently of one another represent —H, —NH$_2$ or —(CH$_2$)$_{0-3}$Z', where Y$^3$ represents —H, —(CH$_2$)$_{0-3}$—CH(NH—C(=O)—CH$_3$)Z', —(CH$_2$)$_{0-3}$—CH(NH$_2$)Z' or —(CH$_2$)$_{0-3}$Z', where Z' represents —H, —SO$_3$H, —NH$_2$ or —COOH where "alkyl" preferably represents C$_{1-10}$-alkyl);

R$^5$ represents -L-BINDER, —H, —NH$_2$, —NO$_2$, halogen (in particular F, Cl, Br), —CN, —CF$_3$, —OCF$_3$, —CH$_2$F, —CH$_2$F, —SH or —(CH$_2$)$_{0-3}$Z, where Z represents —H, —OY$^3$, —SY$^3$, halogen, —NHY$^3$, —C(=O)—NY$^1$Y$^2$ or —C(=O)—OY$^3$, where $Y^1$ and $Y^2$ independently of one another represent —H, —NH$_2$ or —(CH$_2$)$_{0-3}$Z',
where $Y^3$ represents —H or —(CH$_2$)$_{0-3}$Z',
where Z' represents —H, —SO$_3$H, —NH$_2$ or —COOH;
$R^8$ represents C$_{1-10}$-alkyl, fluoro-C$_{1-10}$-alkyl, C$_{2-10}$-alkenyl, fluoro-C$_{2-10}$-alkenyl, C$_{2-10}$-alkynyl, fluoro-C$_{2-10}$-alkynyl, C$_{4-10}$-cycloalkyl, fluoro-C$_{4-10}$-cycloalkyl or —(CH$_2$)$_{0-2}$—(HZ$^2$),
where HZ$^2$ represents a 4- to 7-membered heterocycle having up to two heteroatoms selected from the group consisting of N, O and S (preferably oxetane), where each of these groups may be substituted by —OH, —COOH or —NH$_2$ or -L-BINDER;
where L represents a linker and
BINDER represents a binder or a derivative thereof, where the binder may optionally be attached to a plurality of active compound molecules,
where one representative of $R^1$, $R^2$, $R^3$ $R^4$, $R^5$, $R^8$ and $R^{10}$ represents -L-binder;
$R^6$ and $R^7$ independently of one another represent —H, cyano, C$_{1-10}$-alkyl, fluoro-C$_{1-10}$-alkyl, C$_{2-10}$-alkenyl, fluoro-C$_{2-10}$-alkenyl, C$_{2-10}$-alkynyl, fluoro-C$_{2-10}$-alkynyl, hydroxy, —NO$_2$, —NH$_2$, —COOH or halogen (in particular —F, —Cl, —Br),
-MOD represents —(NR$^{10}$)n-(G1)o-G2-G3,
where $R^{10}$ represents —H or C$_1$-C$_3$-alkyl;
where G1 represents —NH—C(=O)—, —C(=O)—NH— or

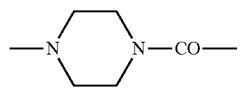

(where, if G1 represents —NH—C(=O)— or

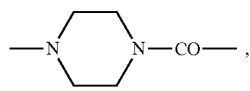

$R^{10}$ does not represent NH$_2$);
where n is 0 or 1;
where o is 0 or 1; and
where G2 represents a linear and/or branched hydrocarbon group which has 1 to 10 carbon atoms and which may be interrupted once or more than once by one or more of the groups —O—, —S—, —S(=O)—, —S(=O)$_2$—, —NR$^y$—, —NR$^y$C(=O)—, —C(=O)—NR$^y$—, —NR$^y$NR$^y$—, —S(=O)$_2$—NR$^y$NR$^y$—, —C(=O)—NR$^y$NR$^y$—,
where R$^y$ represents —H, phenyl, C$_1$-C$_{10}$-alkyl, C$_2$-C$_{10}$-alkenyl or C$_2$-C$_{10}$-alkynyl, each of which may be substituted by —NH—C(=O)—NH$_2$, —COOH, —OH, —NH$_2$, NH—CN—NH$_2$, sulphonamide, sulphone, sulphoxide or sulphonic acid, or represents —C(=O)—, —CR$^x$=N—O—
where R$^x$ represents —H, C$_1$-C$_3$-alkyl or phenyl,
where the hydrocarbon chain including any side chains may be substituted by —NH—C(=O)—NH$_2$, —COOH, —OH, —NH$_2$, NH—CN—NH$_2$, sulphonamide, sulphone, sulphoxide or sulphonic acid,
where G3 represents —H or —COOH, and
where -MOD preferably has at least one group —COOH;

and the salts, solvates, salts of the solvates, and epimers thereof.

DESCRIPTION OF THE FIGURES

FIG. 1 shows alignment of the TWEAKR cysteine-rich domain (amino acids 34 to 68) of various species. (The numbers show the amino acid position in full-length constructs including the signal sequences; "Human" shows amino acids 34 to 68 of SEQ ID NO: 169, "Rat" shows amino acids 7 to 41 of SEQ ID NO: 134, "Mac" shows amino acids 7 to 41 of SEQ ID NO: 133, "Pig" shows amino acids 7 to 41 of SEQ ID NO: 135, "Mouse" shows amino acids 7 to 41 of SEQ ID NO: 137, "Dog" shows amino acids 7 to 41 of SEQ ID NO: 136).

DETAILED DESCRIPTION OF THE INVENTION

Figure 2A:
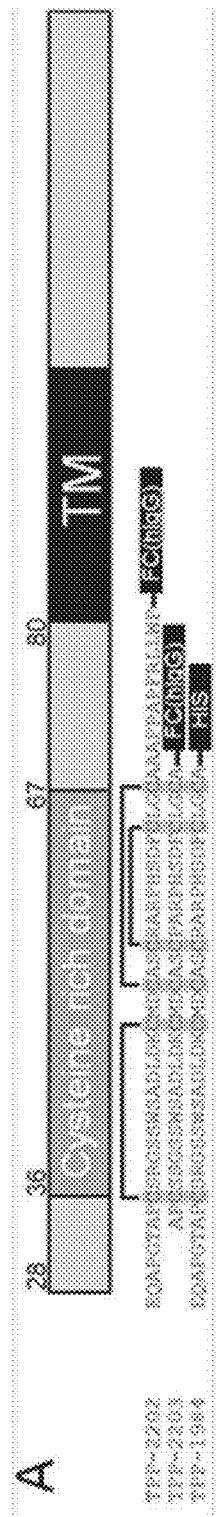
FIG. 2A shows a schematic diagram of the structure of TWEAKR (SEQ ID NO: 169). The diagram shows the extracellular domain (amino acids 28-80) (SEQ ID NO: 168) including the cysteine-rich domain (36-67), the transmembrane domain—TM (81-101) and the intracellular domain (102-129). TPP-2202—the complete ectodomain (28-80), fused to the Fc domain of hIgG1. TPP-2203-extracellular domain with N- and C-terminal truncation (34-68), fused to the Fc domain of hIgG1. Disulphide bridges Cys36-Cys49, Cys52-Cys67 and Cys55-Cys64 are indicated by black bars. N-terminally and C-terminally, TPP-2203 contains two amino acids more and one amino acid more, respectively, than the unmodified cysteine-rich domain to ensure proper folding. TPP-1984-extracellular domain having C-terminal truncation (28-68), fused to an HIS6 tag. All three constructs show comparable binding to the antibodies according to the invention and PDL-192 (TPP-1104). P4A8 (TPP-1324) binds only to the full-length extracellular domain (TPP-2202).

The invention provides site specific homogeneous conjugates of a binder or derivative thereof with one or more active compound molecules, the active compound molecule being a kinesin spindle protein inhibitor (KSP inhibitor) attached to the binder via a linker L and the linker L being conjugated to a specific site at the binder, preferably a glutamine side chain of the binder.

More specifically the invention provides site specific homogeneous conjugates of a binder or derivative thereof with one or more active compound molecules, the active compound molecule being a kinesin spindle protein inhibitor (KSP inhibitor) attached to the binder via a linker L and the linker L being conjugated to a glutamine side chain of the binder using transglutaminases (TGases).

The conjugate according to the invention can be represented by the general formula

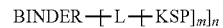

where BINDER represents the binder, preferably an antibody, L represents the linker, KSP represents the KSP inhibitor, m represents a number from 1 to 5, preferably 1, and n represents 2 to 10, preferably 2 to 4, and also preferably 2 or 4. Here, m is the number of KSP inhibitors per linker and n the number of KSP inhibitor/linker conjugates per BINDER. The sum of all KSP present in the conjugate is thus the product of m and n. KSP-L preferably has the formula (IIa) shown above. The binder is preferably a binder peptide or protein such as, for example, an antibody. If the binder is an antibody it comprises an acceptor glutamine, preferentially in the constant region. Such acceptor glutamines can be introduced by mutations of suitable positions into glutamine (e.g. mutation N297Q, Kabat EU numbering) or by generation of deglycosylated or aglycosylated antibodies (e.g. by enzymatic deglycosylation by PNGase F or by mutation of N297X, Kabat EU numbering). In that later case of a deglycosylated or an aglycosylated antibody the glutamine Q295 (Kabat EU numbering) becomes an acceptor glutamine. Highly preferred is an antibody comprising a mutation N297A or N297Q (Kabat EU numbering). Furthermore, the linker is attached to glutamine residues of the binder peptide or protein or derivative thereof. Particular preference is given to binding to glutamine residues of an antibody.

Binders which can be used according to the invention, KSP inhibitors which can be used according to the invention and linkers which can be used according to the invention which can be used in combination without any limitation are described below. In particular, the binders represented in each case as preferred or particularly preferred can be employed in combination with the KSP inhibitors represented in each case as preferred or particularly preferred, optionally in combination with the linkers represented in each case as preferred or particularly preferred.

KSP Inhibitors and their Binder Conjugates

Low-molecular weight KSP inhibitors are known, for example, from WO2006/044825; WO2006/002236; WO2005/051922; WO2006/060737; WO03/060064; WO03/040979; and WO03/049527.

As a rule, KSP inhibitors have the following substructure I(sub):

where
a represents a bond to the rest of the molecule;
$R^{1a}$ represents —H or —$(CH_2)_{0-3}Z$,
   where Z represents —H, halogen, —$NHY^3$, —C(=O)—$NY^1Y^2$ or —C(=O)—$OY^3$,
   where $Y^1$ and $Y^2$ independently of one another represent —H, —$NH_2$, —$(CH_2CH_2O)_{0-3}$—$(CH_2)_{0-3}Z'$ (e.g. —$(CH_2)_{0-3}Z'$) or —CH($CH_2W$)$Z'$,
   where $Y^3$ represents —H or —$(CH_2)_{0-3}Z'$, where Z' represents —H, —SO₃H, —NH₂, —COOH,
—NH—C(=O)—CH₂—CH₂—CH(NH₂)COOH or
—(C(=O)—NH—CHY⁴)₁₋₃COOH,
where W represents —H or —OH,
where Y⁴ represents linear or branched $C_{1-6}$-alkyl which is optionally substituted by —NH—C(=O)—NH₂, or represents aryl or benzyl which are optionally substituted by —NH₂;
$R^{2a}$ represents —H, —C(=O)—CHY⁴—NHY⁵ or —(CH₂)₀₋₃Z,
where Z represents —H, —OY³, —SY³, —NHY³, —C(=O)—NY¹Y² or —C(=O)—OY³,
where Y¹ and Y² independently of one another represent —H, —NH₂ or —(CH₂)₀₋₃Z',
where Y³ represents —H or —(CH₂)₀₋₃Z',
where Z' represents —H, —SO₃H, —NH₂ or —COOH;
where Y⁴ represents linear or branched $C_{1-6}$-alkyl which is optionally substituted by —NH—C(=O)—NH₂, or represents aryl or benzyl which are optionally substituted by —NH₂,
where Y⁵ represents —H or —C(=O)—CHY⁶—NH₂,
where Y⁶ represents linear or branched $C_{1-6}$-alkyl;
$R^{4a}$ represents —H, —C(O)—CHY⁴—NHY⁵ or —(CH₂)₀₋₃Z,
where Z represents —H, —OY³, —SY³, —NHY³, —C(=O)—NY¹Y² or —C(=O)—OY³,
where Y¹ and Y² independently of one another represent —H, —NH₂ or —(CH₂)₀₋₃Z',
where Y³ represents —H or —(CH₂)₀₋₃Z',
where Z' represents —H, —SO₃H, —NH₂ or —COOH;
where Y⁴ represents linear or branched $C_{1-6}$-alkyl which is optionally substituted by —NH—C(=O)—NH₂, or represents aryl or benzyl which are optionally substituted by —NH₂,
where Y⁵ represents —H or —C(=O)—CHY⁶—NH₂,
where Y⁶ represents linear or branched $C_{1-6}$-alkyl,
or
$R^{4a}$ represents a group of $R^{21}$—(C=O)$_{(0-1)}$-(P3)$_{(0-2)}$-P2-NH—CH(CH₂C(=O)—NH₂)—C(=O)— or the cathepsin cleavable group or formula $R^{21}$—(C=O)$_{(0-1)}$-(P3)$_{(0-2)}$-P2-,
where $R^{21}$ represents —H, $C_{1-10}$-alkyl-, $C_{5-10}$-aryl- or $C_{6-10}$-aralkyl-, $C_{5-10}$-heteroalkyl-, $C_{1-10}$-alkyl-O—$C_{6-10}$-aryl-, $C_{5-10}$-heterocycloalkyl-, heteroaryl-, heteroaryl-alkyl-, $C_{1-10}$-alkoxy-, $C_{6-10}$-aryloxy- or $C_{6-10}$-aralkoxy-, $C_{5-10}$-heteroalkoxy-, $C_{1-10}$-alkyl-O—$C_{6-10}$-aryloxy-, $C_{5-10}$-heterocycloalkoxy group, which may be substituted one or more times with —NH₂, —NH-alkyl, —N(alkyl)₂, NH—C(=O)-alkyl, N(alkyl)-C(=O)alkyl, —SO₃H, —SO₂NH₂, —S(=O)₂—N(alkyl)₂, —COOH, —C(=O)—NH₂, —C(=O)—N(alkyl)₂, or —OH; or which represents —H or a group —O$_x$—(CH₂CH₂O)$_y$—R²²,
where x is 0 or 1,
where v is a number from 1 to 20,
where R²² represents —H, -alkyl (preferably $C_{1-12}$-alkyl), —CH₂—COOH, —CH₂—CH₂—COOH, or —CH₂—CH₂—NH₂;
where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;
where P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the corresponding N-alkyl amino acids, preferably N-methyl amino acids;
or
$R^{2a}$ and $R^{4a}$ together represent (with formation of a pyrrolidine ring) —CH₂—CHR¹⁰— or —CHR¹⁰—CH₂—,
where R¹⁰ represents —H, halogen (preferably —F or —Cl), —NH₂, —COOH,
—SO₃H, —SH, $C_{1-4}$-alkyl, halo-$C_{1-4}$-alkyl, $C_{1-4}$-alkoxy, hydroxy substituted $C_{1-4}$-alkyl, —C(=O)—O—($C_{1-4}$-alkyl) or —OH.

Particularly frequently encountered is the following substructur II(sub)

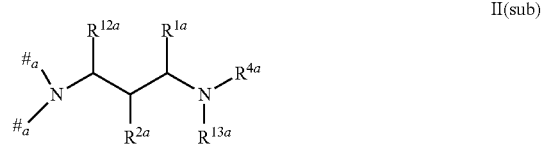

where #a, $R^{1a}$, $R^{2a}$ and $R^{4a}$ have the same meaning as in I(sub) and $R^{12a}$ and $R^{13a}$ represents —H or
$R^{12a}$ and $R^{13a}$ together (with formation of a piperidine ring) represent —CH₂—CHR¹⁰— or —CHR¹⁰—CH₂—,
where R¹⁰ represents —H, —NH₂, —COOH, —SO₃H, —SH or —OH;
where Z represents —H, —OY³, —SY³, —NHY³, —C(=O)—NY¹Y² or —C(=O)—OY³,
where Y¹ and Y² independently of one another represent —H, —NH₂ or —(CH₂CH₂O)₀₋₃—(CH₂)₀₋₃Z' (e.g. —(CH₂)₀₋₃Z'),
where Y³ represents —H or —(CH₂)₀₋₃Z',
where Z' represents —H, —SO₃H, —NH₂, —COOH or —(C=O)—NH—CHY⁴)₁₋₃COOH,
where Y⁴ represents linear or branched $C_{1-6}$-alkyl which is optionally substituted by —NH—C(=O)—NH₂, or represents aryl or benzyl which are optionally substituted by —NH₂.

In particular, a number of KSP inhibitors have the substructur II(sub) where $R^{1a}$, $R^{2a}$, $R^{4a}$, $R^{12a}$ and $R^{13a}$ represent H.

According to the invention, use may be made of KSP inhibitors of the substructure I(sub) or the substructure II(sub). The KSP inhibitors which are used in accordance with the invention also include, for example, ispinesib (Cytokinetics/GSK), MK-0731 (Merck), AZD4877 (AstraZeneca), ARRY-520 (Array BioPharma) and ARQ 621 (ArQule).

KSP inhibitors which are preferred in accordance with the invention have the following basic structure:
Formula (Ia):

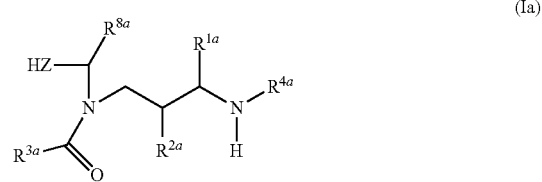

where $R^{1a}$ represents —H, -MOD or —$(CH_2)_{0-3}$Z,
  where Z represents —H, halogen, —$OY^3$, —$SY^3$, —$NHY^3$, —C(=O)—$NY^1Y^2$ or —C(=O)—$OY^3$,
  where $Y^1$ and $Y^2$ independently of one another represent —H, —$NH_2$, —$(CH_2CH_2O)_{0-3}$—$(CH_2)_{0-3}Z'$ (e.g. —$(CH_2)_{0-3}Z'$) or —$CH(CH_2W)Z'$,
  where $Y^3$ represents —H or —$(CH_2)_{0-3}Z'$,
  where Z' represents —H, —$SO_3H$, —$NH_2$, —COOH, —NH—C(=O)—$CH_2$—$CH_2$—$CH(NH_2)COOH$ or —(C(=O)—NH—$CHY^4)_{1-3}COOH$,
  where W represents —H or —OH,
  where $Y^4$ represents linear or branched $C_{1-6}$-alkyl which is optionally substituted by —NH—C(=O)—$NH_2$, or represents aryl or benzyl which are optionally substituted by —$NH_2$;

$R^{2a}$ represents —H, -MOD, —C(=O)—$CHY^4$—$NHY^5$ or —$(CH_2)_{0-3}$Z,
  where Z represents —H, —$OY^3$, —$SY^3$, —$NHY^3$, —C(=O)—$NY^1Y^2$ or —C(=O)—$OY^3$,
  where $Y^1$ and $Y^2$ independently of one another represent —H, —$NH_2$ or —$(CH_2)_{0-3}Z'$,
  where $Y^3$ represents —H or —$(CH_2)_{0-3}Z'$,
  where Z' represents —H, —$SO_3H$, —$NH_2$ or —COOH;
  where $Y^4$ represents linear or branched $C_{1-6}$-alkyl which is optionally substituted by —NH—C(=O)—$NH_2$, or represents aryl or benzyl which are optionally substituted by —$NH_2$,
  where $Y^5$ represents —H or —C(=O)—$CHY^6$—$NH_2$,
  where $Y^6$ represents linear or branched $C_{1-6}$-alkyl;

$R^{4a}$ represents —H, —C(=O)—$CHY^4$—$NHY^5$ or —$(CH_2)_{0-3}$Z,
  where Z represents —H, —$OY^3$, —$SY^3$, —$NHY^3$, —C(=O)—$NY^1Y^2$ or —C(=O)—$OY^3$,
  where $Y^1$ and $Y^2$ independently of one another represent —H, —$NH_2$ or —$(CH_2)_{0-3}Z'$,
  where $Y^3$ represents —H or —$(CH_2)_{0-3}Z'$,
  where Z' represents —H, —$SO_3H$, —$NH_2$ or —COOH;
  where $Y^4$ represents linear or branched $C_{1-6}$-alkyl which is optionally substituted by —NH—C(=O)—$NH_2$, or represents aryl or benzyl which are optionally substituted by —$NH_2$,
  where $Y^5$ represents H or —C(=O)—$CHY^6$—$NH_2$,
  where $Y^6$ represents linear or branched $C_{1-6}$-alkyl,
or
$R^{4a}$ represents a group of $R^{21}$—(C=O)$_{(0-1)}$-(P3)$_{(0-2)}$-P2-NH—CH(CH—(C=O)—$NH_2$)—C(=O)— or $R^{21}$—(C=O)$_{(0-1)}$-(P3)$_{(0-2)}$-P2-NH—CH(CH$_2$COOH)—C(=O)— or the cathepsin cleavable group or formula $R^{21}$—(C=O)$_{(0-1)}$-(P3)$_{(1-2)}$-P2-,
  where $R^{21}$ represents —H, $C_{1-10}$-alkyl-, $C_{5-10}$-aryl- or $C_{6-10}$-aralkyl-, $C_{5-10}$-heteroalkyl-, $C_{1-10}$-alkyl-O—$C_{6-10}$-aryl-, $C_{5-10}$-heterocycloalkyl-, heteroaryl-, heteroaryl-alkyl-, $C_{1-10}$-alkoxy-, $C_{6-10}$-aryloxy- or $C_{6-10}$-aralkoxy-, $C_{5-10}$-heteroalkoxy-, $C_{1-10}$-alkyl-O—$C_{6-10}$-aryloxy-, $C_{5-10}$-heterocycloalkoxy group, which may be substituted one or more times with —$NH_2$, —NH-alkyl, —N(alkyl)$_2$, —NH—C(=O)-alkyl, —N(alkyl)-C(=O)-alkyl, —$SO_3H$, —$SO_2NH_2$, —S(=O)$_2$—N(alkyl)$_2$, —COOH, —C(=O)—$NH_2$, —C(=O)—N(alkyl)$_2$, or —OH; or represents —H or a group —$O_x$—$(CH_2CH_2O)_y$—$R^{22}$,
  where x is 0 or 1
  where v s a number from 1 to 20,
  where $R^{22}$ represents —H, -alkyl (preferably C1-12-alkyl), —$CH_2$—COOH, —$CH_2$—$CH_2$—COOH, or —$CH_2$—$CH_2$—$NH_2$);
  where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;
  where P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the corresponding N-alkyl amino acids, preferably N-methyl amino acids;
or
$R^{2a}$ and $R^{4a}$ together represent (with formation of a pyrrolidine ring) —$CH_2$—$CHR^{10}$— or —$CHR^{10}$—$CH_2$—,
  where $R^{10}$ represents H, halogen (preferably F), —$NH_2$, —COOH, —$SO_3H$, —SH or —OH, and wherein the hydrogen atom of the secondary amino group in the pyrrolidine ring may be replaced by $R^{21}$—C(=O)-P3$_{(0-2)}$-P2-NH—CH($CH_2$C(=O)$NH_2$)—C(=O)-SIG-;
  where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;
  where P3 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the corresponding N-alkyl amino acids, preferably N-methyl amino acids;
  where -SIG is a self-immolative group, which, upon cleavage of the C(=O)-SIG bond provides the free secondary amine;

$R^{3a}$ represents -MOD or an optionally substituted alkyl, cycloalkyl, aryl, heteroaryl, heteroalkyl or heterocycloalkyl group, preferably a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—C(=O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)$_n$-alkyl groups, 1-3 —S(=O)$_2$—NH-alkyl groups, 1-3 —NH-alkyl groups, 1-3 —N(alkyl)$_2$ groups, 1-3 —$NH_2$ groups or 1-3 —$(CH_2)_{0-3}Z$ groups,
  where Z represents —H, halogen, —$OY^3$, —$SY^3$, —$NHY^3$, —C(=O)—$NY^1Y^2$ or —C(=O)—$OY^3$,
  where -MOD is represented as defined infra,
  where n is 0, 1 or 2,
  where $Y^1$ and $Y^2$ independently of one another represent —H, —$NH_2$ or —$(CH_2)_{0-3}Z'$,
  where $Y^3$ represents —H, —$(CH_2)_{0-3}$—CH(NHC(=O)—$CH_3$)Z', —$(CH_2)_{0-3}$—CH($NH_2$)Z' or —$(CH_2)_{0-3}Z'$,
  where Z' represents —H, —$SO_3H$, —$NH_2$ or —COOH
$R^{8a}$ represents $C_{1-10}$-alkyl;
HZ represents a mono- or bicyclic heterocycle which may be substituted by one or more substituents selected from the group consisting of halogen, $C_{1-10}$-alkyl groups, $C_{6-10}$-aryl groups and $C_{6-10}$-aralkyl groups which may optionally be substituted by halogen;
-MOD as defined supra represents —(NR$^{10}$)n-(G1)o-G2-G3, where $R^{10}$ represents —H; halogen or $C_1$-$C_3$-alkyl;
where G1 represents —NH—C(=O)—, —C(=O)—NH— or

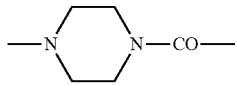

(where, if G1 represents —NHC(=O)— or

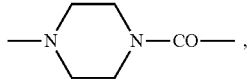

$R^{10}$ does not represent $NH_2$);
where n is 0 or 1;
where o is 0 or 1;
where G2 represents a linear and/or branched hydrocarbon group which has 1 to 10 carbon atoms and which may be interrupted once or more than once by one or more of the groups
—O—, —S—, —S(=O)—, —S(=O)$_2$—, —NR$^y$—, —NR$^y$C(=O)—, —C(=O)—NR—, —NR$^y$NR$^y$—, —S(=O)$_2$—NR$^y$NR$^y$—, —C(=O)—NR$^y$NR$^y$—, —C(=O)—, —CR$^x$=N—O—,
and where the hydrocarbon group including any side chains may be substituted by —NHC(=O)—NH$_2$, —COOH, —OH, —NH$_2$, —NH—CNNH$_2$, sulphonamide, sulphone, sulphoxide or sulphonic acid,
where $R^y$ represents H, phenyl, $C_1$-$C_{10}$-alkyl, $C_2$-$C_{10}$-alkenyl or $C_2$-$C_{10}$-alkynyl, each of which may be substituted by —NHC(=O)—NH$_2$, —COOH, —OH, —NH$_2$, NH—CNNH$_2$, sulphonamide, sulphone, sulphoxide or sulphonic acid,
where $R^x$ represents —H, $C_1$-$C_3$-alkyl or phenyl),
where G3 represents —H or —COOH,
where -MOD preferably has at least one group —COOH;
and the salts, solvates, salts of the solvates, and epimers thereof.
According to the invention, such a kinesin spindle protein inhibitor can be attached to the linker by substitution of a hydrogen atom at $R^{1a}$, $R^{2a}$, $R^{3a}$, $R^{4a}$, $R^{8a}$ or $R^{10}$ or optionally via one of the substituents of HZ, in particular via $R^a$, $R^{2a}$, $R^{3a}$, $R^{4a}$ or $R^{10}$
The substituents of the formula (Ia) preferably have the following meanings, where these preferred meanings are preferably combined with one another:
$R^{1a}$ preferably represents H or —(CH$_2$)$_{0-3}$Z,
where Z represents —H, halogen, —OY$^3$, —SY$^3$, —NHY$^3$, —C(=O)—NY$^1$Y$^2$ or —C(=O)—OY$^3$,
where $Y^1$ and $Y^2$ independently of one another represent —H, —NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z',
where $Y^3$ represents —H or —(CH$_2$)$_{0-3}$Z',
where Z' represents —H, —SO$_3$H, —NH$_2$, —COOH, —NH—C(=O)—CH$_2$—CH$_2$—CH(NH$_2$)COOH or —(C(=O)—NH—CHY$^4$)$_{1-3}$COOH,
where W represents —H or —OH,
where $Y^4$ represents linear or branched $C_{1-6}$-alkyl which is optionally substituted by —NH—C(=O)—NH$_2$, or represents aryl or benzyl which are optionally substituted by —NH$_2$;

$R^{2a}$ and $R^{4a}$ independently of one another preferably represent —H, -L-#1, —C(=O)—CHY$^4$—NHY$^5$ or —(CH$_2$)$_{0-3}$Z, or $R^{2a}$ and $R^{4a}$ together (with formation of a pyrrolidine ring) represent —CH$_2$—CHR$^{10}$— or —CHR$^{10}$—CH$^2$—,
where $R^{10}$ represents —H, —SO$_3$H, —NH$_2$, —COOH, —SH or —OH,
where Z represents —H, halogen, —OY$^3$, —SY$^3$, NHY$^3$, —C(=O)—NY$^1$Y$^2$ or —C(=O)—OY$^3$,
where $Y^1$ and $Y^2$ independently of one another represent —H, —NH$_2$ or —(CH$_2$)$_{0-3}$Z',
where $Y^3$ represents —H or —(CH$_2$)$_{0-3}$Z',
where Z' represents —H, —SO$_3$H, —NH$_2$ or —COOH,
where $Y^4$ independently of one another represents linear or branched $C_{1-6}$-alkyl which is optionally substituted by —NH—C(=O)—NH$_2$, or represents aryl or benzyl which are optionally substituted by —NH$_2$,
where $Y^5$ represents H or —C(=O)—CHY$^6$—NH$_2$,
where $Y^6$ represents linear or branched $C_{1-6}$-alkyl.
Alternatively, $R^{4a}$ may be $R^{21}$—(C=O)$_{(0-1)}$-(P3)$_{(0-2)}$-P2-NH—CH(CH$_2$C(=O)—NH$_2$)—C(=O)— or $R^{21}$(C=O)$_{(0-1)}$-(P3)$_{(0-2)}$-P2-NH—CH(CH$_2$COOH)—C(=O)— or a cathepsin cleavable group of formula $R^{21}$—(C=O)$_{(0-1)}$-(P3)$_{(1-2)}$-P2-. In another alternative, the hydrogen atom of —NH on the pyrrolidine ring is replaced by $R^{21}$—C(=O)-P3-P2-NH—CH(CH$_2$C(=O)—NH$_2$)—C(=O)-SIG-.
The group $R^{21}$—(C=O)$_{(0-1)}$-(P3)$_{(0-2)}$-P2-NH—CH(CH$_2$C(=O)—NH$_2$)—C(=O)—, $R^{21}$—(C=O)$_{(0-1)}$-(P3)$_{(0-2)}$-P2-NH—CH(CH$_2$COOH)—C(=O)— or $R^{21}$—C(=O)-P3-P2-NH—CH(CH$_2$C(=O)—NH$_2$)—C(=O)-SIG- are believed to be cleaved by the enzyme legumain in vivo. In the following, these groups will thus be referred to as "legumain cleavable groups". The legumain cleavable group has the formula —(C=O)$_{(0-1)}$-(P3)$_{(0-2)}$-P2-NH—CH(CH$_2$C(=O)—NH$_2$)—C(=O)— or —(C=O)$_{(0-1)}$-(P3)$_{(0-2)}$-P2-NH—CH(CH$_2$COOH)—C(=O)—. In the conjugates of the present invention, this group has preferably the formula $R^{21}$—(C=O)$_{(0-1)}$-(P3)$_{(0-2)}$-P2-NH—CH(CH$_2$C(=O)—NH$_2$)—C(=O)#, i.e. the legumain cleavable group has a group $R^{21}$ at one end, and at the other end (-#) it binds to the amino group corresponding position $R^{4a}$ in Formula Ia.
—NH—CH(CH$_2$C(=O)—NH$_2$)—C(=O)— (i.e. asparagine) and —NH—CH(CH$_2$COOH)—C(=O)— (i.e. aspartic acid) are present in the natural L-configuration. The legumain cleavable group contains, in addition to asparagine, 1 to 3 additional amino acids (-P2-NH—CH(CH$_2$C(=O)—NH$_2$)—C(=O)—; -P3-P2-NH—CH(CH$_2$C(=O)—NH$_2$)—C(=O)—; -(P3)$_{(2)}$-P2-NH—CH(CH$_2$C(=O)—NH$_2$)—C(=O)—), thus is a di-, tri-, or tetrapeptide or derivative thereof (dipeptide: -P2-NH—CH(CH$_2$C(=O)—NH$_2$)—C(=O)—; tripeptide: -P3-P2-NH—CH(CH$_2$C(=O)NH$_2$)—C(=O)—; tetrapeptide: -(P3)$_2$-P2-NH—CH(CH$_2$C(=O)—NH$_2$)—C(=O)—). The same applies in case the legumain cleavable group contains aspartic acid.
P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline und His, preferably selected from Ala, Gly, Val, Leu, Ile, Pro, Ser, Thr, citrulline und Asn. P2 is generally present in the natural L-configuration. Particularly preferred is L-Ala.
P3 is an amino acid independently selected from Gly, Pro, Ala, Val, Leu, Ile, Met, Phe, Tyr, Trp, Ser, Thr, Cys, Asn, Gln, Asp, Glu, Lys, Arg, citrulline, or its corresponding N-alkyl-amino acids, preferably N-methylamino acids. P3 is preferably selected from His, Pro, Ala, Val, Leu, Ile, Gly, Ser, citrulline und Gln. P3 is generally present in the natural L-configuration vor. Particularly preferred is L-Ala.

A particularly preferred legumain cleavable group is -L-Ala-L-Ala-L-Asn- (e.g. $R^{21}$-L-Ala-L-Ala-L-Asn-#).

$R^{21}$ preferably represents —H, $C_{1-5}$-alkyl, $C_{5-10}$-aralkyl, $C_{1-5}$-alkoxy, $C_{6-10}$-aryloxy, $C_{5-10}$-heteroalkyl-, $C_{5-10}$-heterocycloalkyl-, heteroaryl-, heteroaryl-alkyl-, $C_{5-10}$-heteroalkoxy-, or a $C_{5-10}$-heterocycloalkoxy group, which each may be substituted one or more times with —COOH, —C(=O)—OAlkyl, —C(=O)—O—$NH_2$, —$NH_2$ or —N(Alkyl)$_2$); or represents a group —$O_x$—$(CH_2CH_2O)_y$—$R^{22}$, where x is 0 or 1
where v is a number from 1 to 10, and
where $R^{22}$ represents —H, -alkyl (preferably $C_{1-12}$-alkyl), —$CH_2$—COOH, —$CH_2$—$CH_2$—COOH, or —$CH_2$—$CH_2$—$NH_2$.

"Alkyl" here means an alkyl group with up to 20 carbon atoms, preferably $C_{1-12}$-alkyl.

The cathepsin cleavable group has the formula —(C=O)$_{(0-1)}$-(P3)$_{(1-2)}$-P2-. In the conjugates of the present invention, this group has preferably the formula $R^{21}$—(C=O)$_{(0-1)}$-(P3)$_{(1-2)}$-P2-#, i.e. the cathepsin cleavable group has a group $R^{21}$ at one end, and at the other end (-#) it binds to the amino group corresponding position $R^{4a}$ in Formula Ia. Here $R^{21}$, P2 and P3 have the same meaning as in the legumain cleavable group. Particularly preferred cathepsin cleavable groups are those in which P2 is selected from alanine, lysine und citrulline, und P3 is selected from valine, alanine und phenylalanine, particularly those of formula $R^{21}$—(C=O)$_{(0-1)}$-P3-P2-.

$R^3$ preferably represents an optionally substituted alkyl, aryl, heteroaryl, heteroalkyl, heterocycloalkyl group, -L-#1, -MOD, or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3-O—C(O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)$_n$-alkyl groups, 1-3 —S(=O)$_2$—NH-alkyl groups, 1-3 —NH-alkyl groups, 1-3 —N(alkyl)$_2$ groups, 1-3 —$NH_2$ groups or 1-3 —$(CH_2)_{0-3}$Z groups, where n is 0, 1 or 2,
where Z represents —H, halogen, —$OY^3$, —$SY^3$, —$NHY^3$, —C(=O)—$NY^1Y^2$ or —C(=O)—$OY^3$,
where $Y^1$ and $Y^2$ independently of one another represent —H, —$NH_2$ or —$(CH_2)_{0-3}$Z'
where $Y^3$ represents —H, —$(CH_2)_{0-3}$—CH(NH—C(=O)—$CH_3$)Z', —$(CH_2)_{0-3}$—CH($NH_2$)Z' or —$(CH_2)_{0-3}$Z',
where Z' represents —H, —$SO_3H$, —$NH_2$ or —COOH,
where "alkyl" preferably represents $C_{1-10}$-alkyl.

$R^{8a}$ preferably represents $C_{1-10}$-alkyl.

HZ preferably represents a mono- or bicyclic heterocycle which may be substituted by one or more substituents selected from the group consisting of halogen, $C_{1-10}$-alkyl groups, $C_{6-10}$-aryl groups and $C_{6-10}$-aralkyl groups which may optionally be substituted by halogen.

$C_{1-10}$-Alkyl in the context of the invention (i.e. in the formula above and also in the formulae that follow) represents a linear or branched alkyl radical having 1 to 10 carbon atoms. Examples which may be mentioned as being preferred are: methyl, ethyl, n-propyl, isopropyl, n-butyl, isobutyl, 1-methylpropyl and tert-butyl.

$C_{6-10}$-Aryl- in the context of the invention represents a mono- or bicyclic aromatic homocycle, for example phenyl and naphthyl.

$C_{6-10}$-Aralkyl group in the context of the invention represents a monocyclic aromatic homocycle, by way of example phenyl, to which a $C_1$-$C_4$-alkyl group is attached. An exemplary $C_{6-10}$-aralkyl group is benzyl.

$C_{5-10}$-Heteroaryl in the context of the invention represents a mono- or bicyclic aromatic heterocycle having a total of 6 to 10 ring atoms, where the ring(s) contains/contain one or two ring heteroatoms from the group consisting of N, O, S, SO and $SO_2$ and which is attached via a ring carbon atom or optionally a ring nitrogen atom. Examples which may be mentioned are pyridyl, furanyl, pyrimidyl, imidazolyl, thienyl, thiophenyl, isoxazoyl, isothiazoyl, 1,2,3-oxadiazoyl, furazanyl, 1,2,3-triazoyl, 1,2,4-triazoyl, pyridazyl, pyrrolyl, triazinyl, indolyl, quinolinyl, quinazolinyl, 1,3-benzodioxol, isoindolyl, indazolyl, 1H-pyrazolo[3,4-d]pyrimidyl, benzotriazolyl, isoquinolinyl, cinolinyl, phthalazinyl, pteridinyl, naphthyridinyl, benzimidazolinyl, benzothiazolinyl, benzoxazolinyl, 3,4-methylenedioxyphenyl and benzo[6]furanyl.

Mono- or bicyclic heterocycle in the context of the invention represents a mono- or bicyclic heterocycle having a total of 5 to 10 ring carbon atoms, where the ring(s) contains/contain one to three ring heteroatoms from the group consisting of N, O, S, SO and $SO_2$ and which is attached via a ring carbon atom or optionally a ring nitrogen atom. Examples which may be mentioned are piperidyl, pyrrolinyl, morpholinyl, 3,4-methylenedioxyphenyl and tetrahydrofuranyl.

Halogen atom in the context of the invention represents F, Cl, Br or I.

As used herein, the term "heteroalkyl" refers to a straight or branched alkyl group that contains one or more heteroatoms, that is, an element other than carbon (including but not limited to oxygen, sulfur, nitrogen, phosphorus) in place of one or more carbon atoms.

Whenever a group is described as being "substituted" that group substituted with one or more of the indicated substituents. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, heteroalkyl, aryl, heteroaryl, heteroalicyclyl, aralkyl, heteroaralkyl, (heteroalicyclyl)alkyl, hydroxy, alkoxy, aryloxy, acyl, mercapto, alkylthio, arylthio, cyano, halogen, thiocarbonyl, carbamyl, thiocarbamyl, amido, sulfonamido, sulfonamido, carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

Where the number of substituents is not specified (e.g. haloalkyl), there may be one or more substituents present. For example "haloalkyl" may include one or more of the same or different halogens. As another example, "C~-C~alkoxyphenyl" may include one or more of the same or different alkoxy groups containing one, two or three atoms.

By substitution of a hydrogen atom at $R^{1a}$, $R^{2a}$, $R^{4a}$ or $R^{10}$ in substructure I(sub) or substructure II(sub), or $R^{1a}$, $R^{2a}$, $R^{3a}$, $R^{4a}$, $R^{8a}$ or $R^{10}$ at HZ in formula (Ia), the compound of the formula (Ia) may be attached to a linker in a manner known to the person of average skill. Particularly preferably, the substitution of the hydrogen atom takes place at $R^{1a}$, $R^{2a}$, $R^{3a}$, $R^{4a}$ or at the pyrrolidine ring formed by $R^{2a}$ and $R^{4a}$. This conjugation can take place chemically by various routes, as shown in an exemplary manner in Schemes 2 to 6 in the examples. In particular, it is optionally possible to modify the low-molecular weight KSP inhibitor for the conjugation to the linker, for example by introducing protective groups or leaving groups to facilitate substitution (such that in the reaction said leaving group, and not a hydrogen atom, is substituted by the linker). The KSP inhibitor-linker molecules obtained in this manner (where the linker has a reactive group for coupling to the binder) can then be reacted with the binder to give a binder conjugate according to the invention. In the experimental section, this procedure is illustrated in an exemplary manner by some examples.

Preferred for $R^{1a}$ are —H, —COOH, —C(=O)—NHNH$_2$, —(CH$_2$)$_{1-3}$NH$_2$, —C(=O)—NZ"(CH$_2$)$_{1-3}$—NH$_2$ and —C(=O)—NZ"CH$_2$COOH, where Z" represents —H or —NH$_2$.

Preferred for $R^{2a}$ and $R^{4a}$ are H, or $R^{2a}$ and $R^{4a}$ together (with formation of a pyrrolidine ring) represent —CH$_2$—CHR$^{10}$— or —CHR$^{10}$—CH$_2$—, where $R^{10}$ represents —H.

Preferred for $R^{3a}$ is C$_{1-10}$-alkyl-, which may be substituted by —OH, —O-alkyl, —SH, —S-alkyl, —O—C(=O)-alkyl, —O—C(=O)—NH-alkyl, —NH—C(=O)-alkyl, —NH—C(=O)—NH-alkyl, —S(=O)$_n$-alkyl, —S(=O)$_2$—NH-alkyl, —NH-alkyl, —N(alkyl)$_2$ or —NH$_2$, where alkyl is preferably C$_{1-3}$-alkyl and n is 0, 1 or 2.

Preferred for $R^{8a}$ is a branched C$_{1-5}$-alkyl group, preferably methyl, ethyl, n-propyl, isopropyl, n-butyl, isobutyl, 1-methylpropyl and tert-butyl.

Preferred for HZ is a mono- or bicyclic heterocycle which may be substituted by one or more substituents selected from the group consisting of halogen, C$_{1-10}$-alkyl groups, C$_{6-10}$-aryl groups and C$_{6-10}$-aralkyl groups which may optionally be substituted by halogen.

Particularly preferably, HZ is a substituted pyrrole, pyrazole, imidazole, quinazoline or dihydroquinazoline which is substituted in the ortho-position (with respect to the substituents with R1a etc.) by an optionally substituted benzyl group. Furthermore, the substituted pyrrole, pyrazole, imidazole or quinazoline can preferably be substituted by oxo (in the case of dihydroquinazoline) or a phenyl group substituted by 1 or 2 halogen atoms. Particularly preferably, HZ is a substituted pyrrole.

A KSP inhibitor which is preferably used is ispinesib. A further preferred KSP inhibitor is Arry-520.

Other particularly preferred compounds of the structure KSP-L- have the formula (IIa) or (II) below:

Formula (IIa)

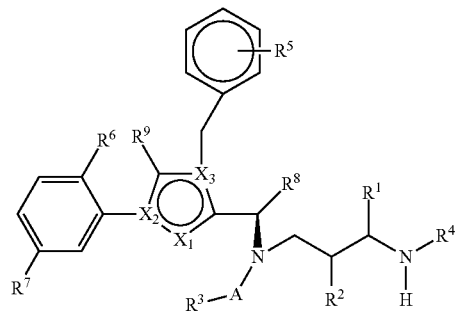

(IIa)

where
$X_1$ represents N, $X_2$ represents N and $X_3$ represents C; or
$X_1$ represents N, $X_2$ represents C and $X_3$ represents N; or
$X_1$ represents CH or CF, $X_2$ represents C and $X_3$ represents N; or
$X_1$ represents NH, $X_2$ represents C and $X_3$ represents C; or
$X_1$ represents CH or CF, $X_2$ represents N and $X_3$ represents C;
(with $X_1$ representing CH, $X_2$ representing C and $X_3$ representing N being preferred);
$R^1$ represents —H, -L-#1, -MOD or —(CH$_2$)$_{0-3}$Z,
  where -L-#1 represents the linker and #1 represents the bond to the binder or derivative thereof.
  where -MOD is represented as defined infra,
  where Z represents —H, halogen, —OY$^3$, —SY$^3$, —NHY$^3$, —C(=O)—NY$^1$Y$^2$ or —C(=O)—OY$^3$,
  where Y$^1$ and Y$^2$ independently of one another represent —H, —NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z',
  where Y$^3$ represents —H or —(CH$_2$)$_{0-3}$Z',
  where Z' represents —H, —NH$_2$, —SO$_3$H, —COOH, —NH—C(=O)—CH$_2$—CH$_2$—CH(NH$_2$)COOH or —(C(=O)—NH—CHY$^4$)$_{1-3}$COOH,
  where W represents —H or —OH,
  where Y$^4$ represents linear or branched C$_{1-6}$-alkyl which is optionally substituted by —NHC(=O)—NH$_2$, or represents aryl or benzyl which are optionally substituted by —NH$_2$;
$R^2$ represents —H, -L-#1, -MOD, —C(=O)—CHY$^4$—NHY$^5$ or —(CH$_2$)$_{0-3}$Z,
  where -L-#1 represents the linker and #1 represents the bond to the binder or derivative thereof,
  where -MOD is represented as defined infra,
  where Z represents —H, halogen, —OY$^3$, —SY$^3$, NHY$^3$, —C(=O)—NY$^1$Y$^2$ or —C(=O)—OY$^3$,
  where Y$^1$ and Y$^2$ independently of one another represent —H, —NH$_2$ or —(CH$_2$)$_{0-3}$Z', and
  where Y$^3$ represents —H or —(CH$_2$)$_{0-3}$Z',
  where Z' represents —H, —SO$_3$H, —NH$_2$ or —COOH;
  where Y$^4$ represents linear or branched C$_{1-6}$-alkyl which is optionally substituted by —NHC(=O)—NH$_2$, or represents aryl or benzyl which are optionally substituted by —NH$_2$,
  where Y$^5$ represents —H or —C(=O)—CHY$^6$—NH$_2$,
  where Y$^6$ represents linear or branched C$_{1-6}$-alkyl;
$R^4$ represents —H, -L-#1, —C(=O)—CHY$^4$—NHY$^5$ or —(CH$_2$)$_{0-3}$Z,
  where -L-#1 represents the linker and #1 represents the bond to the binder or derivative thereof, where Z represents —H, —OY$^3$, —SY$^3$, —NHY$^3$, —C(=O)—NY$^1$Y$^2$ or —C(=O)—OY$^3$, where Y$^1$ and Y$^2$ independently of one another represent —H, —NH$_2$ or —(CH$_2$)$_{0-3}$Z', where Y$^3$ represents —H or —(CH$_2$)$_{0-3}$Z', where Z' represents —H, —SO$_3$H, —NH$_2$ or —COOH;

where Y$^4$ represents linear or branched C$_{1-6}$-alkyl which is optionally substituted by —NHC(=O)—NH$_2$, or represents aryl or benzyl which are optionally substituted by —NH$_2$, and where Y$^5$ represents —H or —C(=O)—CHY$^6$—NH$_2$, where Y$^6$ represents linear or branched C$_{1-6}$-alkyl, or R$^4$ represents a group of R$^{21}$—(C=O)$_{(0-1)}$-(P3)$_{(0-2)}$-P2-NH—CH(CH$_2$C(=O)—NH$_2$)—C(=O)— or R$^{21}$—(C=O)$_{(0-1)}$-(P3)$_{(0-2)}$-P2-NH—CH(CH$_2$COOH)—C(=O)— or the cathepsin cleavable group R$^{21}$—(C=O)$_{(0-1)}$-(P3)$_{(1-2)}$-P2-, where R$^{21}$ represents H, C$_{1-10}$-alkyl-, C$_{5-10}$-aryl- or C$_{6-10}$-aralkyl-, C$_{5-10}$-heteroalkyl-, C$_{1-10}$-alkyl-O—C$_{6-10}$-aryl-, C$_{5-10}$-heterocycloalkyl-, heteroaryl-, heteroaryl-alkyl-, C$_{1-10}$-alkoxy-, C$_{6-10}$-aryloxy- or C$_{6-10}$-aralkoxy-, C$_{5-10}$-heteroalkoxy-, C$_{1-10}$-alkyl-O—C$_{6-10}$-aryloxy-, C$_{5-10}$-heterocloalkoxy group (which may be substituted one or more times with —NH$_2$, —NH-alkyl, —N(alkyl)$_2$, —NH—C(=O)-alkyl, N(alkyl)-C(=O)-alkyl, —SO$_3$H, —SO$_2$NH$_2$, —S(O)$_2$—N(alkyl)$_2$, —COOH, —C(=O)—NH$_2$, —C(=O)—N(alkyl)$_2$, or —OH), —H or a group —(O)$_x$—(CH$_2$CH$_2$O)$_y$—R$^{22}$, where x is 0 or 1 and where v is a number from 1 to 20, where R$^{22}$ represents —H, -alkyl (preferably C$_{1-12}$-alkyl), —CH$_2$—COOH, —CH$_2$—CH$_2$—COOH, or —CH$_2$—CH$_2$—NH$_2$);

where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

where P3 is an amino acid independently selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the corresponding N-alkyl amino acids, preferably N-methyl amino acids; in case there is more than one amino acid P3, P3 may have the same or different amino acids, as defined above;

or

R$^2$ and R$^4$ together (with formation of a pyrrolidine ring) represent —CH$_2$—CHR$^{10}$— or —CHR$^{10}$—CH$_2$—, where R$^{10}$ represents —H, halogen (preferably —F), —NH$_2$, —SO$_3$H, —COOH, —SH or —OH, and wherein the hydrogen atom of the secondary amino group in the pyrrolidine ring may be replaced by R$^{21}$—C(=O)-P3$_{(0-2)}$-P2-NH—CH(CH$_2$C(=O)—NH$_2$)—C(=O)-SIG-;

where L-#1 represents the linker and #1 represents the bond to the binder or derivative thereof, where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

where P3 is an amino acid independently selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the corresponding N-alkyl amino acids, preferably N-methyl amino acids; in case there is more than one amino acid P3, P3 may have the same or different amino acids, as defined above;

where -SIG is a self-immolative group, which, upon cleavage of the —C(=O)-SIG bond provides the free secondary amine;

A represents —C(=O)—, —S(=O)—, —S(=O)$_2$—, —S(=O)$_2$—NH— or —C(=N—NH$_2$)—;

R$^3$ represents -L-#1, -MOD or an optionally substituted alkyl, cycloalkyl, aryl, heteroaryl, heteroalkyl, heterocycloalkyl group, preferably a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—C(=O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)$_n$-alkyl groups, 1-3 —S(=O)$_2$—NH-alkyl groups, 1-3 —NH-alkyl groups, 1-3 —N(alkyl)$_2$ groups, 1-3 —NH((CH$_2$CH$_2$O)$_{1-20}$H) groups, 1-3 —NH$_2$ groups or 1-3 —(CH$_2$)$_{0-3}$Z groups, where -L-#1 represents the linker and #1 represents the bond to the binder or derivative thereof, where -MOD is represented as defined infra, where n represents 0, 1 or 2, where Z represents —H, halogen, —OY$^3$, —SY$^3$, —NHY$^3$, —C(=O)—NY$^1$Y$^2$ or —C(=O)—OY$^3$, where Y$^1$ and Y$^2$ independently of one another represent —H, —NH$_2$ or —(CH$_2$)$_{0-3}$Z' and where Y$^3$ represents —H, —(CH$_2$)$_{0-3}$—CH(NHC(=O)—CH$_3$)Z', —(CH$_2$)$_{0-3}$—CH(NH$_2$)Z' or —(CH$_2$)$_{0-3}$Z', where where Z' represents —H, —SO$_3$H, —NH$_2$ or —COOH R$^5$ represents -L-#1, H, -MOD, —NH$_2$, —NO$_2$, halogen (in particular —F, —Cl, —Br), —CN, —CF$_3$, —OCF$_3$, —CH$_2$F, —CH$_2$F, —SH or —(CH$_2$)$_{0-3}$Z, where Z represents —H, —OY$^3$, —SY$^3$, halogen, —NHY$^3$, —C(=O)—NY$^1$Y$^2$ or —C(=O)—OY$^3$, where Y$^1$ and Y$^2$ independently of one another represent —H, —NH$_2$ or —(CH$_2$)$_{0-3}$Z', where Y$^3$ represents —H or —(CH$_2$)$_{0-3}$Z', where Z' represents —H, —SO$_3$H, —NH$_2$ or —COOH;

R$^6$ and R$^7$ independently of one another represent —H, cyano, C$_{1-10}$-alkyl, fluoro-C$_{1-10}$-alkyl, C$_{2-10}$-alkenyl, fluoro-C$_{2-10}$-alkenyl, C$_{2-10}$-alkynyl, fluoro-C$_{2-10}$-alkynyl, hydroxy, —NO$_2$, —NH$_2$, —COOH or halogen (in particular —F, —Cl, —Br), R$^8$ represents C$_{1-10}$-alkyl, fluoro-C$_{1-10}$-alkyl, C$_{2-10}$-alkenyl, fluoro-C$_{2-10}$-alkenyl, C$_{2-10}$-alkynyl, fluoro-C$_{2-10}$-alkynyl, C$_{4-10}$-cycloalkyl, fluoro-C$_{4-10}$-cycloalkyl, or —(CH$_2$)$_{0-2}$—(HZ$^2$), where HZ$^2$ represents a 4- to 7-membered heterocycle having up to two heteroatoms selected from the group consisting of N, O and S, where each of these groups may be substituted by —OH, —COOH or —NH$_2$ or -L-#1;

where -L-#1 represents the linker and #1 represents the bond to the binder or derivative thereof, where one of the substituents R$^1$, R$^2$, R$^3$, R$^4$ R$^5$, R$^8$ and R$^{10}$ represents (or in the case of R$^8$ contains) -L-#1, R$^9$ represents —H, —F, —CH$_3$, —CF$_3$, —CH$_2$F or —CHF$_2$;

-MOD as defined supra represents —(NR$^{10}$)n-(G1)o-G2-G3,
where R$^{10}$ represents —H or C$_1$-C$_3$-alkyl;
where G1 represents —NH—C(=O)—, —C(=O)—NH— or

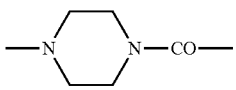

(where, if G1 represents —NH—C(=O)— or

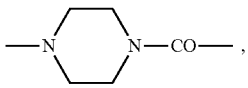

R$^{10}$ does not represent —NH$_2$);
where n is 0 or 1;
where o is 0 or 1;
where G2 represents a linear and/or branched hydrocarbon group which has 1 to 10 carbon atoms and which may be interrupted once or more than once by one or more of the groups —O—, —S—, —S(=O)—, —S(=O)$_2$—, —NR$^y$—, —NR$^y$C(=O)—, —C(=O)—NR—, —NR$^y$NR$^y$—, —S(=O)$_2$—NRyNRy-, —C(=O)—NR$^y$NR$^y$—, —C(=O)—, —CR$^x$=N—O—, and where the hydrocarbon chain including any side chains may be substituted by —NH—C(=O)—NH$_2$, —COOH, —OH, —NH$_2$, NH—CNNH$_2$, sulphonamide, sulphone, sulphoxide or sulphonic acid,
where R$^y$ represents —H, phenyl, C$_1$-C$_{10}$-alkyl, C$_2$-C$_{10}$-alkenyl or C$_2$-C$_{10}$-alkynyl, each of which may be substituted by —NH—C(=O)—NH$_2$, —COOH, —OH, —NH$_2$, NH—CN—NH$_2$, sulphonamide, sulphone, sulphoxide or sulphonic acid,
where R$^x$ represents —H, C$_1$-C$_3$-alkyl or phenyl,
where G3 represents —H or —COOH, and
where -MOD preferably has at least one —COOH group;
and the salts, solvates, salts of the solvates, and epimers thereof.

Formula (II)

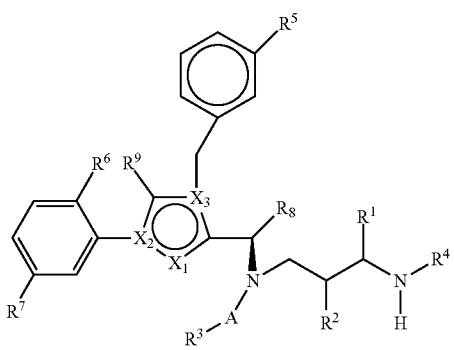

(II)

where
X$_1$ represents N, X$_2$ represents N and X$_3$ represents C; or
X$_1$ represents N, X$_2$ represents C and X$_3$ represents N; or
X$_1$ represents CH or CF, X$_2$ represents C and X$_3$ represents N; or
X$_1$ represents NH, X$_2$ represents C and X$_3$ represents C; or
X$_1$ represents CH, X$_2$ represents N and X$_3$ represents C
R$^1$ represents —H, -MOD, -L-#1 or —(CH$_2$)$_{0-3}$Z,
where -L-#1 represents the linker and #1 represents the bond to the binder or derivative thereof.
where -MOD is represented as defined infra,
where Z represents —H, halogen, —OY$^3$, —SY$^3$, —NHY$^3$, —C(=O)—NY$^1$Y$^2$ or —C(=O)—OY$^3$,
where Y$^1$ and Y$^2$ independently of one another represent —H, —NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z',
where Y$^3$ represents —H or —(CH$_2$)$_{0-3}$Z',
where Z' represents —H, —NH$_2$, —SO$_3$H, —COOH, —NH—C(=O)—CH$_2$—CH$_2$—CH(NH$_2$)COOH or —(C(=O)—NH—CHY$^4$)$_{1-3}$COOH,
where W represents —H or —OH,
where Y$^4$ represents linear or branched C$_{1-6}$-alkyl which is optionally substituted by NH—C(=O)—NH$_2$, or represents aryl or benzyl which are optionally substituted by —NH$_2$;
R$^2$ represents -L-#1, H, -MOD, —C(=O)—CHY$^4$—NHY$^5$ or —(CH$_2$)$_{0-3}$Z,
where -L-#1 represents the linker and #1 represents the bond to the binder or derivative thereof,
where -MOD is represented as defined infra,
where Z represents —H, halogen, —OY$^3$, —SY$^3$, NHY$^3$, —C(=O)—NY$^1$Y$^2$ or —C(=O)—OY$^3$,
where Y$^1$ and Y$^2$ independently of one another represent —H, —NH$_2$ or —(CH$_2$)$_{0-3}$Z', and
where Y$^3$ represents —H or —(CH$_2$)$_{0-3}$Z',
where Z' represents —H, —SO$_3$H, —NH$_2$ or —COOH;
where Y$^4$ represents linear or branched C$_{1-6}$-alkyl which is optionally substituted by —NHC(=O)—NH$_2$, or represents aryl or benzyl which are optionally substituted by —NH$_2$,
where Y$^5$ represents —H or —C(=O)—CHY$^6$—NH$_2$,
where Y$^6$ represents linear or branched C$_{1-6}$-alkyl;
R$^4$ represents -L-#1, —H, —C(=O)—CHY$^4$—NHY$^5$ or —(CH$_2$)$_{0-3}$Z,
where -L-#1 represents the linker and #1 represents the bond to the binder or derivative thereof,
where Z represents —H, —OY$^3$, —SY$^3$, —NHY$^3$, —C(=O)—NY$^1$Y$^2$ or —C(=O)—OY$^3$,
where Y$^1$ and Y$^2$ independently of one another represent —H, —NH$_2$ or —(CH$_2$)$_{0-3}$Z',
where Y$^3$ represents —H or —(CH$_2$)$_{0-3}$Z',
where Z' represents —H, —SO$_3$H, —NH$_2$ or —COOH;
where Y$^4$ represents linear or branched C$_{1-6}$-alkyl which is optionally substituted by NH—C(=O)—NH$_2$, or represents aryl or benzyl which are optionally substituted by —NH$_2$, and
where Y$^5$ represents —H or —C(=O)—CHY$^6$—NH$_2$,
where Y$^6$ represents linear or branched C$_{1-6}$-alkyl, or
R$^4$ represents a group of
R$^{21}$—(C=O)$_{(0-1)}$-(P3)$_{(0-2)}$-P2-NH—CH(CH$_2$C(=O)—NH$_2$)—C(=O)— or
R$^{21}$—(C=O)$_{(0-1)}$-(P3)$_{(0-2)}$-P2-NH—CH(CH$_2$COOH)—C(=O)— or the cathepsin cleavable group R$^{21}$—(C=O)$_{(0-1)}$-(P3)$_{(1-2)}$-P2-,
where R$^{21}$ represents H, C$_{1-10}$-alkyl-, C$_{5-10}$-aryl- or C$_{6-10}$-aralkyl-, C$_{5-10}$-heteroalkyl-, C$_{1-10}$-alkyl-O—C$_{6-10}$-aryl-, C$_{5-10}$-heterocycloalkyl-, heteroaryl-, heteroaryl-alkyl-, $C_{1-10}$-alkoxy-, $C_{6-10}$-aryloxy- or $C_{6-10}$-aralkoxy-, $C_{5-10}$-heteroalkoxy-, $C_{1-10}$-alkyl-O—$C_{6-10}$-aryloxy-, $C_{5-10}$-heterocycloalkoxy group, which may be substituted one or more times with —$NH_2$, —NH-alkyl, —N(alkyl)$_2$, —NH—C(=O)-alkyl, N(alkyl)-C(=O)-alkyl, —$SO_3H$, —S(=O)$_2$$NH_2$, —S(=O)$_2$—N(alkyl)$_2$, —COOH, —C(=O)—$NH_2$, —C(=O)—N(alkyl)$_2$, or —OH, or represent —H or a group —(O)$_x$—(CH$_2$CH$_2$O)$_y$—$R^{22}$, where x is 0 or 1 and where v is a number from 1 to 20, where $R^{22}$ represents —H, -alkyl (preferably $C_{1-12}$-alkyl), —$CH_2$—COOH, —$CH_2$—$CH_2$—COOH, or —$CH_2$—$CH_2$—$NH_2$);

where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

where P3 is an amino acid independently selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the corresponding N-alkyl amino acids, preferably N-methyl amino acids; in case there is more than one amino acid P3, P3 may have the same or different amino acids, as defined above;

or $R^2$ and $R^4$ together (with formation of a pyrrolidine ring) represent —$CH_2$—$CHR^{10}$— or —$CHR^{10}$—$CH_2$—, where $R^{10}$ represents —H, halogen (preferably —F or —Cl), —$NH_2$, —$SO_3H$, —COOH, —SH, $C_{1-4}$-alkyl, $C_{1-4}$-haloalkyl, $C_{1-4}$-alkoxy, hydroxy substituted $C_{1-4}$-alkyl, —C(=O)—O—($C_{1-4}$-alkyl) or —OH, and wherein the hydrogen atom of the secondary amino group in the pyrrolidine ring may be replaced by $R^{21}$—C(=O)-P3$_{(0-2)}$-P2-NH—CH(CH$_2$C(=O)—$NH_2$)—C(=O)-SIG-;

where L-#1 represents the linker and #1 represents the bond to the binder or derivative thereof, where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;

where P3 is an amino acid independently selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the corresponding N-alkyl amino acids, preferably N-methyl amino acids;

where -SIG is a self-immolative group, which, upon cleavage of the —C(=O)-SIG bond provides the free secondary amine;

A represents —C(=O)—, —S(=O)—, —S(=O)$_2$—, —S(=O)$_2$—NH— or —C(=N—$NH_2$)—;

$R^3$ represents -L-#1, -MOD or an optionally substituted alkyl, cycloalkyl, aryl, heteroaryl, heteroalkyl, heterocycloalkyl group, preferably -L-#1 or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 —O-alkyl groups, 1-3 —SH groups, 1-3 —S-alkyl groups, 1-3 —O—C(=O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)$_n$-alkyl groups, 1-3 —S(=O)$_2$—NH-alkyl groups, 1-3 —NH-alkyl groups, 1-3 —N(alkyl)$_2$ groups, 1-3 —$NH_2$ groups or 1-3 —(CH$_2$)$_{0-3}$Z groups, where -L-#1 represents the linker and #1 represents the bond to the binder or derivative thereof, where -MOD is represented as defined infra, where n represents 0, 1 or 2, where Z represents —H, halogen, —$OY^3$, —$SY^3$, —$NHY^3$, —C(=O)—$NY^1Y^2$ or —C(=O)—$OY^3$, where $Y^1$ and $Y^2$ independently of one another represent —H, —$NH_2$ or —(CH$_2$)$_{0-3}$Z' and where $Y^3$ represents —H, —(CH$_2$)$_{0-3}$—CH(NHC(=O)—$CH_3$)Z', —(CH$_2$)$_{0-3}$—CH($NH_2$)Z' or —(CH$_2$)$_{0-3}$Z', where where Z' represents —H, —$SO_3H$, —$NH_2$ or —COOH;

$R^5$ represents —H, —$NH_2$, —$NO_2$, halogen (in particular —F, —Cl, —Br), —SH or —(CH$_2$)$_{0-3}$Z, where Z represents —H, —$OY^3$, —$SY^3$, halogen, —$NHY^3$, —C(O)—$NY^1Y^2$ or —C(O)—$OY^3$, where $Y^1$ and $Y^2$ independently of one another represent —H, —$NH_2$ or —(CH$_2$)$_{0-3}$Z', where $Y^3$ represents —H or —(CH$_2$)$_{0-3}$Z', where Z' represents —H, —$SO_3H$, —$NH_2$ or —COOH;

$R^6$ and $R^7$ independently of one another represent —H, cyano, $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, hydroxy or halogen (in particular —F, —Cl, —Br), $R^8$ represents $C_{1-10}$-alkyl, fluoro-$C_{1-10}$-alkyl, $C_{4-10}$-cycloalkyl, fluoro-$C_{4-10}$-cycloalkyl, or optionally substituted oxetane; and $R^9$ represents —H, —F, —$CH_3$, —$CF_3$, —$CH_2F$ or —$CHF_2$;

and the salts, solvates, salts of the solvates, and epimers thereof.

By substitution of a hydrogen atom at $R^1$, $R^2$, $R^3$, $R^4$, $R^5$ or $R^8$ or at the pyrrolidine ring ($R^{10}$) formed by $R^2$ and $R^4$, in a manner known to the person of average skill the compound of the formula (IIa) or (II) in which none of the substituents $R^1$, $R^2$, $R^3$, $R^4$, $R^5$, $R^8$ and $R^{10}$ represents -L-#1 may be attached to a linker. This gives conjugates of the formula (IIa) or (II) where one of the substituents $R^1$, $R^2$, $R^3$, $R^4$, $R^5$, $R^8$ or $R^{10}$ represents -L-#1, L represents the linker and #1 represents the bond to the binder or the derivative thereof. If the KSP inhibitor according to formula (IIa) or (II) is conjugated with a binder, one of the substituents $R^1$, $R^2$, $R^3$, $R^4$, $R^5$, $R^8$ or $R^{10}$ thus represents -L-#1, where L represents the linker and #1 represents the bond to the binder or the derivative thereof. That is, in the case of the conjugates one of the substituents $R^1$, $R^2$, $R^3$, $R^4$, $R^5$, $R^8$ and $R^{10}$ represents -L-#1, where -L-#1 is attached to the binder, for example an antibody. With particular preference, one of the substituents $R^1$ and $R^3$ represents -L-#1. In this embodiment, it is preferred that $R^4$ represents —H, $R^{21}$—(C=O)$_{(0-1)}$-(P3)$_{(0-2)}$-P2-NH—CH(CH$_2$C(=O)—$NH_2$)—C(=O)— or $R^{21}$—(C=O)$_{(0-1)}$-(P3)$_{(0-2)}$-P2-NH—CH(CH$_2$COOH)—C(=O)— as defined above. In another preferred embodiment, substituent $R^4$ represents -L-#1, wherein the Linker is cleavable at the nitrogen atom binding to $R^4$ such that a primary amino group is generated by cleavage (corresponding to $R^4$=—H). Corresponding cleavable groups are described below.

If $R^1$ is not —H, the carbon atom binding to $R^1$ is a stereocenter, which may be present in the L and/or D configuration, preferably in the L configuration.

If $R^2$ is not —H, the carbon atom binding to $R^2$ is a stereocenter, which may be present in the L and/or D configuration.

The binder is preferably a human, humanized or chimeric monoclonal antibody or an antigen-binding fragment thereof, in particular an anti-TWEAKR antibody or an antigen-binding fragment thereof or an anti-EGFR antibody or an antigen-binding fragment thereof. Particular preference is given to an anti-TWEAKR antibody which binds specifically to amino acid D in position 47 (D47) of TWEAKR (SEQ ID NO: 169), in particular the anti-TWEAKR antibody TPP-2090, or the anti-Her2 antibody trastuzumab. All the antibodies described include aglycosylated variants of these antibodies generated either by deglycosylation by PNGase F or by mutation of N297 (Kabat numbering) of the heavy chain to any amino acid.

The compounds of the formula (IIa) or (II) in which one of the substituents $R^1$, $R^2$, $R^3$, $R^4$, $R^5$ and $R^{10}$ represents -L-#1 and in which $X^1$ represents N, $X_2$ represents N and $X_3$ represents C;
$X_1$ represents CH or CF, $X_2$ represents C and $X_3$ represents N;
$X_1$ represents NH, $X_2$ represents C and $X_3$ represents C; or
$X_1$ represents CH, $X_2$ represents N and $X_3$ represents C
are particularly preferred,
in particular those in which
$X_1$ represents N, $X_2$ represents N and $X_3$ represents C; or $X_1$ represents CH, $X_2$ represents C and $X_3$ represents N. Particular preference is given to compounds in which $X_1$ represents CH, $X_2$ represents C and $X_3$ represents N.

For A, preference is given to —C(=O)—.

Preferred for $R^1$ are -L-#1, —H, —COOH, —C(=O)—NHNH$_2$, —(CH$_2$)$_{1-3}$NH$_2$, —C(=O)—NZ"(CH$_2$)$_{1-3}$ NH$_2$ and —C(=O)—NZ"CH$_2$COOH, where Z" represents —H or —NH$_2$.

$R^2$ and $R^4$ represent —H, or $R^2$ represents —H and $R^4$ represents $R^{21}$—(C=O)$_{(0-1)}$-(P3)$_{(0-2)}$-P2-NH—CH(CH$_2$C(=O)—NH$_2$)—C(=O)— or $R^2$ and $R^4$ together (with formation of a pyrrolidine ring) represent —CH$_2$—CHR$^{10}$— or —CHR$^{10}$—CH$_2$—, where $R^{10}$ represents —H or -L-#1.

Preferred for $R^3$ is -L-#1 or C$_{1-10}$-alkyl-, which may optionally be substituted by —OH, —O-alkyl, —SH, —S-alkyl, —O—C(=O)-alkyl, —O—C(=O)—NH-alkyl, —NH—C(=O)-alkyl, —NH—C(=O)—NH-alkyl, —S(O)$_n$-alkyl, —S(=O)$_2$—NH-alkyl, —NH-alkyl, —N(alkyl)$_2$ or —NH$_2$; where alkyl is preferably C$_{1-3}$-alkyl and n is 0, 1 or 2.

Preferred for $R^5$ is -L-#1, —H or —F.

Preferred for $R^6$ and $R^7$, independently of one another, are —H, (optionally fluorinated) C$_{1-3}$-alkyl, (optionally fluorinated) C$_{2-4}$-alkenyl, (optionally fluorinated) C$_{2-4}$-alkynyl, hydroxy or halogen, Preferred for $R^8$ is a branched C$_{1-5}$-alkyl group, in particular a group of the formula —C(CH$_3$)$_2$—(CH$_2$)$_{0-2}$—R$^y$, where R$^y$ represents —H, —OH, —COOH, —NH$_2$ or -L-#1. Particular preference is given to the group of the formula —C(CH$_3$)$_2$—(CH$_2$)—R$^y$, where R$^y$ represents —H or -L-#1.

Preferred for $R^9$ is —H or —F.

Particular preference is given to compounds of the formula (IIa) or (II) in which none or one of the substituents $R^1$, $R^2$, $R^3$, $R^4$, $R^5$, $R^8$ and $R^{10}$ represents -L-#1, and in which $X_1$ represents N, $X_2$ represents N and $X_3$ represents C;
$X_1$ represents CH or CF, $X_2$ represents C and $X_3$ represents N;
$X_1$ represents NH, $X_2$ represents C and $X_3$ represents C; or
$X_1$ represents CH, $X_2$ represents N and $X_3$ represents C
A represents —C(=O)—;
$R^1$ represents —H, —COOH, —C(=O)—NHNH$_2$, —(CH$_2$)$_{1-3}$NH$_2$, —C(=O)—NZ"(CH$_2$)$_{1-3}$—NH$_2$ and —C(=O)—NZ"CH$_2$COOH, where Z" represents —H or —NH$_2$;
$R^2$ and $R^4$ represent —H, or $R^2$ represents —H and $R^4$ represents $R^{21}$—(C=O)$_{(0-1)}$-(P3)$_{(0-2)}$-P2-NH—CH(CH$_2$C(=O)—NH$_2$)—C(=O)— (where P2 and P3 have the same meaning as defined above), or $R^2$ and $R^4$ together (with formation of a pyrrolidine ring) represent —CH$_2$—CHR$^{10}$— or —CHR$^{10}$—CH$_2$—, where $R^{10}$ represents H or -L-#1;
$R^3$ represents a phenyl group which may be mono- or polysubstituted by halogen (in particular F) or optionally fluorinated C$_{1-3}$-alkyl, or represents an optionally fluorinated C$_{1-10}$-alkyl group which may optionally be substituted by —OY$^4$, —SY$^4$, —O—C(=O)—Y$^4$, —O—C(=O)—NH—Y$^4$, —NH—C(=O)—Y$^4$, —NH—C(=O)—NH—Y$^4$, —S(=O)$_n$—Y$^4$ (where n represents 0, 1 or 2), —S(=O)$_2$—NH—Y$^4$, —NH—Y$^4$ or —N(Y$^4$)$_2$, where Y$^4$ represents —H, phenyl (optionally mono- or polysubstituted by halogen (in particular F) or optionally fluorinated C$_{1-3}$-alkyl), or alkyl (where the alkyl group may be substituted by —OH, —COOH, and/or —NHC(=O)—C$_{1-3}$-alkyl and where alkyl preferably represents C$_{1-3}$-alkyl);
where particularly preferably $R^3$ may be substituted by —OH, —O-alkyl, —SH, —S-alkyl, —O—C(=O)-alkyl, —O—C(=O)—NH-alkyl, —NH—C(=O)-alkyl, —NH—C(=O)—NH-alkyl, —S(=O)$_n$-alkyl (where n represents 0, 1 or 2), —S(=O)$_2$—NH-alkyl, —NH-alkyl, —N(alkyl)$_2$ or —NH$_2$ (where alkyl preferably means C$_{1-3}$-alkyl)
$R^5$ represents —H or —F;
$R^6$ and $R^7$ independently of one another represent —H, (optionally fluorinated) C$_{1-3}$-alkyl, (optionally fluorinated) C$_{2-4}$-alkenyl, (optionally fluorinated) C$_{2-4}$-alkynyl, hydroxy or halogen;
$R^8$ represents a branched C$_{1-5}$-alkyl group; and
$R^9$ represents —H or —F.

Furthermore, it is preferred when (alone or in combination)
$R^1$ represents -L-#1, —COOH or —H,
$R^2$ and $R^4$ independently of one another represent -L-#1 or —H; or $R^2$ represents —H and $R^4$ represents $R^{21}$—(C=O)$_{(0-1)}$-(P3)$_{(0-2)}$-P2-NH—CH(CH$_2$C(=O)—NH$_2$)—C(=O)— (where P2 and P3 have the same meaning as defined above), or $R^2$ and $R^4$ together (with formation of a pyrrolidine ring) represent —CH$_2$—CHR$^{10}$— or —CHR$^{10}$—CH$_2$—, where $R^{10}$ represents —H or -L-#1,
A represents —C(=O)—,
$R^3$ represents —(CH$_2$)OH, —CH(CH$_3$)OH, —CH$_2$—S—CH$_2$CH(COOH)NH—C(=O)—CH$_3$, —CH(CH$_3$)OCH$_3$, a phenyl group which may be substituted by 1-3 halogen atoms, 1-3 amino groups or 1-3 alkyl groups (which may optionally be halogenated), or represents -L-#1,
R represents -L-#1 or —H,
$R^6$ and $R^7$ independently of one another represent —H, C$_{1-3}$-alkyl or halogen; in particular, $R^6$ and $R^7$ represent —F;
$R^8$ represents C$_{1-4}$-alkyl (preferably tert-butyl); and/or
$R^9$ represents —H,
where one of the substituents $R^1$, $R^2$, $R^3$, $R^4$, $R^5$ and $R^{10}$ represents -L-#1.

Additionally, in accordance with the invention it is preferred when $R^1$ represents -L-#1, —COOH or —H, $R^2$ and $R^4$ independently of one another represent -L-#1 or —H, or $R^2$ represents —H and $R^4$ represents $R^{21}$—(C(=O))$_{(0-1)}$-(P3)$_{(0-2)}$-P2-NH—CH(CH$_2$C(=O)—NH$_2$)—C(=O)— (where P2 and P3 have the same meaning as defined above), or $R^2$ and $R^4$ together (with formation of a pyrrolidine ring) represent —CH$_2$—CHR$^{10}$— or —CHR$^{10}$—CH$_2$—, where $R^{10}$ represents —H or -L-#1, A represents —C(=O)—, $R^3$ represents —(CH$_2$)OH, —CH(CH$_3$)OH, —CH$_2$—S—CH$_2$CH(COOH)NH—C(=O)—CH$_3$, —CH(CH$_3$)OCH$_3$, a phenyl group which may be substituted by 1-3 halogen atoms, 1-3 amino groups or 1-3 alkyl groups (which may optionally be halogenated), or represents -L-#1, R represents -L-#1 or —H, $R^6$ and $R^7$ independently of one another represent —H, $C_{1-3}$-alkyl or halogen; in particular, $R^6$ and $R^7$ represent —F;

$R^8$ represents $C_{1-4}$-alkyl (preferably tert-butyl); and $R^9$ represents —H, where one of the substituents $R^1$, $R^2$, $R^3$, $R^4$, $R^5$ and $R^{10}$ represents -L-#1.

Other particularly preferred compounds have the formula (IIIa) or (III) below:

Formula (IIIa)

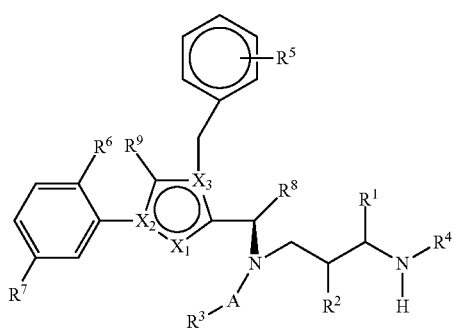

(IIIa)

where $X_1$ represents N, $X_2$ represents N and $X_3$ represents C; or $X_1$ represents N, $X_2$ represents C and $X_3$ represents N; or $X_1$ represents CH or CF, $X_2$ represents C and $X_3$ represents N; or $X_1$ represents NH, $X_2$ represents C and $X_3$ represents C; or $X_1$ represents CH, $X_2$ represents N and $X_3$ represents C (with $X_1$ representing CH, $X_2$ representing C and $X_3$ representing N being preferred);

$R^1$ represents —H, -L-BINDER, -MOD or —(CH$_2$)$_{0-3}$Z,
where Z represents —H, —NHY$^3$, —OY$^3$, —SY$^3$, halogen, —C(=O)—NY$^1$Y$^2$ or —C(=O)—OY$^3$,
where $Y^1$ and $Y^2$ independently of one another represent —H, —NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z', and
where $Y^3$ represents H or —(CH$_2$)$_{0-3}$Z',
where Z' represents —H, —NH$_2$, —SO$_3$H, —COOH, —NH—C(=O)—CH$_2$—CH$_2$—CH(NH$_2$)COOH or —(C(=O)—NH—CHY$^4$)$_{1-3}$COOH,
where W represents —H or —OH,
where $Y^4$ represents linear or branched $C_{1-6}$-alkyl which is optionally substituted by —NH—C(=O)—NH$_2$, or represents aryl or benzyl which are optionally substituted by —NH$_2$;

$R^2$ represents -L-BINDER, —H, -MOD, —C(=O)—CHY$^4$—NHY$^5$ or —(CH$_2$)$_{0-3}$Z,
where Z represents —H, halogen, —OY$^3$, —SY$^3$, —NHY$^3$, —C(=O)—NY$^1$Y$^2$ or —C(=O)—OY$^3$,
where $Y^1$ and $Y^2$ independently of one another represent —H, —NH$_2$ or —(CH$_2$)$_{0-3}$Z',
where $Y^3$ represents —H or —(CH$_2$)$_{0-3}$Z',
where Z' represents —H, —SO$_3$H, —NH$_2$ or —COOH;
where $Y^4$ represents linear or branched $C_{1-6}$-alkyl which is optionally substituted by —NH—C(=O)—NH$_2$, or represents aryl or benzyl which are optionally substituted by —NH$_2$,
where $Y^5$ represents —H or —C(=O)—CHY$^6$—NH$_2$,
where $Y^6$ represents linear or branched $C_{1-6}$-alkyl;

$R^4$ represents -L-BINDER, —H, —C(O)—CHY$^4$—NHY$^5$ or —(CH$_2$)$_{0-3}$Z,
where Z represents —H, —OY$^3$, —SY$^3$, —NHY$^3$, —C(=O)—NY$^1$Y$^2$ or —C(O)—OY$^3$,
where $Y^1$ and $Y^2$ independently of one another represent —H, —NH$_2$ or —(CH$_2$)$_{0-3}$Z',
where $Y^3$ represents —H or —(CH$_2$)$_{0-3}$Z',
where Z' represents —H, —SO$_3$H, —NH$_2$ or —COOH;
where $Y^4$ represents linear or branched $C_{1-6}$-alkyl which is optionally substituted by —NH—C(=O)—NH$_2$, or represents aryl or benzyl which are optionally substituted by —NH$_2$,
where $Y^5$ represents —H or —C(=O)—CHY$^6$—NH$_2$,
where $Y^6$ represents linear or branched $C_{1-6}$-alkyl, or $R^4$ represents a group of $R^{21}$—(C=O)$_{(0-1)}$-(P3)$_{(0-2)}$-P2-NH—CH(CH$_2$C(=O)—NH$_2$)—C(=O)—,
where $R^{21}$ represents —H, $C_{1-10}$-alkyl-, $C_{5-10}$-aryl- or $C_{6-10}$-aralkyl-, $C_{5-10}$-heteroalkyl-, $C_{1-10}$-alkyl-O—$C_{6-10}$-aryl-, $C_{5-10}$-heterocycloalkyl-, heteroaryl-, heteroaryl-alkyl-, $C_{1-10}$-alkoxy-, $C_{6-10}$-aryloxy- or $C_{6-10}$-aralkoxy-, $C_{5-10}$-heteroalkoxy-, $C_{1-10}$-alkyl-O—$C_{6-10}$-aryloxy-, $C_{5-10}$-heterocycloalkoxy group, which may be substituted one or more times with —NH$_2$, —NH-alkyl, —N(alkyl)$_2$, —NH—C(=O)-alkyl, —N(alkyl)-C(=O)-alkyl, —SO$_3$H, —SO$_2$NH$_2$, —S(=O)$_2$—N(alkyl)$_2$, —COOH, —C(=O)—NH$_2$, —C(=O)—N(alkyl)$_2$, or —OH, or is —H or a group —O$_x$—(CH$_2$CH$_2$O)$_y$—R$^{22}$,
where x is 0 or 1,
where v is a number from 1 to 20, and
where $R^{22}$ represents —H, -alkyl (preferably $C_{1-12}$-alkyl), —CH$_2$—COOH, —CH$_2$—CH$_2$—COOH, or —CH$_2$—CH$_2$—NH$_2$;
where P2 is an amino acid selected from Gly, Pro, Ala, Val, Nva, Leu, Ile, Met, Phe, Tyr, Trp, Ser, Thr, Cys, Asn, Gln, Asp, Glu, Lys, Arg, citrulline and His;
where P3 is an amino acid independently selected from Gly, Pro, Ala, Val, Nva, Leu, Ile, Met, Phe, Tyr, Trp, Ser, Thr, Cys, Asn, Gln, Asp, Glu, Lys, Arg, citrulline and His or one of the corresponding N-alkyl amino acids, preferably N-methyl amino acids;

or $R^2$ and $R^4$ together (with formation of a pyrrolidine ring) represent —CH$_2$—CHR$^{10}$— or —CHR$^{10}$—CH$_2$—,
where $R^{10}$ represents -L-BINDER, —H, —NH$_2$, —SO$_3$H, —COOH, —SH or —OH;

A represents —C(=O)—, —S(=O)—, —S(=O)$_2$—, —S(=O)$_2$—NH— or —C(=N—NH$_2$)—;

R³ represents -L-BINDER, -MOD or an optionally substituted alkyl, cycloalkyl, aryl, heteroaryl, heteroalkyl, heterocycloalkyl group, preferably -L-BINDER, or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 —O-alkyl groups, 1-3 —SH groups, 1-3 —S-alkyl groups, 1-3 —O—C(=O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)$_n$-alkyl groups, 1-3 —S(=O)$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups,
where n is 0, 1 or 2,
where Z represents —H, halogen, —OY³, —SY³, —NHY³, —C(=O)—NY¹Y² or —C(O)—OY³,
where Y¹ and Y² independently of one another represent —H, —NH$_2$ or —(CH$_2$)$_{0-3}$Z',
where Y³ represents —H, —(CH$_2$)$_{0-3}$—CH(NH—C(=O)—CH$_3$)Z', —(CH$_2$)$_{0-3}$—CH(NH$_2$)Z' or —(CH$_2$)$_{0-3}$Z',
where Z' represents —H, —SO$_3$H, —NH$_2$ or —COOH
where "alkyl" preferably represents $C_{1-10}$-alkyl);
R⁵ represents -L-BINDER, —H, —NH$_2$, —NO$_2$, halogen (in particular F, Cl, Br), —CN, —CF$_3$, —OCF$_3$, —CH$_2$F, —CHF$_2$, —SH or —(CH$_2$)$_{0-3}$Z,
where Z represents —H, —OY³, —SY³, halogen, —NHY³, —C(=O)—NY¹Y² or —C(=O)—OY³,
where Y¹ and Y² independently of one another represent —H, —NH$_2$ or —(CH$_2$)$_{0-3}$Z',
where Y³ represents —H or —(CH$_2$)$_{0-3}$Z',
where Z' represents —H, —SO$_3$H, —NH$_2$ or —COOH;
R⁶ and R⁷ independently of one another represent —H, cyano, $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, hydroxy, —NO$_2$, —NH$_2$, —COOH or halogen (in particular —F, —Cl, —Br),
R⁸ represents $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, $C_{4-10}$-cycloalkyl, fluoro-$C_{4-10}$-cycloalkyl or —(CH$_2$)$_{0-2}$—(HZ²),
where HZ² represents a 4- to 7-membered heterocycle having up to two heteroatoms selected from the group consisting of N, O and S (preferably oxetane), where each of these groups may be substituted by —OH, —COOH or —NH$_2$ or -L-BINDER;
R⁹ represents —H, —F, —CH$_3$, —CF$_3$, —CH$_2$F or —CHF$_2$;
L represents a linker,
BINDER represents a binder or a derivative thereof, where the binder may optionally be attached to a plurality of active compound molecules,
where one representative of R¹, R², R³ R⁴, R⁵ and R⁸ represents -L-binder;
-MOD represents —(NR¹⁰)$_n$-(G1)$_o$-G2-H, where
where R¹⁰ represents —H or $C_1$-$C_3$-alkyl;
where G1 represents —NHC(=O)—, —C(=O)—NH— or

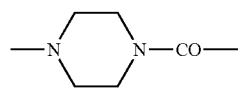

(where, if G1 represents —NH—C(=O)— or

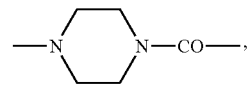

R¹⁰ does not represent NH$_2$);
where n is 0 or 1;
where o is 0 or 1; and
where G2 represents a linear and/or branched hydrocarbon group which has 1 to 10 carbon atoms and which may be interrupted once or more than once by one or more of the groups —O—, —S—, —S(=O)—, —S(=O)$_2$—, —NR^y—, —NR^yC(=O)—, —C(=O)—NR^y—, —NR^yNR^y—, —S(=O)$_2$—NR^yNR^y—, —C(=O)—NR^yNR^y—,
where R^y represents —H, phenyl, $C_1$-$C_{10}$-alkyl, $C_2$-$C_{10}$-alkenyl or $C_2$-$C_{10}$-alkynyl, each of which may be substituted by —NH—C(=O)—NH$_2$, —COOH, —OH, —NH$_2$, NH—CN—NH$_2$, sulphonamide, sulphone, sulphoxide or sulphonic acid, or represents —C(=O)—, —CR^x=N—O—
where R^x represents —H, $C_1$-$C_3$-alkyl or phenyl,
where the hydrocarbon chain including any side chains may be substituted by —NH—C(=O)—NH$_2$, —COOH, —OH, —NH$_2$, NH—CN—NH$_2$, sulphonamide, sulphone, sulphoxide or sulphonic acid,
and where -MOD preferably has at least one group —COOH;
and the salts, solvates and salts of the solvates thereof.

In the case of binder conjugates of the KSP inhibitors of the formula (IIIa), at most one representative of R¹, R², R³ R⁴, R⁵, R⁸ and R¹⁰ (alternatively to one of the conditions given above) may represent -L-BINDER, where L represents a linker and BINDER represents a binder or a derivative thereof, where the binder may optionally be attached to a plurality of active compound molecules.

Formula (III)

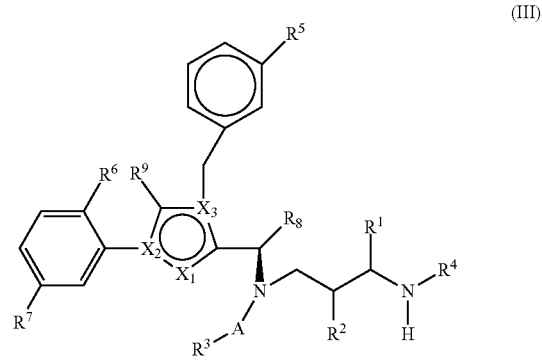

(III)

where
X₁ represent N, X₂ represents N and X₃ represents C, or
X₁ represents CH, X₂ represents C and X₃ represents N or
X₁ represents NH, X₂ represents C and X₃ represents C, or
X₁ represents CH, X₂ represents N and X₃ represents C;
R¹ represents —H, -L-BINDER or —(CH$_2$)$_{0-3}$Z,
where Z represents —H, —NHY³, —OY³, —SY³, halogen, —C(=O)—NY¹Y² or —C(=O)—OY³,
where Y¹ and Y² independently of one another represent —H, —NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z', and where $Y^3$ represents H or —$(CH_2)_{0-3}Z'$,
where $Z'$ represents —H, —$NH_2$, —$SO_3H$, —COOH, —NH—C(=O)—$CH_2$—$CH_2$—CH($NH_2$)COOH or —(C(=O)—NH—$CHY^4)_{1-3}$COOH,
where W represents —H or —OH,
where $Y^4$ represents linear or branched $C_{1-6}$-alkyl which is optionally substituted by —NH—(C=O)—$NH_2$, or represents aryl or benzyl which are optionally substituted by —$NH_2$;

$R^2$ and $R^4$ independently of one another represent -L-BINDER, —H, —C(O)—$CHY^4$—$NHY^5$ or —$(CH_2)_{0-3}$Z,
or
$R^2$ and $R^4$ together (with formation of a pyrrolidine ring) represent —$CH_2$—$CHR^{10}$— or —$CHR^{10}$—$CH_2$—,
where $R^{10}$ represents L-#1, —H, —$NH_2$, —$SO_3H$, —COOH, —SH, or —OH;
where Z represents —H, halogen, —$OY^3$, —$SY^3$, —$NHY^3$, —C(=O)—$NY^1Y^2$ or —C(=O)—$OY^3$,
where $Y^1$ and $Y^2$ independently of one another represent —H, —$NH_2$ or —$(CH_2)_{0-3}Z'$,
where $Y^3$ represents —H or —$(CH_2)_{0-3}Z'$,
where $Z'$ represents —H, —$SO_3H$, —$NH_2$ or —COOH;
where $Y^4$ represents linear or branched $C_{1-6}$-alkyl which is optionally substituted by —NH—C(=O)—$NH_2$, or represents aryl or benzyl which are optionally substituted by —$NH_2$,
where $Y^5$ represents —H or —C(=O)—$CHY^6$—$NH_2$,
where $Y^6$ represents linear or branched $C_{1-6}$-alkyl;
A represents —C(=O)—, —S(=O)—, —S(=O)$_2$—, —S(=O)$_2$—NH— or —C(=N—$NH_2$)—;
$R^3$ represents -L-BINDER or an optionally substituted alkyl, cycloalkyl, aryl, heteroaryl, heteroalkyl, heterocycloalkyl group, preferably -L-BINDER, or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 —O-alkyl groups, 1-3 —SH groups, 1-3 —S-alkyl groups, 1-3 —O—C(=O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)$_n$-alkyl groups, 1-3 —S(=O)$_2$—NH-alkyl groups, 1-3 —NH-alkyl groups, 1-3 —N(alkyl)$_2$ groups, 1-3 —$NH_2$ groups or 1-3 —$(CH_2)_{0-3}$Z groups,
where n is 0, 1 or 2,
where Z represents —H, halogen, —$OY^3$, —$SY^3$, —$NHY^3$, —C(=O)—$NY^1Y^2$ or —C(O)—$OY^3$,
where $Y^1$ and $Y^2$ independently of one another represent —H, —$NH_2$ or —$(CH_2)_{0-3}Z'$,
where $Y^3$ represents —H, —$(CH_2)_{0-3}$—CH(NH—C(=O)—$CH_3$)$Z'$, —$(CH_2)_{0-3}$—CH($NH_2$)$Z'$ or —$(CH_2)_{0-3}Z'$,
where $Z'$ represents —H, —$SO_3H$, —$NH_2$ or —COOH
where "alkyl" preferably represents $C_{1-10}$-alkyl);
$R^5$ represents -L-BINDER, —H, —$NH_2$, —$NO_2$, halogen (in particular F, Cl, Br), —CN, —$CF_3$, —$OCF_3$, —$CH_2F$, —$CH_2F$, —SH or —$(CH_2)_{0-3}$Z,
where Z represents —H, —$OY^3$, —$SY^3$, halogen, —$NHY^3$, —C(=O)—$NY^1Y^2$ or —C(=O)—$OY^3$,
where $Y^1$ and $Y^2$ independently of one another represent —H, —$NH_2$ or —$(CH_2)_{0-3}Z'$,
where $Y^3$ represents —H or —$(CH_2)_{0-3}Z'$,
where $Z'$ represents —H, —$SO_3H$, —$NH_2$ or —COOH;

$R^6$ and $R^7$ independently of one another represent —H, cyano, $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, hydroxy, or halogen (in particular —F, —Cl, —Br);
$R^8$ represents $C_{1-10}$-alkyl, fluoro-$C_{1-10}$-alkyl, $C_{4-10}$-cycloalkyl, fluoro-$C_{4-10}$-cycloalkyl or optionally substituted oxetane;
$R^9$ represents —H, —F, —$CH_3$, —$CF_3$, —$CH_2F$ or —$CHF_2$;
L represents a linker and
BINDER represents a binder or a derivative thereof, where the binder may optionally be attached to a plurality of active compound molecules,
where one representative of $R^1$, $R^2$, $R^3$ $R^4$, $R^5$, $R^8$ and $R^{10}$ represents -L-binder;
and the salts, solvates and salts of the solvates thereof.

Furthermore, preference according to the invention is given to conjugate of the following KSP inhibitors:

Formula (IIIb)

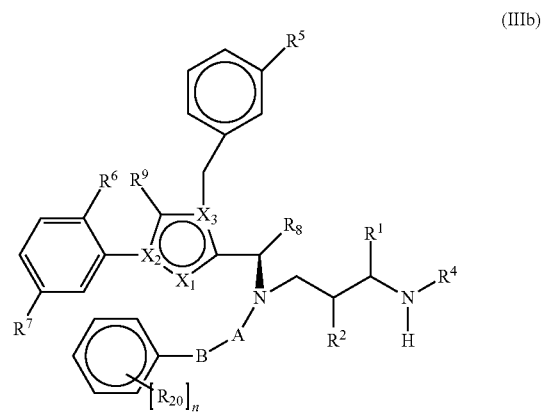

(IIIb)

where $X_1, X_2, X_3$ have the same meaning as in formula (IIIa) or (III) (where preferably $X_1$ represents —CH—, $X_2$ represents —C— and $X_3$ represent —N—), $R^1$, $R^2$, $R^4$, $R^5$, $R^6$, $R^7$, $R^8$ and $R^9$ have the same meaning as in formula (IIIa) or (III), A represents —C(=O)—, B represents a single bond, —O—$CH_2$— or —$CH_2$—O— and $R^{20}$ represents —$NH_2$, —F, —$CF_3$ or —$CH_3$ and n represents 0, 1 or 2.

Formula (IIIc)

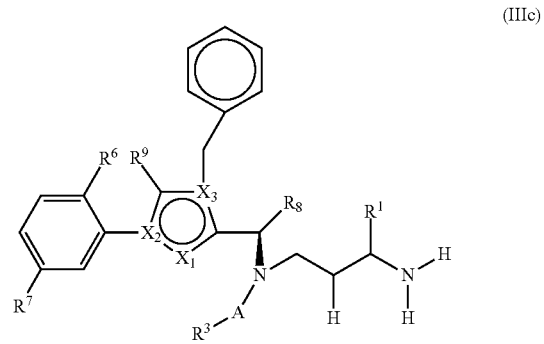

(IIIc)

where $X_1, X_2, X_3$ have the same meaning as in formula (IIIa) or (III) (where preferably $X_1$ represents —CH—, $X_2$ represents —C— and $X_3$ represents —N—);

A, $R^1$, $R^3$, $R^6$, $R^7$, $R^8$ and $R^9$ have the same meaning as in formula (IIIa) or (III), A preferably represents —C(=O)— and $R^3$ represents —CH$_2$OH, —CH$_2$OCH$_3$, —CH(CH$_3$)OH or —CH(CH$_3$)OCH$_3$.

Formula (IIId)

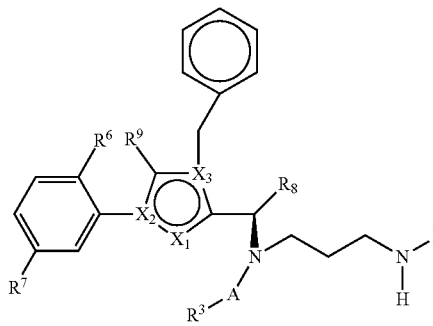

(IIId)

where $X_1$, $X_2$, $X_3$ have the same meaning as in formula (IIIa) or (III) (where preferably $X_1$ represents —CH—, $X_2$ represents —C— and $X_3$ represents —N—);
A, $R^3$, $R^6$, $R^7$, $R^8$ and $R^9$ have the same meaning as in formula (IIIa) or (III), where A preferably represents —C(=O)— and $R^3$ represents —CH$_2$—S$_x$—(CH$_2$)$_{0-4}$—CHY$^5$—COOH, where x is 0 or 1 and $Y^5$ represents —H or —NHY$^6$, where $Y^6$ represents —H or —C(=O)—CH$_3$.

Formula (IIIe)

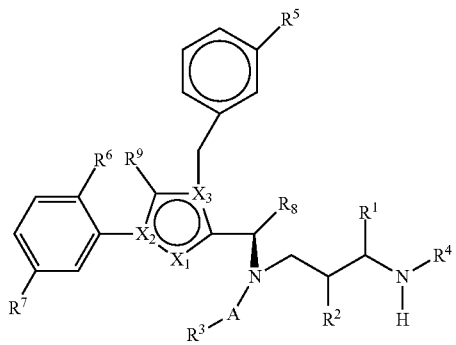

(IIIe)

where $X_1$ represents —CH—, $X_2$ represents —C— and $X_3$ represents —N—;
A, $R^3$, $R^4$, $R^6$, $R^7$, $R^8$ and $R^9$ have the same meaning as in formula (IIIa) or (III) and $R^1$ represents -L-BINDER.

Furthermore, it is preferred when in the compounds of the formulae (III), (IIIa), (IIIb), (IIIc), (IIId) and (IIIe) (alone or in combination):

Z represents Cl or Br;
$R^1$ represents —(CH$_2$)$_{0-3}$Z, where Z represents —C(=O)—NY$^1$Y$^2$, where $Y^2$ represents —(CH$_2$CH$_2$O)$_{0-3}$—(CH$_2$)$_{0-3}$Z' and $Y^1$ represents —H, —NH$_2$ or —(CH$_2$CH$_2$O)$_{03}$—(CH$_2$)$_{0-3}$Z';
$Y^1$ represents —H, $Y^2$ represents —(CH$_2$CH$_2$O)$_3$—CH$_2$CH$_2$Z' and Z' represents —COOH;
$Y^1$ represents —H, $Y^2$ represents —CH$_2$CH$_2$Z' and Z' represents —C(=O)—NHCHY$^4$)$_2$COOH;
$Y^1$ represents —H, $Y^2$ represents —CH$_2$CH$_2$Z', Z' represents —C(=O)—NHCHY$^4$)$_2$COOH and one of the $Y^4$ radicals represents i-propyl and the other —(CH$_2$)$_3$—NH—C(=O)—NH$_2$;
$Y^1$ represents H, $Y^2$ represents —CH$_2$CH$_2$Z', Z' represents —C(=O)—NHCHY$^4$)$_2$COOH and one of the $Y^4$ radicals represents —CH$_3$ and the other —(CH$_2$)$_3$—NH—C(=O)—NH$_2$;
$Y^4$ represents linear or branched C$_{1-6}$-alkyl which is optionally substituted by —NH—C(=O)—NH$_2$;
at least one $Y^4$ representative is selected from the group consisting of i-propyl and —CH$_3$;
$Y^1$ represents —H, $Y^2$ represents —CH$_2$CH$_2$Z', Z' represents —C(=O)—NHCHY$^4$COOH and $Y^4$ represents aryl or benzyl which are optionally substituted by —NH$_2$;
$Y^4$ represents aminobenzyl;
$R^2$ represents —(CH$_2$)$_{0-3}$Z and Z represents —SY$^3$;
$R^4$ represents —C(=O)—CHY$^4$—NHY$^5$ and $Y^5$ represents —H;
$R^4$ represents —C(=O)—CHY$^4$—NHY$^5$ and $Y^5$ represents —C(=O)—CHY$^6$—NH$_2$;
$R^4$ represents $R^{21}$-L-Ala-L-Ala-L-Asn-#;
$Y^4$ represents linear or branched C$_{1-6}$-alkyl which is optionally substituted by —NH—C(=O)—NH$_2$.

Furthermore, it is preferred when $R^1$, $R^2$ or $R^3$ in formula (IIa) or (IIIa) represents -MOD, in particular when $R^4$ represents -L-#1 or -L-BINDER (in particular when -L is a cleavable linker which cleaves directly at —N—$R^4$ or —N-L-#1 or -L-BINDER, such that $R^4$ or L is replaced by —H).

Particularly preferably, $R^3$ represents -MOD and $R^1$ or $R^4$ represents -L-#1 or -L-BINDER,
where -MOD represents —(NR$^{10}$)$_n$-(G1)$_o$-G2-H,
where $R^{10}$ represents —H or C$_1$-C$_3$-alkyl;
where G1 represents —NH—C(=O)—, —C(=O)—NH— or —N⟨piperazine⟩N—CO—

(where, if G1 represents —NH—C(=O)— or

—N⟨piperazine⟩N—CO—, $R^{10}$ does not represent NH$_2$);
where n is 0 or 1;
where o is 0 or 1; and
where G2 represents a linear and/or branched hydrocarbon group which has 1 to 10 carbon atoms and which may be interrupted once or more than once by one or more of the groups —O—, —S—, —S(=O)—, —S(=O)$_2$—, —NR$^y$—, —NR$^y$C(=O)—, —C(=O)—NR—, —NR$^y$NR$^y$—, —S(=O)$_2$—NR$^y$NR$^y$—, —C(=O)—NR$^y$NR$^y$—,
where R$^y$ represents —H, phenyl, C$_1$-C$_{10}$-alkyl, C$_2$-C$_{10}$-alkenyl or C$_2$-C$_{10}$-alkynyl, each of which may be substituted by —NH—C(=O)—NH$_2$, —COOH, —OH, —NH$_2$, NH—CN—NH$_2$, sulphonamide, sulphone, sulphoxide or sulphonic acid, or represents —C(=O)—, —CR$^x$=N—O—
where R$^x$ represents —H, C$_1$-C$_3$-alkyl or phenyl,
where the hydrocarbon chain including any side chains may be substituted by —NH—C(=O)—NH$_2$, —COOH, —OH, —NH$_2$, —NH—CN—NH$_2$, sulphonamide, sulphone, sulphoxide or sulphonic acid, and where -MOD preferably has at least one group —COOH.

Particularly preferably, the group -MOD has a (preferably terminal) —COOH group, for example in a betaine group. Preferably, the group -MOD has the formula —CH$_2$—S$_x$—(CH$_2$)O$_4$—CHY$^5$—COOH where x is 0 or 1, and Y$^5$ represents —H or —NHY$^6$, where Y$^6$ represents —H or —C(=O)—CH$_3$.

Other particularly preferred compounds have the formula (IV) below:

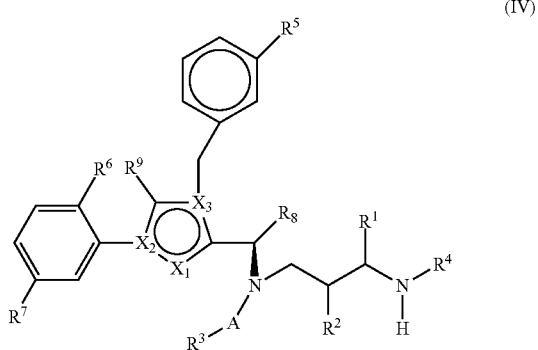

(IV)

where

X$_1$ represents N, X$_2$ represents C and X$_3$ represents N;

R$^1$ represents —H, -L-BINDER or —(CH$_2$)$_{0-3}$Z,
  where Z represents —H, —NHY$^3$, —OY$^3$, —SY$^3$, halogen, —C(=O)—NY$^1$Y$^2$ or —C(=O)—OY$^3$,
  where Y$^1$ and Y$^2$ independently of one another represent —H, —NH$_2$, —(CH$_2$CH$_2$O)$_{0-3}$—(CH$_2$)$_{0-3}$Z' or —CH(CH$_2$W)Z',
  where Y$^3$ represents H or —(CH$_2$)$_{0-3}$Z',
  where Z' represents —H, —NH$_2$, —SO$_3$H, —COOH, —NH—C(=O)—CH$_2$—CH$_2$—CH(NH$_2$)COOH or —(C(=O)—NH—CHY$^4$)$_{1-3}$COOH,
  where W represents —H or —OH,
  where Y$^4$ represents linear or branched C$_{1-6}$-alkyl which is optionally substituted by —NH—(C=O)—NH$_2$, or represents aryl or benzyl which are optionally substituted by —NH$_2$;

R$^2$ and R$^4$ independently of one another represents -L-BINDER, —H, —C(=O)—CHY$^4$—NHY$^5$ or —(CH$_2$)$_{0-3}$Z, or R$^2$ and R$^4$ together (with formation of a pyrrolidine ring) represent —CH$_2$—CHR$^{10}$— or —CHR$^{10}$—CH$_2$—,
  where R$^{10}$ represents L-#1, —H, —NH$_2$, —SO$_3$H, —COOH, —SH, or —OH;
  where Z represents —H, halogen, —OY$^3$, —SY$^3$, —NHY$^3$, —C(=O)—NY$^1$Y$^2$ or —C(=O)—OY$^3$,
  where Y$^1$ and Y$^2$ independently of one another represent —H, —NH$_2$ or —(CH$_2$)$_{0-3}$Z',
  where Y$^3$ represents —H or —(CH$_2$)$_{0-3}$Z',
  where Z' represents —H, —SO$_3$H, —NH$_2$ or —COOH;
  where Y$^4$ represents linear or branched C$_{1-6}$-alkyl which is optionally substituted by —NH—C(=O)—NH$_2$, or represents aryl or benzyl which are optionally substituted by —NH$_2$,
  where Y$^5$ represents —H or —C(=O)—CHY$^6$—NH$_2$,
  where Y$^6$ represents linear or branched C$_{1-6}$-alkyl;

A represents —C(=O)—, —S(=O)—, —S(=O)$_2$—, —S(=O)$_2$—NH— or —C(=N—NH$_2$)—;

R$^3$ represents -L-BINDER or an optionally substituted alkyl, cycloalkyl, aryl, heteroaryl, heteroalkyl, heterocycloalkyl group, or —CH$_2$—S$_x$—(CH$_2$)$_{0-4}$—CHY$^5$—COOH,
  where x is 0 or 1,
  where Y$^5$ represents —H or —NHY$^6$,
  where Y$^6$ represents —H or —C(=O)—CH$_3$,
  preferably -L-BINDER, or a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3 —OH groups, 1-3 halogen atoms, 1-3 halogenated alkyl groups (each having 1-3 halogen atoms), 1-3 —O-alkyl groups, 1-3 —SH groups, 1-3 —S-alkyl groups, 1-3 —O—C(=O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)$_n$-alkyl groups, 1-3 —S(=O)$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups,
  where n is 0, 1 or 2,
  where Z represents —H, halogen, —OY$^3$, —SY$^3$, —NHY$^3$, —C(=O)—NY$^1$Y$^2$ or —C(O)—OY$^3$,
  where Y$^1$ and Y$^2$ independently of one another represent —H, —NH$_2$ or —(CH$_2$)$_{0-3}$Z',
  where Y$^3$ represents —H, —(CH$_2$)$_{0-3}$—CH(NH—C(=O)—CH$_3$)Z', —(CH$_2$)$_{0-3}$—CH(NH$_2$)Z' or —(CH$_2$)$_{0-3}$Z',
  where Z' represents —H, —SO$_3$H, —NH$_2$ or —COOH
  where "alkyl" preferably represents C$_{1-10}$-alkyl);

R$^5$ represents -L-BINDER, —H, —NH$_2$, —NO$_2$, halogen (in particular F, Cl, Br), —SH or —(CH$_2$)$_{0-3}$Z,
  where Z represents —H, —OY$^3$, —SY$^3$, halogen, —NHY$^3$, —C(=O)—NY$^1$Y$^2$ or —C(=O)—OY$^3$,
  where Y$^1$ and Y$^2$ independently of one another represent —H, —NH$_2$ or —(CH$_2$)$_{0-3}$Z',
  where Y$^3$ represents —H or —(CH$_2$)$_{0-3}$Z',
  where Z' represents —H, —SO$_3$H, —NH$_2$ or —COOH;

where L represents a linker,

BINDER represents a binder or a derivative thereof, where the binder may optionally be attached to a plurality of active compound molecules;

R$^6$ and R$^7$ independently of one another represent —H, cyano, C$_{1-10}$-alkyl, fluoro-C$_{1-10}$-alkyl, C$_{2-10}$-alkenyl, fluoro-C$_{2-10}$-alkenyl, C$_{2-10}$-alkynyl, fluoro-C$_{2-10}$-alkynyl, hydroxy or halogen (in particular —F, —Cl, —Br);

R$^8$ represents C$_{1-10}$-alkyl, fluoro-C$_{1-10}$-alkyl, C$_{4-10}$-cycloalkyl, fluoro-C$_{4-10}$-cycloalkyl or optionally substituted oxetane;

R$^9$ represents —H, —F, —CH$_3$, —CF$_3$, —CH$_2$F or —CHF$_2$;

and the salts, solvates, salts of the solvates, and epimers thereof;

with the proviso that R$^1$, R$^2$ and R$^4$ do not simultaneously represent —H.

Furthermore, it is preferred when in the formula (IIa), (II), (III), (IIIa), (IIIb), (IIIc), (IIId), (IIIe) or (IV) (alone or in combination):

Z represents Cl or Br;

R$^1$ represents —(CH$_2$)$_{0-3}$Z, where Z represents —C(=O)—NY$^1$Y$^2$, where Y$^2$ represents —(CH$_2$CH$_2$O)$_{0-3}$—(CH$_2$)O$_{3Z'}$ and Y$^1$ represents H, NH$_2$ or —(CH$_2$CH$_2$O)$_{0-3}$—(CH$_2$)$_{0-3}$Z';

$Y^1$ represents —H, $Y^2$ represents —(CH$_2$CH$_2$O)$_3$—CH$_2$CH$_2$Z' and Z' represents —COOH;

$Y^1$ represents —H, $Y^2$ represents —CH$_2$CH$_2$Z' and Z' represents —(C(=O)—NHCHY$^4$)$_2$COOH;

$Y^1$ represents —H, $Y^2$ represents —CH$_2$CH$_2$Z', Z' represents —(C(=O)—NHCHY$^4$)$_2$COOH and one $Y^4$ representative represents i-propyl and the other represents —(CH$_2$)$_3$—NH—C(=O)—NH$_2$;

$Y^1$ represents —H, $Y^2$ represents —CH$_2$CH$_2$Z', Z' represents —(C(=O)—NHCHY$^4$)$_2$COOH and one $Y^4$ representative represents —CH$_3$ and the other represents —(CH$_2$)$_3$—NH—C(=O)—NH$_2$;

$Y^4$ represents linear or branched $C_{1-6}$-alkyl which is optionally substituted by —NH—C(=O)—NH$_2$;

at least one $Y^4$ representative is selected from the group consisting of i-propyl and —CH$_3$;

$Y^1$ represents —H, $Y^2$ represents —CH$_2$CH$_2$Z', Z' represents —C(=O)—NHCHY$^4$COOH and $Y^4$ represents aryl or benzyl which are optionally substituted by —NH$_2$;

$Y^4$ represents aminobenzyl;

$R^2$ represents —(CH$_2$)$_{0-3}$Z and Z represents —SY$^3$;

$R^4$ represents —C(=O)—CHY$^4$—NHY$^5$ and $Y^5$ represents —H;

$R^4$ represents —C(=O)—CHY$^4$—NHY$^5$ and $Y^5$ represents —C(=O)—CHY$^6$—NH$_2$;

$R^4$ represents $R^{21}$-L-Ala-L-Ala-L-Asn-#;

$Y^4$ represents linear or branched $C_{1-6}$-alkyl which is optionally substituted by —NH—C(=O)—NH$_2$.

Preference is furthermore given to compounds of the formula (IIa), (II), (III), (IIIa), (IIIb), (IIIc), (IIId), (IIIe) or (IV)

where $X_1$ represents N, $X_2$ represents N and $X_3$ represents C; or $X_1$ represents N, $X_2$ represents C and $X_3$ represents N; or $X_1$ represents CH or CF, $X_2$ represents C and $X_3$ represents N; or $X_1$ represents NH, $X_2$ represents C and $X_3$ represents C; or $X_1$ represents CH or CF, $X_2$ represents N and $X_3$ represents C;

(with $X_1$ representing CH, $X_2$ representing C and $X_3$ representing N being preferred);

$R^1$ represents H, -L-#1 or -L-BINDER, -MOD or —(CH$_2$)$_{0-3}$Z, where Z represents —H, —NHY$^3$, —OY$^3$, —SY$^3$, halogen, —C(=O)—NY$^1$Y$^2$ or —C(=O)—OY$^3$, where $Y^1$ and $Y^2$ independently of one another represent —H, —NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z', where $Y^3$ represents H or —(CH$_2$)$_{0-3}$Z', where Z' represents —H, —NH$_2$, —SO$_3$H, —COOH, —NH—C(=O)—CH$_2$—CH$_2$—CH(NH$_2$)COOH or —(C(=O)—NH—CHY$^4$)$_{1-3}$COOH, where W represents —H or —OH, where $Y^4$ represents linear or branched $C_{1-6}$-alkyl which is optionally substituted by —NH—(C=O)—NH$_2$, or represents aryl or benzyl which are optionally substituted by —NH$_2$;

$R^2$ represents —H, —C(=O)—CHY$^4$—NHY$^5$ or —(CH$_2$)$_{0-3}$Z, where Z represents —H, halogen, —OY$^3$, —SY$^3$, —NHY$^3$, —C(=O)—NY$^1$Y$^2$ or —C(=O)—OY$^3$, where $Y^1$ and $Y^2$ independently of one another represent —H, —NH$_2$ or —(CH$_2$)$_{0-3}$Z', where $Y^3$ represents —H or —(CH$_2$)$_{0-3}$Z', where Z' represents —H, —SO$_3$H, —NH$_2$ or —COOH;

where $Y^4$ represents linear or branched $C_{1-6}$-alkyl which is optionally substituted by —NH—C(=O)—NH$_2$, or represents aryl or benzyl which are optionally substituted by —NH$_2$, where $Y^5$ represents —H or —C(=O)—CHY$^6$—NH$_2$, where $Y^6$ represents linear or branched $C_{1-6}$-alkyl;

$R^4$ represents —H or $R^{21}$-L-Ala-L-Ala-L-Asn-;

where $R^{21}$ represents —H, $C_{1-10}$-alkyl-, $C_{5-10}$-aryl- or $C_{6-10}$-aralkyl-, $C_{5-10}$-heteroalkyl-, $C_{1-10}$-alkyl-O—$C_{6-10}$-aryl-, $C_{5-10}$-heterocycloalkyl-, heteroaryl-, heteroaryl-alkyl-, $C_{1-10}$-alkoxy-, $C_{6-10}$-aryloxy-oder $C_{6-10}$-aralkoxy-, $C_{5-10}$-heteroalkoxy-, $C_{1-10}$-alkyl-O—$C_{6-10}$-aryloxy-, $C_{5-10}$-heterocycloalkoxy group, which may be substituted one or more times with —NH$_2$, —NH-alkyl, —N(alkyl)$_2$, —NH—C(=O)-alkyl, —N(alkyl)-C(=O)-alkyl, —SO$_3$H, —SO$_2$NH$_2$, —S(=O)$_2$—N(alkyl)$_2$, —COOH, —C(=O)—NH$_2$, —C(=O)—N(alkyl)$_2$, or —OH, or is —H or a group —O$_x$—(CH$_2$CH$_2$O)$_y$—R$^{22}$, where x is 0 or 1, where v is a number from 1 to 20, and where $R^{22}$ represents —H, -alkyl (preferably $C_{1-12}$-alkyl), —CH$_2$—COOH, —CH$_2$—CH$_2$—COOH, or —CH$_2$—CH$_2$—NH$_2$;

A represents —C(=O)—, —S(=O)—, —S(=O)$_2$—, —S(=O)$_2$—NH— or —C(=N—NH$_2$)—;

$R^3$ represents -L-#1 or -L-BINDER, -MOD or an optionally substituted alkyl, cycloalkyl, aryl, heteroaryl, heteroalkyl, heterocycloalkyl group, preferably -L-BINDER, or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 —O-alkyl groups, 1-3 —SH groups, 1-3 —S-alkyl groups, 1-3 —O—C(=O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)$_n$-alkyl groups, 1-3 —S(=O)$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups, where n is 0, 1 or 2, where Z represents —H, halogen, —OY$^3$, —SY$^3$, —NHY$^3$, —C(=O)—NY$^1$Y$^2$ or —C(O)—OY$^3$, where $Y^1$ and $Y^2$ independently of one another represent —H, —NH$_2$ or —(CH$_2$)$_{0-3}$Z', where $Y^3$ represents —H, —(CH$_2$)$_{0-3}$—CH(NH—C(=O)—CH$_3$)Z', —(CH$_2$)$_{0-3}$—CH(NH$_2$)Z' or —(CH$_2$)$_{0-3}$Z', where Z' represents —H, —SO$_3$H, —NH$_2$ or —COOH where "alkyl" preferably represents $C_{1-10}$-alkyl);

$R^5$ represents —H, -MOD, —NH$_2$, —NO$_2$, halogen (in particular F, Cl, Br), —CN, —CF$_3$, —OCF$_3$, —CH$_2$F, —CH$_2$F, —SH or —(CH$_2$)$_{0-3}$Z, where Z represents —H, —OY$^3$, —SY$^3$, halogen, —NHY$^3$, —C(=O)—NY$^1$Y$^2$ or —C(=O)—OY$^3$, where $Y^1$ and $Y^2$ independently of one another represent —H, —NH$_2$ or —(CH$_2$)$_{0-3}$Z', where $Y^3$ represents —H or —(CH$_2$)$_{0-3}$Z', where Z' represents —H, —SO$_3$H, —NH$_2$ or —COOH;

$R^6$ and $R^7$ independently of one another represent —H, cyano, $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, hydroxy, —NO₂, —NH₂, —COOH or halogen (in particular —F, —Cl, —Br), R⁸ represents $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, $C_{4-10}$-cycloalkyl or fluoro-$C_{4-10}$-cycloalkyl, where one of the substituents R¹ and R³ represents -L-#1 or -L-BINDER, L represents the linker,

1 represents the bond to the binder or derivative thereof,

BINDER represents the binder,

R⁹ represents —H, —F, —CH₃, —CF₃, —CH₂F or —CHF₂;

-MOD represents —(NR¹⁰)ₙ-(G1)o-G2-G3,
 where R¹⁰ represents —H or $C_1$-$C_3$-alkyl;
 where G1 represents —NH—C(=O)—, —C(=O)—NH— or

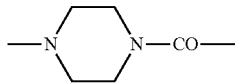

(where, if G1 represents —NH—C(=O)— or

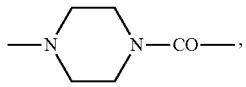

R¹⁰ does not represent —NH₂);
 where n is 0 or 1;
 where o is 0 or 1; and
 where G2 represents a linear and/or branched hydrocarbon group which has 1 to 10 carbon atoms and which may be interrupted once or more than once by one or more of the groups —O—, —S—, —S(=O)—, —S(=O)₂—, —NRʸ—, —NRʸC(=O)—, —C(=O)—NRʸ—, —NRʸNRʸ—, —S(=O)₂—NRʸNRʸ—, —C(=O)—NRʸNRʸ—,
 where Rʸ represents —H, phenyl, $C_1$-$C_{10}$-alkyl, $C_2$-$C_{10}$-alkenyl or $C_2$-$C_{10}$-alkynyl, each of which may be substituted by —NH—C(=O)—NH₂, —COOH, —OH, —NH₂, NH—CN—NH₂, sulphonamide, sulphone, sulphoxide or sulphonic acid, or represents —C(=O)—, —CRˣ=N—O—
 where Rˣ represents —H, $C_1$-$C_3$-alkyl or phenyl,
 where the hydrocarbon chain including any side chains may be substituted by —NH—C(=O)—NH₂, —COOH, —OH, —NH₂, —NH—CN—NH₂, sulphonamide, sulphone, sulphoxide or sulphonic acid,
 where G3 represents —H or —COOH, and
 where -MOD preferably has at least one group —COOH;

and the salts, solvates, salts of the solvates, and epimers thereof.

Preference is furthermore given to compounds of the formula (IIa), (II), (III), (IIIa), (IIIb), (IIIc), (IIId), (IIIe) or (IV) in which $X_1$ represents N, $X_2$ represents N and $X_3$ represents C; or
$X_1$ represents N, $X_2$ represents C and $X_3$ represents N; or
$X_1$ represents CH or CF, $X_2$ represents C and $X_3$ represents N; or
$X_1$ represents NH, $X_2$ represents C and $X_3$ represents C; or
$X_1$ represents CH or CF, $X_2$ represents N and $X_3$ represents C;

(with $X_1$ representing CH, $X_2$ representing C and $X_3$ representing N being preferred);

R¹ represents —H, -L-#1 or -L-BINDER, -MOD or —(CH₂)₀₋₃Z,
 where Z represents —H, —NHY³, —OY³, —SY³, halogen, —C(=O)—NY¹Y² or —C(=O)—OY³,
 where Y¹ and Y² independently of one another represent —H, —NH₂, —(CH₂CH₂O)₀₋₃—(CH₂)₀₋₃Z' (e.g. —(CH₂)₀₋₃Z') or —CH(CH₂W)Z', and
 where Y³ represents H or —(CH₂)₀₋₃Z',
 where Z' represents —H, —NH₂, —SO₃H, —COOH, —NH—C(=O)—CH₂—CH₂—CH(NH₂)COOH or —(C(=O)—NH—CHY⁴)₁₋₃COOH,
 where W represents —H or —OH,
 where Y⁴ represents linear or branched $C_{1-6}$-alkyl which is optionally substituted by —NH—(C=O)—NH₂, or represents aryl or benzyl which are optionally substituted by —NH₂;

R² represents —H, —C(=O)—CHY⁴—NHY⁵ or —(CH₂)₀₋₃Z,
 where Z represents —H, halogen, —OY³, —SY³, —NHY³, —C(=O)—NY¹Y² or —C(=O)—OY³,
 where Y¹ and Y² independently of one another represent —H, —NH₂ or —(CH₂)₀₋₃Z',
 where Y³ represents —H or —(CH₂)₀₋₃Z',
 where Z' represents —H, —SO₃H, —NH₂ or —COOH;
 where Y⁴ represents linear or branched $C_{1-6}$-alkyl which is optionally substituted by —NH—C(=O)—NH₂, or represents aryl or benzyl which are optionally substituted by —NH₂,
 where Y⁵ represents —H or —C(=O)—CHY⁶—NH₂,
 where Y⁶ represents linear or branched $C_{1-6}$-alkyl;

R⁴ represents —H or R²¹-L-Ala-L-Ala-L-Asn-;
 where R²¹ represents —H, $C_{1-10}$-alkyl-, $C_{5-10}$-aryl- or $C_{6-10}$-aralkyl-, $C_{5-10}$-heteroalkyl-, $C_{1-10}$-alkyl-O—$C_{6-10}$-aryl-, $C_{5-10}$-heterocycloalkyl-, heteroaryl-, heteroaryl-alkyl-, $C_{1-10}$-alkoxy-, $C_{6-10}$-aryloxy-oder $C_{6-10}$-aralkoxy-, $C_{5-10}$-heteroalkoxy-, $C_{1-10}$-alkyl-O—$C_{6-10}$-aryloxy-, $C_{5-10}$-heterocyclalkoxy group, which may be substituted one or more times with —NH₂, —NH-alkyl, —N(alkyl)₂, —NH—C(=O)-alkyl, —N(alkyl)-C(=O)-alkyl, —SO₃H, —SO₂NH₂, —S(=O)₂—N(alkyl)₂, —COOH, —C(=O)—NH₂, —C(=O)—N(alkyl)₂, or —OH, or is —H or a group —Oₓ—(CH₂CH₂O)ᵥ—R²²,
 where x is 0 or 1,
 where v is a number from 1 to 20, and
 where R²² represents —H, -alkyl (preferably $C_{1-12}$-alkyl), —CH₂—COOH, —CH₂—CH₂—COOH, or —CH₂—CH₂—NH₂;

A represents —C(=O)—, —S(=O)—, —S(=O)₂—, —S(=O)₂—NH— or —C(=N—NH₂)—;

R³ represents -L-#1 or -L-BINDER, -MOD or an optionally substituted alkyl, cycloalkyl, aryl, heteroaryl, heteroalkyl, heterocycloalkyl group, preferably $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 —O-alkyl groups, 1-3 —SH groups, 1-3 —S-alkyl groups, 1-3 —O—C(=O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)ₙ-alkyl groups, 1-3 —S(=O)₂—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups, where n is 0, 1 or 2, where Z represents —H, halogen, —OY$^3$, —SY$^3$, —NHY$^3$, —C(═O)—NY$^1$Y$^2$ or —C(O)—OY$^3$, where Y$^1$ and Y$^2$ independently of one another represent —H, —NH$_2$ or —(CH$_2$)$_{0-3}$Z', where Y$^3$ represents —H, —(CH$_2$)$_{0-3}$—CH(NH—C(═O)—CH$_3$)Z', —(CH$_2$)$_{0-3}$—CH(NH$_2$)Z' or —(CH$_2$)$_{0-3}$Z', where Z' represents —H, —SO$_3$H, —NH$_2$ or —COOH where "alkyl" preferably represents C$_{1-10}$-alkyl);

R$^5$ represents -MOD, —H, —NH$_2$, —NO$_2$, halogen (in particular F, Cl, Br), —CN, —CF$_3$, —OCF$_3$, —CH$_2$F, —CH$_2$F, —SH or —(CH$_2$)$_{0-3}$Z, where Z represents —H, —OY$^3$, —SY$^3$, halogen, —NHY$^3$, —C(═O)—NY$^1$Y$^2$ or —C(═O)—OY$^3$, where Y$^1$ and Y$^2$ independently of one another represent —H, —NH$_2$ or —(CH$_2$)$_{0-3}$Z', where Y$^3$ represents —H or —(CH$_2$)$_{0-3}$Z', where Z' represents —H, —SO$_3$H, —NH$_2$ or —COOH;

R$^6$ and R$^7$ independently of one another represent —H or halogen (in particular —F, —Cl, —Br), R$^8$ represents C$_{1-10}$-alkyl or fluoro-C$_{1-10}$-alkyl, where one of the substituents R$^1$ and R$^3$ represents -L-#1 or -L-BINDER, L represents the linker,

1 represents the bond to the binder or derivative thereof,

BINDER represents the binder,

R$^9$ represents —H, —F, —CH$_3$, —CF$_3$, —CH$_2$F or —CHF$_2$;

-MOD represents —CH$_2$—S$_x$—(CH$_2$)$_{0-4}$—CHY$^5$—COOH, where x is 0 or 1, where Y$^5$ represents H or NHY$^6$, where Y$^6$ represents H or —C(═O)—CH$_3$, and the salts, solvates, salts of the solvates, and epimers thereof.

Particular preference according to the invention is given to the conjugate of the following compounds of the formulae V, VI and VII, where R$^1$, R$^2$, R$^3$, R$^4$ and R$^5$ have the meanings mentioned above (as mentioned, for example for formula (IIa) or (IIIa)):

Formula V

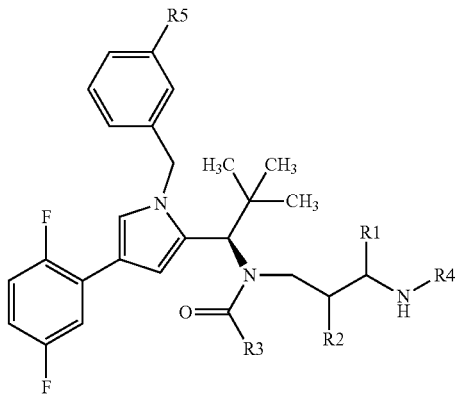

Formula VI

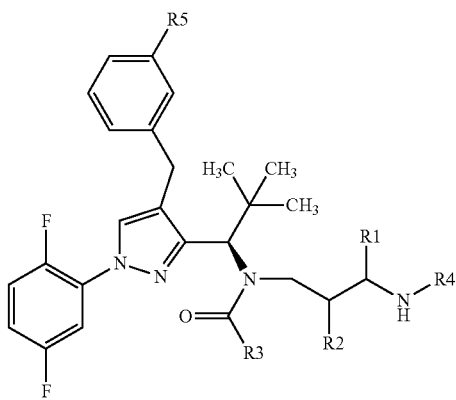

Formula VII

Particular preference is given to the compounds of the formulae V, VI, VII where R$^1$ and R$^5$ represent —H or -L-#1; R$^2$ and R$^4$ independently of one another represent -L-#1 or —H or R$^2$ and R$^4$ together (with formation of a pyrrolidine ring) represent —CH—CHR$^{10}$— or —CHR$^{10}$—CH$_2$—, R$^{10}$ represents —H or -L-#; and R$^3$ represents —CH$_2$OH, —CH(CH$_3$)OH or -L-#1, where one of the substituents R$^1$, R$^2$, R$^3$, R$^4$, R$^5$ and R$^{10}$ represents -L-#1. Especially preferred are the corresponding compounds of the formula VI.

Preferred antibody drug conjugates of the present invention (ADCs) are those of the following Formula VIII:

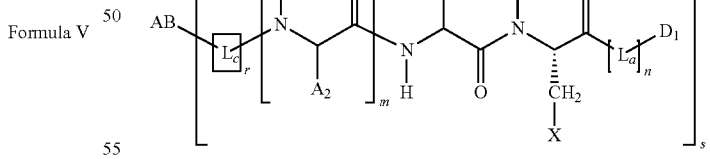

wherein m is a number from 0 to 2st;

n is 0 or 1;

X represents —C(═O)—NH$_2$ or —COOH;

L$_a$ represents a self-immolative linker;

L$_c$ represents a linker.

A$_1$ is a residue derived from one of the amino acids Gly, Pro, Ala, Val, Nva, Leu, Ile, Met, Phe, Tyr, Trp, Ser, Thr, Cys, Asn, Gln, Asp, Glu, Lys, Arg, Citrulline and His;

A$_2$ is a residue derived from one of the amino acids Gly, Pro, Ala, Val, Nva, Leu, Ile, Met, Phe, Tyr, Trp, Ser, Thr, Cys, Asn, Gln, Asp, Glu, Lys, Arg, Citrulline and His or one of the corresponding N-alkyl-amino acids, preferably N-methyl-amino acid (when there is more than one P3, P3 can have different meanings)

D1 is KSP according to Formula II or IIa (ie. without linker L);

R represents $Z_1$—(C=O)q-,
  wherein q is 0 or 1 and
$Z_1$ represents a $C_{1-10}$-alkyl-, $C_{5-10}$-Aryl- or $C_{6-10}$-aralkyl-, $C_{5-10}$-heteroalkyl-, $C_{1-10}$-alkyl-O—$C_{6-10}$-aryl-, $C_{5-10}$-heterocycloalkyl-, heteroaryl-, heteroaryl-alkyl-, $C_{5-10}$-heteroaryl-alkoxy-, $C_{1-10}$-alkoxy-, $C_{6-10}$-aryloxy- or $C_{6-10}$-aralkoxy-, $C_{5-10}$-heteroalkoxy-, $C_{1-10}$-alkyl-O—$C_{6-10}$-aryloxy-, $C_{5-10}$-heterocycloalkoxy group, which may be substituted one or more times with —$NH_2$, —NH-alkyl, —N(alkyl)$_2$, —NH—C(=O)-alkyl, —N(alkyl)-C(=O)-alkyl, —$SO_3H$, —S(=O)$_2$—$NH_2$, —S(=O)$_2$—N(alkyl)$_2$, —COOH, —C(=O)—$NH_2$, —C(=O)—N(alkyl)$_2$, —OH, —H
or a group —$O_x$—(CH$_2$CH$_2$O)$_y$—$R^1$,
  wherein x is 0 or 1,
  wherein v is a number from 1 to 20,
  wherein $R^1$ represents —H, -alkyl (preferably $C_{1-12}$-alkyl), —$CH_2$—COOH, —$CH_2$—$CH_2$—COOH, or —$CH_2$—$CH_2$—$NH_2$,
AB represents an antibody,
s is a number from 1 to 20, preferably 2 to 8, particularly preferred 2 to 4 as e.g. 4.

Preferred antibody prodrug conjugates of the present invention (APDCs) are those of the following Formula IX:

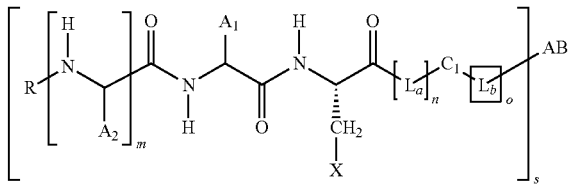

wherein
m is 0, 1 or 2;
n is 0 or 1;
X represents —C(=O)—$NH_2$ or —COOH;
$L_a$ represents a self-immolative linker;
$L_b$ represents a linker.
$A_1$ is a residue derived from one of the amino acids Gly, Pro, Ala, Val, Nva, Leu, Ile, Met, Phe, Tyr, Trp, Ser, Thr, Cys, Asn, Gln, Asp, Glu, Lys, Arg, Citrulline and His;
$A_2$ is a residue derived from one of the amino acids Gly, Pro, Ala, Val, Nva, Leu, Ile, Met, Phe, Tyr, Trp, Ser, Thr, Cys, Asn, Gln, Asp, Glu, Lys, Arg, Citrulline and His or one of the corresponding N-alkyl-amino acids, preferably N-methyl-amino acid (when there is more than one P3, P3 can have different meanings)

$D_1$ is KSP according to Formula II or IIa (ie. without linker L);

R represents $Z_1$—(C=O)q-,
  wherein q is 0 or 1 and
$Z_1$ represents a $C_{1-10}$-alkyl-, $C_{5-10}$-Aryl- or $C_{6-10}$-aralkyl-, $C_{5-10}$-heteroalkyl-, $C_{1-10}$-alkyl-O—$C_{6-10}$-aryl-, $C_{5-10}$-heterocycloalkyl-, heteroaryl-, heteroaryl-alkyl-, $C_{5-10}$-heteroaryl-alkoxy-, $C_{1-10}$-alkoxy-, $C_{6-10}$-aryloxy- or $C_{6-10}$-aralkoxy-, $C_{5-10}$-heteroalkoxy-, $C_{1-10}$-alkyl-O—$C_{6-10}$-aryloxy-, $C_{5-10}$-heterocycloalkoxy group, which may be substituted one or more times with —$NH_2$, —NH-alkyl, —N(alkyl)$_2$, —NH—C(=O)-alkyl, —N(alkyl)-C(=O)-alkyl, —$SO_3H$, —S(=O)$_2$—$NH_2$, —S(=O)$_2$—N(alkyl)$_2$, —COOH, —C(=O)—$NH_2$, —C(=O)—N(alkyl)$_2$, —OH, —H
or a group —$O_x$—(CH$_2$CH$_2$O)$_y$—$R^1$,
  wherein x is 0 or 1,
  wherein v is a number from 1 to 20,
  wherein $R^1$ represents —H, -alkyl (preferably $C_{1-12}$-alkyl), —$CH_2$—COOH, —$CH_2$—$CH_2$—COOH, or —$CH_2$—$CH_2$—$NH_2$,
AB represents an antibody,
s is a number from 1 to 20, preferably 2 to 8, particularly preferred 2 to 4 as e.g. 4.

Linkers

The literature discloses various options for covalently coupling (conjugating) organic molecules to binders in a site specific homogenous manner such as, for example antibodies (see, for example, (Sochaj et al., *Biotechnology Advances*, Article in press (2015), Panowski et al., *MAbs* 6, 34-45 (2014)) Preference according to the invention is given to conjugation of the KSP inhibitors to an antibody via acceptor glutamine residues of the antibody using transglutaminase. Such acceptor glutamines can be introduced by engineering of the antibody by mutations or by generation of aglycosylated antibodies. The number of the said acceptor glutamine residue in the antibody is preferably 2 or 4. For coupling, use is made of linkers. Linkers can be categorized into the group of the linkers which can be cleaved in vivo and the group of the linkers which are stable in vivo (see L. Ducry and B. Stump, *Bioconjugate Chem.* 21, 5-13 (2010)). The linkers which can be cleaved in vivo have a group which can be cleaved in vivo, where, in turn, a distinction may be made between groups which are chemically cleavable in vivo and groups which are enzymatically cleavable in vivo. "Chemically cleavable in vivo" and "enzymatically cleavable in vivo" means that the linkers or groups are stable in circulation and are cleaved only at or in the target cell by the chemically or enzymatically different environment therein (lower pH; elevated glutathione concentration; presence of lysosomal enzymes such as legumain, cathepsin or plasmin, or glycosidases such as, for example, β-glucuronidases), thus releasing the low-molecular weight KSP inhibitor or a derivative thereof. Groups which can be cleaved chemically in vivo are in particular disulphide, hydrazone, acetal and aminal; groups which can be cleaved enzymatically in vivo are in particular the 2-8-oligopeptide group, especially a dipeptide group or glycoside. Peptide cleavage sites are disclosed in *Bioconjugate Chem.* 2002, 13, 855-869, and *Bioorganic &Medicinal Chemistry Letters* 8 (1998) 3341-3346 and also *Bioconjugate Chem.* 1998, 9, 618-626. These include, for example, valine-alanine, valine-lysine, valine-citrulline, alanine-lysine and phenylalanine-lysine (optionally with additional amide group).

Linkers which are stable in vivo are distinguished by a high stability (less than 5% metabolites after 24 hours in plasma) and do not have the chemically or enzymatically in vivo cleavable groups mentioned above.

The linker -L- preferably has one of the basic structures (i) to (iv) below:
(i) —(C=O)$_m$-SG1-L1-L2-
(ii) —(C=O)$_m$-L1-SG-L1-L2-
(iii) —(C=O)$_m$-L1-L2-
(iv) —(C=O)$_m$-L1-SG-L2 where m is 0 or 1; SG is a (chemically or enzymatically) in vivo cleavable group (in particular disulphide, hydrazone, acetal and aminal; or a 2-8-oligopeptide group which can be cleaved by cathepsin or plasmin), SG1 is an oligopeptide group or preferably a dipeptide group, L1 independently of one another represent in vivo stable organic groups, and L2 represents a coupling group to the binder. Particular preference according to the invention is given to the basic linker structure (iii), in particular when the binder is an antibody. Via metabolization, the administration of a conjugate according to the invention having a basic linker structure (iii) and coupling of the linker to a glutamine residue of the binder protein or peptide using transglutaminase leads to glutamine derivatives of the formulae below:

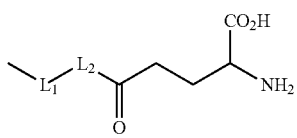

where L1 is in each case attached to the low-molecular weight KSP inhibitor, for example a compound of the formula (I), (IIa), (II), (III), (IIIa), (IIIb), (IIIc), (IIId), (IIIe) or any of (IV) to (IX).

According to the invention, L1 is preferably represented by the formula

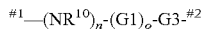

where
$R^{10}$ represents —H, —$NH_2$ or $C_1$-$C_3$-alkyl;
G1 represents —NH—C(=O)—, —C—(=O)—NH— or

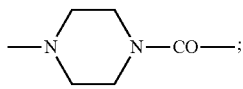

($R^{10}$ is preferably not —$NH_2$, if G1 represents —NH—C(=O)— or

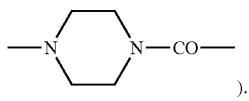

).

n is 0 or 1;
o is 0 or 1; and
G3 represents a bond or an optionally substituted linear or branched hydrocarbon chain which has 1 to 100 carbon atoms from arylene groups and/or linear and/or branched and/or cyclic alkylene groups and which may be interrupted once or more than once by one or more of the groups —O—, —S—, —S(=O)—, —S(=O)$_2$—, —$NR^y$—, —$NR^y$—C(=O)—, —C(NH)$NR^y$—, —C(=O)—$NR^y$—, —$NR^yNR^y$—, —S(=O)$_2$—$NR^yNR^y$—, —C(=O)—$NR^yNR^y$— (where $R^y$ represents —H, phenyl, $C_1$-$C_{10}$-alkyl, $C_2$-$C_{10}$-alkenyl or $C_2$-$C_{10}$-alkynyl, each of which may be substituted by —NH—C(=O)—$NH_2$, —COOH, —OH, —$NH_2$, —NH—$CNNH_2$, sulphonamide, sulphone, sulphoxide or sulphonic acid), —C(=O)—, —$CR^x$=N—O— (where $R^x$ represents —H, $C_1$-$C_3$-alkyl or phenyl) and/or a 3- to 10-membered aromatic or non-aromatic heterocycle having up to 4 heteroatoms selected from the group consisting of N, O and S, —S(=O)— or —S(=O)$_2$— (preferably

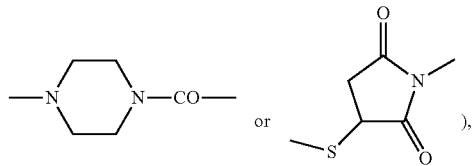

where the hydrocarbon chain including any side chains may be substituted by —NH—C(=O)—$NH_2$, —COOH, —OH, —$NH_2$, —NH—$CNNH_2$, sulphonamide, sulphone, sulphoxide or sulphonic acid.

G3 represents a bond or an optionally substituted linear or branched hydrocarbon chain having 1 to 100 carbon atoms from arylene groups and/or linear and/or branched and/or cyclic alkylene groups and which may be interrupted once or more than once by one or more of the groups —O—, —S—, —S(=O)—, —S(=O)$_2$—, —NH—, —C(=O)—, —NH—C(=O)—, —C(=O)—NH—, —NMe-, —NHNH—, —S(=O)$_2$—NHNH—, —C(=O)—NHNH— and a 5- to 10-membered aromatic or non-aromatic heterocycle having up to 4 heteroatoms selected from the group consisting of N, O and S, or —S(=O)— (preferably

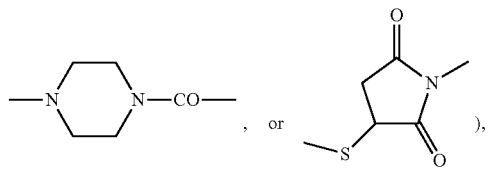

where the side chains, if present, may be substituted by —NH—C(=O)—$NH_2$, —COOH, —OH, —$NH_2$, —NH—$CNNH_2$, sulphonamide, sulphone, sulphoxide or sulphonic acid.

G3 represents a bond or an optionally substituted a linear or branched hydrocarbon chain having 1 to 100 carbon atoms from arylene groups and/or linear and/or branched and/or cyclic alkylene groups and which may be interrupted once or more than once by one or more of the groups —O—, —S—, —S(=O)—, —S(=O)$_2$—, —NH—, —C(=O)—, —NH—C(=O)—, —C(=O)—NH—, —NMe-, —NHNH—, —S(=O)$_2$—NHNH—, —C(=O)—NHNH—, —$CR^x$=N—O— (where $R^x$ represents H, $C_1$-$C_3$-alkyl or phenyl) and a 3- to 10-membered, for example 5- to 10-membered, aromatic or non-aromatic heterocycle having up to 4 heteroatoms selected from the group consisting of N, O and S, —S(=O)— or —S(=O)$_2$— (preferably

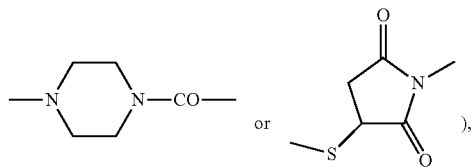

where the hydrocarbon chain including the side chains, if present, may be substituted by —NH—C(=O)—$NH_2$, —COOH, —OH, —$NH_2$, —NH—CN—$NH_2$, sulphonamide, sulphone, sulphoxide or sulphonic acid.

Further interrupting groups in G3 are preferably

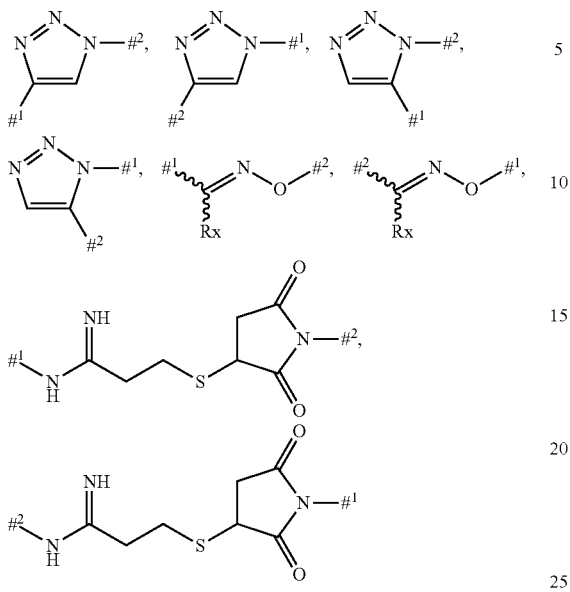

where Rx represents H, C$_1$-C$_3$-alkyl or phenyl.

Here, #1 is the bond to the KSP inhibitor and #² is the bond to the coupling group to the binder (e.g. L2).

A linearlinear or branched hydrocarbon chain of arylen groups and/or linearlinear and/or branched and/or cyclic alkylene groups generally comprises a α,ω-divalent alkyl radical having the respective number of carbon atoms stated. Examples which may be mentioned as being preferred are: methylene, ethane-1,2-diyl (1,2-ethylene), propane-1,3-diyl (1,3-propylene), butane-1,4-diyl (1,4-butylene), pentane-1, 5-diyl (1,5-pentylene), hexane-1,6-diyl (1,6-hexylene), heptane-1,7-diyl (1,7-hexylene), octane-1,8-diyl (1,8-octylene), nonane-1,9-diyl (1,9-nonylene), decane-1,10-diyl (1,10-decylene). However, the alkylene groups in the hydrocarbon chain may also be branched, i.e. one or more hydrogen atoms of the linear alkylene groups mentioned above may optionally be substituted by C$_{1-10}$-alkyl groups, thus forming side chains. The hydrocarbon chain may furthermore contain cyclic alkylene groups (cycloalkanediyl), for example 1,4-cyclohexanediyl or 1,3-cyclopentanediyl. These cyclic groups may be unsaturated. In particular, aromatic groups (arylene groups), for example phenylene, may be present in the hydrocarbon group. In turn, in the cyclic alkylene groups and the arylene groups, too, one or more hydrogen atoms may optionally be substituted by C$_{1-10}$-alkyl groups. In this way, an optionally branched hydrocarbon chain is formed. This hydrocarbon chain has a total of 0 to 100 carbon atoms, preferably 1 to 50, particularly preferably 2 to 25 carbon atoms.

The side chains, if present, may be substituted by —NH—C(=O)—NH$_2$, —COOH, —OH, —NH$_2$, —NH—CN—NH$_2$, sulphonamide, sulphone, sulphoxide or sulphonic acid.

The hydrocarbon chain may be interrupted once or more than once by one or more of the groups —O—, —S—, —S(=O)—, —S(=O)$_2$—, —NH—, —C(=O)—, —NH—C(=O)—, —C(=O)—NH—, —NMe-, —NHNH—, —S(O)$_2$—NHNH—, —C(=O)—NHNH— and a 5- to 10-membered aromatic or non-aromatic heterocycle having up to 4 heteroatoms selected from the group consisting of N, O and S, —S(=O)— or —S(O)$_2$— (preferably

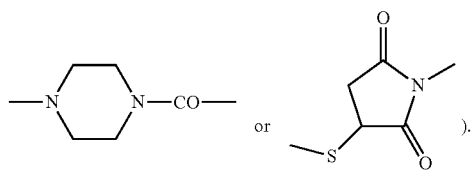

Further interrupting groups in G3 are preferably

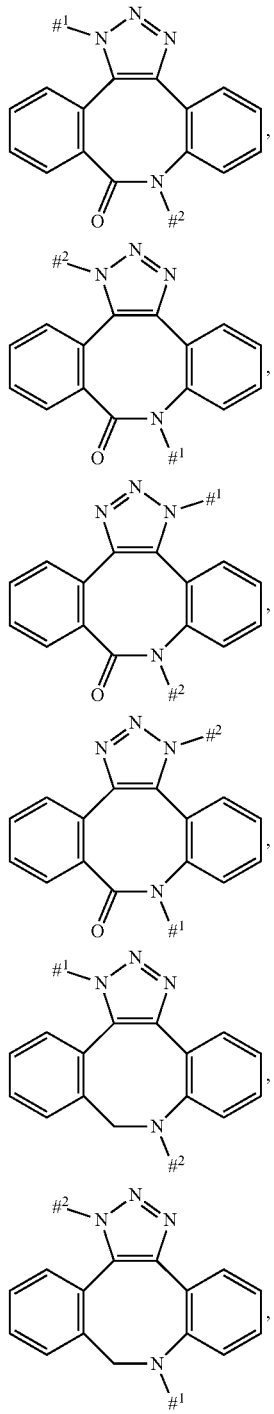

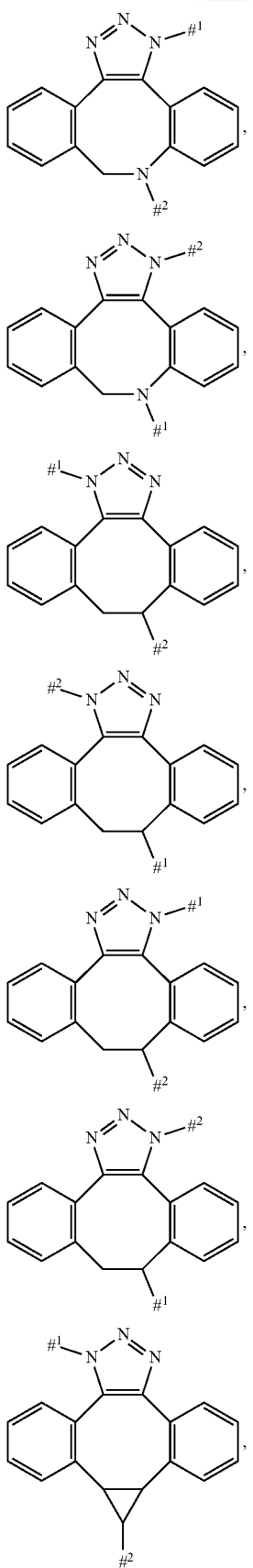

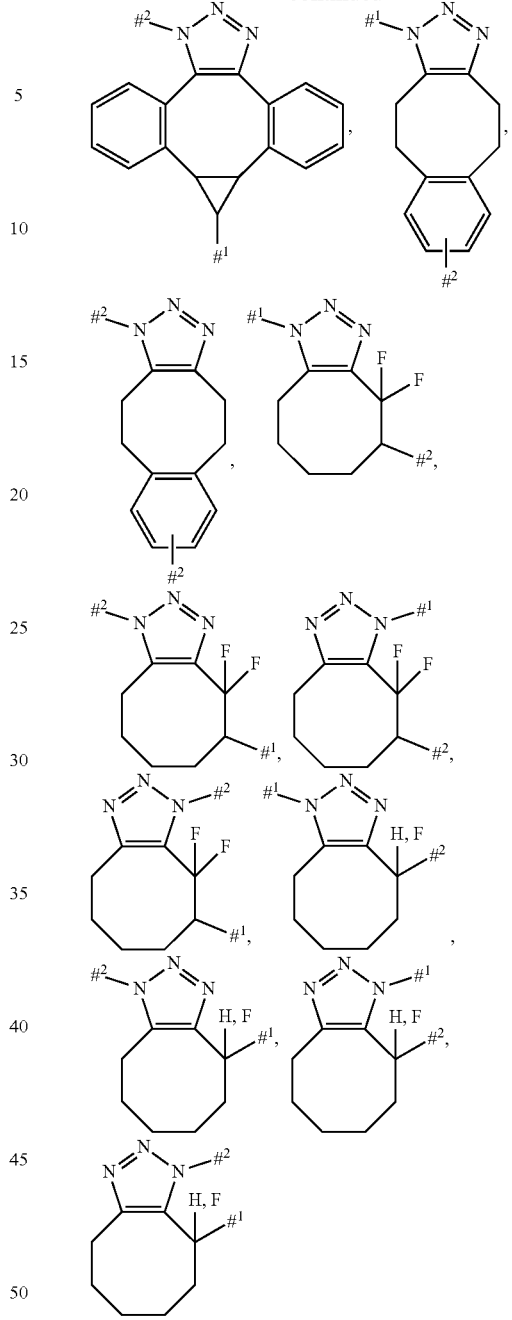

According to the invention, L2 is preferably represented by the formulae:

$\#^1$—(NH)$_p$—(C=O)$_q$-G4-NH-$\#^2$ or $\#^1$—(NH)$_p$—(C=O)$_q$-G4-O—NH-$\#^2$ where p is 0 or 1;
q is 0 or 1; and
G4 represents an optionally substituted alkyl or heteroalkyl chain optionally wherein any carbon of the chain is substituted with an alkoxy, hydroxyl, alkylcarbonyloxy, —S-alkyl, thiol, —C(=O)—S-alkyl, —C(=O)—NH-alkyl, —NH—C(=O)-alkyl, amine, —C(=O)—NH$_2$ where
- #¹ denotes the point of attachment to group L¹,
- #² denotes the point of attachment to the glutamine residue of the binder, Preferably, L2 is one of the groups below:

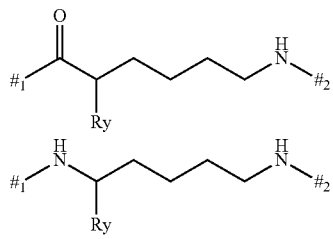

with Ry is —H, —C(=O)—NH-alkyl, —NH—C(=O)-alkyl, —C(=O)—NH₂, —NH₂,
where
- #¹ denotes the point of attachment to group L¹,
- #² denotes the point of attachment to the glutamine residue of the binder.

Preferably Ry is —H or —NH—C(=O)-Me.
Preferably, the linker corresponds to the formula below:

§-(C=O)m-L1-L2-§§ where
m is 0 or 1;
§ represents the bond to the active compound molecule and
§§ represents the bond to the binder peptide or protein, and
L1 and L2 have the meaning given above.

The linkers mentioned above are especially preferred in conjugates of the formula (I) or (II) in which the linker couples by substitution of a hydrogen atom at R¹ or R³ or in combination with a cleavable linker SG1 at R⁴, i.e. R¹ represents -L-#1 or R³ represents -L-#1 or R⁴ represents -SG1-L-#1, where #1 represents the bond to the binder.

Preferred groups L1 in the formula §-(C=O)m-L1-L2-§§ above are those below, where r in each case independently of one another represents a number from 0 to 20, preferably from 0 to 15, particularly preferably from 1 to 20, especially preferably from 2 to 10:

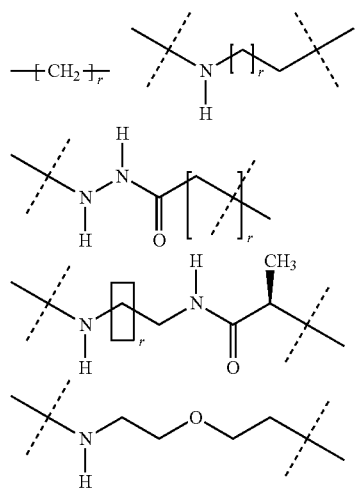

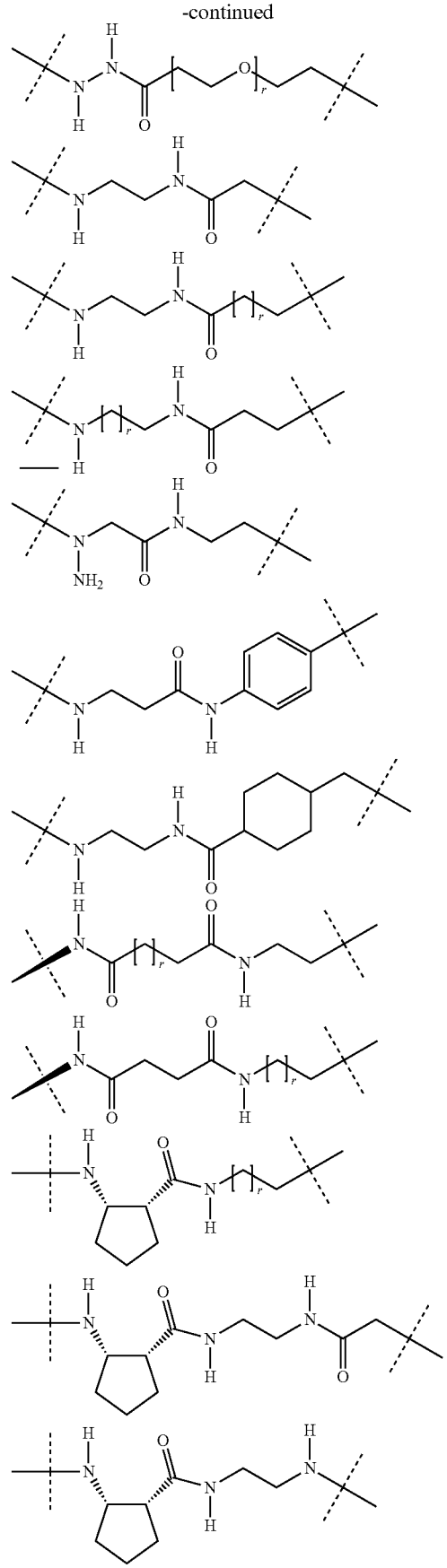

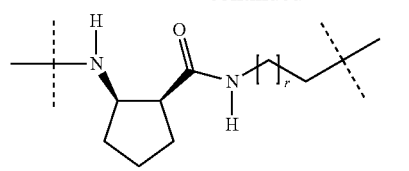
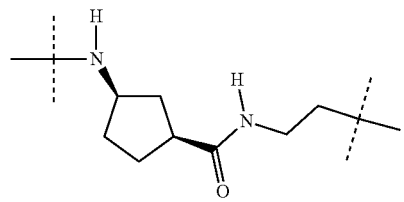
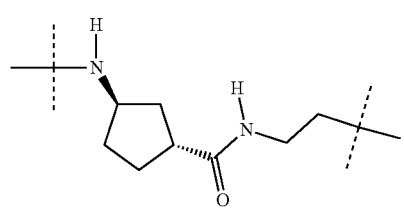
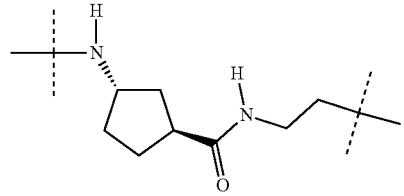
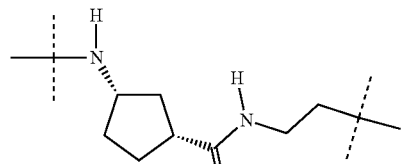
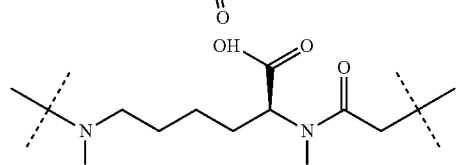
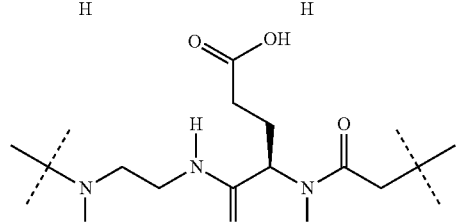
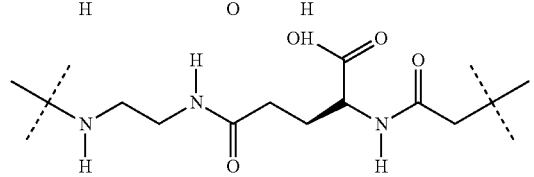
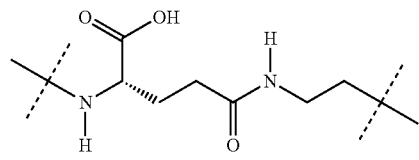
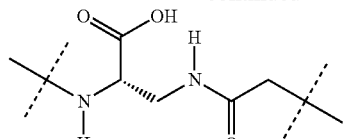
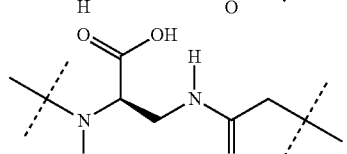
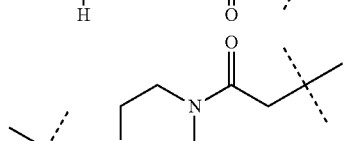
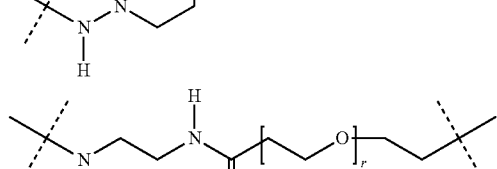
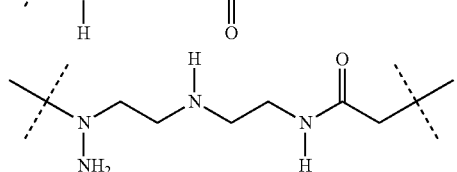
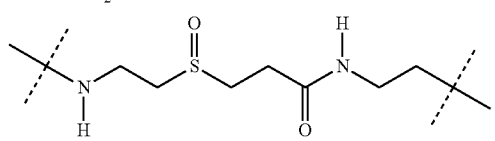
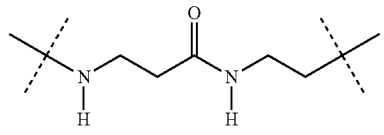
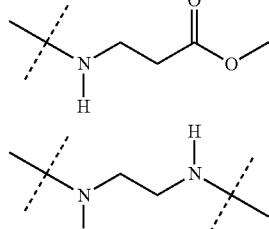
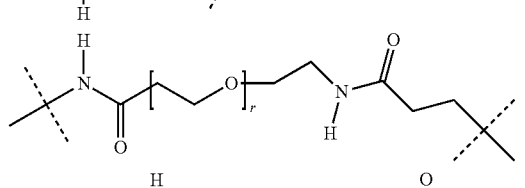
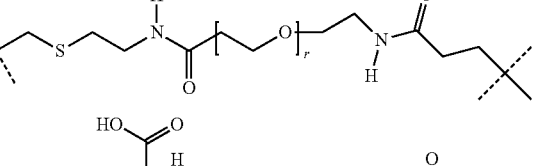

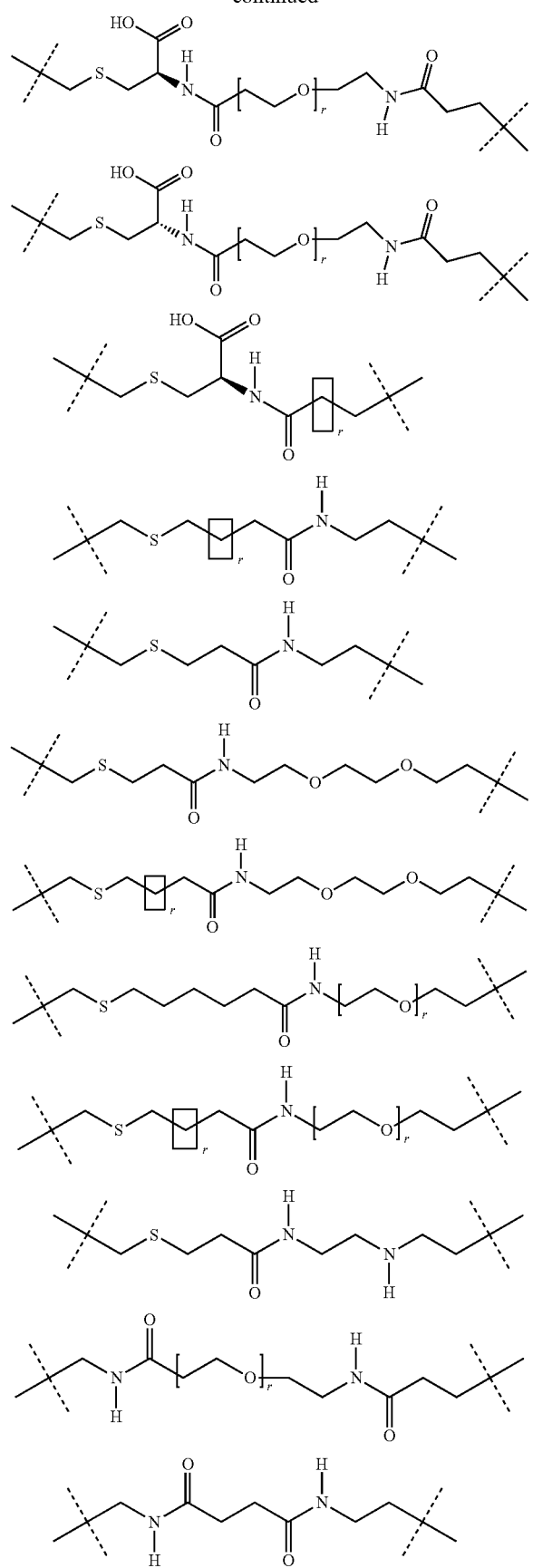
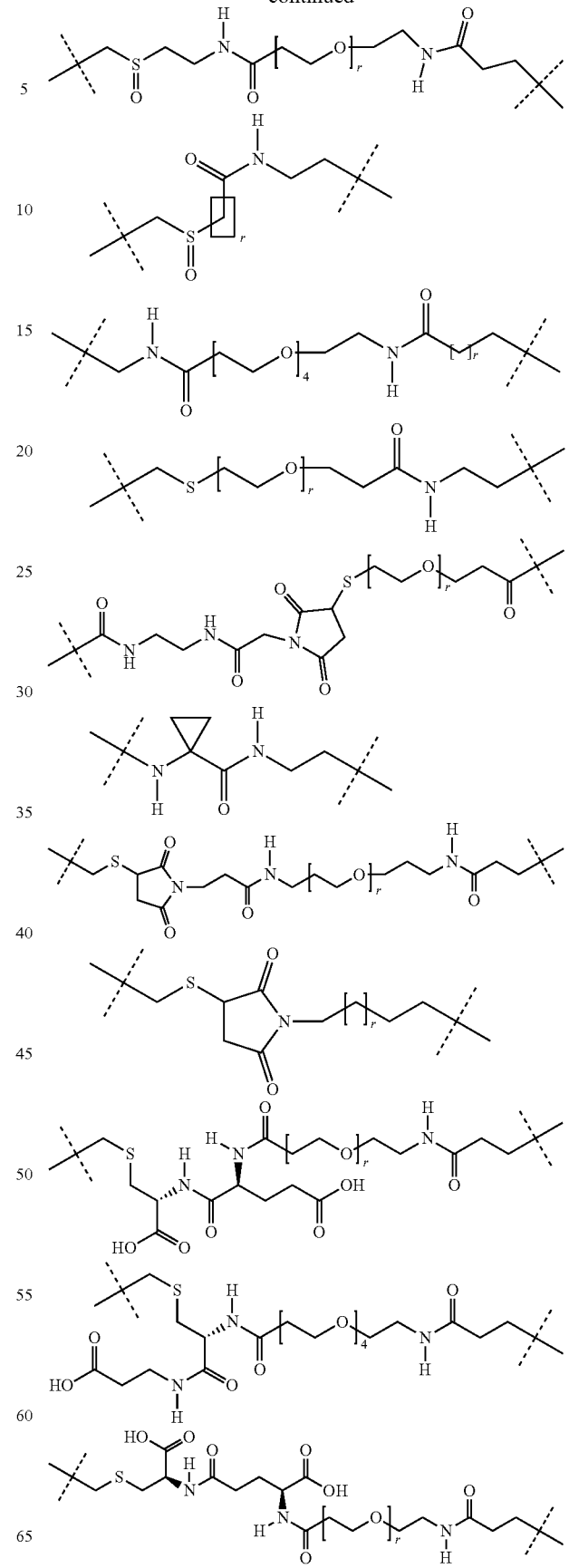

69
-continued
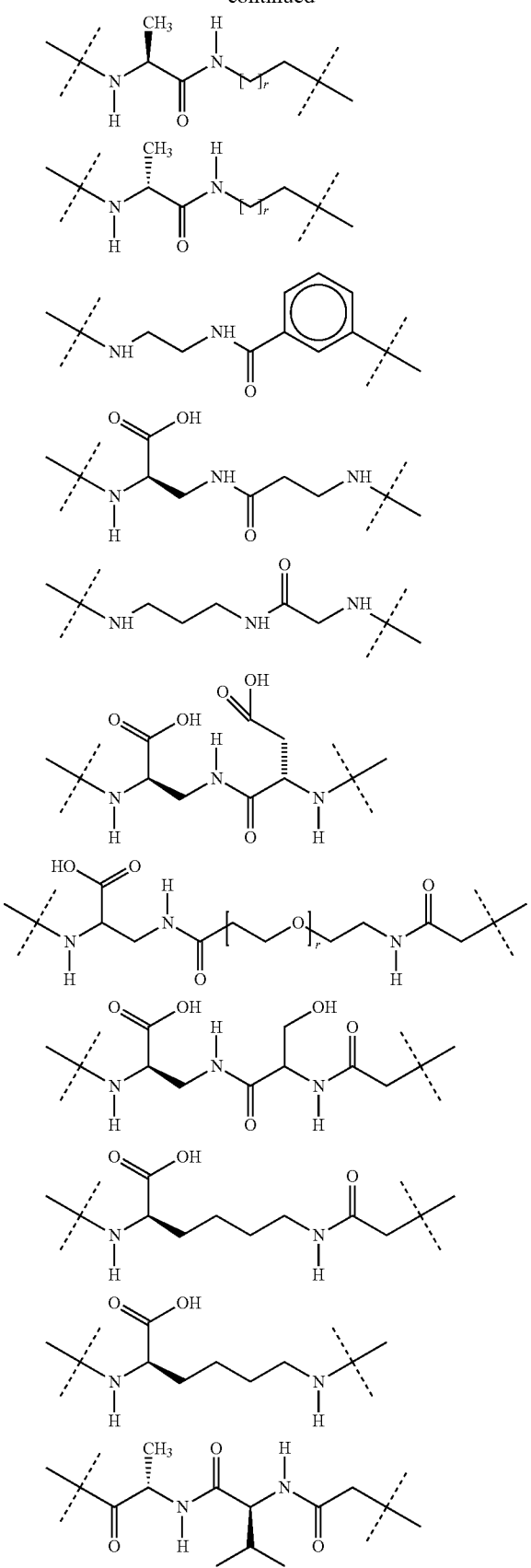
70
-continued
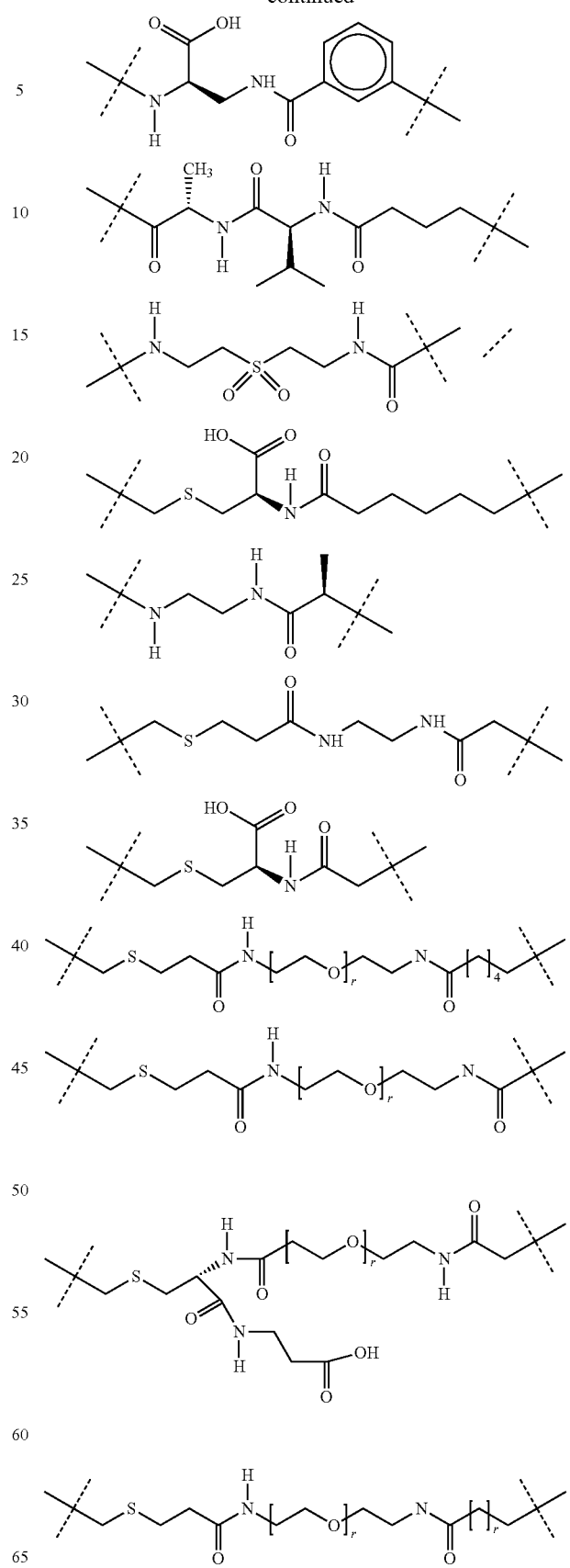

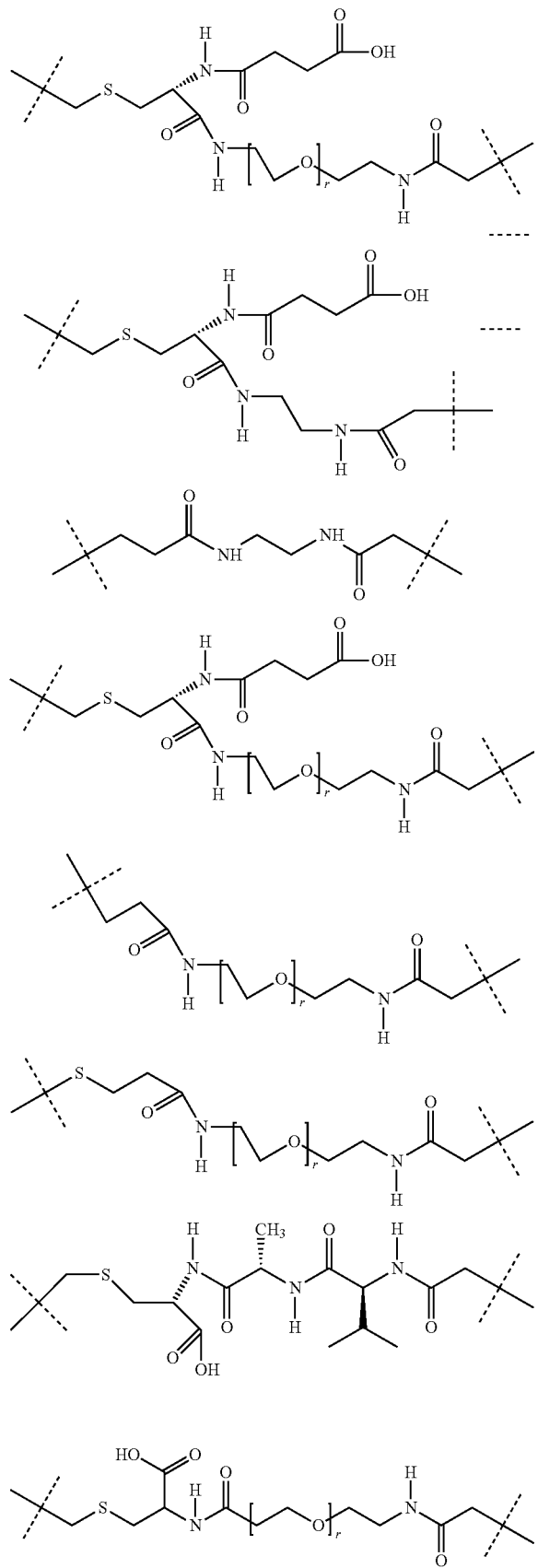
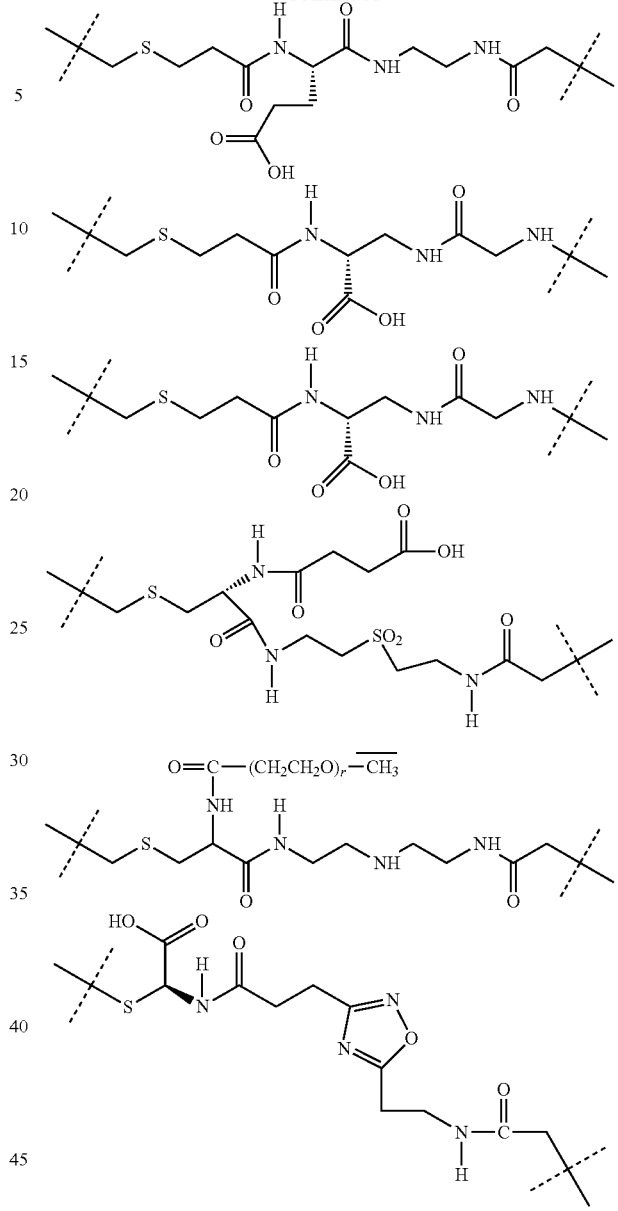

Examples of conjugates having corresponding linkers have the following structures, where X1, X2, X3, Ry and L1 have the meanings given above, AK represents the binder, preferably an antibody conjugated to a glutamine side chain and n is 2 to 10, preferably 2 to 4 and also preferred 2 or 4. With particular preference, AK is a human, humanized or chimeric monoclonal antibody or an antigen-binding fragment thereof, in particular an anti-TWEAKR antibody or an antigen-binding fragment thereof or an anti-EGFR antibody or an antigen-binding fragment thereof. If the binder is an antibody it comprises an acceptor glutamine, preferentially in the constant region. Such acceptor glutamines can be introduced by mutations of suitable positions into glutamine (e.g. mutation N297Q, Kabat EU numbering) or by generation of deglycosylated or aglycosylated antibodies (e.g. by enzymatic deglycosylation by PNGase F or by mutation of N297X, Kabat EU numbering). In that later case of a deglycosylated or an aglycosylated antibody the glutamine Q295 (Kabat EU numbering) becomes an acceptor glutamine. Highly preferred is an antibody comprising a mutation N297A or N297Q (Kabat EU numbering). Particular preference is given to an anti-TWEAKR antibody which binds specifically to amino acid D in position 47 (D47) of TWEAKR (SEQ ID NO: 169), in particular the anti-TWEAKR antibody TPP-2090, or the anti-Her2 antibody. All the antibodies described include aglycosylated variants of these antibodies generated either by deglycosylation by PNGase F or by mutation of N297 (Kabat numbering) of the heavy chain to any amino acid.

SG1 or SG is particularly preferably

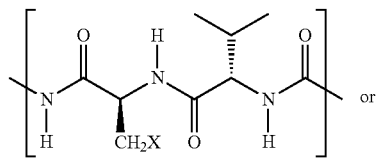

or

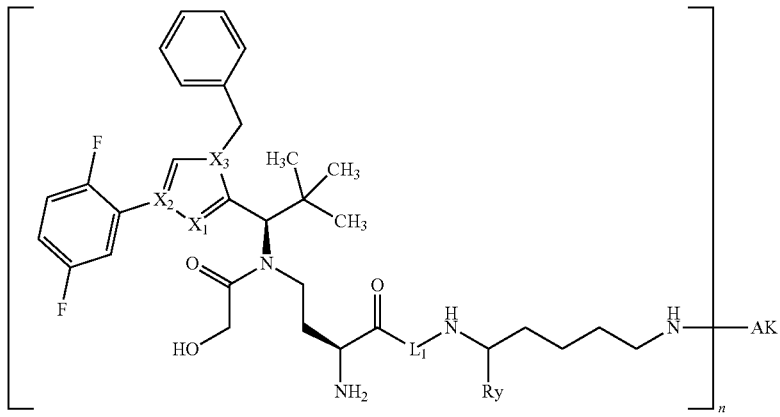

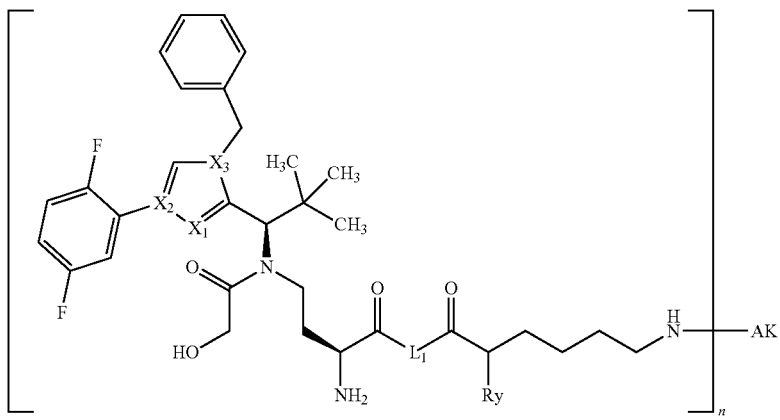

Preference according to the invention is furthermore given to the basic structure (i), (ii) or (iv), where SG1 or SG represents a group which can be cleaved by cathepsin and L1 and L2 have the meanings given above. Particular preference is given to the following groups:

—NH-Val-Ala-CONH— (hereby cleavage of the amide bond at the C-terminal amide of alanine)

—NH-Val-Lys-CONH— (cleavage of the amide bond at the C-terminal amide of lysine)

—NH-Val-Cit-CONH— (cleavage of the amide bond at the C-terminal amide of citrulline)

—NH-Phe-Lys-CONH (cleavage of the amide bond at the C-terminal amide of lysine)

—NH-Ala-Lys-CONH— (cleavage of the amide bond at the C-terminal amide of lysine)

—NH-Ala-Cit-CONH— (cleavage of the amide bond at the C-terminal amide of citrulline)

-continued

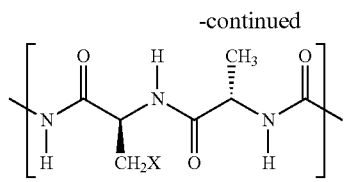

where X represents —H or a $C_{1-10}$-alkyl group which may optionally be substituted by —NH—C(=O)—NH$_2$, —COOH, —OH, NH$_2$, —NH—CNNH$_2$ or sulphonic acid.

The table below gives examples of a linker moiety -SG1-L1- or -L1-SG-L1-, where SG1 and SG are groups which can be cleaved by cathepsin. The L1 group is highlighted in a box. However, these groups L1 can be replaced by one of the groups L1 given for formula §-(C=O)m-L1-L2-§§ above.

-SG1-L1- or -L1-SG-L1-
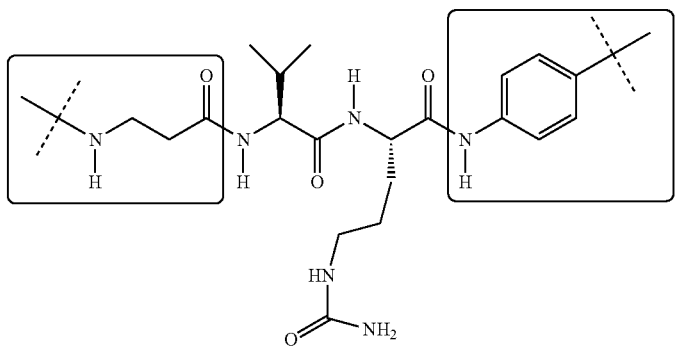
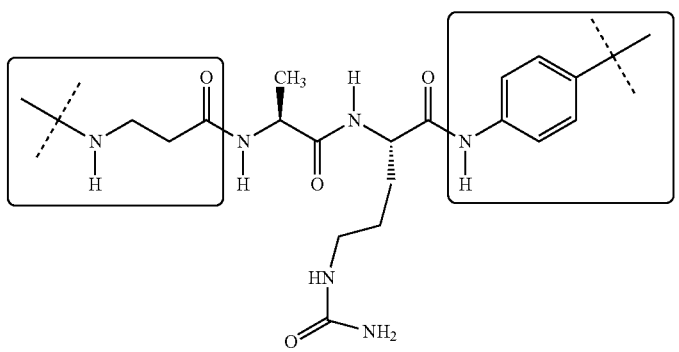
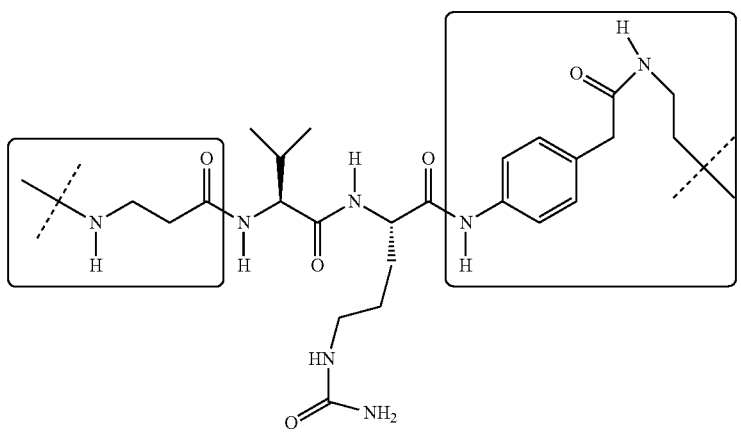

-continued
-SG1-L1- or -L1-SG-L1-
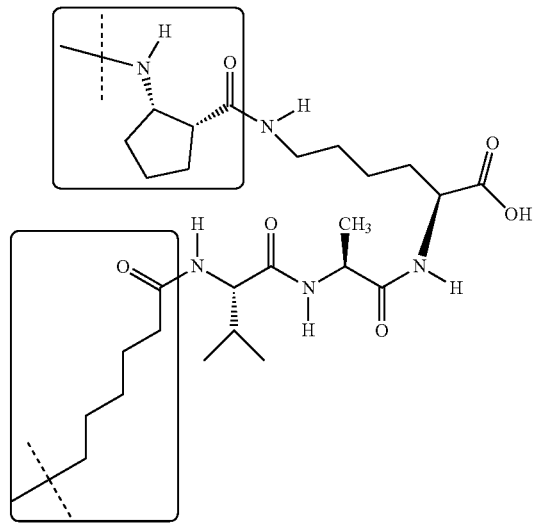
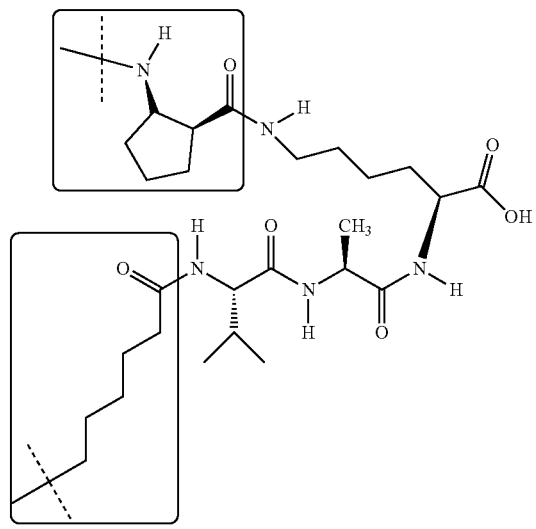
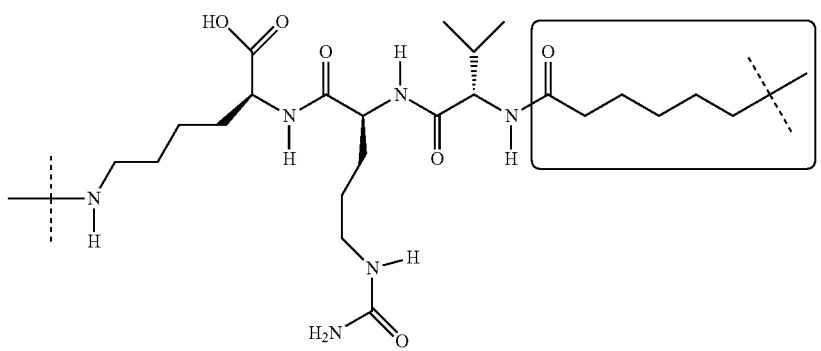

| -SG1-L1- or -L1-SG-L1- |
|---|
| 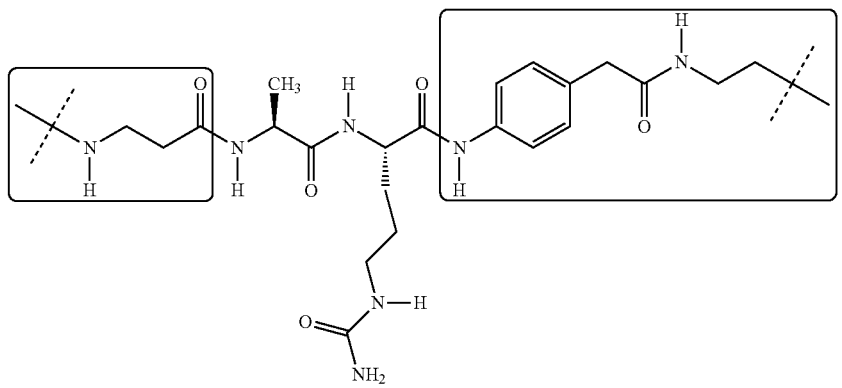 |
| 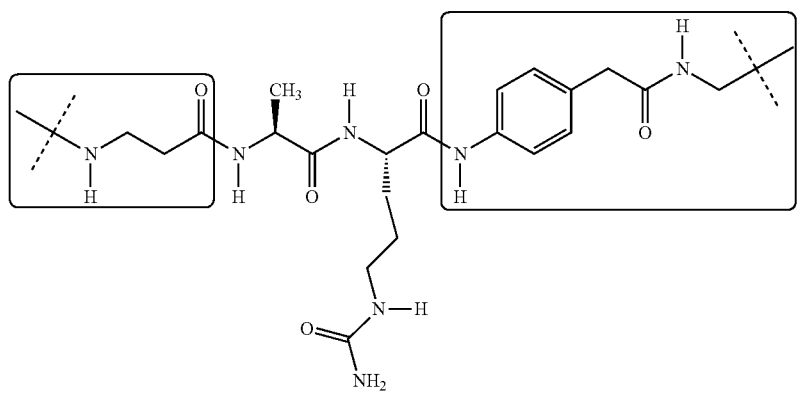 |
| 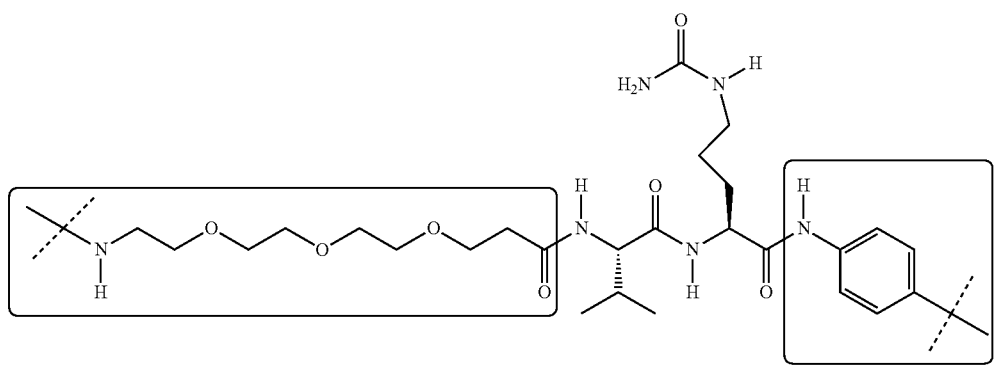 |
| 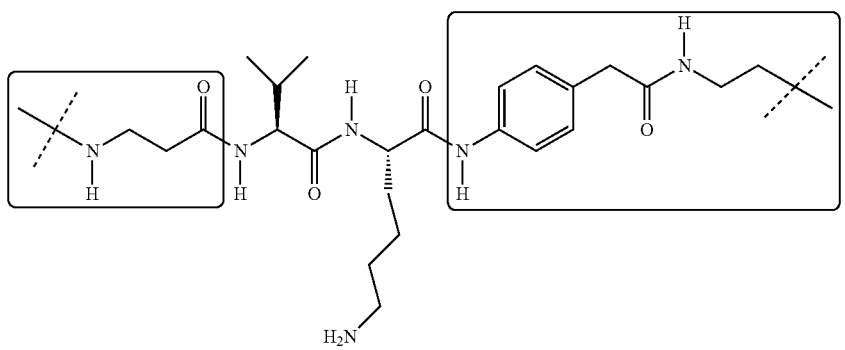 |

| -SG1-L1- or -L1-SG-L1- |
|---|
| 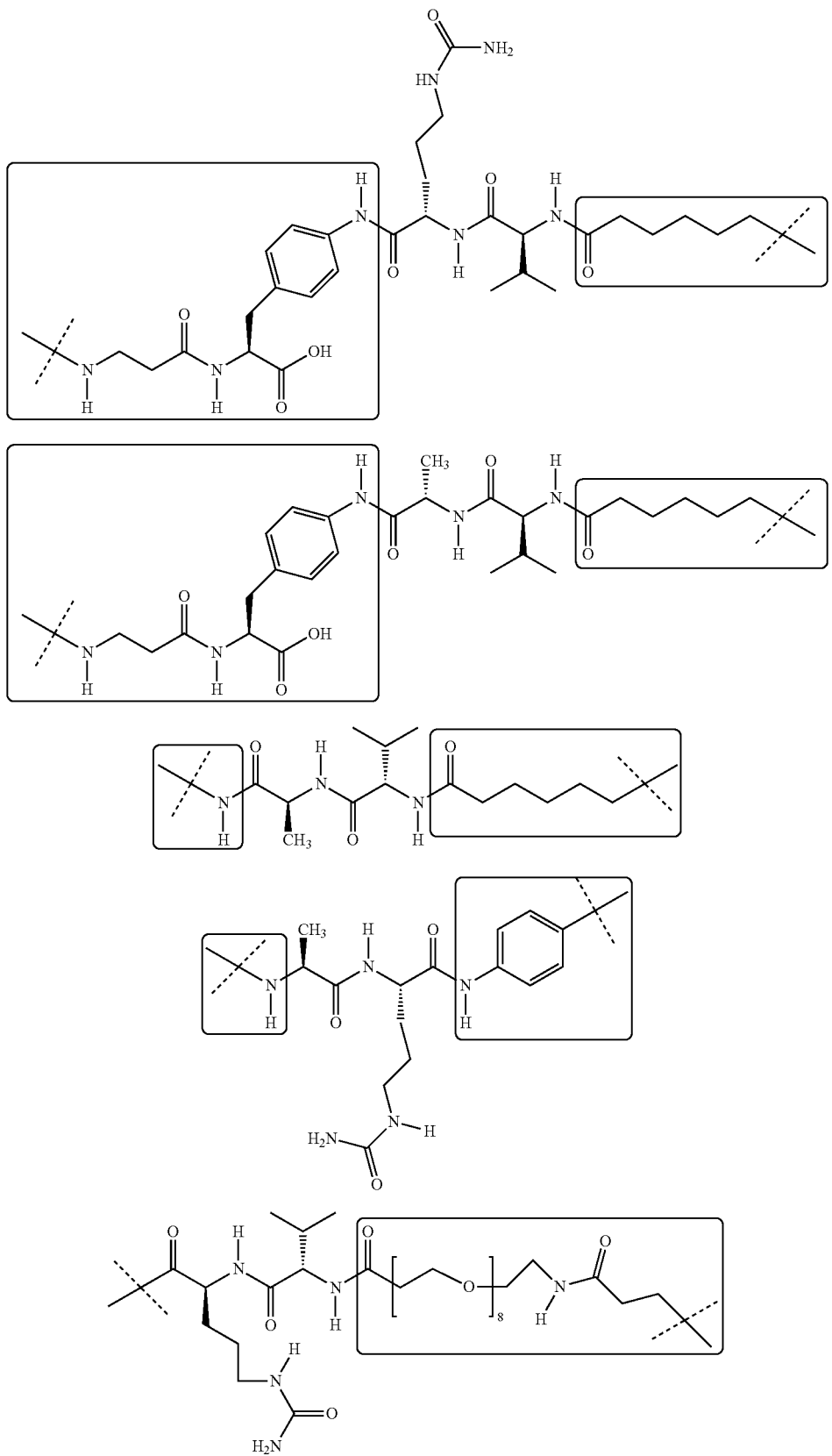 |

-continued
| -SG1-L1- or -L1-SG-L1- |
|---|
| 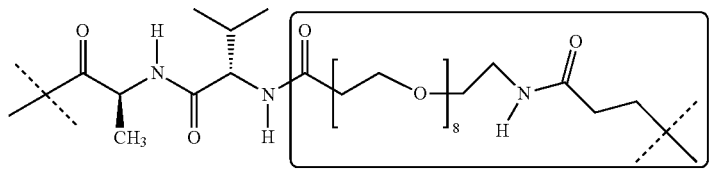 |
| 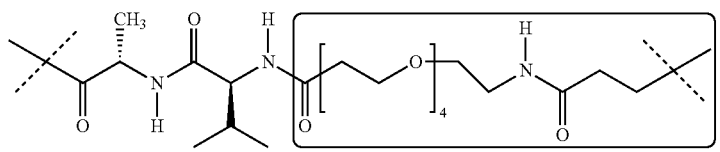 |
| 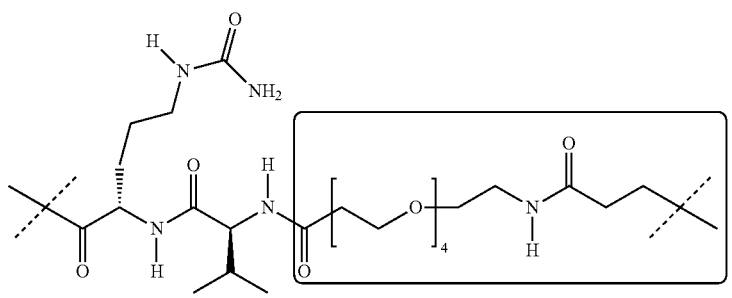 |
| 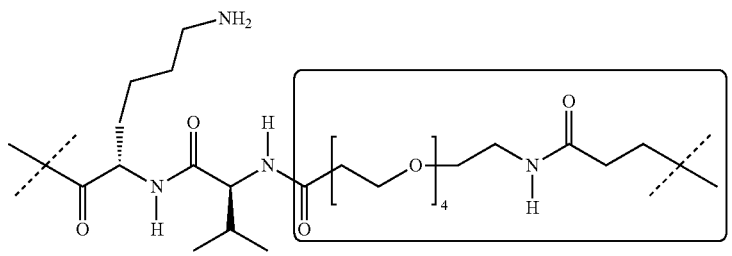 |
| 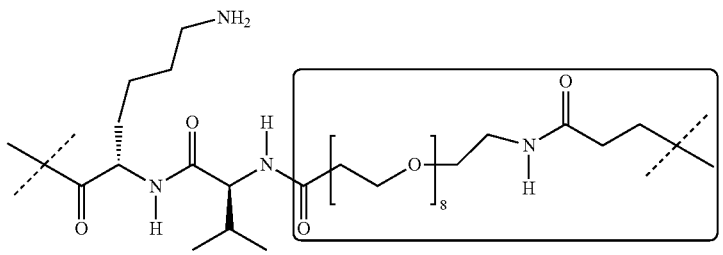 |
| 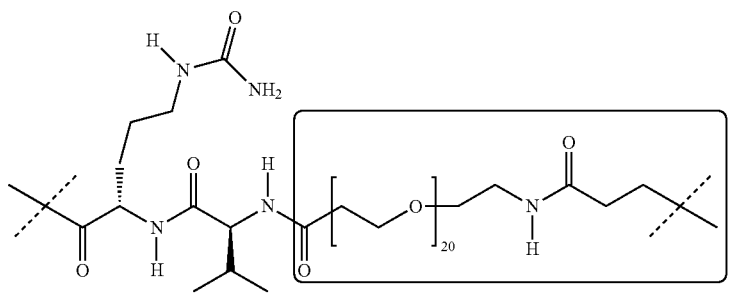 |

-continued
| -SG1-L1- or -L1-SG-L1- |
|---|
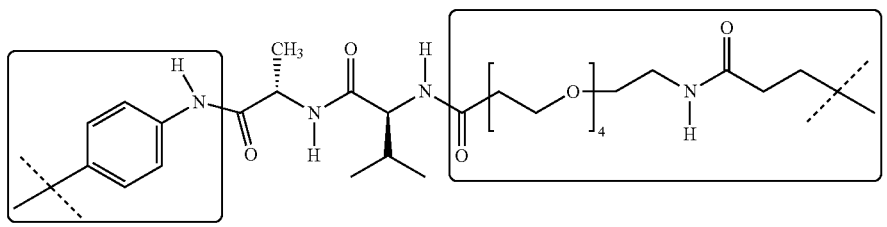
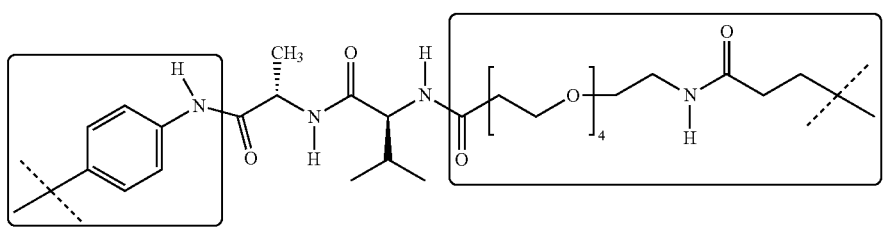
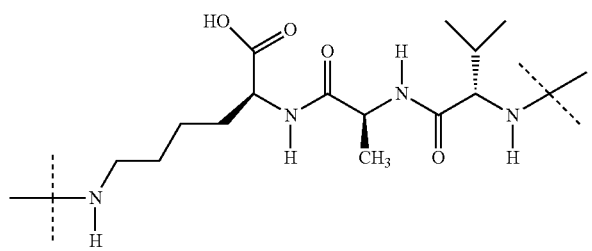
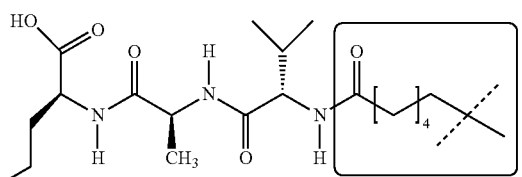
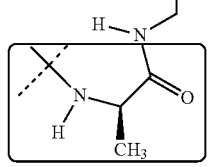
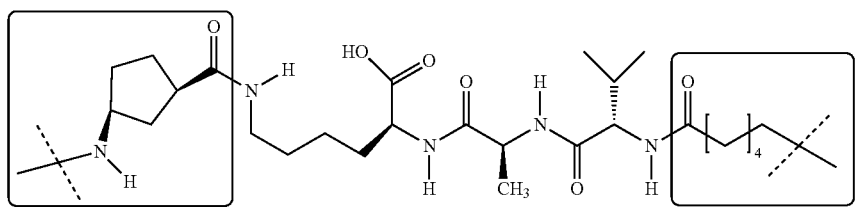
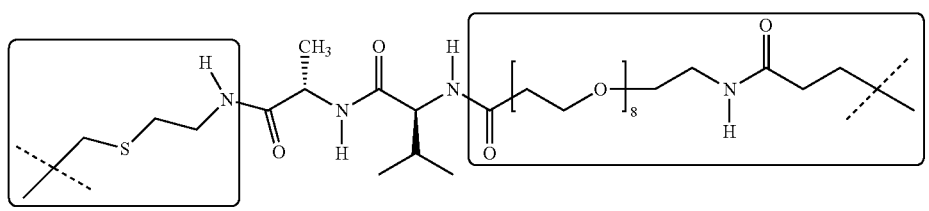

-continued
-SG1-L1- or -L1-SG-L1-
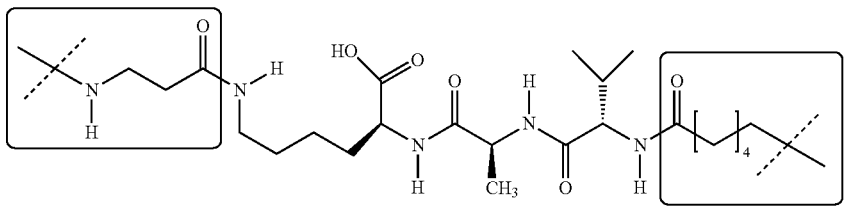
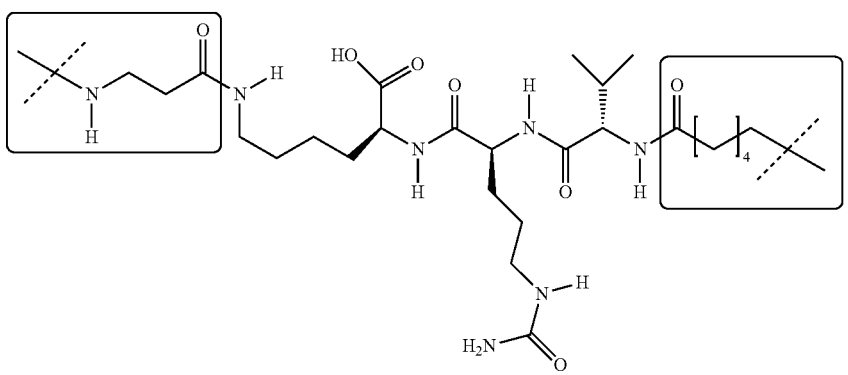
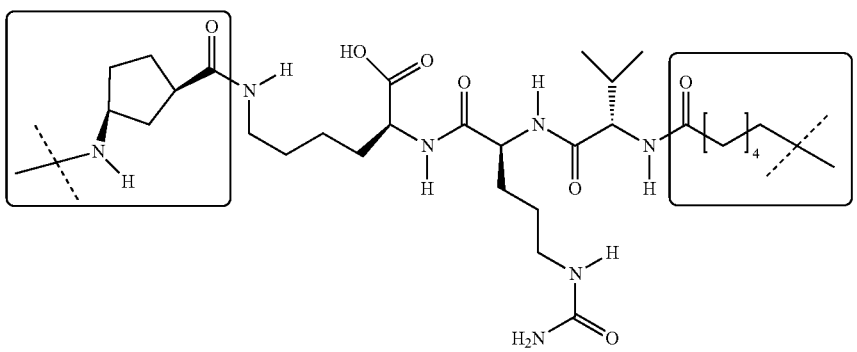
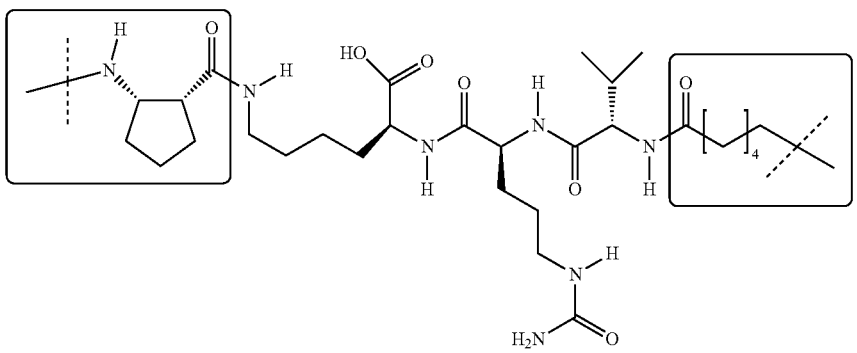

| -SG1-L1- or -L1-SG-L1- |
|---|
| 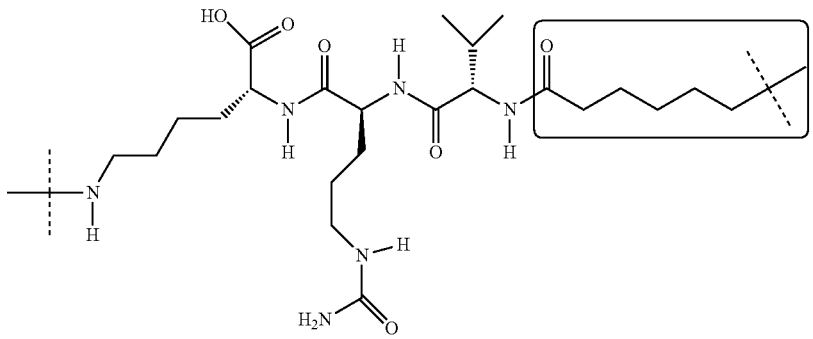 |
| 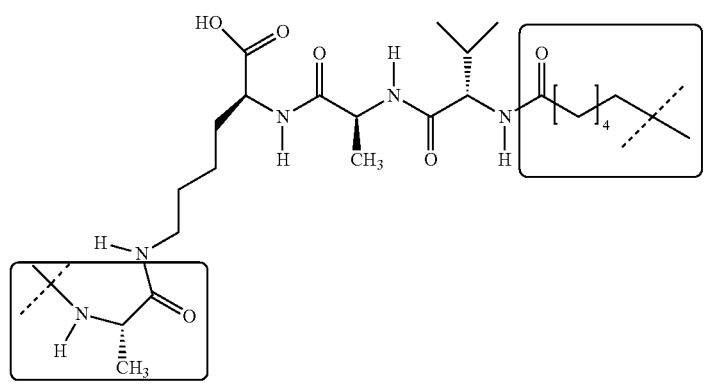 |
| 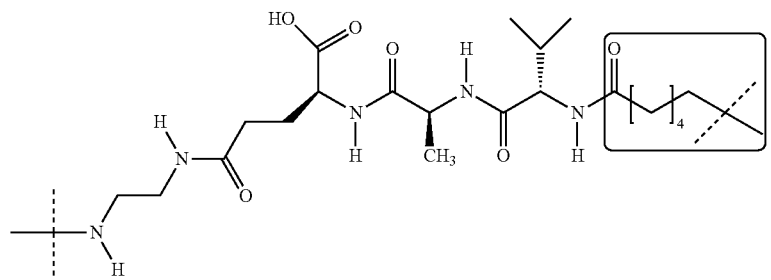 |
| 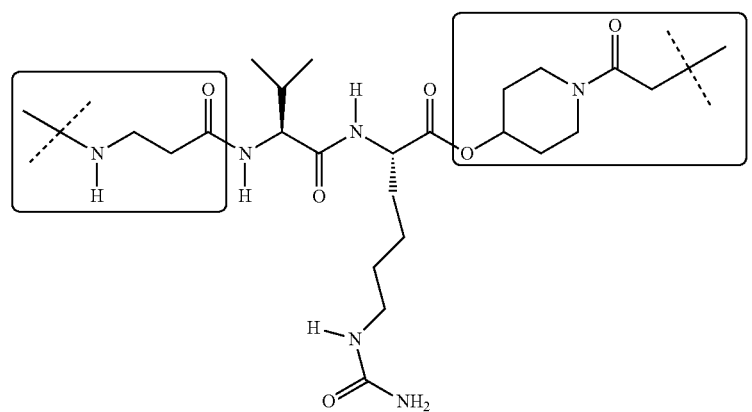 |

-SG1-L1- or -L1-SG-L1-

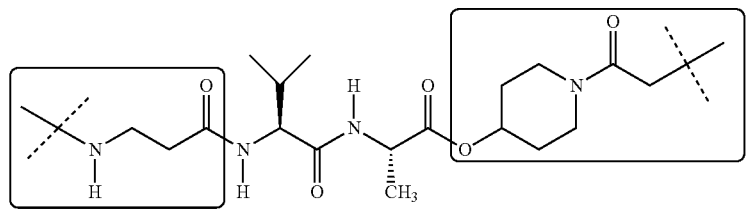

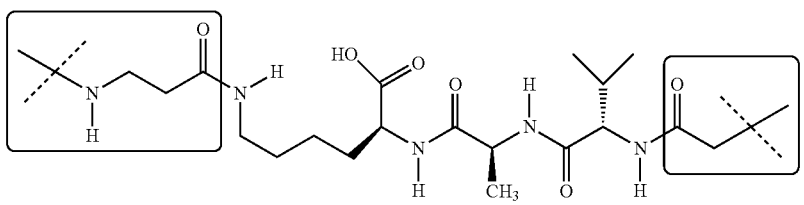

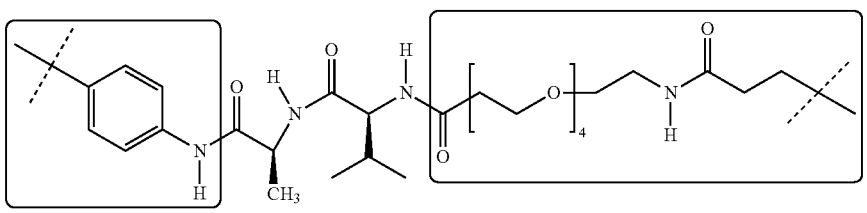

Examples of conjugates having basic structure (i) have the following structure, where X1, X2, X3, R1 and Ry have the meanings given above, AK represents the binder, preferably an antibody conjugated to a glutamine side chain and n is 2 to 10, preferably 2 to 4 and also preferred 2 or 4. Particularly preferably, AK is an anti-TWEAKR antibody, in particular an anti-TWEAKR antibody which binds specifically to amino acid D in position 47 (D47) of TWEAKR (SEQ ID NO: 169), in particular the anti-TWEAKR antibody TPP-2090. All the antibodies described include aglycosylated variants of these antibodies generated either by deglycosylation by PNGase F or by mutation of N297 (Kabat numbering) of the heavy chain to any amino acid.

KSP Inhibitor-Linker-Intermediates and Preparation of the Conjugates

The conjugates according to the invention are prepared by initially providing the low-molecular weight KSP inhibitor with a linker. The intermediate obtained in this manner is then reacted with the binder (preferably an antibody) using transglutaminase.

Preferably, for site specific coupling to a glutamine side chain, one of the compounds below is reacted with the acceptor glutamine-containing binder such as an antibody using transglutaminase.

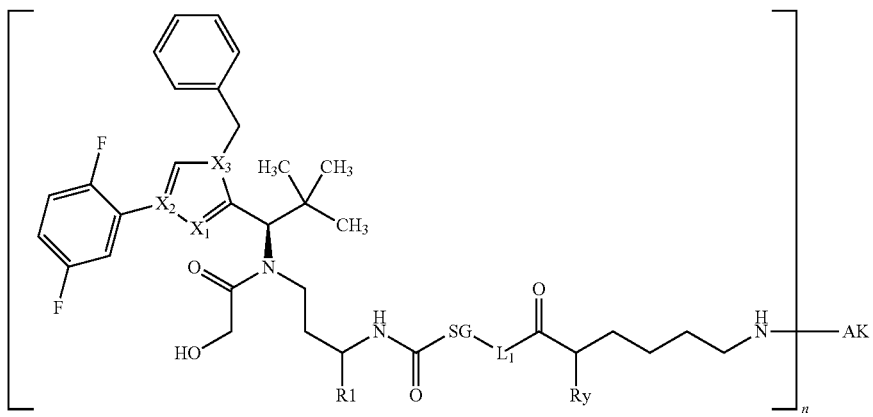

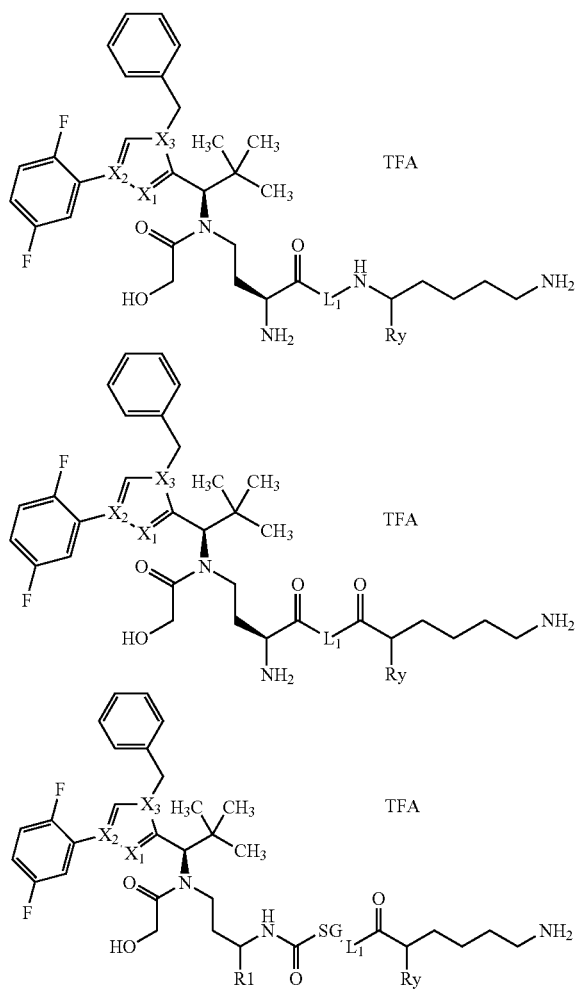

where $X_1$, $X_2$, $X_3$, SG, L1, R1 and Ry have the same meaning as described above. In above-mentioned formulae, instead of a free amino group (—$NH_2$), a group $R^{21}$—(C=)$_{(0-1)}$-(P3)$_{(0-2)}$-P2—NH—CH($CH_2$—C(=O)—$NH_2$)—C(=O)—NH— may be present (wherein $R^{21}$, P2 and P3 have the same meaning as defined above, e.g. with regard to formula (IIa)).

If the binder is an antibody it comprises an acceptor glutamine, preferentially in the constant region. Such acceptor glutamines can be introduced by mutations of suitable positions into glutamine (e.g. mutation N297Q, Kabat EU numbering) or by generation of deglycosylated or aglycosylated antibodies (e.g. by enzymatic deglycosylation by PNGase F or by mutation of N297X, Kabat EU numbering). In that later case of an deglycosylated or aglycosylated antibody the glutamine Q295 (Kabat EU numbering) becomes an acceptor glutamine. Highly preferred is an antibody comprising a mutation N297A or N297Q (Kabat EU numbering).

The compound may be employed, for example, in the form of its trifluoroacetic acid salt. For the reaction with the binder such as, for example, the antibody, the compound is preferably used in a 2 to 100 fold molar excess, more preferably 10 to 100 fold molar excess, even more preferably 50 to 100 fold molar excess, with respect to the binder.

For an intermediate coupling to a glutamine side chain, the reactions can be illustrated as follows: The other intermediates and other antibodies can be reacted correspondingly.

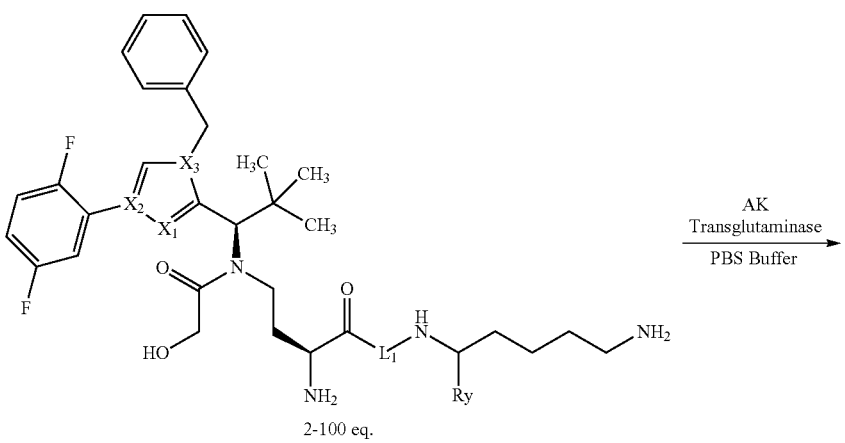

-continued
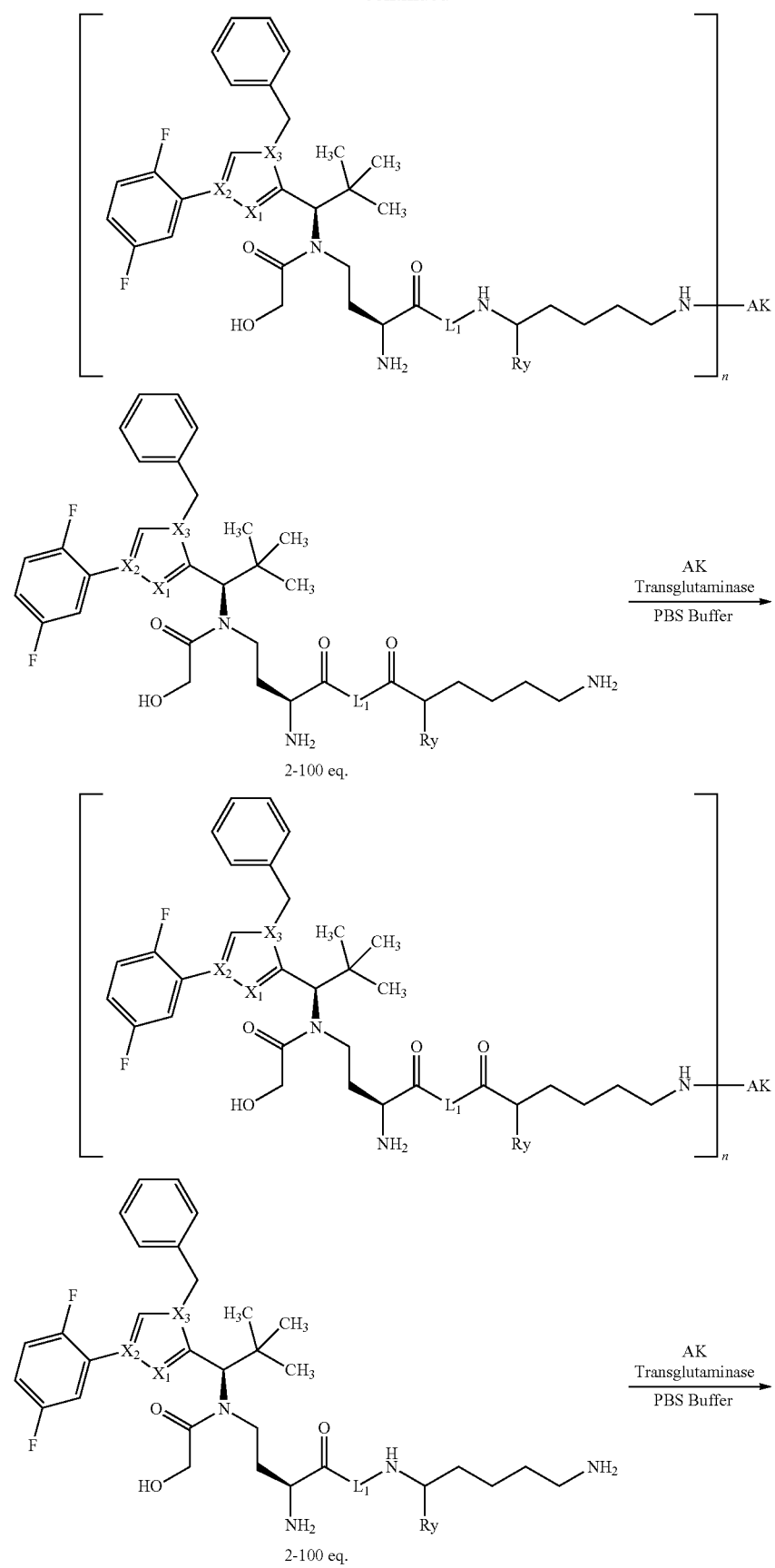

-continued
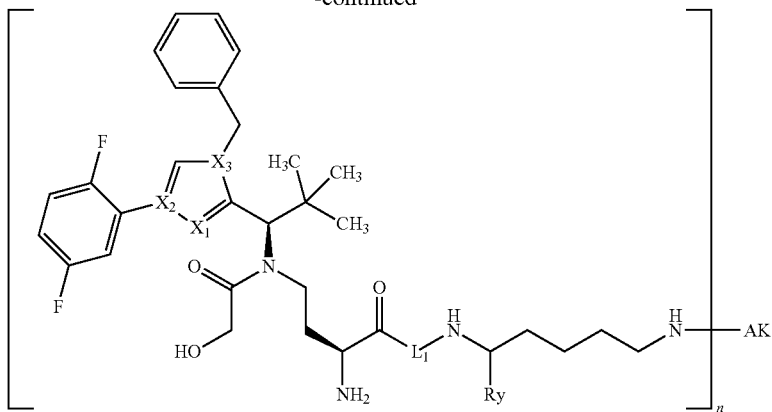
In accordance with the invention, this gives the following conjugates:
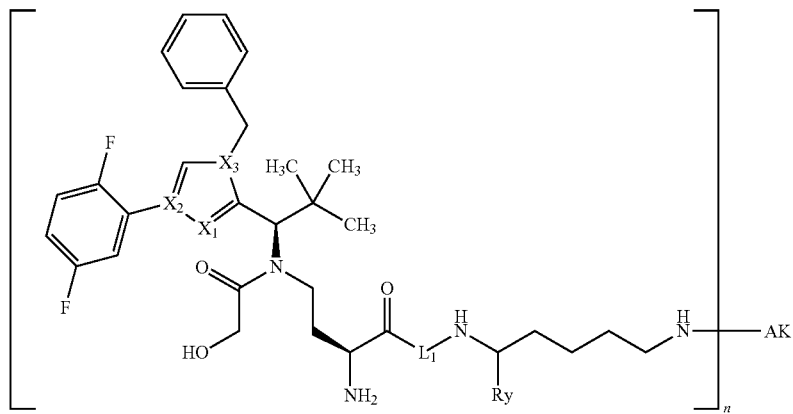
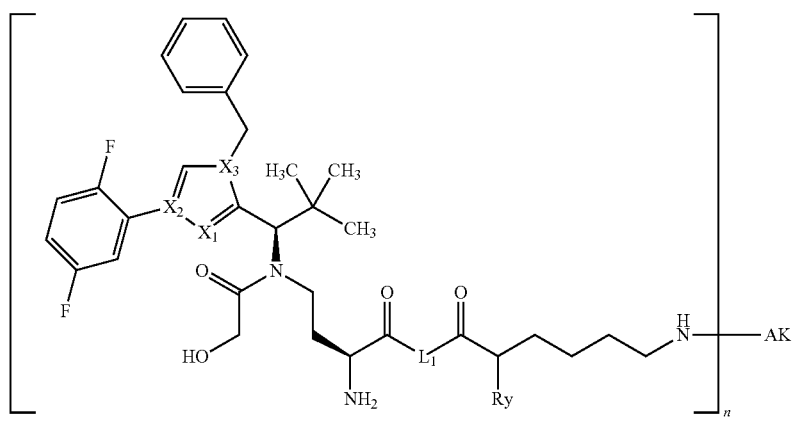

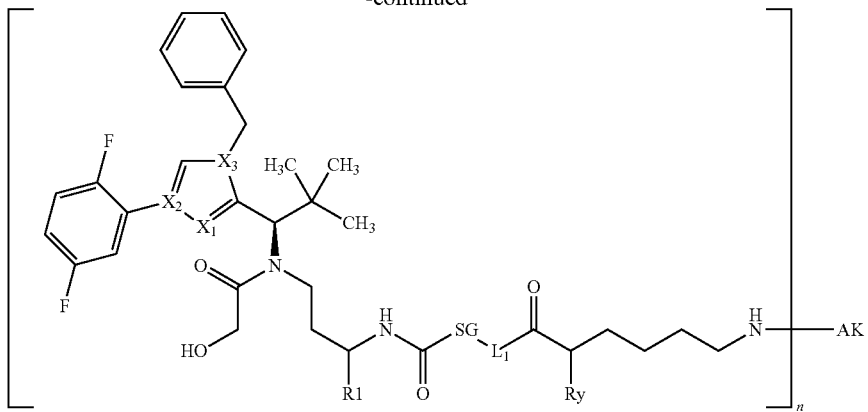

In the above formulae, $X_1$, $X_2$, $X_3$ and R1 have the same meaning as in formula (II), SG, Ry and L1 have the same meaning as described above. AK is an antibody coupled to a glutamine side chain. With particular preference, AK1 is anti-TWEAKR antibodies, in particular antibodies which bind specifically to amino acid D in position 47 (D47) of TWEAKR (SEQ ID NO:169), in particular the anti-TWEAKR antibody TPP-2090. All the antibodies described include aglycosylated variants of these antibodies generated either by deglycosylation by PNGase F or by mutation of N297 (Kabat numbering) of the heavy chain to any amino acid.

Particularly Preferred KSP-Inhibitor-Conjugates

Particularly preferred are the following conjugates, where AK3a, AK3b, AK3d, AK3e, represent the binder, preferably an antibody, and n represents 2 to 10, preferably 2 to 4, and also preferably 2 or 4. Preferred antibodies are those described below in the section Binders, particularly antibody TPP-2090-HC-N297A (particularly as AK3a), antibody TPP-2090-HC-N297Q (particularly as AK3b), Trastuzumab (TPP-7510) (equal to Trastuzumab-HC-N297A) (particularly as AK3d), and Trastuzumab (TPP-7511) (equal to Trastuzumab-HC-N297Q) (particularly as AK3e).

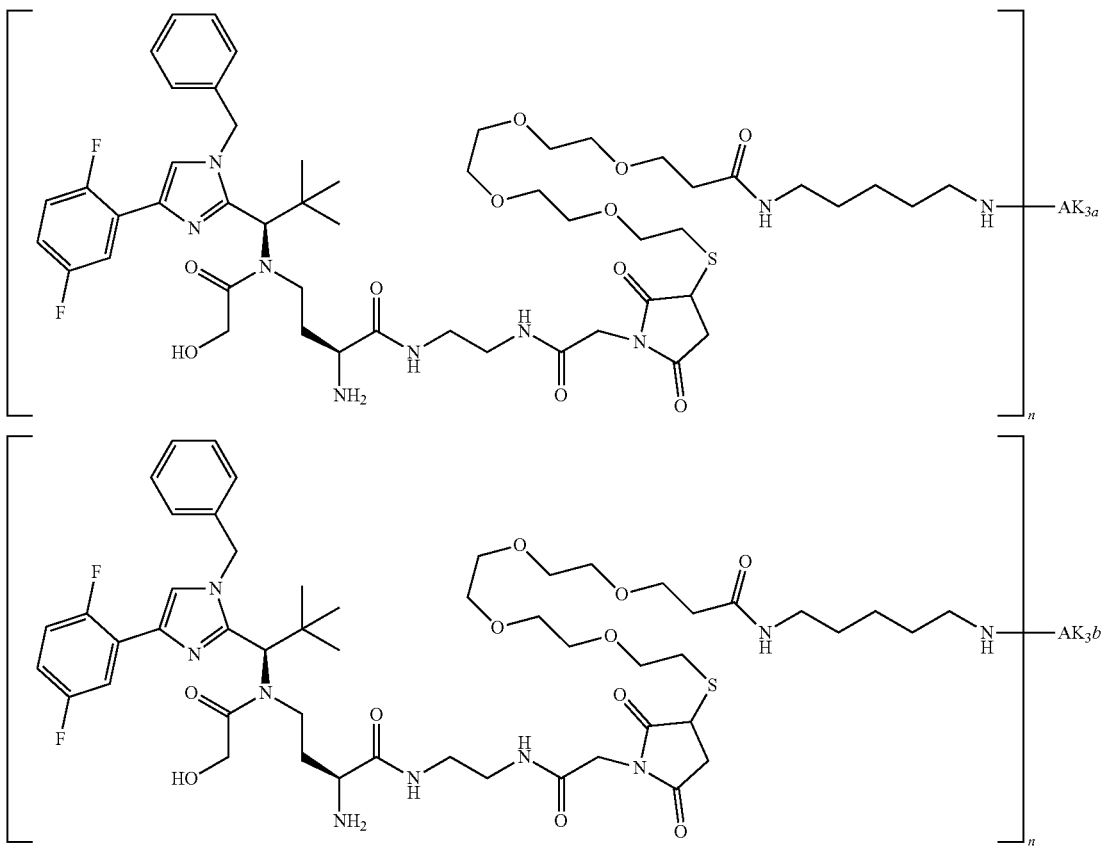

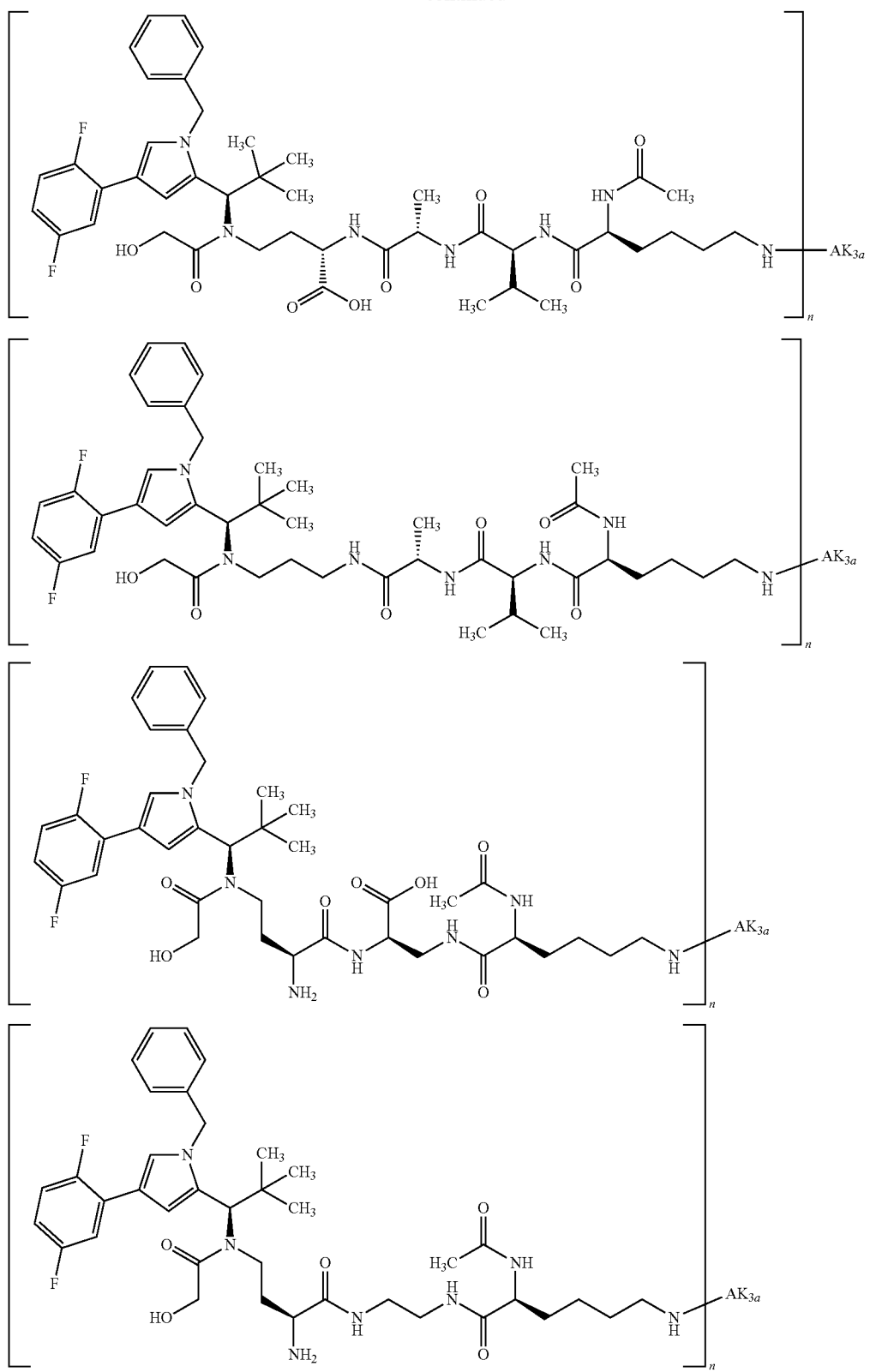

-continued
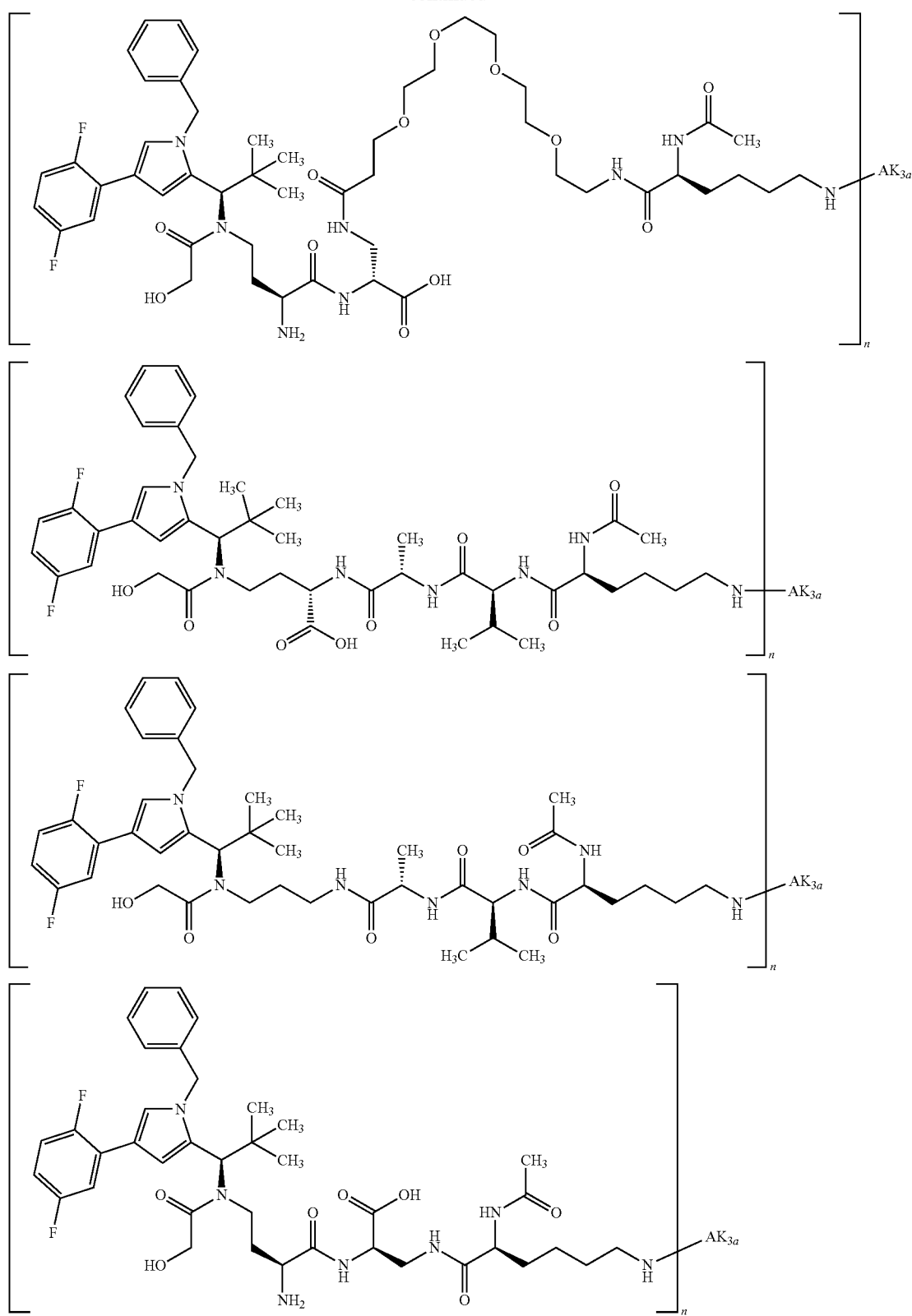

-continued
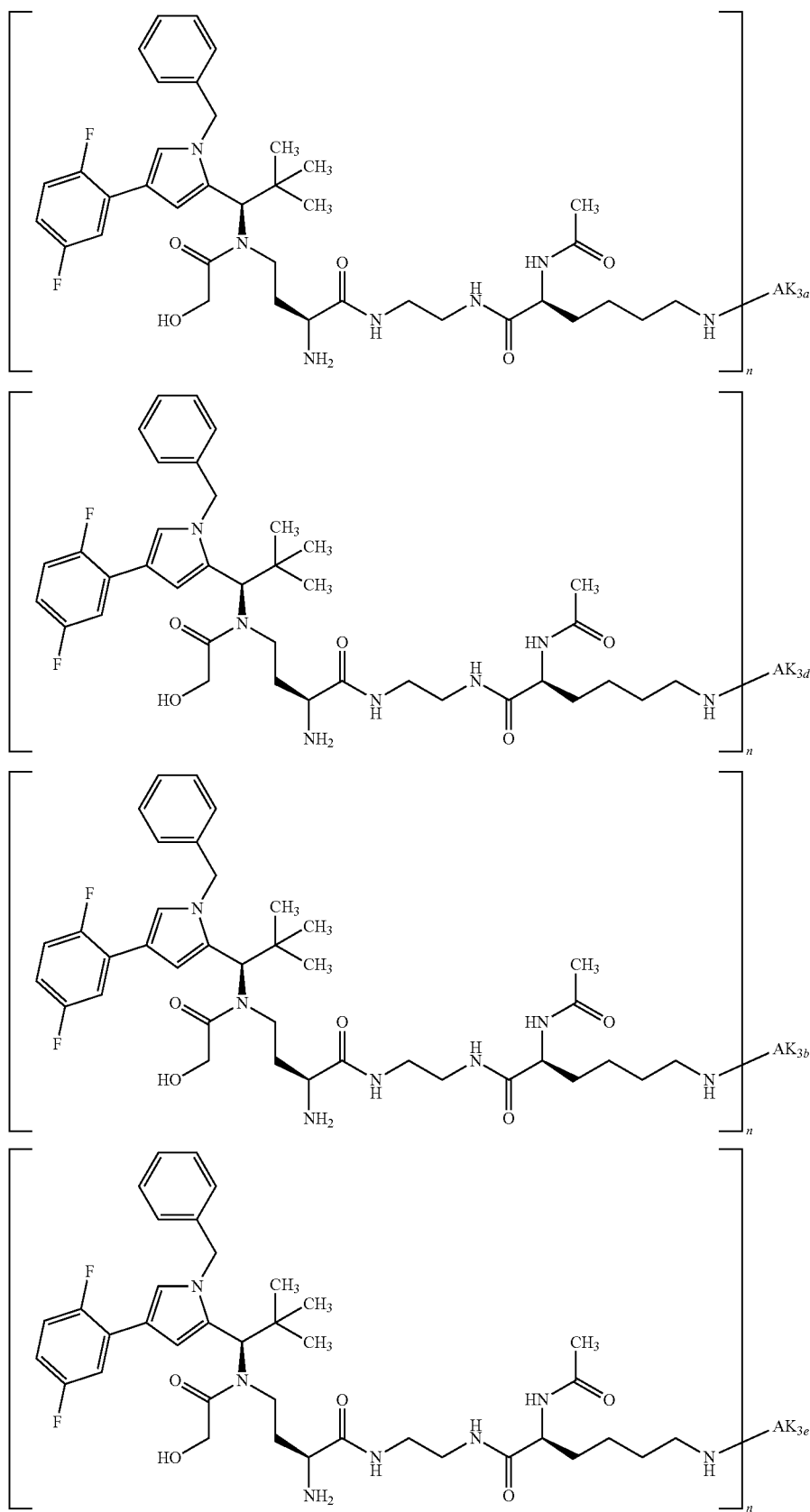

-continued
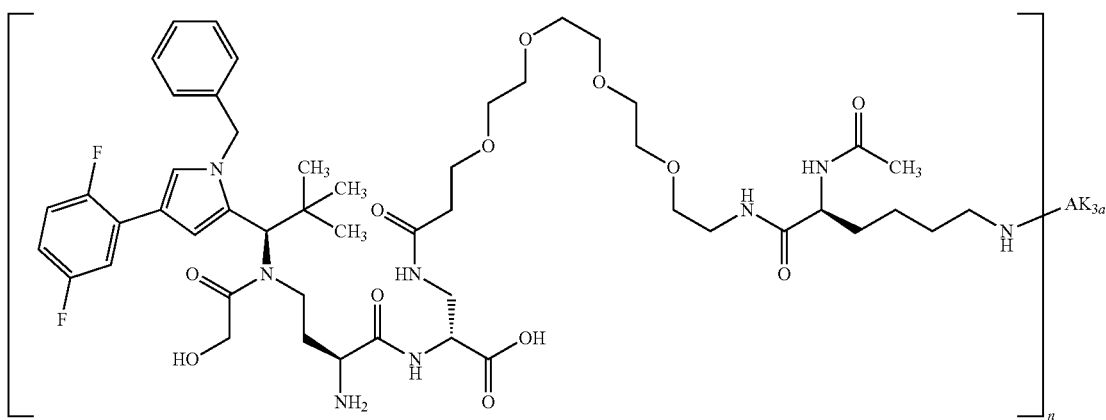
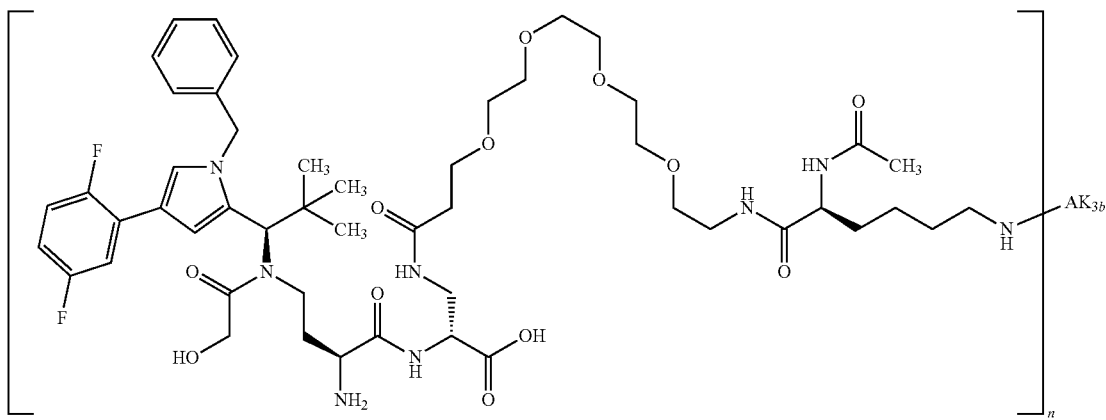
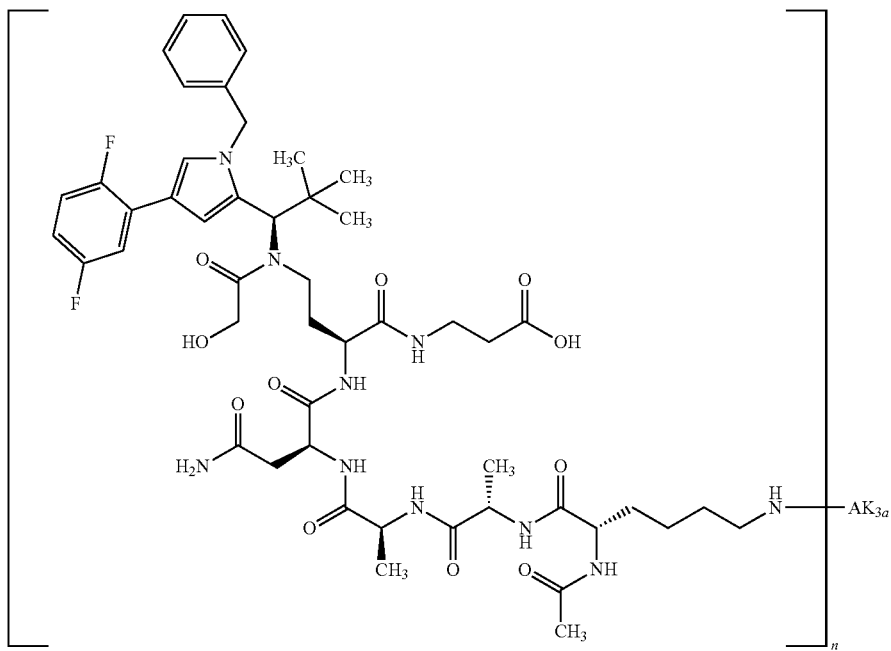

-continued
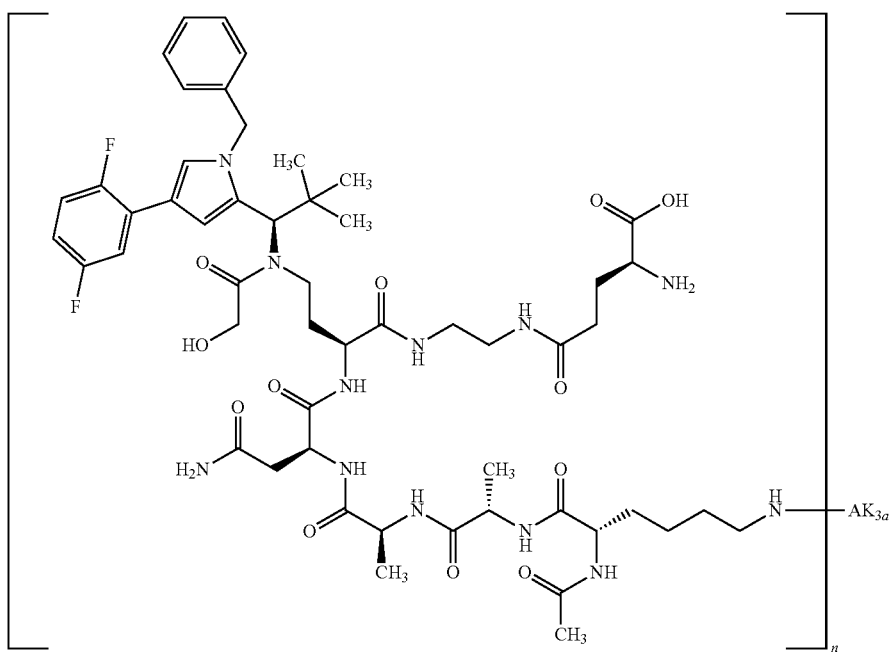
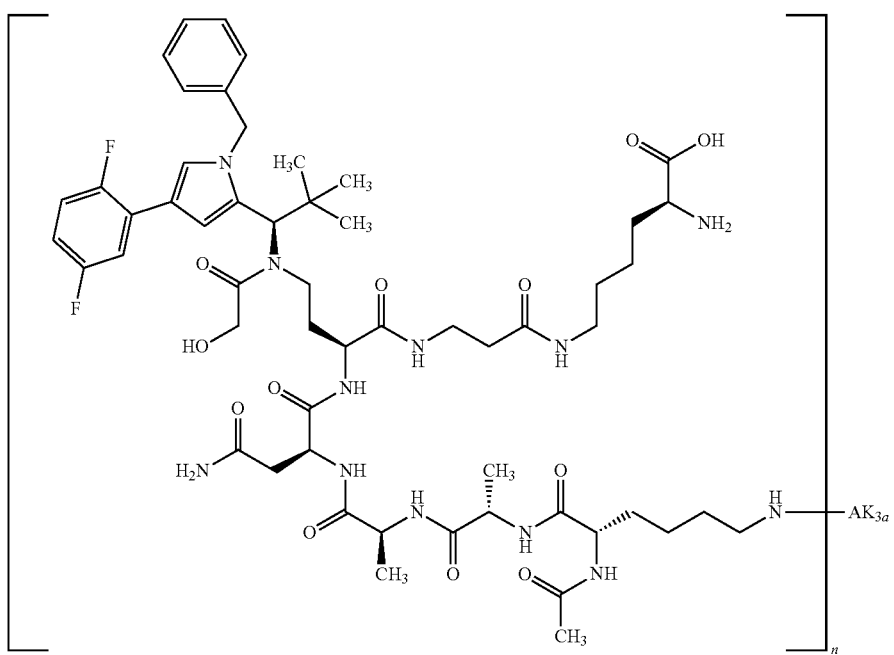

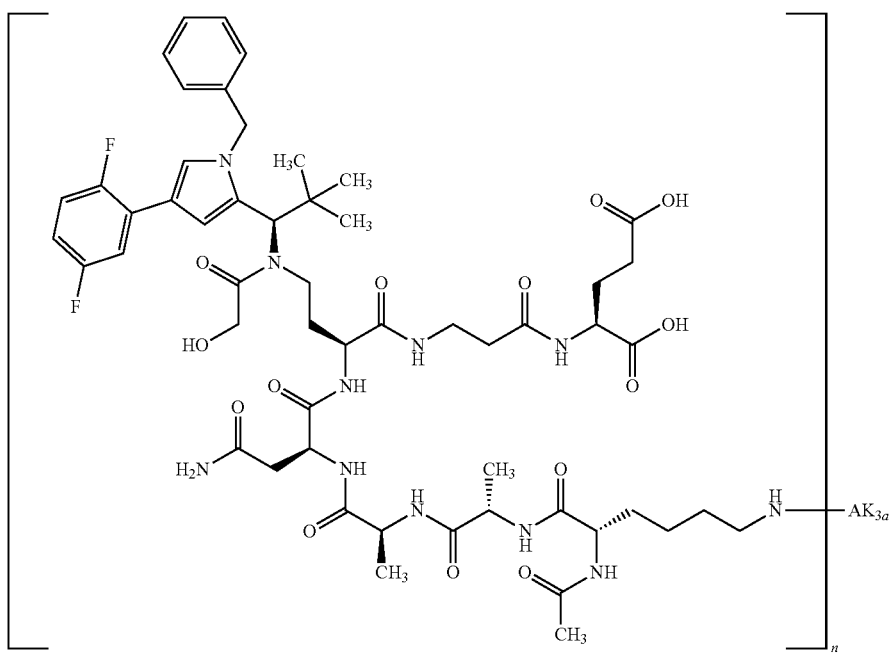
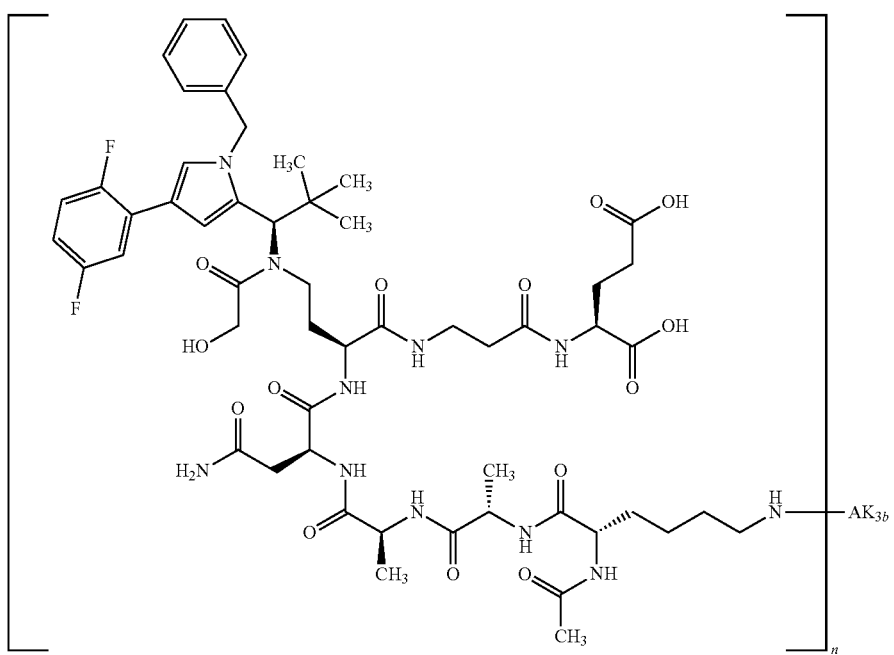

-continued
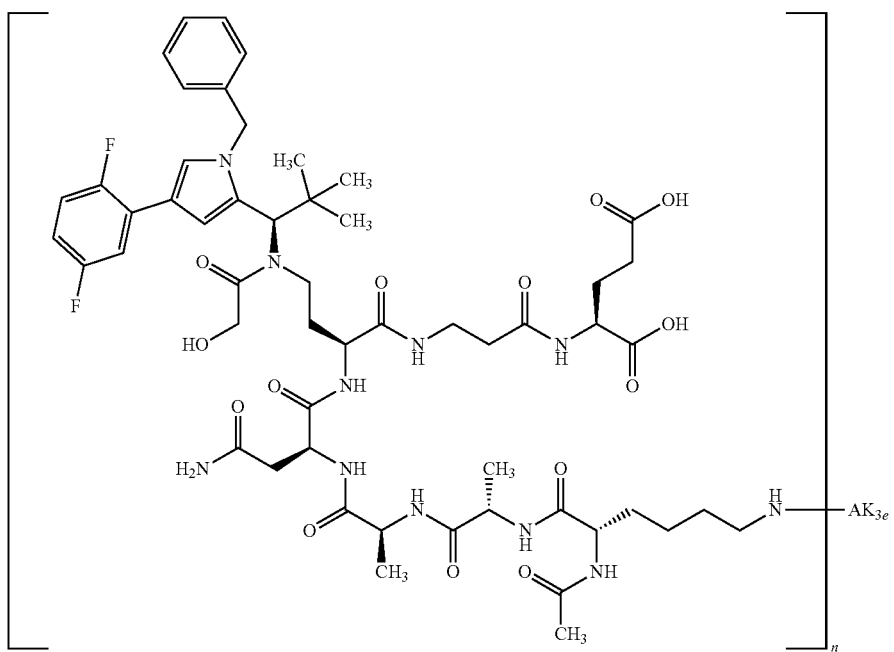
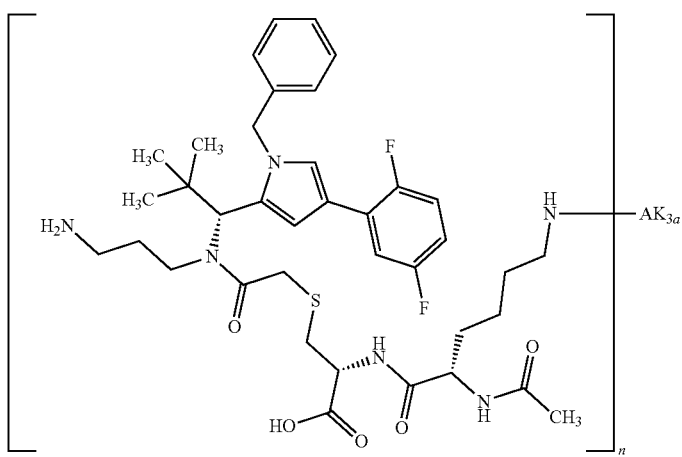
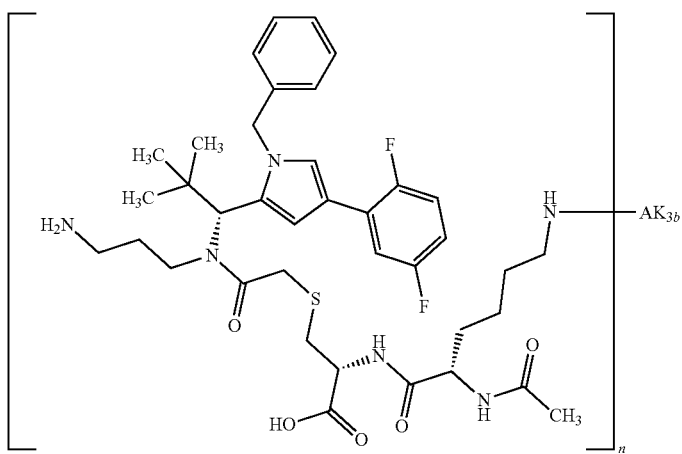

-continued
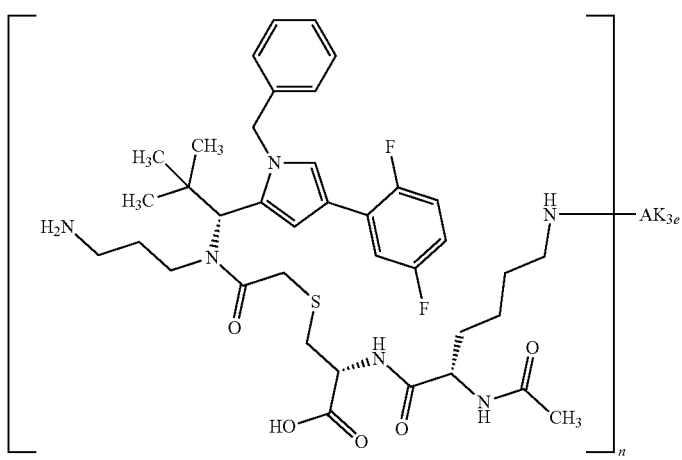
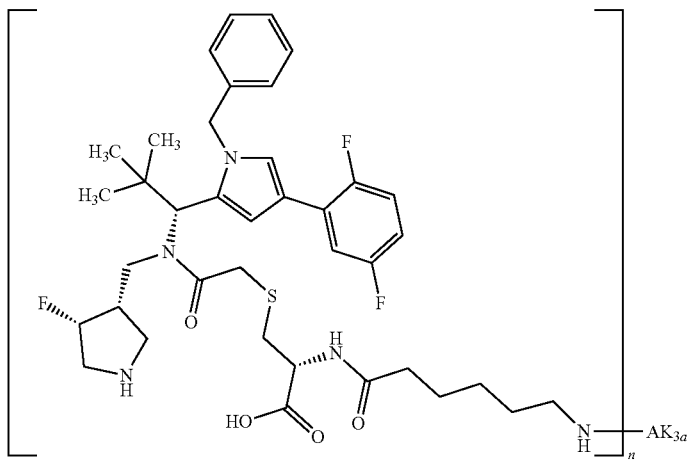
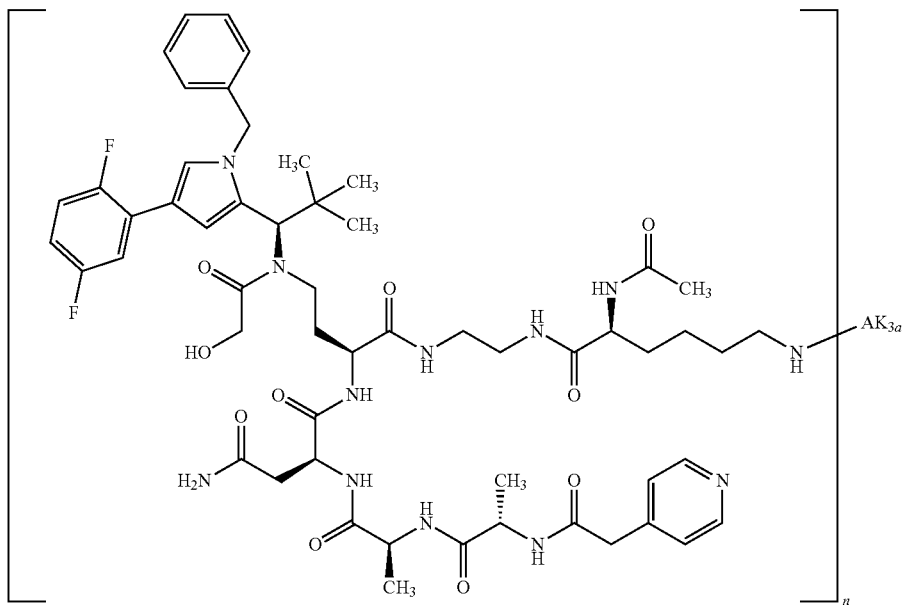

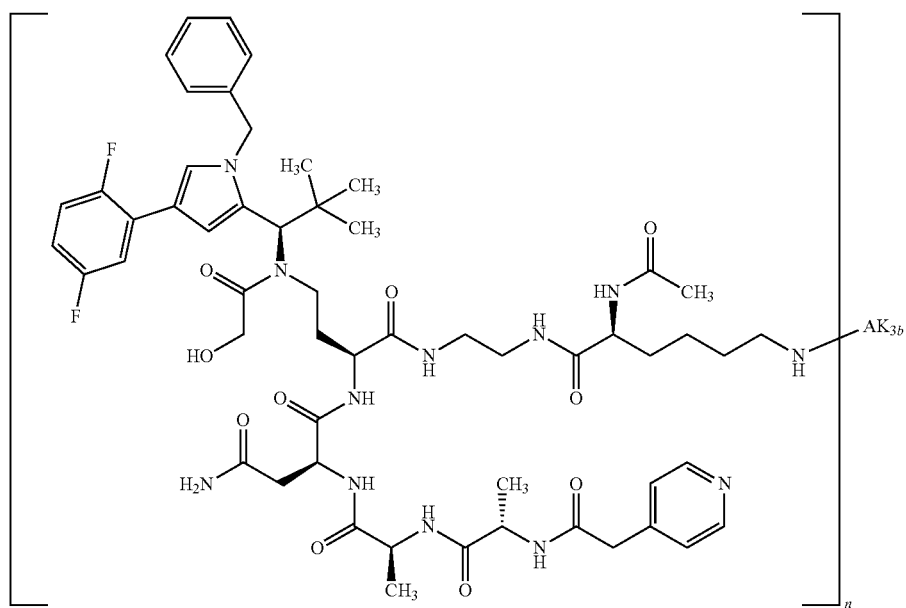
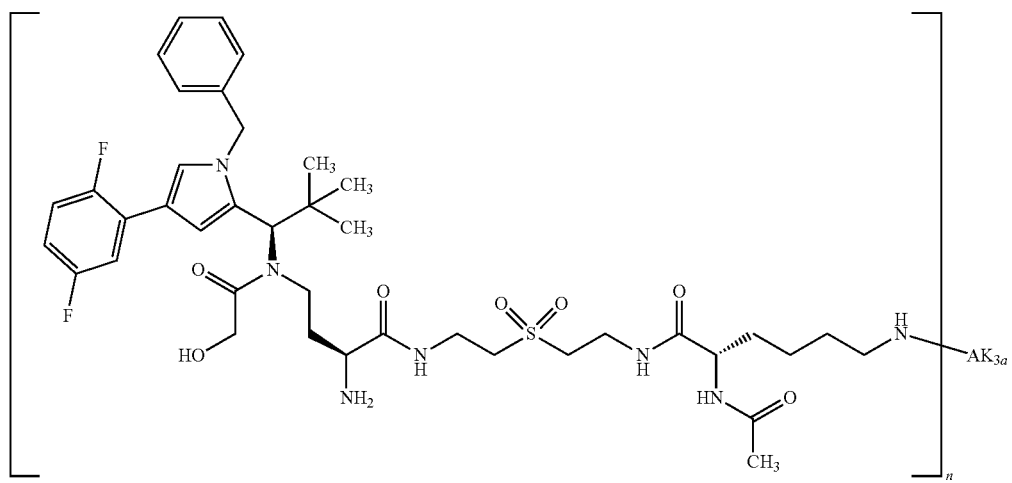
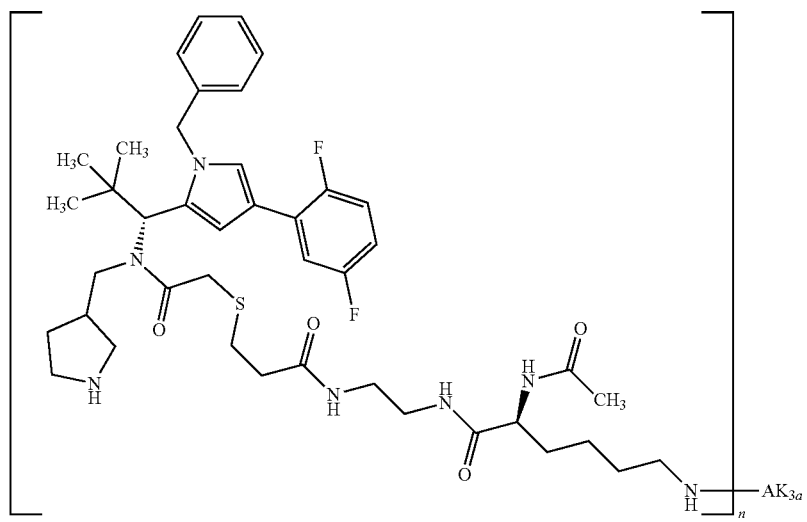

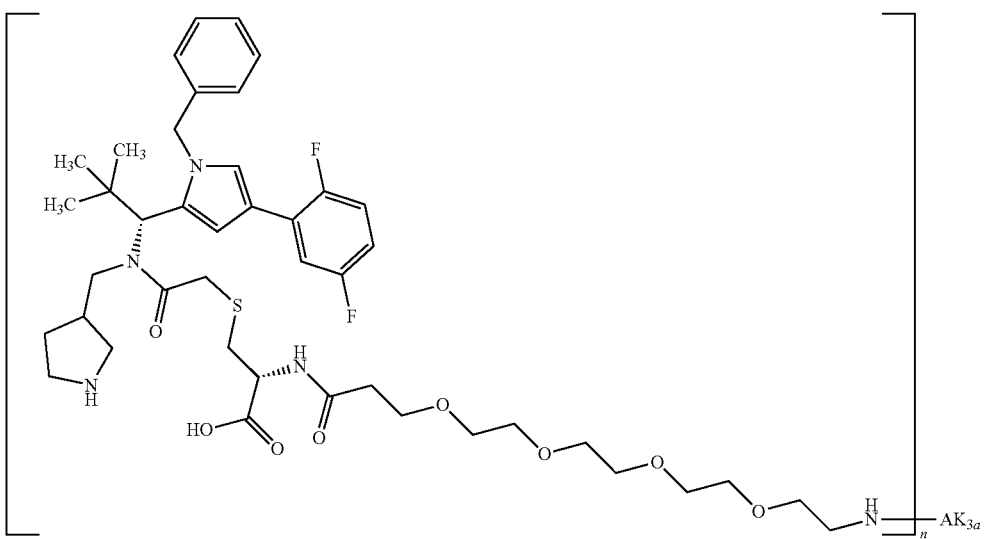
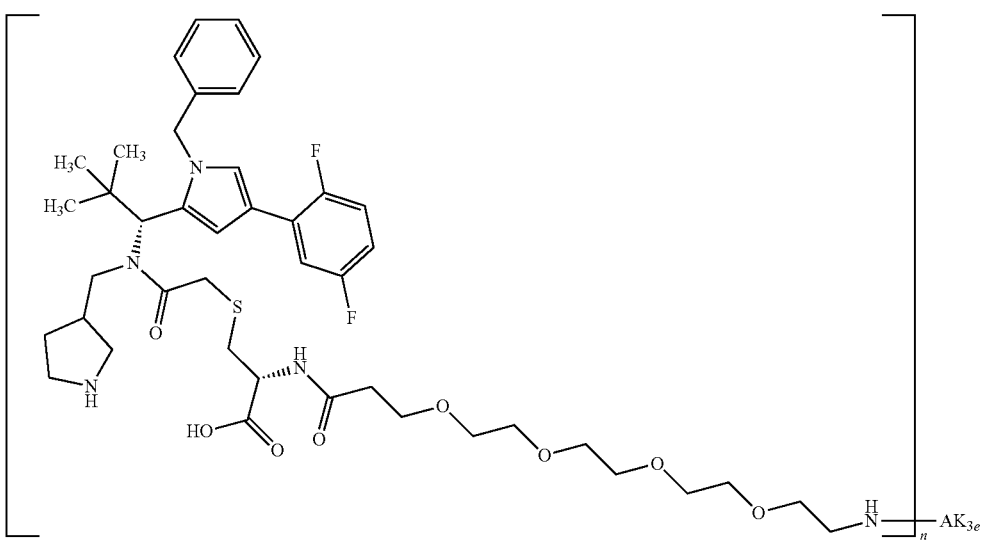
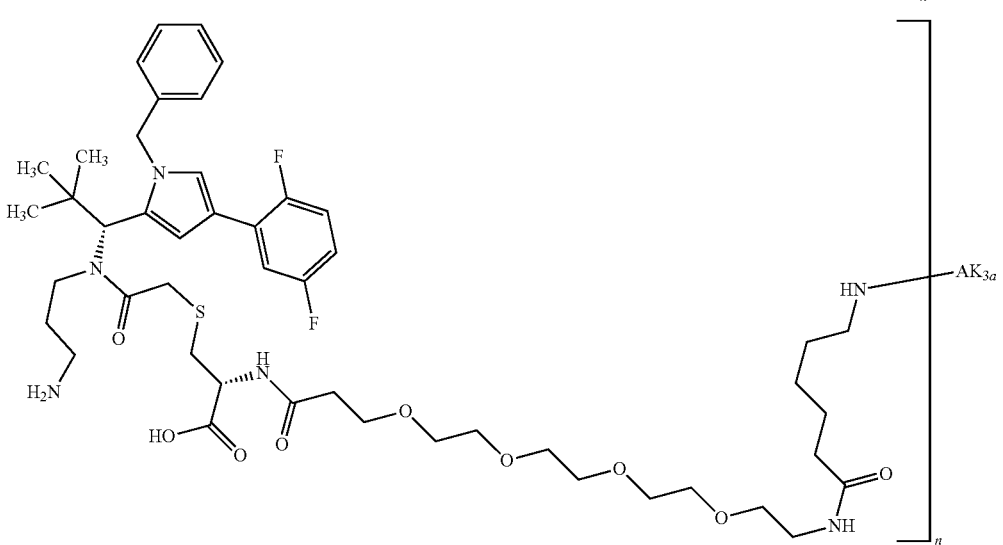

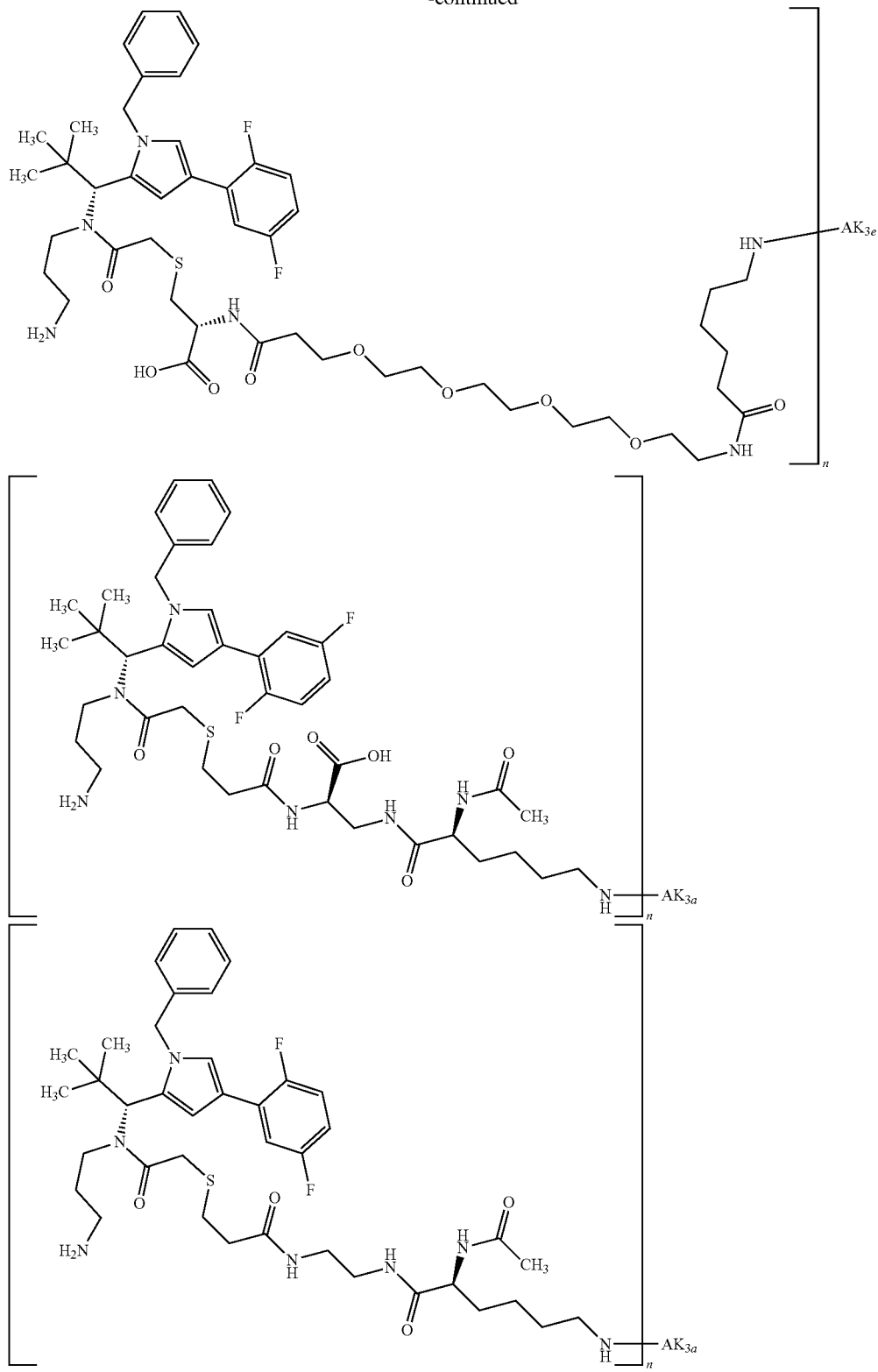
Definitions of Substituents
Alkyl
Alkyl represents a straight-chain or branched saturated monovalent hydrocarbon radical having generally 1 to 10, preferably 1 to 6 ($C_1$-$C_6$-alkyl), more preferably 1 to 4 ($C_1$-$C_4$-alkyl) and particularly preferably 1 to 3 ($C_1$-$C_3$-alkyl) carbon atoms.
Examples which may be mentioned as being preferred are:

methyl-, ethyl-, propyl-, butyl-, pentyl-, hexyl-, isopropyl-, isobutyl-, sec-butyl, tert-butyl-, isopentyl-, 2-methylbutyl-, 1-methylbutyl-, 1-ethylpropyl-, 1,2-dimethylpropyl, neopentyl-, 1,1-dimethylpropyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl-, 1,2-dimethylbutyl-.

Particular preference is given to a methyl, ethyl, propyl, isopropyl or tert-butyl radical.

Heteroalkyl

Heteroalkyl represents alkyl as defined under "Alkyl" above and is interrupted by —O—, —S—, —NH—, —S(=O)—, —S(=O)$_2$—, —S(=O)$_2$—NH—.

Cycloalkyl

Cycloalkyl represents a monocyclic saturated monovalent hydrocarbon radical having generally 3 to 10 ($C_3$-$C_{10}$-cycloalkyl), preferably 3 to 8 ($C_3$-$C_8$-cycloalkyl) and particularly preferably 3 to 7 ($C_3$-$C_7$-cycloalkyl) carbon atoms.

Examples of monocyclic cycloalkyl radicals which may be mentioned as being preferred are: cyclopropyl, cyclobutyl, cyclopentyl, cyclohexyl and cycloheptyl.

Particular preference is given to a cyclopropyl, cyclopentyl or cyclohexyl radical.

Aralkyl

Aryl-$C_1$-$C_6$-alkyl- is understood to mean a group composed of an optionally substituted aryl radical and a $C_1$-$C_6$-alkyl group, and bonded to the rest of the molecule via the $C_1$-$C_6$-alkyl group. Here, the alkyl radical has the meanings given above under alkyl.

Examples which may be mentioned include benzyl, phenylethyl, phenylpropyl, phenylpentyl, with benzyl being preferred.

Alkoxy

Alkoxy represents a straight-chain or branched saturated alkylether radical of the formula —O-alkyl having generally 1 to 6 ($C_1$-$C_6$-alkoxy), preferably 1 to 4 ($C_1$-$C_4$-alkoxy) and particularly preferably 1 to 3 ($C_1$-$C_3$-alkoxy) carbon atoms.

Examples which may be mentioned as being preferred are:
methoxy, ethoxy, n-propoxy, isopropoxy, tert-butoxy, n-pentyloxy and n-hexyloxy.

Aralkoxy

Aralkoxy is understood to mean a group composed of an optionally substituted aryl radical and a $C_1$-$C_6$-alkoxy group, and bonded to the rest of the molecule via the $C_1$-$C_6$-alkox group. Here, the alkoxy radical has the meanings as defined above.

Examples which may be mentioned include benzyloxy, phenylethyloxy, phenylpropyloxy, phenylpentyloxy, with benzyloxy being preferred.

Alkoxyalkyl

Alkoxyalkyl represents an alkyl radical substituted by alkoxy, for example $C_1$-$C_6$-alkoxy-$C_1$-$C_6$-alkyl- or $C_1$-$C_3$-alkoxy-$C_1$-$C_3$-alkyl-.

Here, $C_1$-$C_6$-alkoxy-$C_1$-$C_6$-alkyl- means that the alkoxyalkyl group is attached via the alkyl moiety to the remainder of the molecule.

Heteroatoms

Heteroatoms are understood to mean oxygen, nitrogen or sulphur atoms.

Aryl

Aryl represents a monovalent mono- or bicyclic aromatic ring system which consists of carbon atoms.

Examples are naphthyl- and phenyl-; preference is given to phenyl- or a phenyl radical.

Heteroaryl

Heteroaryl represents a monovalent mono- or bicyclic aromatic ring system having one, two, three or four heteroatoms which may be identical or different. The heteroatoms may be nitrogen atoms, oxygen atoms or sulphur atoms. The binding valency can be at any aromatic carbon atom or at a nitrogen atom.

A monocyclic heteroaryl radical in accordance with the present invention has 5 or 6 ring atoms. Preference is given to heteroaryl radicals having one or two heteroatoms. Here, particular preference is given to one or two nitrogen atoms.

Heteroaryl radicals having 5 ring atoms include, for example, the rings:
thienyl, thiazolyl, furyl, pyrrolyl, oxazolyl, imidazolyl, pyrazolyl, isoxazolyl, isothiazolyl, oxadiazolyl, triazolyl, tetrazolyl and thiadiazolyl.

Heteroaryl radicals having 6 ring atoms include, for example, the rings:
pyridinyl, pyridazinyl, pyrimidinyl, pyrazinyl and triazinyl.

A bicyclic heteroaryl radical in accordance with the present invention has 9 or 10 ring atoms.

Heteroaryl radicals having 9 ring atoms include, for example, the rings:
phthalidyl, thiophthalidyl, indolyl, isoindolyl, indazolyl, benzothiazolyl, benzofuryl, benzothienyl, benzimidazolyl, benzoxazolyl, azocinyl, indolizinyl, purinyl, indolinyl.

Heteroaryl radicals having 10 ring atoms include, for example, the rings:
isochinolinyl, quinolinyl, quinolizinyl, quinazolinyl, quinoxalinyl, cinnolinyl, phthalazinyl, 1,7- and 1,8-naphthyridinyl, pteridinyl, chromanyl.

Heteroaryl further has the meaning of partially saturated bicyclic aryl and partially saturated bicyclic heteroaryl.

Partially Saturated Bicyclic Aryl and Partially Saturated Bicyclic Heteroaryl

A partially saturated bicyclic aryl radical or heteroaryl radical represents a bicyclic group consisting of a phenyl radical or a monocyclic 5- or 6-membered heteroaryl radical which is condensed via two directly adjacent ring atoms in each case to an aliphatic cyclic radical having 4 to 7 ring atoms which may optionally contain one or two heteroatoms which may be identical or different. The heteroatoms may be nitrogen atoms, oxygen atoms or sulphur atoms.

Partially saturated bicyclic aryl radicals include, for example, the groups: tetrahydronaphthyl, 2,3-dihydro-1,4-benzodioxinyl-, 2,3-dihydro-1-benzofuranyl- and 1,3-benzodioxolyl-.

Partially saturated bicyclic heteroaryl radicals include, for example, the groups: 5,6,7,8-tetrahydroquinolinyl- and 5,6,7,8-tetrahydroisoquinolinyl-.

Heterocycloalkyl

Heterocycloalkyl stands for monocyclic heterocyclyl, heterospirocycloalkyl and bridged heterocycloalkyl.

Monocyclic Heterocyclyl

Monocyclic heterocyclyl- means a non-aromatic monocyclic ring system having one, two or three heteroatoms which may be identical or different. The heteroatoms may be nitrogen atoms, oxygen atoms or sulphur atoms.

A monocyclic heterocyclyl ring according to the present invention may have 3 to 8, preferably 4 to 7, particularly preferably 5 or 6 ring atoms.

By way of example and with preference, the following may be mentioned for monocyclic heterocyclyl radicals having 3 ring atoms:
aziridinyl-.

By way of example and with preference, the following may be mentioned for monocyclic heterocyclyl radicals having 4 ring atoms:
azetidinyl-, oxetanyl-.

By way of example and with preference, the following may be mentioned for monocyclic heterocyclyl radicals having 5 ring atoms:
pyrrolidinyl-, imidazolidinyl-, pyrazolidinyl-, pyrrolinyl-, dioxolanyl- and tetrahydrofuranyl-.

By way of example and with preference, the following may be mentioned for monocyclic heterocyclyl radicals having 6 ring atoms:
piperidinyl-, piperazinyl-, morpholinyl-, dioxanyl-, tetrahydropyranyl- and thiomorpholinyl-.

By way of example and with preference, the following may be mentioned for monocyclic heterocyclyl radicals having 7 ring atoms:
azepanyl-, oxepanyl-, 1,3-diazepanyl-, 1,4-diazepanyl-.

By way of example and with preference, the following may be mentioned for monocyclic heterocyclyl radicals having 8 ring atoms:
oxocanyl-, azocanyl-.

From among the monocyclic heterocyclyl radicals, preference is given to 4- to 7-membered saturated heterocyclyl radicals having up to two heteroatoms from the group consisting of O, N and S.

Particular preference is given to morpholinyl-, piperidinyl- and pyrrolidinyl-.

Spirocycloalkyl and Heterospirocycloalkyl $C_5$-$C_{12}$-Spirocycloalkyl or $C_5$-$C_{12}$-heterospirocycloalkyl where one, two, three or four carbon atoms are replaced by heteroatoms as defined above in any combination is understood to mean a fusion of two saturated ring systems which share one common atom. Examples are spiro[2.2]pentyl, spiro[2.3]hexyl, azaspiro[2.3]hexyl, spiro[3.3]heptyl, azaspiro[3.3]heptyl, oxaazaspiro[3.3]heptyl, thiaazaspiro[3.3]heptyl, oxaspiro[3.3]heptyl, oxazaspiro[3.5]nonyl, oxazaspiro[3.4]octyl, oxazaspiro[5.5]undecyl, diazaspiro[3.3]heptyl, thiazaspiro[3.3]heptyl, thiazaspiro[3.4]octyl, azaspiro[5.5]decyl, and the further homologous spiro[3.4], spiro[4.4], spiro[5.5], spiro[6.6], spiro[2.4], spiro[2.5], spiro[2.6], spiro[3.5], spiro[3.6], spiro[4.5], spiro[4.6] and spiro[5.6] systems including the variants modified by heteroatoms as per the definition. Preference is given to $C_6$-$C_{10}$-heterospirocycloalkyl-, by way of example and with particular preference 2-azaspiro[3.3]heptyl-, 1-thia-6-azaspiro[3.3]heptyl-, 2-thia-6-azaspiro[3.3]heptyl-, 2-oxa-6-azaspiro[3.3]heptyl-, 2,6-diazaspiro[3.3]heptyl-, 2-oxa-6-azaspiro[3.4]octyl-, 2-oxa-6-azaspiro[3.5]nonyl-, 2-oxa-7-azaspiro[3.5]nonyl-, 8-azaspiro[4.5]decyl-, 2,8-diazaspiro[4.5]decyl-, 3-oxa-1,8-diazaspiro[4.5]decyl-.

Bicycloalkyl and Heterobicycloalkyl $C_6$-$C_{12}$-Bicycloalkyl or $C_6$-$C_{12}$-heterobicycloalkyl where one, two, three or four carbon atoms are replaced by heteroatoms as defined above in any combination is understood to mean a fusion of two saturated ring systems which share two directly adjacent atoms. Examples are radicals derived from bicyclo[2.2.0]hexyl-, bicyclo[3.3.0]octyl-, bicyclo[4.4.0]decyl-, bicyclo[5.4.0]undecyl-, bicyclo[3.2.0]heptyl-, bicyclo[4.2.0]octyl-, bicyclo[5.2.0]nonyl-, bicyclo[6.2.0]decyl-, bicyclo[4.3.0]nonyl-, bicyclo[5.3.0]decyl-, bicyclo[6.3.0]undecyl- and bicyclo[5.4.0]undecyl-, including the variants modified by heteroatoms, for example azabicyclo[3.3.0]octyl-, azabicyclo[4.3.0]nonyl-, diazabicyclo[4.3.0]nonyl-, oxazabicyclo[4.3.0]nonyl-, thiazabicyclo[4.3.0]nonyl- or azabicyclo[4.4.0]decyl-, and the further possible combinations as per the definition. Preference is given to $C_6$-$C_{10}$-heterobicycloalkyl-, by way of example and with particular preference perhydrocyclopenta[c]pyrrolyl-, perhydrofuro[3,2-c]pyridinyl-, perhydropyrrolo[1,2-a]pyrazinyl-, perhydropyrrolo[3,4-c]pyrrolyl-.

Preferred examples of $C_6$-$C_{12}$-bicycloalkyl- are perhydronaphthalenyl- (decalinyl-), perhydrobenzoannulenyl-, perhydroazulenyl-, perhydroindanyl-, perhydropentalenyl-.

Bridged Cycloalkyl and Bridged Heterocycloalkyl

A bridged $C_6$-$C_{12}$ ring system such as bridged $C_6$-$C_{12}$-cycloalkyl- or bridged $C_6$-$C_{12}$-heterocycloalkyl- is understood to mean a fusion of at least two saturated rings which share two atoms that are not directly adjacent to one another. This may give rise either to a bridged carbocycle (bridged cycloalkyl-) or to a bridged heterocycle (bridged heterocycloalkyl-) where one, two, three or four carbon atoms are replaced by heteroatoms as defined above in any combination. Examples are bicyclo[2.2.1]heptyl-, azabicyclo[2.2.1]heptyl-, oxazabicyclo[2.2.1]heptyl-, thiazabicyclo[2.2.1]heptyl-, diazabicyclo[2.2.1]heptyl-, bicyclo[2.2.2]octyl-, azabicyclo[2.2.2]octyl-, diazabicyclo[2.2.2]octyl-, oxazabicyclo[2.2.2]octyl-, thiazabicyclo[2.2.2]octyl-, bicyclo[3.2.1]octyl-, azabicyclo[3.2.1]octyl-, diazabicyclo[3.2.1]octyl-, oxazabicyclo[3.2.1]octyl-, thiazabicyclo[3.2.1]octyl-, bicyclo[3.3.1]nonyl-, azabicyclo[3.3.1]nonyl-, diazabicyclo[3.3.1]nonyl-oxazabicyclo[3.3.1]nonyl-, thiazabicyclo[3.3.1]nonyl-, bicyclo[4.2.1]nonyl-, azabicyclo[4.2.1]nonyl-, diazabicyclo[4.2.1]nonyl-, oxazabicyclo[4.2.1]nonyl-, thiazabicyclo[4.2.1]nonyl-, bicyclo[3.3.2]decyl-, azabicyclo[3.3.2]decyl-, diazabicyclo[3.3.2]decyl-, oxazabicyclo[3.3.2]decyl-, thiazabicyclo[3.3.2]decyl- or azabicyclo[4.2.2]decyl- and the further possible combinations according to the definition. Preference is given to bridged $C_6$-$C_{10}$-heterocycloalkyl-, by way of example and with particular preference 2-azabicyclo[2.2.1]heptyl-, 2,5-diazabicyclo[2.2.1]heptyl-, 2-oxa-5-azabicyclo[2.2.1]heptyl-, 8-azabicyclo[3.2.1]octyl-, 8-oxa-3-azabicyclo[3.2.1]octyl-, 3,9-diazabicyclo[4.2.1]nonyl-.

Halogenated Alkyl Groups

A halogenated alkyl group represents an alkyl radical having at least one halogen substituent.

A halo-$C_1$-$C_6$-alkyl radical is an alkyl radical having 1-6 carbon atoms and at least one halogen substituent. If a plurality of halogen substituents is present, these may also be different from one another. Preference is given to fluoro-$C_1$-$C_6$-alkyl, fluoro-$C_1$-$C_4$-alkyl and fluoro-$C_1$-$C_3$-alkyl radicals. Examples which may be mentioned as being likewise preferred are:
the trifluoromethyl, 2,2,2-trifluoroethyl, pentafluoroethyl, 4,4,5,5,5-pentafluoropentyl or 3,3,4,4,5,5,5-heptafluoropentyl group.

Preference is given to perfluorinated alkyl radicals such as trifluoromethyl or pentafluoroethyl.

Further Definitions

The term "transglutamrinase", used interchangeably with "TGase" or "TG", refers to an enzyme capable of cross-linking proteins through an acyl-transfer reaction between the γ-carboxamide group of peptide-bound glutamine and the ε-amino group of a lysine or a structurally related primary amine such as amino pentyl group, e.g. a peptide-bound lysine, resulting in a δ-(γ-glutamyl) lysine isopeptide bond. TGases include, inter alia, bacterial transglutaminase (BTG) such as the enzyme having EC reference EC 2.3.2.13 (protein-glutamine-γ-glutamyltransferase).

The term "acceptor glutamine", when referring to an amino acid residue of an antibody, means a glutamine residue that, under suitable conditions, is recognized by a TGase and can be cross-linked by a TGase through a reaction between the glutamine and a lysine or a structurally related primary amine such as amino pentyl group. Optionally the acceptor glutamine is a surface-exposed glutamine.

By "amino acid modification" or by "mutation" herein is meant an amino acid substitution, insertion, and/or deletion in a polypeptide sequence. The preferred amino acid modification herein is a substitution. By "amino acid substitution" or "substitution" herein is meant the replacement of an amino acid at a given position in a protein sequence with another amino acid. For example, the substitution Y50W refers to a variant of a parent polypeptide, in which the tyrosine at position 50 is replaced with tryptophan. A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

The term "site-specific conjugate" refers to a conjugate of a binder, preferably an antibody, and a moiety, preferably a linker-drug-moiety, wherein the binder is functionalized at one or more defined positions, preferably glutamine residues, of the binder. Transglutanminases (TGase) including bacterial transglutaminase (BTG) (EC 2.3.2.13) display strict specificity in recognition of glutamine protein substrates and can catalyze a "site-specific conjugation".

The term "homogeneous conjugate" or "homogeneous ADC" refers to a composition of site specific conjugates wherein at least 60, 70, 80 or 90% of the binders have the same number of conjugated moieties per binder. In case of an antibody the number of conjugated moieties per antibody might be an even number, preferentially 2 or 4.

Binders

In the broadest sense, the term "binder" is understood to mean a molecule which binds to a target molecule present at a certain target cell population to be addressed by the binder/active compound conjugate. The term binder is to be understood in its broadest meaning and also comprises, for example, lectins, proteins capable of binding to certain sugar chains, and phospholipid-binding proteins. Such binders include, for example, high-molecular weight proteins (binding proteins), polypeptides or peptides (binding peptides), non-peptidic (e.g. aptamers (U.S. Pat. No. 5,270,163) review by Keefe A D., et al., Nat. Rev. Drug Discov. 2010; 9:537-550), or vitamins) and all other cell-binding molecules or substances. Binding proteins are, for example, antibodies including aglycosylated variants, and antibody fragments or antibody mimetics such as, for example, affibodies, adnectins, anticalins, DARPins, avimers, nanobodies (review by Gebauer M. et al., Curr. Opinion in Chem. Biol. 2009; 13:245-255; Nuttall S. D. et al., Curr. Opinion in Pharmacology 2008; 8:608-617). Binding peptides are, for example, ligands of a ligand/receptor pair such as, for example, VEGF of the ligand/receptor pair VEGF/KDR, such as transferrin of the ligand/receptor pair transferrin/transferrin receptor or cytokine/cytokine receptor, such as TNFalpha of the ligand/receptor pair TNFalpha/TNFalpha receptor.

The "binder" comprises an acceptor glutamine residue which can be functionalized by a transglutaminase (TGase) including bacterial transglutaminase (BTG) (EC 2.3.2.13). This acceptor glutamine is either naturally occurring without any alteration of the binder or has been generated. An acceptor glutamine might be genetared via insertion of a glutamine residue at a suitable position (e.g. via fusion to a tag comprising an acceptor glutamine), mutation of a suitable position into a glutamine residue, mutation of an amino acid residue wherein the mutation has the effect that a naturally occurring glutamine residue formerly not recognized by an TGase becomes an acceptor glutamine, or changing the post translational modification (e.g. glycosylation) wherein the change has the effect that a naturally occurring glutamine residue formerly not recognized by an TGase becomes an acceptor glutamine. If the binder is an antibody it comprises an acceptor glutamine, preferentially in the constant region. Such acceptor glutamines can be introduced by mutations of suitable positions into glutamine (e.g. mutation N297Q, Kabat EU numbering) or by generation of deglycosylated or aglycosylated antibodies (e.g. by enzymatic deglycosylation by PNGase F or by mutation of N297X, Kabat EU numbering). In that later case of a deglycosylated or an aglycosylated antibody the glutamine Q295 (Kabat EU numbering) becomes an acceptor glutamine. Highly preferred is an antibody comprising a mutation N297A or N297Q (Kabat EU numbering).

The term "aglycosyl antibody" or "aglycosylated antibody" or "deglycosylated antibody" herein is used to define an antibody or an antibody derivative which comprises an Fc region lacking the glycans attached to the conserved N-linked site in the CH2 domains of the Fc region. Aglycosyl antibodies can for example be prepared by mutation of the heavy chain glycosylation site of N297 (using Kabat EU numbering) or by expressing the antibodies in expression systems lacking glycosylation. Methods for enzymatic deglycosylation of antibodies are well known in the art (e.g. Winkelhake & Nicolson (1976), J Biol Chem. 251(4):1074-80). Deglycosylated antibodies may e.g. be prepared by enzymatic deglycosylation using e.g. PNGase F. In one embodiment of this invention, aglycosyl antibodies may be prepared by expression the antibodies in a prokaryotic host. Suitable prokaryotic hosts for include but are not limited to *E. coli, Bacillus subtilis, Salmonella typhimurium* and various species within the genera *Pseudomonas, Streptomyces,* and *Staphylococcus*. In another embodiment of this invention, aglycosyl antibodies may be achieved using mammalian expression systems together with the glycosylation inhibitor tunicamycin (Nose & Wigzell (1983), Proc Natl Acad Sci USA, 80(21):6632-6). That is, the modification is the prevention of glycosylation at the conserved N-linked site in the $CH_2$ domains of the Fc portion of said antibody.

The literature also discloses various options of homogenous site specific covalent coupling (conjugation) of organic molecules to antibodies. Preference according to the invention is given to the conjugation of the toxophores to the antibody via two or four acceptor glutamine residues of the antibody.

A "target molecule" in the broadest sense is understood to mean a molecule which is present in the target cell population and which may be a protein (for example a receptor of a growth factor) or a non-peptidic molecule (for example a sugar or phospholipid). It is preferably a receptor or an antigen.

The term "extracellular" target molecule describes a target molecule, attached to the cell, which is located at the outside of a cell, or the part of a target molecule which is located at the outside of a cell, i.e. a binder may bind on an intact cell to its extracellular target molecule. An extracellular target molecule may be anchored in the cell membrane or be a component of the cell membrane. The person skilled in the art is aware of methods for identifying extracellular target molecules. For proteins, this may be by determining the transmembrane domain(s) and the orientation of the protein in the membrane. These data are usually deposited in protein databases (e.g. SwissProt).

The term "cancer target molecule" describes a target molecule which is more abundantly present on one or more cancer cell species than on non-cancer cells of the same tissue type. Preferably, the cancer target molecule is selectively present on one or more cancer cell species compared with non-cancer cells of the same tissue type, where selectively describes an at least two-fold enrichment on cancer cells compared to non-cancer cells of the same tissue type (a "selective cancer target molecule"). The use of cancer target molecules allows the selective therapy of cancer cells using the conjugates according to the invention.

The binder can be attached to the linker via a bond. Attachment of the binder can be via a carbonyl function of a glutamine side chain. Preferably such glutamine residues are recognized as substrates by bacterial transglutaminase. Glutamine residues according to the invention may be present in the natural binder or are introduced by methods of molecular biology, e.g. by deglycosylation of the antibody by PNGaseF or by introduction of mutations. According to the invention, the attachment of the binder to the toxophor has only a minor effect on the binding activity of the binder with respect to the target molecule. In a preferred embodiment, the attachment has no effect on the binding affinity and specificity of the binder with respect to the target molecule.

In accordance with the present invention, the term "antibody" is to be understood in its broadest meaning and comprises immunoglobulin molecules, for example intact or modified monoclonal antibodies, aglycosylated antibodies, polyclonal antibodies or multispecific antibodies (e.g. bispecific antibodies). An immunoglobulin molecule preferably comprises a molecule having four polypeptide chains, two heavy chains (H chains) and two light chains (L chains) which are typically linked by disulphide bridges. Each heavy chain comprises a variable domain of the heavy chain (abbreviated VH) and a constant domain of the heavy chain. The constant domain of the heavy chain may, for example, comprise three domains CH1, CH2 and CH3. Each light chain comprises a variable domain (abbreviated VL) and a constant domain. The constant domain of the light chain comprises a domain (abbreviated CL). The VH and VL domains may be subdivided further into regions having hypervariability, also referred to as complementarity determining regions (abbreviated CDR) and regions having low sequence variability (framework region, abbreviated FR). Typically, each VH and VL region is composed of three CDRs and up to four FRs. For example from the amino terminus to the carboxy terminus in the following order: FR1, CDR1, FR2, CDR2, FR3, CDR3, FR4. An antibody may be obtained from any suitable species, e.g. rabbit, llama, camel, mouse or rat. In one embodiment, the antibody is of human or murine origin. An antibody may, for example, be human, humanized or chimeric.

The term "monoclonal" antibody refers to antibodies obtained from a population of substantially homogeneous antibodies, i.e. individual antibodies of the population are identical except for naturally occurring mutations, of which there may be a small number. Monoclonal antibodies recognize a single antigenic binding site with high specificity. The term monoclonal antibody does not refer to a particular preparation process.

The term "intact" antibody refers to antibodies comprising both an antigen-binding domain and the constant domain of the light and heavy chain. The constant domain may be a naturally occurring domain or a variant thereof having a number of modified amino acid positions and can be also aglycosylated.

The term "modified intact" antibody refers to intact antibodies fused via their amino terminus or carboxy terminus by means of a covalent bond (e.g. a peptide bond) with a further polypeptide or protein not originating from an antibody. Furthermore, antibodies may be modified such that, at defined positions, reactive cysteines are introduced to facilitate coupling to a toxophor (see Junutula et al. Nat Biotechnol. 2008 August; 26(8):925-32).

The term "human" antibody refers to antibodies which can be obtained from a human or which are synthetic human antibodies. A "synthetic" human antibody is an antibody which is partially or entirely obtainable in silico from synthetic sequences based on the analysis of human antibody sequences. A human antibody can be encoded, for example, by a nucleic acid isolated from a library of antibody sequences of human origin. An example of such an antibody can be found in Söderlind et al., Nature Biotech. 2000, 18:853-856. Such "human" and "synthetic" antibodies also include aglycosylated variants generated either by deglycosylation by PNGase F or by mutation of N297 (Kabat numbering) of the heavy chain to any amino acid.

The term "humanized" or "chimeric" antibody describes antibodies consisting of a non-human and a human portion of the sequence. In these antibodies, part of the sequences of the human immunoglobulin (recipient) are replaced by sequence portions of a non-human immunoglobulin (donor). In many cases, the donor is a murine immunoglobulin. In the case of humanized antibodies, amino acids of the CDR of the recipient are replaced by amino acids of the donor. Sometimes, amino acids of the framework, too, are replaced by corresponding amino acids of the donor. In some cases the humanized antibody contains amino acids present neither in the recepient nor in the donor, which were introduced during the optimization of the antibody. In the case of chimeric antibodies, the variable domains of the donor immunoglobulin are fused with the constant regions of a human antibody. Such "humanized" and "chimeric" antibodies also include aglycosylated variants generated either by deglycosylation by PNGase F or by mutation of N297 (Kabat numbering) of the heavy chain to any amino acid.

The term complementarity determining region (CDR) as used herein refers to those amino acids of a variable antibody domain which are required for binding to the antigen. Typically, each variable region has three CDR regions referred to as CDR1, CDR2 and CDR3. Each CDR region may embrace amino acids according to the definition of Kabat and/or amino acids of a hypervariable loop defined according to Chotia. The definition according to Kabat comprises, for example, the region from about amino acid position 24-34 (CDR1), 50-56 (CDR2) and 89-97 (CDR3) of the variable light chain and 31-35 (CDR1), 50-65 (CDR2) and 95-102 (CDR3) of the variable heavy chain (Kabat et al., Sequences of Proteins of Immunological Interest, 5th Ed. Public Health Service, National Institutes of Health, Bethesda, Md. (1991)). The definition according to Chotia comprises, for example, the region from about amino acid position 26-32 (CDR1), 50-52 (CDR2) and 91-96 (CDR3) of the variable light chain and 26-32 (CDR1), 53-55 (CDR2) and 96-101 (CDR3) of the variable heavy chain (Chothia and Lesk; J Mol Biol 196: 901-917 (1987)). In some cases, a CDR may comprise amino acids from a CDR region defined according to Kabat and Chotia.

Depending on the amino acid sequence of the constant domain of the heavy chain, antibodies may be categorized into different classes. There are five main classes of intact antibodies: IgA, IgD, IgE, IgG and IgM, and several of these can be divided into further subclasses. (Isotypes), e.g. IgG1, IgG2, IgG3, IgG4, IgA1 and IgA2. The constant domains of the heavy chain, which correspond to the different classes, are referred to as [alpha/α], [delta/δ], [epsilon/ε], [gamma/γ] and [my/μ]. Both the three-dimensional structure and the subunit structure of antibodies are known.

The term "functional fragment" or "antigen-binding antibody fragment" of an antibody/immunoglobulin is defined as a fragment of an antibody/immunoglobulin (e.g. the variable domains of an IgG) which still comprise the antigen binding domains of the antibody/immunoglobulin. The "antigen binding domain" of an antibody typically comprises one or more hypervariable regions of an antibody, for example the CDR, CDR2 and/or CDR3 region. However, the "framework" or "skeleton" region of an antibody may also play a role during binding of the antibody to the antigen. The framework region forms the skeleton of the CDRs. Preferably, the antigen binding domain comprises at least amino acids 4 to 103 of the variable light chain and amino acids 5 to 109 of the variable heavy chain, more preferably amino acids 3 to 107 of the variable light chain and 4 to 111 of the variable heavy chain, particularly preferably the complete variable light and heavy chains, i.e. amino acids 1-109 of the VL and 1 to 113 of the VH (numbering according to WO97/08320).

"Functional fragments" or "antigen-binding antibody fragments" of the invention encompass, non-conclusively, Fab, Fab', F(ab')$_2$ and Fv fragments, diabodies, Single Domain Antibodies (DAbs), linear antibodies, individual chains of antibodies (single-chain Fv, abbreviated to scFv); and multispecific antibodies, such as bi and tri-specific antibodies, for example, formed from antibody fragments C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag. Antibodies other than "multispecific" or "multifunctional" antibodies are those having identical binding sites. Multispecific antibodies may be specific for different epitopes of an antigen or may be specific for epitopes of more than one antigen (see, for example WO 93/17715; WO 92/08802; WO 91/00360; WO 92/05793; Tutt, et al., 1991, J. Immunol. 147:60 69; U.S. Pat. Nos. 4,474,893; 4,714,681; 4,925,648; 5,573,920; 5,601,819; or Kostelny et al., 1992, J. Immunol. 148: 1547 1553). An F(ab')$_2$ or Fab molecule may be constructed such that the number of intermolecular disulphide interactions occurring between the Ch1 and the CL domains can be reduced or else completely prevented.

"Epitopes" refer to protein determinants capable of binding specifically to an immunoglobulin or T cell receptors. Epitopic determinants usually consist of chemically active surface groups of molecules such as amino acids or sugar side chains or combinations thereof, and usually have specific 3-dimensional structural properties and also specific charge properties.

"Functional fragments" or "antigen-binding antibody fragments" may be fused with another polypeptide or protein, not originating from an antibody, via the amino terminus or carboxyl terminus thereof, by means of a covalent bond (e.g. a peptide linkage). Furthermore, antibodies and antigen-binding fragments may be modified by introducing reactive cysteines at defined locations, in order to facilitate coupling to a toxophore (see Junutula et al. Nat Biotechnol. 2008 August; 26(8):925-32).

Polyclonal antibodies can be prepared by methods known to a person of ordinary skill in the art. Monoclonal antibodies may be prepared by methods known to a person of ordinary skill in the art (Kohler and Milstein, Nature, 256, 495-497, 1975). Human and humanized monoclonal antibodies may be prepared by methods known to a person of ordinary skill in the art (Olsson et al., Meth Enzymol. 92, 3-16 or Cabilly et al. U.S. Pat. No. 4,816,567 or Boss et al. U.S. Pat. No. 4,816,397).

A person of ordinary skill in the art is aware of diverse methods for preparing human antibodies and fragments thereof, such as, for example, by means of transgenic mice (N Lonberg and D Huszar, Int Rev Immunol. 1995; 13(1): 65-93) or Phage Display Technologien (Clackson et al., Nature. 1991 Aug. 15; 352(6336):624-8). Antibodies of the invention may be obtained from recombinant antibody libraries consisting for example of the amino acid sequences of a multiplicity of antibodies compiled from a large number of healthy volunteers. Antibodies may also be produced by means of known recombinant DNA technologies. The nucleic acid sequence of an antibody can be obtained by routine sequencing or is available from publically accessible databases.

An "isolated" antibody or binder has been purified to remove other constituents of the cell. Contaminating constituents of a cell which may interfere with a diagnostic or therapeutic use are, for example, enzymes, hormones, or other peptidic or non-peptidic constituents of a cell. A preferred antibody or binder is one which has been purified to an extent of more than 95% by weight, relative to the antibody or binder (determined for example by Lowry method, UV-Vis spectroscopy or by SDS capillary gel electrophoresis). Moreover an antibody which has been purified to such an extent that it is possible to determine at least 15 amino acids of the amino terminus or of an internal amino acid sequence, or which has been purified to homogeneity, the homogeneity being determined by SDS-PAGE under reducing or non-reducing conditions (detection may be determined by means of Coomassie Blau staining or preferably by silver coloration). However, an antibody is normally prepared by one or more purification steps.

The term "specific binding" or "binds specifically" refers to an antibody or binder which binds to a predetermined antigen/target molecule. Specific binding of an antibody or binder typically describes an antibody or binder having an affinity of at least $10^{-7}$ M (as Kd value; i.e. preferably those with smaller Kd values than $10^{-7}$ M), with the antibody or binder having an at least two times higher affinity for the predetermined antigen/target molecule than for a non-specific antigen/target molecule (e.g. bovine serum albumin, or casein) which is not the predetermined antigen/target molecule or a closely related antigen/target molecule. The antibodies preferably have an affinity of at least $10^{-7}$ M (as Kd value; in other words preferably those with smaller Kd values than $10^{-7}$ M), preferably of at least $10^{-8}$ M, more preferably in the range from $10^{-9}$ M to $10^{-11}$ M. The Kd values may be determined, for example, by means of surface plasmon resonance spectroscopy.

The antibody-drug conjugates of the invention likewise exhibit affinities in these ranges. The affinity is preferably not substantially affected by the conjugation of the drugs (in general, the affinity is reduced by less than one order of magnitude, in other words, for example, at most from $10^{-8}$ M to $10^{-7}$ M).

The antibodies used in accordance with the invention are also notable preferably for a high selectivity. A high selectivity exists when the antibody of the invention exhibits an affinity for the target protein which is better by a factor of at least 2, preferably by a factor of 5 or more preferably by a factor of 10, than for an independent other antigen, e.g. human serum albumin (the affinity may be determined, for example, by means of surface plasmon resonance spectroscopy).

Furthermore, the antibodies of the invention that are used are preferably cross-reactive. In order to be able to facilitate and better interpret preclinical studies, for example toxicological or activity studies (e.g. in xenograft mice), it is advantageous if the antibody used in accordance with the invention not only binds the human target protein but also binds the species target protein in the species used for the studies. In one embodiment the antibody used in accordance with the invention, in addition to the human target protein, is cross-reactive to the target protein of at least one further species. For toxicological and activity studies it is preferred to use species of the families of rodents, dogs and non-human primates. Preferred rodent species are mouse and rat. Preferred non-human primates are rhesus monkeys, chimpanzees and long-tailed macaques.

In one embodiment the antibody used in accordance with the invention, in addition to the human target protein, is cross-reactive to the target protein of at least one further species selected from the group of species consisting of mouse, rat and long-tailed macaque (*Macaca fascicularis*). Especially preferred are antibodies used in accordance with the invention which in addition to the human target protein are at least cross-reactive to the mouse target protein. Preference is given to cross-reactive antibodies whose affinity for the target protein of the further non-human species differs by a factor of not more than 50, more particularly by a factor of not more than ten, from the affinity for the human target protein.

Antibodies Directed Against a Cancer Target Molecule

The target molecule towards which the binder, for example an antibody or an antigen-binding fragment thereof, is directed is preferably a cancer target molecule. The term "cancer target molecule" describes a target molecule which is more abundantly present on one or more cancer cell species than on non-cancer cells of the same tissue type. Preferably, the cancer target molecule is selectively present on one or more cancer cell species compared with non-cancer cells of the same tissue type, where selectively describes an at least two-fold enrichment on cancer cells compared to non-cancer cells of the same tissue type (a "selective cancer target molecule"). The use of cancer target molecules allows the selective therapy of cancer cells using the conjugates according to the invention.

Antibodies which are specific against an antigen, for example cancer cell antigen, can be prepared by a person of ordinary skill in the art by means of methods with which he or she is familiar (such as recombinant expression, for example) or may be acquired commercially (as for example from Merck KGaA, Germany). Examples of known commercially available antibodies in cancer therapy are Erbitux® (cetuximab, Merck KGaA), Avastin® (bevacizumab, Roche) and Herceptin® (trastuzumab, Genentech). Trastuzumab is a recombinant humanized monoclonal antibody of the IgG1kappa type which in a cell-based assay (Kd=5 nM) binds the extracellular domains of the human epidermal growth receptor with high affinity. The antibody is produced recombinantly in CHO cells. All these antibodies can be also prepared as aglycosylated variants of these antibodies generated either by deglycosylation by PNGase F or by mutation of N297 (Kabat numbering) of the heavy chain to any amino acid.

In a preferred embodiment, the target molecule is a selective cancer target molecule.

In a particularly preferred embodiment, the target molecule is a protein.

In one embodiment, the target molecule is an extracellular target molecule. In a preferred embodiment, the extracellular target molecule is a protein.

Cancer target molecules are known to those skilled in the art. Examples of these are listed below.

Examples of cancer target molecules are:

(1) EGF receptor (NCBI reference sequence NP_005219.2), SEQ ID NO: 213 (1210 amino acids):

```
>gi|29725609|ref|NP_005219.2|EGFR
receptor precursor [Homo sapiens]
MRPSGTAGAALLALLAALCPASRALEEKKVCQGTSNKLTQLGTFEDHFLS

LQRMFNNCEVVLGNLEITYVQRNYDLSFLKTIQEVAGYVLIALNTVERIP

LENLQIIRGNMYYENSYALAVLSNYDANKTGLKELPMRNLQEILHGAVRF

SNNPALCNVESIQWRDIVSSDFLSNMSMDFQNHLGSCQKCDPSCPNGSCW

GAGEENCQKLTKIICAQQCSGRCRGKSPSDCCHNQCAAGCTGPRESDCLV

CRKFRDEATCKDTCPPLMLYNPTTYQMDVNPEGKYSFGATCVKKCPRNYV

VTDHGSCVRACGADSYEMEEDGVRKCKKCEGPCRKVCNGIGIGEFKDSLS

INATNIKHFKNCTSISGDLHILPVAFRGDSFTHTPPLDPQELDILKTVKE

ITGFLLIQAWPENRTDLHAFENLEIIRGRTKQHGQFSLAVVSLNITSLGL

RSLKEISDGDVIISGNKNLCYANTINWKKLFGTSGQKTKIISNRGENSCK

ATGQVCHALCSPEGCWGPEPRDCVSCRNVSRGRECVDKCNLLEGEPREFV

ENSECIQCHPECLPQAMNITCTGRGPDNCIQCAHYIDGPHCVKTCPAGVM

GENNTLVWKYADAGHVCHLCHPNCTYGCTGPGLEGCPTNGPKIPSIATGM

VGALLLLLVVALGIGLFMRRRHIVRKRTLRRLLQERELVEPLTPSGEAPN

QALLRILKETEFKKIKVLGSGAFGTVYKGLWIPEGEKVKIPVAIKELREA

TSPKANKEILDEAYVMASVDNPHVCRLLGICLTSTVQLITQLMPFGCLLD

YVREHKDNIGSQYLLNWCVQIAKGMNYLEDRRLVHRDLAARNVLVKTPQH

VKITDFGLAKLLGAEEKEYHAEGGKVPIKWMALESILHRIYTHQSDVWSY

GVTVWELMTFGSKPYDGIPASEISSILEKGERLPQPPICTIDVYMIMVKC

WMIDADSRPKFRELHEFSKMARDPQRYLVIQGDERMHLPSPTDSNFYRAL

MDEEDMDDVVDADEYLIPQQGFFSSPSTSRTPLLSSLSATSNNSTVACID

RNGLQSCPIKEDSFLQRYSSDPTGALTEDSIDDTFLPVPEYINQSVPKRP

AGSVQNPVYHNQPLNPAPSRDPHYQDPHSTAVGNPEYLNTVQPTCVNSTF

DSPAHWAQKGSHQISLDNPDYQQDFFPKEAKPNGIFKGSTAENAEYLRVA

PQSSEFIGA
```

The extracellular domain is marked by underlining.

(2) mesothelin (SwissProt reference Q13421-3), SEQ ID NO: 214 (622 amino acids):

```
>sp|Q13421-3|MSLN_HUMAN isoform 2
of mesothelin OS=Homo sapiens GN=MSLN
MALPTARPLLGSCGTPALGSLLFLLFSLGWVQPSRTLAGETGQEAAPLDG

VLANPPNISSLSPRQLLGFPCAEVSGLSTERVRELAVALAQKNVKLSTEQ

LRCLAHRLSEPPEDLDALPLDLLLFLNPDAFSGPQACTRFFSRITKANVD
```

-continued

LLPRGAPERQRLLPAALACWGVRGSLLSEADVRALGGLACDLPGRFVAES

AEVLLPRLVSCPGPLDQDQQEAARAALQGGGPPYGPPSTWSVSTMDALRG

LLPVLGQPIIRSIPQGIVAAWRQRSSRDPSWRQPERTILRPRFRREVEKT

ACPSGKKAREIDESLIFYKKWELEACVDAALLATQMDRVNAIPFTYEQLD

VLKHKLDELYPQGYPESVIQHLGYLFLKMSPEDIRKWNVTSLETLKALLE

VNKGHEMSPQVATLIDRFVKGRGQLDKDTLDTLTAFYPGYLCSLSPEELS

SVPPSSIWAVRPQDLDTCDPRQLDVLYPKARLAFQNMNGSEYFVKIQSFL

GGAPTEDLKALSQQNVSMDLATFMKLRTDAVLPLTVAEVQKLLGPHVEGL

KAEERHRPVRDWILRQRQDDLDTLGLGLQGGIPNGYLVLDLSMQEALSGT

PCLLGPGPVLTVLALLLASTLA where mesothelin is encoded by amino acids 296-598. Amino acids 37-286 are coding for the megakaryocyte-potentiating factor. Mesothelin is anchored in the cell membrane via a GPI anchor and is localized extracellularly.

(3) carboanhydrase IX (SwissProt reference Q16790), SEQ ID NO: 215 (459 amino acids):

>sp|Q16790|CAH9_HUMAN carbonic
anhydrase 9 OS=Homo sapiens GN=CA9 PE=1 SV=2
MAPLCPSPWLPLLIPAPAPGLTVQLLLSLLLLVPVHP<u>QRLPRMQEDSPLG

GGSSGEDDPLGEEDLPSEEDSPREEDPPGEEDLPGEEDLPGEEDLPEVKP

KSEEEGSLKLEDLPTVEAPGDPQEPQNNAHRDKEGDDQSHWRYGGDPPWP

RVSPACAGRFQSPVDIRPQLAAFCPALRPLELLGFQLPPLPELRLRNNGH

SVQLTLPPGLEMALGPGREYRALQLHLHWGAAGRPGSEHTVEGHRFPAEI

HVVHLSTAFARVDEALGRPGGLAVLAAFLEEGPEENSAYEQLLSRLEEIA

EEGSETQVPGLDISALLPSDFSRYFQYEGSLTTPPCAQGVIWTVFNQTVM

LSAKQLHTLSDTLWGPGDSRLQLNFRATQPLNGRVIEASFPAGVDSSPRA

AEPVQLNSCLAAGD</u>ILALVFGLLFAVTSVAFLVQMRRQHRRGTKGGVSYR

PAEVAETGA

The extracellular domain is marked by underlining.

(4) C4.4a (NCBI reference sequence NP_055215.2; synonym LYPD3), SEQ ID NO: 216 (346 amino acids):

>gi|93004088|ref|NP_055215.2|ly6/PLAUR domain-
containing protein 3-precursor [Homo sapiens]
MDPARKAGAQAMIWTAGWLLLLLLRGGAQA<u>LECYSCVQKADDGCSPNKMK

TVKCAPGVDVCTEAVGAVETIHGQFSLAVRGCGSGLPGKNDRGLDLHGLL

AFIQLQQCAQDRCNAKLNLTSRALDPAGNESAYPPNGVECYSCVGLSREA

CQGTSPPVVSCYNASDHVYKGCFDGNVTLTAANVTVSLPVRGCVQDEFCT

RDGVTGPGFTLSGSCCQGSRCNSDLRNKTYFSPRIPPLVRLPPPEPTTVA

STTSVTTSTSAPVRPTSTTKPMPAPTSQTPRQGVEHEASRDEEPRLTGGA

AGHQDRSNSGQYPAKGGPQQPHNKGC</u>VAPTAGLAALLLAVAAGVLL

The mature extracellular domain is marked by underlining.

(5) CD52 (NCBI reference sequence NP_001794.2), SEQ ID NO: 217

>gi|68342030|ref|NP_001794.2|
CAMPATH-1 antigen-precursor [Homo sapiens]
MKRFLFLLLTISLLVMVQIQTGLSGQNDTSQTSSPSASSNISGGIFLFFV

ANAIIHLFCFS (6) Her2 (NCBI reference sequence NP_004439.2), SEQ ID NO: 218

>gi|54792096|ref|NP_004439.2| receptor tyrosine-
protein kinase erbB-2 isoform a [Homo sapiens]
MELAALCRWGLLLALLPPGAASTQVCTGTDMKLRLPASPETHLDMLRHLY

QGCQVVQGNLELTYLPTNASLSFLQDIQEVQGYVLIAHNQVRQVPLQRLR

IVRGTQLFEDNYALAVLDNGDPLNNTTPVTGASPGGLRELQLRSLTEILK

GGVLIQRNPQLCYQDTILWKDIFHKNNQLALTLIDTNRSACHPCSPMCK

GSRCWGESSEDCQSLTRTVCAGGCARCKGPLPTDCCHEQCAAGCTGPKHS

DCLACLHFNHSGICELHCPALVTYNTDTFESMPNPEGRYTFGASCVTACP

YNYLSTDVGSCTLVCPLHNQEVTAEDGTQRCEKCSKPCARVCYGLGMEHL

REVRAVTSANIQEFAGCKKIFGSLAFLPESFDGDPASNTAPLQPEQLQVF

ETLEEITGYLYISAWPDSLPDLSVFQNLQVIRGRILHNGAYSLTLQGLGI

SWLGLRSLRELGSGLALIHHNTHLCFVHTVPWDQLFRNPHQALLHTANRP

EDECVGEGLACHQLCARGHCWGPGPTQCVNCSQFLRGQECVEECRVLQGL

PREYVNARHCLPCHPECQPQNGSVTCFGPEADQCVACAHYKDPPFCVARC

PSGVKPDLSYMPIWKFPDEEGACQPCPINCTHSCVDLDDKGCPAEQRASP

LTSIISAVVGILLVVVLGVVFGILIKRRQQKIRKYTMRRLLQETELVEPL

TPSGAMPNQAQMRILKETELRKVKVLGSGAFGTVYKGIWIPDGENVKIPV

AIKVLRENTSPKANKEILDEAYVMAGVGSPYVSRLLGICLTSTVQLVTQL

MPYGCLLDHVRENRGRLGSQDLLNWCMQIAKGMSYLEDVRLVHRDLAARN

VLVKSPNHVKITDFGLARLLDIDETEYHADGGKVPIKWMALESILRRRFT

HQSDVWSYGVTVWELMTFGAKPYDGIPAREIPDLLEKGERLPQPPICTID

VYMIMVKCWMIDSECRPRFRELVSEFSRMARDPQRFVVIQNEDLGPASPL

DSTFYRSLLEDDDMGDLVDAEEYLVPQQGFFCPDPAPGAGGMVHHRHRSS

STRSGGGDLTLGLEPSEEEAPRSPLAPSEGAGSDVFDGDLGMGAAKGLQS

LPTHDPSPLQRYSEDPTVPLPSETDGYVAPLTCSPQPEYVNQPDVRPQPP

SPREGPLPAARPAGATLERPKTLSPGKNGVVKDVFAFGGAVENPEYLTPQ

GGAAPQPHPPPAFSPAFDNLYYWDQDPPERGAPPSTFKGTPTAENPEYLG

LDVPV (7) CD20 (NCBI reference sequence NP_068769.2), SEQ ID NO: 219

>gi|23110987|ref|NP_068769.2| B-
lymphocyte antigen CD20 [Homo sapiens]
MTTPRNSVNGTFPAEPMKGPIAMQSGPKPLFRRMSSLVGPTQSFFMRESK

TLGAVQIMNGLFHIALGGLLMIPAGIYAPICVTVWYPLWGGIMYIISGSL

LAATEKNSRKCLVKGKMIMNSLSLFAAISGMILSIMDILNIKISHFLKME

-continued
SLNFIRAHTPYINIYNCEPANPSEKNSPSTQYCYSIQSLFLGILSVMLIF

AFFQELVIAGIVENEWKRTCSRPKSNIVLLSAEEKKEQTIEIKEEVVGLT

ETSSQPKNEEDIEIIPIQEEEEEETETNFPEPPQDQESSPIENDSSP (8) the lymphocyte activation antigen CD30 (SwissProt ID P28908), SEQ ID NO: 220

>gi|68348711|ref|NP_001234.2|
tumor necrosis factor receptor superfamily
member 8 isoform 1-precursor [Homo sapiens]
MRVLLAALGLLFLGALRAFPQDRPFEDTCHGNPSHYYDKAVRRCCYRCPM

GLFPTQQCPQRPTDCRKQCEPDYYLDEADRCTACVTCSRDDLVEKTPCAW

NSSRVCECRPGMFCSTSAVNSCARCFFHSVCPAGMIVKFPGTAQKNTVCE

PASPGVSPACASPENCKEPSSGTIPQAKPTPVSPATSSASTMPVRGGTRL

AQEAASKLTRAPDSPSSVGRPSSDPGLSPTQPCPEGSGDCRKQCEPDYYL

DEAGRCTACVSCSRDDLVEKTPCAWNSSRTCECRPGMICATSATNSRARC

VPYPICAAETVTKPQDMAEKDTTFEAPPLGTQPDCNPTPENGEAPASTSP

TQSLLVDSQASKTLPIPTSAPVALSSTGKPVLDAGPVLFWVILVLVVVG

SSAFLLCHRRACRKIRQKLHLCYPVQTSQPKLELVDSRPRRSSTQLRSG

ASVTEPVAEERGLMSQPLMETCHSVGAAYLESLPLQDASPAGGPSSPRDL

PEPRVSTEHTNNKIEKIYIMKADTVIVGTVKAELPEGRGLAGPAEPELEE

ELEADHTPHYPEQETEPPLGSCSDVMLSVEEEGKEDPLPTAASGK (9) the lymphocyte adhesion molecule CD22 (SwissProt ID P20273), SEQ ID NO: 221

>gi|157168355|ref|NP_001762.2| B-cell
receptor CD22 isoform 1-precursor [Homo sapiens]
MHLLGPWLLLLVLEYLAFSDSSKWVFEHPETLYAWEGACVWIPCTYRALD

GDLESFILFHNPEYNKNTSKFDGTRLYESTKDGKVPSEQKRVQFLGDKNK

NCTLSIHPVHLNDSGQLGLRMESKTEKWMERIHLNVSERPFPPHIQLPPE

IQESQEVTLTCLLNFSCYGYPIQLQWLLEGVPMRQAAVTSTSLTIKSVFT

RSELKFSPQWSHHGKIVTCQLQDADGKFLSNDTVQLNVKHTPKLEIKVTP

SDAIVREGDSVTMTCEVSSSNPEYTTVSWLKDGTSLKKQNTFTLNLREVT

KDQSGKYCCQVSNDVGPGRSEEVFLQVQYAPEPSTVQILHSPAVEGSQVE

FLCMSLANPLPTNYTWYHNGKEMQGRTEEKVHIPKILPWHAGTYSCVAEN

ILGTGQRGPGAELDVQYPPKKVTTVIQNPMPIREGDTVTLSCNYNSSNPS

VTRYEWKPHGAWEEPSLGVLKIQNVGWDNTTIACAACNSWCSWASPVALN

VQYAPRDVRVRKIKPLSEIHSGNSVSLQCDFSSSHPKEVQFFWEKNGRLL

GKESQLNFDSISPEDAGSYSCWVNNSIGQTASKAWTLEVLYAPRRLRVSM

SPGDQVMEGKSATLTCESDANPPVSHYTWFDWNNQSLPYHSQKLRLEPVK

VQHSGAYWCQGTNSVGKGRSPLSTLTVYYSPETIGRRVAVGLGSCLAILI

LAICGKLQRRWKRTQSQQGLQENSSGQSFFVRNKKVRRAPLSEGPHSLG

CYNPMMEDGISYTTLRFPEMNIPRTGDAESSEMQRPPPDCDDTVTYSALH

KRQVGDYENVIPDFPEDEGIHYSELIQFGVGERPQAQENVDYVILKH

(10) the myloid cell surface antigen CD33 (SwissProt ID P20138), SEQ ID NO: 222

>gi|130979981|ref|NP_001763.3| myeloid
cell surface antigen CD33 isoform 1-precursor
[Homo sapiens]
MPLLLLLPLLWAGALAMDPNFWLQVQESVTVQEGLCVLVPCTFFHPIPYY

DKNSPVHGYWFREGAIISRDSPVATNKLDQEVQEETQGRFRLLGDPSRNN

CSLSIVDARRRDNGSYFFRMERGSTKYSYKSPQLSVHVTDLTHRPKILIP

GTLEPGHSKNLTCSVSWACEQGTPPIFSWLSAAPTSLGPRTTHSSVLIIT

PRPQDHGTNLTCQVKFAGAGVTTERTIQLNVTYVPQNPTTGIFPGDGSGK

QETRAGVVHGAIGGAGVTALLALCLCLIFFIVKTHRRKAARTAVGRNDTH

PTTGSASPKHQKKSKLHGPTETSSCSGAAPTVEMDEELHYASLNFHGMNP

SKDTSTEYSEVRTQ

(11) the transmembrane glycoprotein NMB (SwissProt ID Q14956), SEQ ID NO: 223

>gi|52694752|ref|NP_001005340.1| transmembrane
glycoprotein NMB isoform a-precursor
[Homo sapiens]
MECLYYFLGFLLLAARLPLDAAKRFHDVLGNERPSAYMREHNQLNGWSSD

ENDWNEKLYPVWKRGDMRWKNSWKGGRVQAVLTSDSPALVGSNITFAVNL

IFPRCQKEDANGNIVYEKNCRNEAGLSADPYVYNWTAWSEDSDGENGTGQ

SHHNVFPDGKPFPHHPGWRRWNFIYVFHTLGQYFQKLGRCSVRVSVNTAN

VTLGPQLMEVTVYRRHGRAYVPIAQVKDVYVVTDQIPVFVTMFQKNDRNS

SDETFLKDLPIMFDVLIHDPSHFLNYSTINYKWSFGDNTGLFVSTNHTVN

HTYVLNGTFSLNLTVKAAAPGPCPPPPPPPRPSKPTPSLATTLKSYDSNT

PGPAGDNPLELSRIPDENCQINRYGHFQATITIVEGILEVNIIQMTDVLM

PVPWPESSLIDFVVTCQGSIPTEVCTIISDPTCEITQNTVCSPVDVDEMC

LLTVRRTFNGSGTYCVNLTLGDDTSLALTSTLISVPDRDPASPLRMANSA

LISVGCLAIFVTVISLLVYKKHKEYNPIENSPGNVVRSKGLSVFLNRAKA

VFFPGNQEKDPLLKNQEFKGVS

(12) the adhesion molecule CD56 (SwissProt ID P13591), SEQ ID NO: 224

>gi|94420689|ref|NP_000606.3| neural cell
adhesion molecule 1 isoform 1 [Homo sapiens]
MLQTKDLIWTLFFLGTAVSLQVDIVPSQGEISVGESKFFLCQVAGDAKDK

DISWFSPNGEKLTPNQQRISVVWNDDSSSTLTIYNANIDDAGIYKCVVTG

EDGSESEATVNVKIFQKLMFKNAPTPQEFREGEDAVIVCDVVSSLPPTII

WKHKGRDVILKKDVRFIVLSNNYLQIRGIKKTDEGTYRCEGRILARGEIN

FKDIQVIVNVPPTIQARQNIVNATANLGQSVTLVCDAEGFPEPTMSWTKD

GEQIEQEEDDEKYIFSDDSSQLTIKKVDKNDEAEYICIAENKAGEQDATI

HLKVFAKPKITYVENQTAMELEEQVTLTCEASGDPIPSITWRTSTRNISS

EEKTLDGHMVVRSHARVSSLTLKSIQYTDAGEYICTASNTIGQDSQSMYL

EVQYAPKLQGPVAVYTWEGN

QVNITCEVFAYPSATISWFRDGQLLPSSNYSNIKIYNTPSASYLEVTPDS

-continued
ENDFGNYNCTAVNRIGQESLEFILVQADTPSSPSIDQVEPYSSTAQVQFD
EPEATGGVPILKYKAEWRAVGEEVWHSKWYDAKEASMEGIVTIVGLKPET
TYAVRLAALNGKGLGEISAASEFKTQPVQGEPSAPKLEGQMGEDGNSIKV
NLIKQDDGGSPIRHYLVRYRALSSEWKPEIRLPSGSDHVMLKSLDWNAEY
EVYVVAENQQGKSKAAHFVFRTSAQPTAIPANGSPTSGLSTGAIVGILIV
IFVLLLVVVDITCYFLNKCGLFMCIAVNLCGKAGPGAKGKDMEEGKAAFS
KDESKEPIVEVRTEEERTPNHDGGKHTEPNETTPLTEPEKGPVEAKPECQ
ETETKPAPAEVKTVPNDATQTKENESKA

(13) the surface molecule CD70 (SwissProt ID P32970), SEQ ID NO: 225

>gi|4507605|ref|NP_001243.1| CD70 antigen
[Homo sapiens]
MPEEGSGCSVRRRPYGCVLRAALVPLVAGLVICLVVCIQRFAQAQQQLPL
ESLGWDVAELQLNHTGPQQDPRLYWQGGPALGRSFLHGPELDKGQLRIHR
DGIYMVHIQVTLAICSSTTASRHHPTTLAVGICSPASRSISLLRLSFHQG
CTIASQRLTPLARGDTLCTNLTGTLLPSRNTDETFFGVQWVRP

(14) the surface molecule CD74 (SwissProt ID P04233), SEQ ID NO: 226

>gi|10835071|ref|NP_004346.1| HLA class II
histocompatibility antigen gamma chain isoform b
[Homo sapiens]
MHRRRSRSCREDQKPVMDDQRDLISNNEQLPMLGRRPGAPESKCSRGALY
TGFSILVTLLLAGQATTAYFLYQQQGRLDKLTVTSQNLQLENLRMKLPKP
PKPVSKMRMATPLLMQALPMGALPQGPMQNATKYGNMTEDHVMHLLQNAD
PLKVYPPLKGSFPENLRHLKNTMETIDWKVFESWMHHWLLFEMSRHSLEQ
KPTDAPPKESLELEDPSSGLGVTKQDLGPVPM

(15) the B-lymphocyte antigen CD19 (SwissProt ID P15391), SEQ ID NO: 227

>gi|296010921|ref|NP_001171569.1| B-lymphocyte
antigen CD19 isoform 1-precursor [Homo sapiens]
MPPPRLLFFLLFLTPMEVRPEEPLVVKVEEGDNAVLQCLKGTSDGPTQQL
TWSRESPLKPFLKLSLGLPGLGIHMRPLAIVVLFIFNVSQQMGGFYLCQP
GPPSEKAWQPGWTVNVEGSGELFRWNVSDLGGLGCGLKNRSSEGPSSPSG
KLMSPKLYVWAKDRPEIWEGEPPCLPPRDSLNQSLSQDLTMAPGSTLWLS
CGVPPDSVSRGPLSWTHVHPKGPKSLLSLELKDDRPARDMWVMETGLLLP
RATAQDAGKYYCHRGNLTMSFHLEITARPVLWHWLLRTGGWKVSAVTLAY
LIFCLCSLVGILHLQRALVLRRKRKRMTDPTRRFFKVTPPPGSGPQNQYG
NVLSLPTPTSGLGRAQRWAAGLGGTAPSYGNPSSDVQADGALGSRSPPGV
GPEEEEGEGYEEPDSEEDSEFYENDSNLGQDQLSQDGSGYENPEDEPLGP
EDEDSFSNAESYENEDEELTQPVARTMDFLSPHGSAWDPSREATSLAGSQ
SYEDMRGILYAAPQLRSIRGQPGPNHEEDADSYENMDNPDGPDPAWGGGG
RMGTWSTR

(16) the surface protein mucin-1 (SwissProt ID P15941), SEQ ID NO: 228

>gi|65301117|ref|NP_002447.4| mucin-1 isoform
1-precursor [Homo sapiens]
MTPGTQSPFFLLLLLTVLTVVTGSGHASSTPGGEKETSATQRSSVPSSTE
KNALSTGVSFFFLSFHISNLQFNSSLEDPSTDYYQELQRDISEMFLQIYK
QGGFLGLSNIKFRPGSVVVQLTLAFREGTINVHDVETQFNQYKTEAASRY
NLTISDVSVSDVPFPFSAQSGAGVPGWGIALLVLVCVLVALAIVYLIALA
VCQCRRKNYGQLDIFPARDTYHPMSEYPTYHTHGRYVPPSSTDRSPYEKV
SAGNGGSSLSYTNPAVAATSANL

(17) the surface protein CD138 (SwissProt ID P18827), SEQ ID NO: 229

>gi|29568086|ref|NP_002988.3| syndecan-1-precursor
[Homo sapiens]
MRRAALWLWLCALALSLQPALPQIVATNLPPEDQDGSGDDSDNFSGSGAG
ALQDITLSQQTPSTWKDTQLLTAIPTSPEPTGLEATAASTSTLPAGEGPK
EGEAVVLPEVEPGLTAREQEATPRPRETTQLPTTHQASTTTATTAQEPAT
SHPHRDMQPGHHETSTPAGPSQADLHTPHTEDGGPSATERAAEDGASSQL
PAAEGSGEQDFTFETSGENTAVVAVEPDRRNQSPVDQGATGASQGLLDRK
EVLGGVIAGGLVGLIFAVCLVGFMLYRMKKKDEGSYSLEEPKQANGGAYQ
KPTKQEEFYA

(18) the integrin alphaV (Genbank Accession No.: NP_002201.1), SEQ ID NO: 230

>gi|4504763|ref|NP_002201.1|integrin
alpha-V isoform 1-precursor [Homo sapiens]
MAFPPRRRLRLGPRGLPLLLSGLLLPLCRAFNLDVDSPAEYSGPEGSYFG
FAVDFFVPSASSRMFLLVGAPKANTTQPGIVEGGQVLKCDWSSTRRCQPI
EFDATGNRDYAKDDPLEFKSHQWFGASVRSKQDKILACAPLYHWRTEMKQ
EREPVGTCFLQDGTKTVEYAPCRSQDIDADGQGFCQGGFSIDFTKADRVL
LGGPGSFYWQGQLISDQVAEIVSKYDPNVYSIKYNNQLATRTAQAIFDDS
YLGYSVAVGDFNGDGIDDFVSGVPRAARTLGMVYIYDGKNMSSLYNFTGE
QMAAYFGFSVAATDINGDDYADVFIGAPLFMDRGSDGKLQEVGQVSVSLQ
RASGDFQTTKLNGFEVFARFGSAIAPLGDLDQDGFNDIAIAAPYGGEDKK
GIVYIFNGRSTGLNAVPSQILEGQWAARSMPPSFGYSMKGATDIDKNGYP
DLIVGAFGVDRAILYRARPVITVNAGLEVYPSILNQDNKTCSLPGTALKV
SCFNVRFCLKADGKGVLPRKLNFQVELLLDKLKQKGAIRRALFLYSRSPS
HSKNMTISRGGLMQCEELIAYLRDESEFRDKLTPITIFMEYRLDYRTAAD
TTGLQPILNQFTPANISRQAHILLDCGEDNVCKPKLEVSVDSDQKKIYIG
DDNPLTLIVKAQNQGEGAYEAELIVSIPLQADFIGVVRNNEALARLSCAF
KTENQTRQVVCDLGNPMKAGTQLLAGLRFSVHQQSEMDTSVKFDLQIQSS
NLFDKVSPVVSHKVDLAVLAAVEIRGVSSPDHIFLPIPNWEHKENPETEE
DVGPVVQHIYELRNNGPSSFSKAMLHLQWPYKYNNNTLLYILHYDIDGPM
NCTSDMEINPLRIKISSLQTTEKNDTVAGQGERDHLITKRDLALSEGDIH -continued
TLGCGVAQCLKIVCQVGRLDRGKSAILYVKSLLWTETFMNKENQNHSYSL

KSSASFNVIEFPYKNLPIEDITNSTLVTTNVTWGIQPAPMPVPVWVIILA

VLAGLLLLAVLVFVMYRMGFFKRVRPPQEEQEREQLQPHENGEGNSET

(19) the teratocarcinoma-derived growth factor 1 protein TDGF1 (Genbank Accession No.:

```
>gi|4507425|ref|NP_003203.1| teratocarcinoma-
derived growth factor 1 isoform 1-precursor
[Homo sapiens]
MDCRKMARFSYSVIWIMAISKVFELGLVAGLGHQEFARPSRGYLAFRDDS

IWPQEEPAIRPRSSQRVPPMGIQHSKELNRTCCLNGGTCMLGSFCACPPS

FYGRNCEHDVRKENCGSVPHDTWLPKKCSLCKCWHGQLRCFPQAFLPGCD

GLVMDEHLVASRTPELPPSARTTTFMLVGICLSIQSYY
```

(20) the prostate-specific membrane antigen PSMA (Swiss Prot ID: Q04609), SEQ ID NO: 232

```
>gi|4758398|ref|NP_004467.1| glutamate
carboxypeptidase 2 isoform 1 [Homo sapiens]
MWNLLHETDSAVATARRPRWLCAGALVLAGGFFLLGFLFGWFIKSSNEAT

NITPKHNMKAFLDELKAENIKKFLYNFTQIPHLAGTEQNFQLAKQIQSQW

KEFGLDSVELAHYDVLLSYPNKTHPNYISIINEDGNEIFNTSLFEPPPPG

YENVSDIVPPFSAFSPQGMPEGDLVYVNYARTEDFFKLERDMKINCSGKI

VIARYGKVFRGNKVKNAQLAGAKGVILYSDPADYFAPGVKSYPDGWNLPG

GGVQRGNILNLNGAGDPLTPGYPANEYAYRRGIAEAVGLPSIPVHPIGYY

DAQKLLEKMGGSAPPDSSWRGSLKVPYNVGPGFTGNFSTQKVKMHIHSTN

EVTRIYNVIGTLRGAVEPDRYVILGGHRDSWVFGGIDPQSGAAVVHEIVR

SFGTLKKEGWRPRRTILFASWDAEEFGLLGSTEWAEENSRLLQERGVAYI

NADSSIEGNYTLRVDCTPLMYSLVHNLTKELKSPDEGFEGKSLYESWTKK

SPSPEFSGMPRISKLGSGNDFEVFFQRLGIASGRARYTKNWETNKFSGYP

LYHSVYETYELVEKFYDPMFKYHLTVAQVRGGMVFELANSIVLPFDCRDY

AVVLRKYADKIYSISMKHPQEMKTYSVSFDSLFSAVKNFTEIASKFSERL

QDFDKSNPIVLRMMNDQLMFLERAFIDPLGLPDRPFYRHVIYAPSSHNKY

AGESFPGIYDALFDIESKVDPSKAWGEVKRQIYVAAFTVQAAAETLSEVA
```

(21) the tyrosine protein kinase EPHA2 (Swiss Prot ID: P29317), SEQ ID NO: 233

```
>gi|32967311|ref|NP_004422.2| ephrin
type-A receptor 2-precursor [Homo sapiens]
MELQAARACFALLWGCALAAAAAAQGKEVVLLDFAAAGGELGWLTHPYGK

GWDLMQNIMNDMPIYMYSVCNVMSGDQDNWLRTNWVYRGEAERIFIELKF

TVRDCNSFPGGASSCKETFNLYYAESDLDYGTNFQKRLFTKIDTIAPDEI

TVSSDFEARHVKLNVEERSVGPLTRKGFYLAFQDIGACVALLSVRVYYKK

CPELLQGLAHFPETIAGSDAPSLATVAGTCVDHAVVPPGGEEPRMHCAVD

GEWLVPIGQCLCQAGYEKVEDACQACSPGFFKFEASESPCLECPEHTLPS

PEGATSCECEEGFFRAPQDPASMPCTRPPSAPHYLTAVGMGAKVELRWTP

PQDSGGREDIVYSVTCEQCWPESGECGPCEASVRYSEPPHGLTRTSVTVS

DLEPHMNYTFTVEARNGVSGLVTSRSFRTASVSINQTEPPKVRLEGRSTT

SLSVSWSIPPPQQSRVWKYEVTYRKKGDSNSYNVRRTEGFSVTLDDLAPD

TTYLVQVQALTQEGQGAGSKVHEFQTLSPEGSGNLAVIGGVAVGVVLLLV

LAGVGFFIHRRRKNQRARQSPEDVYFSKSEQLKPLKTYVDPHTYEDPNQA

VLKFTTEIHPSCVTRQKVIGAGEFGEVYKGMLKTSSGKKEVPVAIKTLKA

GYTEKQRVDFLGEAGIMGQFSHHNIIRLEGVISKYKPMMIITEYMENGAL

DKFLREKDGEFSVLQLVGMLRGIAAGMKYLANMNYVHRDLAARNILVNSN

LVCKVSDFGLSRVLEDDPEATYTTSGGKIPIRWTAPEAISYRKFTSASDV

WSFGIVMWEVMTYGERPYWELSNHEVMKAINDGFRLPTPMDCPSAIYQLM

MQCWQQERARRPKFADIVSILDKLIRAPDSLKTLADFDPRVSIRLPSTSG

SEGVPFRTVSEWLESIKMQQYTEHFMAAGYTAIEKVVQMTNDDIKRIGVR

LPGHQKRIAYSLLGLKDQVNTVGIPI
```

(22) the surface protein SLC44A4 (Genbank Accession No: NP_001171515), SEQ ID NO: 234

```
>gi|295849282|ref|NP_001171515.1| choline
transporter-like protein 4 isoform 2
[Homo sapiens]
MGGKQRDEDDEAYGKPVKYDPSFRGPIKNRSCTDVICCVLFLLFILGYIV

VGIVAWLYGDPRQVLYPRNSTGAYCGMGENKDKPYLLYFNIFSCILSSNI

ISVAENGLQCPTPQTVITSLQQELCPSFLLPSAPALGRCFPWTNVTPPAL

PGITNDTTIQQGISGLIDSLNARDISVKIFEDFAQSWYWILVALGVALVL

SLLFILLLRLVAGPLVLVLILGVLGVLAYGIYYCWEEYRVLRDKGASISQ

LGFTTNLSAYQSVQETWLAALIVLAVLEAILLLMLIFLRQRIRIAIALLK

EASKAVGQMMSTMFYPLVTFVLLLICIAYWAMTALYLATSGQPQYVLWAS

NISSPGCEKVPINTSCNPTAHLVNSSCPGLMCVFQGYSSKGLIQRSVFNL

QIYGVLGLFWTLNWVLALGQCVLAGAFASFYWAFHKPQDIPTFPLISAFI

RTLRYHTGSLAFGALILTLVQIARVILEYIDHKLRGVQNPVARCIMCCFK

CCLWCLEKFIKFLNRNAYIMIAIYGKNFCVSAKNAFMLLMRNIVRVVVLD

KVTDLLLFFGKLLVVGGVGVLSFFFFSGRIPGLGKDFKSPHLNYYWLPIM

TSILGAYVIASGFFSVFGMCVDTLFLCFLEDLERNNGSLDRPYYMSKSLL

KILGKKNEAPPDNKKRKK
```

(23) the surface protein BMPR1B (SwissProt: 000238)
(24) the transport protein SLC7A5 (SwissProt: Q01650)
(25) the epithelial prostate antigen STEAP1 (SwissProt: Q9UHE8)
(26) the ovarial carcinoma antigen MUC16 (SwissProt: Q8WXI7)
(27) the transport protein SLC34A2 (SwissProt: O95436)
(28) the surface protein SEMA5b (SwissProt: Q9P283)
(29) the surface protein LYPD1 (SwissProt: Q8N2G4)
(30) the endothelin receptor type B EDNRB (SwissProt: P24530)
(31) the ring finger protein RNF43 (SwissProt: Q68DV7)
(32) the prostate carcinoma-associated protein STEAP2 (SwissProt: Q8NFT2)
(33) the cation channel TRPM4 (SwissProt: Q8TD43)
(34) the complement receptor CD21 (SwissProt: P20023)
(35) the B-cell antigen receptor complex-associated protein CD79b (SwissProt: P40259)

(36) the cell adhesion antigen CEACAM6 (SwissProt: P40199)

(37) the dipeptidase DPEP1 (SwissProt: P16444)

(38) the interleukin receptor IL20Ralpha (SwissProt: Q9UHF4)

(39) the proteoglycan BCAN (SwissProt: Q96GW7)

(40) the ephrin receptor EPHB2 (SwissProt: P29323)

(41) the prostate stem cell-associated protein PSCA (Genbank Accession No: NP_005663.2)

(42) the surface protein LHFPL3 (SwissProt: Q86UP9)

(43) the receptor protein TNFRSF13C (SwissProt: Q96RJ3)

(44) the B-cell antigen receptor complex-associated protein CD79a (SwissProt: P11912)

(45) the receptor protein CXCR5 (SwissProt: P32302)

(46) the ion channel P2X5 (SwissProt: Q93086)

(47) the lymphocyte antigen CD180 (SwissProt: Q99467)

(48) the receptor protein FCRL1 (SwissProt: Q96LA6)

(49) the receptor protein FCRL5 (SwissProt: Q96RD9)

(50) the MHC class II molecule Ia antigen HLA-DOB (Genbank Accession No: NP_002111.1)

(51) the T-cell protein VTCN1 (SwissProt: Q7Z7D3)

(52) TWEAKR (SEQ ID NO: 169 (protein); SEQ ID NO: 170 (DNA).

(53) the lymphocyte antigen CD37 (Swiss Prot: P11049)

(54) the FGF receptor 2; FGFR2 (Gene ID: 2263; official symbol: FGFR2). The FGFR2 receptor occurs in different splice variants (alpha, beta, IIIb, IIIc). All splice variants may act as target molecule.

(55) the transmembrane glycoprotein B7H3 (CD276; Gene ID: 80381.

(56) the B cell receptor BAFFR (CD268; Gene ID: 115650)

(57) the receptor protein ROR 1 (Gene ID: 4919)

(58) the surface receptor IL3RA (CD123; Gene ID: 3561)

(59) the CXC chemokine receptor CXCR5 (CD185; Gene ID 643)

(60) the receptor protein syncytin (Gene ID 30816)

In a preferred subject matter of the invention, the cancer target molecule is selected from the group consisting of the cancer target molecules (1)-(60), in particular (1), (6) and (52).

In a further particularly preferred subject matter of the invention, the binder binds to an extracellular cancer target molecule which is selected from the group consisting of the cancer target molecules (1)-(60), in particular (1), (6) and (52).

In a further particularly preferred subject matter of the invention, the binder binds specifically to an extracellular cancer target molecule which is selected from the group consisting of the cancer target molecules (1)-(60), in particular (1), (6) and (52). In a preferred embodiment the binder is, after binding to its extracellular target molecule on the target cell, internalized by the target cell as a result of the binding. This causes the binder/active compound conjugate, which may be an immunoconjugate or an ADC, to be taken up by the target cell. The binder is then processed, preferably intracellularly, with preference lysosomally.

In one embodiment the binder is a binding protein. In a preferred embodiment the binder is an antibody, an aglycosylated antibody, an antigen-binding antibody fragment, a multispecific antibody or an antibody mimetic.

Preferred antibody mimetics are affibodies, adnectins, anticalins, DARPins, avimers, or nanobodies. Preferred multispecific antibodies are bispecific and trispecific antibodies.

In a preferred embodiment the binder is an antibody or an antigen-binding antibody fragment, more preferably an isolated antibody or an isolated antigen-binding antibody fragment.

Preferred antigen-binding antibody fragments are Fab, Fab', F(ab')$_2$ and Fv fragments, diabodies, DAbs, linear antibodies and scFv. Particularly preferred are Fab, diabodies and scFv.

In a particularly preferred embodiment the binder is an antibody. Particularly preferred are monoclonal antibodies or antigen-binding antibody fragments thereof. Further particularly preferred are human, humanized or chimeric antibodies or antigen-binding antibody fragments thereof.

Antibodies or antigen-binding antibody fragments which bind cancer target molecules may be prepared by a person of ordinary skill in the art using known processes, such as, for example, chemical synthesis or recombinant expression. Binders for cancer target molecules may be acquired commercially or may be prepared by a person of ordinary skill in the art using known processes, such as, for example, chemical synthesis or recombinant expression. Further processes for preparing antibodies or antigen-binding antibody fragments are described in WO 2007/070538 (see page 22 "Antibodies"). The person skilled in the art knows how processes such as phage display libraries (e.g. Morphosys HuCAL Gold) can be compiled and used for discovering antibodies or antigen-binding antibody fragments (see WO 2007/070538, page 24 ff and AK Example 1 on page 70, AK Example 2 on page 72). Further processes for preparing antibodies that use DNA libraries from B cells are described for example on page 26 (WO 2007/070538). Processes for humanizing antibodies are described on page 30-32 of WO2007070538 and in detail in Queen, et al., Pros. Natl. Acad. Sci. USA 86:10029-10033, 1989 or in WO 90/0786. Furthermore, processes for the recombinant expression of proteins in general and of antibodies in particular are known to the person skilled in the art (see, for example, in Berger and Kimrnel (Guide to Molecular Cloning Techniques, Methods in Enzymology, Vol. 152, Academic Press, Inc.); Sambrook, et al., (Molecular Cloning: A Laboratory Manual, (Second Edition, Cold Spring Harbor Laboratory Press; Cold Spring Harbor, N.Y.; 1989) Vol. 1-3); Current Protocols in Molecular Biology, (F. M. Ausabel et al. [Eds.], Current Protocols, Green Publishing Associates, Inc./John Wiley & Sons, Inc.); Harlow et al., (Monoclonal Antibodies: A Laboratory Manual, Cold Spring Harbor Laboratory Press (1988, Paul [Ed.]); Fundamental Immunology, (Lippincott Williams & Wilkins (1998)); and Harlow, et al., (Using Antibodies: A Laboratory Manual, Cold Spring Harbor Laboratory Press (1998)). The person skilled in the art knows the corresponding vectors, promoters and signal peptides which are necessary for the expression of a protein/antibody. Commonplace processes are also described in WO 2007/070538 on pages 41-45. Processes for preparing an IgG1 antibody are described for example in WO 2007/070538 in Example 6 on page 74 ff. Processes which allow the determination of the internalization of an antibody after binding to its antigen are known to the skilled person and are described for example in WO 2007/070538 on page 80. The person skilled in the art is able to use the processes described in WO 2007/070538 that have been used for preparing carboanhydrase IX (Mn) antibodies in analogy for the preparation of antibodies with different target molecule specificity.

Anti-EGFR Antibodies

Examples of antibodies which bind the cancer target molecules EGFR are cetuximab (INN number 7906), panitumumab (INN number 8499) and nimotuzumab (INN number 8545). Cetuximab (Drug Bank Accession Number DB00002) is a chimeric anti-EGFR1 antibody which is produced in SP2/0 mouse myeloma cells and is sold by ImClone Systems Inc/Merck KgaA/Bristol-Myers Squibb Co. Cetuximab is indicated for the treatment of metastasizing, EGFR expressing, colorectal carcinoma with wild type K-Ras gene. It has an affinity of $10^{-10}$M.

Sequence:

```
Cetuximab Light Chain (kappa), SEQ ID NO: 235:
DILLTQSPVILSVSPGERVSFSCRASQSIGTNIHWYQQRTNGSPRLLIKY

ASESISGIPSRFSGSGSGTDFTLSINSVESEDIADYYCQQNNNWPTTFGA

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Cetuximab Heavy Chain, SEQ ID NO: 236:
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK
```

Panitumumab (INN number 8499) (Drug Bank Accession Number DB01269) is a recombinant monoclonal human IgG2 antibody which binds specifically to the human EGF receptor 1 and is sold by Abgenix/Amgen. Panitumumab originates from the immunization of transgenic mice (Xeno-Mouse). These mice are capable of producing human immunoglobulin (light and heavy chains). A specific B-cell clone was selected which produces antibodies against EGFR, and this clone was immortalized with CHO cells (Chinese hamster ovary cells). These cells are now used for the production of a 100% human antibody. Panitumumab is indicated for the treatment of EGFR-expressing, metastasizing colorectal carcinoma, which is resistant to chemotherapeutic treatment with fluoropyrimidine, oxaliplatin and irinotecan. It has an affinity of $10^{-11}$M.

Sequence:

```
Panitumumab Light Chain (kappa), SEQ ID NO: 237:
DIQMTQSPSSLSASVGDRVTITCQASQDISNYLNWYQQKPGKAPKLLIYD

ASNLETGVPSRFSGSGSGTDFTFTISSLQPEDIATYFCQHFDHLPLAFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Panitumumab Heavy Chain, SEQ ID NO: 238:
QVQLQESGPGLVKPSETLSLTCTVSGGSVSSGDYYWTWIRQSPGKGLEWI

GHIYYSGNTNYNPSLKSRLTISIDTSKTQFSLKLSSVTAADTAIYYCVRD
```

-continued
```
RVTGAFDIWGQGTMVTVSSASTKGPSVFPLAPCSRSTSESTAALGCLVKD

YFPEPVTVSWNSGALTSGVHTFPAVLQSSGLYSLSSVVTVPSSNFGTQTY

TCNVDHKPSNTKVDKTVERKCCVECPPCPAPPVAGPSVFLFPPKPKDTLM

ISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLP

PSREEMTKNQVSLTCLVKGFYPSDIAVEWESNGQPENNYKTTPPMLDSDG

SFFLYSKLTVDKSRWQQGNVFSCSVMHEALHNHYTQKSLSLSPG
```

Nimotuzumab (INN number 8545) (EP 00586002, EP 00712863) is a humanized monoclonal IgG1 antibody which binds specifically to the human EGF receptor 1 and is sold by YM BioScienecs Inc. (Mississauga Canada). It is produced in non-secreting NSO cells (mammalian cell line). Nimotuzumab is approved for the treatment of head-and-neck tumours, highly malignant astrocytoma and glioblastoma multiforms (not in EU and US) and pancreatic carcinoma (Orphan drug, EMA). It has an affinity of $10^{-8}$M.

```
Nimotuzumab Light Chain, SEQ ID NO: 239:
DIQMTQSPSSLSASVGDRVTITCRSSQNIVHSNGNTYLDWYQQTPGKAPK

LLIYKVSNRFSGVPSRFSGSGSGTDFTFTISSLQPEDIATYYCFQYSHVP

WTFGQGTKLQITRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

Nimotuzumab Heavy Chain, SEQ ID NO: 240:
QVQLQQSGAEVKKPGSSVKVSCKASGYTFTNYYIYWVRQAPGQGLEWIGG

INPTSGGSNFNEKFKTRVTITADESSTTAYMELSSLRSEDTAFYFCTRQG

LWFDSDGRGFDFWGQGTTVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLS

PGK
```

Further embodiments of EGFR antibodies are as follows:
- Zalutumumab/2F8/HuMax-EGFr, from Genmab A/S (WO 02/100348, WO 2004/056847, INN number 8605)
- Necitumumab/11F8, ImClone/IMC-11F8, from ImClone Systems Inc. [Eli Lilly & Co] (WO 2005/090407 (EP 01735348-A1, US 2007/0264253-A1, U.S. Pat. No. 7,598,350, WO 2005/090407-A1), INN number 9083)
- Matuzumab/anti-EGFR MAb, Merck KGaA/anti-EGFR MAb, Takeda/EMD 72000/EMD-6200/EMD-72000 and EMD-55900/MAb 425/monoclonal antibody 425, from Merck KGaA/Takeda (WO 92/15683, INN number 8103 (Matuzumab))
- RG-7160/GA-201/GA201/R-7160/$R^{7160}$/RG7160/RO-4858696/RO-5083945/RO4858696/RO5083945, from Glycart Biotechnology AG (Roche Holding AG) (WO 2010/112413-A1, WO 2010/115554)

GT-MAB 5.2-GEX/CetuGEX, from Glycotope GmbH (WO 2008/028686-A2 (EP 01900750-A1, EP 01911766-A1, EP 02073842-A2, US 2010/0028947-A1)

ISU-101, from Isu Abxis Inc (ISU Chemical Co Ltd)/ Scancell (WO 2008/004834-A1)

ABT-806/mAb-806/ch-806/anti-EGFR monoclonal antibody 806, from Ludwig Institute for Cancer Research/Abbott/Life Science Pharmaceuticals (WO 02/092771, WO 2005/081854 and WO 2009/023265)

SYM-004 (consists of two chimeric IgG1 antibodies (992 and 1024)), from Symphogen A/S (WO 2010/022736-A2)

MR1-1/MR1-1KDEL, from IVAX Corp (Teva Pharmaceutical Industries Ltd) (Duke University), (patent: WO2001/062931-A2)

Antibody against the deletion mutant, EGFRvIII, from Amgen/Abgenix (WO 2005/010151, U.S. Pat. No. 7,628,986)

SC-100, from Scancell Ltd (WO 01/088138-A1)

MDX-447/EMD 82633/BAB-447/H 447/MAb, EGFR, Medarex/Merck KgaA, from Bristol-Myers Squibb (US)/Merck KGaA (DE)/Takeda (JP), (WO 91/05871, WO 92/15683)

anti-EGFR-Mab, from Xencor (WO 2005/056606)

DXL-1218/anti-EGFR monoclonal antibody (cancer), InNexus, from InNexus Biotechnology Inc, Pharmaprojects PH048638

In a preferred embodiment, the anti-EGFR antibodies are selected from the group consisting of cetuximab, panitumumab, nimotuzumab, zalutumumab, necitumumab, matuzumab, RG-716, GT-MAB 5.2-GEX, ISU-101, ABT-806, SYM-004, MR1-1, SC-100, MDX-447 and DXL-1218.

In a particularly preferred embodiment the anti-EGFR antibodies are selected from the group consisting of cetuximab, panitumumab, nimotuzumab, zalutumumab, necitumumab and matuzumab.

The person skilled in the art knows of processes which can be used to prepare further antibodies, from the CDR regions of the abovementioned antibodies by means of sequence variations, these further antibodies having a similar or better affinity and/or specificity for the target molecule. Furthermore the person skilled in the art knows of processes which can be used to prepare further antibodies, from the CDR regions of the abovementioned antibodies by means of sequence variations, these further antibodies are aglycosylated and/or engineered to contain one or more acceptor glutamine residues for transglutaminase (TGase) catalyzed reactions.

In a further embodiment, the anti-EGFR antibodies or antigen-binding antibody fragments are selected from the group consisting of
antibodies or antigen-binding antibody fragments comprising the three CDR regions of the light chain and the three CDR regions of the heavy chain of one of the following antibodies: cetuximab, panitumumab, nimotuzumab, zalutumumab, necitumumab, matuzumab, RG-716, GT-MAB 5.2-GEX, ISU-101, ABT-806, SYM-004, MR1-1, SC-100, MDX-447 and DXL-1218.

In a further embodiment, the anti-EGFR antibodies or antigen-binding antibody fragments are selected from the group consisting of
antibodies or antigen-binding antibody fragments comprising three CDR regions of the light chain and the three CDR regions of the heavy chain of one of the following antibodies: cetuximab, panitumumab, nimotuzumab, zalutumumab, necitumumab, matuzumab. By reference, these antibodies and antigen-binding fragments thereof are incorporated herein, and they can be used in the context of the present invention.

Anti-Carboanhydrase IX Antibodies

Examples of antibodies which bind the cancer target molecule carbonahydrase IX are described in WO 2007/070538-A2 (e.g. Claims 1-16).

In a preferred embodiment the anti-carboanhydrase IX antibodies or antigen-binding antibody fragments are selected from the group consisting of anti-carboanhydrase IX antibodies or antigen-binding antibody fragments 3ee9 (Claim 4 (a) in WO 2007/070538-A2), 3ef2 (Claim 4 (b) in WO2007/070538-A2), 1e4 (Claim 4 (c) in WO 2007/070538-A2), 3a4 (Claim 4 (d) in WO 2007/070538-A2), 3ab4 (Claim 4 (e) in WO 2007/070538-A2), 3ah10 (Claim 4 (f) in WO 2007/070538-A2), 3bb2 (Claim 4 (g) in WO 2007/070538-A2), 1aa1 (Claim 4 (h) in WO 2007/070538-A2), 5a6 (Claim 4 (i) in WO 2007/070538-A2) and 5aa3 (Claim 4 (j) in WO 2007/070538-A2).

Anti-C4.4a Antibodies:

According to the invention, use may be made of C4.4a antibodies.

Examples of C4.4a antibodies and antigen-binding fragments are described in WO 2012/143499 A2. By reference, all antibodies of WO 2012/143499 A2 are hereby incorporated into the description of the present invention, and they can be used in the present invention. The sequences of the antibodies are given in Table 1 of WO 2012/143499 A2, where each row shows the respective CDR amino acid sequences of the variable light chain or the variable heavy chain of the antibody listed in column 1.

In one embodiment, the anti-C4.4a antibodies or antigen-binding antibody fragments thereof are, after binding to a cell expressing C4.4a, internalized by the cell.

In a further embodiment, the anti-C4.4a antibodies or antigen-binding antibody fragments comprise at least one, two or three CDR amino acid sequences of an antibody listed in Table 1 of WO 2012/143499 A2 or Table 2 of WO 2012/143499 A2. Preferred embodiments of such antibodies are likewise listed in WO 2012/143499 A2 and incorporated herein by reference.

Anti-HER2 Antibodies:

An example of an antibody binding to the cancer target molecule Her2 is trastuzumab (Genentech). Trastuzumab is a humanized antibody used inter alia for the treatment of breast cancer.

Further examples of antibodies binding to HER2 are, in addition to trastuzumab (INN 7637, CAS No.: RN: 180288-69-1) and Pertuzumab (CAS No.: 380610-27-5), the antibodies disclosed in WO 2009/123894-A2, WO 200/8140603-A2 or in WO 2011/044368-A2. An example of an anti-HER2 conjugate is trastuzumab-emtansine (INN-No. 9295). By reference, these antibodies and antigen-binding fragments thereof are incorporated herein, and they can be used in the context of the present invention.

Anti-CD20 Antibodies:

An example of an antibody binding to the cancer target molecule CD20 is rituximab (Genentech).

Rituximab (CAS Number: 174722-31-7) is a chimeric antibody used for the treatment of non-Hodgkin lymphoma. By reference, these antibodies and antigen-binding fragments thereof are incorporated herein, and they can be used in the context of the present invention.

Anti-CD52 Antibodies:

An example of an antibody binding to the cancer target molecule CD52 is alemtuzumab (Genzyme). Alemtuzumab (CAS Number: 216503-57-0) is a humanized antibody used for the treatment of chronic lymphocytic leukaemia. By reference, these antibodies and antigen-binding fragments thereof are incorporated herein, and they can be used in the context of the present invention.

Anti-Mesothelin Antibodies:

Examples of anti-mesothelin antibodies are described, for example, in WO 2009/068204. By reference, all antibodies described in WO 2009/068204 are hereby incorporated into the present description, such that these antibodies can be used in the context of the invention disclosed herein.

The anti-mesothelin antibodies used in accordance with the invention are also notable preferably for an invariant binding to mesothelin. Invariant binding is characterized, for example, in that the antibody used in accordance with the invention binds to an epitope of mesothelin which cannot be masked by a further extracellular protein. Such a further extracellular protein is, for example, the protein ovarian cancer antigen 125 (CA125). Antibodies which are used with preference are characterized in that their binding to mesothelin is not blocked by CA125.

Anti-CD30 Antibodies

Examples of antibodies which bind the cancer target molecule CD30 and can be used for the treatment of cancer, for example Hodgkin lymphoma, are brentuximab, iratumumab and antibodies disclosed in WO 2008/092117, WO 2008/036688 or WO 2006/089232. An example of an anti-CD30 conjugate is brentuximab vedotin (INN No. 9144). By reference, these antibodies and antigen-binding fragments thereof are incorporated herein, and they can be used in the context of the present invention.

Anti-CD22 Antibodies

Examples of antibodies which bind the cancer target molecule CD22 and can be used for the treatment of cancer, for example lymphoma, are inotuzumab and epratuzumab. Examples of anti-CD22 conjugates are inotuzumab ozagamycin (INN No. 8574) or anti-CD22-MMAE and anti-CD22-MC-MMAE (CAS RN: 139504-50-0 and 474645-27-7, respectively). By reference, these antibodies and antigen-binding fragments thereof are incorporated herein, and they can be used in the context of the present invention.

Anti-CD33 Antibodies

Examples of antibodies which bind the cancer target molecule CD33 and can be used for the treatment of cancer, for example leukaemia, are gemtuzumab and lintuzumab (INN 7580). An example of an anti-CD33 conjugate is gemtuzumab-ozagamycin. By reference, these antibodies and antigen-binding fragments thereof are incorporated herein, and they can be used in the context of the present invention.

Anti-NMB Antibodies

An example of an antibody which binds the cancer target molecule NMB and can be used for the treatment of cancer, for example melanoma or breast cancer, is glembatumumab (INN 9199). An example of an anti-NMB conjugate is glembatumumab vedotin (CAS RN: 474645-27-7). By reference, these antibodies and antigen-binding fragments thereof are incorporated herein, and they can be used in the context of the present invention.

Anti-CD56 Antibodies

An example of an antibody which binds the cancer target molecule CD56 and can be used for the treatment of cancer, for example multiple myeloma, small-cell lung carcinoma, MCC or ovarial carcinoma is lorvotuzumab. An example of an anti-CD56 conjugate is lorvotuzumab mertansine (CAS RN: 139504-50-0). By reference, these antibodies and antigen-binding fragments thereof are incorporated herein, and they can be used in the context of the present invention.

Anti-CD70 Antibodies

Examples of antibodies which bind the cancer target molecule CD70 and can be used for the treatment of cancer, for example non-Hodgkin lymphoma or renal cell cancer, are disclosed in WO 2007/038637-A2 and WO 2008/070593-A2. An example of an anti-CD70 conjugate is SGN-75 (CD70 MMAF). By reference, these antibodies and antigen-binding fragments thereof are incorporated herein, and they can be used in the context of the present invention.

Anti-CD74 Antibodies

An example of an antibody which binds the cancer target molecule CD74 and can be used for the treatment of cancer, for example multiple myeloma, is milatuzumab. An example of an anti-CD74 conjugate is milatuzumab-doxorubicin (CAS RN: 23214-92-8). By reference, these antibodies and antigen-binding fragments thereof are incorporated herein, and they can be used in the context of the present invention.

Anti-CD19 Antibodies

An example of an antibody which binds the cancer target molecule CD19 and can be used for the treatment of cancer, for example non-Hodgkin lymphoma, is disclosed in WO 2008/031056-A2. Further antibodies and examples of an anti-CD19 conjugate (SAR3419) are disclosed in WO 2008/047242-A2. By reference, these antibodies and antigen-binding fragments thereof are incorporated herein, and they can be used in the context of the present invention.

Anti-Mucin Antibodies

Examples of antibodies which bind the cancer target molecule mucin-1 and can be used for the treatment of cancer, for example non-Hodgkin lymphoma, are clivatuzumab and the antibodies disclosed in WO 2003/106495-A2, WO 2008/028686-A2. Examples of anti-mucin conjugates are disclosed in WO 2005/009369-A2. By reference, these antibodies and antigen-binding fragments thereof are incorporated herein, and they can be used in the context of the present invention.

Anti-CD138 Antibodies

Examples of antibodies which bind the cancer target molecule CD138 and conjugates thereof, which can be used for the treatment of cancer, for example multiple myeloma, are disclosed in WO 2009/080829-A1, WO 2009/080830-A1. By reference, these antibodies and antigen-binding fragments thereof are incorporated herein, and they can be used in the context of the present invention.

Anti-Integrin-alphaV Antibodies

Examples of antibodies which bind the cancer target molecule integrin alphaV and can be used for the treatment of cancer, for example melanoma, sarcoma or carcinoma, are intetumumab (CAS RN: 725735-28-4), abciximab (CAS RN: 143653-53-6), etaracizumab (CAS RN: 892553-42-3) and the antibodies disclosed in U.S. Pat. No. 7,465,449, EP 719859-A1, WO 2002/012501-A1 and WO2006/062779-A2. Examples of anti-integrin AlphaV conjugates are intetumumab-DM4 and other ADCs disclosed in WO 2007/024536-A2. By reference, these antibodies and antigen-binding fragments thereof are incorporated herein, and they can be used in the context of the present invention.

Anti-TDGF1 Antibodies

Examples of antibodies which bind the cancer target molecule TDGF1 and can be used for the treatment of cancer are the antibodies disclosed in WO 02/077033-A1, U.S. Pat. No. 7,318,924, WO 2003/083041-A2 and WO 2002/088170-A2. Examples of anti-TDGF1 conjugates are disclosed in WO 2002/088170-A2. By reference, these antibodies and antigen-binding fragments thereof are incorporated herein, and they can be used in the context of the present invention.

Anti-PSMA Antibodies

Examples of antibodies which bind the cancer target molecule PSMA and can be used for the treatment of cancer, for example prostate carcinoma, are the antibodies disclosed in WO 97/35616-A1, WO 99/47554-A1, WO 01/009192-A1 and WO2003/034903. Examples of anti-PSMA conjugates are disclosed in WO 2009/026274-A1 and WO 2007/002222. By reference, these antibodies and antigen-binding fragments thereof are incorporated herein, and they can be used in the context of the present invention.

Anti-EPHA2 Antibodies

Examples of antibodies which bind the cancer target molecule EPHA2 and can be used for preparing a conjugate and for the treatment of cancer are disclosed in WO 2004/091375-A2. By reference, these antibodies and antigen-binding fragments thereof are incorporated herein, and they can be used in the context of the present invention.

Anti-SLC44A4 Antibodies

Examples of antibodies which bind the cancer target molecule SLC44A4 and can be used for preparing a conjugate and for the treatment of cancer, for example pancreas or prostate carcinoma, are disclosed in WO2009/033094-A2 and US2009/0175796-A1. By reference, these antibodies and antigen-binding fragments thereof are incorporated herein, and they can be used in the context of the present invention.

Anti-HLA-DOB Antibodies

An example of an antibody binding to the cancer target molecule HLA-DOB is the antibody Lym-1 (CAS RN: 301344-99-0) which can be used for the treatment of cancer, for example non-Hodgkin lymphoma. Examples of anti-HLA-DOB conjugates are disclosed, for example, in WO 2005/081711-A2. By reference, these antibodies and antigen-binding fragments thereof are incorporated herein, and they can be used in the context of the present invention.

Anti-VTCN1 Antibodies

Examples of antibodies which bind the cancer target molecule VTCN1 and can be used for preparing a conjugate and for the treatment of cancer, for example ovarial carcinoma, pancreas, lung or breast cancer, are disclosed in WO 2006/074418-A2. By reference, these antibodies and antigen-binding fragments thereof are incorporated herein, and they can be used in the context of the present invention.

Anti-FGFR2 Antibodies

According to the invention, use may be made of anti-FGFR2 antibodies.

Examples of anti-FGFR2 antibodies and antigen-binding fragments are described in WO2013076186.

By reference, all antibodies of WO2013076186 are hereby incorporated into the description of the present invention, and they can be used in the present invention. The sequences of the antibodies are shown in Table 9 and Table 10 of WO2013076186. Preference is given to antibodies, antigen-binding fragments and variants of the antibodies derived from the antibodies referred to as M048-D01 and M047-D08. Preferred anti-FGFR2 bind to the various splice variants known of FGFR2.

In one embodiment, the anti-FGFR2 antibodies or antigen-binding antibody fragments thereof are, after binding to a cell expressing FGFR2, internalized by the cell.

In a further embodiment, the anti-FGFR2 antibodies or antigen-binding antibody fragments comprise at least one, two or three CDR amino acid sequences of an antibody listed in Table 9 or Table 10 of WO2013076186. Preferred embodiments of such antibodies are likewise listed in WO2013076186 and incorporated herein by reference.

Anti-TWEAKR Antibodies

In a preferred embodiment, when an anti-TWEAKR antibody or an antigen-binding fragment thereof is used in the processes according to the present invention, this antibody or fragment is selected from those described below. In addition, antibodies which bind to TWEAKR are known to the person skilled in the art, see, for example, WO 2015/189143 (A1), WO 2014/198817 (A1), WO2009/020933 (A2) or WO2009140177 (A2). In addition, aglycosylated variants of the described anti-TWEAKR antibodies generated either by deglycosylation by PNGase F or by mutation of N297 (Kabat numbering) of the heavy chain to any amino acid are used in the processes according to the present invention. Furthermore variants of these antibodies being engineered to contain one or more acceptor glutamine residues for transglutaminase (TGase) catalyzed reactions.

The invention relates in particular to conjugates with antibodies or antigen-binding antibody fragments thereof or variants thereof which lead to strong activation of the TWEAKR (SEQ ID NO: 169 (protein); SEQ ID NO:170 (DNA)), resulting in a strong induction of apoptosis in various cancer cells overexpressing TWEAKR.

The agonistic activity of TWEAKR with regard to the induction of apoptosis and inhibition of the proliferation of the anti-TWEAKR antibodies already described (e.g. PDL-192) is limited and does not reach the efficacy of the endogenous ligand TWEAK. This lack of agonistic activity is not based on reduced affinity, since these antibodies bind at the TWEAKR with affinities which, compared to the endogenous ligand TWEAK, are in a similar range (Michaelson J S et al, MAbs. 2011 July-August; 3(4):362-75; Culp P A et al, Clin Cancer Res. 2010 Jan. 15; 16(2):497-508), and even antibodies having a higher binding affinity do not necessarily display a more effective signalling activity (Culp P A, et al, Clin Cancer Res. 2010 Jan. 15; 16(2):497-508). In addition, it has been shown that the antitumour activity of the antibodies already described depends on the Fc effector function, and it was shown that ADCC plays an important role for the in-vivo efficacy in mouse models.

Generation of the Anti-TWEAKR Antibodies

A complete human antibody phage library (Hoet R M et al, Nat Biotechnol 2005; 23(3):344-8) was employed to isolate TWEAKR-specific human monoclonal antibodies of the present invention by protein panning (Hoogenboom H. R., Nat Biotechnol 2005; 23(3):1105-16) using dimeric Fc-fused extracellular domains of human and mouse TWEAKR as immobilized target. 11 different Fab phages were identified, and the corresponding antibodies were cloned into a mammalian EgG expression vector which provides the CH2-CH3 domains missing in the soluble FAb. Following identification of preferred antibodies, these were expressed as full-length IgGs. Aglycosylated variants of the described antibodies were generated by introducing the mutation N297A or N297Q in the heavy chain of the respective antibody. The constructs were expressed, for example, transiently in mammalian cells as described by Tom et al., Chapter 12 in Methods Express: Expression Systems edited by Micheal R. Dyson and Yves Durocher, Scion Publishing Ltd, 2007 (see AK-Example 1). The antibodies were purified by protein-A chromatography and characterized further by their binding affinity to soluble monomeric TWEAKR using ELISA and BIAcore analysis, as described in AK-Example 2. To determine the cell binding characteristics of the anti-TWEAKR antibodies, binding was tested by flow cytometry on a number of cell lines (HT29, HS68, HS578). NFκB reporter gene assays were carried out to examine the agonistic activity of all 11 antibodies identified (human IgG1). The antibody having the highest in vitro activity (TPP-883) was selected for further activity and affinity maturation (see AK-Example 1 for details). A single substitution variant having improved agonistic activity was detected: G102T of CDR-H3. In the end, 7 variants were selected based on increased affinity compared to the best single substitution variant G102T. The corresponding DNA thereof was cloned into a mammalian IgG expression vector and examined for functional activity in the NF-kappaB reporter gene assay mentioned above. Finally, the sequences obtained were compared with human germ line sequences, and deviations without any significant effect on the affinity and the efficacy were adapted. The following antibodies were obtained by antibody library screening and by affinity and/or activity maturation. "TPP-2090", "TPP-2149", "TPP-2093", "TPP-2148", "TPP-2084", "TPP-2077", "TPP-1538", "TPP-883", "TPP-1854", "TPP-1853", "TPP-1857" and "TPP-1858".

Antibodies of the invention can furthermore be obtained by methods known in the art such as antibody phage display screening (see, for example, Hoet R M et al., Nat Biotechnol 2005; 23(3):344-8), the well-established hybridoma technology (see, for example, Köhler and Milstein Nature. 1975 Aug. 7; 256(5517):495-7) or immunization of mice, inter alia immunization of hMAb mice (e.g. VelocImmune Mouse®).

Particular Embodiments of Anti-TWEAKR Antibodies

One embodiment of the invention is the provision of antibodies or antigen-binding antibody fragments thereof or variants thereof showing strong induction of caspase 3/7 in one or more TWEAKR-expressing cell lines (see also WO 2015/189143 A1 and WO 2014/198817 A1). In a preferred embodiment, the one or more TWEAKR-expressing cell line(s) is/are present in the group consisting of WiDr, A253, NCI-H322, HT29 and 786-O. "Induction of caspase 3/7" can be measured by customary methods known in the art, including those described herein. In one embodiment, the "induction of caspase 3/7" is determined in accordance with the present invention using the activity determination with capase 3/7 solution (Promega, #G8093) and reading the luminescence on a VICTOR V (Perkin Elmer). At the end of the incubation time, the caspase 3/7 activity was determined and the induction factor of caspase 3/7 was determined in comparison to untreated cells. An antibody is said to show "strong induction" of caspase 3/7 when the induction factor is greater than 1.2, preferably greater than 1.5, even more preferably greater than 1.8, even more preferably greater than 2.1, even more preferably greater than 2.5. What is provided are anti-TWEAKR antibodies leading to stronger induction of caspase 3/7 in HT29 cells compared to agonistic antibodies already described [e.g. PDL-192(TPP-1104), P4A8(TPP-1324), 136.1(TPP-2194)] and also compared to 300 ng/ml recombinant human TWEAK. This strong activity of inducing caspase 3/7 in cancer cells was also observed in WiDr, A253, NIC-H322 and 786-0 cells where in most experiments the antibodies of the invention examined induced higher factors of change compared to the reference antibodies [PDL-192(TPP-1104), P4A8(TPP-1324)] and to 300 ng/ml TWEAK. Some antibodies of the invention bind to the TWEAKR only with morate affinity (>10 nM) which is clearly less than the affinity of the endogenous ligand TWEAK, and also less compared to other known agonistic antibodies. This property offers further possible advantages such as, for example, potentially deeper penetration into the tumour.

In this regard, one embodiment of the invention is the provision of antibodies or antigen-binding antibody fragments thereof binding specifically to a TWEAKR at a novel epitope characterized by selective binding to aspartate (D) at position 47 (D47) of TWEAKR (SEQ ID NO: 169; see also FIG. 1). The dependencies identified for certain TWEAKR amino acids for antibody interaction correlate with the agonistic activity determined for these antibodies. The native ligand TWEAK shows an effective activation of the TWEAKR and binds depending on leucine 46 in the cysteine-rich domain of TWEAKR (Pellegrini et al, FEBS 280: 1818-1829). P4A8 displays a very low agonistic activity and interacts at least partially with domains outside of the cysteine-rich domain of TWEAKR. PDL-192 displays a morate agonistic activity and binds depending on $R^{56}$ to the cysteine-rich domain, but opposite the TWEAK ligand site. Antibodies of the present invention (e.g. TPP-2090) bind depending on D47, and TWEAK binds depending on L46. Thus, TWEAK binds to a similar but different binding site FIG. 7). Accordingly, the antibodies of the present invention displaying strong agonistic activity bind to a novel epitope (D47-dependent) for antibodies associated with very high agonistic activity.

The amino acid at position 47 (D47) of TWEAKR (SEQ ID NO: 169) is considered to be critical for binding of the antibodies according to the invention, which means that the antibody binds specifically to the D at position 47 (D47) of TWEAKR (SEQ ID NO:169) when the antibody loses more than 20%, alternatively more than 30%, alternatively more than 40%, alternatively more than 50%, alternatively more than 60%, alternatively more than 70%, alternatively more than 80%, alternatively more than 90%, alternatively 100% of its ELISA signal by modification of this residue into alanine, as described in AK-Example 2 and FIG. 6. Alternatively, an antibody binds specifically to the D at position 47 (D47) of TWEAKR (SEQ ID NO: 169) when the antibody loses more than 20%, alternatively more than 30%, alternatively more than 40%, alternatively more than 50%, alternatively more than 60%, alternatively more than 70%, alternatively more than 80%, alternatively more than 90%, alternatively 100% of its ELISA signal for TPP-2614 compared to TPP-2203. Preferably, an antibody binds specifically to the D at position 47 (D47) of TWEAKR (SEQ ID NO: 169) when the antibody loses more than 80% of its ELISA signal for TPP-2614 compared to TPP-2203.

In the present application, reference is made to the following preferred antibodies of the invention, as shown in the table below: "TPP-2090", "TPP-2149", "TPP-2093", "TPP-2148", "TPP-2084", "TPP-2077", "TPP-1538", "TPP-883", "TPP-1854", "TPP-1853", "TPP-1857", "TPP-1858".

TABLE

Protein sequences of the antibodies:

| | SEQ ID NO: IgG1 light chain | SEQ ID NO: IgG1 heavy chain | SEQ ID NO: L-CDR1 | SEQ ID NO: L-CDR2 | SEQ ID NO: L-CDR3 | SEQ ID NO: H-CDR1 | SEQ ID NO: H-CDR2 | SEQ ID NO: H-CDR3 | SEQ ID NO: VL protein | SEQ ID NO: VH protein |
|---|---|---|---|---|---|---|---|---|---|---|
| Anti-TWEAKR antibodies according to the invention: | | | | | | | | | | |
| TPP-2090 | 1 | 2 | 3 | 4 | 5 | 6 | 7 | 8 | 9 | 10 |
| TPP-2149 | 11 | 12 | 13 | 14 | 15 | 16 | 17 | 18 | 19 | 20 |
| TPP-2093 | 21 | 22 | 23 | 24 | 25 | 26 | 27 | 28 | 29 | 30 |
| TPP-2148 | 31 | 32 | 33 | 34 | 35 | 36 | 37 | 38 | 39 | 40 |
| TPP-2084 | 41 | 42 | 43 | 44 | 45 | 46 | 47 | 48 | 49 | 50 |
| TPP-2077 | 51 | 52 | 53 | 54 | 55 | 56 | 57 | 58 | 59 | 60 |
| TPP-1538 | 61 | 62 | 63 | 64 | 65 | 66 | 67 | 68 | 69 | 70 |
| TPP-883 | 71 | 72 | 73 | 74 | 75 | 76 | 77 | 78 | 79 | 80 |
| TPP-1854 | 81 | 82 | 83 | 84 | 85 | 86 | 87 | 88 | 89 | 90 |
| TPP-1853 | 91 | 92 | 93 | 94 | 95 | 96 | 97 | 98 | 99 | 100 |
| TPP-1857 | 101 | 102 | 103 | 104 | 105 | 106 | 107 | 108 | 109 | 110 |
| TPP-1858 | 111 | 112 | 113 | 114 | 115 | 116 | 117 | 118 | 119 | 120 |
| TPP-2658 | 1 | 241 | 3 | 4 | 5 | 6 | 7 | 8 | 9 | 10 |
| TPP-5442 | 1 | 242 | 3 | 4 | 5 | 6 | 7 | 8 | 9 | 10 |
| TPP-8825 | 1 | 243 | 3 | 4 | 5 | 6 | 7 | 8 | 9 | 10 |
| Comparative antibodies: | | | | | | | | | | |
| P3G5(TPP-2195) | 121 | 122 | | | | | | | | |
| 136.1(TPP-2194) | 123 | 124 | | | | | | | | |
| P4A8(TPP-1324) | 125 | 126 | | | | | | | | |
| PDL-192(TPP-1104) | 127 | 128 | | | | | | | | |
| 18.3.3(TPP-2193) | 129 | 130 | | | | | | | | |
| P2D3(TPP-2196 | 131 | 132 | | | | | | | | |

TPP-2090 is: an antibody which comprises a region of the heavy chain corresponding to SEQ ID NO: 2 and a region of the light chain corresponding to SEQ ID NO: 1.

TPP-2658 is: an antibody which comprises a region of the heavy chain corresponding to SEQ ID NO: 241 and a region of the light chain corresponding to SEQ ID NO: 1.

TPP-5442 is: an antibody which comprises a region of the heavy chain corresponding to SEQ ID NO: 242 and a region of the light chain corresponding to SEQ ID NO: 1.

TPP-8825 is: an antibody which comprises a region of the heavy chain corresponding to SEQ ID NO: 243 and a region of the light chain corresponding to SEQ ID NO: 1.

TPP-2149 is: an antibody which comprises a region of the heavy chain corresponding to SEQ ID NO: 12 and a region of the light chain corresponding to SEQ ID NO: 11.

TPP-2093 is: an antibody which comprises a region of the heavy chain corresponding to SEQ ID NO: 22 and a region of the light chain corresponding to SEQ ID NO: 21.

TPP-2148 is: an antibody which comprises a region of the heavy chain corresponding to SEQ ID NO: 32 and a region of the light chain corresponding to SEQ ID NO: 31.

TPP-2084 is: an antibody which comprises a region of the heavy chain corresponding to SEQ ID NO: 42 and a region of the light chain corresponding to SEQ ID NO: 41.

TPP-2077 is: an antibody which comprises a region of the heavy chain corresponding to SEQ ID NO: 52 and a region of the light chain corresponding to SEQ ID NO: 51.

TPP-1538 is: an antibody which comprises a region of the heavy chain corresponding to SEQ ID NO: 62 and a region of the light chain corresponding to SEQ ID NO: 61.

TPP-883 is: an antibody which comprises a region of the heavy chain corresponding to SEQ ID NO: 72 and a region of the light chain corresponding to SEQ ID NO: 71.

TPP-1854 is: an antibody which comprises a region of the heavy chain corresponding to SEQ ID NO: 82 and a region of the light chain corresponding to SEQ ID NO: 81.

TPP-1853 is: an antibody which comprises a region of the heavy chain corresponding to SEQ ID NO: 92 and a region of the light chain corresponding to SEQ ID NO: 91.

TPP-1857 is: an antibody which comprises a region of the heavy chain corresponding to SEQ ID NO: 102 and a region of the light chain corresponding to SEQ ID NO: 101.

TPP-1858 is: an antibody which comprises a region of the heavy chain corresponding to SEQ ID NO: 112 and a region of the light chain corresponding to SEQ ID NO: 111.

TPP-2090 is: an antibody which comprises a variable region of the heavy chain corresponding to SEQ ID NO: 10 and a variable region of the light chain corresponding to SEQ ID NO: 9.

TPP-2149 is: an antibody which comprises a variable region of the heavy chain corresponding to SEQ ID NO: 20 and a variable region of the light chain corresponding to SEQ ID NO: 19.

TPP-2093 is: an antibody which comprises a variable region of the heavy chain corresponding to SEQ ID NO: 30 and a variable region of the light chain corresponding to SEQ ID NO: 29.

TPP-2148 is: an antibody which comprises a variable region of the heavy chain corresponding to SEQ ID NO: 40 and a variable region of the light chain corresponding to SEQ ID NO: 39.

TPP-2084 is: an antibody which comprises a variable region of the heavy chain corresponding to SEQ ID NO: 50 and a variable region of the light chain corresponding to SEQ ID NO: 49.

TPP-2077 is: an antibody which comprises a variable region of the heavy chain corresponding to SEQ ID NO: 60 and a variable region of the light chain corresponding to SEQ ID NO: 59.

TPP-1538 is: an antibody which comprises a variable region of the heavy chain corresponding to SEQ ID NO: 70 and a variable region of the light chain corresponding to SEQ ID NO: 69.

TPP-883 is: an antibody which comprises a variable region of the heavy chain corresponding to SEQ ID NO: 80 and a variable region of the light chain corresponding to SEQ ID NO: 79.

TPP-1854 is: an antibody which comprises a variable region of the heavy chain corresponding to SEQ ID NO: 90 and a variable region of the light chain corresponding to SEQ ID NO: 89.

TPP-1853 is: an antibody which comprises a variable region of the heavy chain corresponding to SEQ ID NO: 100 and a variable region of the light chain corresponding to SEQ ID NO: 99.

TPP-1857 is: an antibody which comprises a variable region of the heavy chain corresponding to SEQ ID NO: 110 and a variable region of the light chain corresponding to SEQ ID NO: 109.

TPP-1858 is: an antibody which comprises a variable region of the heavy chain corresponding to SEQ ID NO: 120 and a variable region of the light chain corresponding to SEQ ID NO: 119.

TABLE

DNA sequences of antibodies according to the invention

| Antibody | SEQ ID NO: IgG1 light chain | SEQ ID NO: IgG1 heavy chain |
|---|---|---|
| Antibodies according to the invention: | | |
| TPP-2090 | 177 | 178 |
| TPP-2149 | 179 | 180 |
| TPP-2093 | 181 | 182 |
| TPP-2148 | 183 | 184 |
| TPP-2084 | 185 | 186 |
| TPP-2077 | 187 | 188 |
| TPP-1538 | 189 | 190 |
| TPP-883 | 191 | 192 |
| TPP-1854 | 193 | 194 |
| TPP-1853 | 195 | 196 |
| TPP-1857 | 197 | 198 |
| TPP-1858 | 199 | 200 |
| Comparative antibodies: | | |
| P3G5(TPP-2195) | 201 | 202 |
| 136.1(TPP-2194) | 203 | 204 |
| P4A8(TPP-1324) | 205 | 206 |
| PDL-192(TPP-1104) | 207 | 208 |
| 18.3.3(TPP-2193) | 209 | 210 |
| P2D3(TPP-2196) | 211 | 212 |

Preferred embodiments of the anti-TWEAKR antibody are those below:
1. An anti-TWEAKR antibody, an aglycosylated variant, or an antigen-binding fragment thereof which binds specifically to the D at position 47 (D47) of the TWEAKR (SEQ ID NO: 169).
2. The antibody or an antigen-binding fragment thereof according to embodiment 1 where the antibody is an agonistic antibody.
3. The antibody or an antigen-binding fragment thereof according to embodiment 1 or 2 which comprises:
 a variable heavy chain comprising:
 (a) a CDR1 of the heavy chain encoded by an amino acid sequence comprising the formula PYPMX (SEQ ID NO: 171), where X is 1 or M;
 (b) a CDR2 of the heavy chain encoded by an amino acid sequence comprising the formula YISPSGGXTHYADSVKG (SEQ ID NO: 172), where X is S or K; and
 (c) a CDR3 of the heavy chain encoded by an amino acid sequence comprising the formula GGDTYFDYFDY (SEQ ID NO: 173);
 and a variable light chain comprising:
 (a) a CDR1 of the light chain encoded by an amino acid sequence comprising the formula RASQSISXYLN (SEQ ID NO: 174), where X is G or S;
 (b) a CDR2 of the light chain encoded by an amino acid sequence comprising the formula XASSLQS (SEQ ID NO: 175), where X is Q, A or N; and
 (c) a CDR3 of the light chain encoded by an amino acid sequence comprising the formula QQSYXXPXIT (SEQ ID NO: 176), where X at position 5 is T or S, X at position 6 is T or S and X at position 8 is G or F.
4. The antibody or an antigen-binding fragment thereof according to any of the preceding embodiments, comprising:
 a. a variable heavy chain comprising the variable CDR1 sequence of the heavy chain, as shown in SEQ ID NO: 6, the variable CDR2 sequence of the heavy chain, as shown in SEQ ID NO: 7 and the variable CDR3 sequence of the heavy chain, as shown in SEQ ID NO: 8, and also
 a variable light chain comprising the variable CDR1 sequence of the light chain shown in SEQ ID NO: 3, the variable CDR2 sequence of the light chain shown in SEQ ID NO: 4 and the variable CDR3 sequence of the light chain shown in SEQ ID NO: 5 or
 b. a variable heavy chain comprising the variable CDR1 sequence of the heavy chain, as shown in SEQ ID NO: 16, the variable CDR2 sequence of the heavy chain, as shown in SEQ ID NO: 17, the variable CDR3 sequence of the heavy chain, as shown in SEQ ID NO:18, and also
 a variable light chain comprising the variable CDR1 sequence of the light chain shown in SEQ ID NO: 13, the variable CDR2 sequence of the light chain shown in SEQ ID NO: 14 and the variable CDR3 sequence of the light chain shown in SEQ ID NO: 15 or
 c. a variable heavy chain comprising the variable CDR1 sequence of the heavy chain, as shown in SEQ ID NO: 26, the variable CDR2 sequence of the heavy chain, as shown in SEQ ID NO: 27, the variable CDR3 sequence of the heavy chain, as shown in SEQ ID NO:28, and also
 a variable light chain comprising the variable CDR1 sequence of the light chain shown in SEQ ID NO: 23, the variable CDR2 sequence of the light chain shown in SEQ ID NO: 24 and the variable CDR3 sequence of the light chain shown in SEQ ID NO:25 or
 d. a variable heavy chain comprising the variable CDR1 sequence of the heavy chain, as shown in SEQ ID NO: 36, the variable CDR2 sequence of the heavy chain, as shown in SEQ ID NO: 37, the variable CDR3 sequence of the heavy chain, as shown in SEQ ID NO:38, and also a variable light chain comprising the variable CDR1 sequence of the light chain shown in SEQ ID NO: 33, the variable CDR2 sequence of the light chain shown in SEQ ID NO: 34 and the variable CDR3 sequence of the light chain shown in SEQ ID NO:35 or e. a variable heavy chain comprising the variable CDR1 sequence of the heavy chain, as shown in SEQ ID NO: 46, the variable CDR2 sequence of the heavy chain, as shown in SEQ ID NO: 47, the variable CDR3 sequence of the heavy chain, as shown in SEQ ID NO:48, and also a variable light chain comprising the variable CDR1 sequence of the light chain shown in SEQ ID NO: 43, the variable CDR2 sequence of the light chain shown in SEQ ID NO: 44 and the variable CDR3 sequence of the light chain shown in SEQ ID NO:45 or f. a variable heavy chain comprising the variable CDR1 sequence of the heavy chain, as shown in SEQ ID NO: 56, the variable CDR2 sequence of the heavy chain, as shown in SEQ ID NO: 57, the variable CDR3 sequence of the heavy chain, as shown in SEQ ID NO:58, and also a variable light chain comprising the variable CDR1 sequence of the light chain shown in SEQ ID NO: 53, the variable CDR2 sequence of the light chain shown in SEQ ID NO: 54 and the variable CDR3 sequence of the light chain shown in SEQ ID NO:55 or g. a variable heavy chain comprising the variable CDR1 sequence of the heavy chain, as shown in SEQ ID NO: 66, the variable CDR2 sequence of the heavy chain, as shown in SEQ ID NO: 67, the variable CDR3 sequence of the heavy chain, as shown in SEQ ID NO:68, and also a variable light chain comprising the variable CDR1 sequence of the light chain shown in SEQ ID NO: 63, the variable CDR2 sequence of the light chain shown in SEQ ID NO: 64 and the variable CDR3 sequence of the light chain shown in SEQ ID NO:65 or h. a variable heavy chain comprising the variable CDR1 sequence of the heavy chain, as shown in SEQ ID NO: 76, the variable CDR2 sequence of the heavy chain, as shown in SEQ ID NO: 77, the variable CDR3 sequence of the heavy chain, as shown in SEQ ID NO:78, and also a variable light chain comprising the variable CDR1 sequence of the light chain shown in SEQ ID NO: 73, the variable CDR2 sequence of the light chain shown in SEQ ID NO: 74 and the variable CDR3 sequence of the light chain shown in SEQ ID NO:75 or i. a variable heavy chain comprising the variable CDR1 sequence of the heavy chain, as shown in SEQ ID NO: 86, the variable CDR2 sequence of the heavy chain, as shown in SEQ ID NO: 87, the variable CDR3 sequence of the heavy chain, as shown in SEQ ID NO:88, and also a variable light chain comprising the variable CDR1 sequence of the light chain shown in SEQ ID NO: 83, the variable CDR2 sequence of the light chain shown in SEQ ID NO: 84 and the variable CDR3 sequence of the light chain shown in SEQ ID NO:85 or j. a variable heavy chain comprising the variable CDR1 sequence of the heavy chain, as shown in SEQ ID NO: 96, the variable CDR2 sequence of the heavy chain, as shown in SEQ ID NO: 97, the variable CDR3 sequence of the heavy chain, as shown in SEQ ID NO:98, and also a variable light chain comprising the variable CDR1 sequence of the light chain shown in SEQ ID NO: 93, the variable CDR2 sequence of the light chain shown in SEQ ID NO: 94 and the variable CDR3 sequence of the light chain shown in SEQ ID NO:95 or k. a variable heavy chain comprising the variable CDR1 sequence of the heavy chain, as shown in SEQ ID NO: 106, the variable CDR2 sequence of the heavy chain, as shown in SEQ ID NO: 107, the variable CDR3 sequence of the heavy chain, as shown in SEQ ID NO:108, and also a variable light chain comprising the variable CDR1 sequence of the light chain shown in SEQ ID NO: 103, the variable CDR2 sequence of the light chain shown in SEQ ID NO: 104 and the variable CDR3 sequence of the light chain shown in SEQ ID NO: 105 or l. a variable heavy chain comprising the variable CDR1 sequence of the heavy chain, as shown in SEQ ID NO: 116, the variable CDR2 sequence of the heavy chain, as shown in SEQ ID NO: 117, the variable CDR3 sequence of the heavy chain, as shown in SEQ ID NO:118, and also a variable light chain comprising the variable CDR1 sequence of the light chain shown in SEQ ID NO: 113, the variable CDR2 sequence of the light chain shown in SEQ ID NO: 114 and the variable CDR3 sequence of the light chain shown in SEQ ID NO: 115.

5. The antibody or the antigen-binding fragment thereof according to any of the preceding embodiments, comprising:

a. a variable sequence of the heavy chain, as shown in SEQ ID NO:10, and also a variable sequence of the light chain, as shown in SEQ ID NO:9, or b. a variable sequence of the heavy chain, as shown in SEQ ID NO:20, and also a variable sequence of the light chain, as shown in SEQ ID NO: 19, or c. a variable sequence of the heavy chain, as shown in SEQ ID NO:30, and also a variable sequence of the light chain, as shown in SEQ ID NO:29, or d. a variable sequence of the heavy chain, as shown in SEQ ID NO:40, and also a variable sequence of the light chain, as shown in SEQ ID NO:39, or e. a variable sequence of the heavy chain, as shown in SEQ ID NO:50, and also a variable sequence of the light chain, as shown in SEQ ID NO:49, or f. a variable sequence of the heavy chain, as shown in SEQ ID NO:60, and also a variable sequence of the light chain, as shown in SEQ ID NO:59, or g. a variable sequence of the heavy chain, as shown in SEQ ID NO:70, and also a variable sequence of the light chain, as shown in SEQ ID NO:69, or h. a variable sequence of the heavy chain, as shown in SEQ ID NO:80, and also a variable sequence of the light chain, as shown in SEQ ID NO:79, or i. a variable sequence of the heavy chain, as shown in SEQ ID NO:90, and also a variable sequence of the light chain, as shown in SEQ ID NO:89, or j. a variable sequence of the heavy chain, as shown in SEQ ID NO:100, and also a variable sequence of the light chain, as shown in SEQ ID NO:99, or k. a variable sequence of the heavy chain, as shown in SEQ ID NO:110, and also a variable sequence of the light chain, as shown in SEQ ID NO: 109, or l. a variable sequence of the heavy chain, as shown in SEQ ID NO:120, and also a variable sequence of the light chain, as shown in SEQ ID NO: 119.

6. The antibody according to any of the preceding embodiments which is an IgG antibody.

7. The antibody according to any of the preceding embodiments, comprising:
   a. a sequence of the heavy chain, as shown in SEQ ID NO:2, and also a sequence of the light chain, as shown in SEQ ID NO:1, or
   b. a sequence of the heavy chain, as shown in SEQ ID NO: 12, and also a sequence of the light chain, as shown in SEQ ID NO: 11, or
   c. a sequence of the heavy chain, as shown in SEQ ID NO:22, and also a sequence of the light chain, as shown in SEQ ID NO:21, or
   d. a sequence of the heavy chain, as shown in SEQ ID NO:32, and also a sequence of the light chain, as shown in SEQ ID NO:31, or
   e. a sequence of the heavy chain, as shown in SEQ ID NO:42, and also a sequence of the light chain, as shown in SEQ ID NO:41, or
   f. a sequence of the heavy chain, as shown in SEQ ID NO:52, and also a sequence of the light chain, as shown in SEQ ID NO:51, or
   g. a sequence of the heavy chain, as shown in SEQ ID NO:62, and also a sequence of the light chain, as shown in SEQ ID NO:61, or
   h. a sequence of the heavy chain, as shown in SEQ ID NO:72, and also a sequence of the light chain, as shown in SEQ ID NO:71, or
   i. a sequence of the heavy chain, as shown in SEQ ID NO:82, and also a sequence of the light chain, as shown in SEQ ID NO:81, or
   j. a sequence of the heavy chain, as shown in SEQ ID NO:92, and also a sequence of the light chain, as shown in SEQ ID NO:91, or
   k. a sequence of the heavy chain, as shown in SEQ ID NO: 102, and also a sequence of the light chain, as shown in SEQ ID NO:101, or
   l. a sequence of the heavy chain, as shown in SEQ ID NO:112, and also a sequence of the light chain, as shown in SEQ ID NO:111.

8. The antigen-binding fragment according to any of the preceding embodiments or an antigen-binding fragment of an antibody according to any of the preceding embodiments which is an scFv, Fab, Fab' fragment or a F(ab')₂ fragment.

9. The antibody or the antigen-binding fragment according to any of the preceding embodiments which is a monoclonal antibody or an antigen-binding fragment thereof.

10. The antibody or the antigen-binding fragment according to any of the preceding embodiments which is a human, humanized or chimeric antibody or an antigen-binding fragment.

Particular preference is given to the anti-TWEAKR antibody TPP-2090.

It is an embodiment of this invention to provide antibodies suitable for transglutaminase (TGase)-mediated conjugation of a kinesin spindle protein inhibitor.

Wild-type full-length IgG antibodies of human isotype possess a conserved acceptor glutamine at residue 295 (Kabat EU numbering) of the heavy chain which is accessible and reactive in presence of a TGase, to form a conjugate from the antibody and the suitable compound, when the antibody is in a non-glycosylated form. Such an "aglycosyl antibody" or "aglycosylated antibody" or "deglycosylated antibody" comprises an Fc region lacking the glycans attached to the conserved N-linked site in the CH2 domains of the Fc region.

Aglycosyl antibodies can for example be generated by expressing the antibodies in expression systems lacking glycosylation. Aglycosyl antibodies may be prepared by expression the antibodies in a prokaryotic host. Suitable prokaryotic hosts for include but are not limited to *E. coli, Bacillus subtilis, Salmonella typhimurium* and various species within the genera *Pseudomonas, Streptomyces*, and *Staphylococcus*. In another embodiment of this invention, aglycosyl antibodies may be achieved using mammalian expression systems together with the glycosylation inhibitor tunicamycin (Nose & Wigzell (1983), Proc Natl Acad Sci USA, 80(21):6632-6). That is, the modification is the prevention of glycosylation at the conserved N-linked site in the CH2 domains of the Fc portion of said antibody. In another embodiment of the invention the glycans attached to the conserved N-linked site in the CH2 domains of the Fc region antibody are removed, which means the antibody is deglycosylated. Methods for enzymatic deglycosylation of antibodies are well known in the art (e.g. Winkelhake & Nicolson (1976), J Biol Chem. 251(4):1074-80). Deglycosylated antibodies may e.g. be prepared by enzymatic deglycosylation using e.g. PNGase F.

In another embodiment of the invention aglycosylated antibodies are prepared by mutation of the heavy chain glycosylation site of N297 (using Kabat EU numbering). Enzymatic conjugation of such engineered aglycosylated antibodies was described for aglycosylated antibody variants bearing the mutations N297D, N297Q (Jeger et al., Angewandte Chemie Int. Ed. Engl 49, 9995-9997 (2010)), or N297S (see patent applications WO2013092998A1 and WO2013092983A2). Furthermore this invention shows that transglutaminase could efficiently catalyze conjugation to aglycosylated antibody variants bearing the mutation N297A (Kabat EUnumbering).

Additional or alternative sites reactive in the presence of a TGase can be created by engineering the antibodies. The compounds of the invention include glutamine engineered antibodies where one or more amino acids of a wild-type or parent antibody are replaced with (substituted by) a glutamine amino acid, or where a glutamine residue, optionally together with other amino acid residues (e.g. a tag comprising the acceptor glutamine residue), is introduced or added to a wild-type or parent.

A single site mutation that provides a glutamine that is accessible to a TGase may yield more than one engineered glutamine residue that can be conjugated if the antibody comprises more than one engineered chain. For example, a single site mutation will yield two engineered glutamine residues in an IgG due to the dimeric nature of the IgG antibody.

The glutamine amino acid residues of an antibody that are reactive, in the presence of a TGase under suitable conditions may be located in the heavy chain, typically in the constant domain. In one embodiment, an asparagine at amino acid position 297 (Kabat EU numbering) is replace with a residue different from glutamine. Preferred are N297D, N297Q, N297S or N297A, highly preferred is N297A. The antibody will have a constant region with a N297X substitution. An antibody having a N297X substitution and a glutamine at residue 295 (Kabat EU numbering) will therefore have one acceptor glutamine and thus one conjugation sites per heavy chain. The complete IgG form will therefore have two conjugates per antibody.

The glutamine amino acid residues of an antibody that are reactive, in the presence of a TGase under suitable conditions may be located in the heavy chain, typically in the constant domain. In one embodiment, an asparagine at amino acid position 297 (Kabat EU numbering) is substituted with a glutamine residue. The antibody will have a constant region with a N297Q substitution. An antibody having a N297Q substitution and a glutamine at residue 295 (Kabat EU numbering) will therefore have two acceptor glutamines and thus two conjugation sites per heavy chain. The complete IgG form will therefore have four conjugates per antibody.

The glutamine amino acid residues of an antibody that are reactive, in the presence of a TGase under suitable conditions may be located in the heavy chain, typically in the constant domain. In one embodiment, an asparagine at amino acid position 297 (Kabat EU numbering) is substituted with a glutamine residue and at position 295 (Kabat EU numbering) the glutamine is replaced. The antibody will have a constant region with a N297Q and Q295X substitution. Preferred is a Q295N substitution. An antibody having a N297Q substitution and no glutamine at residue 295 (EU Numbering) will therefore have one acceptor glutamine and thus one conjugation sites per heavy chain. The complete IgG form will therefore have two conjugates per antibody.

Preferred antibodies suitable for transglutaminase (TGase)-mediated conjugation comprise a:
i. N297X substitution wherein X is any amino acid but asparagine; even more preferred are N297D, N297Q, N297S or N297A, highly preferred are N297A and N297Q.
ii. N297Q substitution and a Q295X substitution wherein X is any amino acid but glutamine, preferred is Q295N.

An advantageous approach for preparing conjugated antibodies will thus involve providing as starting materials antibodies lacking N297-linked glycosylation (such N-linked glycosylation interferes with TGase coupling).

Isotopes, Salts, Solvates, Isotopic Variants

The present invention also encompasses all suitable isotopic variants of the compounds according to the invention. An isotopic variant of a compound according to the invention is understood here as meaning a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by the processes known to those skilled in the art, for example by the methods described below and the procedures described in the working examples, by using corresponding isotopic modifications of the respective reagents and/or starting compounds.

Preferred salts in the context of the present invention are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, benzenesulphonic acid, toluenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylpiperidine, N-methylmorpholine, arginine, lysine and 1,2-ethylenediamine.

Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

In addition, the present invention also encompasses prodrugs of the compounds according to the invention. The term "prodrugs" here denotes compounds which may themselves be biologically active or inactive, but are converted (for example by metabolic or hydrolytic means) to inventive compounds during their residence time in the body.

PARTICULAR EMBODIMENTS

The following embodiments are particularly preferred:

Embodiment A

An ADC (or APDC) of the formula

BINDER—[L—KSP]$_n$ where KSP-L- is a compound of the formula (II), (IIa), (IIIb), (IIIc), (IIId), (IIIe), any of (IV) to (IX), or the formula (IIf) below, the binder is an anti-TWEAKR antibody comprising an acceptor glutamine residue (particularly preferably an anti-TWEAKR antibody or a variant thereof which binds specifically to amino acid D in position 47 (D47) of TWEAKR (SEQ ID NO: 169), especially the anti-TWEAKR antibody TPP-2090), aglycosylated variants of these antibodies generated either by deglycosylation by PNGase F or by mutation of N297 (Kabat numbering) of the heavy chain to any amino acid, and variants of the described antibodies being engineered to contain solvent accessible glutamine residues being substrates for bacterial transglutaminase,
and n is 2 or 4 formula (IIf)

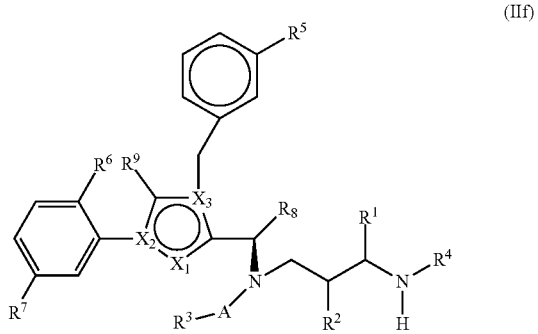

where
$X_1$ represents N, $X_2$ represents N and $X_3$ represents C;
$X_1$ represents CH, $X_2$ represents C and $X_3$ represents N;
$X_1$ represents NH, $X_2$ represents C and $X_3$ represents C; or
$X_1$ represents CH, $X_2$ represents N and $X_3$ represents C;
A represents C(=O);
$R^1$ represents -L-#1, —H, —COOH, —C(=O)—NHNH$_2$, —(CH2)$_{1-3}$NH$_2$, —C(=O)—NZ"(CH2)$_{1-3}$NH$_2$ and —C(=O)—NZ"CH$_2$COOH, where Z" represents —H or —NH$_2$;
$R^2$ and $R^4$ represent —H or -L-#1, or $R^2$ represents —H and $R^4$ represents $R^{21}$—(C=O)$_{(0-1)}$-(P3)$_{(0-2)}$-P2-NH—CH(CH$_2$C(=O)—NH$_2$)—C(=O)— (where P2 and Pe have the same meaning as defined above, e.g. as shown with respect to formula (IIa)), or $R^2$ and $R^4$ together (with formation of a pyrrolidine ring) represent —CH$_2$—CHR$^{10}$— or —CHR$^{10}$—CH$_2$—, where $R^{10}$ represents —H or -L-#1;
$R^3$ represents -L-#1 or a $C_{1-10}$-alkyl-, which may optionally be substituted by —OH, —O-alkyl, —SH, —S-alkyl, —O—C(O)-alkyl, —O—C(=O)—NH-alkyl, —NH—C(=O)-alkyl, —NH—C(=O)—NH-alkyl, —S(=O)$_n$-alkyl, —S(=O)$_2$—NH-alkyl, —NH-alkyl, —N(alkyl)$_2$ or —NH$_2$ (where alkyl is preferably $C_{1-3}$-alkyl);
$R^5$ represents -L-#1, H or F;
$R^6$ and $R^7$ independently of one another represent —H, $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, hydroxy or halogen (in particular —F, —Cl, —Br),
$R^8$ represents a branched $C_{1-5}$-alkyl group which may be substituted by -L-#1; and
$R^9$ represents H or F,
where one of the substituents $R^1$, $R^2$, $R^3$, $R^4$, $R^5$, $R^8$ and $R^{10}$ represents -L-#1, and
-L- represents the linker and #1 represents the bond to the antibody,
and salts, solvates and salts of the solvates of the ADC.

The linker is preferably a linker

§-(C=O)$m$-L1-L2-§§ where
m is 0 or 1;
§ represents the bond to KSP and
§§ represents the bond to the antibody, and
L2 represents:

$^1$—(NH)$_p$—(C=O)$_q$-G4-NH-#$^2$ or #$^1$—(NH)$_p$—(C=O)$_q$-G4-O—NH-#$^2$ where
p is 0 or 1;
q is 0 or 1; and
G4 represents an optionally substituted alkyl or heteroalkyl chain optionally wherein any carbon of the chain is substituted with an alkoxy, hydroxyl, alkylcarbonyloxy, —S-alkyl, thiol, —C(=O)—S-alkyl, —C(=O)—NH-alkyl, —NH—C(=O)-alkyl, amine, —C(=O)—NH$_2$
where
$^1$ denotes the point of attachment to group $L^1$,
$^2$ denotes the point of attachment to the glutamine residue of the binder,
and L1 is represented by formula

1-(NR$^{10}$)$_n$-(G1)$_o$-G3-#$^2$ where
$R^{10}$ represents —H, —NH$_2$ or $C_1$-$C_3$-alkyl;
G1 represents —NH—C(=O)— or

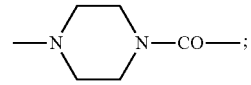

n is 0 or 1;
o is 0 or 1; and
G3 represents a bond or an optionally substituted linear or branched hydrocarbon chain having 1 to 100 carbon atoms from arylene groups and/or linear and/or branched and/or cyclic alkylene groups and which may be interrupted once or more than once by one or more of the groups —O—, —S—, —S(=O)—, —S(=O)$_2$, —NH—, —C(=O)—, —NH—C(=O)—, —C(=O)—NH—, —NMe-, —NHNH—, —S(=O)$_2$—NHNH—, —C(=O)—NHNH— and a 3- to 10-membered aromatic or non-aromatic heterocycle having up to 4 heteroatoms selected from the group consisting of N, O and S, or —S(=O)— (preferably

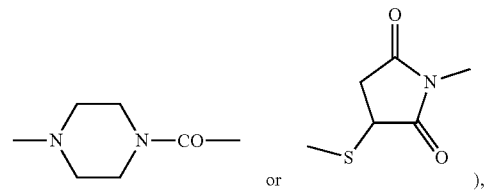

where the side chains, if present, may be substituted by —NH—C(=O)—NH$_2$, —COOH, —OH, —NH$_2$, —NH—CNNH$_2$, sulphonamide, sulphone, sulphoxide or sulphonic acid.
Here, #1 is the bond to the KSP inhibitor and #2 is the bond to the coupling group to the binder (e.g. L2).

Embodiment B

An ADC of the formula

BINDER—[L—KSP]$_n$ where KSP-L- is a compound of the formula (II), (IIa), (IIIb), (IIIc), (IIId), (IIIe), (IIf), any of (IV) to (IX) or of the formula (IIg) below, the binder is an antibody comprising an acceptor glutamine residue and n is 2 or 4:

formula (IIg)

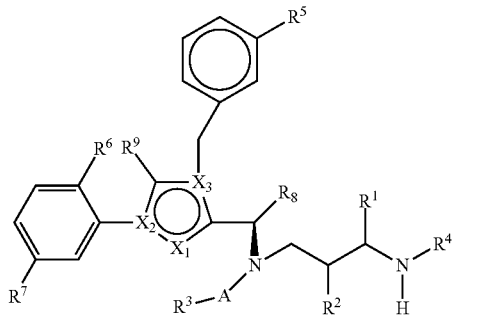

(IIg)

where
$X_1$ represents N, $X_2$ represents N and $X_3$ represents C;
$X_1$ represents CH, $X_2$ represents C and $X_3$ represents N;
$X_1$ represents NH, $X_2$ represents C and $X_3$ represents C; or
$X_1$ represents CH, $X_2$ represents N and $X_3$ represents C;
A represents —C(=O)—;
$R^1$ represents -L-#1, —H, —COOH, —C(=O)—NHNH$_2$, —(CH$_2$)$_{1-3}$NH$_2$, —C(=O)—NZ"(CH$_2$)$_{1-3}$NH$_2$ and —C(=O)—NZ"CH$_2$COOH, where Z" represents —H or —NH$_2$;
$R^2$ and $R^4$ represent —H or -L-#1, or $R^2$ represents —H and $R^4$ represents $R^{21}$—(C=O)$_{(0-1)}$-(P3)$_{(0-2)}$-P2-NH—CH (CH$_2$C(=O)—NH$_2$)—C(=O)— (where P2 and Pe have the same meaning as defined above, e.g. as shown with respect to formula (IIa)), or $R^2$ and $R^4$ together (with formation of a pyrrolidine ring) represent —CH$_2$—CHR$^{10}$— or —CHR$^{10}$—CH$_2$—, where $R^{10}$ represents —H or -L-#1;
$R^3$ represents -L-#1 or a $C_{1-10}$-alkyl-, which may optionally be substituted by —OH, —O-alkyl, —SH, —S-alkyl, —O—C(=O)-alkyl, —O—C(=O)—NH-alkyl, —NH—C (=O)-alkyl, —NH—C(=O)—NH-alkyl, —S(=O)$_n$-alkyl, —S(=O)$_2$—NH-alkyl, —NH-alkyl, —N(alkyl)$_2$ or —NH$_2$ (where alkyl is preferably $C_{1-3}$-alkyl);
$R^5$ represents -L-#1, H or F;
$R^6$ and $R^7$ independently of one another represent —H, $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, hydroxy or halogen (in particular —F, —Cl, —Br),
$R^8$ represents a branched $C_{1-5}$-alkyl group; and
$R^9$ represents H or F,
where one of the substituents $R^1$, $R^2$, $R^3$, $R^4$, $R^5$ and $R^{10}$ represents -L-#1, and
-L- represents the linker and #1 represents the bond to the antibody,
where -L- is represented by §-(C=O)$m$-L1-L2-§§ where
m is 0 or 1;
§ represents the bond to KSP and
§§ represents the bond to the antibody, and
L2 represents:

$^1$—(NH)$_p$—(C=O)$_q$-G4-NH-#$^2$ or #$^1$—(NH)$_p$—(C=O)$_q$-G4-O—NH-#$^2$ where
p is 0 or 1;
q is 0 or 1; and
G4 represents an optionally substituted alkyl or heteroalkyl chain optionally wherein any carbon of the chain is substituted with an alkoxy, hydroxyl, alkylcarbonyloxy, —S-alkyl, thiol, —C(=O)—S-alkyl, —C(=O)—NH-alkyl, —NH—C(=O)-alkyl, amine, —C(=O)—NH$_2$
where
$^1$ denotes the point of attachment to group $L^1$,
$^2$ denotes the point of attachment to the glutamine residue of the binder,
and L1 is represented by formula

$^1$—(NR$^{10}$)$_n$-(G1)$_o$-G3-#$^2$ where
$R^{10}$ represents —H, —NH$_2$ or $C_1$-$C_3$-alkyl;
G1 represents —NH—C(=O)— or

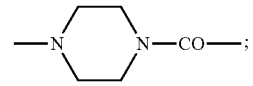

n is 0 or 1;
o is 0 or 1; and
G3 represents a bond or an optionally substituted linear or branched hydrocarbon chain having 1 to 100 carbon atoms from arylene groups and/or linear and/or branched and/or cyclic alkylene groups and which may be interrupted once or more than once by one or more of the groups —O—, —S—, —S(=O)—, —S(=O)$_2$, —NH—, —C(=O)—, —NH—C (=O)—, —C(=O)—NH—, —NMe-, —NHNH—, —S(=O)$_2$—NHNH—, —C(=O)—NHNH— and a 3- to 10-membered aromatic or non-aromatic heterocycle having up to 4 heteroatoms selected from the group consisting of N, O and S, or —S(=O)— (preferably

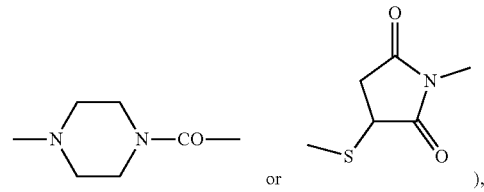

where the side chains, if present, may be substituted by —NH—C(=O)—NH$_2$, —COOH, —OH, —NH$_2$, —NH—CNNH$_2$, sulphonamide, sulphone, sulphoxide or sulphonic acid. #$^1$ is the bond to the KSP inhibitor and #$^2$ is the bond to the coupling group to the antibody (e.g. L2), and salts, solvates and salts of the solvates of the ADC, Embodiment C An ADC of the formula BINDER—[L—KSP]$_n$ where KSP-L- is a compound having the substructure I(sub) below, the binder is an anti-TWEAKR antibody comprising an acceptor glutamine residue (particularly preferably Trastuzumab or an anti-TWEAKR antibody which binds specifically to amino acid D in position 47 (D47) of TWEAKR (SEQ ID NO:169), especially the anti-TWEAK R antibody TPP-2090), anti-HER2 antibody or anti-EGRF antibody (preferably nimotuzumab), aglycosylated variants of these antibodies generated either by deglycosylation by PNGase F or by mutation of N297 (Kabat numbering) of the heavy chain to any amino acid, and variants of the described antibodies being engineered to contain one or more acceptor glutamine residues for transglutaminase (TGase) catalyzed reactions, and n is 2 or 4:

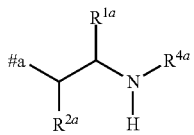

I(sub)

where

\#a represents a bond to the remainder of the molecule;

$R^{1a}$ represents -L-$\#^1$, —H or —$(CH_2)_{0-3}$Z, where Z represents —H, halogen, —$NHY^3$, —C(=O)—$NY^1Y^2$ or —C(=O)—$OY^3$, where $Y^1$ and $Y^2$ independently of one another represent —H, —$NH_2$ or —$(CH_2)_{0-3}$Z', where $Y^3$ represents —H or —$(CH_2)_{0-3}$Z', where Z' represents —H, —$NH_2$, —$SO_3H$, —COOH, where $Y^4$ represents linear or branched $C_{1-6}$-alkyl which is optionally substituted by —NH—C(=O)—$NH_2$, or represents aryl or benzyl which are optionally substituted by —$NH_2$;

$R^{2a}$ and $R^{4a}$ independently of one another represent -L-$\#^1$, H, —C(=O)—$CHY^4$—$NHY^5$ or —$(CH_2)_{0-3}$Z, where Z represents —H, halogen, —$OY^3$, —$SY^3$, $NHY^3$, —C(=O)—$NY^1Y^2$ or —C(=O)—$OY^3$, where $Y^4$ represents linear or branched $C_{1-6}$-alkyl which is optionally substituted by —NHC(=O)—$NH_2$, or represents aryl or benzyl which are optionally substituted by —$NH_2$, where $Y^5$ represents —H or —C(=O)—$CHY^6$—$NH_2$, where $Y^6$ represents linear or branched $C_{1-6}$-alkyl, or $R^{2a}$ represents —H and $R^{4a}$ represents $R^{21}$—$(C=O)_{(0-1)}$-$(P3)_{(0-2)}$-P2-NH—CH$(CH_2C(=O)$—$NH_2)$—C(=O)— where P2 and P3 have the same meaning as defined above, e.g. as shown with respect to formula (IIa), where $R^{21}$ represents H, $C_{1-10}$-alkyl-, $C_{5-10}$-aryl- or $C_{6-10}$-aralkyl-, $C_{5-10}$-heteroalkyl-, $C_{1-10}$-alkyl-O—$C_{6-10}$-aryl-, $C_{5-10}$-heterocycloalkyl-, heteroaryl-, heteroaryl-alkyl-, $C_{1-10}$-alkoxy-, $C_{6-10}$-aryloxy- or $C_{6-10}$-aralkoxy-, $C_{5-10}$-heteroalkoxy-, $C_{1-10}$-alkyl-O—$C_{6-10}$-aryloxy-, $C_{5-10}$-heterocycloalkoxy group, which may be substituted one or more times with —$NH_2$,
—NH-alkyl, —N(alkyl)$_2$, —NH—C(=O)-alkyl, N(alkyl)-C(=O)-alkyl, —$SO_3H$, —S(=O)$_2NH_2$, —S(=O)$_2$—N(alkyl)$_2$, —COOH, —C(=O)—$NH_2$, —C(=O)—N(alkyl)$_2$, or —OH, or represent —H or a group —$(O)_x$—$(CH_2CH_2O)_y$—$R^{22}$, where x is 0 or 1 and where v is a number from 1 to 20, where $R^{22}$ represents —H, -alkyl (preferably $C_{1-12}$-alkyl), —$CH_2$—COOH, —$CH_2$—$CH_2$—COOH, or —$CH_2$—$CH_2$—$NH_2$);

or $R^{2a}$ and $R^{4a}$ together (with formation of a pyrrolidine ring) represent —$CH_2$—$CHR^0$— or —$CHR^{10}$—$CH_2$—, where $R^{10}$ represents —H, -L-$\#^1$, —$NH_2$, —$SO_3H$, —COOH, —SH, —$SO_3H$ or —OH, where one of the substituents $R^{1a}$, $R^{2a}$, $R^{4a}$ or $R^{10}$ represents -L-$\#^1$, L- represents the linker and $\#^1$ represents the bond to the antibody, where -L- is represented by §-(C=O)$m$-L1-L2-§§ where m is 0 or 1;

§ represents the bond to KSP and

§§ represents the bond to the antibody, and

L2 represents $\#^1$—$(NH)_p$—$(C=O)_q$-G4-NH-$\#^2$ or $\#^1$—$(NH)_p$—$(C=O)_q$-G4-O—NH-$\#^2$ where p is 0 or 1;

q is 0 or 1; and

G4 represents an optionally substituted alkyl or heteroalkyl chain optionally wherein any carbon of the chain is substituted with an alkoxy, hydroxyl, alkylcarbonyloxy, —S-alkyl, thiol, —C(=O)—S-alkyl, —C(=O)—NH-alkyl, —NH—C(=O)-alkyl, amine, —C(=O)—$NH_2$ where $\#^1$ denotes the point of attachment to group $L^1$, $\#^2$ denotes the point of attachment to the glutamine residue of the binder, and L1 is represented by formula $\#^1$-(NR$^{10}$)$_n$-(G1)$_o$-G3-$\#^2$ where $R^{10}$ represents —H, —$NH_2$ or $C_1$-$C_3$-alkyl;

G1 represents —NH—C(=O)— or

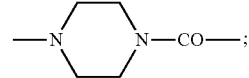

n is 0 or 1;

o is 0 or 1; and

G3 represents a bond or an optionally substituted linear or branched hydrocarbon chain having 1 to 100 carbon atoms from arylene groups and/or linear and/or branched and/or cyclic alkylene groups and which may be interrupted once or more than once by one or more of the groups —O—, —S—, —S(=O)—, —S(=O)$_2$—, —NH—, —C(=O)—, —NH—C(=O)—, —C(=O)—NH—, —NMe-, —NHNH—, —S(=O)$_2$—NHNH—, —C(=O)—NHNH— and a 3- to 10-membered aromatic or non-aromatic heterocycle having up to 4 heteroatoms selected from the group consisting of N, O and S, or —S(=O)— (preferably

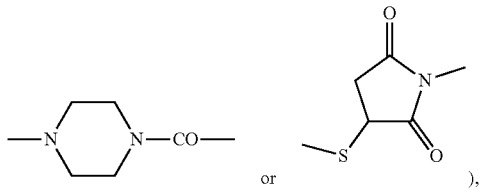

where the side chains, if present, may be substituted by —NH—C(=O)—NH$_2$, —COOH, —OH, —NH$_2$, —NH—CN—NH$_2$, sulphonamide, sulphone, sulphoxide or sulphonic acid.

Here, #$^1$ is the bond to the KSP inhibitor and #$^2$ is the bond to the coupling group to the binder (e.g. L2). and salts, solvates and salts of the solvates of the ADC.

Embodiment D

An ADC of the formula

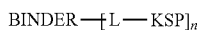

where KSP-L- is a compound of the formula (II), (IIa), (IIIb), (IIIc), (IIId), (IIe), (IIf), (IIg), any of (III) to (IX), or of the formula (IIh) below, the binder is an antibody comprising an acceptor glutamine residue and n is a number 2 or 4:

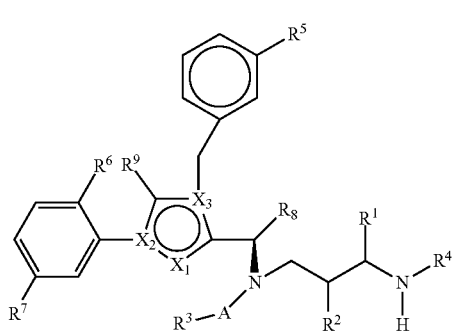

(IIh)

where
$X_1$ represents N, $X_2$ represents N and $X_3$ represents C;
$X_1$ represents CH, $X_2$ represents C and $X_3$ represents N;
$X_1$ represents NH, $X_2$ represents C and $X_3$ represents C; or
$X_1$ represents CH, $X_2$ represents N and $X_3$ represents C;
A represents —C(=O)—;
$R^1$ represents -L-#$^1$;
$R^2$ and $R^4$ represent —H,
or
$R^2$ represents —H and
$R^4$ represents $R^{21}$—C(=O)-P3$_{(0-2)}$-P2-NH—CH(CH$_2$C(=O)—NH$_2$)—C(=O)—
where P2 and P3 have the same meaning as defined above, e.g. as shown with respect to formula (IIa), or
$R^2$ and $R^4$ together (with formation of a pyrrolidine ring) represent —CH$_2$—CHR$^{10}$— or —CHR$^{10}$—CH$_2$—, where $R^{10}$ represents H;
$R^3$ represents $C_{1-10}$-alkyl, which may be substituted by 1-3 —OH groups, 1-3 —O-alkyl groups, 1-3 —SH groups, 1-3 —S-alkyl groups, 1-3 —O—C(=O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)$_n$-alkyl groups, 1-3 —S(=O)$_2$—NH-alkyl groups, 1-3 —NH-alkyl groups, 1-3 —N(alkyl)$_2$ groups or 1-3 —NH$_2$ groups,
where alkyl is preferably $C_{1-3}$-alkyl or -MOD
where -MOD represents —(NR$^{10}$)$_n$-(G1)$_o$-G2-H,
where
$R^{10}$ represents —H or $C_1$-$C_3$-alkyl;
where G1 represents —NH—C(=O)—, —C(=O)—NH— or

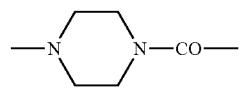

(where, if G1 represents —NH—C(=O)— or

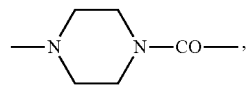

$R^{10}$ does not represent NH$_2$);
where n is 0 or 1;
where o is 0 or 1; and
where G2 represents a linear and/or branched hydrocarbon group which has 1 to 10 carbon atoms and which may be interrupted once or more than once by one or more of the groups —O—, —S—, —S(=O)—, —S(=O)$_2$—, —NR$^y$—, —NR$^y$C(=O)—, —C(=O)—NR$^y$—, —NR$^y$NR$^y$—, —S(=O)$_2$—NR$^y$NR$^y$—, —C(=O)—NR$^y$NR$^y$—,
where R$^y$ represents —H, phenyl, $C_1$-$C_{10}$-alkyl, $C_2$-$C_{10}$-alkenyl or $C_2$-$C_{10}$-alkynyl, each of which may be substituted by —NH—C(=O)—NH$_2$, —COOH, —OH, —NH$_2$, NH—CN—NH$_2$, sulphonamide, sulphone, sulphoxide or sulphonic acid, or represents —C(=O)—, —CR$^x$=N—O—
where R$^x$ represents —H, $C_1$-$C_3$-alkyl or phenyl,
where the hydrocarbon chain including any side chains may be substituted by —NH—C(=O)—NH$_2$, —COOH, —OH, —NH$_2$, NH—CN—NH$_2$, sulphonamide, sulphone, sulphoxide or sulphonic acid,
where -MOD preferably has at least one group —COOH;
$R^5$ represents H or F;
$R^6$ and $R^7$ independently of one another represent —H, $C_{1-3}$-alkyl, fluoro-$C_{1-3}$-alkyl, $C_{2-4}$-alkenyl, fluoro-$C_{2-4}$-alkenyl, $C_{2-4}$-alkynyl, fluoro-$C_{2-4}$-alkynyl, hydroxy or halogen (in particular —F, —Cl, —Br),
$R^8$ represents a branched $C_{1-5}$-alkyl group; and
$R^9$ represents H or F,
where -L- represents the linker and #1 represents the bond to the antibody,
where -L- is represented by §-(C=O)$m$-L1-L2-§§ where
m is 0 or 1;
§ represents the bond to KSP and
§§ represents the bond to the antibody, and
L2 represents:

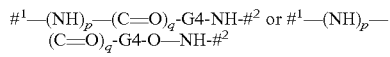

where
p is 0 or 1;
q is 0 or 1; and
G4 represents an optionally substituted alkyl or heteroalkyl chain optionally wherein any carbon of the chain is substituted with an alkoxy, hydroxyl, alkylcarbonyloxy, —S-alkyl, thiol, —C(=O)—S-alkyl, —C(=O)—NH-alkyl, —NH—C(=O)-alkyl, amine, —C(=O)—NH$_2$
where
$^1$ denotes the point of attachment to group L$^1$,
$^2$ denotes the point of attachment to the glutamine residue of the binder,
and L1 is represented by formula

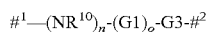

where
R$^{10}$ represents —H, —NH$_2$ or C$_1$-C$_3$-alkyl;
G1 represents —NH—C(=O)— or

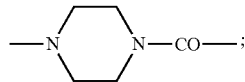

n is 0 or 1;
o is 0 or 1; and
G3 represents a bond or an optionally substituted linear or branched hydrocarbon chain having 1 to 100 carbon atoms from arylene groups and/or linear and/or branched and/or cyclic alkylene groups and which may be interrupted once or more than once by one or more of the groups —O—, —S—, —S(=O)—, —S(=O)$_2$, —NH—, —C(=O)—, —NH—C(=O)—, —C(=O)—NH—, —NMe-, —NHNH—, —S(=O)$_2$—NHNH—, —C(=O)—NHNH— and a 3- to 10-membered aromatic or non-aromatic heterocycle having up to 4 heteroatoms selected from the group consisting of N, O and S, or —S(=O)— (preferably

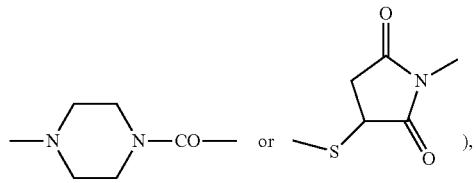

where the hydrocarbon chain including the side chains, if present, may be substituted by —NH—C(=O)—NH$_2$, —COOH, —OH, —NH$_2$, —NH—CNNH$_2$, sulphonamide, sulphone, sulphoxide or sulphonic acid.
where #$^1$ is the bond to the KSP inhibitor and #$^2$ is the bond to the coupling group to the antibody (e.g. L2), and salts, solvates, salts of the solvates and epimers of the ADC.

Embodiment E

A site specific and homogenous ADC of the formula

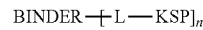

where KSP-L- is a compound of the formula (II), (IIa), (IIIb), (IIIc), (IIId), (IIe), (IIf), (IIg), or any of (III) to (IX), or of the formula (IIh) and salts, solvates and salts of the solvates of the ADC.

One embodiment of the invention is a conjugate of a binder or derivative thereof with one or more active compound molecules, the active compound molecule being a kinesin spindle protein inhibitor attached to the binder via a linker L, where the linker L is attached to a glutamine side chain of the binder, where 1 to 5 kinesin spindle protein inhibitors are attached to the linker L, where the kinesin spindle protein inhibitor has the formula (IIa) below:

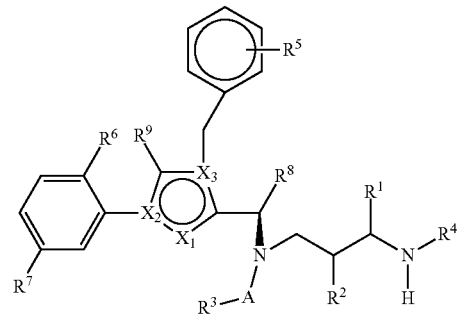

(IIa)

where
X$_1$ represents N, X$_2$ represents N and X$_3$ represents C; or
X$_1$ represents N, X$_2$ represents C and X$_3$ represents N; or
X$_1$ represents CH or CF, X$_2$ represents C and X$_3$ represents N; or
X$_1$ represents NH, X$_2$ represents C and X$_3$ represents C; or
X$_1$ represents CH, X$_2$ represents N and X$_3$ represents C (with X$_1$ representing CH, X$_2$ representing C and X$_3$ representing N being preferred);
R$^1$ represents —H, -MOD, -L-#1 or —(CH$_2$)$_{0-3}$Z,
where -L-#1 represents the linker and #1 represents the bond to the binder or derivative thereof.
where -MOD is represented as defined infra,
where Z represents —H, halogen, —OY$^3$, —SY$^3$, —NHY$^3$, —C(=O)—NY$^1$Y$^2$ or —C(=O)—OY$^3$,
where Y$^1$ and Y$^2$ independently of one another represent —H, —NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z',
where Y$^3$ represents —H or —(CH$_2$)$_{0-3}$Z',
where Z' represents —H, —NH$_2$, —SO$_3$H, —COOH, —NH—C(=O)—CH$_2$—CH$_2$—CH(NH$_2$)COOH or —(C(=O)—NH—CHY$^4$)$_{1-3}$COOH,
where W represents —H or —OH,
where Y$^4$ represents linear or branched C$_{1-6}$-alkyl which is optionally substituted by —NH—C(=O)—NH$_2$, or represents aryl or benzyl which are optionally substituted by —NH$_2$;

$R^2$ represents -L-#1, H, -MOD, —C(=O)—CHY$^4$—NHY$^5$ or —(CH$_2$)$_{0-3}$Z,
  where -L-#1 represents the linker and #1 represents the bond to the binder or derivative thereof,
  where -MOD is represented as defined infra,
  where Z represents —H, halogen, —OY$^3$, —SY$^3$, NHY$^3$, —C(=O)—NY$^1$Y$^2$ or —C(=O)—OY$^3$,
  where Y$^1$ and Y$^2$ independently of one another represent —H, —NH$_2$ or —(CH$_2$)$_{0-3}$Z', and
  where Y$^3$ represents —H or —(CH$_2$)$_{0-3}$Z',
  where Z' represents —H, —SO$_3$H, —NH$_2$ or —COOH;
  where Y$^4$ represents linear or branched C$_{1-6}$-alkyl which is optionally substituted by —NHC(=O)—NH$_2$, or represents aryl or benzyl which are optionally substituted by —NH$_2$,
  where Y$^5$ represents —H or —C(=O)—CHY$^6$—NH$_2$,
  where Y$^6$ represents linear or branched C$_{1-6}$-alkyl;
$R^4$ represents -L-#1, —H, —C(=O)—CHY$^4$—NHY$^5$ or —(CH$_2$)$_{0-3}$Z,
  where -L-#1 represents the linker and #1 represents the bond to the binder or derivative thereof,
  where Z represents —H, —OY$^3$, —SY$^3$, —NHY$^3$, —C(=O)—NY$^1$Y$^2$ or —C(=O)—OY$^3$,
  where Y$^1$ and Y$^2$ independently of one another represent —H, —NH$_2$ or —(CH$_2$)$_{0-3}$Z',
  where Y$^3$ represents —H or —(CH$_2$)$_{0-3}$Z',
  where Z' represents —H, —SO$_3$H, —NH$_2$ or —COOH;
  where Y$^4$ represents linear or branched C$_{1-6}$-alkyl which is optionally substituted by —NH—C(=O)—NH$_2$, or represents aryl or benzyl which are optionally substituted by —NH$_2$, and
  where Y$^5$ represents —H or —C(=O)—CHY$^6$—NH$_2$,
  where Y$^6$ represents linear or branched C$_{1-6}$-alkyl,
or
$R^2$ and $R^4$ together (with formation of a pyrrolidine ring) represent —CH$_2$—CHR$^{10}$— or —CHR$^{10}$—CH$_2$—,
  where R$^{10}$ represents L-#1, —H, —NH$_2$, —SO$_3$H, —COOH, —SH or —OH,
A represents —C(=O)—, —S(=O)—, —S(=O)$_2$—, —S(=O)$_2$—NH— or —C(=N—NH$_2$)—;
$R^3$ represents -L-#1, -MOD or an optionally substituted alkyl, cycloalkyl, aryl, heteroaryl, heteroalkyl, heterocycloalkyl group, preferably -L-#1 or a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3 —OH groups, 1-3 halogen atoms, 1-3 halogenated alkyl groups (each having 1-3 halogen atoms), 1-3 —O-alkyl groups, 1-3 —SH groups, 1-3 —S-alkyl groups, 1-3 —O—C(=O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)$_n$-alkyl groups, 1-3 —S(=O)$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups,
  where -L-#1 represents the linker and #1 represents the bond to the binder or derivative thereof,
  where n represents 0, 1 or 2,
  where Z represents —H, halogen, —OY$^3$, —SY$^3$, —NHY$^3$, —C(=O)—NY$^1$Y$^2$ or —C(=O)—OY$^3$,
  where Y$^1$ and Y$^2$ independently of one another represent —H, —NH$_2$ or —(CH$_2$)$_{0-3}$Z' and
  where Y$^3$ represents —H, —(CH$_2$)$_{0-3}$—CH(NHC(=O)—CH$_3$)Z', —(CH$_2$)$_{0-3}$—CH(NH$_2$)Z' or —(CH$_2$)$_{0-3}$Z', where
  where Z' represents —H, —SO$_3$H, —NH$_2$ or —COOH;
$R^5$ represents —H, —NH$_2$, —NO$_2$, halogen (in particular —F, —Cl, —Br), —SH or —(CH$_2$)$_{0-3}$Z,
  where Z represents —H, —OY$^3$, —SY$^3$, halogen, —NHY$^3$, —C(O)—NY$^1$Y$^2$ or —C(O)—OY$^3$,
  where Y$^1$ and Y$^2$ independently of one another represent —H, —NH$_2$ or —(CH$_2$)$_{0-3}$Z',
  where Y$^3$ represents —H or —(CH$_2$)$_{0-3}$Z',
  where Z' represents —H, —SO$_3$H, —NH$_2$ or —COOH
$R^6$ and $R^7$ independently of one another represent —H, cyano, C$_{1-10}$-alkyl, fluoro-C$_{1-10}$-alkyl, C$_{2-10}$-alkenyl, fluoro-C$_{2-10}$-alkenyl, C$_{2-10}$-alkynyl, fluoro-C$_{2-10}$-alkynyl, hydroxy, —NO$_2$, —NH$_2$, —COOH or halogen (in particular —F, —Cl, —Br),
$R^8$ represents C$_{1-10}$-alkyl, fluoro-C$_{1-10}$-alkyl, C$_{2-10}$-alkenyl, fluoro-C$_{2-10}$-alkenyl, C$_{2-10}$-alkynyl, fluoro-C$_{2-10}$-alkynyl, C$_{4-10}$-cycloalkyl, fluoro-C$_{4-10}$-cycloalkyl or —(CH$_2$)$_{0-2}$-(HZ$^2$),
  where HZ$^2$ represents a 4- to 7-membered heterocycle having up to two heteroatoms selected from the group consisting of N, O and S (preferably oxetane), where each of these groups may be substituted by —OH, —COOH, —NH$_2$ or -L-#1;
where one or none of the substituents R$^1$, R$^2$, R$^3$, R$^4$ R$^5$, R$^8$ and R$^{10}$ represents or (in the case of R$^8$) contains -L-#1,
where L represents the linker and
where #1 represents the bond to the binder or derivative thereof,
where -MOD represents —(NR$^{10}$)$_n$-(G1)-G2-H,
  where R$^{10}$ represents —H or C$_1$-C$_3$-alkyl;
  where G1 represents —NH—C(=O)—, —C(=O)—NH— or

—N⟨   ⟩N—CO—

(where, if G1 represents —NH—C(=O)— or

—N⟨   ⟩N—CO—,

R$^{10}$ does not represent NH$_2$);
  where n is 0 or 1;
  where o is 0 or 1; and
  where G2 represents a linear and/or branched hydrocarbon group which has 1 to 10 carbon atoms and which may be interrupted once or more than once by one or more of the groups —O—, —S—, —S(=O)—, —S(=O)$_2$—, —NR$^y$—, —NR$^y$C(=O)—, —C(=O)—NR$^y$—, —NR$^y$NR$^y$—, —S(=O)$_2$—NR$^y$NR$^y$—, —C(=O)—NR$^y$NR$^y$—,
  where R$^y$ represents —H, phenyl, C$_1$-C$_{10}$-alkyl, C$_2$-C$_{10}$-alkenyl or C$_2$-C$_{10}$-alkynyl, each of which may be substituted by —NH—C(=O)—NH$_2$, —COOH, —OH, —NH$_2$, NH—CN—NH$_2$, sulphonamide, sulphone, sulphoxide or sulphonic acid, or represents —C(=O)—, —CR$^x$=N—O—
  where R$^x$ represents —H, C$_1$-C$_3$-alkyl or phenyl,
  where the hydrocarbon chain including any side chains may be substituted by —NH—C(=O)—NH$_2$, —COOH, —OH, —NH$_2$, NH—CN—NH$_2$, sulphonamide, sulphone, sulphoxide or sulphonic acid,
where G3 represents —H or —COOH, and
where -MOD preferably has at least one group —COOH;
and the salts, solvates, salts of the solvates, and epimers thereof.

Another embodiment of the invention is a conjugate as defined above where $X_1$ represents CH, $X_2$ represents C and $X_3$ represents N.

Another embodiment of the invention is a conjugate as defined above where the substituent $R^1$ represents -L-#1.

Another embodiment of the invention is a conjugate of a binder or derivative thereof with the active compound molecule being a kinesin spindle protein inhibitor attached to the binder via a linker L, where the linker L is attached to a glutamine side chain of the binder, where the kinesin spindle protein inhibitor has the substructure below:

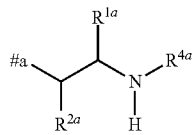

where
a represents a bond to the rest of the molecule;
$R^{1a}$ represents H or —(CH$_2$)$_{0-3}$Z,
    where Z represents —H, halogen, —OY$^3$, —SY$^3$, —NHY$^3$, —C(=O)—NY$^1$Y$^2$ or —C(=O)—OY$^3$,
    where Y$^1$ and Y$^2$ independently of one another represent —H, —NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z',
    where Y$^3$ represents —H or —(CH$_2$)$_{0-3}$Z',
    where Z' represents —H, —NH$_2$, —SO$_3$H, —COOH, —NH—C(=O)—CH$_2$—CH$_2$—CH(NH$_2$)COOH or —(C(=O)—NH—CHY$^4$)$_{1-3}$COOH,
    where W represents —H or —OH,
    where Y$^4$ represents linear or branched C$_{1-6}$-alkyl which is optionally substituted by —NH—(C=O)—NH$_2$, or represents aryl or benzyl which are optionally substituted by —NH$_2$;
$R^{2a}$ and $R^{4a}$ independently of one another represent —H, —C(=O)—CHY$^4$—NHY$^5$ or —(CH$_2$)$_{0-3}$Z, or
$R^2$ and $R^4$ together (with formation of a pyrrolidine ring) represent —CH$_2$—CHR$^{10}$— or —CHR$^{10}$—CH$_2$—,
    where R$^{10}$ represents —H, —NH$_2$, —SO$_3$H, —COOH, —SH, or —OH;
    where Z represents —H, halogen, —OY$^3$, —SY$^3$, —NHY$^3$, —C(=O)—NY$^1$Y$^2$ or —C(=O)—OY$^3$,
    where Y$^1$ and Y$^2$ independently of one another represent —H, —NH$_2$ or —(CH$_2$)$_{0-3}$Z',
    where Y$^3$ represents —H or —(CH$_2$)$_{0-3}$Z',
    where Z' represents —H, —SO$_3$H, —NH$_2$ or —COOH;
    where Y$^4$ represents linear or branched C$_{1-6}$-alkyl which is optionally substituted by —NH—C(=O)—NH$_2$, or represents aryl or benzyl which are optionally substituted by —NH$_2$,
    where Y$^5$ represents —H or —C(=O)—CHY$^6$—NH$_2$,
    where Y$^6$ represents linear or branched C$_{1-6}$-alkyl;
where the kinesin spindle protein inhibitor is attached to the linker by substitution of a hydrogen atom at $R^{1a}$, $R^{2a}$, $R^{4a}$ or at the pyrrolidine ring formed by $R^{2a}$ and $R^{4a}$ and the salts, solvates, salts of the solvates, and epimers thereof.

Another embodiment of the invention is a conjugate as defined above where the kinesin spindle protein inhibitor is represented by general formula (I):

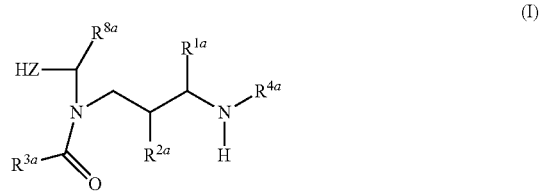

where
$R^{1a}$ represents —H or —(CH$_2$)$_{0-3}$Z,
    where Z represents —H, —NHY$^3$, —OY$^3$, —SY$^3$, halogen, —C(=O)—NY$^1$Y$^2$ or —C(=O)—OY$^3$,
    where Y$^1$ and Y$^2$ independently of one another represent —H, —NH$_2$, —(CH$_2$CH$_2$O)$_{0-3}$—(CH$_2$)$_{0-3}$Z' or —CH(CH$_2$W)Z', and
    where Y$^3$ represents —H or —(CH$_2$)$_{0-3}$Z',
    where Z' represents —H, —NH$_2$, —SO$_3$H, —COOH, —NH—C(=O)—CH$_2$—CH$_2$—CH(NH$_2$)COOH or —(C(=O)—NH—CHY$^4$)$_{1-3}$COOH,
    where W represents —H or —OH,
    where Y$^4$ represents linear or branched C$_{1-6}$-alkyl which is optionally substituted by —NH—(C=O)—NH$_2$, or represents aryl or benzyl which are optionally substituted by —NH$_2$;
$R^{2a}$ and $R^{4a}$ independently of one another represent —H, —C(=O)—CHY$^4$—NHY$^5$ or —(CH$_2$)$_{0-3}$Z, or
$R^{2a}$ and $R^{4a}$ together (with formation of a pyrrolidine ring) represent —CH$_2$—CHR$^{10}$— or —CHR$^{10}$—CH$_2$—,
    where R$^{10}$ represents —H, —NH$_2$, —SO$_3$H, —COOH, —SH, or —OH;
    where Z represents —H, halogen, —OY$^3$, —SY$^3$, —NHY$^3$, —C(=O)—NY$^1$Y$^2$ or —C(=O)—OY$^3$,
    where Y$^1$ and Y$^2$ independently of one another represent —H, —NH$_2$ or —(CH$_2$)$_{0-3}$Z',
    where Y$^3$ represents —H or —(CH$_2$)$_{0-3}$Z',
    where Z' represents —H, —SO$_3$H, —NH$_2$ or —COOH;
    where Y$^4$ represents linear or branched C$_{1-6}$-alkyl which is optionally substituted by —NH—C(=O)—NH$_2$, or represents aryl or benzyl which are optionally substituted by —NH$_2$,
    where Y$^5$ represents —H or —C(=O)—CHY$^6$—NH$_2$,
    where Y$^6$ represents linear or branched C$_{1-6}$-alkyl;
$R^{3a}$ represents an optionally substituted alkyl, cycloalkyl, aryl, heteroaryl, heteroalkyl, heterocycloalkyl group, preferably -L-BINDER, or a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3 —OH groups, 1-3 halogen atoms, 1-3 halogenated alkyl groups (each having 1-3 halogen atoms), 1-3 —O-alkyl groups, 1-3 —SH groups, 1-3 —S-alkyl groups, 1-3 —O—C(=O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)$_n$-alkyl groups, 1-3 —S(=O)$_2$—

NH-alkyl groups, 1-3 —NH-alkyl groups, 1-3 —N(alkyl)$_2$ groups, 1-3 —NH$_2$ groups or 1-3 —(CH$_2$)$_{0-3}$Z groups, where n is 0, 1 or 2, where Z represents —H, halogen, —OY$^3$, —SY$^3$, —NHY$^3$, —C(=O)—NY$^1$Y$^2$ or —C(O)—OY$^3$, where Y$^1$ and Y$^2$ independently of one another represent —H, —NH$_2$ or —(CH$_2$)$_{0-3}$Z', where Y$^3$ represents —H, —(CH$_2$)$_{0-3}$—CH(NH—C(=O)—CH$_3$)Z', —(CH$_2$)$_{0-3}$—CH(NH$_2$)Z' or —(CH$_2$)$_{0-3}$Z', where Z' represents —H, —SO$_3$H, —NH$_2$ or —COOH where "alkyl" preferably represents C$_{1-10}$-alkyl);

R$^a$ represents C$_{1-10}$-alkyl;

HZ represents a mono- or bicyclic heterocycle which may be substituted by one or more substituents selected from the group consisting of halogen, C$_{1-10}$-alkyl groups, C$_{6-10}$-aryl groups and C$_{6-10}$-aralkyl groups which may optionally be substituted by halogen;

where the kinesin spindle protein inhibitor is attached to the linker by substitution of a hydrogen atom at R$^{1a}$, R$^{2a}$, R$^{3a}$, R$^{4a}$, R$^{8a}$ or at the pyrrolidine ring formed by R$^{2a}$ and R$^{4a}$ and the salts, solvates and salts of the solvates thereof.

Another embodiment of the invention is a conjugate as defined above, where the linker L is attached to a glutamine side chain of the binder, where 1 to 5 kinesin spindle protein inhibitors are attached to the linker L, where the active compound molecule linker is represented by general formula (II):

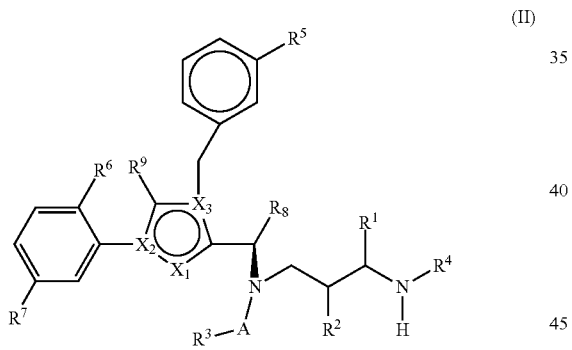

(II)

where

X$_1$ represents N, X$_2$ represents N and X$_3$ represents C; or

X$_1$ represents N, X$_2$ represents C and X$_3$ represents N; or

X$_1$ represents CH, X$_2$ represents C and X$_3$ represents N; or

X$_1$ represents NH, X$_2$ represents C and X$_3$ represents C; or

X$_1$ represents CH, X$_2$ represents N and X$_3$ represents C

R$^1$ represents —H, -L-#1 or —(CH$_2$)$_{0-3}$Z, where -L-#1 represents the linker and #1 represents the bond to the binder or derivative thereof.

where Z represents —H, halogen, —OY$^3$, —SY$^3$, —NHY$^3$, —C(=O)—NY$^1$Y$^2$ or —C(=O)—OY$^3$, where Y$^1$ and Y$^2$ independently of one another represent —H, —NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z', where Y$^3$ represents —H or —(CH$_2$)$_{0-3}$Z', where Z' represents —H, —NH$_2$, —SO$_3$H, —COOH, —NH—C(=O)—CH$_2$—CH$_2$—CH(NH$_2$)COOH or —(C(=O)—NH—CHY$^4$)$_{1-3}$COOH, where W represents —H or —OH, where Y$^4$ represents linear or branched C$_{1-6}$-alkyl which is optionally substituted by NH—C(=O)—NH$_2$, or represents aryl or benzyl which are optionally substituted by —NH$_2$;

R$^2$ and R$^4$ independently of one another represents -L-#1, —H, —C(=O)—CHY$^4$—NHY$^5$ or —(CH$_2$)$_{0-3}$Z, where Y$^4$ represents linear or branched C$_{1-6}$-alkyl which is optionally substituted by NH—C(=O)—NH$_2$, or represents aryl or benzyl which are optionally substituted by —NH$_2$, and where Y$^5$ represents —H or —C(=O)—CHY$^6$—NH$_2$, where Y$^6$ represents linear or branched C$_{1-6}$-alkyl, or R$^2$ represents —H and R$^4$ represents a group of

R$^{21}$—(C=O)$_{(0-1)}$-(P3)$_{(0-2)}$-P2-NH—CH(CH$_2$C(=O)—NH$_2$)—C(=O)— where R$^{21}$ represents H, C$_{1-10}$-alkyl-, C$_{5-10}$-aryl- or C$_{6-10}$-aralkyl-, C$_{5-10}$-heteroalkyl-, C$_{1-10}$-alkyl-O—C$_{6-10}$-aryl-, C$_{5-10}$-heterocycloalkyl-, heteroaryl-, heteroaryl-alkyl-, C$_{1-10}$-alkoxy-, C$_{6-10}$-aryloxy- or C$_{6-10}$-aralkoxy-, C$_{5-10}$-heteroalkoxy-, C$_{1-10}$-alkyl-O—C$_{6-10}$-aryloxy-, C$_{5-10}$-heterocycloalkoxy group, which may be substituted one or more times with —NH$_2$, —NH-alkyl, —N(alkyl)$_2$, —NH—C(=O)-alkyl, N(alkyl)-C(=O)-alkyl, —SO$_3$H, —S(=O)$_2$NH$_2$, —S(=O)$_2$—N(alkyl)$_2$, —COOH, —C(=O)—NH$_2$, —C(=O)—N(alkyl)$_2$, or —OH, or represent —H or a group —(O)$_x$—(CH$_2$CH$_2$O)$_y$—R$^{22}$, where x is 0 or 1 and where v is a number from 1 to 20, where R$^{22}$ represents —H, -alkyl (preferably C$_{1-12}$-alkyl), —CH$_2$—COOH, —CH$_2$—CH$_2$—COOH, or —CH$_2$—CH$_2$—NH$_2$);

where P2 and P3 have the same meaning as defined above, e.g. as shown with respect to formula (IIa), or R$^2$ and R$^4$ together (with formation of a pyrrolidine ring) represent —CH$_2$—CHR$^{10}$— or —CHR$^{10}$—CH$_2$—, where R$^{10}$ represents L-#1, —H, —NH$_2$, —SO$_3$H, —COOH, —SH or —OH, where Z represents —H, —OY$^3$, —SY$^3$, halogen, —NHY$^3$, —C(=O)—NY$^1$Y$^2$ or —C(=O)—OY$^3$, where Y$^1$ and Y$^2$ independently of one another represent —H, —NH$_2$ or —(CH$_2$)$_{0-3}$Z', where Y$^3$ represents —H or —(CH$_2$)$_{0-3}$Z', where Z' represents —H, —SO$_3$H, —NH$_2$ or —COOH;

A represents —C(=O)—, —S(=O)—, —S(=O)$_2$—, —S(=O)$_2$—NH— or —C(=N—NH$_2$)—;

R$^3$ represents -L-#1 or an optionally substituted alkyl, aryl, heteroaryl, or heterocycloalkyl group, preferably -L-#1 or a C$_{1-10}$-alkyl, C$_{6-10}$-aryl, C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3 —OH groups, 1-3 halogen atoms, 1-3 halogenated alkyl groups (each having 1-3 halogen atoms), 1-3 —O-alkyl groups, 1-3 —SH groups, 1-3 —S-alkyl groups, 1-3 —O—C(=O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)$_n$-alkyl groups, 1-3 —S(=O)$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups, where -L-#1 represents the linker and #1 represents the bond to the binder or derivative thereof, where n represents 0, 1 or 2, where Z represents —H, halogen, —$OY^3$, —$SY^3$, —$NHY^3$, —C(=O)—$NY^1Y^2$ or —C(=O)—$OY^3$, where $Y^1$ and $Y^2$ independently of one another represent —H, —$NH_2$ or —$(CH_2)_{0-3}Z'$ and where $Y^3$ represents —H, —$(CH_2)_{0-3}$—CH(NHC(=O)—$CH_3$)$Z'$, —$(CH_2)_{0-3}$—CH($NH_2$)$Z'$ or —$(CH_2)_{0-3}Z'$, where where $Z'$ represents —H, —$SO_3H$, —$NH_2$ or —COOH;

$R^5$ represents -L-#1, —H, —F, —$NH_2$, —$NO_2$, halogen (in particular —F, —Cl, —Br), —SH or —$(CH_2)_{0-3}Z$, where Z represents —H, —$OY^3$, —$SY^3$, halogen, —$NHY^3$, —C(=O)—$NY^1Y^2$ or —C(=O)—$OY^3$, where $Y^1$ and $Y^2$ independently of one another represent —H, —$NH_2$ or —$(CH_2)_{0-3}Z'$, where $Y^3$ represents —H or —$(CH_2)_{0-3}Z'$, where $Z'$ represents —H, —$SO_3H$, —$NH_2$ or —COOH;

where one of the substituents $R^1$, $R^2$, $R^3$, $R^4$ and $R^5$ represents -L-#1, L represents the linker and #1 represents the bond to the binder or derivative thereof, $R^6$ and $R^7$ independently of one another represent —H, cyano, $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, hydroxy or halogen (in particular —F, —Cl, —Br), $R^8$ represents $C_{1-10}$-alkyl, fluoro-$C_{1-10}$-alkyl, $C_{4-10}$-cycloalkyl, fluoro-$C_{4-10}$-cycloalkyl, or optionally substituted oxetane; and $R^9$ represents —H, —F, —$CH_3$, —$CF_3$, —$CH_2F$ or —$CHF_2$;

and the salts, solvates, salts of the solvates, and epimers thereof.

Another embodiment of the invention is a conjugate as defined above, $R^1$ represents —H, -L-#1 or —$(CH_2)_{0-3}Z$, where -L-#1 represents the linker and #1 represents the bond to the binder or derivative thereof.

where Z represents —H, —$OY^3$, —$SY^3$, —$NHY^3$, —C(=O)—$NY^1Y^2$ or —C(=O)—$OY^3$, where $Y^1$ and $Y^2$ independently of one another represent —H, —$NH_2$, —$(CH_2CH_2O)_{0-3}$—$(CH_2)_{0-3}Z'$ or —CH($CH_2W$)$Z'$, where $Y^3$ represents —H or —$(CH_2)_{0-3}Z'$, where $Z'$ represents —H, —$NH_2$, —COOH, —NH—C(=O)—$CH_2$—$CH_2$—CH($NH_2$)COOH or —(C(=O)—NH—CHY$^4$)$_{1-3}$COOH, where W represents —H or —OH, where $Y^4$ represents linear or branched $C_{1-6}$-alkyl which is optionally substituted by NH—C(=O)—$NH_2$, or represents aryl or benzyl which are optionally substituted by —$NH_2$;

$R^2$ and $R^4$ independently of one another represent -L-#1, —H or —C(=O)—CHY$^4$—NHY$^5$, or $R^2$ and $R^4$ together (with formation of a pyrrolidine ring) represent —$CH_2$—CHR$^{10}$—, where $R^{10}$ represents —H, -L-#1, —$NH_2$, —COOH, —SH, —OH or —$SO_3H$, where $Y^4$ represents linear or branched $C_{1-6}$-alkyl which is optionally substituted by NH—C(=O)—$NH_2$, or represents aryl or benzyl which are optionally substituted by —$NH_2$, and where $Y^5$ represents —H or —C(=O)—CHY$^6$—$NH_2$, where $Y^6$ represents linear or branched $C_{1-6}$-alkyl, A represents —C(=O)—, $R^3$ represents —($CH_2$)OH or -L-#1, and $R^5$ represents -L-#1 or —H, where one of the substituents $R^1$, $R^2$, $R^3$, $R^4$ and $R^5$ represents -L-#1, and the salts, solvates, salts of the solvates, and epimers thereof.

Another embodiment of the invention is a conjugate as defined above where $R^6$ and $R^7$ independently of one another represent —H, $C_{1-3}$-alkyl or halogen.

Another embodiment of the invention is a conjugate as defined above where $R^8$ represents $C_{1-4}$-alkyl (preferably tert-butyl).

Another embodiment of the invention is a conjugate as defined above where $R^9$ represents —H.

Another embodiment of the invention is a conjugate as defined above where $R^6$ and $R^7$ represent —F.

Another embodiment of the invention is a conjugate as defined above where the binder or derivative thereof is a binder peptide or protein or a derivative of a binder peptide or protein.

Another embodiment of the invention is a conjugate as defined above where the conjugate has 2 conjugation sites per binder.

Another embodiment of the invention is a conjugate according as defined above where the conjugate has 4 conjugation sites per binder.

Another embodiment of the invention is a conjugate as defined above where the binder peptide or protein represents an antibody or the derivative of the binder peptide or protein comprising an acceptor glutamine side chain which can be recognized by transglutaminase.

Another embodiment of the invention is a conjugate as defined above produced by transglutaminase mediated conjugation.

Another embodiment of the invention is a conjugate as defined above produced using Transglutaminase originated from *Streptomyces Mobaraensis*.

Another embodiment of the invention is a conjugate as defined above where the binder binds to a cancer target molecule.

Another embodiment of the invention is a conjugate as defined above where the binder binds to an extracellular target molecule.

Another embodiment of the invention is a conjugate as defined above where the binder, after binding to the extracellular target molecule, is internalized and processed intracellularly (preferably lysosomally) by the cell expressing the target molecule.

Another embodiment of the invention is a conjugate s defined above where the binder peptide or protein is a human, humanized or chimeric monoclonal antibody or an antigen-binding fragment thereof.

Another embodiment of the invention is a conjugate as defined above where the binder peptide or protein is an antibody bearing acceptor glutamine residue(s) in its heavy chain, optionally within the CH2 domain.

Another embodiment of the invention is a conjugate as defined above where the binder peptide or protein is an antibody bearing acceptor glutamine residue is in its heavy chain at position 295 (KABAT numbering system).

Another embodiment of the invention is a conjugate as defined above where the binder peptide or protein is an antibody comprising a N297X substitution wherein X is any amino acid but asparagine; even more preferred are N297D, N297Q, N297S or N297A, highly preferred are N297A and N297Q.

Another embodiment of the invention is a conjugate as defined above where the binder peptide or protein is an antibody comprising N297Q substitution and a Q295X substitution wherein X is any amino acid but glutamine, preferred is Q295N.

Another embodiment of the invention is a conjugate as defined above where the binder peptide or protein is an antibody comprising an asparagine at residue 297 that substantially lacks N-linked glycosylation.

Another embodiment of the invention is a conjugate as defined above where the binder peptide or protein is an antibody produced in a host cell that produces antibodies lacking N-linked glycosylation at amino acid residue N297.

Another embodiment of the invention is a conjugate as defined above where the binder peptide or protein is an anti-HER2 antibody, an anti-EGFR antibody, an anti-TWEAKR antibody or an antigen-binding fragment thereof.

Another embodiment of the invention is a conjugate as defined above where the anti-TWEAKR antibody binds specifically to amino acid D in position 47 (D47) of TWEAKR (SEQ ID NO: 169), preferably the anti-TWEAKR antibody TPP2090 and aglycosylated variants thereof.

Another embodiment of the invention is a conjugate as defined above where the anti-TWEAKR antibody binds specifically to amino acid D in position 47 (D47) of TWEAKR (SEQ ID NO: 169), preferably the anti-TWEAKR antibody TPP-2090-HC-N297A or TPP-2090-HC-N297Q.

Another embodiment of the invention is a conjugate as defined above, where the linker L is attached to a glutamine side chain of the binder, where 1 to 5 kinesin spindle protein inhibitors are attached to the linker L, where the linker L has one of the basic structures (i) to (iv) below:
  (i) —(C=O)$_m$—SG1-L1-L2-
  (ii) —(C=O)$_m$-L1-SG-L1-L2-
  (iii) —(C=O)$_m$-L1-L2-
  (iv) —(C=O)$_m$-L1-SG-L2
  where m is 0 or 1, SG and SG1 are in vivo cleavable groups, L1 independently of one another represent organic groups not cleavable in vivo, and L2 represents a coupling group to the binder.

Another embodiment of the invention is a conjugate as defined above, where the linker L is attached to a glutamine side chain of the binder, where 1 to 5 kinesin spindle protein inhibitors are attached to the linker L, where the in vivo cleavable group SG is a 2-8 oligopeptide group, preferably dipeptide group or a disulphide, a hydrazone, an acetal or an aminal and SG1 is a 2-8 oligopeptide group, preferably a dipeptide group.

Another embodiment of the invention is a conjugate as defined above where the linker is attached to a glutamine side chain and has the formula below:

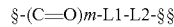

where
m is 0 or 1;
§ represents the bond to the active compound molecule and
§§ represents the bond to the binder peptide or protein, and
L1 represents —(NR$^{10}$)$_n$-(G1)o-G3-, where R$^{10}$ represents —H, —H$_2$ or C$_1$-C$_3$-alkyl;
G1 represents —NH—C(=O)— or

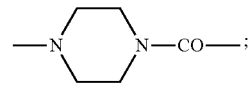

n is 0 or 1;
o is 0 or 1; and
G3 represents a bond or an optionally substituted linear or branched hydrocarbon chain having 1 to 100 carbon atoms from arylene groups and/or linear and/or branched and/or cyclic alkylene groups and which may be interrupted once or more than once by one or more of the groups —O—, —S—, —S(=O)—, —S(=O)$_2$, —NH—, —C(=O)—, —NH—C(=O)—, —C(=O)—NH—, —NMe-, —NHNH—, —S(=O)$_2$—NHNH—, —C(=O)—NHNH— and a 3- to 10-membered aromatic or non-aromatic heterocycle having up to 4 heteroatoms selected from the group consisting of N, O and S, or —S(=O)— (preferably

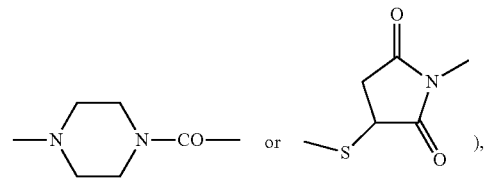

where the hydrocarbon chain including the side chains, if present, may be substituted by —NH—C(=O)—NH$_2$, —COOH, —OH, —NH$_2$, —NH—CN—NH$_2$, sulphonamide, sulphone, sulphoxide or sulphonic acid.
or represents one of the groups below:

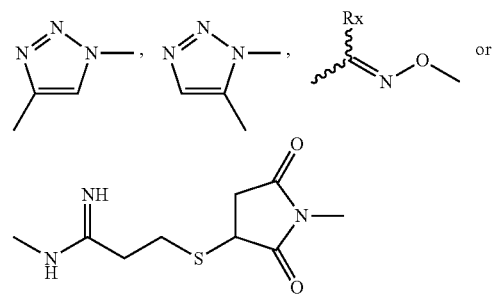

where Rx represents —H, C$_1$-C$_3$-alkyl or phenyl.
L2 represents #1-(NH)$_p$—(C=O)$_q$-G4-NH-#2 or #1-(NH)$_p$—(C=O)$_q$-G4-O—NH-#2 where
p is 0 or 1;
q is 0 or 1; and
G4 represents an optionally substituted alkyl or heteroalkyl chain optionally wherein any carbon of the chain is substituted with an alkoxy, hydroxyl, alkylcarbonyloxy, —S— alkyl, thiol, —C(=O)—S-alkyl, —C(=O)—NH-alkyl, —NH—C(=O)-alkyl, amine, —C(=O)—NH$_2$
where
$^1$ denotes the point of attachment to group L$^1$,
$^2$ denotes the point of attachment to the glutamine residue of the binder,
Another embodiment of the invention is a conjugate as defined above where the hydrocarbon chain is interrupted by one of the groups below:

185

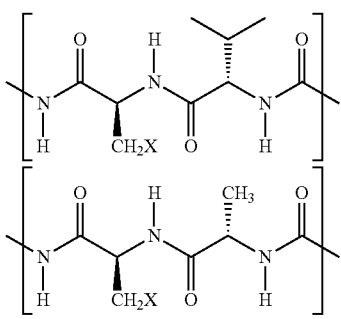

where X represents —H or a $C_{1-10}$-alkyl group which may optionally be substituted by —NH—C(=O)—NH$_2$, —COOH, —OH, —NH$_2$, —NH—CN—NH$_2$, sulphone, sulphoxide or sulphonic acid.

Another embodiment of the invention is a conjugate as defined above where L2 is one of the groups below:
L2 is

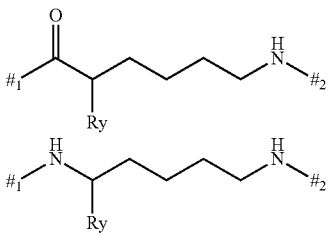

with Ry is —H, —C(=O)—NH-alkyl, —NH—C(=O)-alkyl, —C(=O)—NH$_2$, or —NH$_2$.
where
$^1$ denotes the point of attachment to group $L^1$,
$^2$ denotes the point of attachment to the glutamine residue of the binder.

Another embodiment of the invention is a conjugate as defined above where Ry is H or NHCOMe Another embodiment of the invention is a conjugate as defined above where $R^1$ or $R^4$ represents -L-#1.

Another embodiment of the invention is a conjugate as defined above where the anti-TWEAKR antibody is an agonistic antibody.

Another embodiment of the invention is a conjugate as defined above which comprises:
a variable heavy chain comprising:
a. a CDR1 of the heavy chain encoded by an amino acid sequence comprising the formula PYPMX (SEQ ID NO: 171), where X is I or M;
b. a CDR2 of the heavy chain encoded by an amino acid sequence comprising the formula YISPSGGXTHYADSVKG (SEQ ID NO: 172), where X is S or K; and
c. a CDR3 of the heavy chain encoded by an amino acid sequence comprising the formula GGDTYFDYFDY (SEQ ID NO: 173);
and a variable light chain comprising:
d. a CDR1 of the light chain encoded by an amino acid sequence comprising the formula RASQSISXYLN (SEQ ID NO: 174), where X is G or S;
e. a CDR2 of the light chain encoded by an amino acid sequence comprising the formula XASSLQS (SEQ ID NO: 175), where X is Q, A or N; and

186 f. a CDR3 of the light chain encoded by an amino acid sequence comprising the formula QQSYXXPXIT (SEQ ID NO: 176), where X at position 5 is T or S, X at position 6 is T or S and X at position 8 is G or F.

Another embodiment of the invention is a conjugate as defined above which comprises:
a. a variable sequence of the heavy chain, as shown in SEQ ID NO:10, and also a variable sequence of the light chain, as shown in SEQ ID NO:9, or
b. a variable sequence of the heavy chain, as shown in SEQ ID NO:20, and also a variable sequence of the light chain, as shown in SEQ ID NO: 19, or
c. a variable sequence of the heavy chain, as shown in SEQ ID NO:30, and also a variable sequence of the light chain, as shown in SEQ ID NO:29, or
d. a variable sequence of the heavy chain, as shown in SEQ ID NO:40, and also a variable sequence of the light chain, as shown in SEQ ID NO:39, or
e. a variable sequence of the heavy chain, as shown in SEQ ID NO:50, and also a variable sequence of the light chain, as shown in SEQ ID NO:49, or
f. a variable sequence of the heavy chain, as shown in SEQ ID NO:60, and also a variable sequence of the light chain, as shown in SEQ ID NO:59, or
g. a variable sequence of the heavy chain, as shown in SEQ ID NO:70, and also a variable sequence of the light chain, as shown in SEQ ID NO:69, or
h. a variable sequence of the heavy chain, as shown in SEQ ID NO:80, and also a variable sequence of the light chain, as shown in SEQ ID NO:79, or
i. a variable sequence of the heavy chain, as shown in SEQ ID NO:90, and also a variable sequence of the light chain, as shown in SEQ ID NO:89, or
j. a variable sequence of the heavy chain, as shown in SEQ ID NO:100, and also a variable sequence of the light chain, as shown in SEQ ID NO:99, or
k. a variable sequence of the heavy chain, as shown in SEQ ID NO: 110, and also a variable sequence of the light chain, as shown in SEQ ID NO: 109, or
l. a variable sequence of the heavy chain, as shown in SEQ ID NO:120, and also a variable sequence of the light chain, as shown in SEQ ID NO: 119.

Another embodiment of the invention is a conjugate as defined above where the antibody is an IgG antibody.

Another embodiment of the invention is a process for preparing the conjugate as defined above where a compound of one of the formulae below, preferably in the form of its trifluoroacetic acid salt, is conjugated to a residue of a binder peptide or protein using transglutaminase, where the compound is preferably employed in a 2- to 100-fold molar excess with respect to the binder peptide or protein:

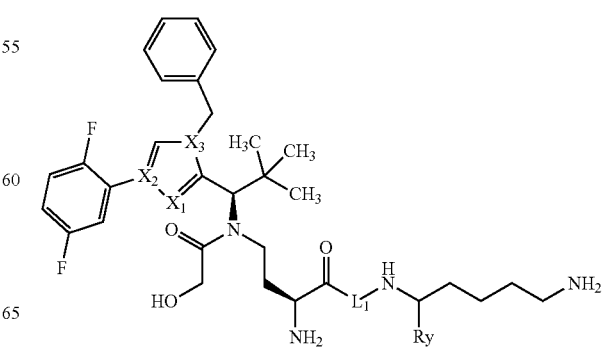

187
-continued

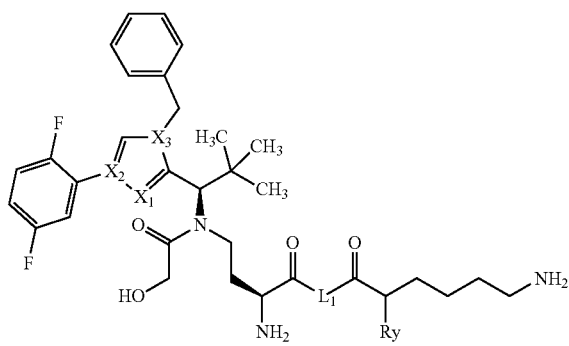

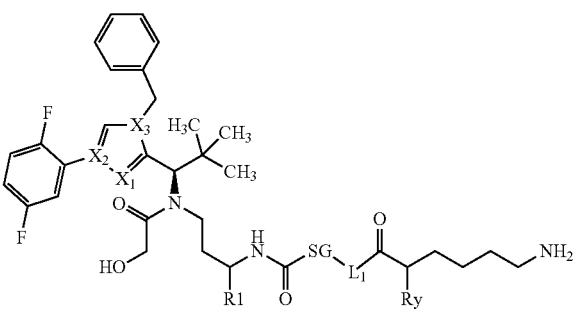

where $X_1$, $X_2$, $X_3$, SG, L1, R1 have the same meaning as above, e.g. in Formula (IIa), and Ry is —H, —C(=O)—NH-alkyl, —NH—C(=O)-alkyl, —C(=O)—NH$_2$, or —NH$_2$.

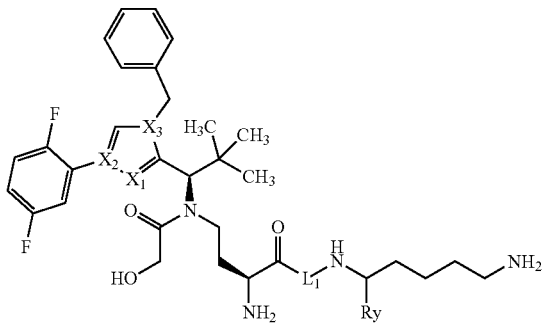

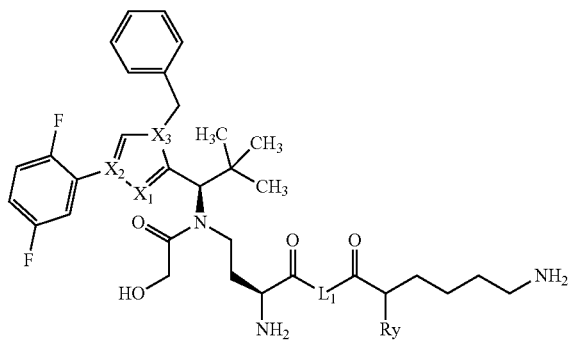

188
-continued

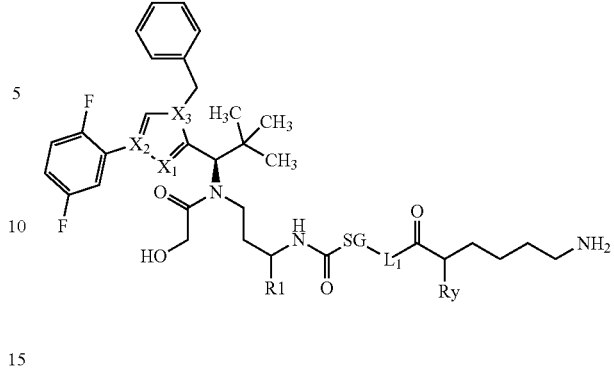

where $X_1$, $X_2$, $X_3$, SG, L1, R1 and Rx have the same meaning as defined above.

Another embodiment of the invention is a conjugate as defined above where the binder peptide or protein represents an antibody or the derivative of the binder peptide or protein according to the following formula

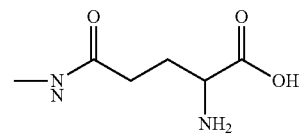

Another embodiment of the invention is a pharmaceutical composition comprising a conjugate as defined above or a compound as defined above in combination with an inert non-toxic pharmaceutically suitable auxiliary.

Another embodiment of the invention is a conjugate as defined above or compound as defined above for use in a method for the treatment and/or prophylaxis of diseases.

Another embodiment of the invention is a conjugate as defined above or compound as defined above for use in a method for the treatment of hyperproliferative and/or angiogenic disorders.

Another embodiment of the invention is a method for the treatment and/or prophylaxis of hyperproliferative and/or angiogenic disorders in humans and animals using an effective amount of at least one conjugate as defined above or compound as defined above.

Particularly preferred embodiments are conjugates according to one of the following formulae, where Ak3a, Ak3b, AD3d, Ak3e, represent a binder, preferably an antibody, and n represents 2 to 10, preferably 2 to 4, and also preferably 2 or 4:

189                                                                 190
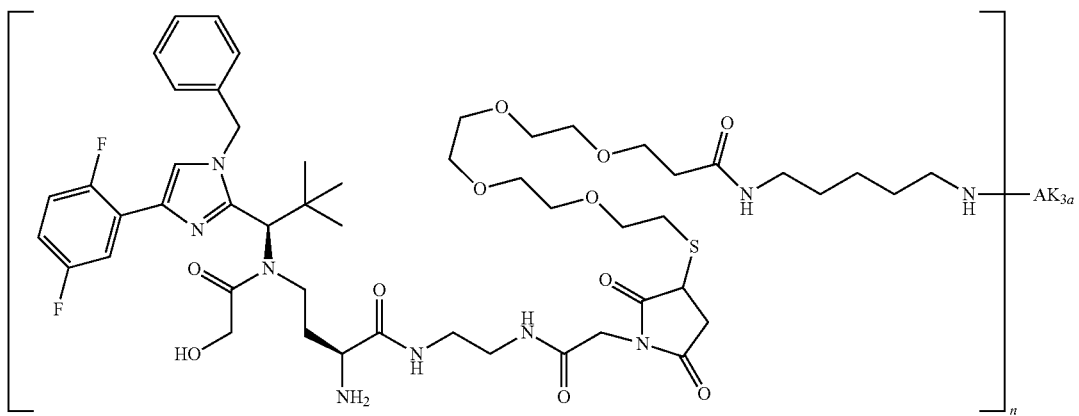
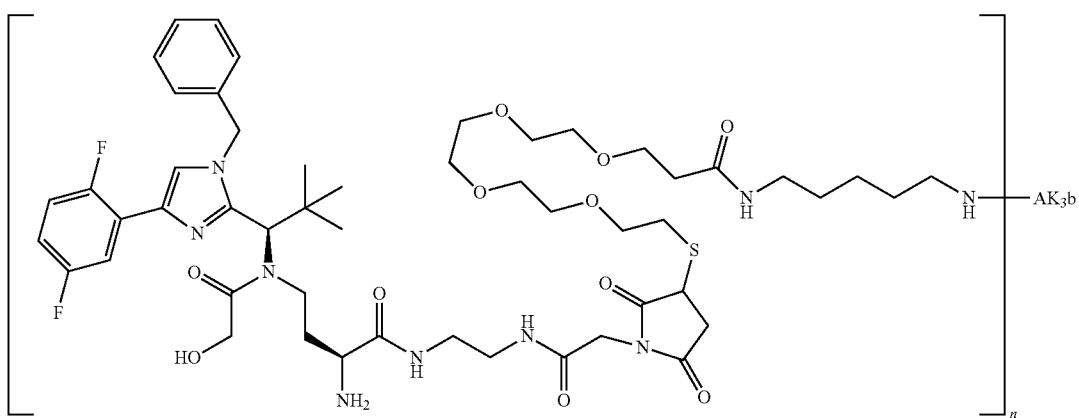
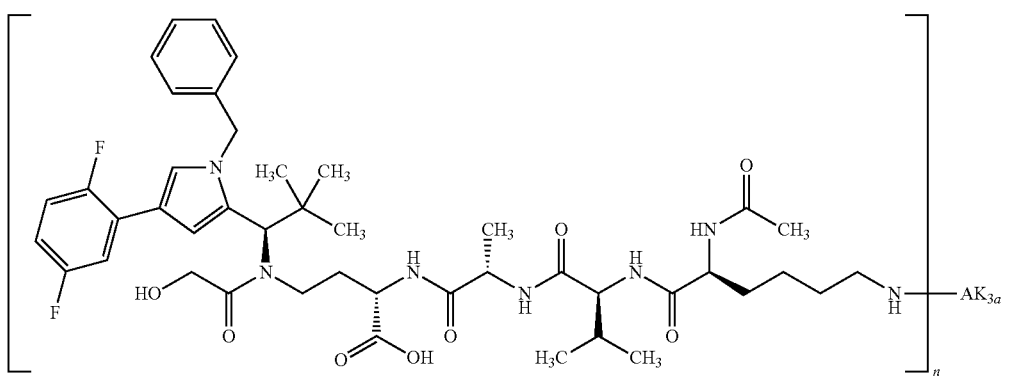
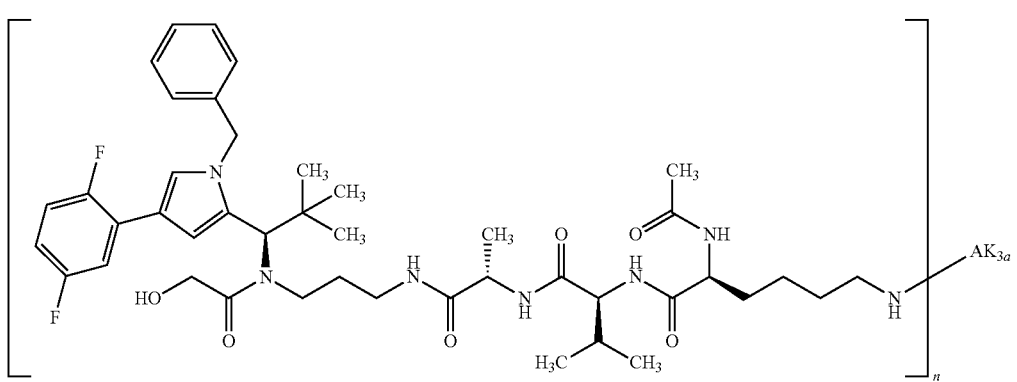

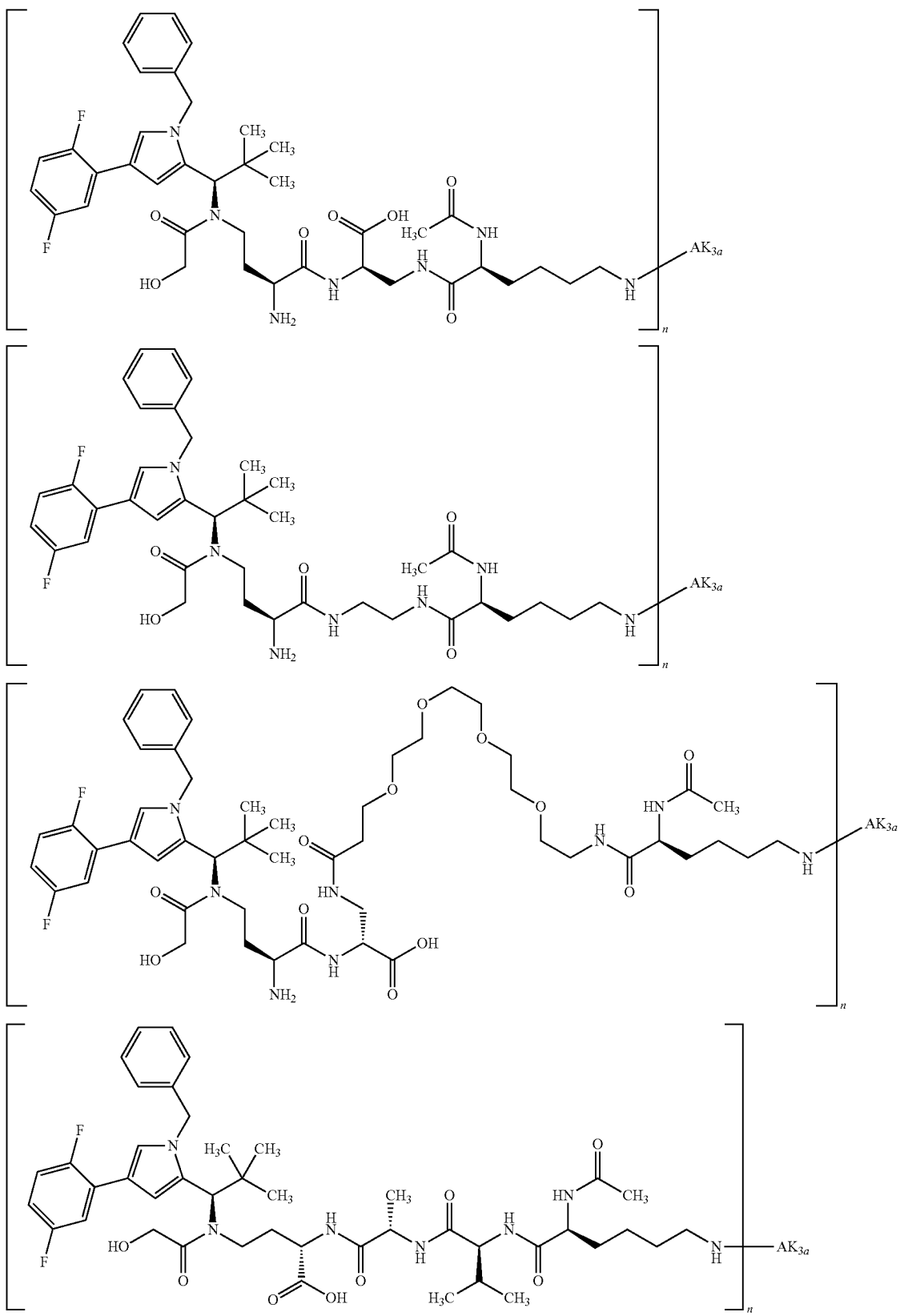

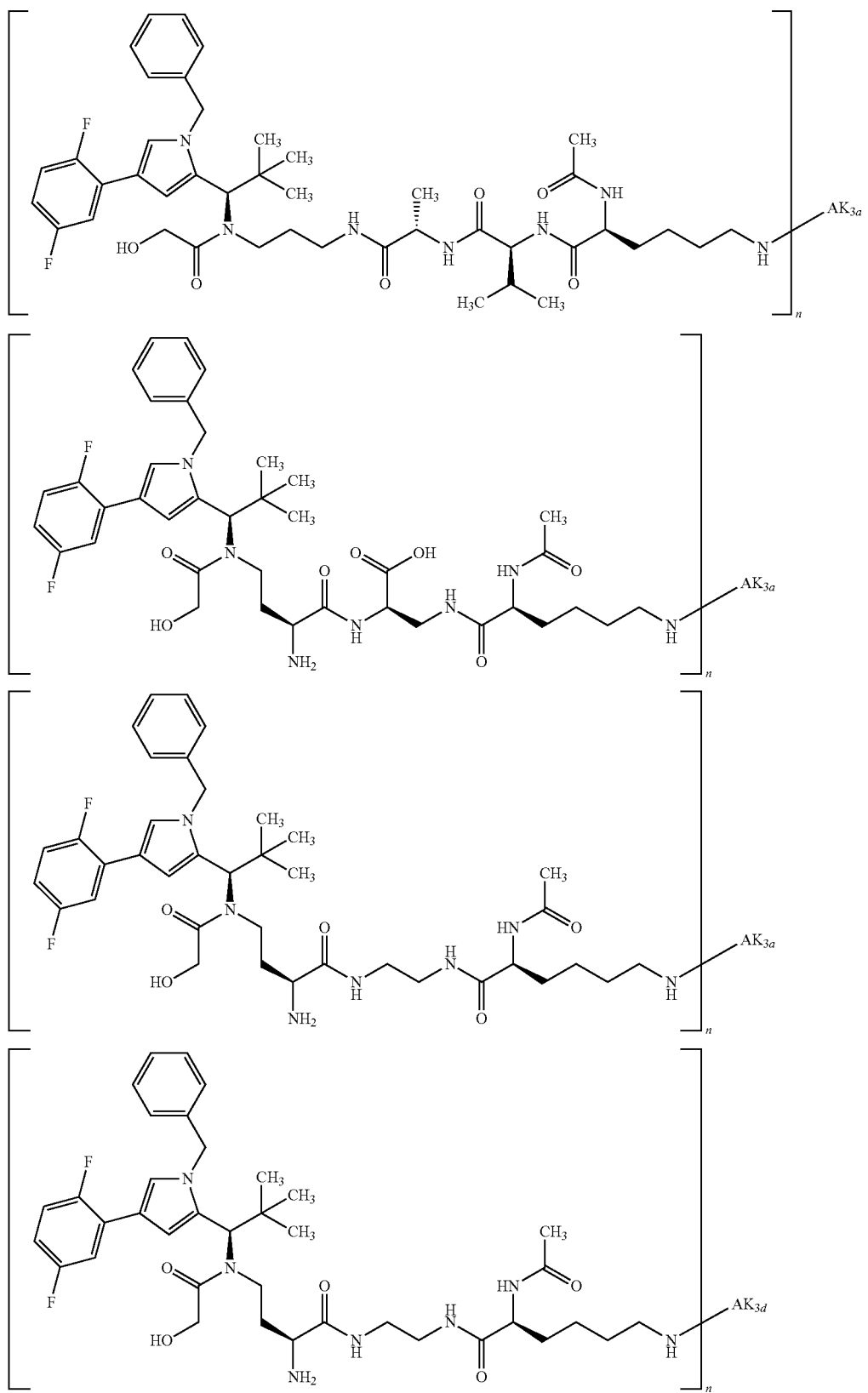

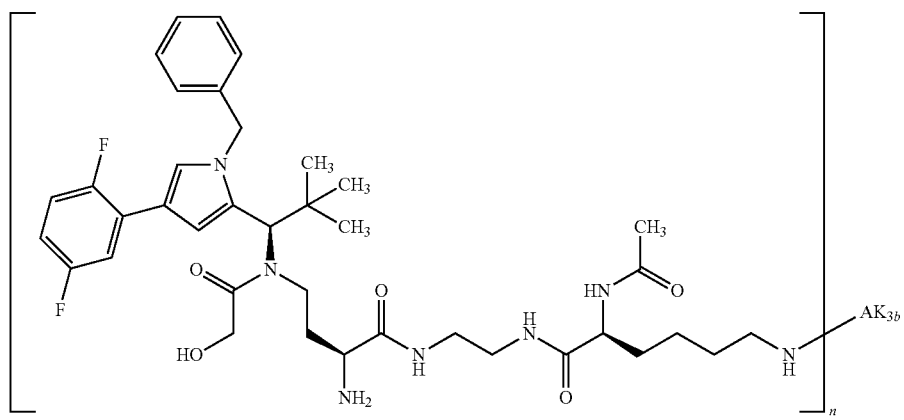
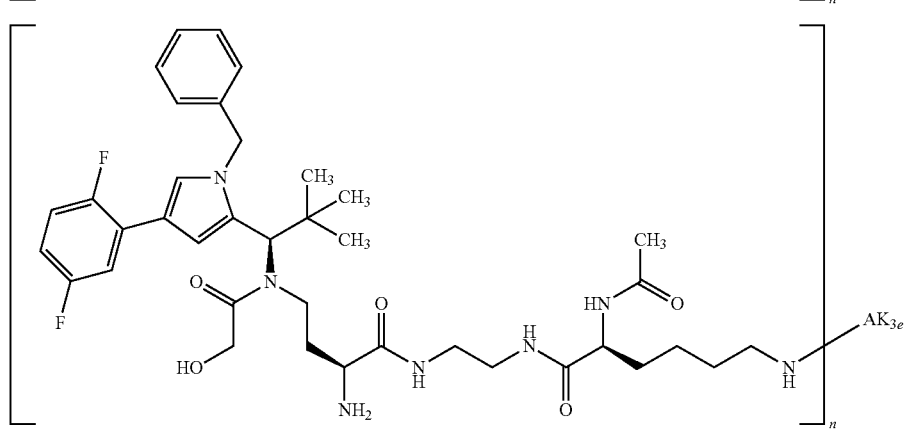
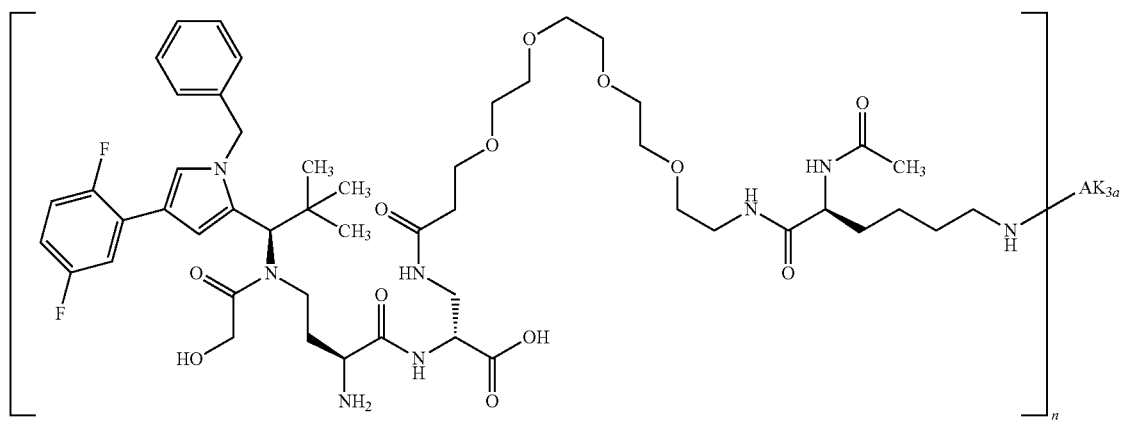
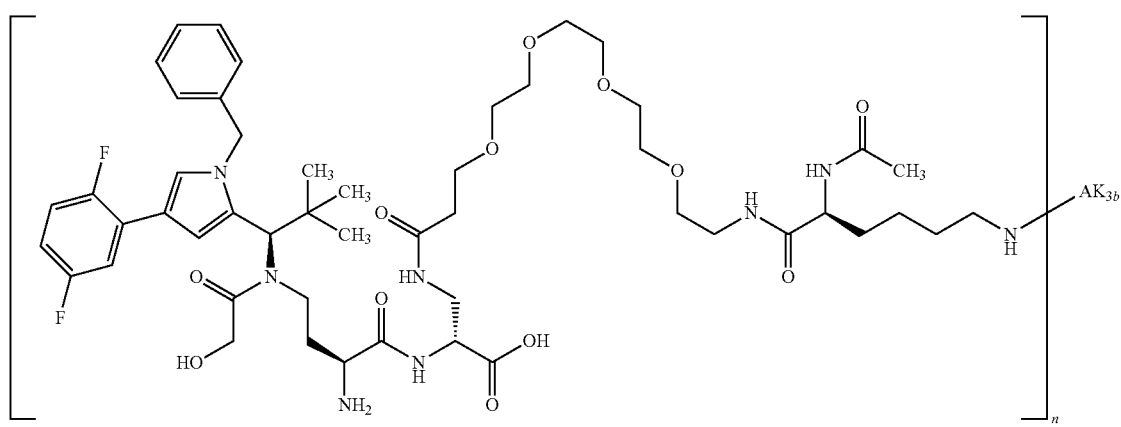

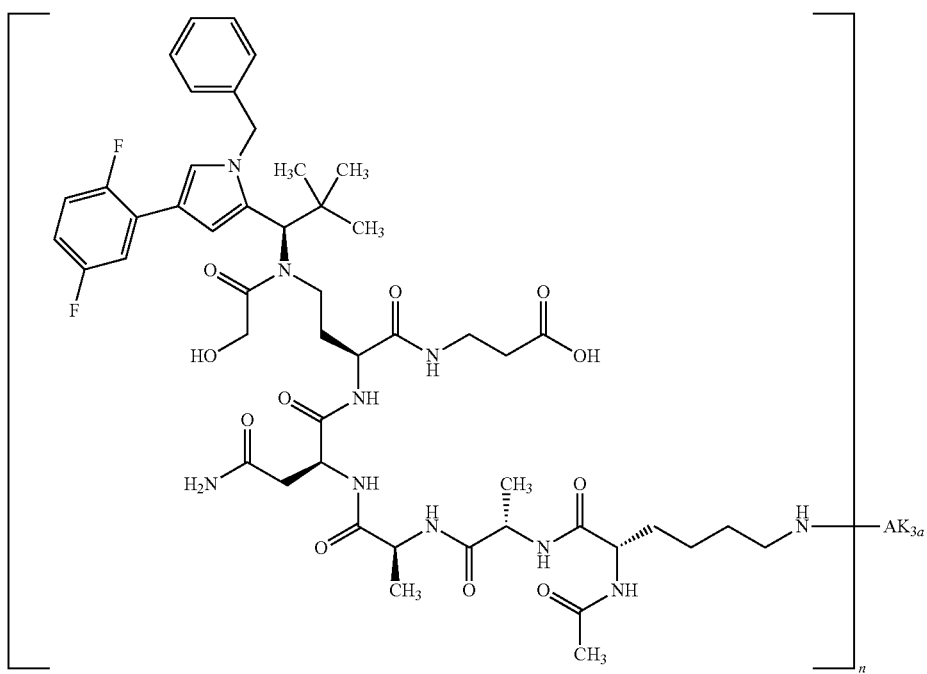
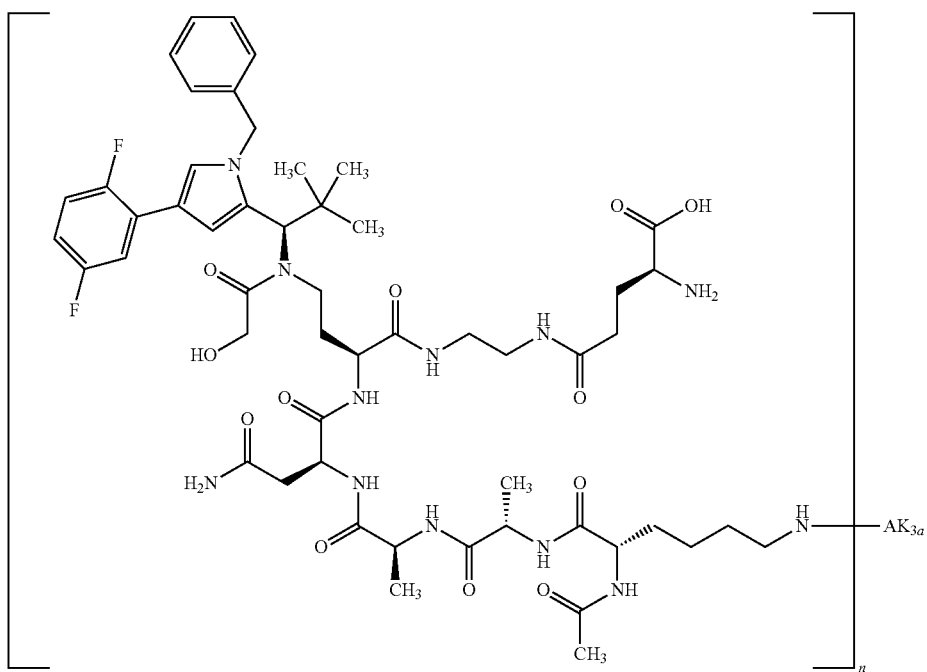

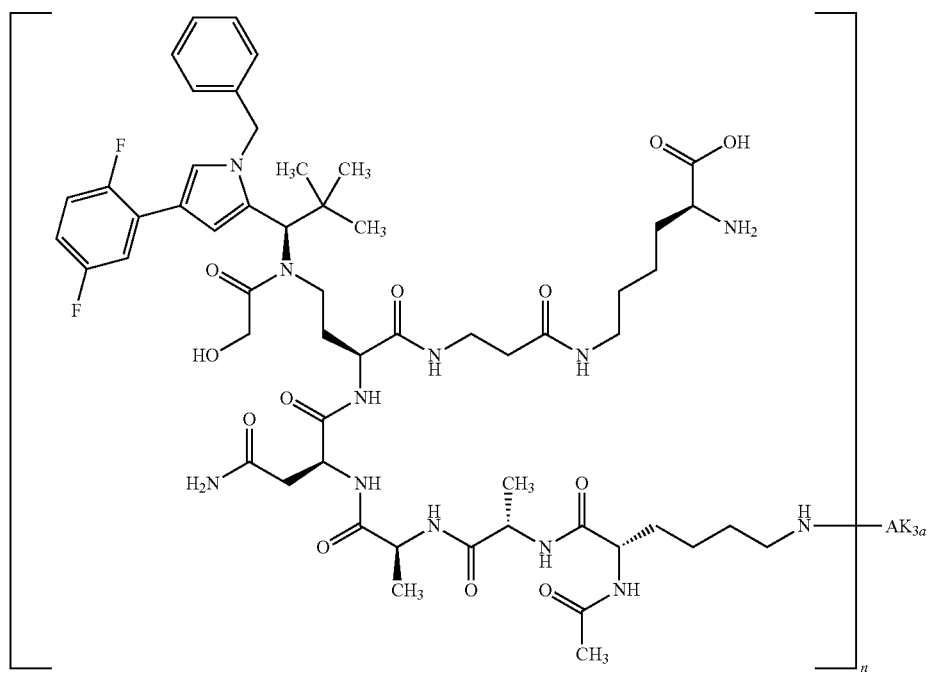
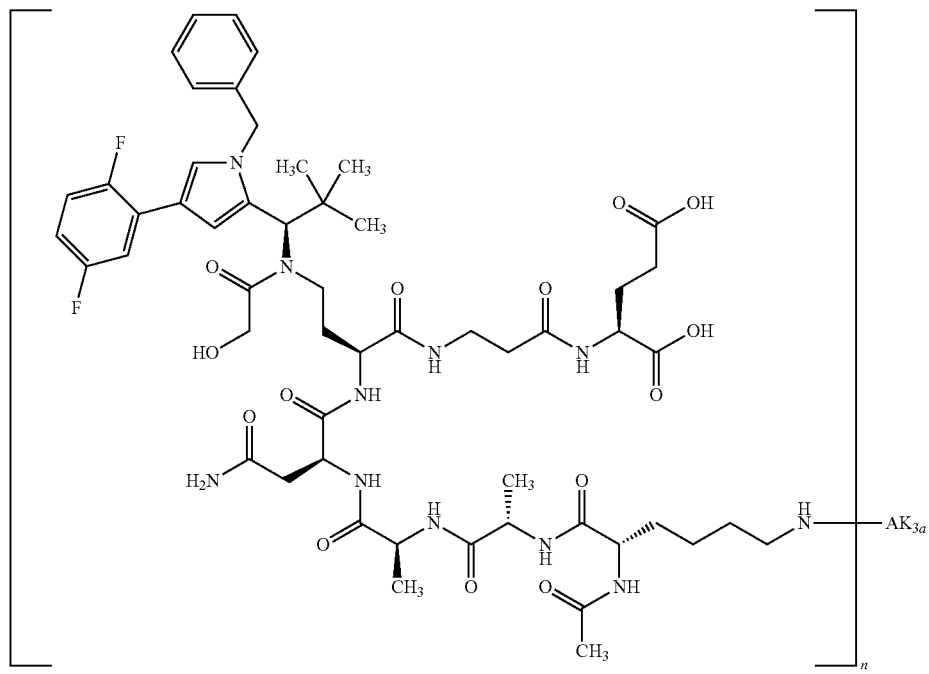

201 202
-continued
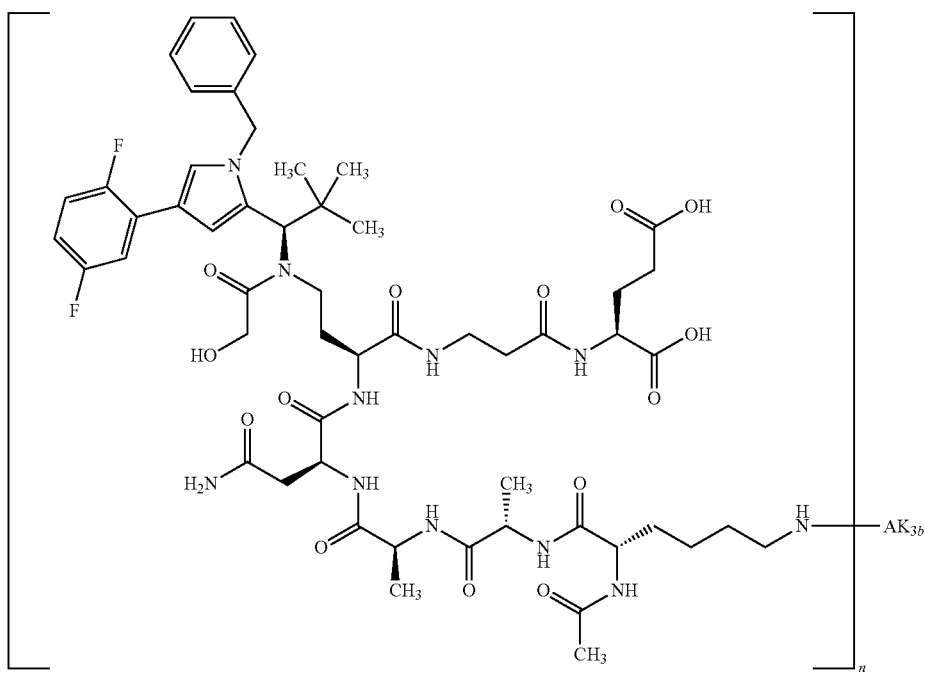
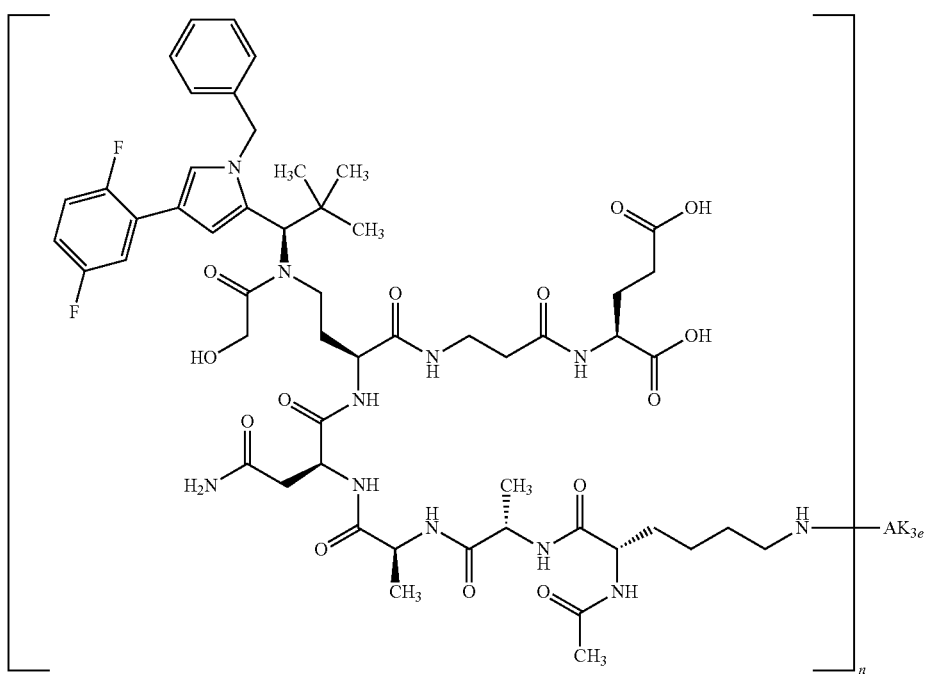

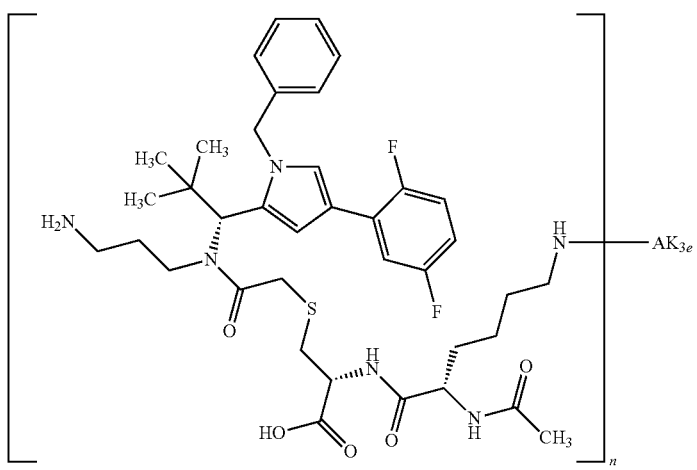
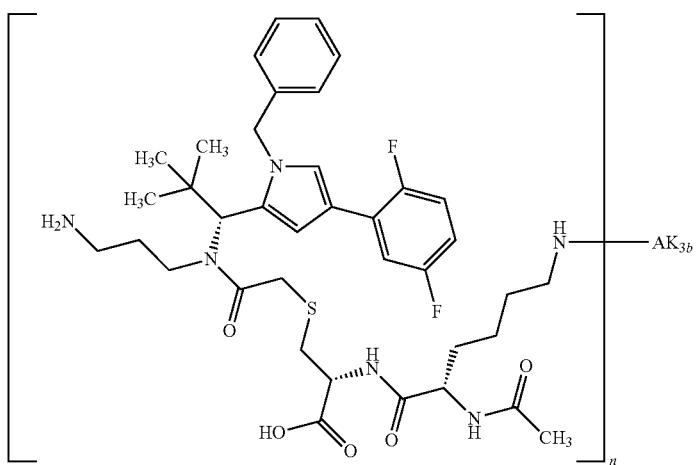
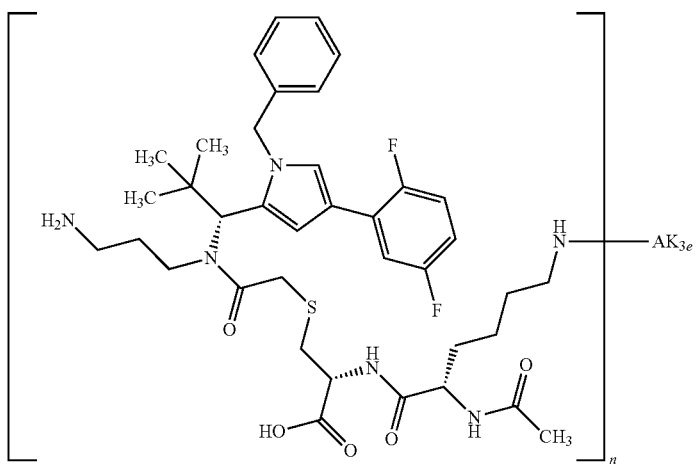

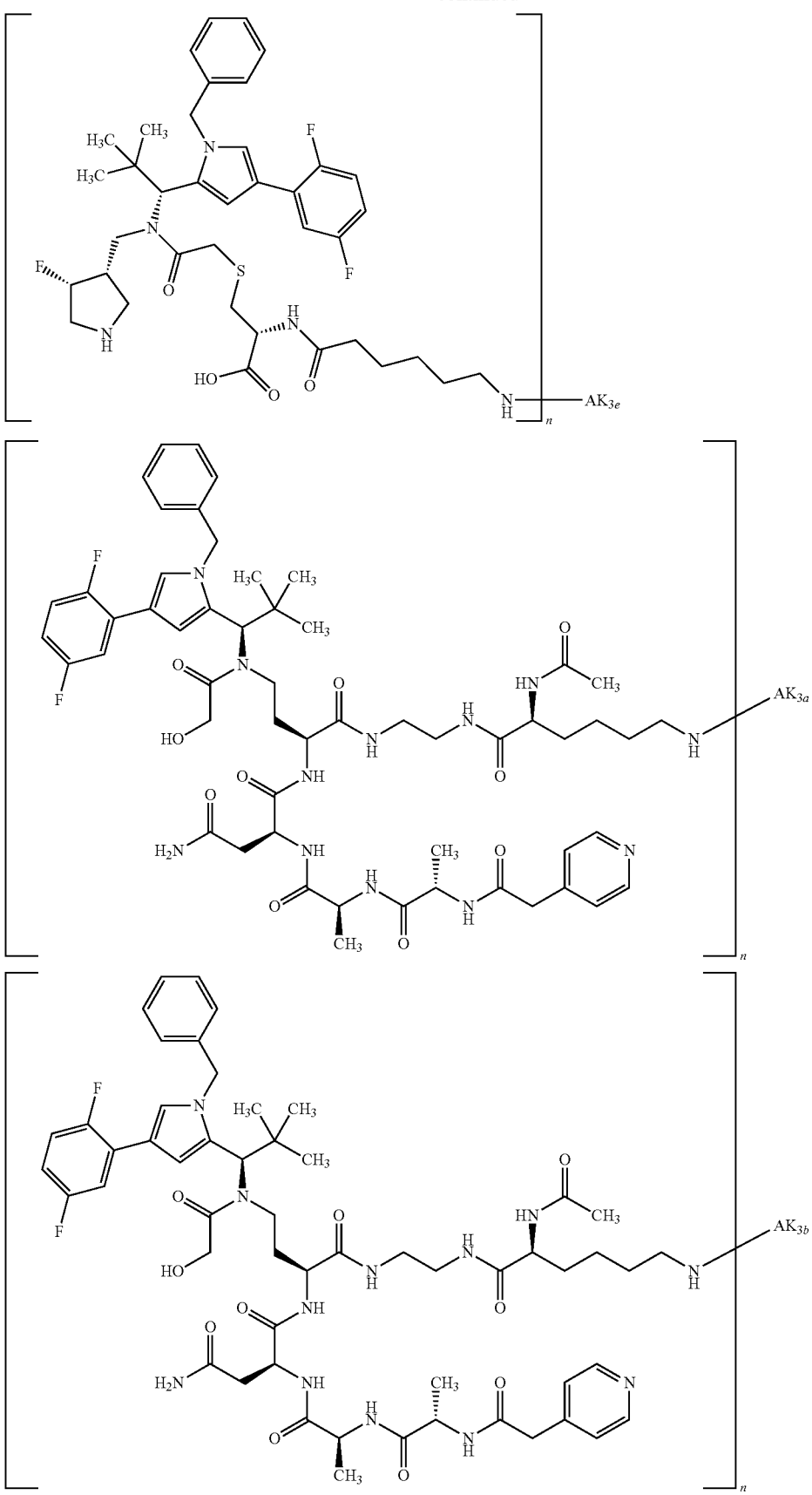

-continued
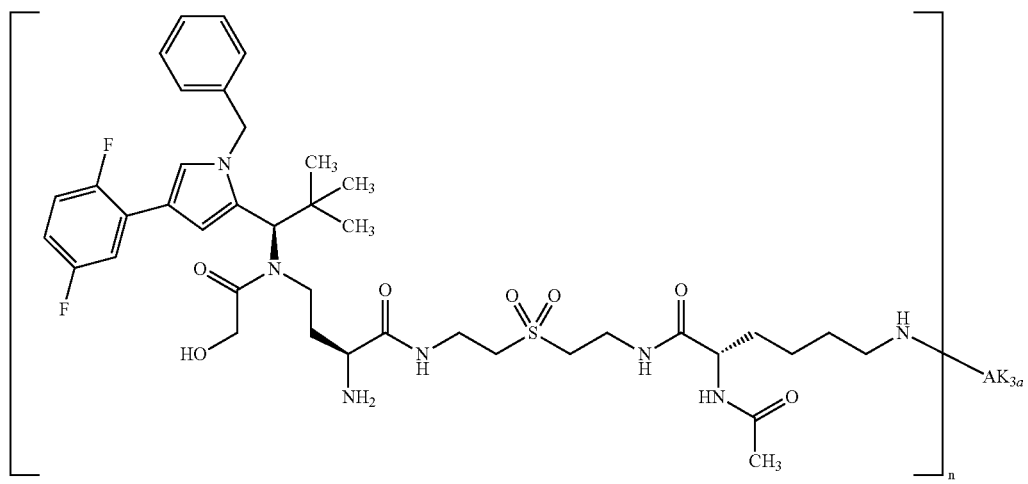
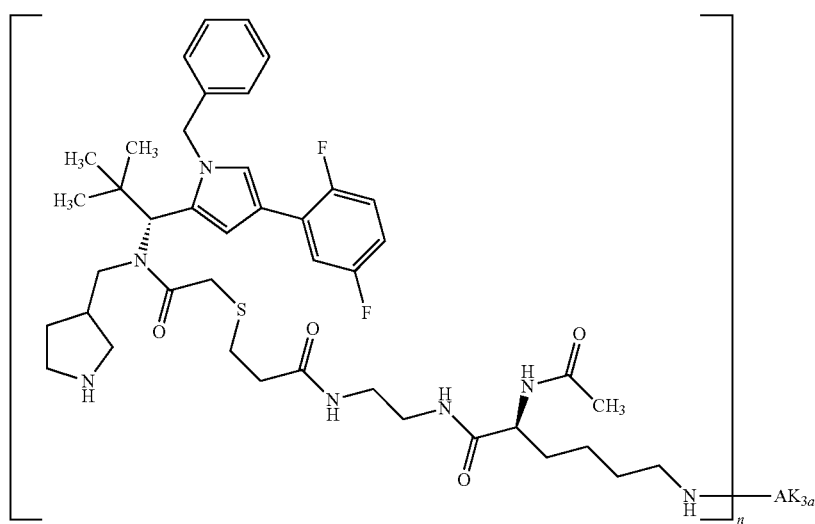
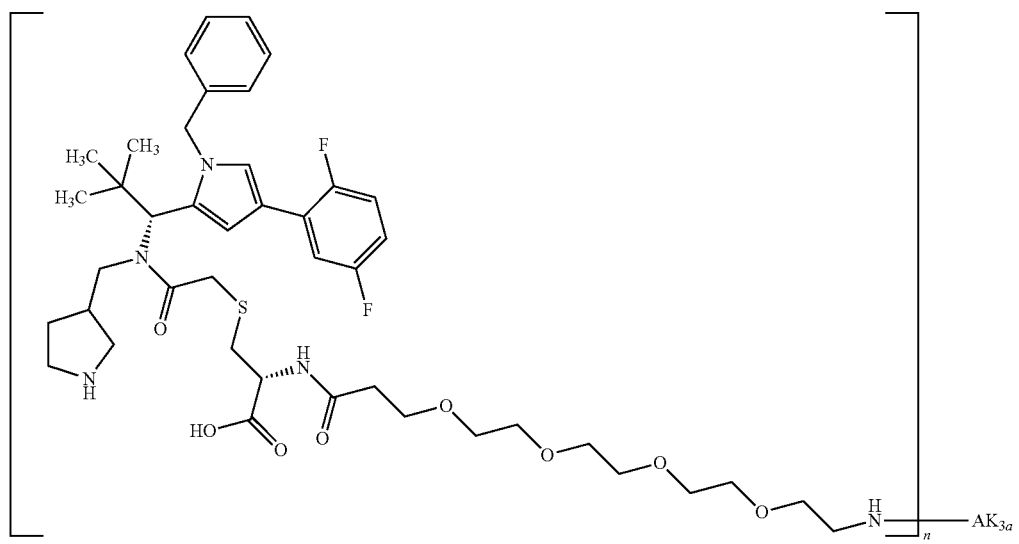

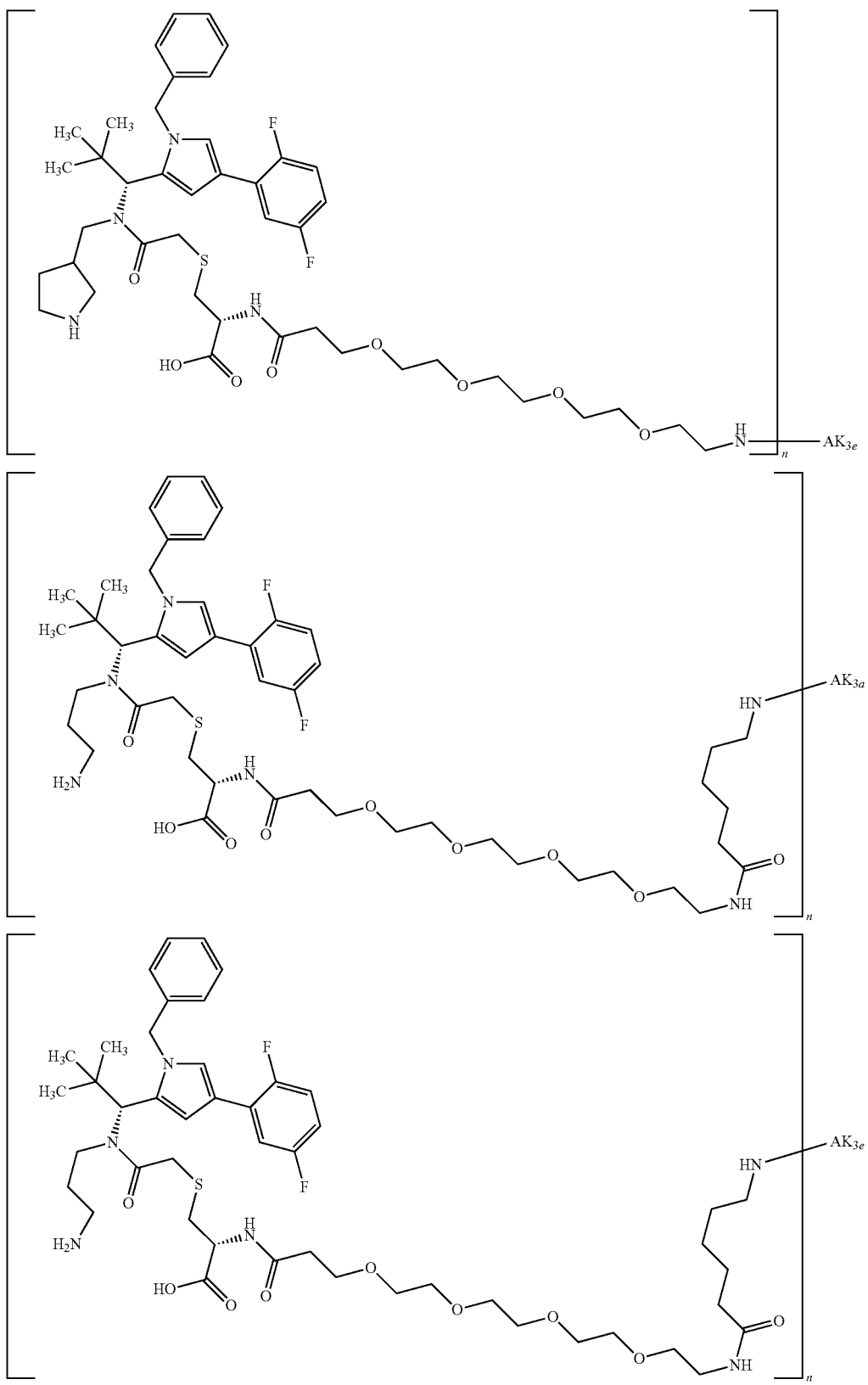

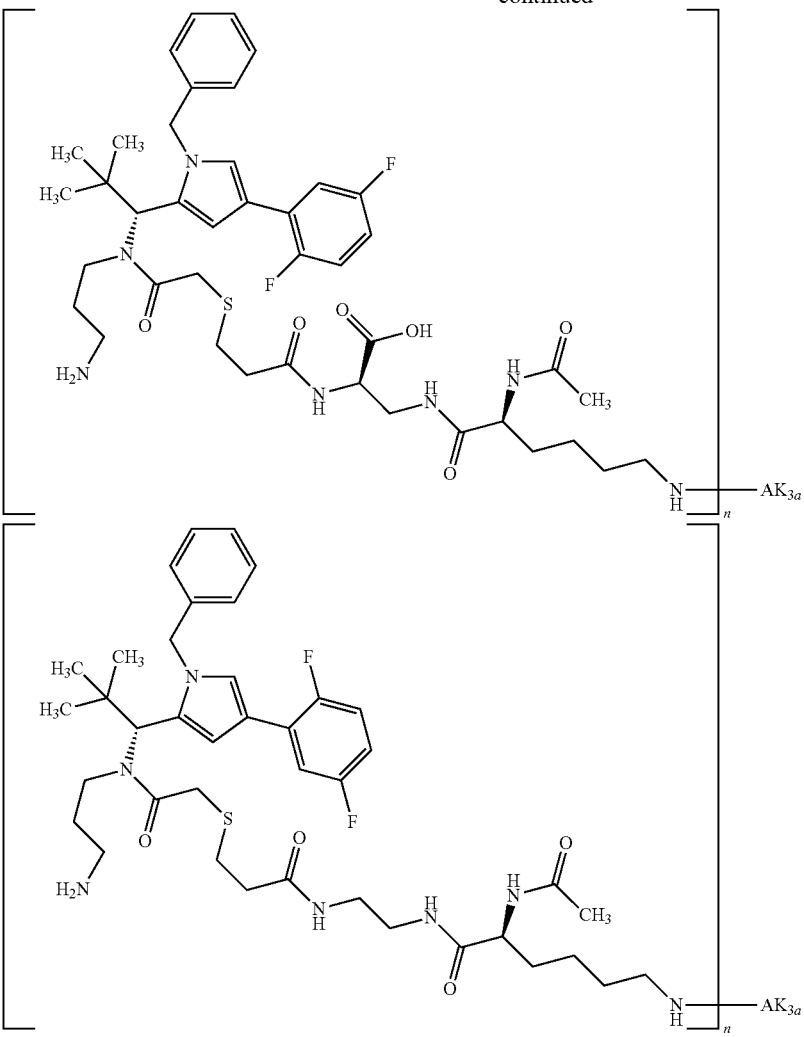

Therapeutic Use

The hyper-proliferative diseases, for the treatment of which the compounds according to the invention may be employed, include in particular the group of cancer and tumour diseases. In the context of the present invention, these are understood to mean especially the following diseases, but without any limitation thereto: mammary carcinomas and mammary tumours (mammary carcinomas including ductal and lobular forms, also in situ), tumours of the respiratory tract (small-cell and non-small cell carcinoma, bronchial carcinoma), cerebral tumours (e.g. of the brain stem and of the hypothalamus, astrocytoma, ependymoma, glioblastoma, glioma, medulloblastoma, meningioma and neuro-ectormal and pineal tumours), tumours of the digestive organs (carcinomas of the oesophagus, stomach, gall bladder, small intestine, large intestine, rectum and anal carcinomas), liver tumours (inter alia hepatocellular carcinoma, cholangiocarcinoma and mixed hepatocellular cholangiocarcinoma), tumours of the head and neck region (larynx, hypopharynx, nasopharynx, oropharynx, lips and oral cavity carcinomas, oral melanomas), skin tumours (basaliomas, spinaliomas, squamous cell carcinomas, Kaposi's sarcoma, malignant melanoma, non-melanomatous skin cancer, Merkel cell skin cancer, mast cell tumours), tumours of soft tissue (inter alia soft tissue sarcomas, osteosarcomas, malignant fibrous histiocytomas, chondrosarcomas, fibrosarcomas, hemangiosarcomas, leiomyosarcomas, liposarcomas, lymphosarcomas and rhabdomyosarcomas), tumours of the eyes (inter alia intraocular melanoma and retinoblastoma), tumours of the endocrine and exocrine glands (e.g. of the thyroid and parathyroid glands, pancreas and salivary gland carcinomas, adenocarcinomas), tumours of the urinary tract (tumours of the bladder, penis, kidney, renal pelvis and ureter) and tumours of the reproductive organs (carcinomas of the endometrium, cervix, ovary, vagina, vulva and uterus in women and carcinomas of the prostate and testes in men). These also include proliferative blood diseases of the blood, the lymph system and the spinal cord, in solid form and as circulating cells, such as leukaemias, lymphomas and myeloproliferative diseases, for example acute myeloid, acute lymphoblastic, chronic lymphocytic, chronic myelogenous and hairy cell leukaemia, and AIDS-correlated lymphomas, Hodgkin's lymphomas, non-Hodgkin's lymphomas, cutaneous T cell lymphomas, Burkitt's lymphomas and lymphomas in the central nervous system.

These well-characterized diseases in humans can also occur with a comparable aetiology in other mammals and can likewise be treated there with the compounds of the present invention.

The treatment of the cancer diseases mentioned above with the compounds according to the invention comprises both a treatment of the solid tumors and a treatment of metastasizing or circulating forms thereof.

In the context of this invention, the term "treatment" or "treat" is used in the conventional sense and means attending to, caring for and nursing a patient with the aim of combating, reducing, attenuating or alleviating a disease or health abnormality, and improving the living conditions impaired by this disease, as, for example, in the event of a cancer.

The present invention thus further provides for the use of the compounds according to the invention for the treatment and/or prevention of disorders, in particular the disorders mentioned above.

The present invention further provides for the use of the compounds according to the invention for producing a medicament for the treatment and/or prevention of disorders, in particular the disorders mentioned above.

The present invention further provides for the use of the compounds according to the invention in a method for treatment and/or prevention of disorders, in particular the disorders mentioned above.

The present invention further provides a method for treatment and/or prevention of disorders, in particular the disorders mentioned above, using an effective amount of at least one of the compounds according to the invention.

The compounds according to the invention can be used alone or, if required, in combination with one or more other pharmacologically active substances, provided that this combination does not lead to undesirable and unacceptable side effects. The present invention furthermore therefore provides medicaments containing at least one of the compounds according to the invention and one or more further active compounds, in particular for treatment and/or prevention of the abovementioned disorders.

For example, the compounds of the present invention can be combined with known anti-hyper-proliferative, cytostatic or cytotoxic substances for the treatment of cancer diseases. Examples of suitable combination active compounds include:

131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, lanreotide, lapatinib, lasocholine, lenalidomide, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

In addition, the compounds of the present invention can be combined, for example, with binders which, by way of example, can bind to the following targets: OX-40, CD137/4-1BB, DR3, IDO1/IDO2, LAG-3, CD40.

In addition, the compounds according to the invention can also be used in combination with radiotherapy and/or surgical intervention.

Generally, the following aims can be pursued with the combination of compounds of the present invention with other cytostatically or cytotoxically active agents:
- improved efficacy in slowing the growth of a tumour, in reducing its size or even in the complete elimination thereof, compared with treatment with an individual active compound;
- the possibility of using the chemotherapeutics used in a lower dosage than in the case of monotherapy;
- the possibility of a more tolerable therapy with fewer side effects compared with individual administration;
- the possibility of treatment of a broader spectrum of tumour diseases;
- the achievement of a higher rate of response to the therapy;
- a longer survival time of the patient compared with present-day standard therapy.

In addition, the compounds according to the invention can also be used in combination with radiotherapy and/or surgical intervention.

The present invention further provides medicaments which comprise at least one compound according to the invention, typically together with one or more inert, non-toxic, pharmaceutically suitable excipients, and the use thereof for the aforementioned purposes.

The compounds according to the invention can act systemically and/or locally. For this purpose, they can be administered in a suitable manner, for example parenterally, possibly inhalatively or as implants or stents.

The compounds according to the invention can be administered in suitable administration forms for these administration routes.

Parenteral administration can bypass an absorption step (for example intravenously, intraarterially, intracardially, intraspinally or intralumbally) or include an absorption (for example intramuscularly, subcutaneously, intracutaneously, percutaneously or intraperitoneally). Administration forms suitable for parenteral administration include preparations for injection and infusion in the form of solutions, suspensions, emulsions or lyophilizates. Preference is given to parenteral administration, especially intravenous administration.

In general, it has been found to be advantageous in the case of parenteral administration to administer amounts of from about 0.001 to 1 mg/kg, preferably about 0.01 to 0.5 mg/kg, of body weight to achieve effective results.

It may nevertheless be necessary where appropriate to deviate from the stated amounts, specifically as a function of body weight, route of administration, individual response to the active compound, nature of the preparation and time or interval over which administration takes place. Thus, in some cases less than the abovementioned minimum amount may be sufficient, while in other cases the upper limit mentioned must be exceeded. In the case of administration of greater amounts, it may be advisable to divide them into several individual doses over the day.

EXAMPLES

The examples which follow illustrate the invention. The invention is not restricted to the examples.

Unless stated otherwise, the percentages in the tests and examples which follow are percentages by weight; parts are parts by weight. Solvent ratios, dilution ratios and concentration data for the liquid/liquid solutions are in each case based on volume.

Synthesis Routes:

Examplary for the working examples, the schemes below show exemplary synthesis routes leading to the working examples:

Scheme 1: Synthesis of glutamine-linked ADCs

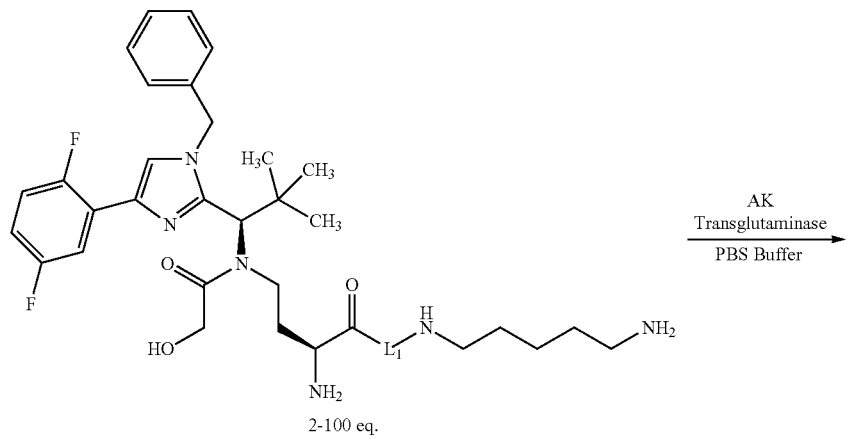

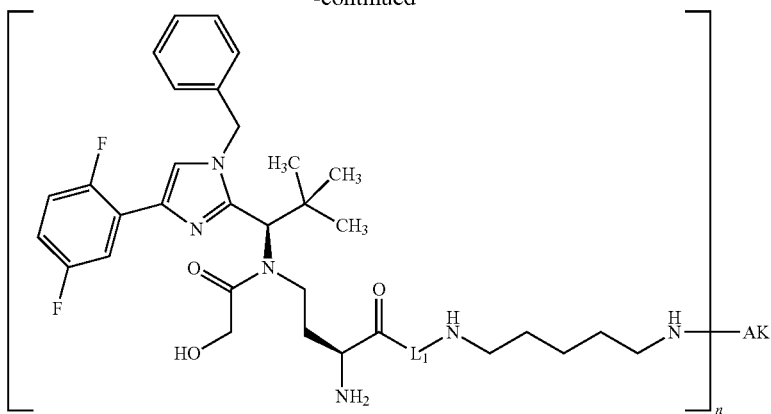
with n is 2 or 4.
Scheme 2
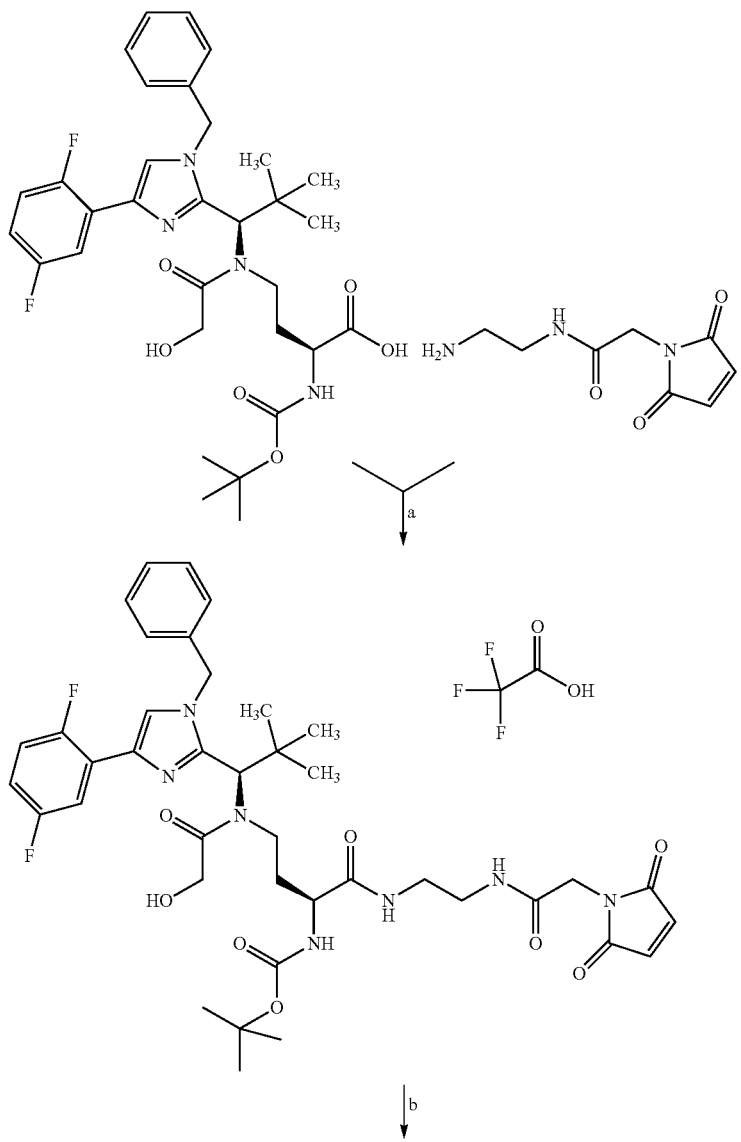

-continued
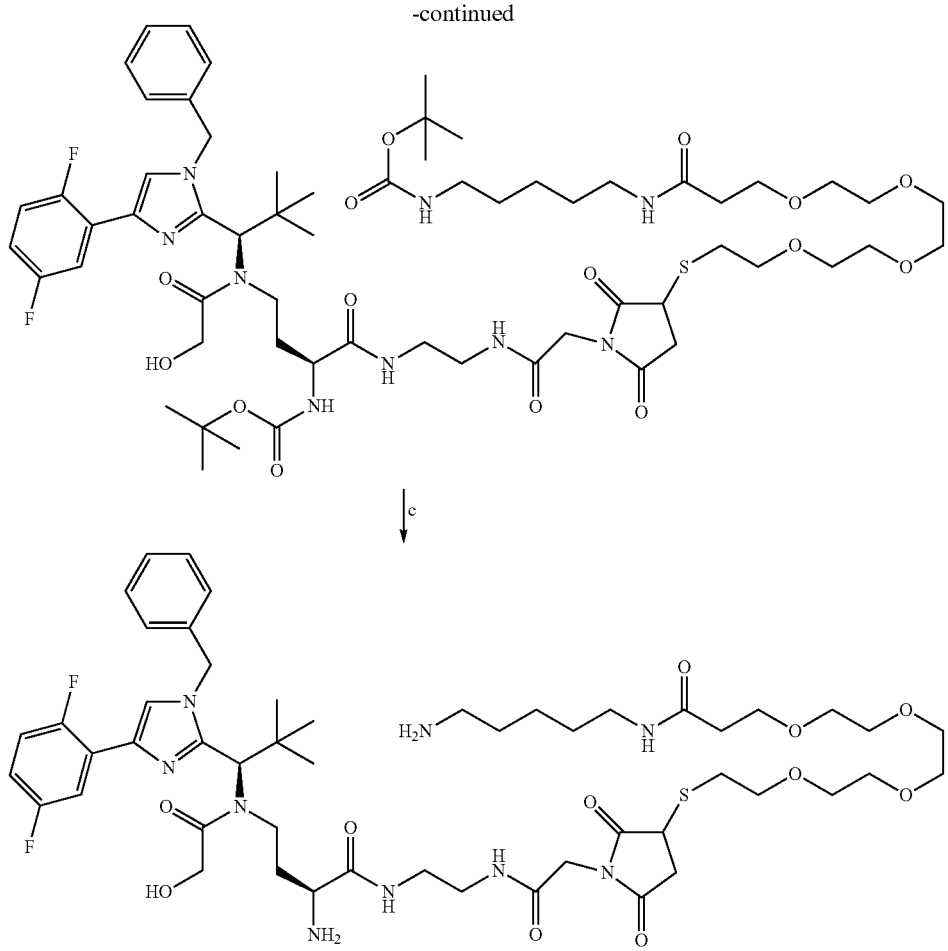
a. HATU, DIPEA, DMF, rt; b. ACN, Buffer pH8, rt; c. HCl 4M, dioxane, rt
Scheme 3: Synthesis of glutamine-linked ADCs
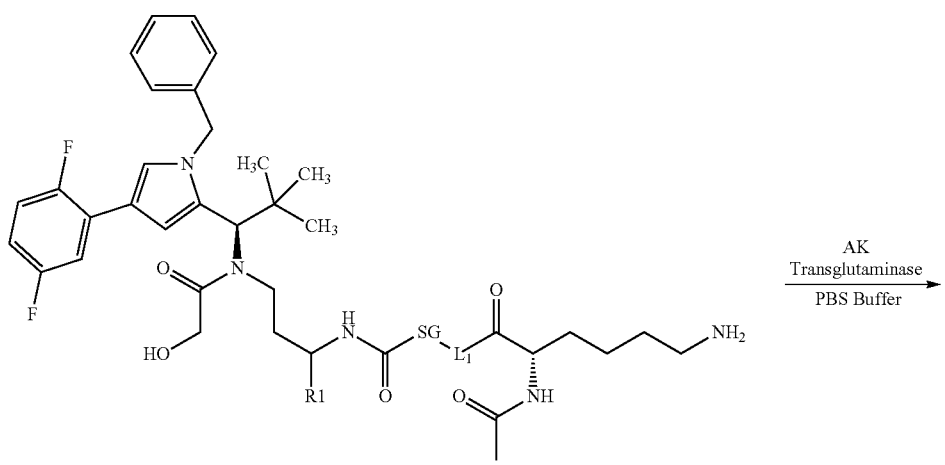
2-100 eq.

221 222
-continued
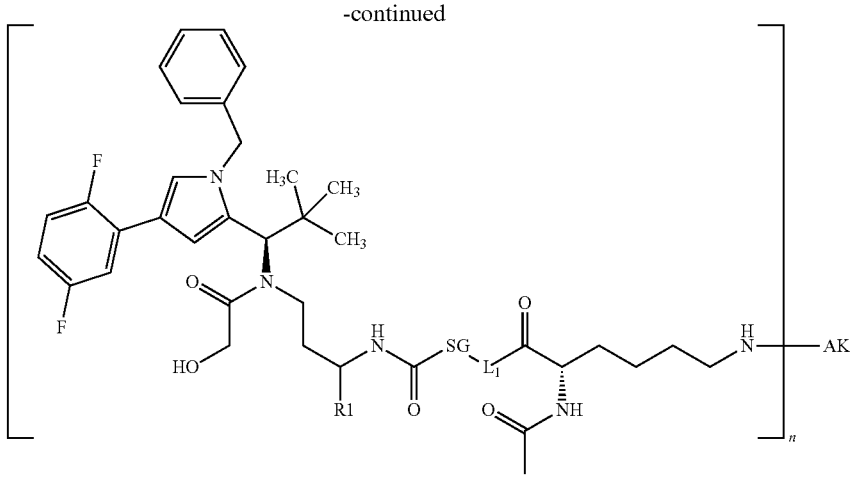
with n is 2 or 4.
Scheme 4
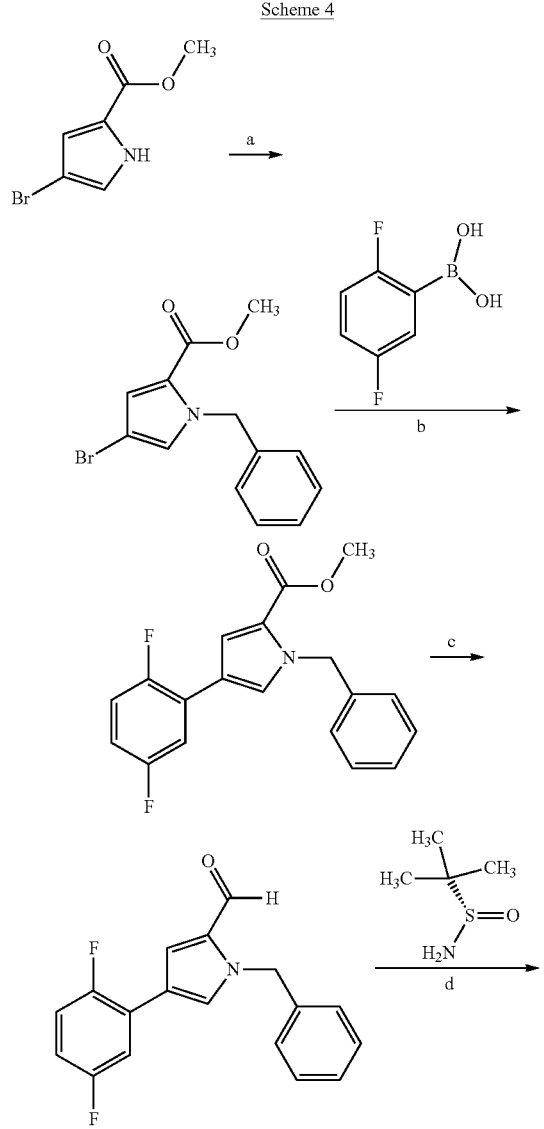
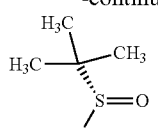
-continued
[a): for example benzyl bromide, Cs$_2$CO$_3$, DMF, RT; b) for example Pd(dppf)$_2$Cl$_2$, DMF, Na$_2$CO$_3$, 85° C.; c) for example LiAlH$_4$, THF, 0° C.; MnO$_2$, DCM, RT;
d) for example Ti(iOPr)$_4$, THF, RT; e) for example tBuLi, THF, −78° C.; MeOH, NH$_4$Cl; f) for example HCl/1,4-dioxane]

Scheme 5
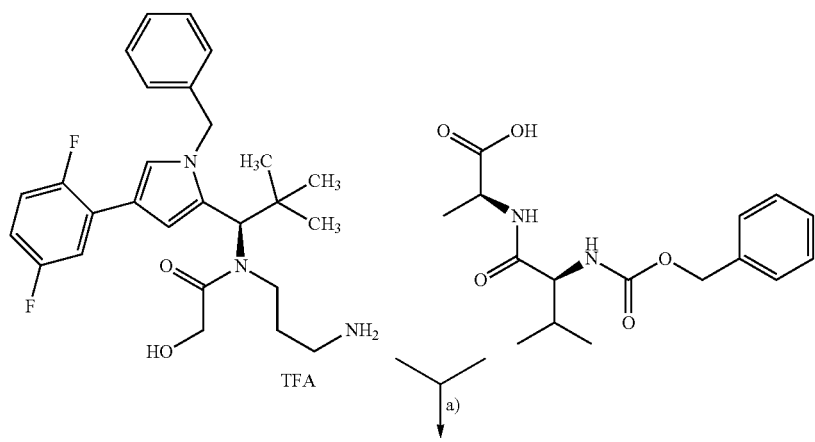
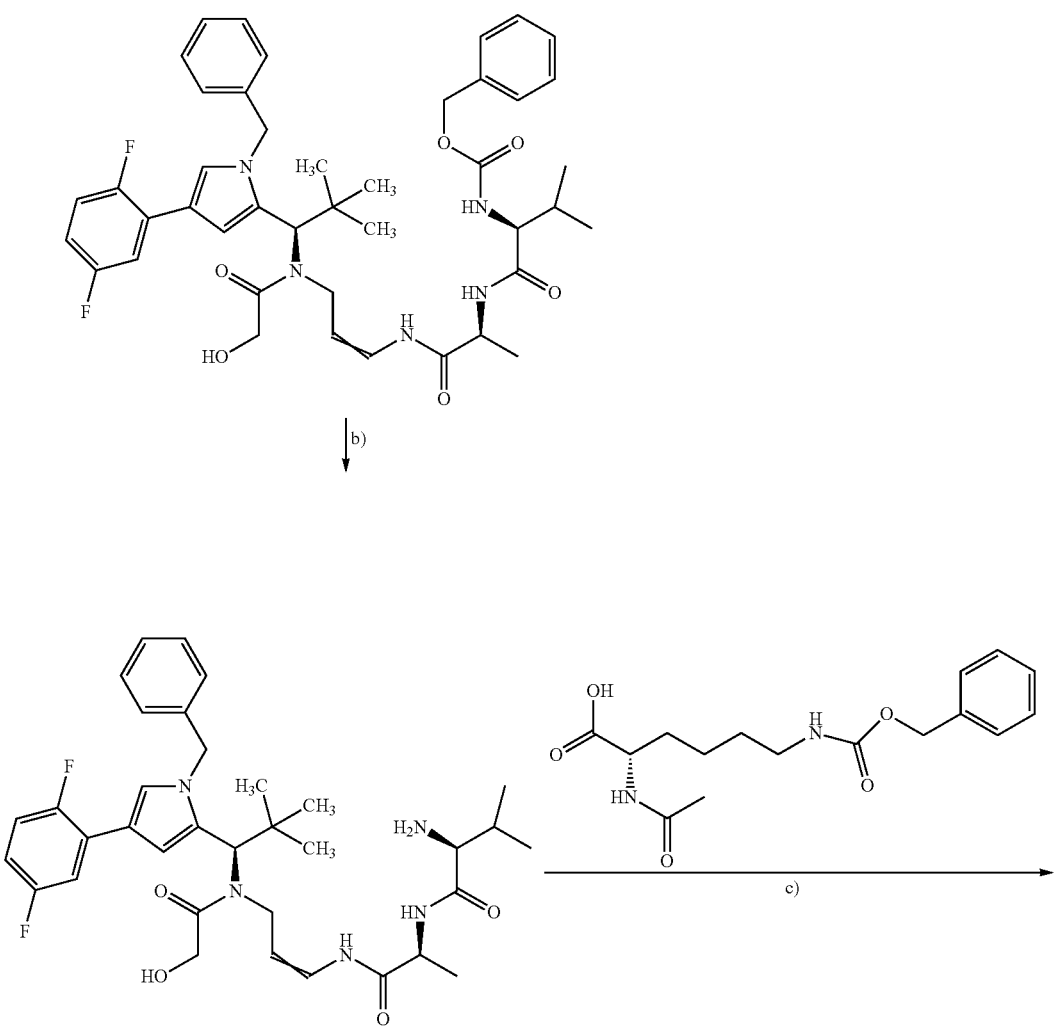

-continued
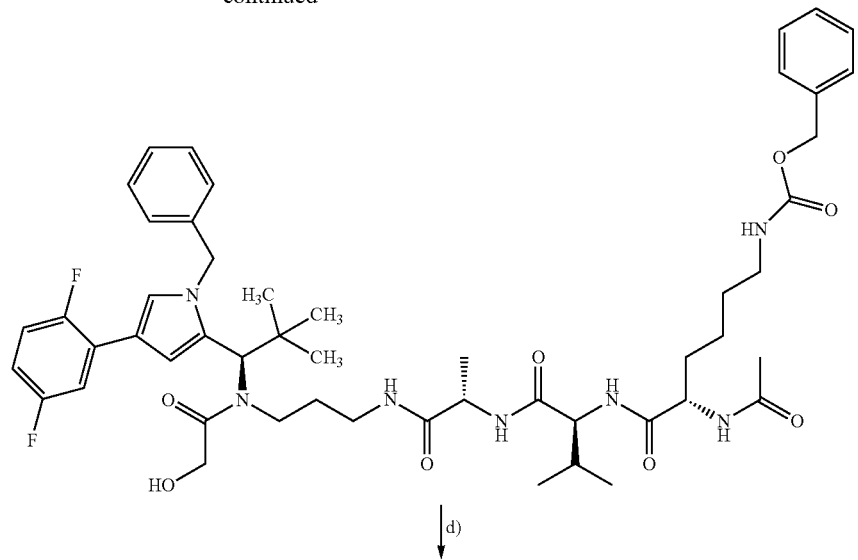
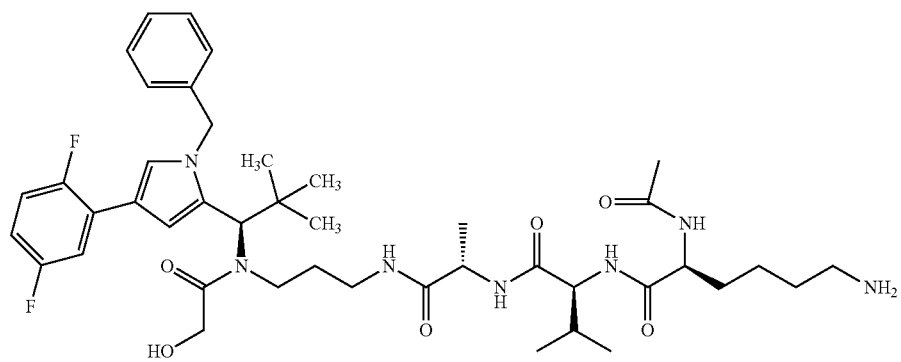
a. HATU, DIPEA, DMF, rt; b) Pd/C 10%, MeOH; c) HATU, DIPEA, DMF, rt, d) Pd/C 10%, MeOH
Scheme 6
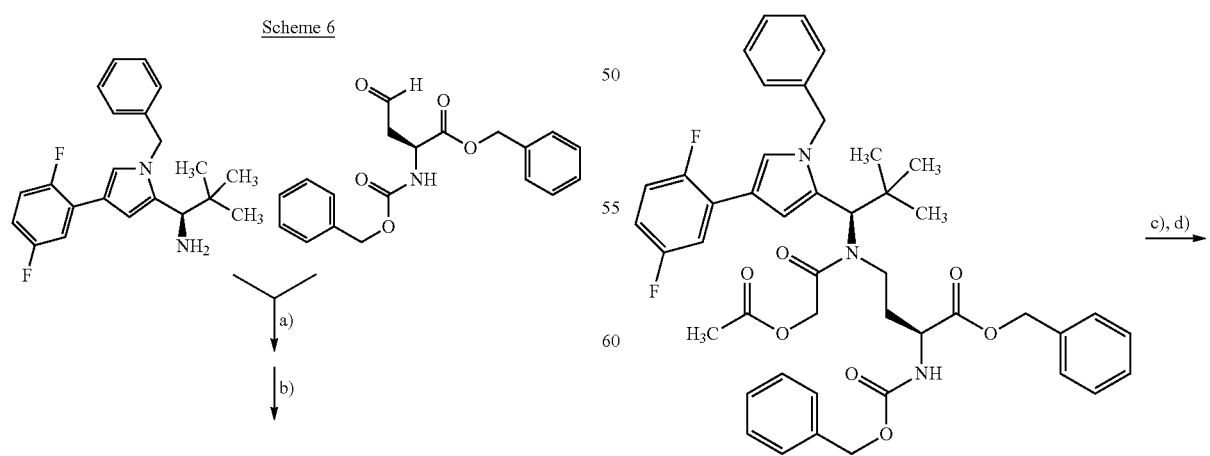

227
-continued
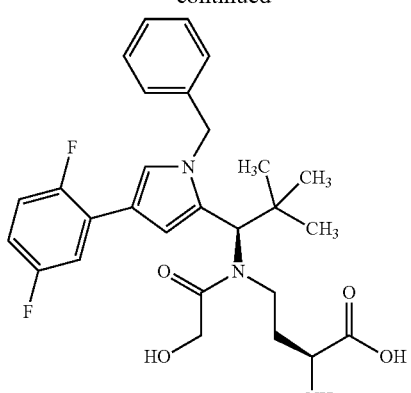
e) ↙   f) ↘
228
-continued
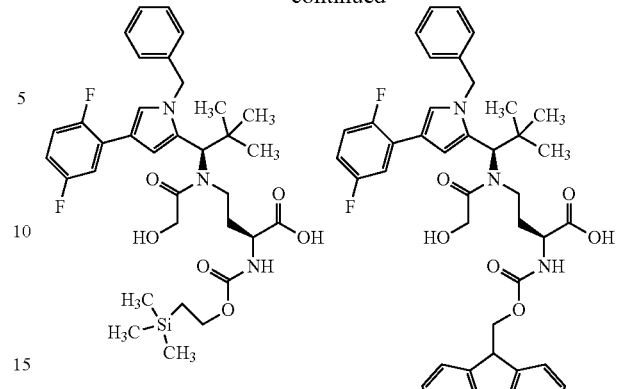
[a]: for example sodium triacetoxyborohydride, acetic acid, DCM, RT; b) for example acetoxyacetyl chloride, NEt₃, DCM, RT; c) for example LiOH, THF/water, RT; d) for example H₂, Pd—C, EtOH, RT; e) for example Teoc—OSu, NEt₃, dioxane, RT; f) for example Fmoc—Cl, diisopropylethylamine, dioxane/water 2:1, RT]
Scheme 7:
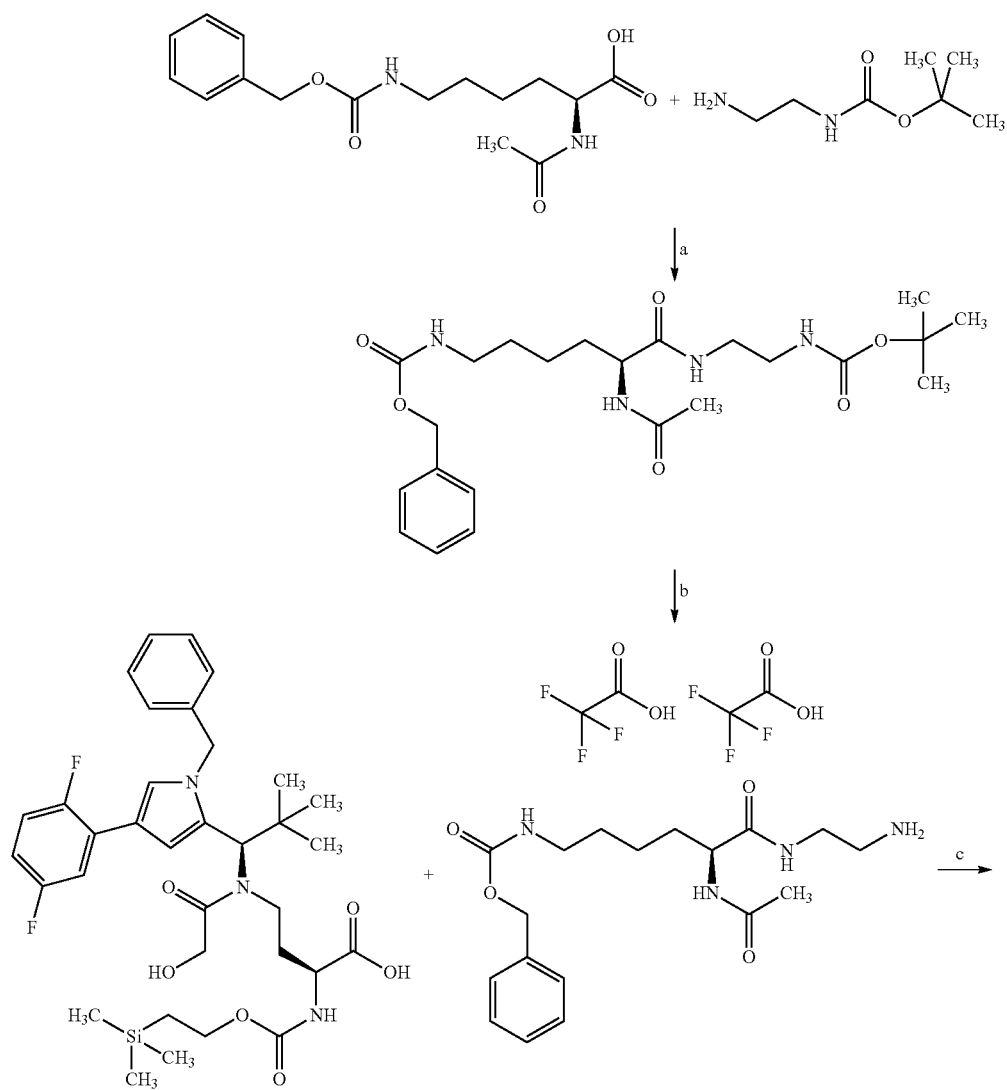

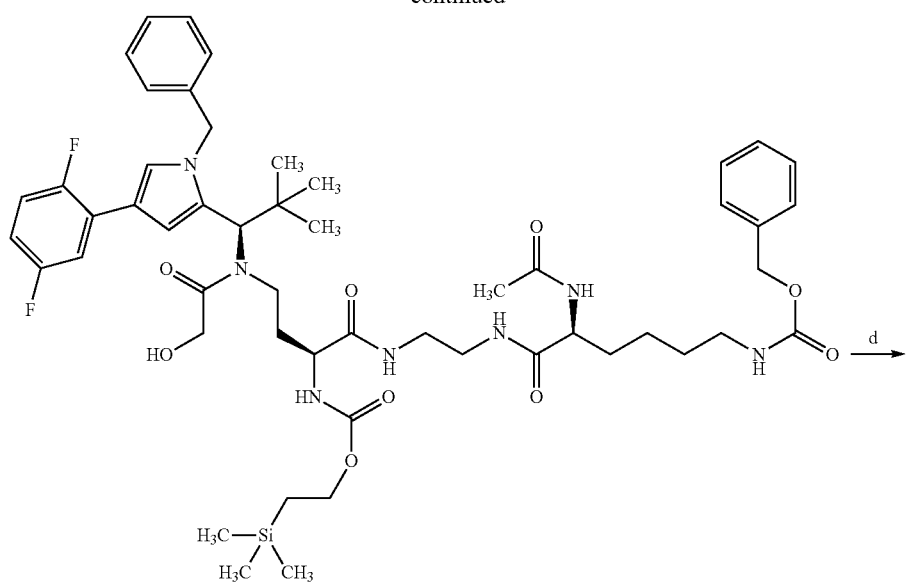
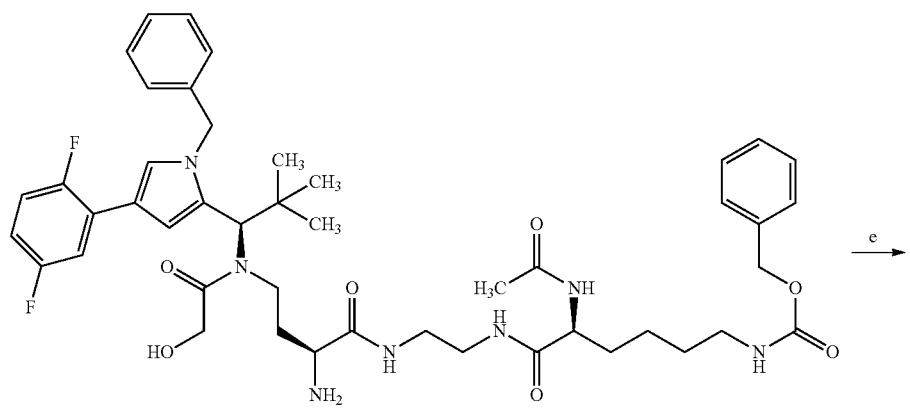
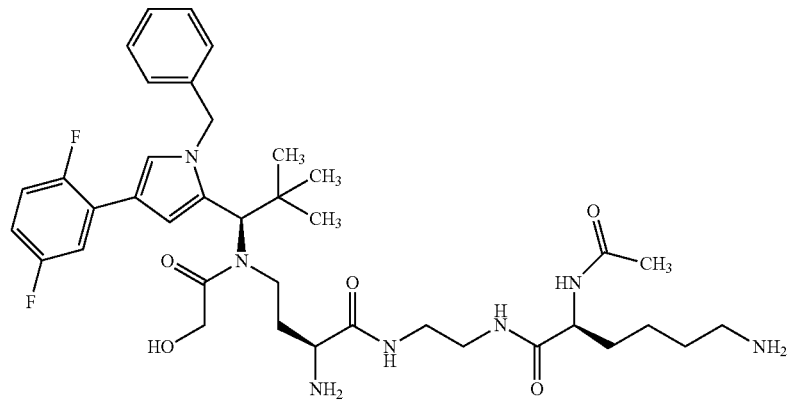
[a) HATU, DMF, diisopropylethylamine, RT; b) TFA, DCM, RT; c) HATU, DMF, diisopropylethylamine, RT; d) zinc chloride, trifluorethanol, 50° C.; e) H$_2$, Pd/C, THF/water, RT]

Scheme 8
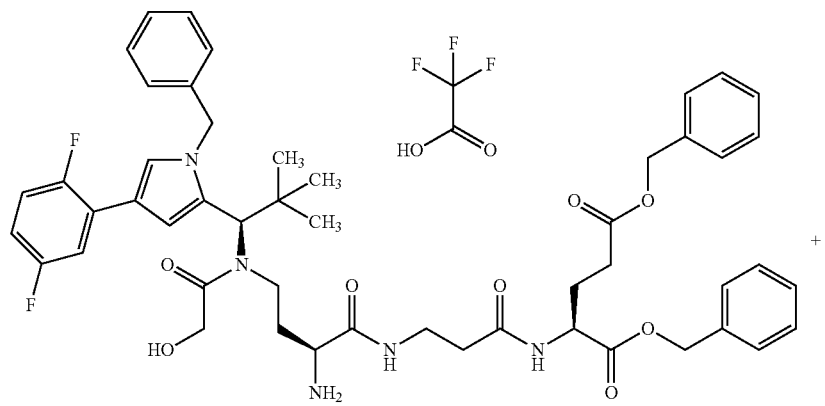
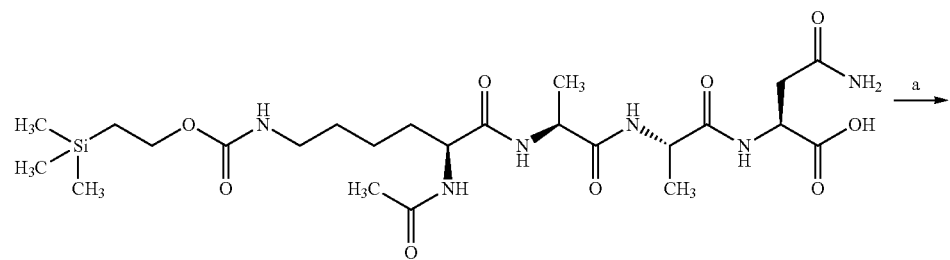
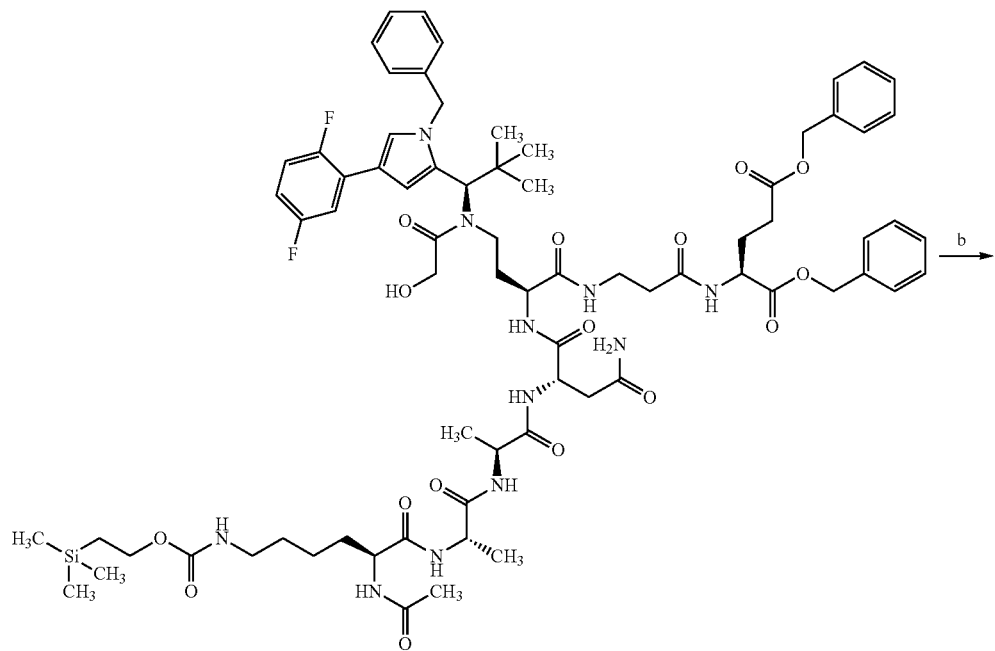

-continued
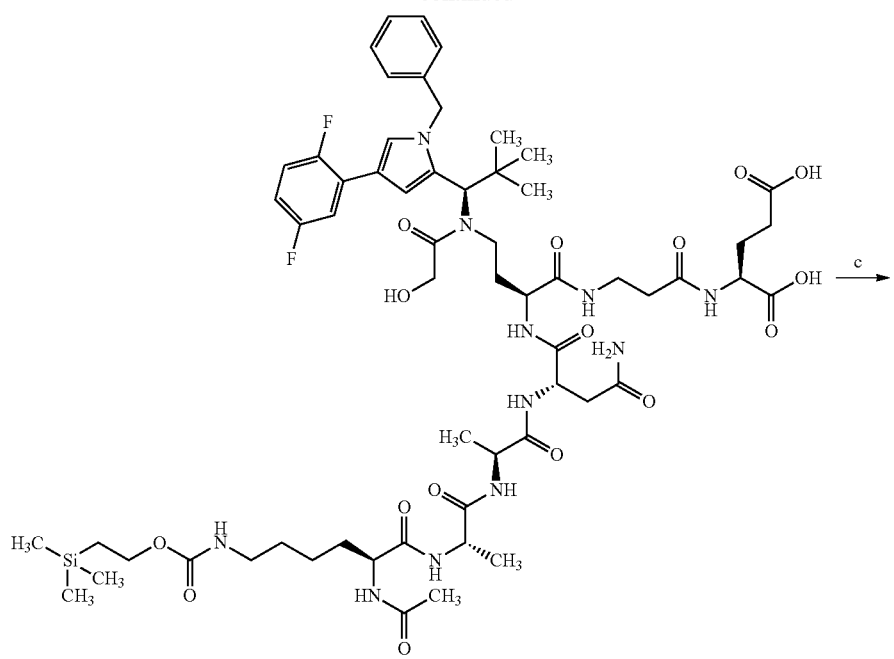
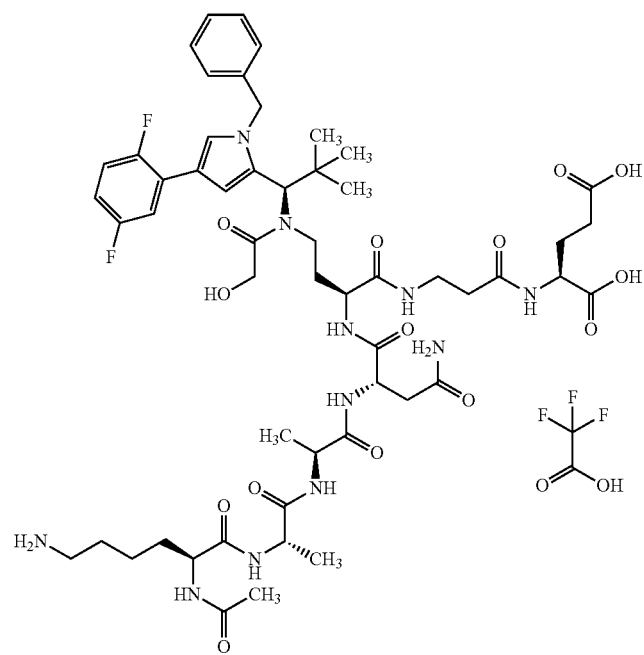
[a) HATU, DMF, diisopropylethylamine, RT; b) H₂, Pd/C, THF/water, RT; c) zinc chloride, trifluorethanol, 50° C.]

235
Scheme 9: Synthesis of glutamine-linked ADCs
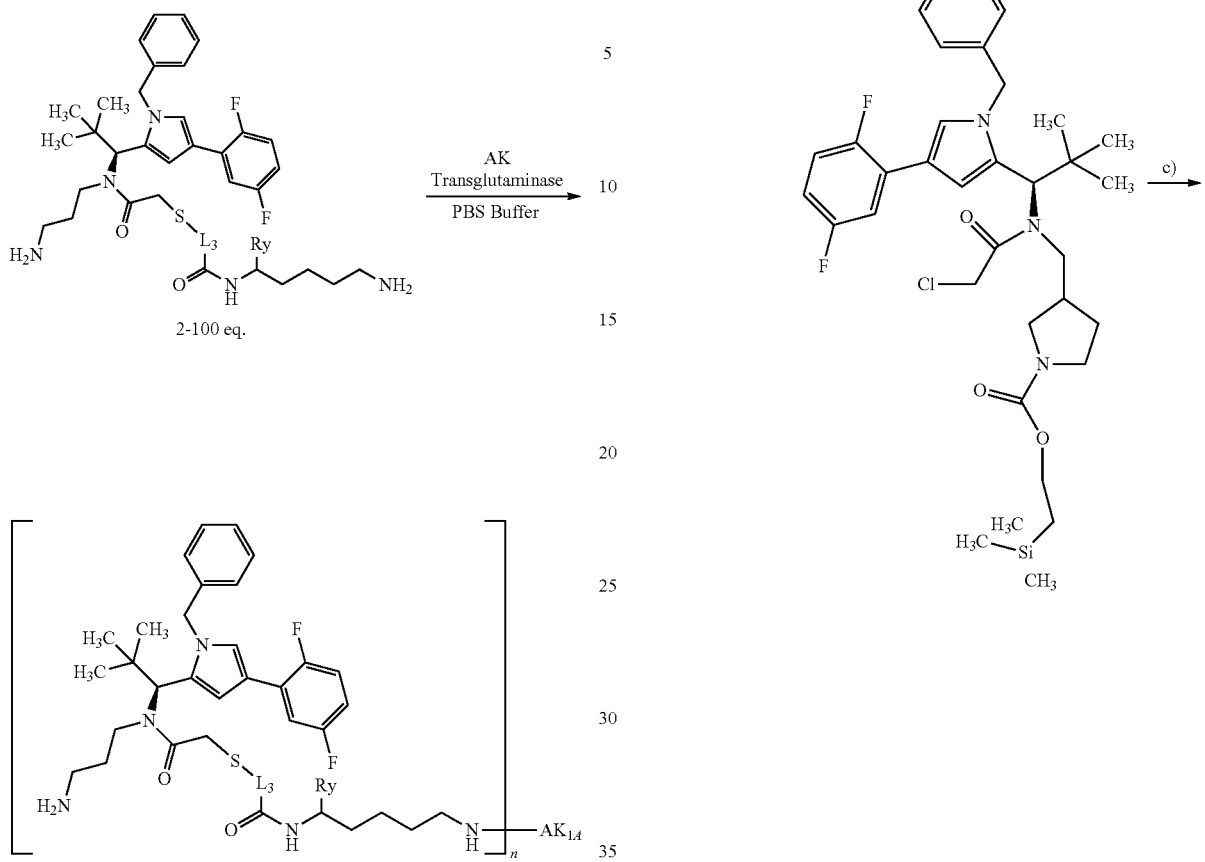
with n is 2 or 4.
Scheme 10
236
-continued
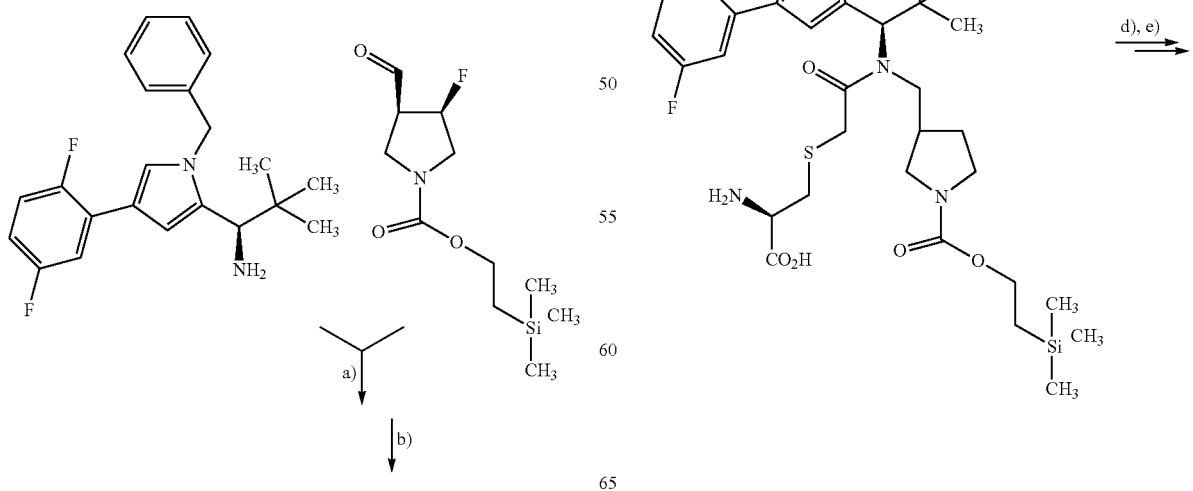

-continued

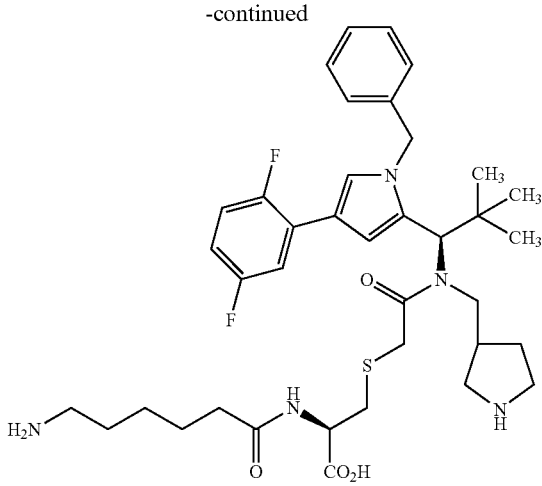

[a) sodium triacetoxyborhydride, acetic acid, DCM, RT; b) acetoxyacetylchloride, triethylamine, DCM, RT; c) L-Csytein, NaHCO₃, DBU, isopropanol/water, RT; d) Boc-6-aminocaproic acid, HATU, DMF, Diisopropylethylamin, RT; e) Zinkchlorid, Trifluorethanol, 50° C., EDTA.]

A. Examples

Abbreviations and Acronyms

A431NS human tumour cell line
A549 human tumour cell line
ABCB1 ATP-binding cassette sub-family B member 1 (synonym for P-gp and MDR1)
abs. absolute
Ac acetyl
ACN acetonitrile
aq. aqueous, aqueous solution
ATP adenosine triphosphate
BCRP breast cancer resistance protein, an efflux transporter
BEP 2-bromo-1-ethylpyridinium tetrafluoroborate
Boc tert-butoxycarbonyl
br. broad (in NMR)
Ex. Example
CI chemical ionization (in MS)
D doublet (in NMR)
D day(s)
TLC thin-layer chromatography
DCI direct chemical ionization (in MS)
Dd doublet of doublets (in NMR)
DMAP 4-N,N-dimethylaminopyridine
DME 1,2-dimethoxyethane
DMEM Dulbecco's Modified Eagle Medium (standardized nutrient medium for cell culture)
DMF N,N-dimethylformamide
DMSO dimethyl sulphoxide
DPBS, D-PBS, PBS Dulbecco's phosphate-buffered salt solution
  PBS=DPBS=D-PBS, pH 7.4, from Sigma, No D8537
  composition:
  0.2 g KCl
  0.2 g $KH_2PO_4$ (anhyd)
  8.0 g NaCl
  1.15 g $Na_2HPO_4$ (anhyd)
  made up ad 1 l with $H_2O$
Dt doublet of triplets (in NMR)
DTT DL-dithiothreitol
EDC N'-(3-dimethylaminopropyl)-N-ethylcarbodiimide hydrochloride
EGFR epidermal growth factor receptor
EI electron impact ionization (in MS)
ELISA enzyme-linked immunosorbent assay
eq. equivalent(s)
ESI electrospray ionization (in MS)
ESI-MicroTofq ESI-MicroTofq (name of the mass spectrometer with Tof=time of flight and q=quadrupol)
FCS foetal calf serum
Fmoc (9H-fluoren-9-ylmethoxy)carbonyl
GTP guanosine-5'-triphosphate
H hour(s)
HATU O-(7-azabenzotriazol-1-yl)-N,N,N',N'-tetramethyluronium hexafluorophosphate
HCT-116 human tumour cell line
HEPES 4-(2-hydroxyethyl)piperazine-1-ethanesulphonic acid
HOAc acetic acid
HOAt 1-hydroxy-7-azabenzotriazole
HOBt 1-hydroxy-1H-benzotriazole hydrate
HOSu N-hydroxysuccinimide
HPLC high-pressure high-performance liquid chromatography
HT29 human tumour cell line
$IC_{50}$ half-maximal inhibitory concentration
i.m. intramuscularly, administration into the muscle
i.v. intravenously, administration into the vein
conc. concentrated
LC-MS liquid chromatography-coupled mass spectroscopy
LLC-PK1 cells Lewis lung carcinoma pork kidney cell line
L-MDR human MDR1 transfected LLC-PK1 cells
M multiplet (in NMR)
MDR1 multidrug resistance protein 1
MeCN acetonitrile
Me methyl
Min minute(s)
MS mass spectrometry
MTT 3-(4,5-dimethylthiazol-2-yl)-2,5-diphenyl-2H-tetrazolium bromide
NCI-H292 human tumour cell line
NCI-H520 human tumour cell line
NMM N-methylmorpholine
NMP N-methyl-2-pyrrolidinone
NMR nuclear magnetic resonance spectrometry
NMRI mouse strain, originates from the Naval Medical Research Institute (NMRI)
NSCLC non small cell lung cancer
PBS phosphate-buffered salt solution
Pd/C palladium on activated carbon
P-gp P-gycoprotein, a transporter protein
PNGaseF enzyme for cleaving sugar
quant. quantitative (in yield)
Quart quartet (in NMR)
Quint quintet (in NMR)
$R_f$ retention index (in TLC)
RT room temperature
$R_t$ retention time (in HPLC)
S singlet (in NMR)
s.c. subcutaneously, administration under the skin
SCC-4 human tumour cell line
SCC-9 human tumour cell line
SCID mice test mice with severe combined immunodeficiency
t triplet (in NMR)
TBAF tetra-n-butylammonium fluoride
TEMPO (2,2,6,6-tetramethylpiperidin-1-yl)oxy tert. tertiary
TFA trifluoroacetic acid
THF tetrahydrofuran
T3P® 2,4,6-tripropyl-1,3,5,2,4,6-trioxatriphosphinane 2,4,6-trioxide
UV ultraviolet spectrometry
v/v ratio by volume (of a solution)
Z benzyloxycarbonyl Amino Acid Abbreviations Ala=Alanine
Arg=Arginine
Asn=Asparagine
Asp=Aspartic acid
Cys=Cysteine
Glu=Glutamic acid
Gln=Glutamine
Gly=Glycine
His=Histidine
Ile=Isoleucine
Leu=Leucine
Lys=Lysine
Met=Methionine
Nva=Norvaline
Phe=Phenylalanine
Pro=Proline
Ser=Serine
Thr=Threonine
Trp=Tryptophan
Tyr=Tyrosine
Val=Valine If, in the context of the present disclosure, no temperature is given in the description of a reaction, room temperature should always be assumed.

HPLC and LC-MS Methods:

Method 1 (LC-MS):
Instrument: Waters ACQUITY SQD UPLC system; column: Waters Acquity UPLC HSS T3 1.8μ50×1 mm; mobile phase A: 1 l of water+0.25 ml of 99% strength formic acid; mobile phase B: 1 l of acetonitrile+0.25 ml of 99% strength formic acid; gradient: 0.0 min 90% A→1.2 min 5% A→2.0 min 5% A oven: 50° C.; flow rate: 0.40 ml/min; UV detection: 208-400 nm.

Method 2 (LC-MS):
MS instrument type: Waters Synapt G2S; UPLC instrument type: Waters Acquity I-CLASS; column: Waters, BEH300, 2.1×150 mm, C18 1.7 μm; mobile phase A: 1 l of water+0.01% formic acid; mobile phase B: 1 l of acetonitrile+0.01% formic acid; gradient: 0.0 min 2% B→1.5 min 2% B→8.5 min 95% B→10.0 min 95% B; oven: 50° C.; flow rate: 0.50 ml/min; UV detection: 220 nm.

Method 3 (LC-MS):
MS instrument: Waters (Micromass) QM; HPLC instrument: Agilent 1100 series; column: Agilent ZORBAX Extend-C18 3.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 4 (LC-MS):
MS instrument type: Waters Synapt G2S; UPLC instrument type: Waters Acquity I-CLASS; column: Waters, HSST3, 2.1×50 mm, C18 1.8 μm; mobile phase A: 1 l of water+0.01% formic acid; mobile phase B: 1 l of acetonitrile+0.01% formic acid; gradient: 0.0 min 10% B→0.3 min 10% B→1.7 min 95% B→2.5 min 95% B; oven: 50° C.; flow rate: 1.20 ml/min; UV detection: 210 nm.

Method 5 (LC-MS):
Instrument: Waters ACQUITY SQD UPLC system; column: Waters Acquity UPLC HSS T3 1.8μ 50×1 mm; mobile phase A: 1 l of water+0.25 ml of 99% strength formic acid; mobile phase B: 1 l of acetonitrile+0.25 ml of 99% strength formic acid; gradient: 0.0 min 95% A→6.0 min 5% A→7.5 min 5% A oven: 50° C.; flow rate: 0.35 ml/min; UV detection: 210-400 nm.

Method 6 (LC-MS):
Instrument: Micromass Quattro Premier with Waters UPLC Acquity; column: Thermo Hypersil GOLD 1.9μ 50×1 mm; mobile phase A: 1 l of water+0.5 ml of 50% strength formic acid; mobile phase B: 1 l of acetonitrile+0.5 ml of 50% strength formic acid; gradient: 0.0 min 97% A→0.5 min 97% A→3.2 min 5% A→4.0 min 5% A; oven: 50° C.; flow rate: 0.3 ml/min; UV detection: 210 nm.

Method 7 (LC-MS):
Instrument: Agilent MS Quad 6150; HPLC: Agilent 1290; column: Waters Acquity UPLC HSS T3 1.8μ 50×2.1 mm; mobile phase A: 1 l of water+0.25 ml of 99% strength formic acid; mobile phase B: 1 l of acetonitrile+0.25 ml of 99% strength formic acid; gradient: 0.0 min 90% A→0.3 min 90% A→1.7 min 5% A→3.0 min 5% A; oven: 50° C.; flow rate: 1.20 ml/min; UV detection: 205-305 nm.

Method 8 (LC-MS):
MS instrument type: Waters Synapt G2S; UPLC instrument type: Waters Acquity I-CLASS; column: Waters, HSST3, 2.1×50 mm, C18 1.8 μm; mobile phase A: 1 l of water+0.01% formic acid; mobile phase B: 1 l of acetonitrile+0.01% formic acid; gradient: 0.0 min 2% B→2.0 min 2% B→13.0 min 90% B→15.0 min 90% B; oven: 50° C.; flow rate: 1.20 ml/min; UV detection: 210 nm.

Method 9: LC-MS-Prep Purification Method for Examples 181-191 (Method LIND-LC-MS-Prep)
MS instrument: Waters; HPLC instrument: Waters (column Waters X-Bridge C18, 19 mm×50 mm, 5 μm, mobile phase A: water+0.05% ammonia, mobile phase B: acetonitrile (ULC) with gradient; flow rate: 40 ml/min; UV detection: DAD; 210-400 nm).
or:
MS instrument: Waters; HPLC instrument: Waters (column Phenomenex Luna 5μ C18(2) 100A, AXIA Tech. 50×21.2 mm, mobile phase A: water+0.05% formic acid, mobile phase B: acetonitrile (ULC) with gradient; flow rate: 40 ml/min; UV detection: DAD; 210-400 nm).

Method 10: LC-MS Analysis Method for Examples 181-191 (LIND_SQD_SB_AQ)
MS instrument: Waters SQD; HPLC instrument: Waters UPLC; column: Zorbax SB-Aq (Agilent), 50 mm×2.1 mm, 1.8 μm; mobile phase A: water+0.025% formic acid, mobile phase B: acetonitrile (ULC)+0.025% formic acid; gradient: 0.0 min 98% A-0.9 min 25% A-1.0 min 5% A-1.4 min 5% A-1.41 min 98% A-1.5 min 98% A; oven: 40° C.; flow rate: 0.600 ml/min; UV detection: DAD; 210 nm.

Method 11 (HPLC):
Instrument: HP1100 Series
Column: Merck Chromolith SpeedROD RP-18e, 50-4.6 mm, Cat.
No. 1.51450.0001, precolumn Chromolith Guard Cartridge Kit, RP-18e,
5-4.6 mm, Cat. No. 1.51470.0001
Gradient: flow rate 5 ml/min
injection volume 5 μl
solvent A: $HClO_4$ (70% strength) in water (4 ml/l)
solvent B: acetonitrile start 20% B 0.50 min 20% B 3.00 min 90% B 3.50 min 90% B 3.51 min 20% B 4.00 min 20% B column temperature: 40° C.

Wavelength: 210 nm

All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

Method 12 (LC-MS):

Instrument MS: Thermo Scientific FT-MS; Instrument UHPLC+: Thermo Scientific UltiMate 3000; Säule: Waters, HSST3, 2.1×75 mm, C18 1.8 µm; Eluent A: 1 l Wasser+ 0.01% Ameisensäure; Eluent B: 1 l Acetonitril+0.01% Ameisensäure; Gradient: 0.0 min 10% B→2.5 min 95% B→3.5 min 95% B; Ofen: 50° C.; Fluss: 0.90 ml/min; UV-Detektion: 210 nm/Optimum Integration Path 210-300 nm.

Method 13: (LC-MS):

Instrument MS: Waters (Micromass) Quattro Micro; Instrument Waters UPLC Acquity; Säule: Waters BEH C18 1.7µ 50×2.1 mm; Eluent A: 1 l Wasser+0.01 mol Ammoniumformiat, Eluent B: 1 l Acetonitril; Gradient: 0.0 min 95% A→0.1 min 95% A→2.0 min 15% A→2.5 min 15% A→2.51 min 10% A→3.0 min 10% A; Ofen: 40° C.; Fluss: 0.5 ml/min; UV-Detektion: 210 nm.

Starting Materials and Intermediates

Intermediate C1

Trifluoroacetic acid-(1R)-1-[1-benzyl-4-(2,5-difluorophenyl)-1H-imidazol-2-yl]-2,2-dimethylpropan-1-amine (1:1)

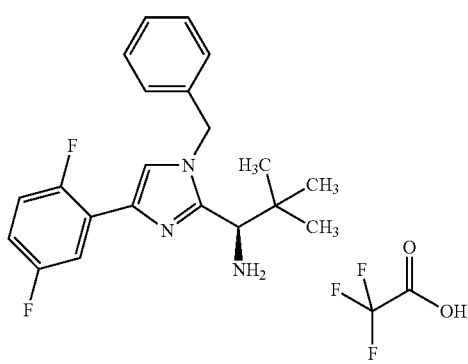 [SMILES: CC(C)(C)[C@@H](N)c1nc(-c2cc(F)ccc2F)cn1Cc1ccccc1 ; O=C(O)C(F)(F)F]

The title compound was prepared as described in WO2006/002326.

Intermediate C2 tert-Butyl(2S)-4-({(1R)-1-[1-benzyl-4-(2,5-difluorophenyl)-1H-imidazol-2-yl]-2,2-dimethylpropyl}amino)-2-[(tert-butoxycarbonyl)amino]butanoate

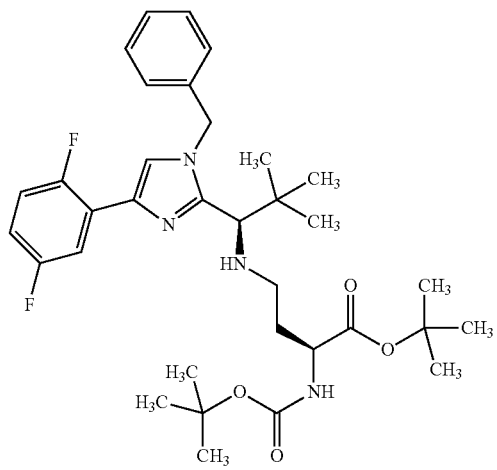 [SMILES: CC(C)(C)OC(=O)N[C@@H](CCN[C@@H](c1nc(-c2cc(F)ccc2F)cn1Cc1ccccc1)C(C)(C)C)C(=O)OC(C)(C)C]

4.22 g (14.5 mmol) of tert-butyl N-(tert-butoxycarbonyl)-L-homoserinate were dissolved in 180 ml of dichloromethane, and 3.5 ml of pyridine and 9.2 g (21.7 mmol) of 1,1,1-triacetoxy-1lambda$^5$,2-benziodoxol-3(1H)-one were then added. The reaction was stirred at RT for 1 h and then diluted with 500 ml of dichloromethane and extracted twice with 10% strength sodium thiosulphate solution and then extracted successively twice with 5% strength citric acid and twice with 10% strength sodium bicarbonate solution. The organic phase was separated off, dried over magnesium sulphate and then dried under reduced pressure. The residue was taken up in diethyl ether, and HCl (solution in diethyl ether) was added. The precipitate was filtered off and the filtrate was then concentrated and lyophilized from acetonitrile/water. This gave 3.7 g (93%) of tert-butyl (2S)-2-[(tert-butoxycarbonyl)amino]-4-oxobutanoate which were used without further purification for the next step. ($R_f$: 0.5 (DCM/methanol 95/5).

3.5 g (9.85 mmol) of Intermediate C1 were dissolved in 160 ml of DCM, and 3.13 g (14.77 mmol) of sodium triacetoxyborohydride and 0.7 ml of acetic acid were added. After 5 min of stirring at RT, 3.23 g (11.85 mmol) of tert-butyl (2S)-2-[(tert-butoxycarbonyl)amino]-4-oxobutanoate were added and the reaction was stirred at RT for a further 30 min. The solvent was then evaporated under reduced pressure and the residue was taken up in acetonitrile/water. The precipitated solid was filtered off and dried, giving 5.46 g (84%) of the title compound.

HPLC (Method 11): $R_t$=2.5 min;

LC-MS (Method 1): $R_t$=1.13 min; MS (ESIpos): m/z=613 (M+H)$^+$.

Intermediate C3

(2S)-4-[(Acetoxyacetyl) {(1R)-1-[1-benzyl-4-(2,5-difluorophenyl)-1H-imidazol-2-yl]-2,2-dimethylpropyl}amino]-2-[(tert-butoxycarbonyl)amino]butanoic acid

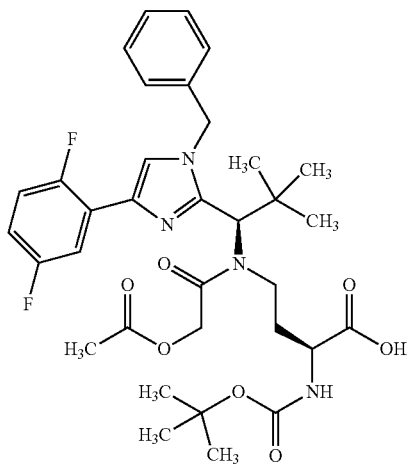 [SMILES: CC(=O)OCC(=O)N(CC[C@H](NC(=O)OC(C)(C)C)C(=O)O)[C@@H](c1nc(-c2cc(F)ccc2F)cn1Cc1ccccc1)C(C)(C)C]

5.46 g (8.24 mmol) of Intermediate C2 were dissolved in 160 ml of DCM, and 4.8 ml of triethylamine and 2.2 ml (20.6 mmol) of acetoxyacetyl chloride then were added. The reaction was stirred at RT overnight and then concentrated under reduced pressure. The residue was taken up in ethyl acetate and extracted three times with saturated sodium bicarbonate solution and then with saturated sodium chloride solution. The organic phase was dried over sodium sulphate and then concentrated. The residue was purified by column chromatography on Biotage/Isolera (SNAP 340 g) using the mobile phase cyclohexane/ethyl acetate 2:1. This gave 4.57 g (75%) of the acylated intermediate.

LC-MS (Method 1): $R_t$=1.49 min; MS (ESIpos): m/z=713 (M+H)$^+$.

1 g (1.36 mmol) of this intermediate was dissolved in 20 ml of DCM, and 20 ml of TFA were added. After 5 h of stirring at RT, the mixture was concentrated and the residue was triturated twice with n-pentane. In each case, the n-pentane was decanted off and the solid that remained was dried under high vacuum. This gave 1.1 g of (2S)-4-[(acetoxyacetyl){(1R)-1-[1-benzyl-4-(2,5-difluorophenyl)-1H-imidazol-2-yl]-2,2-dimethylpropyl}amino]-2-aminobutanoic acid/trifluoroacetic acid (1:1). LC-MS (Method 1): $R_t$=0.93 min; MS (ESIpos): m/z=557 (M+H)$^+$.

0.91 g (1.57 mmol) of this intermediate were dissolved in 70 ml of DCM, and 3.43 g (15.7 mmol) of di-tert-butyl dicarbonate and 4.1 ml of N,N-diisopropylethylamine were added. After 30 min of stirring at RT, the reaction was diluted with DCM and extracted with 5% strength citric acid. The organic phase was dried over sodium sulphate and concentrated. The residue was triturated twice with n-pentane and in each case the n-pentane was decanted off. The solid that remained was lyophilized from acetonitrile/water 1:1, giving 1.11 g of the title compound.

HPLC (Method 11): $R_t$=2.55 min;

LC-MS (Method 1): $R_t$=1.3 min; MS (ESIpos): m/z=657 (M+H)$^+$.

Intermediate C4

(2S)-2-Amino-4-[{(1R)-1-[1-benzyl-4-(2,5-difluorophenyl)-1H-imidazol-2-yl]-2,2-dimethylpropyl}(glycoloyl)amino]butanoic acid/trifluoroacetic acid (1:1)

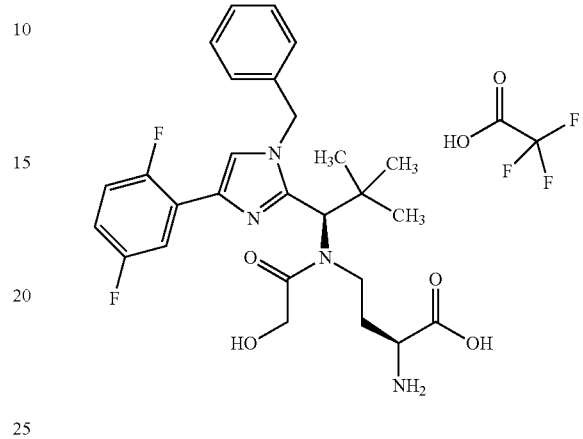

5.46 g (8.24 mmol) of Intermediate C2 were dissolved in 160 ml of DCM, and 4.8 ml of triethylamine and 2.2 ml (20.6 mmol) of acetoxyacetyl chloride were added. The reaction was stirred at RT overnight and then concentrated under reduced pressure. The residue was taken up in ethyl acetate and extracted three times with saturated sodium bicarbonate solution and then with saturated sodium chloride solution. The organic phase was dried over sodium sulphate and then concentrated. The residue was purified by column chromatography on Biotage/Isolera (SNAP 340 g) using the mobile phase cyclohexane/ethyl acetate 2:1. This gave 4.57 g (75%) of the acylated intermediate.

LC-MS (Method 1): $R_t$=1.49 min; MS (ESIpos): m/z=713 (M+H)$^+$.

1.5 g (2.035 mmol) of this intermediate were taken up in 50 ml of ethanol, and 5.8 ml of a 40% strength solution of methanamine in water was added. The reaction was stirred at 50° C. for 4 h and then concentrated. The residue was taken up in DCM and washed twice with water. The organic phase was dried over magnesium sulphate and then concentrated.

The residue was dried under high vacuum. This gave 1.235 mg of this intermediate, which were reacted further without further purification.

1.235 mg (1.5 mmol) of this intermediate were dissolved in 15 ml of DCM, and 15 ml of TFA were added. After 4 h of stirring at RT, the mixture was concentrated. The residue was purified by preparative HPLC. The appropriate fractions were concentrated and the residue was lyophilized from acetonitrile.

This gave 1.04 g (quant) of the title compound.

HPLC (Method 11): $R_t$=1.9 min;

LC-MS (Method 1): $R_t$=0.89 min; MS (ESIpos): m/z=515 (M+H)$^+$.

Intermediate C5

(2S)-4-[{(1R)-1-[1-Benzyl-4-(2,5-difluorophenyl)-1H-imidazol-2-yl]-2,2-dimethylpropyl}(glycoloyl)amino]-2-[(tert-butoxycarbonyl)amino]butanoic acid

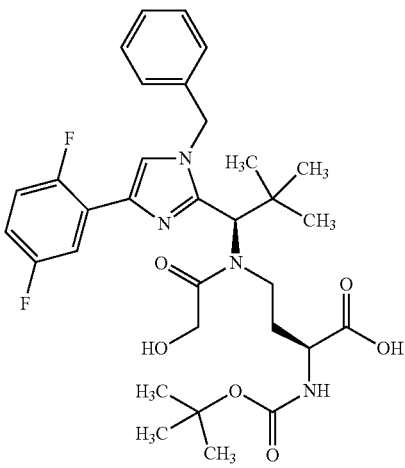 [SMILES: CC(C)(C)OC(=O)N[C@@H](CCN(C(=O)CO)[C@@H](c1nc(-c2cc(F)ccc2F)cn1Cc1ccccc1)C(C)(C)C)C(=O)O]

0.9 g (1.24 mmol) of Intermediate C4 was dissolved in 60 ml of DCM, and 2.7 g (12.5 mmol) of di-tert-butyl dicarbonate and 3.3 ml of N,N-diisopropylethylamine were added. After 45 min of stirring at RT, the reaction was concentrated and the residue was taken up in diethyl ether, and n-pentane was added until the mixture started to get cloudy. The reaction was cooled to 0° C. and then decanted. Once more, n-pentane was added to the residue and the mixture was decanted. The solid that remained was lyophilized from acetonitrile/water 1:1, giving 0.95 g (quant) of the title compound.

HPLC (Method 11): $R_t$=2.5 min;
LC-MS (Method 1): $R_t$=1.27 min; MS (ESIpos): m/z=615 (M+H)$^+$.

Intermediate C52

(1R)-1-[1-Benzyl-4-(2,5-difluorophenyl)-1H-pyrrol-2-yl]-2,2-dimethylpropan-1-amine

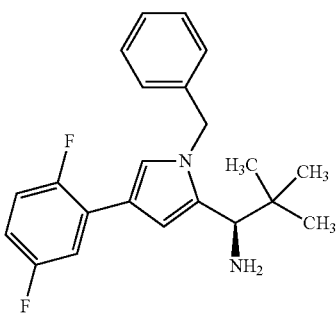 [SMILES: CC(C)(C)[C@@H](N)c1cc(-c2cc(F)ccc2F)cn1Cc1ccccc1]

10.00 g (49.01 mmol) of methyl 4-bromo-1H-pyrrole-2-carboxylate were initially charged in 100.0 ml of DMF, and 20.76 g (63.72 mmol) of caesium carbonate and 9.22 g (53.91 mmol) of benzyl bromide were added. The reaction mixture was stirred at RT overnight. The reaction mixture was partitioned between water and ethyl acetate and the aqueous phase was extracted with ethyl acetate. The combined organic phases were dried over magnesium sulphate and the solvent was evaporated under reduced pressure. The reaction was repeated with 90.0 g of methyl 4-bromo-1H-pyrrole-2-carboxylate. The two combined reactions were purified by preparative RP-HPLC (column: Daiso 300×100; 10μ, flow rate: 250 ml/min, MeCN/water). The solvents were evaporated under reduced pressure and the residue was dried under high vacuum. This gave 125.15 g (87% of theory) of the compound methyl 1-benzyl-4-bromo-1H-pyrrole-2-carboxylate.

LC-MS (Method 1): $R_t$=1.18 min; MS (ESIpos): m/z=295 [M+H]$^+$.

Under argon, 4.80 g (16.32 mmol) of methyl 1-benzyl-4-bromo-1H-pyrrole-2-carboxylate were initially charged in DMF, and 3.61 g (22.85 mmol) of (2,5-difluorophenyl)boronic acid, 19.20 ml of saturated sodium carbonate solution and 1.33 g (1.63 mmol) of [1,1'-bis(diphenylphosphino)ferrocene]-dichloropalladium(II):dichloromethane were added. The reaction mixture was stirred at 85° C. overnight. The reaction mixture was filtered through Celite and the filter cake was washed with ethyl acetate. The organic phase was extracted with water and then washed with saturated NaCl solution. The organic phase was dried over magnesium sulphate and the solvent was evaporated under reduced pressure. The residue was purified on silica gel (mobile phase: cyclohexane/ethyl acetate 100:3). The solvents were evaporated under reduced pressure and the residue was dried under high vacuum. This gave 3.60 g (67% of theory) of the compound methyl 1-benzyl-4-(2,5-difluorophenyl)-1H-pyrrole-2-carboxylate.

LC-MS (Method 7): $R_t$=1.59 min; MS (ESIpos): m/z=328 [M+H]$^+$.

3.60 g (11.00 mmol) of methyl 1-benzyl-4-(2,5-difluorophenyl)-1H-pyrrole-2-carboxylate were initially charged in 90.0 ml of THF, and 1.04 g (27.50 mmol) of lithium aluminium hydride (2.4 M in THF) were added at 0° C. The reaction mixture was stirred at 0° C. for 30 minutes. At 0° C., saturated potassium sodium tartrate solution was added, and ethyl acetate was added to the reaction mixture. The organic phase was extracted three times with saturated potassium sodium tartrate solution. The organic phase was washed once with saturated NaCl solution and dried over magnesium sulphate. The solvent was evaporated under reduced pressure and the residue was dissolved in 30.0 ml of dichloromethane. 3.38 g (32.99 mmol) of manganese(IV) oxide were added and the mixture was stirred at RT for 48 h. Another 2.20 g (21.47 mmol) of manganese(IV) oxide were added and the mixture was stirred at RT overnight. The reaction mixture was filtered through Celite and the filter cake was washed with dichloromethane. The solvent was evaporated under reduced pressure and the residue 2.80 g of (1-benzyl-4-(2,5-difluorophenyl)-1H-pyrrole-2-carbaldehyde) was used without further purification in the next step of the synthesis.

LC-MS (Method 7): $R_t$=1.48 min; MS (ESIpos): m/z=298 [M+H]$^+$.

28.21 g (94.88 mmol) of 1-benzyl-4-(2,5-difluorophenyl)-1H-pyrrole-2-carbaldehyde together with 23.00 g (189.77 mmol) of (R)-2-methylpropane-2-sulphinamide were initially charged in 403.0 ml of absolute THF, and 7.42 g (237.21 mmol) of titanium(IV) isopropoxide were added and the mixture was stirred at RT overnight. 500.0 ml of saturated NaCl solution and 1000.0 ml of ethyl acetate were added, and the mixture was stirred at RT for 1 h. The mixture was filtered through kieselguhr and the filtrate was washed twice with saturated NaCl solution. The organic phase was dried over magnesium sulphate, the solvent was evaporated under reduced pressure and the residue was purified using Biotage Isolera (silica gel, column 1500+340 g SNAP, flow rate 200 ml/min, ethyl acetate/cyclohexane 1:10).

LC-MS (Method 7): $R_t$=1.63 min; MS (ESIpos): m/z=401 [M+H]$^+$.

25.00 g (62.42 mmol) of (R)-N-{(E/Z)-[1-benzyl-4-(2,5-difluorophenyl)-1H-pyrrol-2-yl]methylene}-2-methylpropane-2-sulphinamide were initially charged in absolute THF under argon and cooled to −78° C. 12.00 g (187.27 mmol) of tert-butyllithium (1.7 M solution in pentane) were then added at −78° C. and the mixture was stirred at this temperature for 3 h. At −78° C., 71.4 ml of methanol and 214.3 ml of saturated ammonium chloride solution were then added in succession, and the reaction mixture was allowed to warm to RT and stirred at RT for 1 h. The mixture was diluted with ethyl acetate and washed with water. The organic phase was dried over magnesium sulphate and the solvent was evaporated under reduced pressure. The residue (R)-N-{(1R)-1-[1-benzyl-4-(2,5-difluorophenyl)-1H-pyrrol-2-yl]-2,2-dimethylpropyl}-2-methylpropane-2-sulphinamide was used without further purification in the next step of the synthesis.

LC-MS (Method 6): $R_t$=2.97 min; MS (ESIpos): m/z=459 [M+H]$^+$.

28.00 g (61.05 mmol) of (R)-N-{(1R)-1-[1-benzyl-4-(2,5-difluorophenyl)-1H-pyrrol-2-yl]-2,2-dimethylpropyl}-2-methylpropane-2-sulphinamide were initially charged in 186.7 ml of 1,4-dioxane, and 45.8 ml of HCl in 1,4-dioxane solution (4.0 M) were then added. The reaction mixture was stirred at RT for 2 h and the solvent was evaporated under reduced pressure. The residue was purified by preparative RP-HPLC (column: (column: Kinetix 100×30; flow rate: 60 ml/min, MeCN/water). The acetonitrile was evaporated under reduced pressure and dichloromethane was added to the aqueous residue. The organic phase was washed with sodium bicarbonate solution and dried over magnesium sulphate. The solvent was evaporated under reduced pressure and the residue was dried under high vacuum. This gave 16.2 g (75% of theory) of the title compound.

LC-MS (Method 6): $R_t$=2.10 min; MS (ESIpos): m/z=338 [M-NH$_2$]+, 709 [2M+H]$^+$.

$^1$H NMR (400 MHz, DMSO-d$_6$): δ [ppm]=0.87 (s, 9H), 1.53 (s, 2H), 3.59 (s, 1H), 5.24 (d, 2H), 6.56 (s, 1H), 6.94 (m, 1H), 7.10 (d, 2H), 7.20 (m, 1H), 7.26 (m, 2H), 7.34 (m, 2H), 7.46 (m, 1H).

Intermediate C53

(2S)-4-[{(1R)-1-[1-Benzyl-4-(2,5-difluorophenyl)-1H-pyrrol-2-yl]-2,2-dimethylpropyl}(glycoloyl)amino]-2-{[(9H-fluoren-9-ylmethoxy)carbonyl]amino}butanoic acid

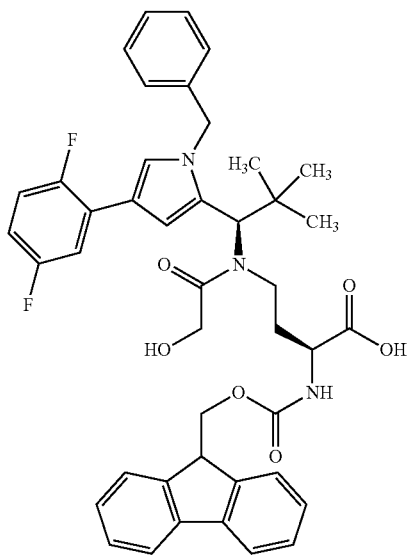 [SMILES: CC(C)(C)[C@H](c1cc(-c2cc(F)ccc2F)cn1Cc1ccccc1)N(CC[C@H](NC(=O)OCC1c2ccccc2-c2ccccc21)C(=O)O)C(=O)CO]

First, Intermediate C52 was reductively alkylated with benzyl (2S)-2-{[(benzyloxy)carbonyl]amino}-4-oxobutanoate analogously to C2. The secondary amino group was then acylated with 2-chloro-2-oxoethyl acetate and the two ester groups were then hydrolysed with 2M lithium hydroxide solution in methanol. The intermediate obtained in this manner was dissolved in ethanol, palladium on carbon (10%) was added and the mixture was hydrogenated at RT with hydrogen under standard pressure for 1 h. The deprotected compound was taken up in dioxane/water 2:1 and in the last step the Fmoc protective group was introduced using 9H-fluoren-9-ylmethyl chlorocarbonate in the presence of N,N-diisopropylethylamine.

LC-MS (Method 1): $R_t$=1.37 min; MS (ESIpos): m/z=734 (M−H)$^−$.

Intermediate C58

(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoic acid

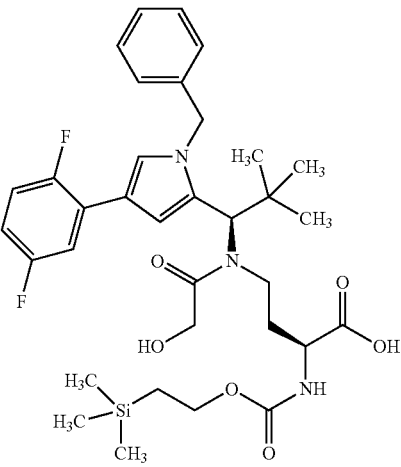 [SMILES: CC(C)(C)[C@H](c1cc(-c2cc(F)ccc2F)cn1Cc1ccccc1)N(CC[C@H](NC(=O)OCC[Si](C)(C)C)C(=O)O)C(=O)CO]

First, Intermediate C52 was reductively alkylated with benzyl (2S)-2-{[(benzyloxy)carbonyl]amino}-4-oxobutanoate analogously to Intermediate C2. First, Intermediate C52 was reductively alkylated with benzyl (2S)-2-{[(benzyloxy)carbonyl]amino}-4-oxobutanoate analogously to C2. The secondary amino group was then acylated with 2-chloro-2-oxoethyl acetate as described for Intermediate C27, and the two ester groups were then hydrolysed with 2M lithium hydroxide solution in methanol. The intermediate obtained in this manner was dissolved in ethanol, palladium on carbon (10%) was added and the mixture was hydrogenated at RT with hydrogen under standard pressure for 1 h.

500 mg (0.886 mmol) of this fully deprotected intermediate were taken up in 60 ml of dioxane, and 253 mg (0.975 mmol) of 1-({[2-(trimethylsilyl)ethoxy]carbonyl}oxy)pyrrolidine-2,5-dione and 198 µl of triethylamine were added. After 24 h of stirring at RT, the reaction was concentrated and the residue was purified by preparative HPLC. Combination of the appropriate fractions, concentration under reduced pressure and drying under high vacuum gave 312 mg (50% of theory) of the title compound.

LC-MS (Method 5): $R_t$=4.61 min; MS (ESIpos): m/z=658 (M+H)$^−$.

Intermediate C61

N-[(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-beta-alanine

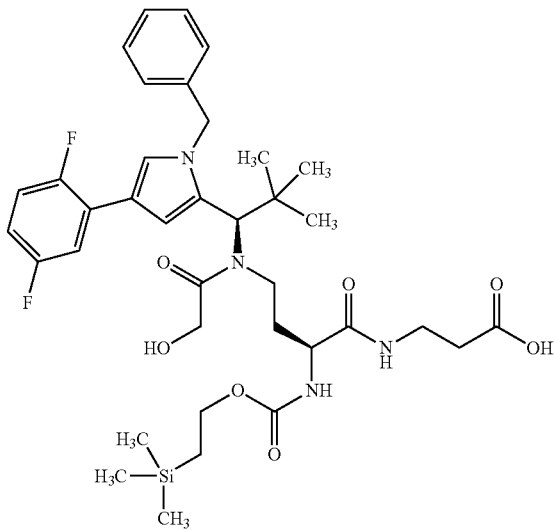 [SMILES: CC(C)(C)[C@H](c1cc(-c2cc(F)ccc2F)cn1Cc1ccccc1)N(CC[C@H](NC(=O)OCC[Si](C)(C)C)C(=O)NCCC(=O)O)C(=O)CO]

The title compound was prepared by coupling 60 mg (0.091 mmol) of Intermediate C58 with methyl B-alaninate, followed by ester cleavage with 2M lithium hydroxide solution. This gave 67 mg (61% of theory) of the title compound over 2 steps.

LC-MS (Method 1): $R_t$=1.29 min; MS (ESIpos): m/z=729 (M+H)+.

Intermediate C69

11-{(1R)-1-[1-Benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid

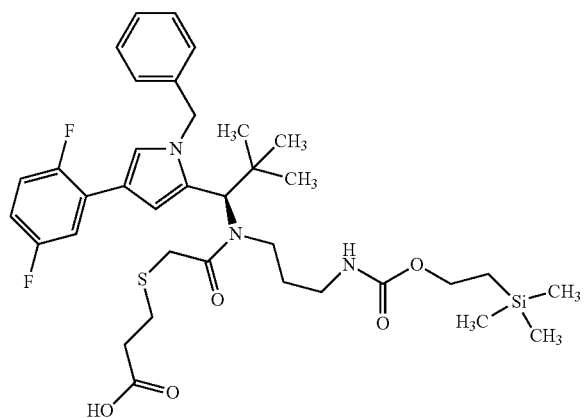 [SMILES: CC(C)(C)[C@H](c1cc(-c2cc(F)ccc2F)cn1Cc1ccccc1)N(CCCNC(=O)OCC[Si](C)(C)C)C(=O)CSCCC(=O)O]

117.0 mg (0.19 mmol) of (2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C70) and 21.6 mg (0.20 mmol) of 3-sulphanylpropanoic acid were initially charged in 3.0 ml of methanol, 89.5 mg (0.65 mmol) of potassium carbonate were added and the mixture was stirred at 50° C. for 4 h. The reaction mixture was diluted with ethyl acetate and the organic phase was washed with water and saturated NaCl solution. The organic phase was dried over magnesium sulfate, the solvent was evaporated under reduced pressure and the residue was dried under high vacuum. The residue was used without further purification in the next step of the synthesis. This gave 106.1 mg (73% of theory) of the title compound.

LC-MS (Method 1): $R_t$=1.42 min; MS (ESIneg): m/z=700 (M−H)⁻.

Intermediate C70

(2-(Trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate

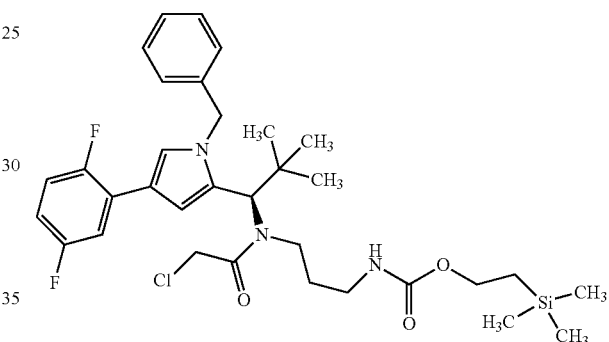

990.0 mg (2.79 mmol) of (1R)-1-[1-benzyl-4-(2,5-difluorophenyl)-1H-pyrrol-2-yl]-2,2-dimethylpropan-1-amine (intermediate C52) were initially charged in 15.0 ml of dichloromethane, and 828.8 mg (3.91 mmol) of sodium triacetoxyborohydride and 129.9 mg (3.21 mmol) of acetic acid were added, and the mixture was stirred at RT for 5 min. 698.1 mg (3.21 mmol) of 2-(trimethylsilyl)ethyl (3-oxopropyl)carbamate (Intermediate L15) dissolved in 15.0 ml of dichloromethane were added, and the reaction mixture was stirred at RT overnight. The reaction mixture was diluted with ethyl acetate and the organic phase was washed in each case twice with saturated sodium carbonate solution and saturated NaCl solution. The organic phase was dried over magnesium sulphate and the solvent was evaporated under reduced pressure. The residue was purified using silica gel (mobile phase: dichloromethane/methanol 100:2). The solvents were evaporated under reduced pressure and the residue was dried under high vacuum. This gave 1.25 g (73% of theory) of the compound 2-(trimethylsilyl)ethyl [3-({(1R)-1-[1-benzyl-4-(2,5-difluorophenyl)-1H-pyrrol-2-yl]-2,2-dimethylpropyl}amino)propyl]carbamate.

LC-MS (Method 1): $R_t$=1.09 min; MS (ESIpos): m/z=556 (M+H)⁺.

908.1 mg (1.63 mmol) of 2-(trimethylsilyl)ethyl [3-({(1R)-1-[1-benzyl-4-(2,5-difluorophenyl)-1H-pyrrol-2-yl]-2,2-dimethylpropyl}amino)propyl]carbamate and 545.6 mg (5.39 mmol) of triethylamine were initially charged in 10.0 ml of dichloromethane, and the mixture was cooled to 0° C. At this temperature, 590.5 mg (5.23 mmol) of chloroacetyl chloride were added and the mixture was stirred at RT overnight. The reaction mixture was diluted with ethyl acetate and the organic phase was washed in each case three times with saturated sodium bicarbonate solution and saturated ammonium chloride solution. The organic phase was washed with saturated NaCl solution and dried over magnesium sulphate. The residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 673.8 mg (65% of theory) of the title compound.

LC-MS (Method 1): $R_t$=1.53 min; MS (ESIneg): m/z=676 $(M+HCOO^-)^-$.

Intermediate C71

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1)

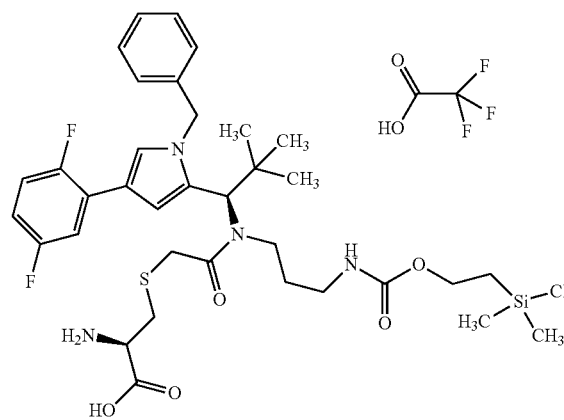

536.6 mg (4.43 mmol) of L-cysteine were suspended in 2.5 ml of water together with 531.5 mg (6.33 mmol) of sodium bicarbonate. 400.0 mg (0.63 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C70) dissolved in 25.0 ml of isopropanol and 1.16 g (7.59 mmol) of 1,8-diazabicyclo[5.4.0]undec-7-ene were added. The reaction mixture was stirred at 50° C. for 1.5 h. Ethyl acetate was added to the reaction mixture and the organic phase was washed repeatedly with saturated sodium bicarbonate solution and once with sat. NaCl solution. The organic phase was dried over magnesium sulphate, the solvent was evaporated under reduced pressure and the residue was dried under high vacuum. The residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 449.5 mg (86% of theory) of the title compound.

LC-MS (Method 1): $R_t$=1.20 min; MS (ESIpos): m/z=717 $(M+H)^+$.

Intermediate C74

2-(Trimethylsilyl)ethyl 3-amino-N-[(2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-D-alaninate trifluoroacetate (1:1)

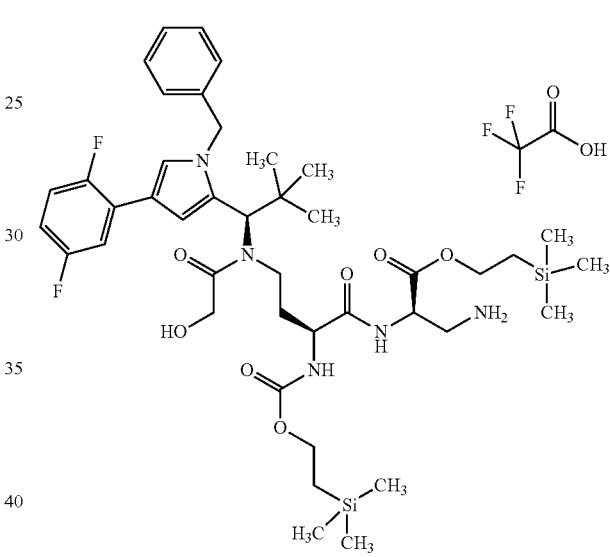

75 mg (0.114 mmol) of intermediate C58 were dissolved in 12.5 ml DMF and coupled with 78 mg (0.171 mmol) of intermediate L6 in the presence of 65 mg (0.11 mmol) HATU and 79 μL N,N-diisopropylethylamine. After purification via preparative HPLC, the residue was dissolved in 20 mL ethanol and hydrogenated for 1 h in presence of 10% Pd/C at room temperature at atmospheric pressure. After filtration of the catalyst, the solvent was evaporated under reduced pressure. The residue was purified over preparative HPLC and lyophilized to afford 63 mg (64% over 2 steps) of the title compound.

LC-MS (Method 1): $R_t$=1.16 min; MS (EIpos): m/z=844 $[M+H]^+$.

Intermediate C75

Methyl (2S)-4-[(acetoxyacetyl){(1R)-1-[1-benzyl-4-(2,5-difluorophenyl)-1H-pyrrol-2-yl]-2,2-dimethylpropyl}amino]-2-({[2-(trimethylsilyl)ethoxy]carbonyl}amino)butanoate

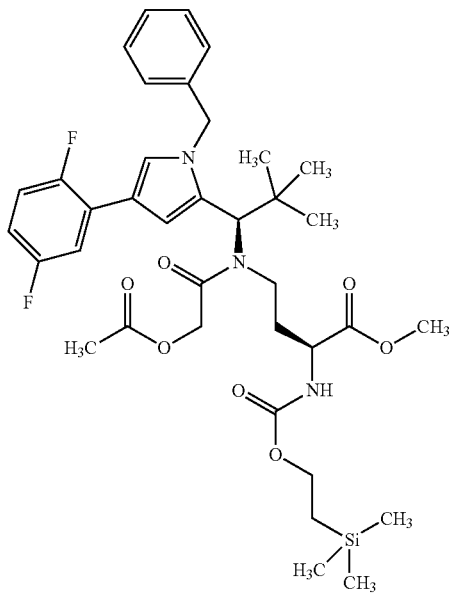 [SMILES: COC(=O)[C@H](CCN(C(=O)COC(C)=O)[C@@H](c1cc(-c2cc(F)ccc2F)cn1Cc1ccccc1)C(C)(C)C)NC(=O)OCC[Si](C)(C)C]

To a solution of 4.3 g (12.2 mmol) of intermediate C52 in 525 mL DCM was added 3.63 g (17.12 mmol) sodium triacetoxyborhydride and 8.4 mL acetic acid. After stirring the mixture at room temperature for 5 min, a solution of 3.23 g (11.85 mmol) methyl-(2S)-4-oxo-2-({[2-(trimethylsilyl)ethoxy]carbonyl}amino)butanoate (prepared from (3S)-3-amino-4-methoxy-4-oxobutanoic acid using classical method) in 175 mL DCM was added and the reaction mixture was stirred for 45 min at room temperature. The crude mixture was diluted with DCM and washed twice with 100 mL of a saturated sodium hydrogen carbonate solution and then with brine. The organic layer was dried over magnesium sulfate and evaporated. The residue was purified over preparative HPLC to afford 4.6 g (61%) methyl (2S)-4-({(1R)-1-[1-benzyl-4-(2,5-difluorophenyl)-1H-pyrrol-2-yl]-2,2-dimethylpropyl}amino)-2-({[2-(trimethylsilyl)ethoxy]carbonyl}amino)butanoate.

LC-MS (Method 12): $R_t$=1.97 min; MS (ESIpos): m/z=614.32 (M+H)$^+$.

To a solution of 200 mg (0.33 mmol) methyl (2S)-4-({(1R)-1-[1-benzyl-4-(2,5-difluorophenyl)-1H-pyrrol-2-yl]-2,2-dimethylpropyl}amino)-2-({[2-(trimethylsilyl)ethoxy]carbonyl}amino)butanoate 10 mL DCM were added 105 μL triethylamine and 77 μL (0.717 mmol) acetoxyacetylchloride. The reaction mixture was stirred overnight at room temperature diluted with ethyl acetate and washed twice with a saturated sodium hydrogen carbonate solution and then with brine. The organic layer was dried over magnesium sulfate and evaporated to afford 213 mg (75%) of the title compound.

LC-MS (Method 1): $R_t$=1.46 min; MS (ESIpos): m/z=714 (M+H)$^+$.

Intermediate C88 tert-Butyl (3R)-3-[({(1R)-1-[1-benzyl-4-(2,5-difluorophenyl)-1H-pyrrol-2-yl]-2,2-dimethylpropyl}amino)methyl]pyrrolidine-1-carboxylate trifluoroacetate (1:1) (Mixture of Stereoisomers)

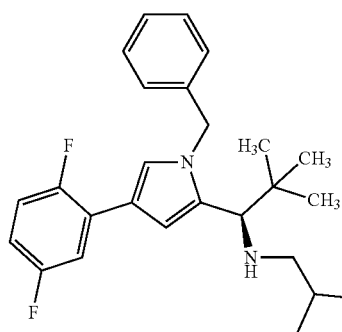
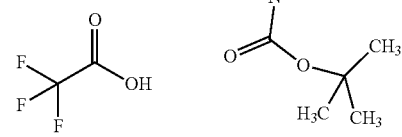

To a solution of 2.04 g (5.75 mmol) tert-butyl (3R)-3-[({(1R)-1-[1-benzyl-4-(2,5-difluorophenyl)-1H-pyrrol-2-yl]-2,2-dimethylpropyl}amino)methyl]pyrrolidine-1-carboxylate trifluoroacetate (1:1) (intermediate C52) in 51 ml dichlormethane were added 1.71 g (8.05 mmol) sodium triacetoxyborhydride and 0.40 g (6.61 mmol) acetic acid and the reaction mixture was stirred at room temperature for 5 min. A solution of 1.32 g (6.61 mmol) tert-butyl 3-formylpyrrolidine-1-carboxylate in 20 ml dichlormethane was then added and the mixture was stirred overnight at room temperature. Ethyl acetate was then added and the organic phase was washed with a saturated sodium carbonate solution and brine. The organic phase was dried over magnesium sulfate, the solvent was evaporated under reduced pressure and the residue was dried under high vacuum. The residue was used without further purification in the next step of the synthesis. This gave 1.86 g (50% of theory) of the title compound.

LC-MS (Method 1): $R_t$=0.99 min; MS (ESIpos): m/z=538 (M+H-CF$_3$CO$_2$H)$^+$.

Intermediate C89 tert-Butyl (3R)-3-{[{(1R)-1-[1-benzyl-4-(2,5-difluorophenyl)-1H-pyrrol-2-yl]-2,2-dimethylpropyl}(chloroacetyl)amino]methyl}pyrrolidine-1-carboxylate

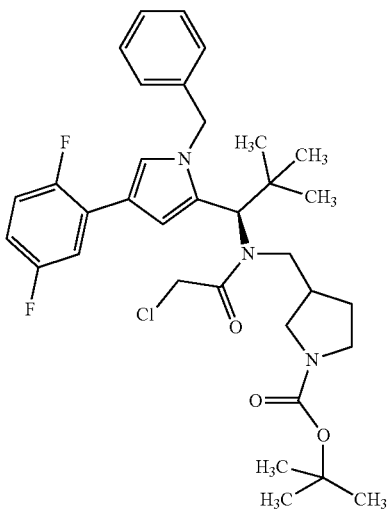 [SMILES: CC(C)(C)OC(=O)N1CCC(CN(C(=O)CCl)[C@@H](c2cc(-c3cc(F)ccc3F)cn2Cc2ccccc2)C(C)(C)C)C1]

To a solution of 2.89 g (4.19 mmol, 80% purity) of tert-butyl (3R)-3-[({(1R)-1-[1-benzyl-4-(2,5-difluorophenyl)-1H-pyrrol-2-yl]-2,2-dimethylpropyl}amino)methyl]pyrrolidine-1-carboxylate (intermediate C88) in 42 ml dichlormethane with 4 Å molecular sieves were added 1.36 g (13.42 mmol) triethylamine and 2.13 g (18.87 mmol) of chloracetyl chloride. The reaction mixture was stirred at room temperature for 5 h and the solvent was then evaporated. The residue was purified over preparative HPLC to afford 449 mg (17% d. Th.) of isomere 1 and 442 mg (17% d. Th) of isomere 2 of the title compound.

Isomere 1 LC-MS (Method 1): $R_t$=2.74 min; MS (ESIpos): m/z=614 (M+H)$^+$.

Isomere 2 LC-MS (Method 1): $R_t$=2.78 min; MS (ESIpos): m/z=614 (M+H)$^+$.

Intermediate C90

S-[2-({(1R)-1-[1-Benzyl-4-(2,5-difluorophenyl)-1H-pyrrol-2-yl]-2,2-dimethylpropyl}{[(3R)-1-(tert-butoxycarbonyl)pyrrolidin-3-yl]methyl}amino)-2-oxoethyl]-L-cysteine (isomere 1)

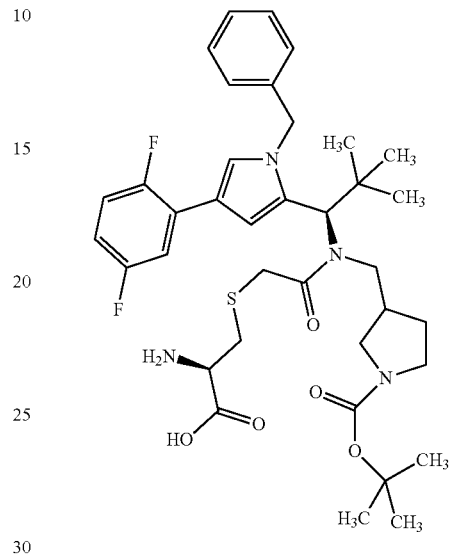

To a solution of 493 mg (4.07 mmol) L-cysteine in 2.3 mL water were added 489 mg (5.82 mmol) of sodium hydrogencarbonate followed by a solution of 357 mg (0.58 mmol) of tert-butyl (3R)-3-{[{(1R)-1-[1-benzyl-4-(2,5-difluorophenyl)-1H-pyrrol-2-yl]-2,2-dimethylpropyl}(chloroacetyl)amino]methyl}pyrrolidine-1-carboxylate (intermediate C89, isomere 1) in 23.0 mL iso-propanol and 1.06 g (6.98 mmol) of 1,8-diazabicyclo(5.4.0)undec-7-ene. The reaction mixture was stirred at 50° C. for 3 h. Ethyl acetate was then added and the organic phase was washed with a saturated sodium carbonate solution and brine. The organic phase was dried over magnesium sulfate, the solvent was evaporated under reduced pressure and the residue was dried under high vacuum. The residue was used without further purification in the next step of the synthesis. This gave 255 mg (62% of theory) of the title compound.

LC-MS (Method 1): $R_t$=1.09 min; MS (ESIpos): m/z=699 (M+H)$^+$.

Intermediate C95

3-{[2-({(1R)-1-[1-Benzyl-4-(2,5-difluorophenyl)-1H-pyrrol-2-yl]-2,2-dimethylpropyl}{[(3R)-1-(tert-butoxycarbonyl)pyrrolidin-3-yl]methyl}amino)-2-oxoethyl]sulfanyl}propanoic acid (isomer 1)

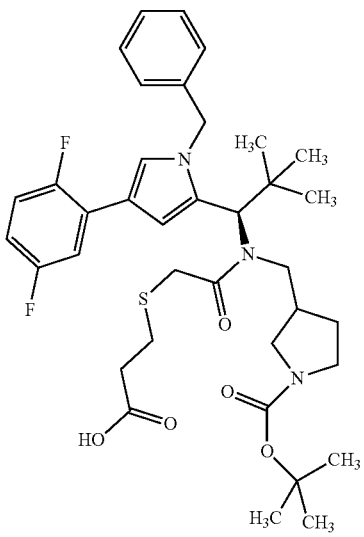 [SMILES: CC(C)(C)OC(=O)N1CCC(CN(C(=O)CSCCC(=O)O)[C@@H](c2cc(-c3cc(F)ccc3F)cn2Cc2ccccc2)C(C)(C)C)C1]

To a mixture of 384.0 mg (0.62 mmol) of tert-butyl (3R)-3-{[{(1R)-1-[1-benzyl-4-(2,5-difluorophenyl)-1H-pyrrol-2-yl]-2,2-dimethylpropyl}(chloroacetyl)amino]methyl}pyrrolidine-1-carboxylate (intermediate C89, isomere 1) and 73.0 mg (0.69 mmol) of 3-sulfanylpropanoic acid in 14 ml Methanol and one drop water was added 302.5 mg (2.19 mmol) of potassium carbonate. The reaction mixture was stirred at 50° C. for 2.5 h. Ethyl acetate was then added and the organic phase was then washed with water and brine, dried over magnesium sulfate and evaporated. under reduced pressure. The residue was dried under high vacuum and used without further purification in the next step of the synthesis. This gave 358.0 mg (84% of theory) of the title compound.

LC-MS (Method 1): $R_t$=1.33 min; MS (ESIpos): m/z=684 (M+H)$^+$.

Intermediate C101

N-(3-Aminopropyl)-N-{(1R)-1-[1-benzyl-4-(2,5-difluorophenyl)-1H-pyrrol-2-yl]-2,2-dimethylpropyl}-2-hydroxyacetamide

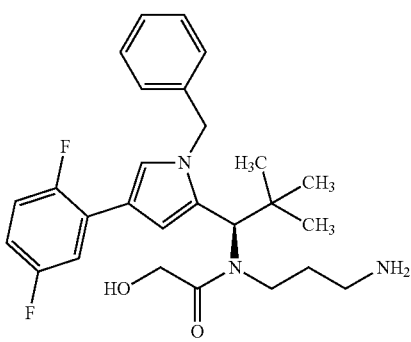 [SMILES: CC(C)(C)[C@H](c1cc(-c2cc(F)ccc2F)cn1Cc1ccccc1)N(CCCN)C(=O)CO]

150.0 mg (0.42 mmol) of (1R)-1-[1-benzyl-4-(2,5-difluorophenyl)-1H-pyrrol-2-yl]-2,2-dimethylpropan-1-amine (intermediate C52) were initially charged in 2.0 ml of dichloromethane, and 29.2 mg (0.49 mmol) of HOAc and 125.6 mg (0.59 mmol) of sodium triacetoxyborohydride were added and the mixture was stirred at RT for 5 min. 98.9 mg (0.49 mmol) of 3-(1,3-dioxo-1,3-dihydro-2H-isoindol-2-yl) propanal were added. The reaction mixture was stirred at RT overnight. The reaction mixture was then diluted with ethyl acetate and the organic phase was washed twice with saturated sodium carbonate solution and once with saturated NaCl solution. After drying over magnesium sulphate, the solvent was evaporated under reduced pressure and the residue was purified using silica gel (mobile phase: dichloromethane/methanol 100:1). The solvents were evaporated under reduced pressure and the residue was dried under high vacuum. This gave 188.6 mg (74%) of the compound 2-[3-({(1R)-1-[1-benzyl-4-(2,5-difluorophenyl)-1H-pyrrol-2-yl]-2,2-dimethylpropyl}amino)propyl]-1H-isoindole-1,3(2H)-dione.

LC-MS (Method 1): $R_t$=1.00 min; MS (ESIpos): m/z=541 [M+H]$^+$.

171.2 mg (0.32 mmol) of 2-[3-({(1R)-1-[1-benzyl-4-(2,5-difluorophenyl)-1H-pyrrol-2-yl]-2,2-dimethylpropyl}amino)propyl]-1H-isoindole-1,3(2H)-dione were initially charged in 5.0 ml of dichloromethane, and 73.6 mg (0.73 mmol) of triethylamine were added. At 0° C., 94.9 mg (0.70 mmol) of acetoxyacetyl chloride were added, and the reaction mixture was stirred at RT overnight. The reaction mixture was diluted with ethyl acetate and the organic phase was washed twice with saturated sodium bicarbonate solution and once with sat. NaCl solution. After drying over magnesium sulphate, the solvent was evaporated under reduced pressure and the residue was purified using Biotage Isolera (silica gel, column 10 g SNAP, flow rate 12 ml/min, ethyl acetate/cyclohexane 1:3). The solvents were evaporated under reduced pressure and the residue was dried under high vacuum. This gave 159.0 mg (77%) of the compound 2-({(1R)-1-[1-benzyl-4-(2,5-difluorophenyl)-1H-pyrrol-2-yl]-2,2-dimethylpropyl}[3-(1,3-dioxo-1,3-dihydro-2H-isoindol-2-yl)propyl]amino)-2-oxoethyl acetate.

LC-MS (Method 1): $R_t$=1.35 min; MS (ESIpos): m/z=642 [M+H]$^+$.

147.2 mg (0.23 mmol) of 2-({(1R)-1-[1-benzyl-4-(2,5-difluorophenyl)-1H-pyrrol-2-yl]-2,2-dimethylpropyl}[3-(1,3-dioxo-1,3-dihydro-2H-isoindol-2-yl)propyl]amino)-2-oxoethyl acetate were initially charged in 4.0 ml of ethanol, and 356.2 mg (4.59 mmol) of methanamine (40% in water) were added. The reaction mixture was stirred at 50° C. overnight. The solvent was evaporated under reduced pressure and the residue was co-distilled with toluene three times. The residue was purified using silica gel (mobile phase: dichloromethane/methanol 10:1). The solvents were evaporated under reduced pressure and the residue was dried under high vacuum. This gave 67.4 mg (63%) of the title compound.

LC-MS (Method 1): $R_t$=0.91 min; MS (ESIpos): m/z=470 [M+H]$^+$.

Intermediate C102 tert-butyl {(2S)-4-[{(1R)-1-[1-benzyl-4-(2,5-difluorophenyl)-1H-imidazol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}carbamate

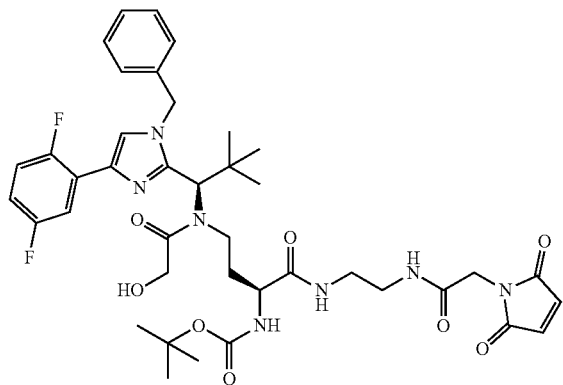 [SMILES: CC(C)(C)OC(=O)N[C@@H](CCN(C(=O)CO)[C@@H](c1nc(-c2cc(F)ccc2F)cn1Cc1ccccc1)C(C)(C)C)C(=O)NCCNC(=O)CN1C(=O)C=CC1=O]

20.0 mg (32.54 µmol) (2S)-4-[{(1R)-1-[1-benzyl-4-(2,5-difluorophenyl)-1H-imidazol-2-yl]-2,2-dimethylpropyl}(glycoloyl)amino]-2-[(tert-butoxycarbonyl)amino]butanoic acid (intermediate C5), 10.1 mg (32.54 µmol) N-(2-aminoethyl)-2-(2,5-dioxo-2,5-dihydro-1H-pyrrol-1-yl)acetamide trifluoroacetate (1:1) (intermediate L1) and 18.6 mg (48.81 µmol) HATU were dissolved in 2.5 ml DMF. 16.8 mg (23 µl, 130.15 µmol) N,N-diisopropylethylamine were added and the mixture was stirred at room temperature for 1 h. The mixture was purified directly via preparative HPLC (eluent: acetonitrile/water+0.1% TFA, gradient 35:65→95:5) followed by freeze-drying to give 15 mg (58%) of the target compound.

LC-MS (Method 1): $R_t$=1.23 min; MS (EIpos): m/z=794 [M+H]$^+$.

Intermediate C103 tert-butyl [(2S)-4-[{(1R)-1-[1-benzyl-4-(2,5-difluorophenyl)-1H-imidazol-2-yl]-2,2-dimethylpropyl}(glycoloyl)amino]-1-({2-[({3-[(2,2-dimethyl-4,12-dioxo-3,15,18,21,24-pentaoxa-5,11-diazahexacosan-26-yl)sulfanyl]-2,5-dioxopyrrolidin-1-yl}acetyl)amino]ethyl}amino)-1-oxobutan-2-yl]carbamate 15 mg (18.90 µmol) tert-butyl {(2S)-4-[{(1R)-1-[1-benzyl-4-(2,5-difluorophenyl)-1H-imidazol-2-yl]-2,2-dimethylpropyl}(glycoloyl)amino]-1-[(2-{[(2,5-dioxo-2,5-dihydro-1H-pyrrol-1-yl)acetyl]amino}-ethyl)amino]-1-oxobutan-2-yl}carbamate (intermediate C102) were dissolved in 500 µl acetonitrile. 12.3 mg (26.45 µmol) tert-butyl (7-oxo-21-sulfanyl-10,13,16,19-tetraoxa-6-azahenicos-1-yl)carbamate (intermediate L2) dissolved in 275 µl phosphate-buffered saline (pH=7) were added to the mixture. The pH of the solution was adjusted to pH=8 by adding some drops of 1N sodium hydroxide solution. The mixture was stirred for 30 min. at room temperature. The mixture was purified via preparative HPLC (eluent: acetonitrile/water+0.1% TFA, gradient 35:65-95:5) followed by freeze-drying to give 20 mg (84%) of the target compound.

LC-MS (Method 1): $R_t$=1.26 min; MS (EIpos): m/z=1261 [M+H]$^+$.

Intermediate C104

(2S)-4-[{(1R)-1-[1-benzyl-4-(2,5-difluorophenyl)-1H-pyrrol-2-yl]-2,2-dimethylpropyl}(glycoloyl)amino]-2-{[(benzyloxy)carbonyl]amino}butanoic acid

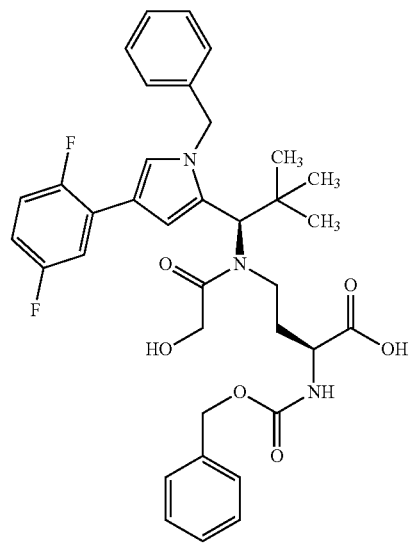

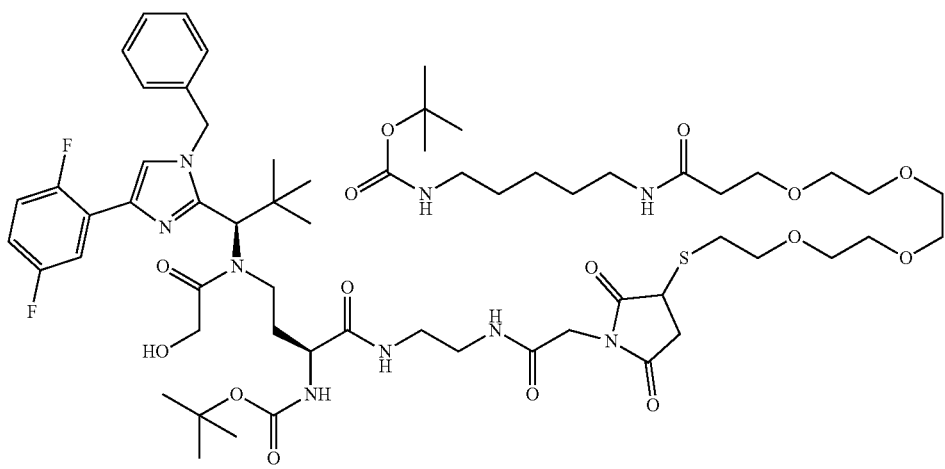 [SMILES: CC(C)(C)OC(=O)NCCCCCNC(=O)CCOCCOCCOCCOCCSC1CC(=O)N(CC(=O)NCCNC(=O)[C@H](CCN(C(=O)CO)[C@@H](c2nc(-c3cc(F)ccc3F)cn2Cc2ccccc2)C(C)(C)C)NC(=O)OC(C)(C)C)C1=O]

Intermediate C52 was reductively alkylated with benzyl-(2S)-2-{[(benzyloxy)carbonyl]amino}-4-oxobutanoate in analogy to intermediate C2. Subsequently the secondary amino group was acylated with 2-chloro-2-oxoethylacetate. In the final step, the two ester groups were cleaved using 2M lithium hydroxide solution in methanol.

LC-MS (Method 1): $R_t$=1.31 min; MS (ESIpos): m/z=646 (M−H)⁻.

Intermediate C105

Benzyl N-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alaninate trifluoroacetate (1:1)

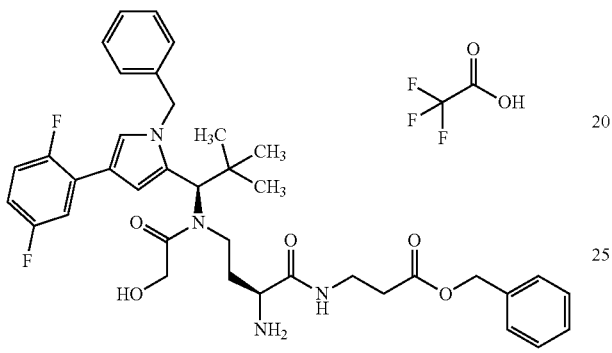

200 mg of intermediate C58 were coupled with benzyl beta-alaninate in DMF in the presence of HATU and N,N-diisopropylethylamine and subsequently the Teoc-protecting group was cleaved using 4 equivalents of zinc chloride in 2,2,2 trifluorethanol under heating for 40 min to 50° C. After addition of 4 equivalents of EDTA the product was purified by HPLC.

LC-MS (Method 12): $R_t$=1.7 min; MS (ESIpos): m/z=675 (M+H)⁺.

Intermediate C106

2-(Trimethylsilyl)ethyl N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-N2-{[2-(trimethylsilyl)ethoxy]carbonyl}-L-glutaminate

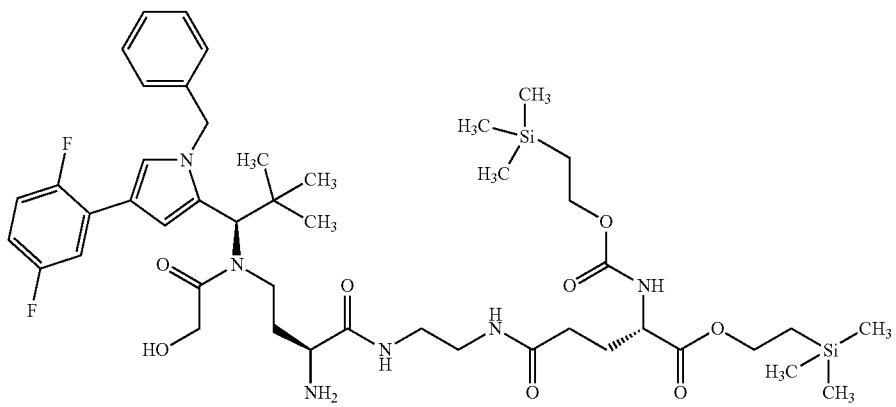 [SMILES: CC(C)(C)[C@H](c1cc(-c2cc(F)ccc2F)cn1Cc1ccccc1)N(CC[C@H](N)C(=O)NCCNC(=O)CC[C@H](NC(=O)OCC[Si](C)(C)C)C(=O)OCC[Si](C)(C)C)C(=O)CO]

151 mg (0.23 mmol) of intermediate C104 were coupled with 128 mg (0.234 mmol) of intermediate L9 in DMF in the presence of HATU and N,N-diisopropylethylamine. Subsequently the Z-protecting group was cleaved by hydrogenation over 10% palladium/activated charcoal under normal pressure.

Yield: 30% of th. over 2 steps

LC-MS (Method 1): $R_t$=1.14 min; MS (ESIpos): m/z=929 (M+H)$^+$.

Intermediate C108

2-(Trimethylsilyl)ethyl $N^6$—(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-$N^2$-{[2-(trimethylsilyl) ethoxy]carbonyl}-L-lysinate

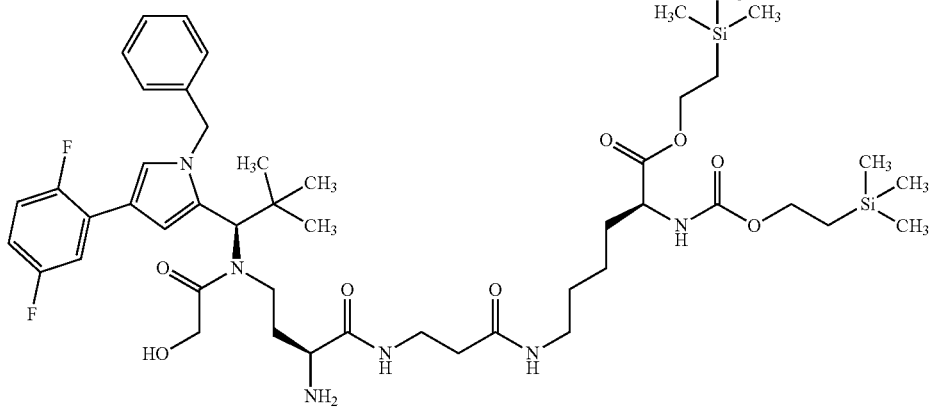

103 mg (0.16 mmol) of intermediate C104 were coupled with 110 mg (0.175 mmol) of 2-(Trimethylsilyl)ethyl $N^6$-beta-alanyl-$N^2$-{[2-(trimethylsilyl)ethoxy]carbonyl}-L-lysinat (intermediate L11) in DMF in the presence of EDC, HOBT and N,N-diisopropylethylamine. Subsequently the Z-protecting group was cleaved by hydrogenation in DCM-methanol 1:1 over 10% palladium/activated charcoal under normal pressure. The title compound was obtained in a yield of 113 mg (75% over 2 steps).

LC-MS (Method 1): $R_t$=1.17 min; MS (ESIpos): m/z=957 (M+H)$^+$.

Intermediate C109 dibenzyl N-({(2S)-2-amino-4-[{(1R)-1-[1-benzyl-4-(2,5-difluorophenyl)-1H-pyrrol-2-yl]-2,2-dimethyl propyl}(glycoloyl)amino]butanoyl}-beta-alanyl-L-glutamate

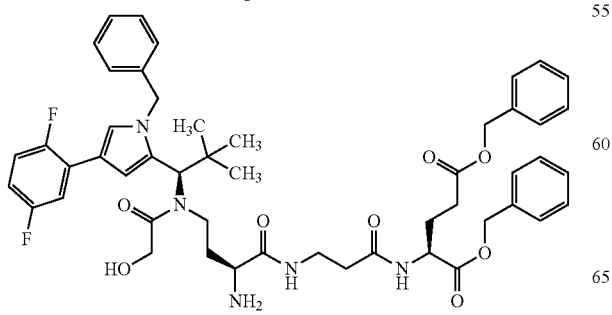

The title compound was obtained by coupling of intermediate C61 with dibenzyl L-glutamate in DMF in the presence of HATU and N,N-diisopropylethylamine and subsequent removal of the Teoc protecting group using 10 equivalents of zinc chloride in 2,2,2 trifluorethanol under heating for 1 h to 50° C. in trifluoroethanol.

LC-MS (Method 1): $R_t$=1.09 min; MS (ESIpos): m/z=894 (M+H)$^+$.

Intermediate C110

N2-acetyl-N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-N6-(tert-butoxycarbonyl)-L-lysinamide

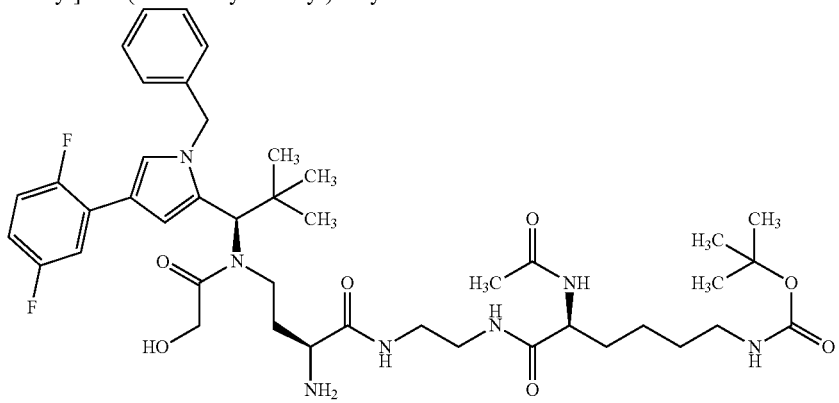

The title compound was obtained by coupling of intermediate C104 with intermediate L13 in DMF in the presence of HATU and N,N-diisopropylethylamine and subsequent removal of the Z-protecting by hydrogenation in DCM-methanol 1:1 over 10% palladium/activated charcoal under normal pressure.

LC-MS (Method 1): $R_t$=0.96 min; MS (ESIpos): m/z=826 (M+H)$^+$.

Intermediate C111

2-(Trimethylsilyl)ethyl (3R,4R)-3-[({(1R)-1-[1-benzyl-4-(2,5-difluorophenyl)-1H-pyrrol-2-yl]-2,2-dimethylpropyl}amino)methyl]-4-fluoropyrrolidine-1-carboxylate trifluoroacetate (1:1)

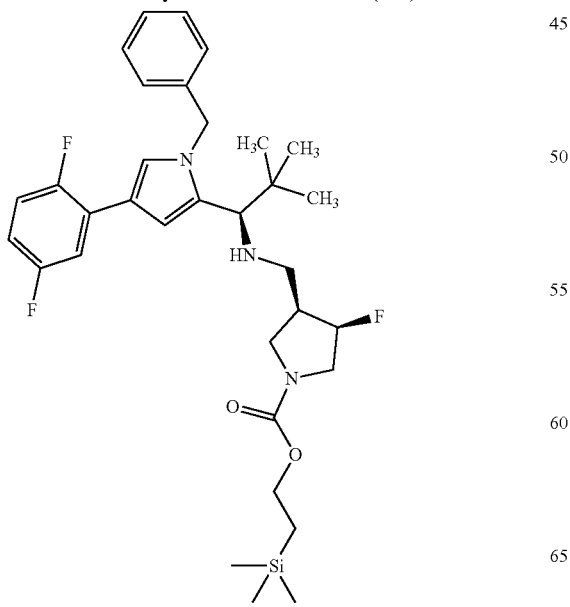

To a solution of (1R)-1-[1-benzyl-4-(2,5-difluorophenyl)-1H-pyrrol-2-yl]-2,2-dimethylpropan-1-amine (108 mg, 304 µmol) (intermediate C52) in 56.0 ml DCM an mol. sieves 4 Å was added sodium triacetoxyborhydrid (90.2 mg, 426 µmol). The mixture was stirred at RT for 15 min and 2-(trimethylsilyl)ethyl (3R,4S)-3-fluoro-4-formylpyrrolidine-1-carboxylate (97.3 mg, 98% purity, 365 µmol) (Ref: WO 2014/151030A1) was then added. The reaction mixture was stirred at RT for 3.5 h and then diluted with DCM. The organic layer was washed with sat. sodium hydrogencarbonate and water. The organic layer was then dried over sodium sulfate and evaporated. The residue was purified by preparative RP-HPLC to afford 1.39 g (24% of theory) of the title compound.

LC-MS (Method 1): $R_t$=1.15 min; MS (ESIpos): m/z=600 $(M+H)^+$.

Intermediate C112

2-(Trimethylsilyl)ethyl (3R,4R)-3-{[{(1R)-1-[1-benzyl-4-(2,5-difluorophenyl)-1H-pyrrol-2-yl]-2,2-dimethylpropyl}(chloroacetyl)amino]methyl}-4-fluoropyrrolidine-1-carboxylate

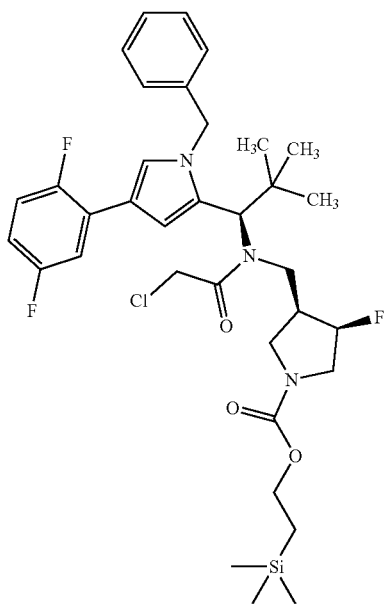 [SMILES: CC(C)(C)[C@H](c1cc(-c2cc(F)ccc2F)cn1Cc1ccccc1)N(C[C@@H]1CN(C(=O)OCC[Si](C)(C)C)C[C@@H]1F)C(=O)CCl]

To a solution of 692.8 mg (0.88 mmol) 2-(trimethylsilyl)ethyl (3R,4R)-3-[({(1R)-1-[1-benzyl-4-(2,5-difluorophenyl)-1H-pyrrol-2-yl]-2,2-dimethylpropyl}amino)methyl]-4-fluoropyrrolidine-1-carboxylate trifluoroacetate (1:1) (Intermediate C111) in 8.7 ml DCM with mol. sieves 4 Å were added 295.0 mg (2.91 mmol) triethylamine and 418.9 mg (3.71 mmol) chloracetylchloride. The reaction mixture was stirred at RT for 2.5 h and then diluted with DCM. The organic layer was washed with sat. sodium hydrogencarbonate and sat. ammonium chloride. The organic layer was then dried over sodium sulfate and evaporated. The residue was diluted in 8.7 ml DCM and mol. sieves 4 Å, 295.0 mg (2.91 mmol) triethylamine and 418.9 mg (3.71 mmol) chloracetylchloride were added. The reaction mixture was stirred at RT for 3 h and was then diluted with DCM. The organic layer was washed with sat. sodium hydrogencarbonate and sat. ammonium chloride. The organic layer was then dried over sodium sulfate and evaporated to afford 691 mg (74% of theory) of the title compound which was used in the next step without further purification.

LC-MS (Method 1): $R_t$=1.78 min; MS (ESIpos): m/z=676 $(M+H)^+$.

Intermediate C113

S-[2-({(1R)-1-[1-Benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]-L-cysteine

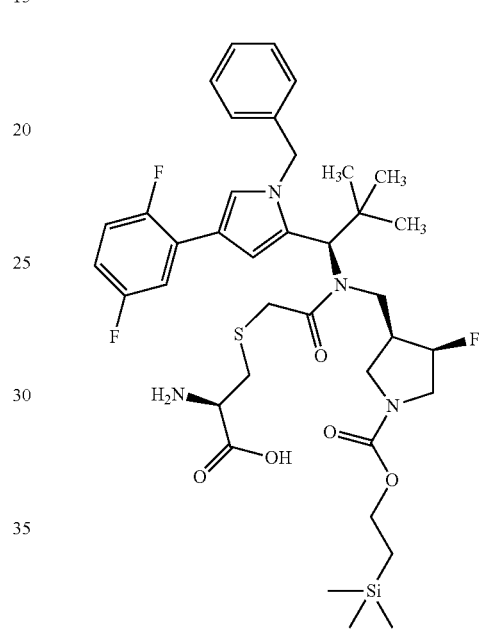

To a suspension of 203.6 mg (1.68 mmol) L-cysteine and 201.7 mg (2.40 mmol) sodium hydrogencarbonate in 0.95 mL of water was added a solution of 170.0 mg (0.24 mmol) 2-(trimethylsilyl)ethyl (3R,4R)-3-{[{(1R)-1-[1-benzyl-4-(2,5-difluorophenyl)-1H-pyrrol-2-yl]-2,2-dimethylpropyl}(chloroacetyl)amino]methyl}-4-fluoropyrrolidine-1-carboxylate (intermediate C112) in 9.5 mL iso-propanol and 438.5 mg (2.40 mmol) 1,8-diazabicyclo(5.4.0)undec-7-ene. The reaction mixture was stirred at 50° C. for 3 h. The reaction mixture was then diluted with ethyl acetate and the organic layer was washed with sat. sodium hydrogencarbonate and brine. The organic layer was then dried over sodium sulfate and the solvent was evaporated to afford 152 mg (83% of theory) of the title compound which was used in the next step without further purification.

LC-MS (Method 1): $R_t$=1.26 min; MS (ESIpos): m/z=762 $(M+H)^+$.

Intermediate L1

Trifluoroacetic acid/N-(2-aminoethyl)-2-(2,5-dioxo-2,5-dihydro-1H-pyrrol-1-yl)acetamide (1:1)

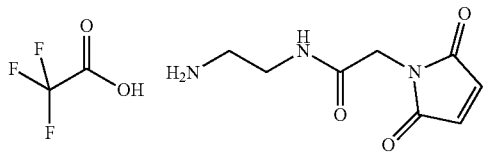 [SMILES: O=C(O)C(F)(F)F ; NCCNC(=O)CN1C(=O)C=CC1=O]

The title compound was prepared by classical methods of peptide chemistry starting from commercially available (2,5-dioxo-2,5-dihydro-1H-pyrrol-1-yl)acetic acid and tert-butyl (2-aminoethyl)carbamate.

HPLC (Method 11): $R_t$=0.19 min;
LC-MS (Method 1): $R_t$=0.17 min; MS (ESIpos): m/z=198 (M+H)⁺.

Intermediate L2

Tert-butyl (7-oxo-21-sulfanyl-10,13,16,19-tetraoxa-6-azahenicos-1-yl)carbamate

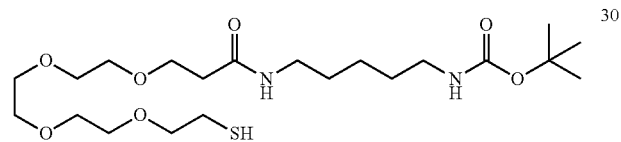

356 mg (1.757 mmol) tert-butyl (5-aminopentyl)carbamate, 496 mg (1.757 mmol) 1-sulfanyl-3,6,9,12-tetraoxapentadecan-15-oic acid and 801 mg (2.108 mmol) HATU were dissolved in 5.95 ml DMF. The reaction mixture was cooled with an ice bath and 681 mg (920 µl, 5.272 mmol) N,N-diisopropylethylamine was added. The mixture was stirred at room temperature for 4 h and stored overnight in a refrigerator at 4° C. The mixture was purified directly via preparative HPLC (eluent: acetonitrile/water+0.1% TFA, gradient 20:80→80:20) followed by freeze-drying to give 255 mg (29%) of the target compound.

LC-MS (Method 1): $R_t$=0.87 min; MS (EIpos): m/z=467 [M+H]⁺.

Intermediate L3

N²-acetyl-N⁶-[(benzyloxy)carbonyl]-L-lysine

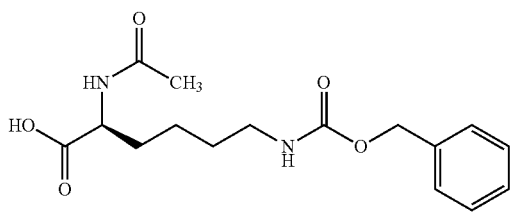 [SMILES: CC(=O)N[C@@H](CCCCNC(=O)OCc1ccccc1)C(=O)O]

This intermediate was obtained by recating benzyl carbonochloridate with N²-acetyl-L-lysine.

LC-MS (Method 1): $R_t$=0.71 min; MS (ESIpos): m/z=323 (M+H)⁺.

Intermediate L4

N²-acetyl-N⁶-{[2-(trimethylsilyl)ethoxy]carbonyl}-L-lysine

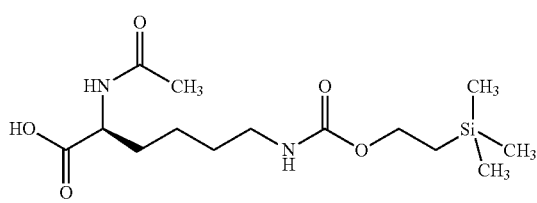 [SMILES: CC(=O)N[C@@H](CCCCNC(=O)OCC[Si](C)(C)C)C(=O)O]

This intermediate was obtained by recating 1-({[2-(trimethylsilyl)ethoxy]carbonyl}oxy) pyrrolidine-2,5-dione with N2-acetyl-L-lysine.

LC-MS (Method 1): $R_t$=0.87 min; MS (ESIpos): m/z=333 (M+H)⁺.

Intermediate L5

9H-Fluoren-9-ylmethyl {(5S)-5-acetamido-6-[(2-aminoethyl)amino]-6-oxohexyl}carbamate trifluoroacetate (1:1)

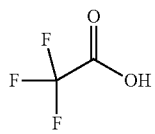

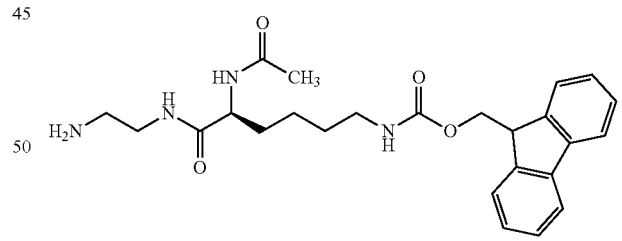

This intermediate was obtained by reacting commercially available N²-acetyl-N⁶-[(9H-fluoren-9-ylmethoxy)carbonyl]-L-lysine with tert-butyl (2-aminoethyl)carbamate and subsequent removal of the Boc-group with trifluoroacetic acid.

LC-MS (Method 13): $R_t$=0.87 min; MS (ESIpos): m/z=453 (M+H)⁺.

Intermediate L6

2-(Trimethylsilyl)ethyl 3-{[(benzyloxy)carbonyl]amino}-D-alaninate trifluoroacetate (1:1)

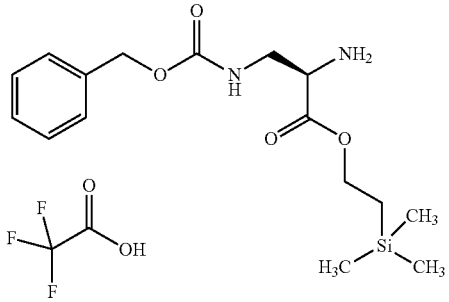 [SMILES: O=C(O)C(F)(F)F ; C[Si](C)(C)CCOC(=O)[C@H](N)CNC(=O)OCc1ccccc1]

The title compound was prepared starting from 3-{[(benzyloxy)carbonyl]amino}-N-(tert-butoxycarbonyl)-D-alanine using classical peptide chemistry methods. Esterification with 2-(trimethylsilyl)ethanol using EDC/DMAP followed by deprotection of the Boc group by TFA provided 405 mg (58% over 2 steps) of the title compound.

LC-MS (Method 1): $R_t$=0.75 min; MS (ESIpos): m/z=339 (M+H)$^+$.

Intermediate L7

$N^2$-acetyl-$N^6$-[(benzyloxy)carbonyl]-L-lysyl-L-alanyl-L-alanyl-L-asparagine

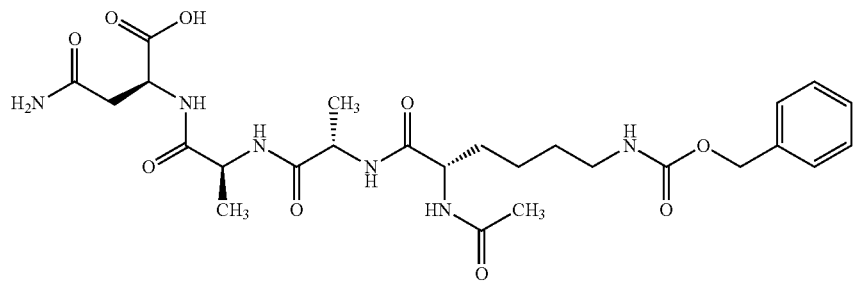 [SMILES: CC(=O)N[C@@H](CCCCNC(=O)OCc1ccccc1)C(=O)N[C@@H](C)C(=O)N[C@@H](C)C(=O)N[C@@H](CC(N)=O)C(=O)O]

The synthesis of the title compound started with coupling of N-[(benzyloxy)carbonyl]-L-alanyl-L-alanine and tert-butyl L-asparaginate in DMF in the presence of HATU and N,N-diisopropylethylamine and subsequent removal of the Z-protecting group by hydrogenation in methanol with 10% palladium on activated charcoal. The intermediate obtained was then coupled with intermediate L3 in DMF in the presence of HATU and N,N-diisopropylethylamine and in the final step the tert-butylester group was cleaved with trifluoroacetic acid in DCM.

LC-MS (Method 1): $R_t$=0.59 min; MS (ESIpos): m/z=579 (M+H)$^+$.

Intermediate L8

$N^2$-acetyl-$N^6$-{[2-(trimethylsilyl)ethoxy]carbonyl}-L-lysyl-L-alanyl-L-alanyl-L-asparagine

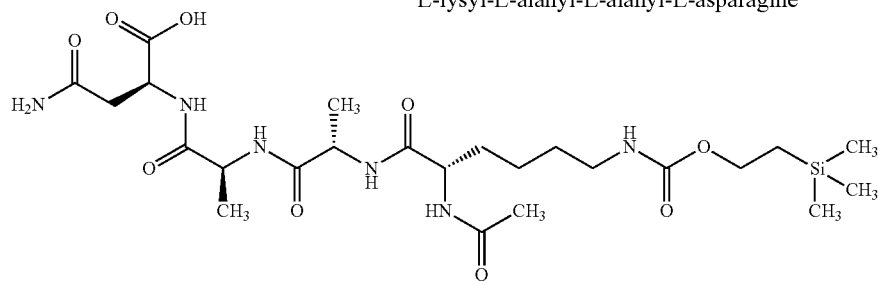

The synthesis of the title compound started with coupling of N-[(benzyloxy)carbonyl]-L-alanyl-L-alanine and tert-butyl L-asparaginate in DMF in the presence of HATU and N,N-diisopropylethylamine and subsequent removal of the Z-protecting group by hydrogenation in methanol over 10% palladium/activated charcoal under normal pressure. The intermediate obtained was then coupled with intermediate L4 in DMF in the presence of HATU and N,N-diisopropylethylamine and subsequently both protecting groups were removed under stirring for 1 h in 7.5% trifluoroacetic acid in DCM. In the final step the amino group was again protected using 1-({[2-(trimethylsilyl)ethoxy]carbonyl}oxy)pyrrolidine-2,5-dione in the presence of N,N-diisopropylethylamine in DMF.

LC-MS (Method 1): $R_t$=0.71 min; MS (ESIpos): m/z=589 (M+H)$^+$.

Intermediate L9

2,2-Dimethylpropanoic acid-2-(trimethylsilyl)ethyl-N-(2-aminoethyl)-N$^2$-{[2-(trimethylsilyl) ethoxy]carbonyl}-L-glutaminate (1:1)

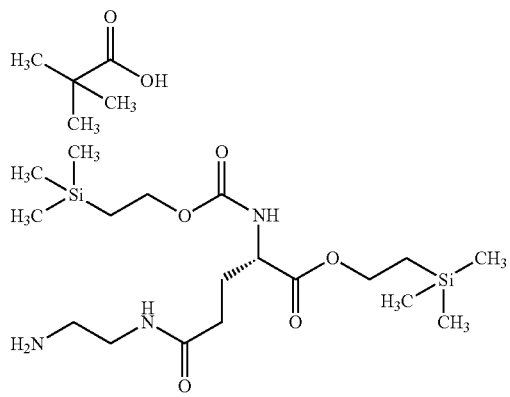

First (4S)-5-tert-butoxy-4-[(tert-butoxycarbonyl)amino]-5-oxopentanoic acid was coupled with benzyl-(2-aminoethyl)carbamate in the presence of HATU and N,N-diisopropylethylamine. Subsequently both, the Boc group and the tert-butylester group were cleaved using trifluoro acetic acid. Then first the amino group was protected again by reaction with trimethylsilyl)ethoxy]carbonyl}oxy)pyrrolidine-2,5-dione in DMF/water in the presence of N,N-diisopropylethylamine and then the carboxy group was esterified with 2-(trimethylsilyl)ethanol in DCM using EDC/DMAP. In the final step the Z-protecting group was removed by hydrogenation over 10% palladium/activated charcoal under normal pressure and the title compound was obtained and purified by HPLC.

LC-MS (Method 1): $R_t$=0.82 min; MS (ESIpos): m/z=434 (M+H)$^+$.

Intermediate L10 tert-butyl N-[(benzyloxy)carbonyl]-L-alanyl-L-alanyl-L-asparaginate

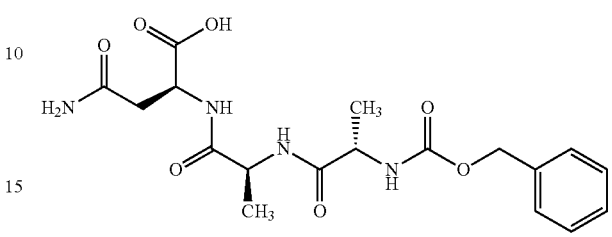

The title compound was obtained by coupling of N-[(benzyloxy)carbonyl]-L-alanyl-L-alanine with tert-butyl L-asparaginate in DMF in the presence of HATU and N,N-diisopropylethylamine and subsequent removal of the tert-butylester group by trifluoroacetic acid in DCM.

LC-MS (Method 1): $R_t$=0.5 min; MS (ESIpos): m/z=409 (M+H)$^+$.

Intermediate L11

2-(trimethylsilyl)ethyl N$^6$-beta-alanyl-N$^2$-{[2-(trimethylsilyl)ethoxy]carbonyl}-L-lysinate

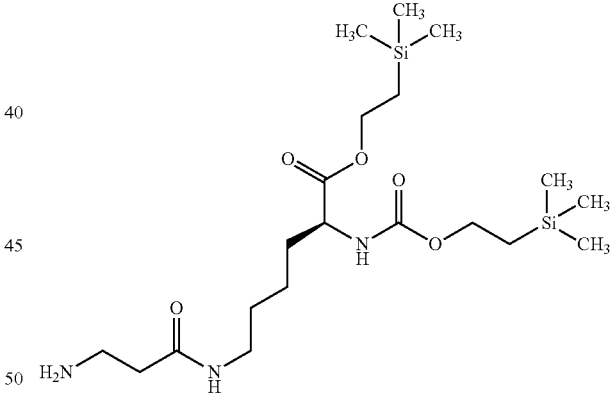

The title compound was synthesized with classical methods of peptide chemistry starting with the coupling of N-(tert-butoxycarbonyl)-beta-alanine with 2-(trimethylsilyl) ethyl N-[(benzyloxy)carbonyl]-L-lysinate with HATU and N,N-diisopropylethylamine, removal of the Z-protecting group by hydrogenation over 10% palladium/activated charcoal under normal pressure, introduction of the trimethylsilyl-ethyloxy carbonyl(Teoc)-protecting group with 1-({[2-(trimethylsilyl)ethoxy]carbonyl}oxy)pyrrolidine-2,5-dione and finally mild removal of the Boc-protecting group by stirring for 45 minutes in a 7.5% solution of trifluoro acetic acid in dichloromethane.

LC-MS (Method 1): $R_t$=0.83 min; MS (ESIpos): m/z=462 (M+H)$^+$.

Intermediate L12

Benzyl (2S)-5-({(5S)-5-acetamido-6-[(2-aminoethyl)amino]-6-oxohexyl}amino)-2-{[(benzyloxy)carbonyl]amino}-5-oxopentanoate trifluoroacetate (1:1)

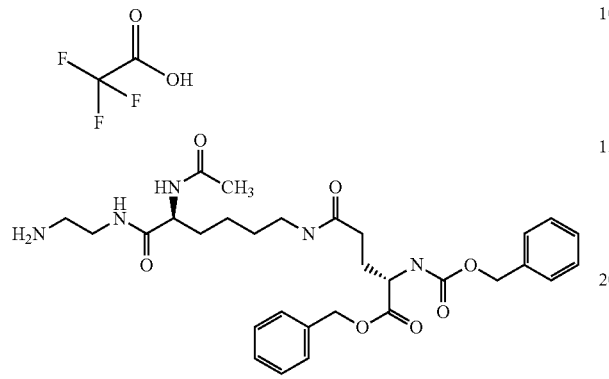

The title compound was synthesized with classical methods of peptide chemistry starting with coupling of tert-butyl (2-aminoethyl)carbamate with intermediate L3 with HATU and N,N-diisopropylethylamine, removal of the Z-protecting group by hydrogenation in DCM/methanol 1:1 over 10% palladium/activated charcoal under normal pressure, coupling of the obtained intermediate with (4S)-5-(benzyloxy)-4-{[(benzyloxy)carbonyl]amino}-5-oxopentanoic acid with HATU and N,N-diisopropylethylamine and finally removal of the Boc-protecting group by stirring for 1 h in a 25% solution of trifluoro acetic acid in dichloromethane.

LC-MS (Method 1): $R_t$=0.66 min; MS (ESIpos): m/z=584 $(M+H)^+$.

Intermediate L13

Benzyl (2S)-5-({(5S)-5-acetamido-6-[(2-aminoethyl)amino]-6-oxohexyl}amino)-2-{[(benzyloxy)carbonyl]amino}-5-oxopentanoate trifluoroacetate (1:1)

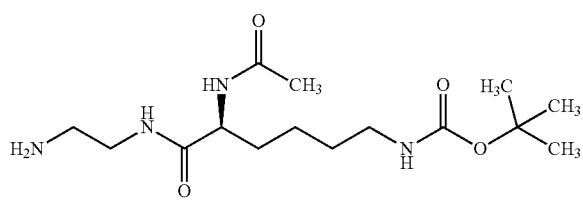 [SMILES: CC(=O)N[C@@H](CCCCNC(=O)OC(C)(C)C)C(=O)NCCN]

The title compound was synthesized with classical methods of peptide chemistry starting with coupling of N2-acetyl-N6-(tert-butoxycarbonyl)-L-lysine with benzyl (2-aminoethyl)carbamate hydrochloride (1:1) with HATU and N,N-diisopropylethylamine and subsequent removal of the Z-protecting group by hydrogenation in DCM/methanol 1:1 over 10% palladium/activated charcoal under normal pressure.

LC-MS (Method 1): $R_t$=0.43 min; MS (ESIpos): m/z=331 $(M+H)^+$.

Intermediate L14

N-(pyridin-4-ylacetyl)-L-alanyl-L-alanyl-L-asparagine trifluoroacetate (1:1)

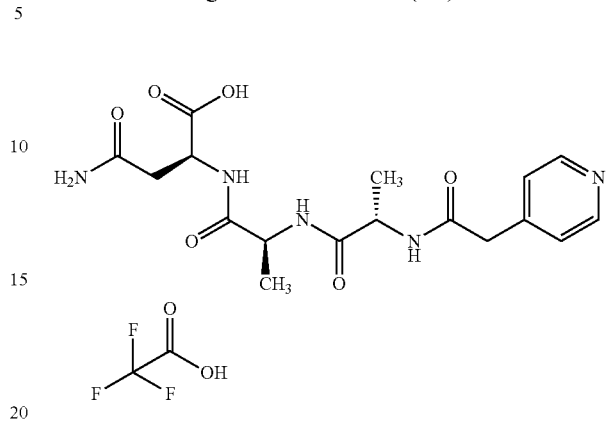

The title compound was synthesized applying classical methods of peptide chemistry starting with coupling of pyridin-4-ylacetic acid hydrochloride (1:1) with commercially available tert-butyl L-alanyl-L-alaninate hydrochloride (1:1) with HATU and N,N-diisopropylethylamine and subsequent removal of the tert-butylester with trifluoroacetic acid in DCM. The obtained intermediate was coupled with tert-butyl L-asparaginate in the presence of HATU and N,N-diisopropylethylamine and finally the tert-butylester with cleaved with trifluoroacetic acid in DCM.

LC-MS (Method 1): $R_t$=0.15 min; MS (ESIpos): m/z=394 $(M+H)^+$.

Intermediate L15

2-(Trimethylsilyl)ethyl (3-oxopropyl)carbamate

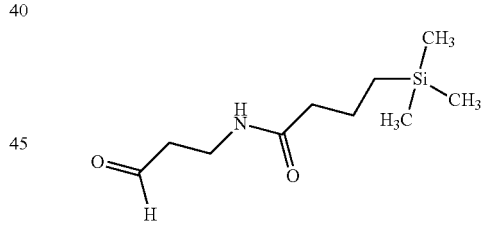

434.4 mg (5.78 mmol) of 3-amino-1-propanol and 1.50 g (5.78 mmol) of 2-(trimethylsilyl)ethyl 2,5-dioxopyrrolidine-1-carboxylate were dissolved in 10.0 ml of dichloromethane, 585.3 mg (5.78 mmol) of triethylamine were added and the mixture was stirred at RT overnight. The reaction mixture was diluted with dichloromethane and the organic phase was washed with water and saturated sodium bicarbonate solution and then dried over magnesium sulphate. The solvent was evaporated under reduced pressure. The residue 2-(trimethylsilyl)ethyl (3-hydroxypropyl)carbamate (996.4 mg, 79% of theory) was dried under high vacuum and used without further purification in the next step of the synthesis. 807.0 mg (3.68 mmol) of 2-(trimethylsilyl)ethyl (3-hydroxypropyl)carbamate were initially charged in 15.0 ml of chloroform and 15.0 ml of 0.05 N potassium carbonate/0.05 N sodium bicarbonate solution (1:1). 102.2 mg (0.37 mmol) of tetra-n-butylammonium chloride, 736.9 mg (5.52 mmol) of N-chlorosuccinimide and 57.5 mg (0.37 mmol) of TEMPO were then added and the reaction mixture was stirred vigorously at RT overnight. The reaction mixture was diluted with dichloromethane and the organic phase was washed with water and saturated NaCl solution. The organic phase was dried over magnesium sulphate and the solvent was evaporated under reduced pressure. The residue was dried under high vacuum and used without further purification in the next step of the synthesis (890.3 mg).

Intermediate L16

2,2-dimethyl-4,11-dioxo-3,15,18,21,24-pentaoxa-5,12-diazaheptacosan-27-oic acid

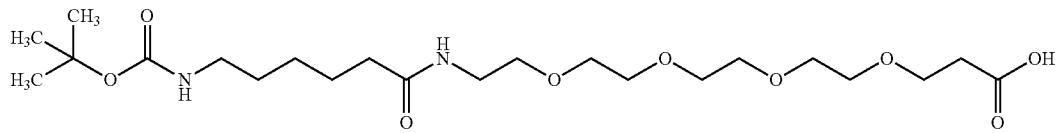 [SMILES: CC(C)(C)OC(=O)NCCCCCC(=O)NCCOCCOCCOCCOCCC(=O)O]

The title compound was obtained by coupling of methyl 1-amino-3,6,9,12-tetraoxapentadecan-15-oate with 6-[(tert-butoxycarbonyl)amino]hexanoic acid in DMF in the presence of HATU and N,N-diisopropylethylamine and subsequent saponification of the ester group using 5 equivalents of lithium hydroxide in THF:Water (1:1) at room temperature for 1 h.

LC-MS (Method 12): $R_t$=1.25 min; MS (ESIpos): m/z=479 [M+H]+

Intermediate L17

2-(trimethylsilyl)ethyl 3-{[$N^2$-acetyl-$N^6$-(tert-butoxycarbonyl)-L-lysyl]amino}-D-alaninate

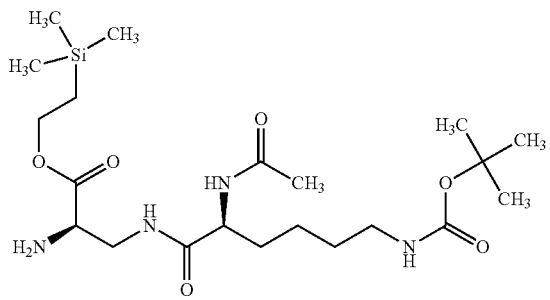 [SMILES: CC(=O)N[C@@H](CCCCNC(=O)OC(C)(C)C)C(=O)NC[C@@H](N)C(=O)OCC[Si](C)(C)C]

The title compound was obtained by coupling of 3-amino-N-[(benzyloxy)carbonyl]-D-alanine and 2,5-dioxopyrrolidin-1-yl $N^2$-acetyl-$N^6$-(tert-butoxycarbonyl)-L-lysinate in DMF in the presence of N,N-diisopropylethylamine, followed by coupling of the carboxylic acid group with 2-(trimethylsilyl)ethanol in acetonitrile in the presence of pyridine and 1,3-dicyclohexylcarbodiimide and subsequent deprotection of the benzyloxycarbonyl group by hydrogenation in methanol in presence of 10% Pd/C at room temperature for 2 h.

LC-MS (Method 1): $R_t$=0.70 min; MS (ESIpos): m/z=475 (M+H)$^+$.

Intermediate L81 benzyl {2-[(2-aminoethyl)sulfonyl]ethyl}carbamate trifluoroacetate (1:1)

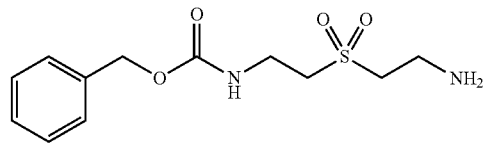

-continued

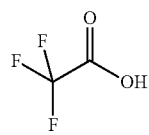

250 mg (1.11 mmol) 2,2'-Sulfonyldiethanamine were coupled with 92.3 mg (0.37 mmol) 1-{[(Benzyloxy)carbonyl]oxy}pyrrolidin-2,5-dion in the presence of N, N-diisopropylethylamine in DMF. After HPLC purification 70 mg (47% d. Th.) of the title compound were obtained.

LC-MS (Method 12): $R_t$=0.64 min; MS (ESIpos): m/z=257.11 (M+H)$^+$.

Intermediate L108

$N^2$-Acetyl-N-(2-aminoethyl)-$N^6$-(tert-butoxycarbonyl)-L-lysinamide

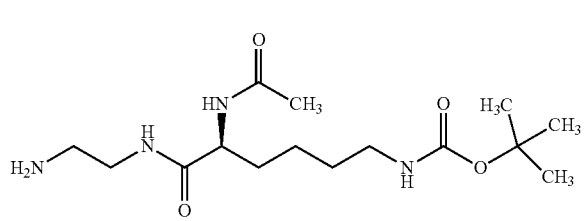 [SMILES: CC(=O)N[C@@H](CCCCNC(=O)OC(C)(C)C)C(=O)NCCN]

The title compound was obtained by coupling of $N^2$-acetyl-$N^6$-(tert-butoxycarbonyl)-L-lysine and benzyl (2-aminoethyl)carbamate hydrochloride (1:1) in DMF in the presence of HATU and N,N-diisopropylethylamine and subsequent deprotection of the benzyloxycarbonyl group by hydrognenation in dichloromethane/methanol 1:1 in presence of 10% Pd/C at room temperature for 1 h.

LC-MS (Method 1): $R_t$=0.43 min; MS (ESIpos): m/z=331 (M+H)$^+$.

Intermediate F1

1-{[1-(2-{[2-({(2S)-2-amino-4-[{(1R)-1-[1-benzyl-4-(2,5-difluorophenyl)-1H-imidazol-2-yl]-2,2-dimethylpropyl}(glycoloyl)amino]butanoyl}amino)ethyl]amino}-2-oxoethyl)-2,5-dioxopyrrolidin-3-yl]sulfanyl}-N-(5-aminopentyl)-3,6,9,12-tetraoxapentadecan-15-amide dihydrochloride

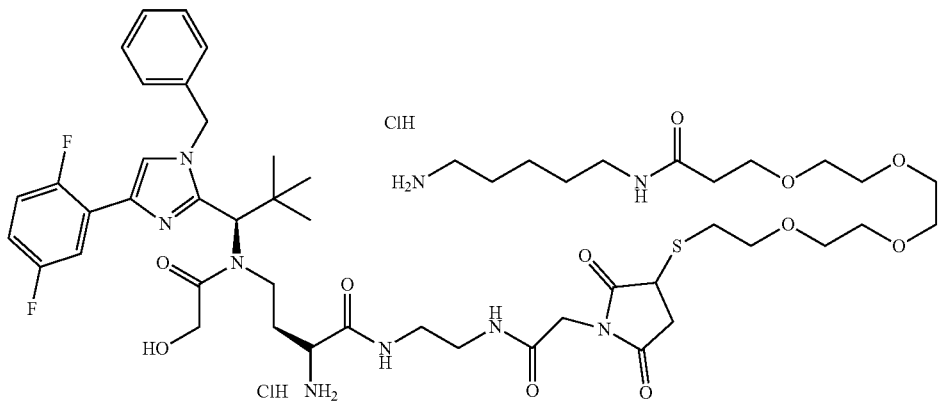

19 mg (15.07 μmol) tert-butyl [(2S)-4-[{(1R)-1-[1-benzyl-4-(2,5-difluorophenyl)-1H-imidazol-2-yl]-2,2-dimethylpropyl}(glycoloyl)amino]-1-({2-[({3-[(2,2-dimethyl-4,12-dioxo-3,15,18,21,24-pentaoxa-5,11-diazahexacosan-26-yl)sulfanyl]-2,5-dioxopyrrolidin-1-yl}acetyl)amino]ethyl}amino)-1-oxobutan-2-yl]carbamate (intermediate C103) were dissolved in 300 μl DCM. 113 μl hydrogen chloride solution 4M in dioxane were added and the mixture was stirred at room temperature for 1 h. Additional 100 μl hydrogen chloride solution 4 M in dioxane were added and the mixture was again stirred for 1 h.

The solvent was evaporated and the residue was solidified by freeze-drying from a mixture of acetonitrile and water to yield 11 mg (64%) of the target compound.

LC-MS (Method 4): $R_t$=5.86 min; MS (EIpos): m/z=1060 [M+H]$^+$.

Intermediate F2

$N^2$-acetyl-L-lysyl-L-valyl-N-{(1S)-3-[{(1R)-1-[1-benzyl-4-(2,5-difluorophenyl)-1H-pyrrol-2-yl]-2,2-dimethylpropyl}(glycoloyl)amino]-1-carboxypropyl}-L-alaninamide trifluoroacetate (1:1)

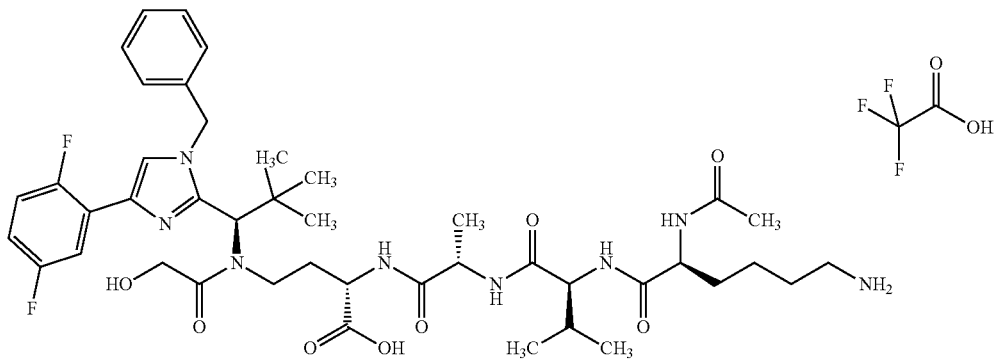 [SMILES: CC(=O)N[C@@H](CCCCN)C(=O)N[C@H](C(=O)N[C@@H](C)C(=O)N[C@@H](CCN(C(=O)CO)[C@@H](c1nc(-c2cc(F)ccc2F)cn1Cc1ccccc1)C(C)(C)C)C(=O)O)C(C)C ; O=C(O)C(F)(F)F]

The title compound was prepared using classical methods well known in peptide synthesis starting from methyl-(2S)-4-[(acetoxyacetyl){(1R)-1-[1-benzyl-4-(2,5-difluorphenyl)-1H-pyrrol-2-yl]-2,2-dimethylpropyl}amino]-2-({[2-(trimethylsilyl)ethoxy]carbonyl}amino)butanoat (intermediate C75). First the Teoc group was cleaved using 6 equivalents of zinc chloride in 2,2,2 trifluorethanol under heating for 2 h to 50° C. in trifluoroethanol. Subsequently the deprotected intermediate was reacted with N-[(benzyloxy)carbonyl]-L-valyl-L-alanine in the presence of HATU und N,N-diisopropylethylamine in DMF. In the next step the Z-protecting group was removed by hydrogenation over 10% palladium/activated charcoal under normal pressure. The intermediate obtained was reacted with intermediate L3 in the presence of HATU and N,N-diisopropylethylamine in DMF. Subsequent ester cleavage with 2M Lithiumhydroxide solution in water/THF 2:1 and final removal of the Z-protecting group by hydrogenation over 10% palladium/activated charcoal under normal pressure gave the title compound.

LC-MS (Method 1): $R_t$=0.9 min; MS (ESIpos): m/z=854 (M+H)$^+$.

Intermediate F3

$N^2$-acetyl-L-lysyl-L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide trifluoroacetate (1:1)

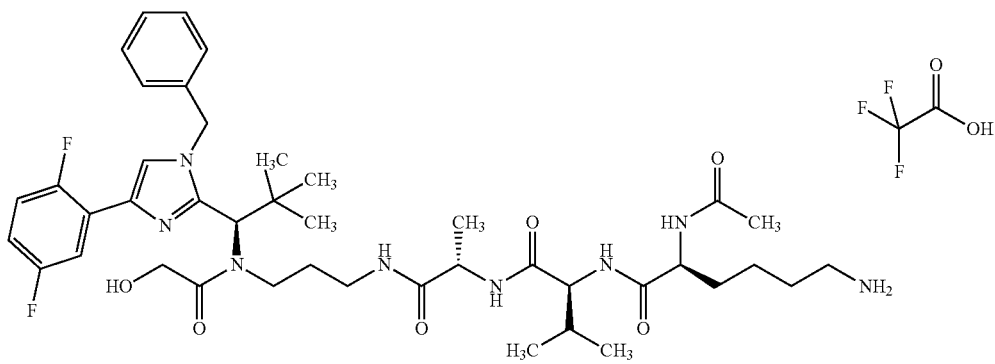 [SMILES: CC(=O)N[C@@H](CCCCN)C(=O)N[C@H](C(=O)N[C@@H](C)C(=O)NCCCN(C(=O)CO)[C@@H](c1nc(-c2cc(F)ccc2F)cn1Cc1ccccc1)C(C)(C)C)C(C)C ; O=C(O)C(F)(F)F]

The title compound was synthesized using classical methods well known in peptide synthesis starting from N-(3-aminopropyl)-N-{(1R)-1-[1-benzyl-4-(2,5-difluorophenyl)-1H-pyrrol-2-yl]-2,2-dimethyl propyl}-2-hydroxyacetamide (intermediate C101) by coupling with benzyloxy)carbonyl]-L-valyl-L-alanine in the presence of HATU und N,N-diisopropylethylamine in DMF. In the next step the Z-protecting group was removed by hydrogenation over 10% palladium/activated charcoal under normal pressure. The intermediate obtained was reacted with intermediate L3 in the presence of HATU and N,N-diisopropylethylamine in DMF. Finally by hydrogenation over 10% palladium/activated charcoal under normal pressure the title compound was obtained.

LC-MS (Method 1): $R_t$=0.90 min; MS (ESIpos): m/z=810 (M+H)$^+$.

Intermediate F4

3-[(N²-acetyl-L-lysyl)amino]-N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-D-alanine trifluoroacetate (1:1)

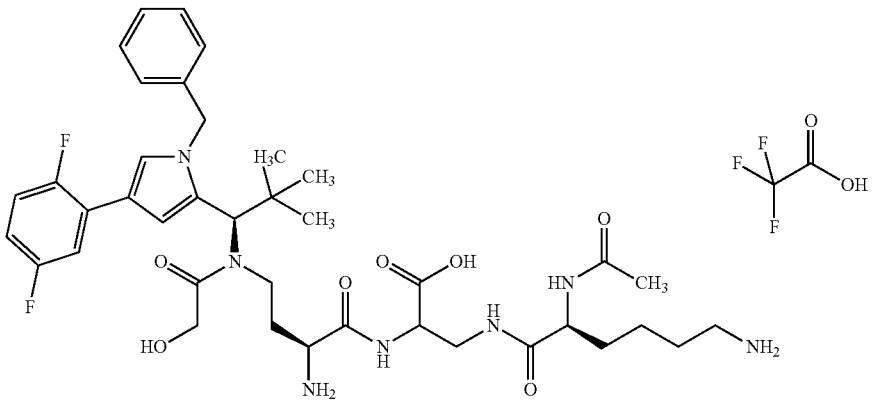 [SMILES: CC(=O)N[C@@H](CCCCN)C(=O)NCC(NC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

25 mg (0.026 mmol) of intermediate C74 were dissolved in 3.75 mL DMF and coupled with 13 mg (0.031 mmol) of commercially available N2-acetyl-N6-[(9H-fluoren-9-yl-methoxy)carbonyl]-L-lysine in the presence of 12 mg (0.031 mmol) HATU and 3 equivalents of N, N diisopropylethylamine. In the second step the Fmoc protecting group was cleaved with 100 equivalents of DABCO in 5 ml DMF. Finally the Teoc protecting group was cleaved with 6 equivalents of zinc chloride under heating for 2 h to 50° C. in trifluoroethanol. After HPLC purification 4.5 mg (20%) of the title compound were obtained.

LC-MS (Method 1): $R_t$=0.76 min; MS (ESIpos): m/z=770 (M+H)⁺.

Intermediate F5

N²-acetyl-N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-L-lysinamide trifluoroacetate (1:1)

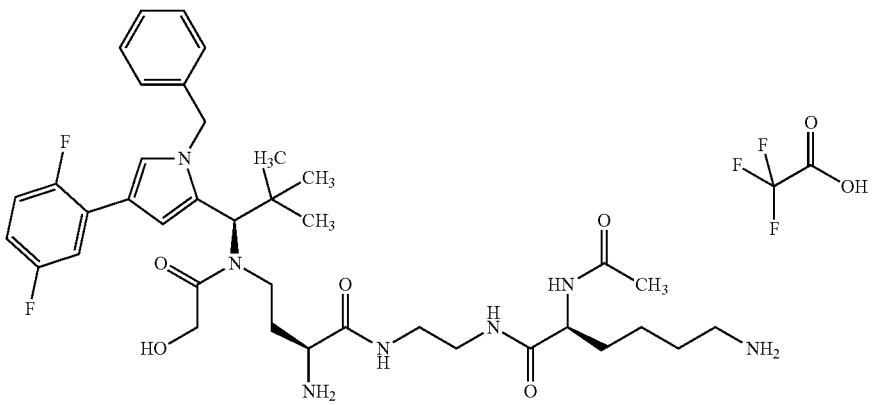 [SMILES: CC(=O)N[C@@H](CCCCN)C(=O)NCCNC(=O)[C@@H](N)CCN(C(=O)CO)[C@@H](c1cc(-c2cc(F)ccc2F)cn1Cc1ccccc1)C(C)(C)C ; O=C(O)C(F)(F)F]

The title compound was obtained by coupling of (2S)-4-[{(1R)-1-[1-benzyl-4-(2,5-difluorophenyl)-1H-pyrrol-2-yl]-2,2-dimethylpropyl}(glycoloyl)amino]-2-{[(9H-fluoren-9-ylmethoxy)carbonyl]amino}butanoic acid (Intermediate C53) with Intermediate L5 and subsequent removal of the Fmoc protecting groups with 100 equivalents of DABCO in DMF.

LC-MS (Method 12): $R_t$=1.11 min; MS (EIpos): m/z=724.40 $[M+H]^+$.

Intermediate F6

3-({15-[($N^2$-acetyl-L-lysyl)amino]-4,7,10,13-tetraoxapentadecan-1-oyl}amino)-N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-D-alanine trifluoroacetate (1:1)

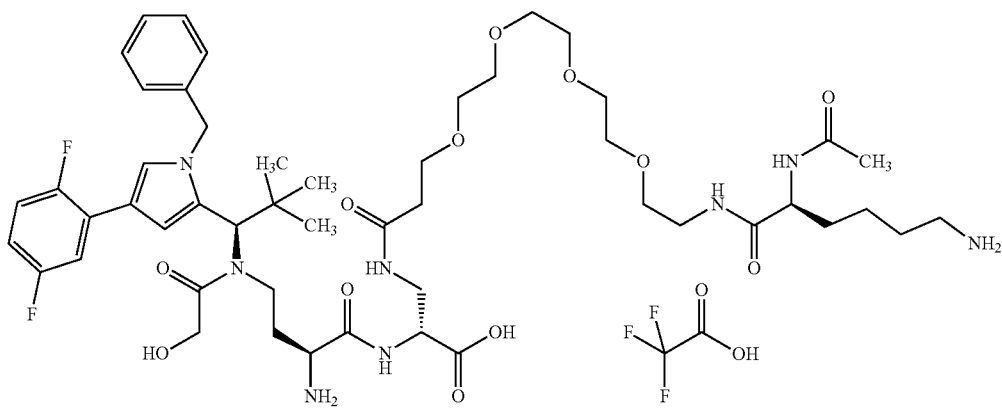

In the initial step intermediate C74 was coupled with commercially available 9H-fluoren-9-ylmethyl {(15-[(2,5-dioxopyrrolidin-1-yl)oxy]-15-oxo-3,6,9,12-tetraoxapentadec-1-yl}carbamate in the presence of N, N diisopropylethylamine in DMF. Subsequently the Fmoc protecting group was cleaved with 100 equivalents of DABCO in DMF and the intermediate obtained was coupled with L4 in the presence of 1.1 equivalents of HATU and 3 equivalents of N, N diisopropylethylamine in DMF. Finally the Teoc protecting groups and the trimethylsilylethylester were cleaved with 12 equivalents of zinc chloride under heating for 1 h to 50° C. in trifluoroethanol. After HPLC purification 2.3 mg of the title compound were obtained.

LC-MS (Method 1): $R_t$=0.72 min; MS (EIpos): m/z=1017 $[M+H]^+$.

Intermediate F7

N²-acetyl-L-lysyl-L-alanyl-L-alanyl-N¹-{(2S)-4-[{(1R)-1-[1-benzyl-4-(2,5-difluorophenyl)-1H-pyrrol-2-yl]-2,2-dimethylpropyl}(glycoloyl)amino]-1-[(2-carboxyethyl)amino]-1-oxobutan-2-yl}-L-aspartamide

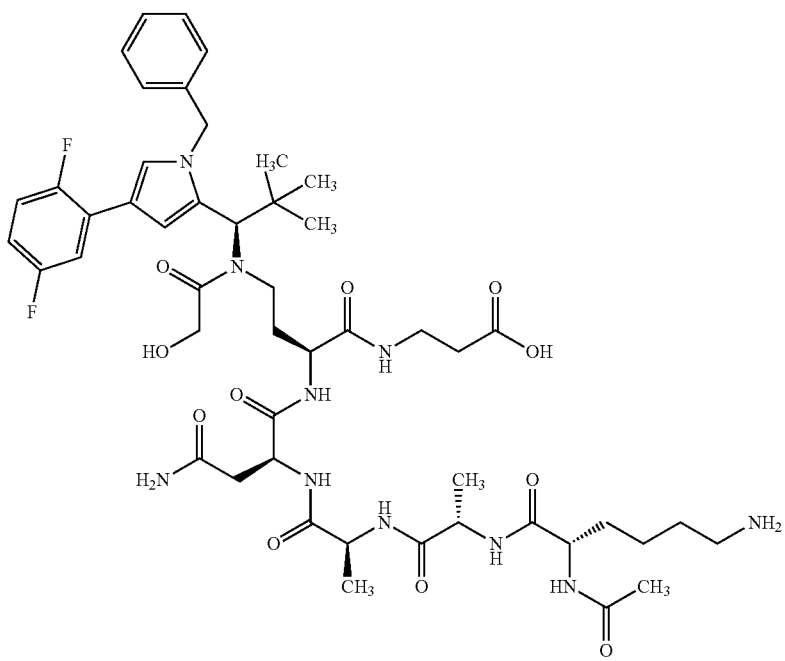 [SMILES: CC(=O)N[C@@H](CCCCN)C(=O)N[C@@H](C)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCC(=O)O]

The title compound was obtained by coupling of intermediate C105 with intermediate L7 in DMF in the presence of HATU and N,N-diisopropylethylamine and subsequent simultaneous removal of the Z-protecting group and the benzyl ester by hydrogenation in DCM-methanol 1:1 with 10% palladium on activated charcoal and HPLC purification.

LC-MS (Method 1): $R_t$=0.82 min; MS (ESIpos): m/z=1011 (M+H)⁺.

Intermediate F8

N²-acetyl-L-lysyl-L-alanyl-alanyl-N-[(2S)-4-[{(1R)-1-[1-benzyl-4-(2,5-difluorophenyl)-1H-pyrrol-2-yl]-2,2-dimethylpropyl}(glycoloyl)amino]-1-{[2-(L-gamma-glutamylamino)ethyl]amino}-1-oxobutan-2-yl]-L-aspartamide trifluoroacetate (1:1)

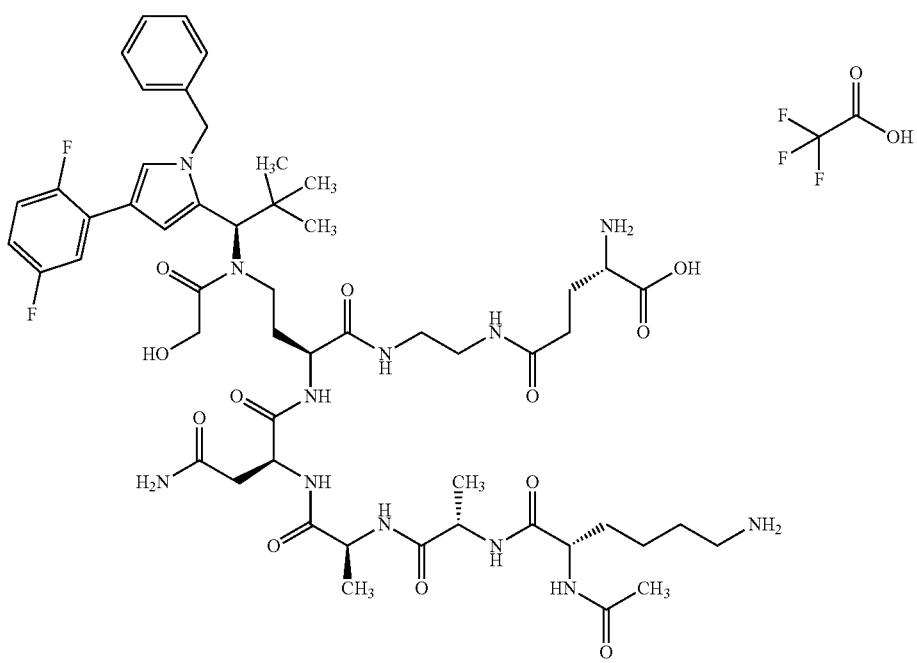 [SMILES: CC(=O)N[C@@H](CCCCN)C(=O)N[C@@H](C)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CC[C@H](N)C(=O)O ; O=C(O)C(F)(F)F]

The title compound was obtained by coupling of intermediate C106 with intermediate L8 in DMF in the presence of HATU and N,N-diisopropylethylamine and subsequent simultaneous removal of all protecting groups using 10 equivalents of zinc chloride in 2,2,2 trifluorethanol under heating for 6 h to 50° C. After addition of 6 equivalents of EDTA the product was purified by HPLC.

LC-MS (Method 1): $R_t$=0.72 min; MS (ESIpos): m/z=1111 (M+H)⁺.

Intermediate F9

N²-acetyl-L-lysyl-L-alanyl-L-alanyl-N¹-{(2S)-1-[(3-{[(5S)-5-amino-5-carboxypentyl]amino}-3-oxopropyl)amino]-4-[{(1R)-1-[1-benzyl-4-(2,5-difluorophenyl)-1H-pyrrol-2-yl]-2,2-dimethylpropyl}(glycoloyl)amino]-1-oxobutan-2-yl}-L-aspartamide trifluoroacetate (1:1)

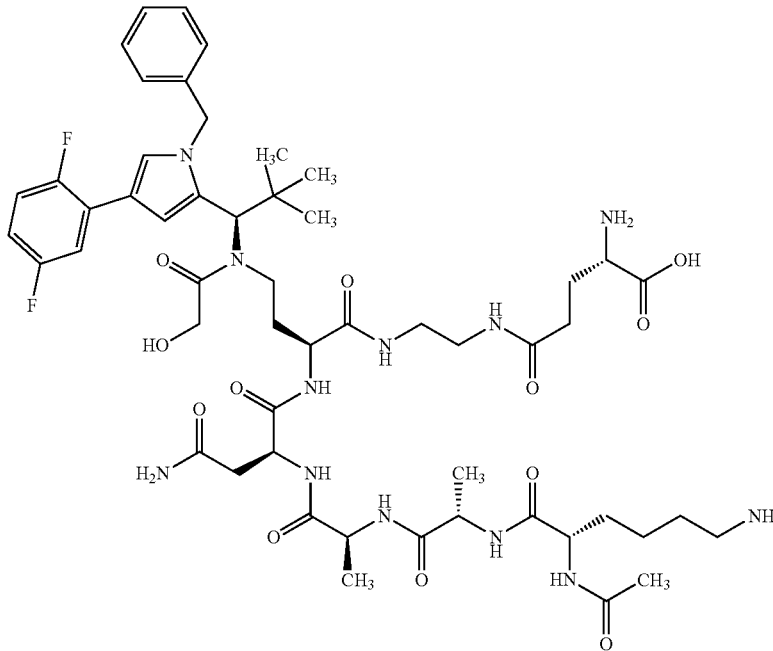
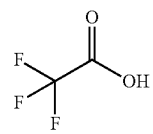

The title compound was obtained by coupling of intermediate C108 with intermediate L10 in DMF in the presence of HATU and N,N-diisopropylethylamine, subsequent removal of the Z-protecting group by hydrogenation in DCM/methanol 1:1 over 10% palladium/activated charcoal under normal pressure, then coupling with intermediate L4 in DMF in the presence of HATU and N,N-diisopropylethylamine and finally simultaneous removal of all protecting groups using 12 equivalents of zinc chloride in 2,2,2 trifluorethanol under heating for 2 h to 50° C. After addition of 12 equivalents of EDTA the product is purified by HPLC.

LC-MS (Method 12): $R_t$=11.7 min; MS (ESIneg): m/z=1137 (M−H)⁻.

Intermediate F10

N²-acetyl-L-lysyl-L-alanyl-L-alanyl-N¹-{(2S)-4-[{(1R)-1-[1-benzyl-4-(2,5-difluorophenyl)-1H-pyrrol-2-yl]-2,2-dimethylpropyl}(glycoloyl)amino]-1-[(3-{[(1S)-1,3-dicarboxypropyl]amino}-3-oxopropyl)amino]-1-oxobutan-2-yl}-L-aspartamide trifluoroacetate (1:1)

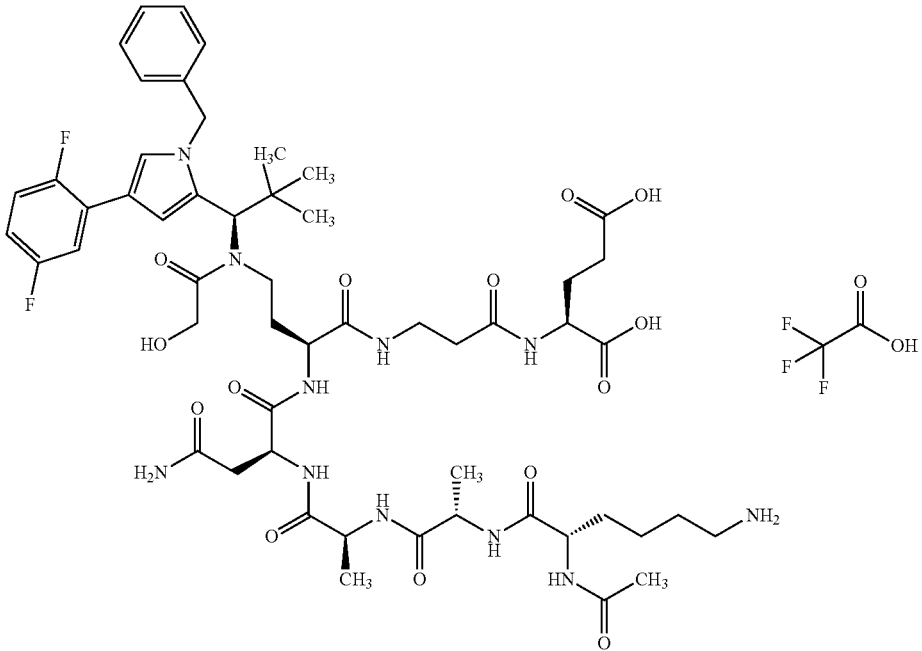 [SMILES: CC(=O)N[C@@H](CCCCN)C(=O)N[C@@H](C)C(=O)N[C@@H](C)C(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCC(=O)N[C@@H](CCC(=O)O)C(=O)O ; O=C(O)C(F)(F)F]

The title compound was obtained by coupling of intermediate C109 with intermediate L8 in DMF in the presence of HATU and N,N-diisopropylethylamine, subsequent removal of the benzyl ester protecting groups by hydrogenation in methanol over 10% palladium/activated charcoal under normal pressure and finally removal of the Teoc protecting group using 6 equivalents of zinc chloride in 2,2,2 trifluorethanol under heating for 6 h to 50° C. After addition of 6 equivalents of EDTA the product was purified by HPLC.

LC-MS (Method 12): $R_t$=1.31 min; MS (ESIpos): m/z=1140 (M+H)⁺.

Intermediate I1

N²-acetyl-L-lysyl-S-{2-[(3-aminopropyl) {(1R)-1-[1-benzyl-4-(2,5-difluorophenyl)-1H-pyrrol-2-yl]-2,2-dimethylpropyl}amino]-2-oxoethyl}-L-cysteine trifluoroacetate (1:2)

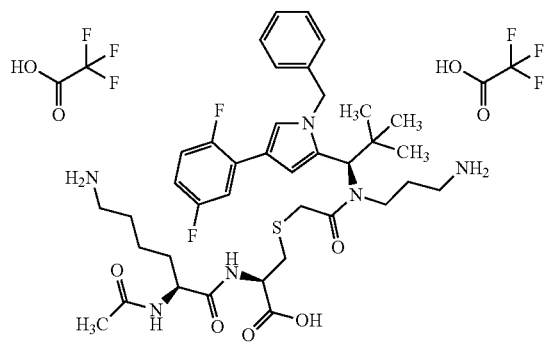 [SMILES: O=C(O)C(F)(F)F ; CC(=O)N[C@@H](CCCCN)C(=O)N[C@@H](CSCC(=O)N(CCCN)[C@@H](c1cc(-c2cc(F)ccc2F)cn1Cc1ccccc1)C(C)(C)C)C(=O)O ; O=C(O)C(F)(F)F]

To a solution of S-(11-{(1R)-1-[1-benzyl-4-(2,5-difluorophenyl)-1H-pyrrol-2-yl]-2,2-dimethypropyl}-2,2-dimethyl-6,12-dioxo-5-oxa-7,11-diaza-2-silatridecan-13-yl)-L-cysteine trifluoroacetate (1:1) (20.0 mg, 24.1 μmol) (intermediate C71) and N²-acetyl-N⁶-(tert-butoxycarbonyl)-L-lysine (9.02 mg, 31.3 μmol) in acetonitrile (2.0 ml) were added N,N-diisopropylethylamine (34 μl, 190 μmol) and 2,4,6-tripropyl-1,3,5,2,4,6-trioxatriphosphinane 2,4,6-trioxide (19 μl, 50% purity, 31 μmol). The mixture was stirred over night at room temperature and purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 5.2 mg (22% of theory) of N²-acetyl-N⁶-(tert-butoxycarbonyl)-L-lysyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine. The product contained around 15% of its epimer.

To a solution of N²-acetyl-N⁶-(tert-butoxycarbonyl)-L-lysyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine (61.6 mg, 62.4 μmol) in 2,2,2-Trifluorethanol (6.0 ml) was added Zinkchlorid (51.0 mg, 374 μmol) and the mixture was stirred at 50° C. for 1 h. Zinkchlorid (51.0 mg, 374 μmol) was then added and the mixture was stirred at 50° C. for 1 h. The mixture was stirred for 5 min with EDTA (218 mg, 748 μmol) and purified by preparative RP-HPLC (column: Reprosil 250×30; 10μ, flow rate: 50 ml/min, MeCN/water, 0.1% TFA). The solvents were evaporated under reduced pressure and the residue was lyophilized. This gave 41.6 mg (69% of theory) of the title compound.

LC-MS (Method 12): $R_t$=1.32 min; MS (ESIneg): m/z=741 [M−H]⁻

Intermediate F12

N-(6-aminohexanoyl)-S-[2-({(1R)-1-[1-benzyl-4-(2,5-difluorophenyl)-1H-pyrrol-2-yl]-2,2-dimethylpropyl}{[(3S,4R)-4-fluoropyrrolidin-3-yl]methyl}amino)-2-oxoethyl]-L-cysteine trifluoroacetate (1:1)

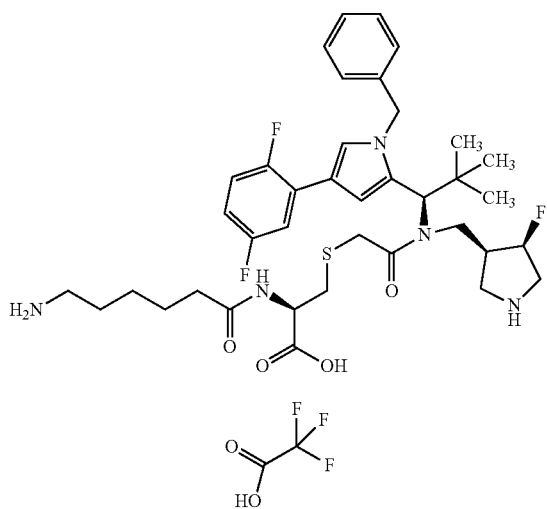 [SMILES: CC(C)(C)[C@H](c1cc(-c2cc(F)ccc2F)cn1Cc1ccccc1)N(C[C@@H]1CNC[C@@H]1F)C(=O)CSC[C@H](NC(=O)CCCCCN)C(=O)O ; O=C(O)C(F)(F)F]

To a solution of 6-[(tert-butoxycarbonyl)amino]hexanoic acid (29.2 mg, 126 µmol) in 1.4 ml DMF were added N,N-diisopropylethylamine (21 µl, 120 µmol) and HATU (46.2 mg, 122 µmol). The reaction mixture was stirred at RT for 10 min and a solution of S-[2-({(1R)-1-[1-benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]-L-cysteine (37.0 mg, 48.6 µmol) (intermediate C107) in 1.4 ml DMF was then added. The reaction mixture was then stirred overnight at RT. Water and DCM were then added and the organic phase was separated, further washed with water, dried over magnesium sulfate and evaporated to afford 49.7 mg (85% of theory) of S-[2-({(1R)-1-[1-benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]-N-{6-[(tert-butoxycarbonyl)amino]hexanoyl}-L-cysteine which was used in the next step without further purification.

LC-MS (Method 1): Rt=1.47 min; MS (ESIpos): m/z=974 [M+H]$^+$

To a solution of S-[2-({(1R)-1-[1-benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]-N-{6-[(tert-butoxycarbonyl)amino]hexanoyl}-L-cysteine (49.7 mg, 81% purity, 41.4 µmol) in 3.5 ml trifluorethanol, was added (45.2 mg, 332 µmol) and the reaction mixture was stirred at 50° C. for 2 h. EDTA (96.9 mg, 332 µmol) was then added and the resulting mixture was stirred at RT for 15 min. Ethyl acetate was then added and the organic phase was washed with water and brine, dried over magnesium sulfate and evaporated. The residue was purified by preparative RP-HPLC (MeCN/water, 0.1% TFA) to afford 4.5 mg (13% of theory) of the title compound.

LC-MS (Method 1): Rt=0.79 min; MS (ESIpos): m/z=730 [M+H]+

Intermediate F13

N-(pyridin-4-ylacetyl)-L-alanyl-L-alanyl-N$^1$-{(2S)-1-({2-[(N$^2$-acetyl-L-lysyl)amino]ethyl}amino)-4-[{(1R)-1-[1-benzyl-4-(2,5-difluorophenyl)-1H-pyrrol-2-yl]-2,2-dimethylpropyl}(glycoloyl)amino]-1-oxobutan-2-yl}-L-aspartamide trifluoroacetate (1:1)

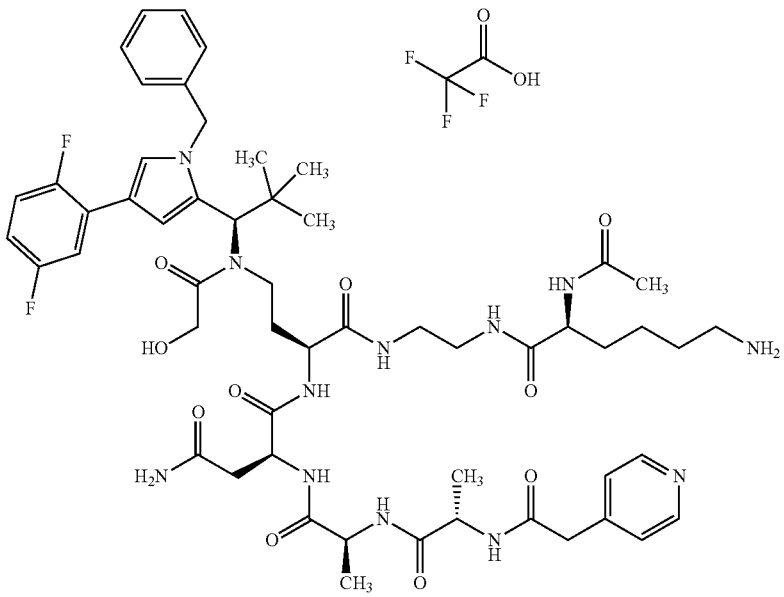 [SMILES: CC(=O)N[C@@H](CCCCN)C(=O)NCCNC(=O)[C@H](CCN(C(=O)CO)[C@@H](c1cc(-c2cc(F)ccc2F)cn1Cc1ccccc1)C(C)(C)C)NC(=O)[C@H](CC(N)=O)NC(=O)[C@H](C)NC(=O)[C@H](C)NC(=O)Cc1ccncc1 ; O=C(O)C(F)(F)F]

The title compound was obtained by coupling of intermediate C110 with intermediate L14 in DMF in the presence of HATU and N,N-diisopropylethylamine and subsequent removal of the Boc group using 6 equivalents of zinc chloride in 2,2,2 trifluorethanol under heating for 0.5 h to 50° C. After addition of 6 equivalents of EDTA the product was purified by HPLC.

LC-MS (Method 1): $R_t$=0.76 min; MS (ESIpos): m/z=1101 (M+H)$^+$.

Intermediate F14

N$^2$-acetyl-N-(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]sulfonyl}ethyl)-L-lysinamide trifluoroacetate (1:2)

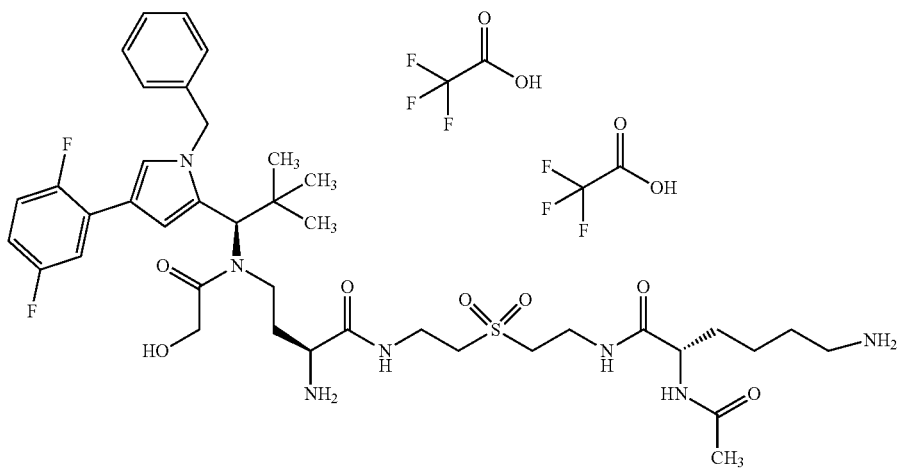 [SMILES: CC(=O)N[C@@H](CCCCN)C(=O)NCCS(=O)(=O)CCNC(=O)[C@@H](N)CCN(C(=O)CO)[C@@H](c1cc(-c2cc(F)ccc2F)cn1Cc1ccccc1)C(C)(C)C ; O=C(O)C(F)(F)F ; O=C(O)C(F)(F)F]

Initially intermediate L81 was coupled with intermediate C58 in the presence of HATU and N,N-diisopropylethylamine. Subsequently the Z protecting group was removed by hydrogenation in DCM/methanol 1:1 over 10% palladium/activated charcoal under normal pressure. The intermediate obtained was coupled with intermediate L4 in the presence of HATU and N,N-diisopropylethylamine.

Finally the Teoc protecting groups were cleaved using 6 equivalents of zinc chloride in 2,2,2 trifluorethanol under heating for 2 h to 50° C. After addition of 6 equivalents of EDTA the product was purified by HPLC.

LC-MS (Method 12): $R_t$=0.7 min; MS (ESIpos): m/z=818 (M+H)$^+$.

Intermediate F15

N²-acetyl-N-{2-[(3-{[2-({(1R)-1-[1-benzyl-4-(2,5-difluorophenyl)-1H-pyrrol-2-yl]-2,2-dimethylpropyl}[pyrrolidin-3-ylmethyl]amino)-2-oxoethyl]sulfanyl}propanoyl)amino]ethyl}-L-lysinamide trifluoroacetate (1:2) (isomer 1)

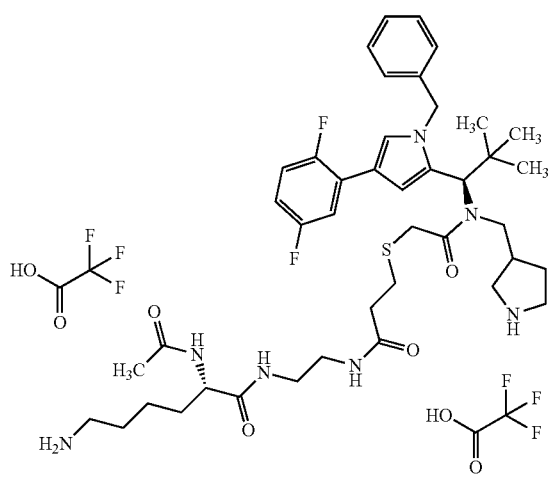

The title compound was obtained by coupling of intermediate C95 with intermediate L108 in DMF in the presence of HATU and N,N-diisopropylethylamine and subsequent removal of the Boc groups using 6 equivalents of zinc chloride in 2,2,2 trifluorethanol under heating for 1 h to 50° C. After addition of 6 equivalents of EDTA the product was purified by HPLC.

LC-MS (Method 1): $R_t$=0.74 min; MS (ESIpos): m/z=796 (M+H)⁺.

Intermediate F16

N-(15-amino-4,7,10,13-tetraoxapentadecan-1-oyl)-S-[2-({(1R)-1-[1-benzyl-4-(2,5-difluorophenyl)-1H-pyrrol-2-yl]-2,2-dimethylpropyl}[pyrrolidin-3-ylmethyl]amino)-2-oxoethyl]cystein trifluoroacetat (1:2) (Isomer 1)

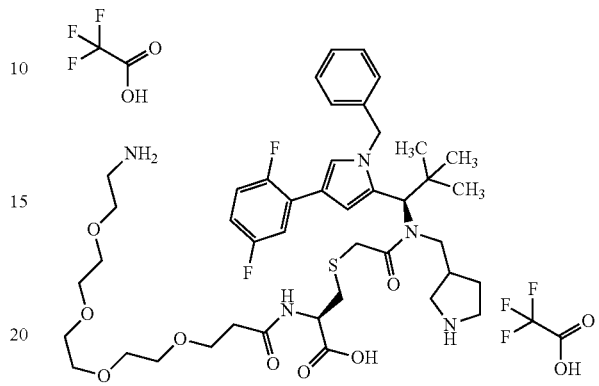

The title compound was obtained by coupling of intermediate C90 with 2,2-dimethyl-4-oxo-3,8,11,14,17-pentaoxa-5-azaicosan-20-oic acid in DMF in the presence of HATU and N,N-diisopropylethylamine and subsequent removal of the Boc groups using 6 equivalents of zinc chloride in 2,2,2 trifluorethanol under heating for 3 h to 50° C. After addition of 6 equivalents of EDTA the product was purified by HPLC.

LC-MS (Method 1): $R_t$=0.80 min; MS (ESIpos): m/z=846 (M+H)⁺.

Intermediate F17

N-(22-amino-17-oxo-4,7,10,13-tetraoxa-16-azadocosan-1-oyl)-S-{2-[(3-aminopropyl){(1R)-1-[1-benzyl-4-(2,5-difluorophenyl)-1H-pyrrol-2-yl]-2,2-dimethylpropyl}amino]-2-oxoethyl}-L-cystein trifluoroacetat (1:2)

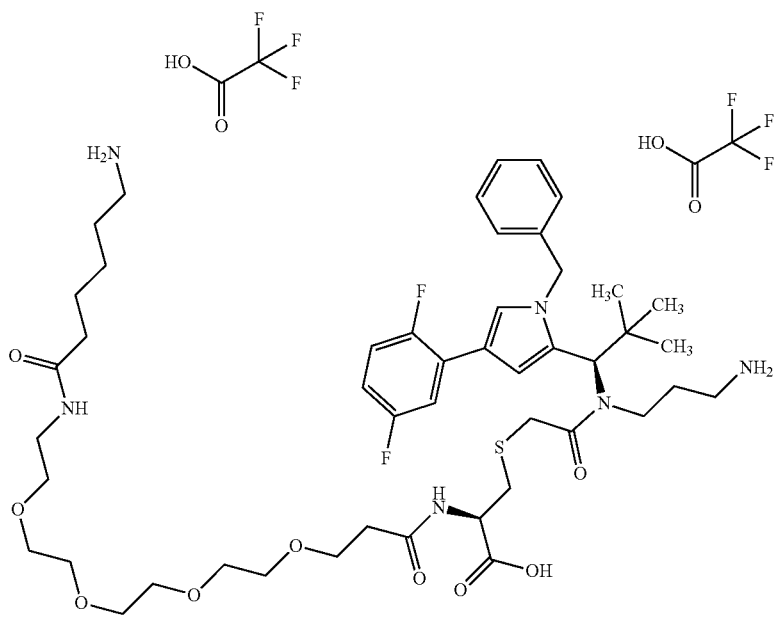 [SMILES: CC(C)(C)[C@H](c1cc(-c2cc(F)ccc2F)cn1Cc1ccccc1)N(CCCN)C(=O)CSC[C@H](NC(=O)CCOCCOCCOCCOCCNC(=O)CCCCCN)C(=O)O ; O=C(O)C(F)(F)F ; O=C(O)C(F)(F)F]

The title compound was obtained by coupling of intermediate C71 with intermediate L16 in DMF in the presence of HATU and N,N-diisopropylethylamine and subsequent removal of the protecting groups using 6 equivalents of zinc chloride in 2,2,2 trifluorethanol under heating for 1 h to 50° C. After addition of 6 equivalents of EDTA the product was purified by HPLC.

LC-MS (Method 1): $R_t$=0.78 min; MS (ESIpos): m/z=933 (M+H)$^+$.

Intermediate F18

3-[(N$^2$-acetyl-L-lysyl)amino]-N-[3-({2-[(3-aminopropyl) {(1R)-1-[1-benzyl-4-(2,5-difluorophenyl)-1H-pyrrol-2-yl]-2,2-dimethylpropyl}amino]-2-oxoethyl}sulfanyl)propanoyl]-D-alanin trifluoroacetat (1:2)

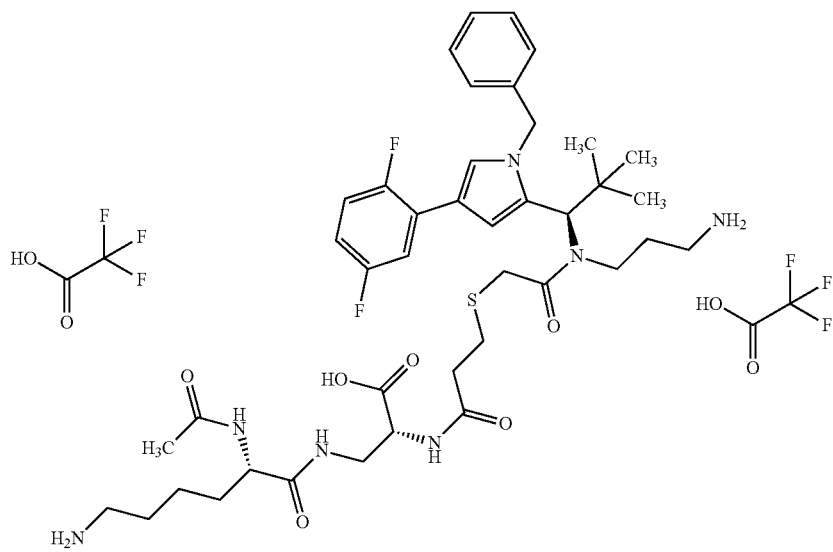 [SMILES: O=C(O)C(F)(F)F ; CC(=O)N[C@@H](CCCCN)C(=O)NC[C@@H](NC(=O)CCSCC(=O)N(CCCN)[C@@H](c1cc(-c2cc(F)ccc2F)cn1Cc1ccccc1)C(C)(C)C)C(=O)O ; O=C(O)C(F)(F)F]

The title compound was obtained by coupling of intermediate C69 with intermediate L17 in DMF in the presence of HATU and N,N-diisopropylethylamine and subsequent removal of the protecting groups using 6 equivalents of zinc chloride in 2,2,2 trifluorethanol under heating for 1 h to 50° C. After addition of 6 equivalents of EDTA the product was purified by HPLC.

LC-MS (Method 1): $R_t$=0.76 min; MS (ESIpos): m/z=814 (M+H)$^+$.

Intermediate F19

N²-acetyl-N-(2-{[3-({2-[(3-aminopropyl){(1R)-1-[1-benzyl-4-(2,5-difluorophenyl)-1H-pyrrol-2-yl]-2,2-dimethylpropyl}amino]-2-oxoethyl}sulfanyl)propanoyl]amino}ethyl)-L-lysinamid trifluoroacetat (1:2)

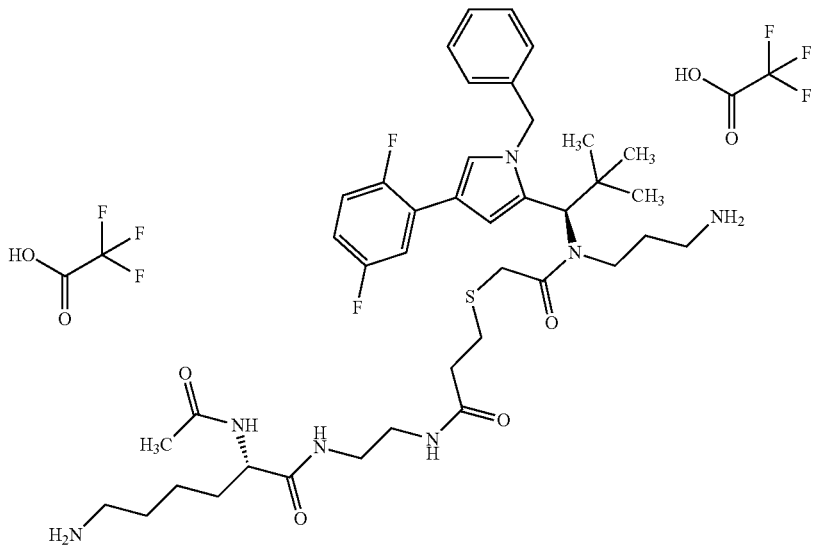 [SMILES: O=C(O)C(F)(F)F ; CC(=O)N[C@@H](CCCCN)C(=O)NCCNC(=O)CCSCC(=O)N(CCCN)[C@@H](c1cc(-c2cc(F)ccc2F)cn1Cc1ccccc1)C(C)(C)C ; O=C(O)C(F)(F)F]

The title compound was obtained by coupling of intermediate L108 with intermediate C69 in DMF in the presence of HATU and N,N-diisopropylethylamine and subsequent removal of the protecting groups using 6 equivalents of zinc chloride in 2,2,2 trifluorethanol under heating for 1 h to 50° C. After addition of 6 equivalents of EDTA the product was purified by HPLC.

LC-MS (Method 1): $R_t$=0.79 min; MS (ESIpos): m/z=770 (M+H)⁺.

B: Preparation of Antibody/Active Compound Conjugates (ADC)

B-1. General Process for Generating Anti-TWEAKR Antibodies

The anti-TWEAKR antibodies were generated, for example, by screening of a phage display library for recombinant human TWEAKR SEQ ID NO: 138 and murine TWEAKR SEQ ID NO: 137. Particularly the antibody TPP-2090 is an important example. The antibodies obtained in this manner were reformatted into the human IgG1 format. The aglycosylated variant TPP-2090-HC-N297A was generated by introducing the mutation N297A in the heavy chain of TPP-2090 (Kabat numbering system of immunoglobulins). The aglycosylated variant TPP-2090-HC-N297Q was generated by introducing the mutation N297Q in the heavy chain of TPP-2090 (Kabat numbering system of immunoglobulins). These two antibodies were used for the working examples described here (see also WO 2015/189143 A1 and WO 2014/198817 A1). In addition, antibodies which bind to TWEAKR are known to the person skilled in the art, see, for example, WO2009/020933(A2) or WO2009140177 (A2).

```
SEQ ID NO: 138 (polypeptide):
EQAPGTAPCSRGSSWSADLDKCMDCASCRARPHSDFCLGCAAAPPAPFRL
LWPRSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKS
RWQQGNVFSCSVMHEALHNHYTQKSLSLSPGK SEQ ID NO: 137 (polypeptide):
EQAPGTSPCSSGSSWSADLDKCMDCASCPARPHSDFCLGCAAAPPAHFRL
LWPRSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKS
RWQQGNVFSCSVMHEALHNHYTQKSLSLSPGK
```

B-2. General Process for Expressing Anti-TWEAKR Antibodies in Mammalian Cells The antibodies, for example TPP-2090 and the aglycosylated variants TPP-2090-HC-N297A, TPP-2090-HC-N297Q, Trastuzumab-HC-N297A (equal to TPP-7510), Trastuzumab-HC-N297Q (equal to TPP-7511) were produced in transient mammalian cell cultures as described by Tom et al., Chapter 12 in Methods Express: Expression Systems edited by Micheal R. Dyson and Yves Durocher, Scion Publishing Ltd, 2007 (see AK-Example 1).

B-3. General Process for Purifying Antibodies from Cell Supernatants

The antibodies, for example TPP-2090 and the aglycosylated variants TPP-2090-HC-N297A, TPP-2090-HC- N297Q, Trastuzumab-HC-N297A (equal to TPP-7510), Trastuzumab-HC-N297Q (equal to TPP-7511) were obtained from the cell culture supernatants. The cell supernatants were clarified by centrifugation of cells. The cell supernatant was then purified by affinity chromatography on a MabSelect Sure (GE Healthcare) chromatography column. To this end, the column was equilibrated in DPBS pH 7.4 (Sigma/Aldrich), the cell supernatant was applied and the column was washed with about 10 column volumes of DPBS pH 7.4+500 mM sodium chloride. The antibodies were eluted in 50 mM sodium acetate pH 3.5+500 mM sodium chloride and then purified further by gel filtration chromatography on a Superdex 200 column (GE Healthcare) in DPBS pH 7.4.

The commercially available antibody cetuximab (trade name Erbitux) was purified from the commercial product by standard chromatographic methods (protein A, preparative SEC).

The commercially available antibody trastuzumab (trade name Herceptin) was purified from the commercial product by standard chromatographic methods (protein A, preparative SEC).

Trastuzumab-HC-N297A (equal to TPP-7510) comprises a heavy chain represented by SEQ ID NO: 244. The light chain is identical with the one of Trastuzumab.

Trastuzumab-HC-N297Q (equal to TPP-7511) comprises a heavy chain represented by SEQ ID NO: 245. The light chain is identical with the one of Trastuzumab.

From the commercial product (trade name CIMAher), the antibody nimotuzumab was purified from the commercial product by standard chromatographic methods (protein A, preparative SEC).

From the commercial product (trade name Vectibix), the antibody panitumumab was purified from the commercial product by standard chromatographic methods (protein A, preparative SEC).

B-4. General Processes for Coupling to Glutamine

General Procedure a for Transglutaminase Coupling Employed in the Following Examples to Achieve a Maximum DAR of 2:

For the reactions of the ADC working examples the following antibodies were used (the following nomenclature Antibody-HC-N297Z means the antibody with the replacement of N297 (kabat numbering) by the amino acid Z in both heavy chains of the antibody, the nomenclature TPP-XXXX-HC-Q295N—HC-N297Q means the antibody with the TPP-XXXX with a replacement of the amino acid Q295 (kabat numbering) by the amino acid N in both heavy chains of the antibody and a replacement of the amino acid N297 (kabat numbering) by the amino acid Q (Kabat numbering) in both heavy chins of the antibody. The name of the antibody can be declared as name (e.g. Trastuzumab) or as TPP-XXXX (the antibody with the TPP-number XXXX):

$AK_{3a}$: TPP-2090-HC-N297A (equal to anti-TWEAKR antibody TPP-2658)
$AK_{3c}$: TPP-2090-HC-Q295N-HC-N297Q (equal to anti-TWEAKR antibody TPP-8825)
$AK_{3d}$: Trastuzumab-HC-N297A (equal to TPP-7510)

To a solution of 5 mg of the aglyco variant (HC-N297A or HC-Q295N-HC-N297Q) of respective antibody in DPBS pH 7.4 (c~5-15 mg/mL) 20 μL (6 equivalents) of a solution of the respective precursor intermediate F (10 mM in DMSO) were added. After 5 min incubation at 37° C. 50 μL (1.25 U) of a solution of recombinant microbial (bacterial) transglutaminase in water (Product number T001 from Zedira GmbH, Darmstadt, Germany) (25 U/mL) were added. The reaction mixture was incubated at 37° C. for 24 hours and subsequently diluted with DPBS pH 7.4 to a volume of 2.5 mL. The ADC solution was purified by gel filtration over PD 10-columns (Sephadex® G-25, GE Healthcare) equilibrated with DPBS-Puffer pH 7.4 which also was used for elution. Subsequently, the ADC solution was concentrated using Amicon Ultracel-30K centrifugation devices (Millipore) and re-diluted to a volume of about 2.5 mL. Finally 0.00625 μmol of b-transglutaminase blocker Zedira C100 in 12.5 μL DPBS were added. For the ADC solutions obtained the protein concentration was determined as given in the individual examples. Drug load was determined with the methods described in chapter B5. The ADC batches were characterized as pointed out in the examples.

General Procedure B for Transglutaminase Coupling Employed in the Following Examples to Achieve a Maximum DAR of 4:

For the reactions of the ADC working examples the following antibodies were used (the following nomenclature as used above):
$AK_{3b}$: TPP-2090-HC-N297Q (equal to anti-TWEAKR antibody TPP-5442)
$AK_{3e}$: Trastuzumab-HC-N297Q (equal to TPP-7511)

To a solution of 5 mg of the aglyco variant (HC-N297Q) of respective antibody in DPBS pH 7.4 (c~5-15 mg/mL) 16-24 equivalents of a solution of the respective precursor intermediate F (10 mM in DMSO) were added. After 5 min incubation at 37° C. 400 μL (10 U) of a solution of recombinant microbial (bacterial) transglutaminase in water (Product number T001 from Zedira GmbH, Darmstadt, Germany) (25 U/mL) were added. The reaction mixture was incubated at 37° C. for 24 hours and subsequently diluted with DPBS pH 7.4 to a volume of 2.5 mL. The ADC solution was purified by gel filtration over PD 10-columns (Sephadex® G-25, GE Healthcare) equilibrated with DPBS-Puffer pH 7.4 which also was used for elution. Subsequently, the ADC solution was concentrated using Amicon Ultracel-30K centrifugation devices (Millipore) and re-diluted to a volume of about 2.5 mL. Finally 0.1 μmol of b-transglutaminase blocker Zedira C100 in 200 μL DPBS were added. For the ADC solutions obtained the protein concentration was determined as given in the individual examples. Drug load was determined with the methods described in chapter B7. The ADC batches were characterized as pointed out in the examples.

General Procedure C for Transglutaminase Coupling in Larger Scale Employed in the Following Examples to Achieve a Maximum DAR of 2:

To a solution of 30 mg of the aglyco variant (HC-N297A or HC-Q295N-HC-N297Q) of respective antibody in DPBS pH 7.4 (c~5-15 mg/mL) 6 equivalents of a solution of the respective precursor intermediate F (10 mM in DMSO) were added. After 5 min incubation at 37° C. 200 μL (7.5 U) of a solution of recombinant microbial (bacterial) transglutaminase in water (Product number T001 from Zedira GmbH, Darmstadt, Germany) (25 U/mL) were added. The reaction mixture was incubated at 37° C. for 24 hours. The ADC was purified by gel filtration chromatography on a Superdex 200 column (GE Healthcare) in DPBS pH 7.4 to remove small molecules and the transglutaminase from the ADC, and finally concentrated using Amicon Ultracel-30K centrifugation devices (Millipore) to final concentrations between 5-25 mg/mL. The solution was then sterile filtered.

The respective protein concentrations, stated in the working examples, of the ADC solutions were determined. Drug load was determined with the methods described in chapter B5. The ADC batches were characterized as pointed out in the examples.

General Procedure D for Transglutaminase Coupling in Larger Scale Employed in the Following Examples to Achieve a Maximum DAR of 4:

To a solution of 30 mg of the aglyco variant (HC-N297Q) of respective antibody in DPBS pH 7.4 (c~5-15 mg/mL) 16-24 equivalents of a solution of the respective precursor intermediate F (10 mM in DMSO) were added. After 5 min incubation at 37° C. 2400 µL (60 U) of a solution of recombinant microbial (bacterial) transglutaminase in water (Product number T001 from Zedira GmbH, Darmstadt, Germany) (25 U/mL) were added. The reaction mixture was incubated at 37° C. for 24 hours. The ADC was purified by gel filtration chromatography on a Superdex 200 column (GE Healthcare) in DPBS pH 7.4 to remove small molecules and the transglutaminase from the ADC, and finally concentrated using Amicon Ultracel-30K centrifugation devices (Millipore) to final concentrations between 5-25 mg/mL. The solution was then sterile filtered.

The respective protein concentrations, stated in the working examples, of the ADC solutions were determined. Drug load was determined with the methods described in chapter B5. The ADC batches were characterized as pointed out in the examples.

B-5. Determination of the Antibody, the Toxophor Loading and the Determination of Conjugation Site For protein identification in addition to molecular weight determination after deglycosylation and/or denaturing, a tryptic digestion was carried out, which, after denaturing, reduction and derivatization, confirms the identity of the protein via the tryptic peptides found. Furthermore this approach could be used for the identification of the coupling site by detection of conjugated tryptic peptides.

The toxophor loading of the PBS buffer solutions obtained of the conjugates described in the working example was determined as follows:

Determination of toxophor loading of glutamine-linked ADCs was carried out by mass spectrometric determination of the molecular weights of the individual conjugate species. Here, the sample was acidified and after HPLC separation/desalting over a short C4 column (GromSil 300 Butyl-1 ST, 5 µm, 5 mm×500 µm), analysed by mass spectrometry using an ESI-MicroTofQ System (Bruker Daltonik). All spectra over the signal in the TIC (Total Ion Chromatogram) were added and the molecular weight of the different conjugate species was calculated based on MaxEnt deconvolution. The DAR (=drug/antibody ratio) was then calculated out of the sum of toxophor number weighted coupled species divided by the sum of the singly weighted integration results of each species.

In addition, based on the species distribution the homogeneity (prercentage of D2>85% for DAR2) of the bTG coupling method could be exemplary demonstrated comparing four different preparations of example 5A in the following table.

TABLE distribution comparison of four different preparations of example 5A (DAR2)

| Example 5A | Conc. | | % distribution | | |
|---|---|---|---|---|---|
| Prep. No | [mg/mL] | DAR | D0 | D1 | D2 |
| prep. 4 | 1.6 | 1.9 | 0.5 | 9.8 | 89.7 |
| prep. 6 | 1.4 | 2.0 | 0.3 | 2.9 | 96.8 |
| prep. 7 | 1.6 | 1.9 | 0.5 | 12.0 | 87.5 |
| prep. 11 | 1.5 | 1.9 | 0.5 | 7.9 | 91.6 |

A comparable homogeneous distribution can be received with other bTG coupled Toxophor-Linker constructs. This was exemplary demonstrated at four different ADC compounds in the following table.

TABLE distribution of four different ADC examples (DAR2)

| | Conc. | | % distribution | | | |
|---|---|---|---|---|---|---|
| Example | [mg/mL] | DAR | D0 | D1 | D2 | D3 |
| 5A | 1.4 | 2.0 | 0.3 | 2.9 | 96.8 | |
| 13A | 2.1 | 1.8 | 2.4 | 12.8 | 84.8 | |
| 8A | 1.7 | 1.9 | | 8.0 | 90.8 | 1.2 |
| 9A | 1.8 | 2.0 | | 7.7 | 89.7 | 2.6 |

Based on a N297Q substitution within an Antibody a bTG based coupling with a result of DAR4 is possible. The homogeneity of this ADC's (percentage of D4>70%) and transferability on different antibodies was exemplary demonstrated at three different ADC compounds in the following table.

TABLE distribution of two different ADC examples (DAR4)

| | Conc. | | % distribution | | | | | |
|---|---|---|---|---|---|---|---|---|
| Example | [mg/mL] | DAR | D0 | D1 | D2 | D3 | D4 | D5 | D6 |
| 6a4 | 1.63 | 4.1 | | | 0.8 | 3.4 | 77.6 | 18.2 | |
| 10e4 | 1.56 | 3.9 | | | 2.4 | 6.7 | 89.1 | 1.8 | |

Alternatively, the toxophor loading of glutamine-linked conjugates was determined by reversed-phase chromatography of the reduced and denatured ADCs. Guanidinium hydrochloride (GuHCl) (28.6 mg) and a solution of DL-dithiothreitol (DTT) (500 mM, 3 µl) were added to the ADC solution (1 mg/ml, 50 µl). The mixture was incubated at 55° C. for one hour and analysed by HPLC.

HPLC analysis was carried out on an Agilent 1260 HPLC system with detection at 220 nm. A Polymer Laboratories PLRP-S polymeric reversed-phase column (catalogue number PL1912-3802) (2.1×150 mm, 8 µm particle size, 1000 Å) was used at a flow rate of 1.2 ml/min with the following gradient: 0 min, 31% B; 1 min, 31% B; 14 min, 38% B; 16 min, 95% B. Mobile phase A consisted of 0.05% trifluoroacetic acid (TFA) in water, mobile phase B of 0.05% trifluoroacetic acid in acetonitrile.

The detected peaks were assigned by retention time comparison with the light chain (L0) and the heavy chain (H0) of the non-conjugated antibody. Peaks detected exclusively in the conjugated sample were assigned to the heavy chains with one or two toxophors (H1, H2).

Average loading of the antibody with toxophors was calculated from the peak areas determined by integration as double the sum of the HC-Load and the LC-load, whereas the HC-load is the sum of toxophor number weighted integration results of all heavy chain (HC)-peaks divided by the sum of the singly weighted integration results of the HC-peaks and whereas the LC-load is the sum of toxophor number weighted integration results of the light chain (LC)-peaks divided by the sum of the singly weighted integration results of all LC peaks.

B-6. Checking the Antigen-Binding of the ADCs

The capability of the binder of binding to the target molecule was checked after coupling had taken place. The person skilled in the art is familiar with multifarious methods which can be used for this purpose; for example, the affinity of the conjugate can be checked using ELISA technology or surface plasmon resonance analysis (BIAcore™ measurement). The conjugate concentration can be measured by the person skilled in the art using customary methods, for example for antibody conjugates by protein determination. (see also Doronina et al.; Nature Biotechnol. 2003; 21:778-784 and Polson et al., Blood 2007; 1102:616-623).

Working Examples ADCs

The Following Examples were Synthesized Following General Procedure C for Transglutaminase Coupling (See Chapter B-4)

Example 1A

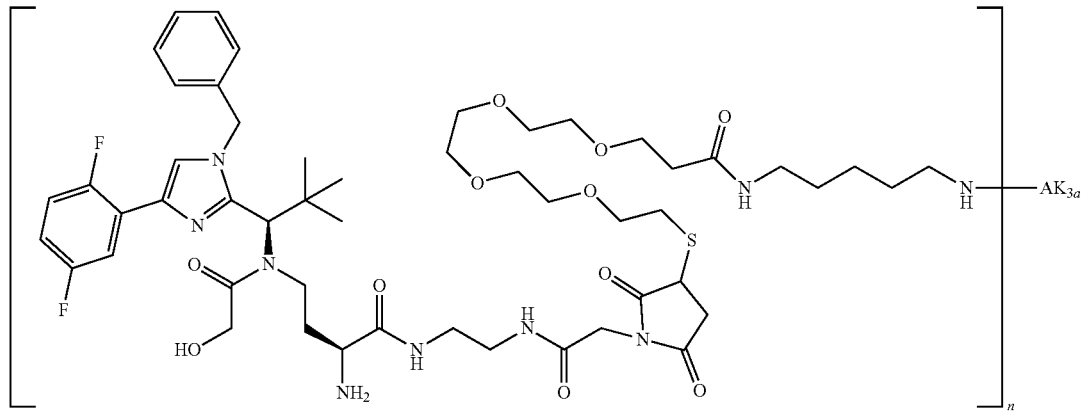

Here, 2250 µL DPBS pH 7.4, 200 µL of a solution of intermediate F1 (10 mM in DMSO), and 50 µL of a solution of recombinant microbial (bacterial) transglutaminase (Product number T001 from Zedira GmbH, Darmstadt, Germany) (100 U/mL) were added to 2500 µL of a solution of the antibody TPP-2090-HC-N297A (2 mg/mL). The reaction mixture was incubated at 37° C. for 24 hours. The ADC was purified by gel filtration chromatography on a Superdex 200 column (GE Healthcare) in DPBS pH 7.4 to remove small molecules and the transglutaminase from the ADC, and finally concentrated using Amicon Ultracel-30K centrifugation devices (Millipore).

Protein concentration: 1.65 mg/ml

Drug/mAb ratio: 1.9

Example 1A4

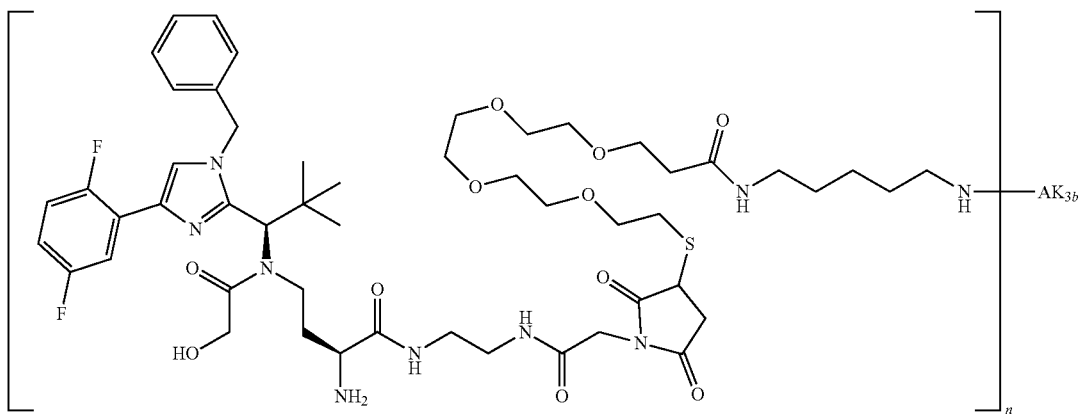

Here, 450 µL DPBS pH 7.4, 40 µL of a solution of intermediate F1(10 mM in DMSO), and 10 µL of a solution of recombinant microbial (bacterial) transglutaminase (Product number T001 from Zedira GmbH, Darmstadt, Germany) (100 U/mL) were added to 500 µL of a solution of the antibody TPP-2090-HC-N297Q (2 mg/mL). The reaction mixture was incubated at 37° C. for 24 hours and afterwards directly analyzed for drug antibody ratio without further purification.

Protein concentration in the reaction mixture: 1 mg/ml
Drug/mAb ratio: 3.5

Example 2A

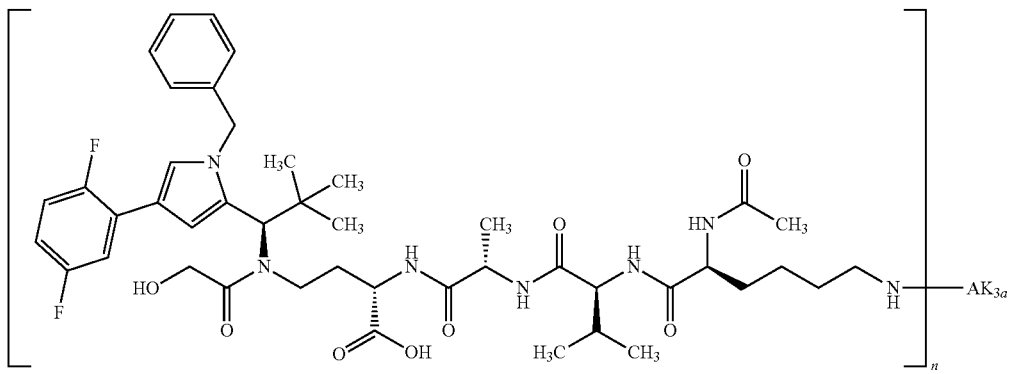

50 µL DPBS pH 7.4, 40 µL of a solution of intermediate F2 (10 mM in DMSO), and 10 µL of a solution of recombinant microbial (bacterial) transglutaminase (Product number T001 from Zedira GmbH, Darmstadt, Germany) (100 U/mL) were added to 500 µL of a solution of the antibody TPP-2090-HC-N297A (2 mg/mL). The reaction mixture was incubated at 37° C. for 24 hours. The ADC was purified by gel filtration chromatography on a Superdex 200 column (GE Healthcare) in DPBS pH 7.4 to remove small molecules and the transglutaminase from the ADC, and finally concentrated using Amicon Ultracel-30K centrifugation devices (Millipore).

Protein concentration: 1.26 mg/ml
Drug/mAb ratio: 1.6

Example 3A

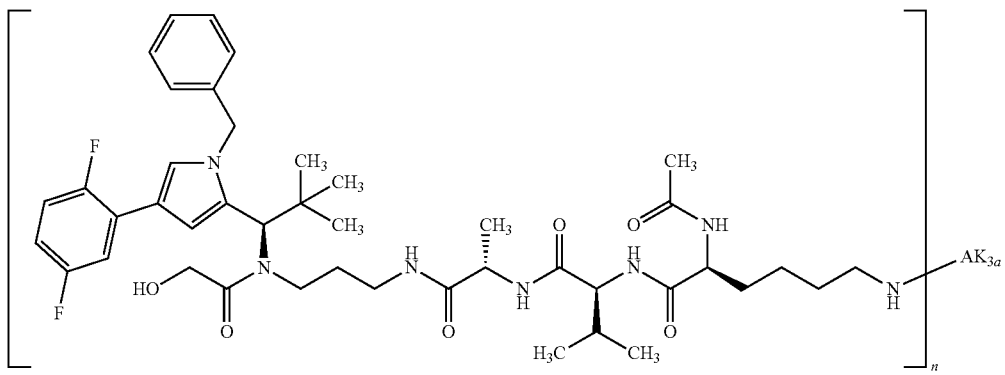

Here, 450 μL DPBS pH 7.4, 40 μL of a solution of intermediate F3 (10 mM in DMSO), and 10 μL of a solution of recombinant microbial (bacterial) transglutaminase (Product number T001 from Zedira GmbH, Darmstadt, Germany) (100 U/mL) were added to 500 μL of a solution of the antibody TPP-2090-HC-N297A (2 mg/mL). The reaction mixture was incubated at 37° C. for 24 hours. The ADC was purified by gel filtration chromatography on a Superdex 200 column (GE Healthcare) in DPBS pH 7.4 to remove small molecules and the transglutaminase from the ADC, and finally concentrated using Amicon Ultracel-30K centrifugation devices (Millipore).

Protein concentration: 1.06 mg/ml
Drug/mAb ratio: 2.0

Example 4A

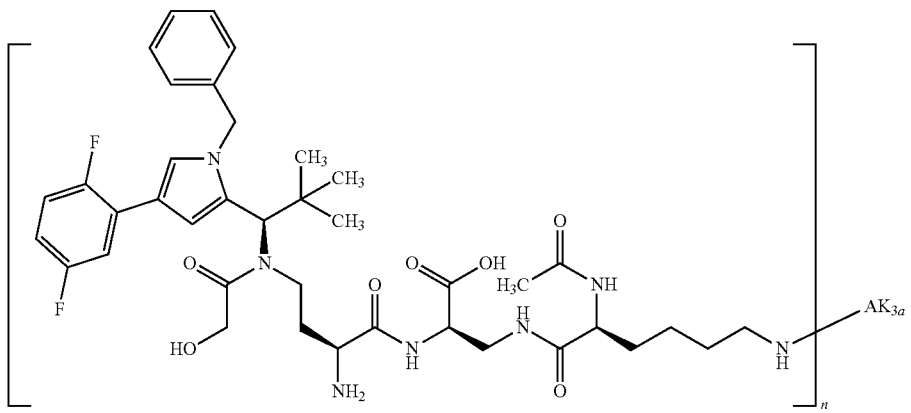

Here, 900 μL DPBS pH 7.4, 80 μL of a solution of intermediate F4 (10 mM in DMSO), and 20 μL of a solution of recombinant microbial (bacterial) transglutaminase (Product number T001 from Zedira GmbH, Darmstadt, Germany) (100 U/mL) were added to 1000 μL of a solution of the antibody TPP-2090-HC-N297A (2 mg/mL). The reaction mixture was incubated at 37° C. for 24 hours. The ADC was purified by gel filtration chromatography on a Superdex 200 column (GE Healthcare) in DPBS pH 7.4 to remove small molecules and the transglutaminase from the ADC, and finally concentrated using Amicon Ultracel-30K centrifugation devices (Millipore).

Protein concentration: 2.18 mg/ml
Drug/mAb ratio: 1.7

Example 5A

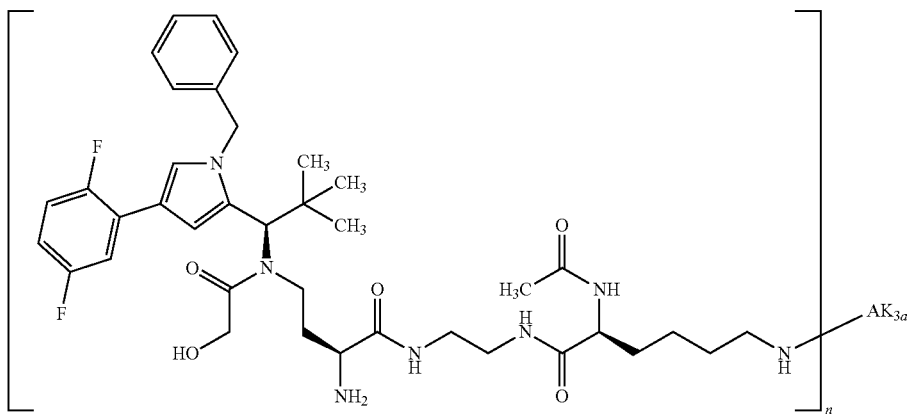

Here, 900 μL DPBS pH 7.4, 80 μL of a solution of intermediate F5 (10 mM in DMSO), and 20 μL of a solution of recombinant microbial (bacterial) transglutaminase (Product number T001 from Zedira GmbH, Darmstadt, Germany) (100 U/mL) were added to 1000 μL of a solution of the antibody TPP-2090-HC-N297A (2 mg/mL). The reaction mixture was incubated at 37° C. for 24 hours. The ADC was purified by gel filtration chromatography on a Superdex 200 column (GE Healthcare) in DPBS pH 7.4 to remove small molecules and the transglutaminase from the ADC, and finally concentrated using Amicon Ultracel-30K centrifugation devices (Millipore).

Protein concentration: 2.24 mg/ml
Drug/mAb ratio: 1.9

Example 6A

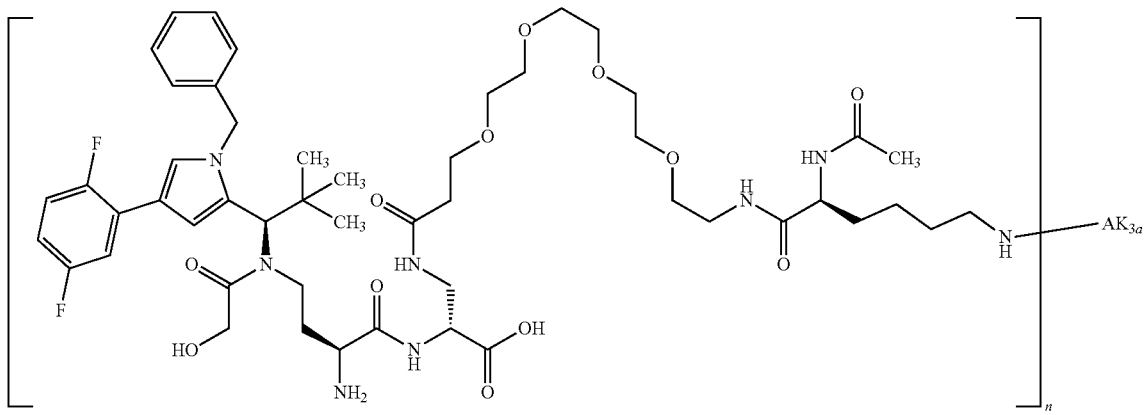

Here, 900 μL DPBS pH 7.4, 80 μL of a solution of intermediate F6 (10 mM in DMSO), and 20 μL of a solution of recombinant microbial (bacterial) transglutaminase (Product number T001 from Zedira GmbH, Darmstadt, Germany) (100 U/mL) were added to 1000 μL of a solution of the antibody TPP-2090-HC-N297A (2/mg/mL). The reaction mixture was incubated at 37° C. for 24 hours and afterwards directly analyzed for drug antibody ratio without further purification.

Protein concentration in the reaction mixture: 2.22 mg/ml
Drug/mAb ratio: 2.0

The Following Examples were Synthesized Following General Procedure A or B for Transglutaminase Coupling in 5 mg Scale and Following Procedures C or D in Larger Scale (See Chapter B-4)

Example 2A

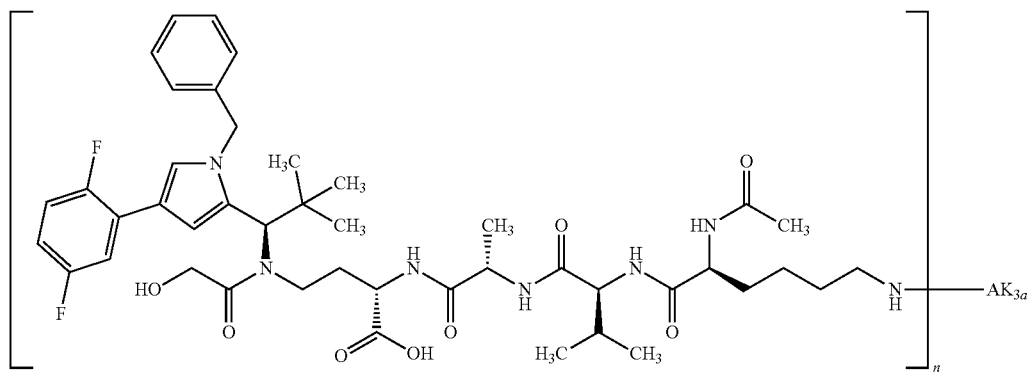

Precursor: F2, general procedure A, anti-TWEAKR antibody TPP-2658 (equal to TPP-2090-HC-N297A)
Protein concentration: 1.66 mg/ml
Drug/mAb ratio: 1.7

Example 3A

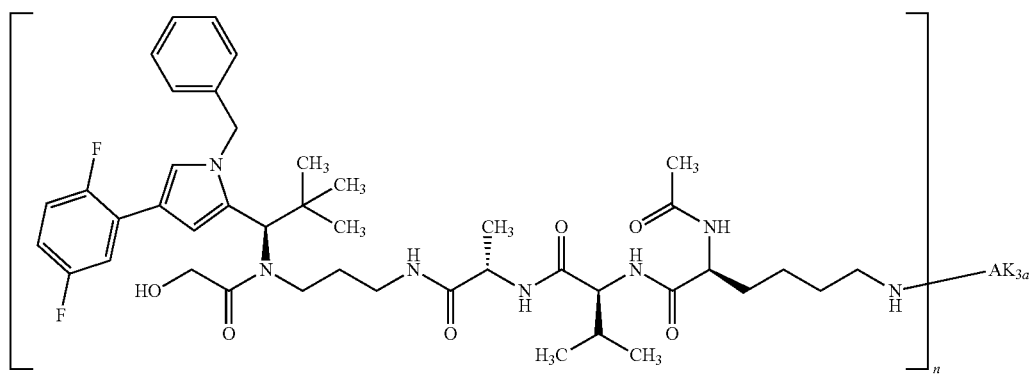

Precursor: F3, general procedure A, anti-TWEAKR antibody TPP-2658 (equal to TPP-2090-HC-N297A)
Protein concentration: 1.71 mg/ml
Drug/mAb ratio: 1.8

Example 4A
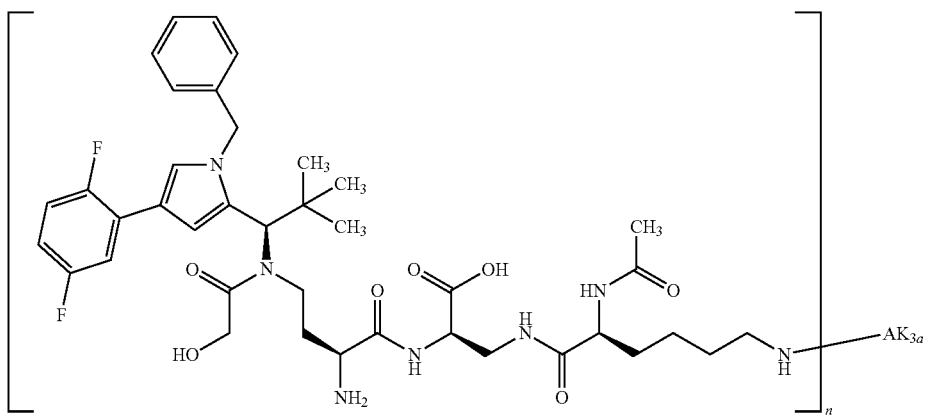
Precursor: F4, general procedure A, anti-TWEAKR antibody TPP-2658 (equal to TPP-2090-HC-N297A)
Protein concentration: 1.71 mg/ml
Drug/mAb ratio: 1.8
Example 4A4
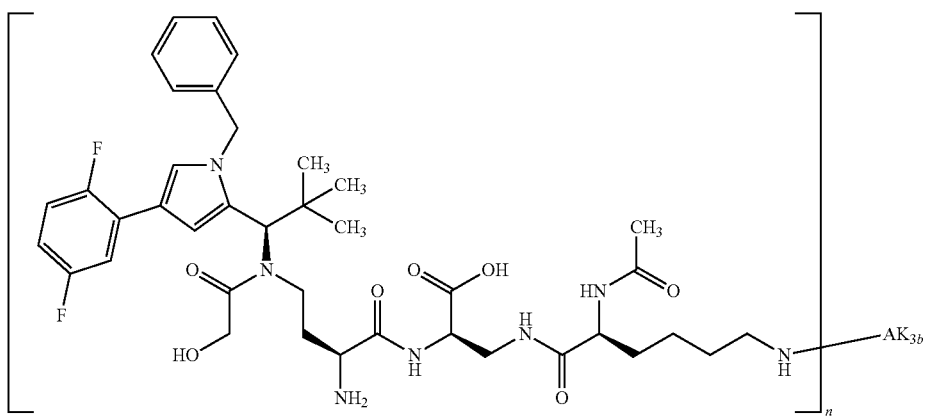
Precursor: F4, general procedure B, anti-TWEAKR antibody TPP-5442 (equal to TPP-2090-HC-N297Q)
Protein concentration: 1.49 mg/ml
Drug/mAb ratio: 3.4

Example 5A

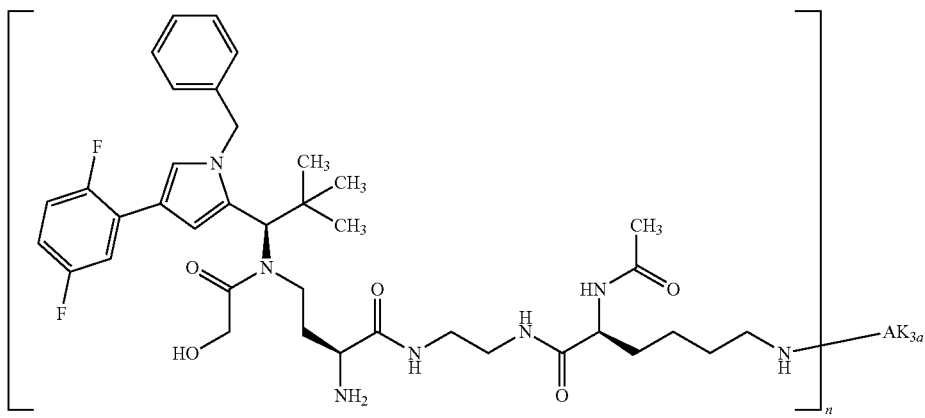

Precursor: F5, general procedure A, anti-TWEAKR antibody TPP-2658 (equal to TPP-2090-HC-N297A)
Protein concentration: 1.35 mg/ml
Drug/mAb ratio: 2.0
Coupling of this ADC was also performed in 30 mg scale following the general procedure C in chapter B4:
Protein concentration: 11.2 mg/ml
Drug/mAb ratio: 2.0

Example 5A4

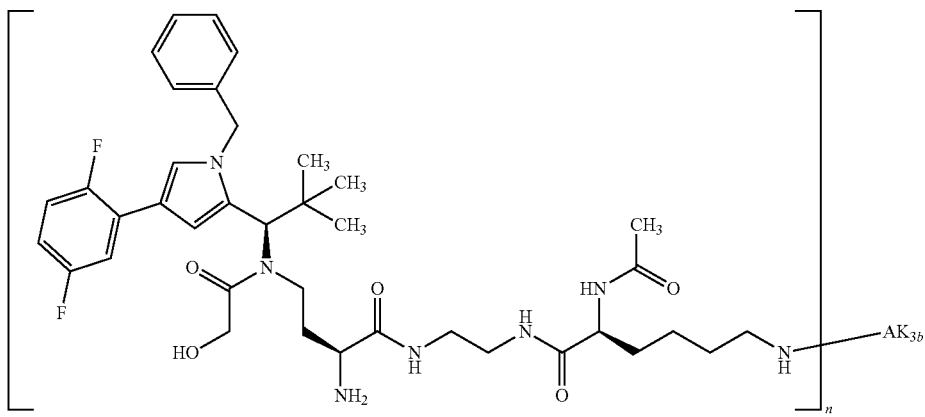

Precursor: F5, general procedure B, anti-TWEAKR antibody TPP-5442 (equal to TPP-2090-HC-N297Q)
Protein concentration: 0.83 mg/ml
Drug/mAb ratio: 3.6
Coupling of this ADC was also performed in 30 mg scale following the general procedure D in chapter B4:
Protein concentration: 10.0 mg/ml
Drug/mAb ratio: 3.8

Example 5E
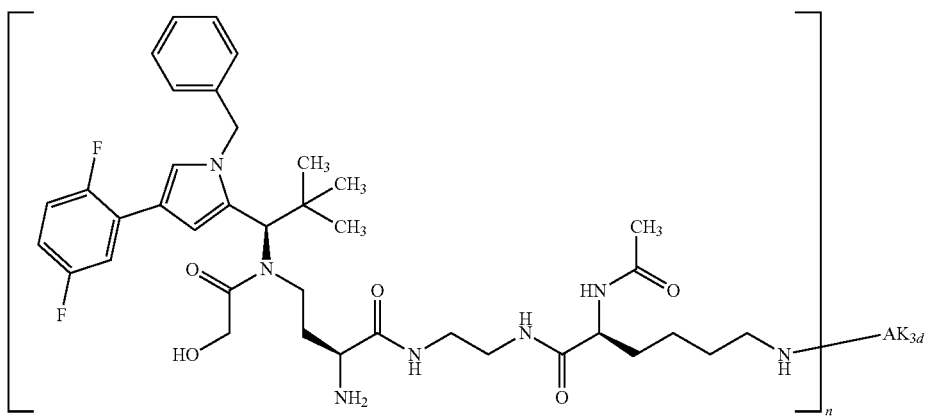
Precursor: F5, general procedure A, Trastuzumab-HC-N297A (equal to TPP-7510)
Protein concentration: 2.44 mg/ml
Drug/mAb ratio: 1.6
Example 5E4
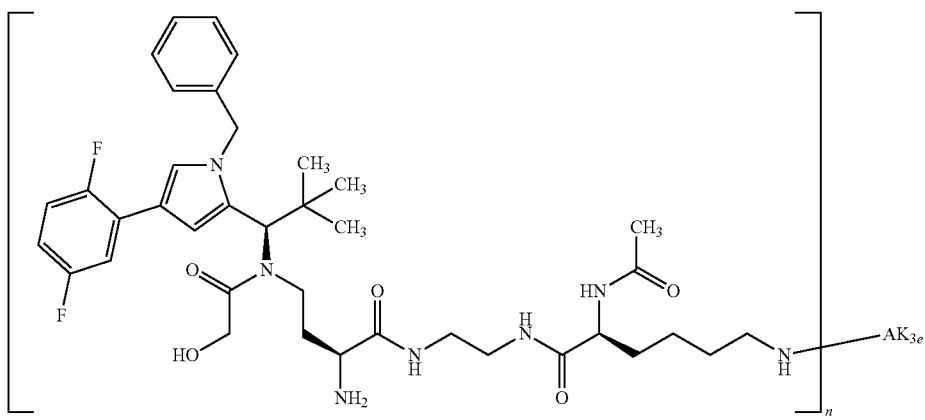
Precursor: F5, general procedure B, Trastuzumab-HC-N297Q (equal to TPP-7511)
Protein concentration: 2.85 mg/ml
Drug/mAb ratio: 3.6

Example 6A

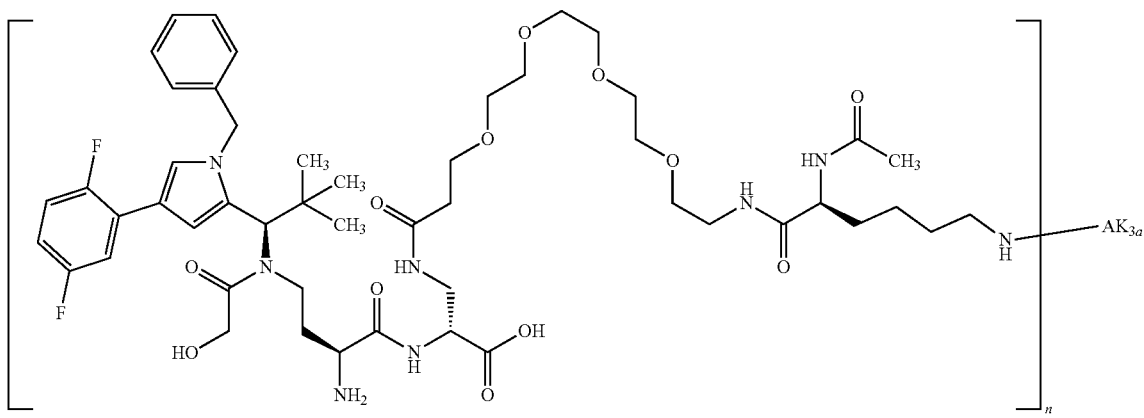

Precursor: F6, general procedure A, anti-TWEAKR antibody TPP-2658 (equal to TPP-2090-HC-N297A)
Protein concentration: 1.63 mg/ml
Drug/mAb ratio: 1.8
Coupling of this ADC was also performed in 30 mg scale following the general procedure C in chapter B4:
Protein concentration: 13.2 mg/ml
Drug/mAb ratio: 1.9

Example 6A4

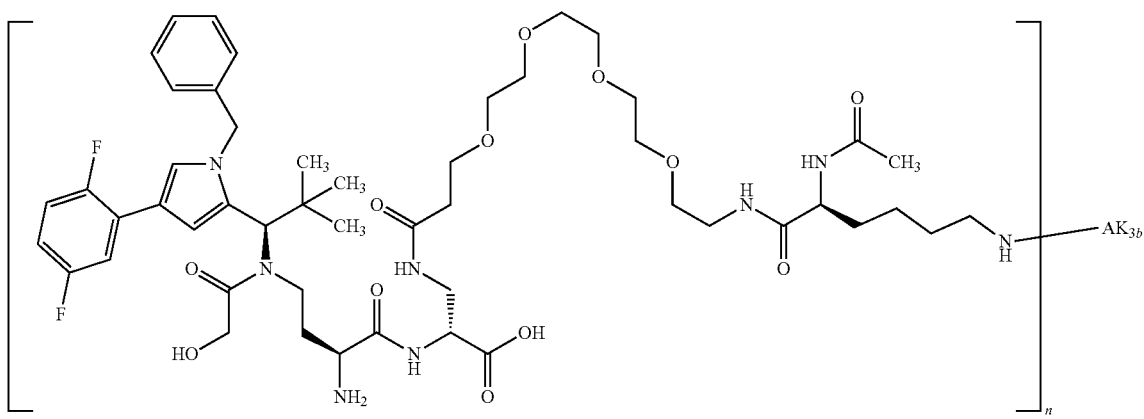

Precursor: F6, general procedure B, anti-TWEAKR antibody TPP-5442 (equal to TPP-2090-HC-N297Q)
Protein concentration: 1.63 mg/ml
Drug/mAb ratio: 4.1
Coupling of this ADC was also performed in 30 mg scale following the general procedure D in chapter B4:
Protein concentration: 11.8 mg/ml
Drug/mAb ratio: 3.7

Example 7A
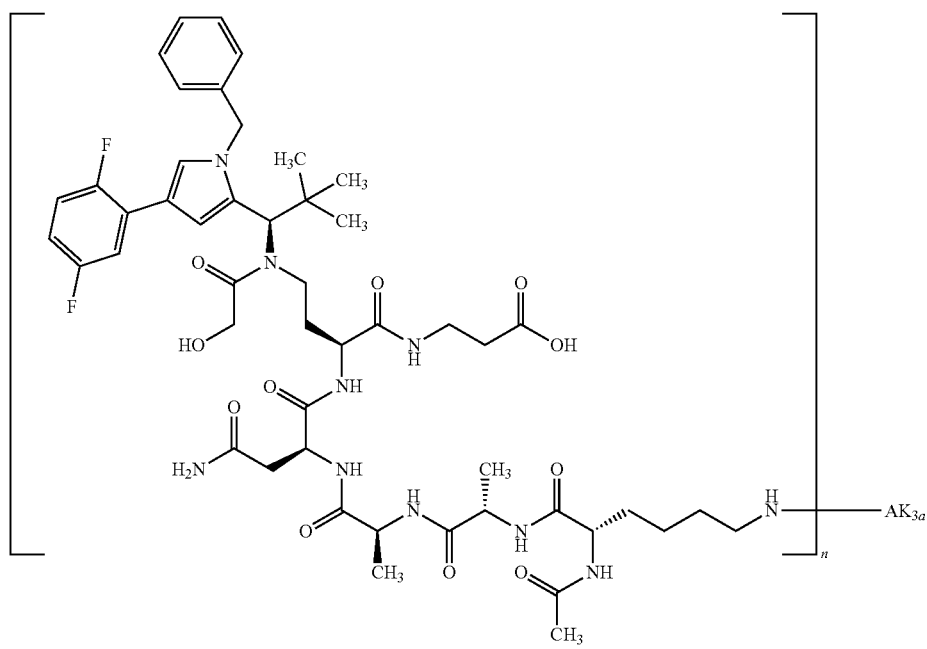
Precursor: F7, general procedure A, anti-TWEAKR antibody TPP-2658 (equal to TPP-2090-HC-N297A)
Protein concentration: 1.66 mg/ml
Drug/mAb ratio: 1.9
Example 8A
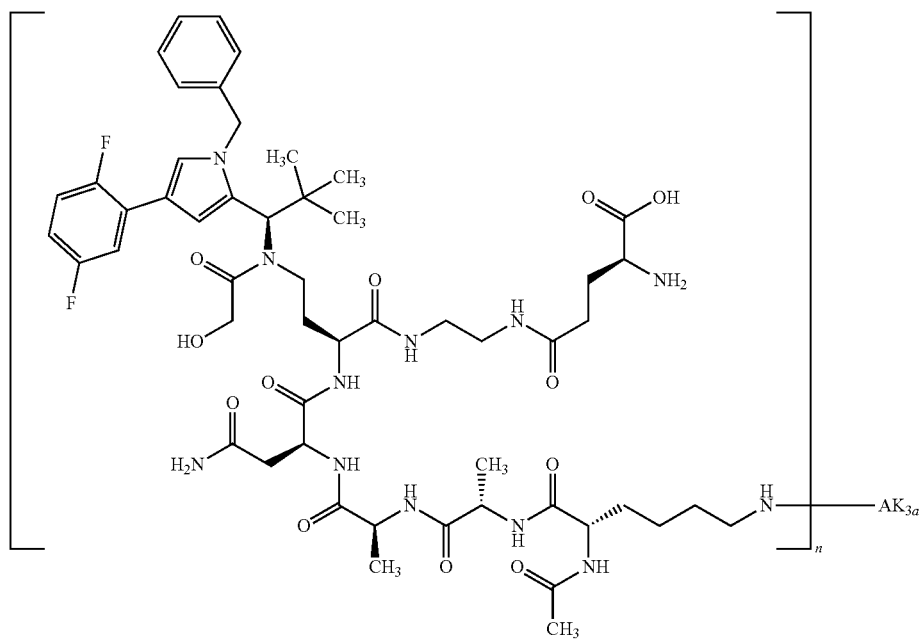
Precursor: F8, general procedure A, anti-TWEAKR antibody TPP-2658 (equal to TPP-2090-HC-N297A)
Protein concentration: 1.68 mg/ml
Drug/mAb ratio: 1.9

Example 9A
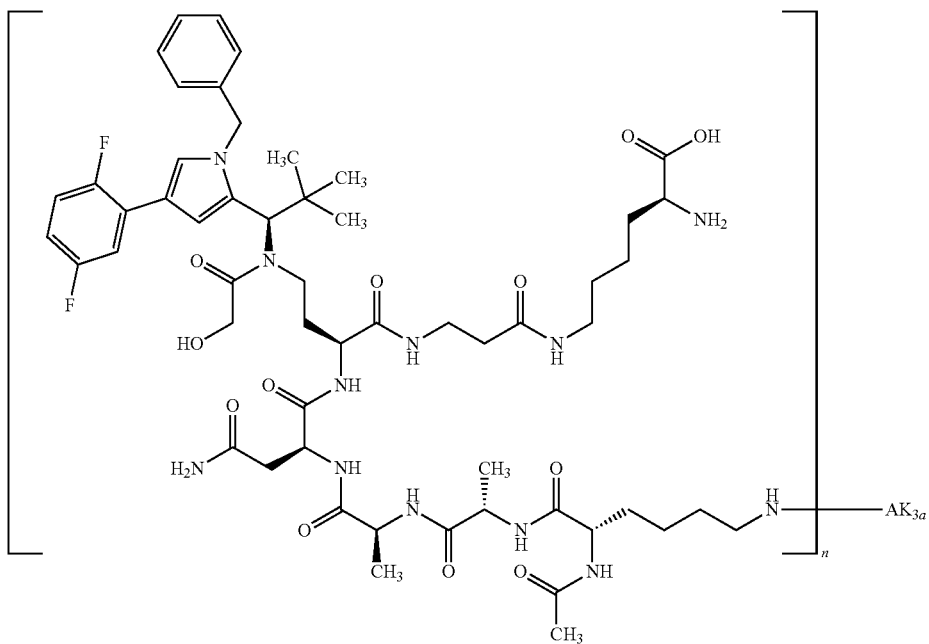
Precursor: F9, general procedure A, anti-TWEAKR antibody TPP-2658 (equal to TPP-2090-HC-N297A)
Protein concentration: 1.8 mg/ml
Drug/mAb ratio: 2.0
Example 10A
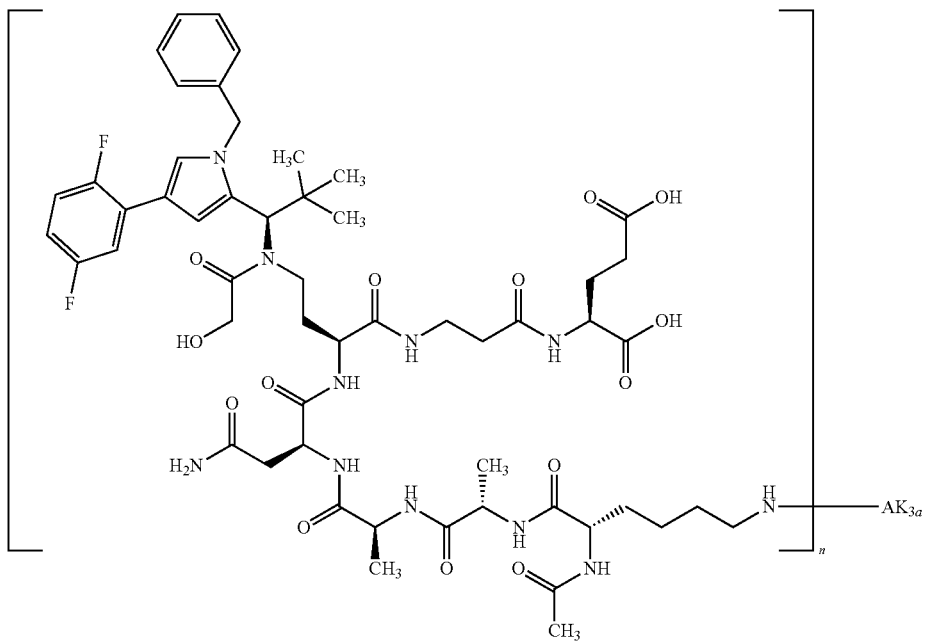
Precursor: F10, general procedure A, anti-TWEAKR antibody TPP-2658 (equal to TPP-2090-HC-N297A)
Protein concentration: 1.73 mg/ml
Drug/mAb ratio: 1.8

Example 10A4
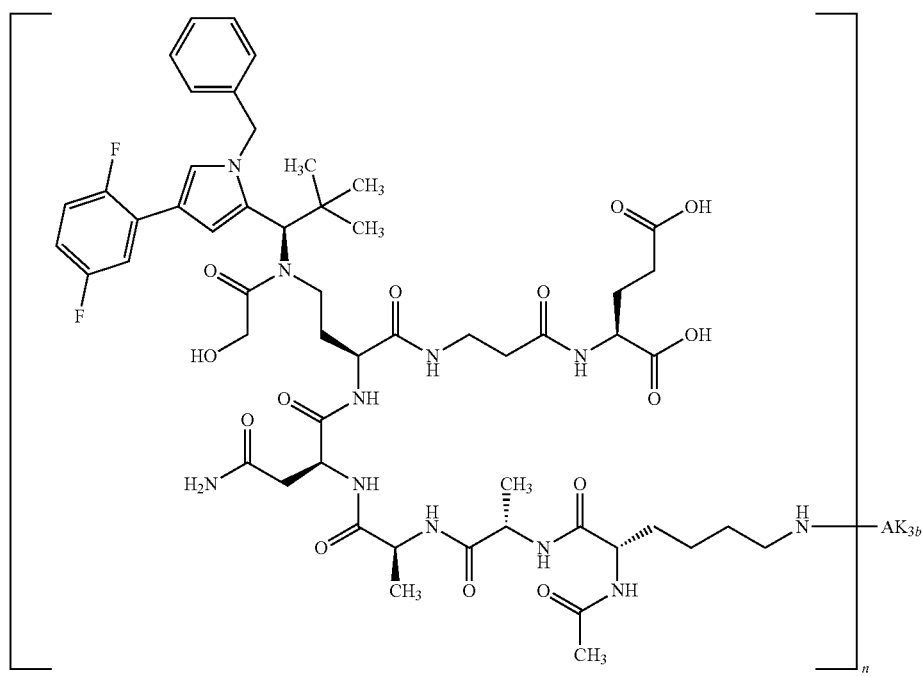
Precursor: F10, general procedure B, anti-TWEAKR antibody TPP-5442 (equal to TPP-2090-HC-N297Q)
Protein concentration: 1.76 mg/ml
Drug/mAb ratio: 3.9
Example 10E4
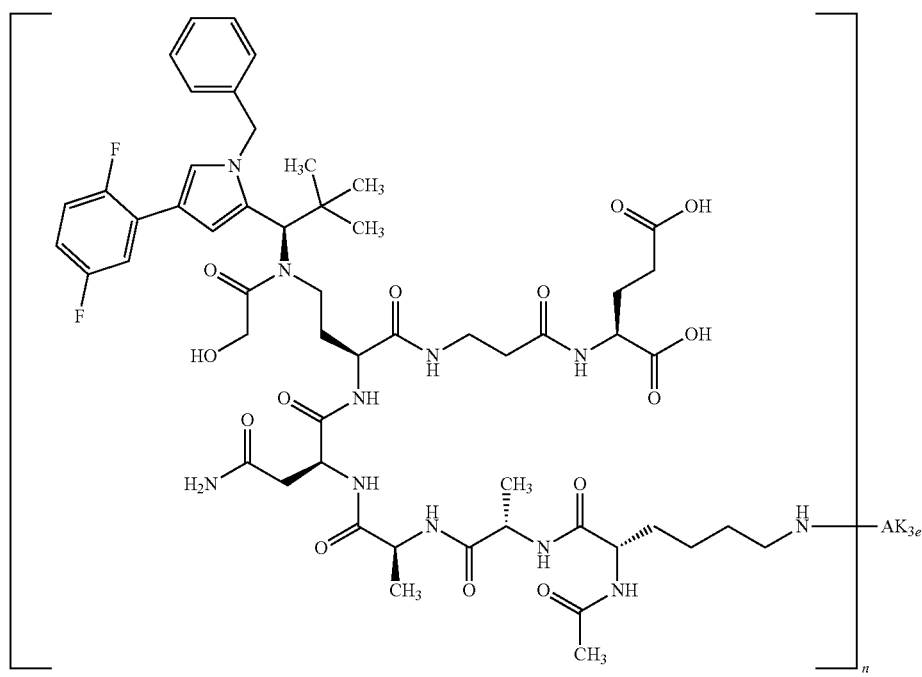
Precursor: F10, general procedure B, Trastuzumab-HC-N297Q (equal to TPP-7511)
Protein concentration: 1.56 mg/ml
Drug/mAb ratio: 3.9

333
Example 11A

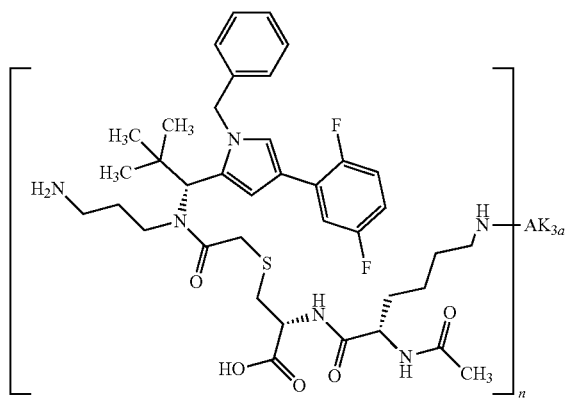

Precursor: F11, general procedure A, anti-TWEAKR antibody TPP-2658 (equal to TPP-2090-HC-N297A)
Protein concentration: 1.82 mg/ml
Drug/mAb ratio: 1.9

Example 11A4

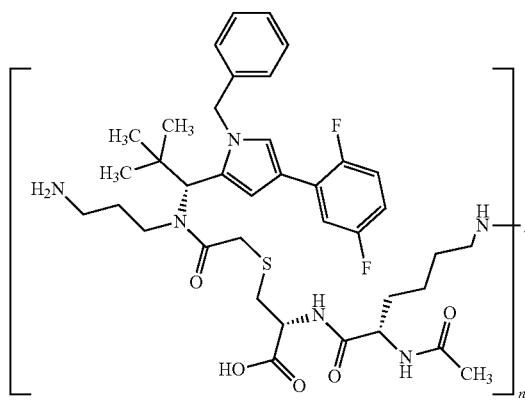

Precursor: F11, general procedure B, anti-TWEAKR antibody TPP-5442 (equal to TPP-2090-HC-N297Q)
Protein concentration: 1.1 mg/ml
Drug/mAb ratio: 3.6

334
Example 11E4

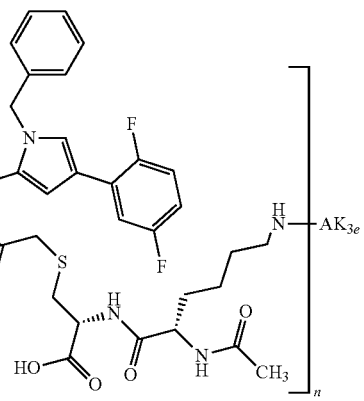

Precursor: F11, general procedure B, Trastuzumab-HC-N297Q (equal to TPP-7511).
Protein concentration: 1.75 mg/ml
Drug/mAb ratio: 3.8

Example 12A

Precursor: F12, general procedure A, anti-TWEAKR antibody TPP-2658 (equal to TPP-2090-HC-N297A)
Protein concentration: 1.77 mg/ml
Drug/mAb ratio: 1.8

Example 13A

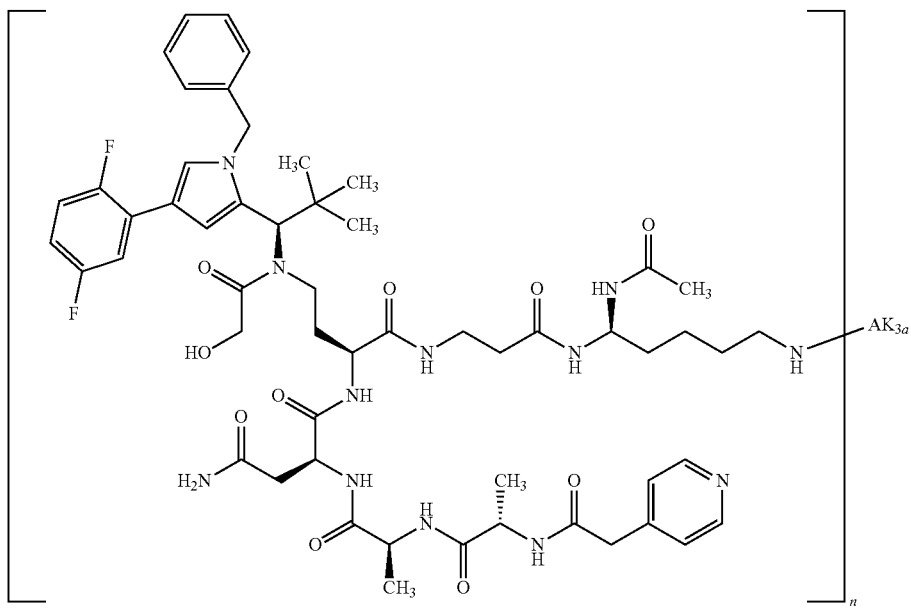

Precursor: F13, general procedure A, anti-TWEAKR antibody TPP-2658 (equal to TPP-2090-HC-N297A)
Protein concentration: 2.11 mg/ml
Drug/mAb ratio: 1.8
Coupling of this ADC was also performed in 30 mg scale following the general procedure C in chapter B4:
Protein concentration: 11.88 mg/ml
Drug/mAb ratio: 2.0

Example 13A4

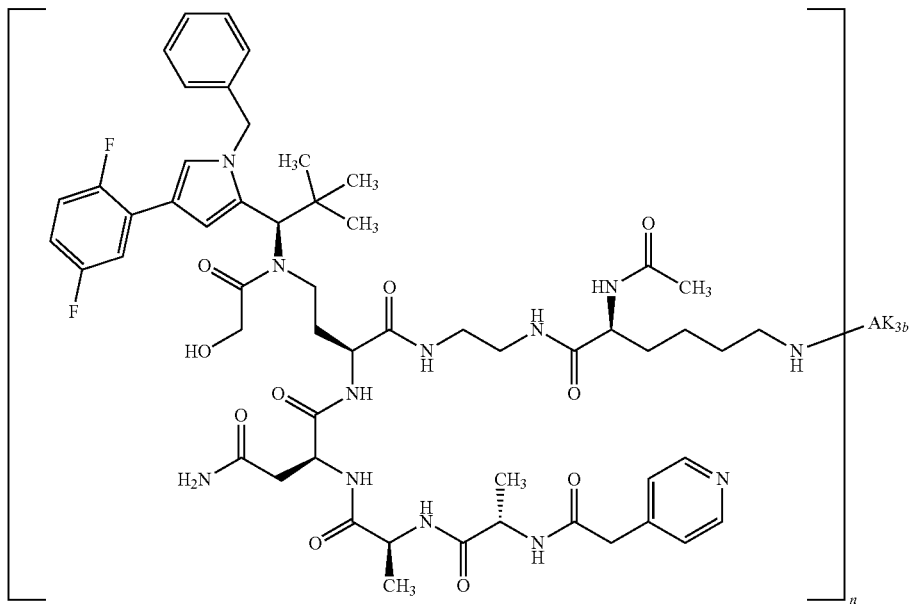

Precursor: F13, general procedure D, anti-TWEAKR antibody TPP-5442 (equal to TPP-2090-HC-N297Q)
Coupling of this ADC was performed in 30 mg scale following the general procedure C in chapter B4:
Protein concentration: 12.0 mg/ml
Drug/mAb ratio: 3.8

Example 14A
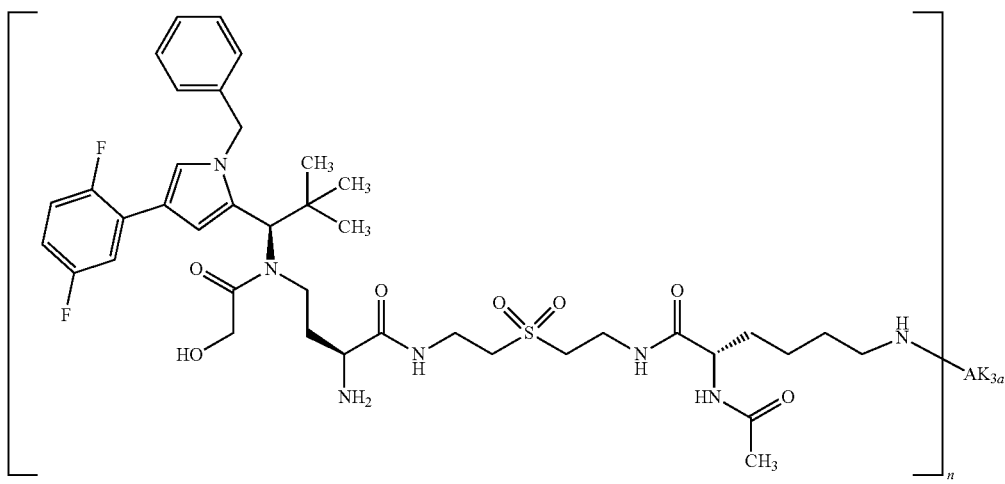
Precursor: F14, general procedure A, anti-TWEAKR antibody TPP-2658 (equal to TPP-2090-HC-N297A)
Protein concentration: 1.58 mg/ml
Drug/mAb ratio: 1.7
Example 15A4
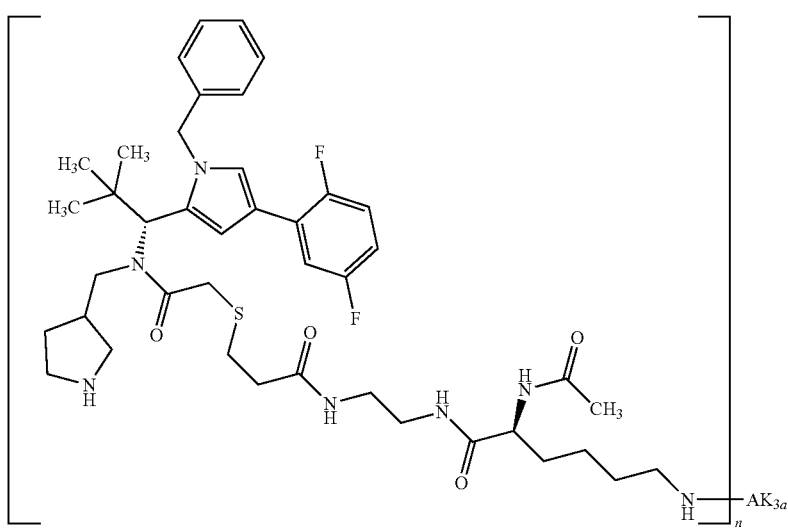
Precursor: F15, general procedure B, anti-TWEAKR antibody TPP-5442 (equal to TPP-2090-HC-N297Q)
Protein concentration: 1.05 mg/ml
Drug/mAb ratio: 3.6

Example 16A4
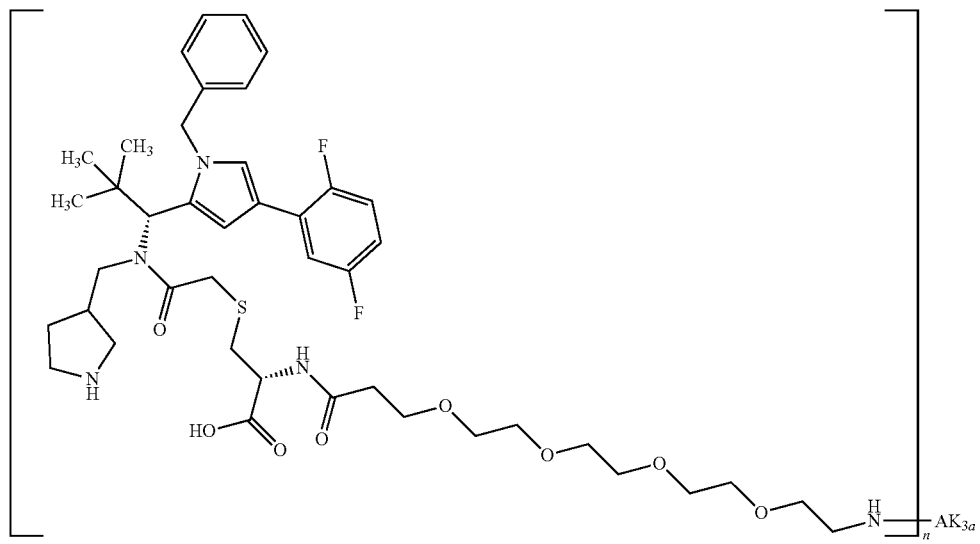
Precursor: F16, general procedure B, anti-TWEAKR antibody TPP-5442 (equal to TPP-2090-HC-N297Q)
Protein concentration: 1.78 mg/ml
Drug/mAb ratio: 3.8
Example 16E4
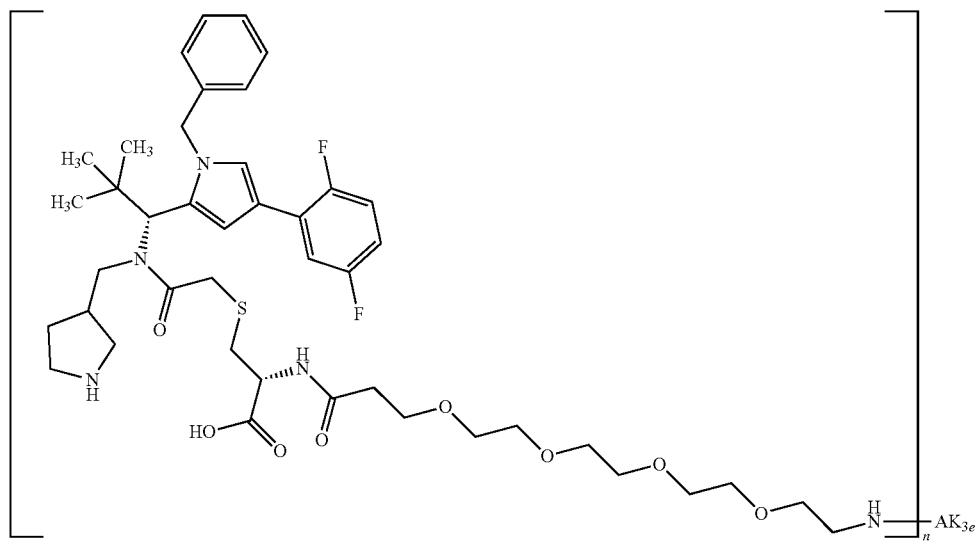
Precursor: F16, general procedure B, Trastuzumab-HC-N297Q (equal to TPP-7511)
Protein concentration: 1.82 mg/ml
Drug/mAb ratio: 3.8

Example 17A4
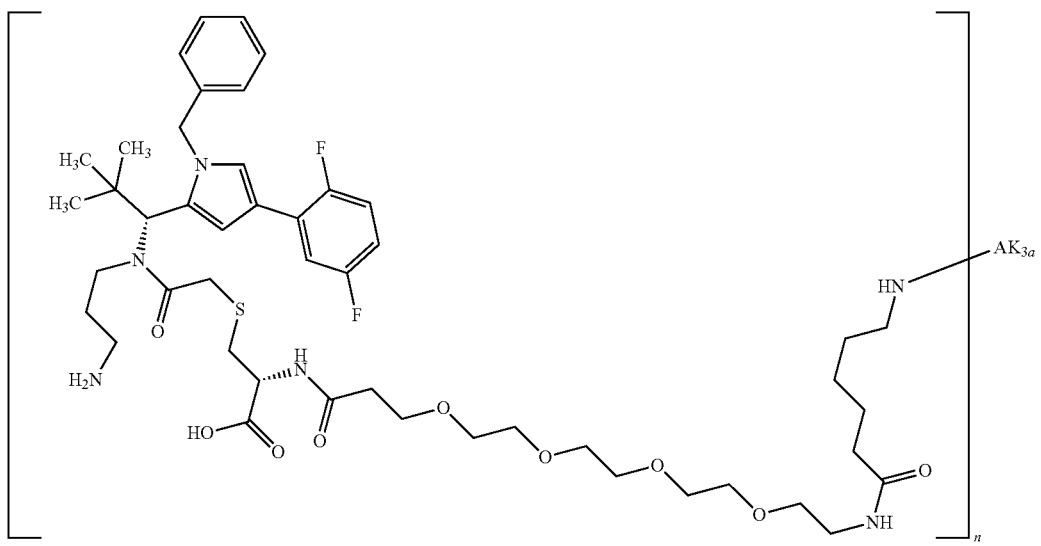
Precursor: F17, general procedure B, anti-TWEAKR antibody TPP-5442 (equal to TPP-2090-HC-N297Q)
  Protein concentration: 1.71 mg/ml
  Drug/mAb ratio: 3.8
Example 17E4
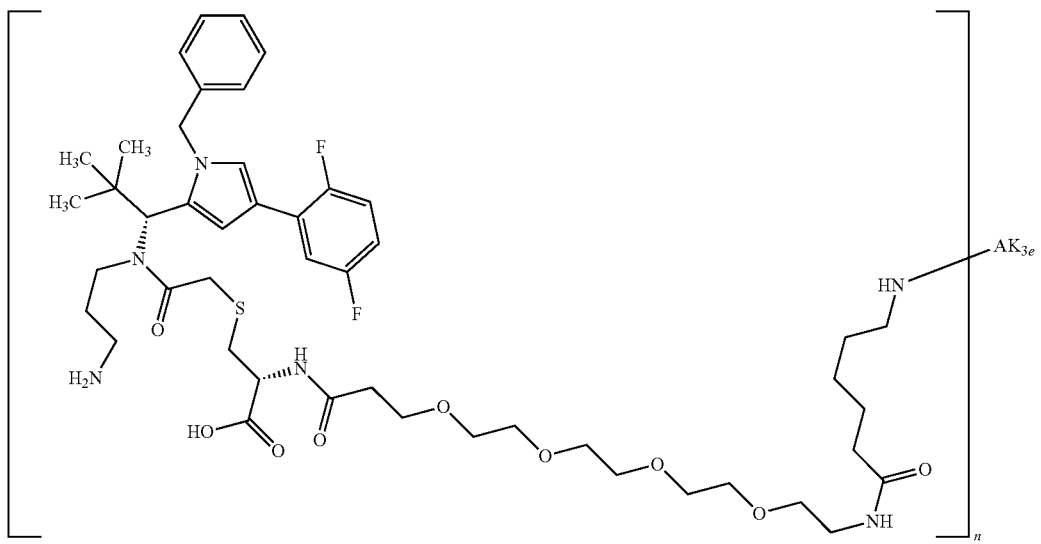
Precursor: F17, general procedure B, Trastuzumab-HC-N297Q (equal to TPP-7511)
  Protein concentration: 1.90 mg/ml
  Drug/mAb ratio: 3.8

Example 18A4
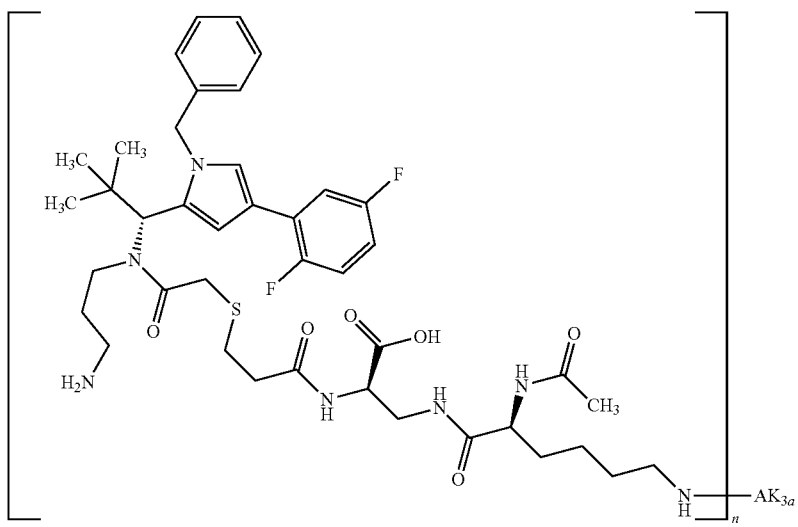
Precursor: F18, general procedure B, anti-TWEAKR antibody TPP-5442 (equal to TPP-2090-HC-N297Q)
Protein concentration: 1.07 mg/ml
Drug/mAb ratio: 3.7
Example 19A4
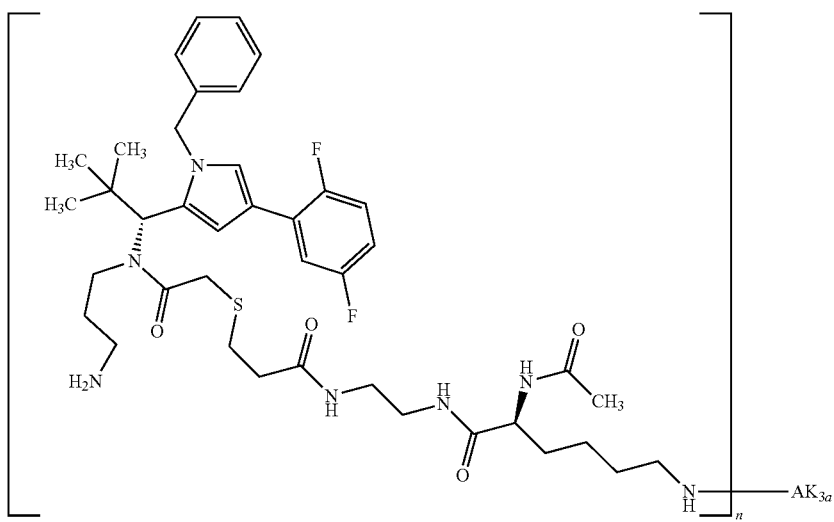
Precursor: F19, general procedure B, anti-TWEAKR antibody TPP-5442 (equal to TPP-2090-HC-N297Q)
Protein concentration: 0.92 mg/ml
Drug/mAb ratio: 3.3

Metabolite Example M100

N[6]-L-gamma-glutamyl-N[2]-acetyl-N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-L-lysinamide trifluoro acetate (1:1)

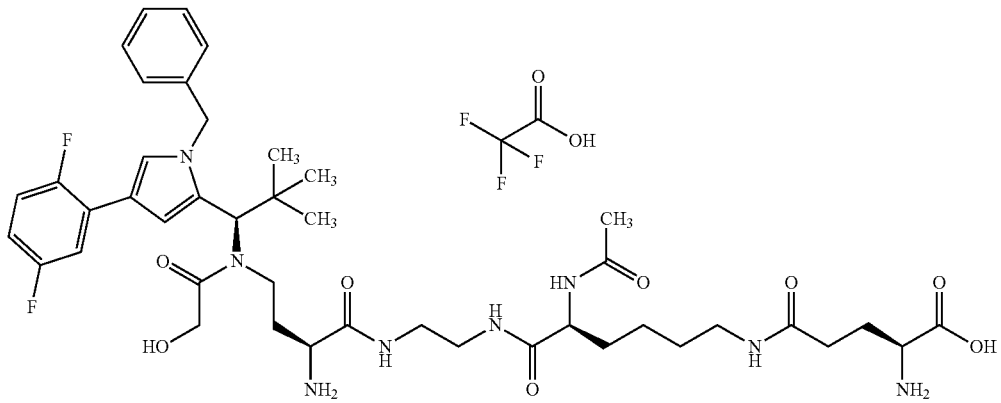 [SMILES: CC(=O)N[C@@H](CCCCNC(=O)CC[C@H](N)C(=O)O)C(=O)NCCNC(=O)[C@@H](N)CCN(C(=O)CO)[C@@H](c1cc(-c2cc(F)ccc2F)cn1Cc1ccccc1)C(C)(C)C ; O=C(O)C(F)(F)F]

First intermediate C58 was coupled with intermediate L12 in DMF in the presence of HATU and N,N-diisopropylethylamine; subsequently the Teoc-protecting group was cleaved using 4 equivalents of zinc chloride in 2,2,2 trifluoroethanol under heating for 2 h to 50° C. and after addition of 4 equivalents of EDTA the product was purified by HPLC. Finally the Z protecting group and the benzyl ester were cleaved by hydrogenation in methanol over 10% palladium/activated charcoal under normal pressure.

LC-MS (Method 1): $R_t$=0.74 min; MS (ESIpos): m/z=855 (M+H)$^+$.

C: ASSESSMENT OF BIOLOGICAL EFFICACY

The biological activity of the compounds according to the invention can be shown in the assays described below:

C-1a Determination of the Cytotoxic Effects of the ADCs Directed Against TWEAKR

The analysis of the cytotoxic effects of the anti-TWEAKR-ADCs was carried out with various cell lines:

NCI-H292: human mucoepidermoid lung carcinoma cells, ATCC-CRL-1848, standard medium: RPMI 1640 (Biochrom; #FG1215, stab. glutamine)+10% FCS (Biochrom; #S0415), TWEAKR-positive, EGFR-positive.

SK-HEP-1: human liver carcinoma cells, ATCC No. HTB-52, standard medium: MEM with Earle's salt+Glutamax I (Invitrogen 41090)+10% heat inactivated FCS (Fa. gibco, No. 10500-064); EGFR-positive, TWEAKR positive.

LoVo: human colorectal carcinoma cells, ATCC No. CCL-229, standard medium: Kaighn's+L-Glutamin (Invitrogen 21127)+10% heat inactivated FCS (Fa. gibco, No. 10500-064), TWEAKR-positive BxPC3: human pancreas carcinoma cells, ATCC-CRL-1687, standard medium: RPMI 1640 (Biochrom; #FG1215, stab. glutamine)+10% FCS (Biochrom; #S0415), TWEAKR-positive.

KPL4: human breast carcinoma cells, standard medium: RPMI 1640+GlutaMAX I+10% FBS, cell bank, Bayer Pharma AG (identity checked and confirmed on 19 Jul. 2012 at DSMZ), Berlin, ERBB2-positive.

The cells are cultivated by a standard method, as indicated in the American Tissue Type Collection (ATCC) for the respective cell lines.

MTT Assay

The test was carried out by detaching the cells with a solution of Accutase in PBS (Biochrom AG #L2143), pelleting, resuspending in culture medium, counting and seeding the cells into a 96-well culture plate with white bottom (Costar #3610, LoVo:1000 cells/well, SK-HEP-1:1200 cell/well, NCI H292: 1500 cell/well in a total volume of 100 µL). The cells were then incubated in an incubator at 37° C. and 5% carbon dioxide. After 48 h, the antibody drug conjugates were added in 10 µL of culture medium in concentrations of from 10$^{-5}$M to 10$^{-13}$M to the cells (triplicates) and incubated in an incubator at 37° C. and 5% carbon dioxide. After 96 h, the proliferation was measured using the MTT assay (ATCC, Manassas, Va., USA, catalogue No. 30-1010K). At the end of the selected incubation time, the MTT reagent was added and incubated with the cells for 4 h, followed by lysis of the cells overnight by addition of the detergent. The dye formed was detected at 570 nm (Infinite M1000 pro, Fa. Tecan). Based on the measured data the IC$_{50}$ value was determined from the DRC (dose response curve). The proliferation of cells which were not treated with test substance but were otherwise treated identically was defined as the 100% value. The data derived from a selected example are summarized in Tabelle 1.

TABLE 1

| example | NCI-H292 IC$_{50}$ [M] MTT Assay | SK-HEP-1 IC$_{50}$ [M] MTT Assay |
|---|---|---|
| 1A | 1.19E−09 | 3.35E−09 |
| 2A | 5.00E−07 | 7.85E−08 |
| 3A | 4.34E−09 | 3.84E−08 |
| 4A | 5.90E−10 | 2.26E−10 |
| 4A4 | 2.99E−10 | 7.88E−11 |
| 5A | 2.20E−09 | 1.49E−09 |
| 5A4 | 8.26E−10 | 1.52E−10 |
| 6A | 3.98E−10 | 7.43E−10 |
| 6A4 | 1.07E−10 | 3.93E−11 |
| 7A | 5.00E−07 | 5.00E−07 |
| 8A | 3.07E−09 | 1.34E−09 |

TABLE 1-continued

| example | NCI-H292 IC$_{50}$ [M] MTT Assay | SK-HEP-1 IC$_{50}$ [M] MTT Assay |
|---|---|---|
| 9A | 2.09E-09 | 2.12E-09 |
| 10A | 8.51E-10 | 8.87E-10 |
| 10A4 | 1.84E-10 | 1.71E-10 |
| 11A | 3.12E-09 | 6.53E-10 |
| 11A4 | 3.61E-10 | 3.34E-11 |
| 12A | 3.18E-10 | 1.77E-10 |
| 13A | 1.50E-09 | 1.92E-09 |
| 14A | 2.49E-09 | 3.13E-09 |
| 15A4 | 1.31E-11 | 3.04E-11 |
| 16A4 | 2.26E-10 | 8.71E-11 |
| 17A4 | 1.84E-10 | 1.13E-10 |
| 18A4 | 4.53E-10 | 1.23E10 |
| 19A4 | 1.90E-10 | 4.03E-10 |

TABLE 2

| Beispiel | KPL4 IC$_{50}$ [M] MTT Assay |
|---|---|
| 5E | 5E-07 |
| 5E4 | 2.74E-10 |
| 10E4 | 3.29E-10 |
| 11E4 | 2.68E-11 |
| 16E4 | 5.21E-11 |
| 17E4 | 3.66E-11 |

C-1b Determination of the Inhibition of the Kinesin Spindle Protein KSP/Eg5

The motor domain of the human kinesin spindle protein KSP/Eg5 (from tebu-bio/Cytoskeleton Inc, No. 027EG01-XL) is incubated at a concentration of 10 nM with 50 µg/ml taxol-(from Sigma No. T7191-5MG) stabilized microtubuli (bovine or porcine, from tebu-bio/Cytoskeleton Inc) for 5 min at RT in 15 mM PIPES, pH 6.8 (5 mM MgCl$_2$ and 10 mM DTT, from Sigma). The freshly prepared mixture was aliquoted into a 384-well MTP. The inhibitors to be examined at concentrations of $1.0 \times 10^{-6}$ M to $1.0 \times 10^{-13}$ M and ATP (final concentration 500 µM, from Sigma) were then added. Incubation was carried out at RT for 2 h. ATPase activity was detected by detecting the inorganic phosphate formed using malachite green (from Biomol). After additon of the reagent, the assay was incubated at RT for 50 minutes prior to detection of the absorption at a wavelength of 620 nm. Monastrol (Fa. Sigma, M8515-1 mg) and Ispinesib (from Adooq A10486) were used as positive control. The individual data of the dose-activity curve are octuple determinations. The IC$_{50}$ values are means of three independent experiments. The 100% control was the sample which had not been treated with inhibitors.

In the following table 2 IC$_{50}$-values of representative examples derived from the described assay and the corresponding cytotoxicity data (MTT-Assay) are summarized:

TABLE 2

| Beispiele | KSP-Assay IC$_{50}$ [M] | NCI-H292 IC$_{50}$ [M] MTT Assay | KPL-4 IC$_{50}$ [M] MTT Assay |
|---|---|---|---|
| M100 | 2.45E-09 | >5.00E-07 | >5.00E-07 |

C-2 Internalisation Assay

Internalisation is a key process which enables specific and efficient provision of the cytotoxic payload in antigen-expressing cancer cells via antibody drug conjugates (ADC). This process is monitored via fluorescent labelling of specific TWEAKR antibodies and an isotype control antibody. First, the fluorescent dye is conjugated to lysines of the antibody. Conjugation is carried out using a two-fold molar excess of CypHer 5E mono NHS ester (Batch 357392, GE Healthcare) at pH 8.3. After the coupling, the reaction mixture was purified using gelchromatography (Zeba Spin Desalting Columns, 40K, Fa. Thermo Scientific, No. 87768; Elutionspuffer: DULBECCO'S PBS, Fa. Sima-Aldrich, No. D8537), to remove excess dye and to adjust the pH. The protein solution was then concentrated (VIVASPIN 500, from Sartorius stedim biotec). Determination of the dye load of the antibody was by spectrophotometric analysis (NanoDrop) and subsequent calculation (D:P=A$_{dye}$ ε$_{protein}$:(A$_{280}$-0.16A$_{dye}$)ε$_{dye}$). The dye load of the TWEAKR antibody examined here and the isotype control were of a comparable order. In cell binding assays, it was confirmed that the conjugation did not lead to a change in the affinity of the antibody.

The labelled antibodies were used for the internalisation assay. Prior to the start of the treatment, the cells ($2 \times 10^4$/well) were seeded in 100 µL medium in a 96-well MTP (fat, black, clear bottom No 4308776, from Applied Biosystems). After 18 h of incubation at 37° C./5% CO$_2$, the medium was replaced and labelled anti-TWEAKR antibodies were added in different concentrations (10, 5, 2.5, 1, 0.1 µg/mL). The same treatment protocol was applied to the labelled isotype control (negative control). The chosen incubation times are 0 h, 0.25 h, 0.5 h, 1 h, 1.5 h, 2 h, 3 h, 6 h and 24 h. The fluorescence measurement was carried out using the InCellanalyser 1000 (from GE Healthcare). This was followed by kinetic evaluation via measurement of the parameters granule counts/cell and total granule intensity/cell.

Following binding to the TWEAKR, TWEAKR antibodies were examined for the internalisation ability. For this purpose, cells with different TWEAKR expression levels were chosen. A target-mediated specific internalisation was observed with the TWEAKR antibodies, whereas the isotype control showed no internalisation.

The commercially available antibodies (Cetuximab, Nimotuzumab, Herceptin) were treated identical and internalization was performed as described above using the respective Target-expressing cells. For all antibodies a target-dependent internalization could be observed while the isotype control showed no internalization.

C-3 In Vitro Tests for Determining Cell Permeability

The cell permeability of a substance can be investigated by means of in vitro testing in a flux assay using Caco-2 cells [M. D. Troutman and D. R. Thakker, Pharm. Res. 20 (8), 1210-1224 (2003)]. For this purpose, the cells were cultured for 15-16 days on 24-well filter plates. For the determination of permeation, the respective working example was applied in a HEPES buffer to the cells either apically (A) or basally (B) and incubated for 2 hours. After 0 hours and after 2 hours, samples were taken from the cis and trans compartments. The samples were separated by HPLC (Agilent 1200, Böblingen, Germany) using reverse phase columns. The HPLC system was coupled via a Turbo Ion Spray Interface to a Triple Quadropol mass spectrometer API 4000 (Applied Biosystems Applera, Darmstadt, Germany). The permeability was evaluated on the basis of a Papp value, which was calculated using the formula published by Schwab et al. [D. Schwab et al., J. Med. Chem. 46, 1716-1725 (2003)]. A substance was classified as actively transported when the ratio of P$_{app}$ (B-A) to P$_{app}$ (A-B) (efflux ratio) was >2 or <0.5.

Of critical importance for toxophores which are released intracellularly is the permeability from B to A [$P_{app}$ (B-A)] and the ratio of $P_{app}$ (B-A) to $P_{app}$ (A-B) (efflux ratio): the lower this permeability, the slower the active and passive transport processes of the substance through the monolayer of Caco-2 cells. If additionally the efflux ratio does not indicate any active transport, the substance may, following intracellular release, remain longer in the cell. Hence, there is also more time available for interaction with the biochemical target (in this case: kinesin spindle protein, KSP/Eg5).

TABLE 3

| Metabolite example | $P_{app}$ (B-A) [nm/s] | Efflux ratio |
|---|---|---|
| M100 | 1.2 | 0.7 |

C-4 In Vitro Tests for Determining the Substrate Properties for P-Glycoprotein (P-Gp)

Many tumour cells express transporter proteins for drugs, and this frequently accompanies the development of resistance towards cytostatics. Substances which are not substrates of such transporter proteins, such as P-glycoprotein (P-gp) or BCRP, for example, could therefore exhibit an improved activity profile.

The substrate properties of a substance for P-gp (ABCB1) were determined by means of a flux assay using LLC-PK1 cells which overexpress P-gp (L-MDR1 cells) [A. H. Schinkel et al., *J. Clin. Invest.* 96, 1698-1705 (1995)]. For this purpose, the LLC-PK1 cells or L MDR1 cells were cultured on 96-well filter plates for 3-4 days. For determination of the permeation, the respective test substance, alone or in the presence of an inhibitor (such as ivermectin or verapamil, for example), was applied in a HEPES buffer to the cells either apically (A) or basally (B) and incubated for 2 hours. After 0 hours and after 2 hours, samples were taken from the cis and trans compartments. The samples were separated by HPLC using reverse phase columns. The HPLC system was coupled via a Turbo Ion Spray Interface to a Triple Quadropol mass spectrometer API 3000 (Applied Biosystems Applera, Darmstadt, Germany). The permeability was evaluated on the basis of a Papp value, which was calculated using the formula published by Schwab et al. [D. Schwab et al., *J. Med. Chem.* 46, 1716-1725 (2003)]. A substance was classified as P=gp substrate when the efflux ratio of $P_{app}$ (B-A) to $P_{app}$ (A-B) was >2. As further criteria for the evaluation of the P-gp substrate properties, the efflux ratios in L-MDR1 and LLC-PK1 cells or the efflux ratio in the presence or absence of an inhibitor may be compared. If these values differ by a factor of more than 2, the substance in question is a P-gp substrate.

C-5 Pharmakokinetics

C5a: Identification of the ADC Metabolites after Internalisation In Vitro

Description of the Method:

Internalisation studies with immunoconjugates are carried out to analyse metabolites formed intracellularly. To this end, human lung tumour cells NCI H292 ($3\times10^5$/well) are sown in 6-well plates and incubated overnight (37° C., 5% $CO_2$). The cells are treated with 10 µg/ml of the ADC to be examined. Internalisation is carried out at 37° C. and 5% $CO_2$. At various time points (0, 4, 24, 48, 72 h), cell samples are taken for further analysis. First, the supernatants (about 5 ml) are harvested and, after centrifugation (2 min, RT, 1000 rpm Heraeus Variofuge 3.0R), stored at −80° C. The cells are washed with PBS and detached with Accutase, and the cell number is determined. After another washing, a defined number of cells ($2\times10^5$) is treated with 100 µl of lysis buffer (Mammalian Cell Lysis Kit (Sigma MCL1) and incubated with continuous shaking (Thermomixer, 15 min, 4° C., 650 rpm) in Protein LoBind tubes (eppendorf Cat. No. 0030 108.116). After the incubation, the lysate is centrifuged (10 min, 4° C., 12000 g, eppendorf 5415R) and the supernatant is harvested. The supernatant obtained is stored at −80° C. All samples are then analysed as follows.

Measurement of the compounds in the culture supernatant or cell lysate is carried out after precipitation of the proteins with methanol or acetonitrile by high-pressure liquid chromatography (HPLC) coupled to a triple-quadrupole mass spectrometer (MS).

For work-up of 50 µl of culture supernatant/cell lysate, 150 µl of precipitation reagent (generally acetonitrile) are added and the mixture is shaken for 10 seconds. The precipitation reagent contains an internal standard (ISTD) in a suitable concentration (generally in the range of 20-100 ng/ml). After 3 minutes of centrifugation at 16000 g, the supernatant is transferred into an autosampler vial, made up with 500 µl of a buffer suitable for the mobile phase and shaken again.

The two matrix samples are then measured using the HPLC-coupled triple-quadrupol mass spectrometer API6500 from AB SCIEX Deutschland GmbH.

For calibration, concentrations of 0.5-2000 µg/l are added to plasma samples. The detection limit (LOQ) is about 2 µg/l. The linear range extends from 2 to 1000 µg/l.

For calibration of the tumour samples, concentrations of 0.5-200 µg/l are added to the supernatant of untreated tumours. The detection limit is 4 µg/l. The linear range extends from 4 to 200 µg/l. Quality controls for testing validity contain 5 and 50 µg/l.

C5b: Identification of the ADC Metabolites In Vivo

After i.v. administration of 3-30 mg/kg of different ADCs, the plasma and tumour concentrations of the ADCs and any metabolites occurring can be measured, and the pharmacokinetic parameters such as clearance (CL), area under the curve (AUC) and half-times ($t_{1/2}$) can be calculated.

Analysis for Quantification of any Metabolites Occurring

Measurement of the compounds in plasma and tumour is carried out after precipitation of the proteins with methanol or acetonitrile by high-pressure liquid chromatography (HPLC) coupled to a triple-quadrupole mass spectrometer (MS).

For work-up of 50 µl of plasma, 250 µl of precipitation reagent (generally acetonitrile) are added and the mixture is shaken for 10 seconds. The precipitation reagent contains an internal standard (ISTD) in a suitable concentration (generally in the range of 20-100 ng/ml). After 3 minutes of centrifugation at 16000 g, the supernatant is transferred into an autosampler vial, made up with 500 µl of a buffer suitable for the mobile phase and shaken again.

During the work-up of a tumour, the latter is treated with 3 times the amount of extraction buffer. The extraction buffer contains 50 ml of Tissue Protein Extraction Reagent (Pierce, Rockford, Ill.), two pellets of Complete-Protease-Inhibitor-Cocktail (Roche Diagnostics GmbH, Mannheim, Germany) and phenylmethylsulphonyl fluoride (Sigma, St. Louis, Mo.) in a final concentration of 1 mM. The sample is homogenized twice for 20 minutes in a Tissuelyser II (Qiagen), at maximum stroke number. 50 µl of the homogenate are transferred into an autosampler vial and made up with 150 µl of methanol including ISTD. After 3 minutes of centrifugation at 16000 g, 10 µl of the supernatant are made up with 180 µl of a buffer suitable for the mobile phase and shaken again. The tumour sample is then ready for measuring.

The two matrix samples are then measured using the HPLC-coupled triple-quadrupol mass spectrometer API6500 from AB SCIEX Deutschland GmbH.

For calibration, concentrations of 0.5-2000 µg/l are added to plasma samples. The detection limit (LOQ) is about 2 µg/l. The linear range extends from 2 to 1000 µg/l.

For calibration of the tumour samples, concentrations of 0.5-2000 µg/l are added to the supernatant of untreated tumours. The detection limit is 5 µg/l. The linear range extends from 5 to 200 µg/l.

Quality controls for testing validity contain 5 and 50 µg/l, in plasma additionally 500 µg/l.

Analysis for Quantification of the Antibodies Used

The antibody part of the ADCs was determined using a ligand binding assay (ELISA) as total IgG concentration in plasma samples and tumour lysates. Here, the sandwich ELISA format was used. This ELISA had been qualified and validated for the determination in plasma and tumour samples. The ELISA plates were coated with anti-human goat IgG Fc antibodies. After incubation with the sample, the plates were washed and incubated with a detector conjugate of simian anti-human IgG(H+L) antibody and horseradish peroxidase (HRP). After a further washing step, the HRP substrate was added to OPD and the colour development was monitored via absorption at 490 nm. Standard samples having a known IgG concentration were fitted using a 4-parameter equation. Within the lower (LLOQ) and upper (ULOQ) quantification limits, the unknown concentrations were determined by interpolation.

C-6 Activity Test In Vivo

The activity of the conjugates according to the invention was tested, for example, using xenograft models. The person skilled in the art is familiar with methods in the prior art which allow the activity of the compounds according to the invention to be tested (see, for example, WO 2005/081711; Polson et al., Cancer Res. 2009 Mar. 15; 69(6):2358-64). To this end, a tumour cell line expressing the target molecule of the binder was implanted into rodents (for example mice). A conjugate according to the invention, an isotype control conjugate, a control antibody or isotonic saline was then administered to the implant animals. The administration took place once or more than once. Following an incubation time of several days, the size of the tumour was determined by comparing conjugate-treated animals and the control group. The conjugate-treated animals displayed a smaller tumour size.

Growth Inhibition/Regression of Experimental Tumours in the Mouse

Human tumour cells expressing the antigen for the antibody drug conjugate are inoculated subcutaneously into the flank of immunosuppressed mice, for example NMRi nude or SCID mice. 1-10 million cells are detached from the cell culture, centrifuged and resuspended in medium or medium/matrigel. The cell suspension is injected under the skin of the mouse.

Within a few days, a tumour grows. Treatment is commenced after the tumour is established, at a tumour size of approximately 40 mm$^2$. To examine the effect on larger tumours, treatment may be initiated only at a tumour size of 50-100 mm$^2$.

Treatment with ADCs is carried out via the intravenouse route into the tail vein of the mouse. The ADC is administered in a volume of 5 ml/kg.

The treatment protocol depends on the pharmacokinetics of the antibody. As standard, treatment takes place three times in succession every fourth day. For a quick assessment, a protocol with a single treatment may be employed. However, the treatment may also be continued, or a second cycle of three treatment days may follow at a later time.

As standard, 8 animals are used per treatment group. In addition to the groups to which the active substances are administered, one group is treated as control group only with the buffer, according to the same protocol.

During the experiment, the tumour area is measured regularly in two dimensions (length/width) using a caliper. The tumour area is determined as length×width. The ratio of the mean tumour area of the treatment group to that of the control group is stated as T/C area.

When after the end of the treatment all groups of the experiment are terminated at the same time, the tumours can be removed and weighed. The ratio of the mean tumour weights of the treatment group to that of the control group is stated as T/C weight.

D. Working Examples of Pharmaceutical Compositions

The compounds according to the invention can be converted to pharmaceutical formulations as follows:

i.v. Solution:

The compound according to the invention is dissolved in a concentration below the saturation solubility in a physiologically acceptable solvent (e.g. isotonic saline solution, D-PBS, or a formulation with glycine and sodium chloride in citrate buffer with addition of polysorbate 80). The solution is subjected to sterile filtration and dispensed into sterile and pyrogen-free injection vessels.

i.v. Solution:

The compounds according to the invention can be converted to the administration forms mentioned.

This can be accomplished in a manner known per se by "mixing with" or "dissolving in" inert, non-toxic, pharmaceutically suitable excipients (e.g. buffer substances, stabilizers, solubilizers, preservatives). The following, for example, may be present: amino acids (glycine, histidine, methionine, arginine, lysine, leucine, isoleucine, threonine, glutamic acid, phenylalanine and others), sugars and related compounds (glucose, saccharose, mannitol, trehalose, sucrose, mannose, lactose, sorbitol), glycerol, sodium salts, potassium, ammonium salts and calcium salts (e.g. sodium chloride, potassium chloride or disodiumhydrogenphosphate and many others), acetate/acetic acid buffer systems, phosphate buffer systems, citric acid and citrate buffer systems, trometamol (TRIS and TRIS salts), Polysorbates (e.g. Polysorbate 80 and Polysorbate 20), Poloxamers (e.g. Poloxamer 188 and Poloxamer 171), Macrogols (PEG derivatives, e.g. 3350), Triton X-100, EDTA salts, glutathione, albumins (e.g. human), urea, benzyl alcohol, phenol, chlorocresol, metacresol, benzalkonium chloride and many others.

Lyophilizate for Subsequent Conversion into an i.v., s.c. Or i.m. Solution:

Alternatively the compounds of the invention may be converted into a stable lyophilizate (possibly with the aid of abovementioned excipients) and, before being administered, reconstituted with a suitable solvent (e.g. injection-grade water, isotonic saline solution) and administered.

Working Examples of Anti-Tweakr Antibodies

All examples were carried out using standard methods known to the person skilled in the art, unless described here in detail. Routine methods of molecular biology of the examples that follow can be carried out as described in standard laboratory textbooks such as Sambrook et al., Molecular Cloning: a Laboratory Manual, 2. Edition; Cold Spring Harbor Laboratory Press, Cold Spring Harbor, N.Y., 1989.

AK Example 1: Antibody Preparation Using an Antibody Library

A complete human phage display library (Hoet R M et al, Nat Biotechnol 2005; 23(3):344-8) was employed to isolate TWEAKR-specific human monoclonal antibodies of the present invention by protein panning (Hoogenboom H. R., Nat Biotechnol 2005; 23(3):1105-16), where dimeric Fc-fused extracellular domains of human and murine TWEAKR were immobilized as target.

TABLE AK-1

List of recombinant antigens used for antibody selection

| Nomenclature | Description | SEQ ID NO |
|---|---|---|
| TPP-599 | HUMAN-TNFRSF12Aaa28-80-hIgG1-Fc | 138 |
| TPP-601 | MURIN-TNFRSF12Aaa28-80-hIgG1-Fc | 137 |

The antigens were biotinylated using an about 2-fold molar excess of biotin-LC-NHS (Pierce; Cat. No. 21347) according to the instructions of the manufacturer and desalted using Zeba desalting columns (Pierce; Cat. No. 89889). Washed magnetic beads (DynaBeads) were incubated overnight with 200 nM biotinylated antigen at 4° C. and blocked for 1 h at 4° C. with blocking buffer (PBS with 3% BSA, 0.05% Tween-20). The blocked Fab phage library was added to the blocked TWEAKR beads (DynaBeads Streptavidin-M280-Invitrogen 112-06D) and incubated at room temperature for 30 min. After stringent washing (3× with blocking buffer and 9× with PBS (150 mM NaCl; 8 mM Na2HPO4; 1.5 mM KH2PO4; adjusted to pH=7.4-7.6) with 0.05% Tween-20), Fab phages binding specifically to biotinylated TWEAKR beads (DynaBeads Streptavidin-M280-Invitrogen 112-06D) were resuspended in PBS and, for amplification, used directly for infecting *Escherichia coli* strain TG1. In the second selection round, two murine TWEAKR (200 nM) were used to select for cross-reactive binders, and in the third selection round the concentration of human TWEAKR was reduced (100 nM) to increase the selection pressure for high-affinity binders.

11 different Fab phages were identified and the corresponding antibodies were cloned into a mammalian IgG expression vector which provided the missing $CH_2$—$CH_3$ domains not present in the soluble Fab. The resulting IgGs were expressed transiently in mammalian cells as described in Tom et al., Chapter 12 in Methods Express: Expression Systems edited by Micheal R. Dyson and Yves Durocher, Scion Publishing Ltd, 2007. Briefly, a CMV promoter-based expression plasmid was transfected into HEK293-6E cells and incubated in Fernbach bottles or Wave bags. Expression took place at 37° C. for 5 to 6 days in F17 medium (Invitrogen). 1% Ultra-Low IgG FCS (Invitrogen) and 0.5 mM valproic acid (Sigma) were added as supplements 24 h after the transfection. The antibodies were purified by protein-A chromatography and characterized further by their binding affinity to soluble monomeric TWEAKR using ELISA and BIAcore analysis, as described in AK-Example 2.

TABLE AK-2

List of recombinant antigen used for the affinity measurement

| Nomenclature | Description | Origin | Cat. No. (Fitzgerald Inc) | SEQ ID NO |
|---|---|---|---|---|
| TPP-2305 | hTNFRSF12 amino acids a28-80 | human | 30R-AT080 | 168 |

To determine the cell binding characteristics of the anti-TWEAKR antibodies, binding to a number of cell lines (HT29, HS68, HS578) was examined by flow cytometry. The cells were suspended in dilutions of the antibodies (5 µg/ml) in FACS buffer and incubated on ice for 1 h. A second antibody (PE goat-anti-human IgG, Dianova #109-115-098) was then added. After 1 h of incubation on ice, the cells were analysed by flow cytometry using an FACS array (BD Biosciences).

NF-kappaB reporter gene assays were carried out to assess the agonistic activity of all 11 antibodies identified (human IgG1). HEK293 cells were transiently transfected with an NF-kappaB reporter construct (BioCat, Cat. No. LR-0051-PA) using 293fectin according to the instructions of the manufacturer. Transfected cells were sown in F17 media (serum-free; Invitrogen) at 37 C, 5% CO2 into white polylysine-coated 384-well plates (BD). The next day, the cells were stimulated with various concentrations of purified antibodies for 6 h, and a luciferase assay was then carried out using standard methods.

Internalisation was monitored via fluorescence labelling of anti-TWEAKR antibodies (CypHer 5E mono NHS ester; GE Healthcare). Prior to the treatment, HT29 cells were sown ($2\times10^4$/well) in 100 µl of medium in 96-well MTP plates (thick, black, transparent botton, No. 4308776, Applied Biosystems). After 18 h of incubation at 37° C./5% $CO_2$, the medium was replaced and labelled anti-TWEAKR antibodies were added in different concentrations (10, 5, 2.5, 1, 0.1 µg/ml). The chosen incubation time was 0, 0.25, 0.5, 1, 1.5, 2, 3, 6 and 24 h. Fluorescence measurement was carried out in an InCell-analyser 1000 (GE Healthcare).

The antibody having the highest in vitro activity (TPP-883) was selected for further activity and affinity maturation.

TPP-883

SEQ ID NO. 71

AQDIQMTQSPATLSASVGDRVTITC<u>RASQSISSYLN</u>WYQQKPGKAPKLLI

Y<u>AASSLQS</u>GVPSRFSGSGSGTDFTLTISSLQPEDFATYYC<u>QQSYSSPGIT</u>

FGPGTKVEIKRTVAAPSVFIFPPSDEQLKSGTASVVCLLNNEYPREAKVQ

WKVDNALQSGNSQESVIEQDSKDSTYSLSSTLTLSKADYEKHKLYACEVT

HQGLSSPVTKSFNRGEC

SEQ ID NO. 72

EVQLLESGGGLVQPGGSLRLSCAASGFTFS<u>PYPMMW</u>VRQAPGKGLEWVS<u>Y</u>

<u>ISPSGGKTHYADS</u>VKGRFTISRDNSKNTLYLQMNSLRAEDTAVYYCAR<u>GG</u>

<u>DGYFDYFDY</u>WGQGTLVTVSSASTKGPSVFPLAPSSKSTSGGTAALGCLVK

DYFPEPVIVSWNSGALTSGVHTFPAVLQSSGLYSLSSVVIVPSSSLGTQT

YICNVNHKPSNIKVDKRVEPKSCDKTHICPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

-continued
VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG

Amino acid sequences of the light (SEQ ID NO.71) and heavy (SEQ ID NO.72) chains of TPP-883; CDRs both of the heavy and the light chain are underlined.

Maturation was carried out in a first mutations collection round, followed by recombination of those amino acid modifications which increased affinity and activity most. For collecting mutations NNK (N=AGCT, K=G or T), randomization was carried out at the following individual amino acid positions by site-directed mutagenesis using synthetic oligonucleotides including NNK codon diversification (continuous amino acid nomenclature): S35, S36, Y37 and N39 in CDR-L1; A51, S53, S54, Q56 and S57 in CDR-L2; S92, Y93, S94, S95, G97 and I98 in CDR-L3; P31, Y32, P33, M34 and M35 in CDR-H1; Y50, S52, P53, S54, G56, K57 and H59 in CDR-H2; G99, G100, D101, G102, Y103, F104, D105 and Y106 in CDR-H3. The DNA of all individual NNK saturation mutagenesis libraries was cloned into a mammalian IgG expression vector for activity maturation or into a phagemid vector for affinity maturation. Affinity maturation was carried out by phage panning. Washed magnetic beads (DynaBeads) were incubated overnight with 10 nM, 1 nM, 100 µM or 10 µM biotinylated antigen at 4° C. and blocked for 1 h at 4° C. with blocking buffer (PBS with 3% BSA, 0.05% Tween-20). The blocked Fab phage library was added in 10000-fold, 1000-fold or 100-fold excess, compared to the theoretical library complexity, to the blocked TWEAKR-DynaBeads and incubated at room temperature for 30 min. That means that 12 strategies were followed in total (4 antigen concentrations×3 Fab phage titres). After stringent washing (3× with blocking buffer and 9× with PBS with 0.05% Tween-20), Fab phages binding specifically to biotinylated TWEAKR DynaBeads (DynaBeads Streptavidin-M280-Invitrogen 112-06D) were resuspended in PBS and, for amplification, used directly for infecting Escherichia coli strain TG1. In selection round two, the concentration of human TWEAKR-Fc was reduced (1 nM, 100 µM, 10 µM and 1 µM), and the same Fab phage titre was used for all 12 strategies ($4.4\times10^{11}$). For the expression of soluble Fab, the phagemid vector was digested with MluI to remove the gene-III membrane anchor sequence required for the Fab display on the phage, and the vector was re-ligated. 96 variants of each of the 12 selection pools were expressed as soluble Fabs and examined in an ELISA format. To this end, 2.5 nM biotinylated TWEAKR-Fc were antigen-coated, and binding of soluble Fabs was demonstrated using anti-c-Myc antibodies (Abcam ab62928). 7 single substitution variants (consecutive amino acid nomenclature) with improved binding to TWEAKR-Fc (Seq ID No 138) were demonstrated: S36G of CDR-L1, A51Q and S57K of CDR-L2, S94T and G97F of CDR-L3, M35I of CDR-H1 and G102T of CDR-H3. For the activity maturation, HEK293 cells were transfected with an NF-kappaB reporter (BioCat, Cat. No. LR-0051-PA). Transfected cells were sown in F17 media (serum-free; Invitrogen) in white, polylysine-coated 384-well plates (BD), and individual variants of the NNK-diversified position antibodies (human IgG1) libraries were expressed transiently in mammalian cells. The next day, NF-kappaB reporter cells were stimulated with the individual NNK antibody variants expressed for 6 h, and a luciferase assay was then carried out using standard methods. 1 single substitution variant having improved agonistic activity was detected: G102T of CDR-H3. This variant was also obtained by affinity maturation, and there, too, it showed the highest enhancement of affinity. After mutation collection by affinity and activity screening, all 7 favourable individual substitutions (library complexity: 128 variants) were recombined into a recombination library. To this end, oligonucleotides were synthesized to introduce selected mutations or the corresponding wild type amino acid at each selected position. The library was established using successive rounds of overlap extension PCR. The final PCR product was ligated into a bacterial soluble Fab expression vector, and 528 variants were selected at random (~4-fold excess of the sample taken) for an equilibrium ELISA screen with soluble Fabs, as described above. In the end, 7 variants were selected based on increased affinity compared to the best single substitution variant G102T. The corresponding DNA of these was cloned into a mammalian IgG expression vector and examined for functional activity in the above-mentioned NF-kappaB reporter cell assay. Finally, the sequences obtained were compared with human germ line sequences, and deviations without any significant effect on the affinity and the efficacy were adapted. Antibodies having the sequences below were obtained by antibody library screening and by affinity and/or activity maturation:

TPP-2090
SEQ ID NO. 1:
DIQMTQSPSSLSASVGDRVTITC<u>RASQSISGYLN</u>WYQQKPGKAPKLLIYQ

<u>ASSLQSGV</u>PSRFSGSGSGTDFTLTISSLQPEDFATYYC<u>QQSYTSPFIT</u>FG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

SEQ ID NO. 2:
EVQLLESGGGLVQPGGSLRLSCAASGFTFS<u>PYPMI</u>WVRQAPGKGLEWVS<u>Y</u>

<u>ISPSGGSTHYADS</u>VKGRFTISRDNSKNTLYLQMNSLRAEDTAVYYCAR<u>GG</u>

<u>DTYFDYFDY</u>WGQGTLVTVSSASTKGPSVFPLAPSSKSTSGGTAALGCLVK

DYFPEPVTVSWNSGALTSGVHTFPAVLQSSGLYSLSSVVIVPSSSLGTQT

YICNVNHKPSNIKVDKKVEPKSCDKTHICPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

Amino acid sequences of the light (SEQ ID NO.1) and heavy (SEQ ID NO.2) chains of TPP-2090; CDRs both of the heavy and the light chain are underlined. Based on the sequence of TPP-2090, the aglycosylated antibodies TPP-2090-HC-N297A (comprising the mutation in the heavy chain N297A (Kabat, EU numbering) and TPP-2090-HC-N-297Q (comprising the mutation in the heavy chain N297Q (Kabat, EU numbering) were generated by site directed mutagenesis:

TPP-2090-HC-N297A
Light chain (SEQ ID NO: 1):
DIQMTQSPSSLSASVGDRVTITCRASQSISGYLNWYQQKPGKAPKLLIYQ

ASSLQSGVPSRFSGSGSGTDFTLTISSLQPEDFATYYCQQSYTSPFITFG

QGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC

Heavy chain (SEQ ID NO. 241):
EVQLLESGGGLVQPGGSLRLSCAASGFTFSPYPMIWVRQAPGKGLEWVSY
ISPSGGSTHYADSVKGRFTISRDNSKNTLYLQMNSLRAEDTAVYYCARGG
DTYFDYFDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG TPP-2090-HC-N297Q
Light chain (SEQ ID NO. 1):
DIQMTQSPSSLSASVGDRVTITC<u>RASQSISGYLN</u>WYQQKPGKAPKLLIYQ
<u>ASSLQS</u>GVPSRFSGSGSGTDFTLTISSLQPEDFATYYC<u>QQSYTSPFIT</u>FG
QGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC Heavy chain (SEQ ID NO. 242):
EVQLLESGGGLVQPGGSLRLSCAASGFTFS<u>PYPMI</u>WVRQAPGKGLEWVS<u>Y</u>
<u>ISPSGGSTHYADSVKG</u>RFTISRDNSKNTLYLQMNSLRAEDTAVYYCAR<u>GG</u>
<u>DTYFDYFDY</u>WGQGTLVTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYQ
STYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG TPP-2149
                                        SEQ ID NO. 11
DIQMTQSPATLSASVGDRVTITC<u>RASQSISGYLN</u>WYQQKPGKAPKLLIYQ
<u>ASSLQS</u>GVPSRFSGSGSGTDFTLTISSLQPEDFATYYC<u>QQSYTSPFIT</u>FG
PGTKVEIKRTVAAPSVFIFPPSDEQLKSGTASVVCLLNNFYPREAKVQWK
VDNALQSGNSQESVTEQDSKDSTYSLSSTLTLSKADYEKHKLYACEVTHQ
GLSSPVTKSFNRGEC SEQ ID NO. 12
EVQLLESGGGLVQPGGSLRLSCAASGFTFS<u>PYPMI</u>WVRQAPGKGLEWVS<u>Y</u>
<u>ISPSGGKTHYADSVKG</u>RFTISRDNSKNTLYLQMNSLRAEDTAVYYCAR<u>GG</u>
<u>DTYFDYFDY</u>WGQGTLVTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG Amino acid sequences of the light (SEQ ID NO.11) and heavy (SEQ ID NO.12) chains of TPP-2149; CDRs both of the heavy and the light chain are underlined.

TPP-2093
                                        SEQ ID NO. 21
DIQMTQSPSSLSASVGDRVTITC<u>RASQSISSYLN</u>WYQQKPGKAPKLLIYQ
<u>ASSLQS</u>GVPSRFSGSGSGTDFTLTISSLQPEDFATYYC<u>QQSYTSPFIT</u>FG
QGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC

SEQ ID NO. 22
EVQLLESGGGLVQPGGSLRLSCAASGFTFS<u>PYPMM</u>WVRQAPGKGLEWVS<u>Y</u>
<u>ISPSGGSTHYADSVKG</u>RFTISRDNSKNTLYLQMNSLRAEDTAVYYCAR<u>GG</u>
<u>DTYFDYFDY</u>WGQGTLVTVSSASTKGPSVFPLAPSSKSTSGGTAALGCLVK
DYFPEPVTVSWNSGALTSGVHTFPAVLQSSGLYSLSSVVIVPSSSLGTQT
YICNVNHKPSNIKVDKKVEPKSCDKTHICPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG

Amino acid sequences of the light (SEQ ID NO.21) and heavy (SEQ ID NO.22) chains of TPP-2093; CDRs both of the heavy and the light chain are underlined.

TPP-2148
                                        SEQ ID NO. 31
DIQMTQSPATLSASVGDRVTITC<u>RASQSISSYLN</u>WYQQKPGKAPKLLIYQ
<u>ASSLQS</u>GVPSRFSGSGSGTDFTLTISSLQPEDFATYYC<u>QQSYTSPFIT</u>FG
PGTKVEIKRTVAAPSVFIFPPSDEQLKSGTASVVCLLNNFYPREAKVQWK
VDNALQSGNSQESVTEQDSKDSTYSLSSTLTLSKADYEKHKLYACEVTHQ
GLSSPVTKSFNRGEC

SEQ ID NO. 32
EVQLLESGGGLVQPGGSLRLSCAASGFTFS<u>PYPMM</u>WVRQAPGKGLEWVS<u>Y</u>
<u>ISPSGGKTHYADSVKG</u>RFTISRDNSKNTLYLQMNSLRAEDTAVYYCAR<u>GG</u>
<u>DTYFDYFDY</u>WGQGTLVTVSSASTKGPSVFPLAPSSKSTSGGTAALGCLVK
DYFPEPVTVSWNSGALTSGVHTFPAVLQSSGLYSLSSVVIVPSSSLGTQT
YICNVNHKPSNIKVDKKVEPKSCDKTHICPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG

Amino acid sequences of the light (SEQ ID NO.31) and heavy (SEQ ID NO.32) chains of TPP-2148; CDRs both of the heavy and the light chain are underlined.

TPP-2084

SEQ ID NO. 41
DIQMTQSPSSLSASVGDRVTITC<u>RASQSISSYLN</u>WYQQKPGKAPKLLIY<u>A</u>
<u>ASSLQS</u>GVPSRFSGSGSGTDFTLTISSLQPEDFATYYC<u>QQSYSTPGIT</u>FG
QGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC

SEQ ID NO. 42
EVQLLESGGGLVQPGGSLRLSCAASGFTFS<u>PYPMM</u>WVRQAPGKGLEWVS<u>Y</u>
<u>ISPSGGSTHYADSVKG</u>RFTISRDNSKNTLYLQMNSLRAEDTAVYYCAR<u>GG</u>
<u>DTYFDYFDY</u>WGQGTLVTVSSASTKGPSVFPLAPSSKSTSGGTAALGCLVK
DYFPEPVTVSWNSGALTSGVHTFPAVLQSSGLYSLSSVVIVPSSSLGTQT
YICNVNHKPSNIKVDKKVEPKSCDKTHICPPCPAPELLGGPSVFLFPPKP
KDTLMISRTPEVTCVVVDVSHEDPEVKFNWYVDGVEVHNAKTKPREEQYN
STYRVVSVLIVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG

Amino acid sequences of the light (SEQ ID NO.41) and heavy (SEQ ID NO.42) chains of TPP-2084; CDRs both of the heavy and the light chain are underlined.

TPP-2077

SEQ ID NO. 51
DIQMTQSPATLSASVGDRVTITC<u>RASQSISSYLN</u>WYQQKPGKAPKLLIY<u>A</u>
<u>ASSLQS</u>GVPSRFSGSGSGTDFTLTISSLQPEDFATYYC<u>QQSYSSPGIT</u>FG
PGTKVEIKRTVAAPSVFIFPPSDEQLKSGTASVVCLLNNFYPREAKVQWK
VDNALQSGNSQESVTEQDSKDSTYSLSSTLTLSKADYEKHKLYACEVTHQ
GLSSPVTKSFNRGEC

SEQ ID NO. 52
EVQLLESGGGLVQPGGSLRLSCAASGFTFS<u>PYPMM</u>WVRQAPGKGLEWVS<u>Y</u>
<u>ISPSGGKTHYADSVKG</u>RFTISRDNSKNTLYLQMNSLRAEDTAVYYCAR<u>GG</u>
<u>DTYFDYFDY</u>WGQGTLVTVSSASTKGPSVFPLAPSSKSTSGGTAALGCLVK
DYFPEPVTVSWNSGALTSGVHTFPAVLQSSGLYSLSSVVIVPSSSLGTQT
YICNVNHKPSNIKVDKKVEPKSCDKTHICPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG

Amino acid sequences of the light (SEQ ID NO.51) and heavy (SEQ ID NO.52) chains of TPP-2077; CDRs both of the heavy and the light chain are underlined.

TPP-1538

SEQ ID NO. 61
AQDIQMTQSPATLSASVGDRVTITC<u>RASQSISSYLN</u>WYQQKPGKAPKLLI
Y<u>AASSLQS</u>GVPSRFSGSGSGTDFTLTISSLQPEDFATYYC<u>QQSYSSPGIT</u>
FGPGTKVEIKRTVAAPSVFIFPPSDEQLKSGTASVVCLLNNEYPREAKVQ
WKVDNALQSGNSQESVIEQDSKDSTYSLSSTLTLSKADYEKHKLYACEVT
HQGLSSPVTKSFNRGEC

SEQ ID NO. 62
EVQLLESGGGLVQPGGSLRLSCAASGFTFS<u>PYPMM</u>WVRQAPGKGLEWVS<u>Y</u>
<u>ISPSGGKTHYADSVKG</u>RFTISRDNSKNTLYLQMNSLRAEDTAVYYCAR<u>GG</u>
<u>DTYFDYFDY</u>WGQGTLVTVSSASTKGPSVFPLAPSSKSTSGGTAALGCLVK
DYFPEPVTVSWNSGALTSGVHTFPAVLQSSGLYSLSSVVIVPSSSLGTQT
YICNVNHKPSNIKVDKKVEPKSCDKTHICPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG

Amino acid sequences of the light (SEQ ID NO.61) and heavy (SEQ ID NO.62) chains of TPP-1538; CDRs both of the heavy and the light chain are underlined.

TPP-1854

SEQ ID NO. 81
AQDIQMTQSPATLSASVGDRVTITC<u>RASQSISGYLN</u>WYQQKPGKAPKLLI
Y<u>NASSLQS</u>GVPSRFSGSGSGTDFTLTISSLQPEDFATYYC<u>QQSYTSPFIT</u>
FGPGTKVEIKRTVAAPSVFIFPPSDEQLKSGTASVVCLLNNEYPREAKVQ
WKVDNALQSGNSQESVIEQDSKDSTYSLSSTLTLSKADYEKHKLYACEVT
HQGLSSPVTKSFNRGEC

SEQ ID NO. 82
EVQLLESGGGLVQPGGSLRLSCAASGFTFS<u>PYPMI</u>WVRQAPGKGLEWVS<u>Y</u>
<u>ISPSGGKTHYADSVKG</u>RFTISRDNSKNTLYLQMNSLRAEDTAVYYCAR<u>GG</u>
<u>DTYFDYFDY</u>WGQGTLVTVSSASTKGPSVFPLAPSSKSTSGGTAALGCLVK
DYFPEPVTVSWNSGALTSGVHTFPAVLQSSGLYSLSSVVIVPSSSLGTQT
YICNVNHKPSNIKVDKKVEPKSCDKTHICPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPG

Amino acid sequences of the light (SEQ ID NO.81) and heavy (SEQ ID NO.82) chains of TPP-1854; CDRs both of the heavy and the light chain are underlined.

TPP-1853

SEQ ID NO. 91
AQDIQMTQSPATLSASVGDRVTITC<u>RASQSISSYLN</u>WYQQKPGKAPKLLI
Y<u>NASSLQS</u>GVPSRFSGSGSGTDFTLTISSLQPEDFATYYC<u>QQSYTSPGIT</u>
FGPGTKVEIKRTVAAPSVFIFPPSDEQLKSGTASVVCLLNNEYPREAKVQ

-continued

WKVDNALQSGNSQESVIEQDSKDSTYSLSSTLTLSKADYEKHKLYACEVT

HQGLSSPVTKSFNRGEC

SEQ ID NO. 92
EVQLLESGGGLVQPGGSLRLSCAASGFTFS<u>PYPMM</u>WVRQAPGKGLEWVS<u>Y</u>

<u>ISPSGGKTHYADSVKG</u>RFTISRDNSKNTLYLQMNSLRAEDTAVYYCAR<u>GG</u>

<u>DTYFDYFDY</u>WGQGTLVTVSSASTKGPSVFPLAPSSKSTSGGTAALGCLVK

DYFPEPVTVSWNSGALTSGVHTFPAVLQSSGLYSLSSVVIVPSSSLGTQT

YICNVNHKPSNIKVDKKVEPKSCDKTHICPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

Amino acid sequences of the light (SEQ ID NO.91) and heavy (SEQ ID NO.92) chains of TPP-1853; CDRs both of the heavy and the light chain are underlined.

TPP-1857

SEQ ID NO. 101
AQDIQMTQSPATLSASVGDRVTITC<u>RASQSISGYLN</u>WYQQKPGKAPKLLI

Y<u>NASSLQS</u>GVPSRFSGSGSGTDFTLTISSLQPEDFATYYC<u>QQSYTSPGIT</u>

FGPGTKVEIKRTVAAPSVFIFPPSDEQLKSGTASVVCLLNNFYPREAKVQ

WKVDNALQSGNSQESVTEQDSKDSTYSLSSTLTLSKADYEKHKLYACEVT

HQGLSSPVTKSFNRGEC

SEQ ID NO. 102
EVQLLESGGGLVQPGGSLRLSCAASGFTFS<u>PYPMM</u>WVRQAPGKGLEWVS<u>Y</u>

<u>ISPSGGKTHYADSVKG</u>RFTISRDNSKNTLYLQMNSLRAEDTAVYYCAR<u>GG</u>

<u>DTYFDYFDY</u>WGQGTLVTVSSASTKGPSVFPLAPSSKSTSGGTAALGCLVK

DYFPEPVTVSWNSGALTSGVHTFPAVLQSSGLYSLSSVVIVPSSSLGTQT

YICNVNHKPSNIKVDKKVEPKSCDKTHICPPCPAPELLGGPSVFLFPPKP

KDTLMISRTPEVTCVVVDVSHEDPEVKFNWYVDGVEVHNAKTKPREEQYN

STYRVVSVLIVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

Amino acid sequences of the light (SEQ ID NO.101) and heavy (SEQ ID NO.102) chains of TPP-1857; CDRs both of the heavy and the light chain are underlined.

TPP-1858

SEQ ID NO. 111
AQDIQMTQSPATLSASVGDRVTITC<u>RASQSISSYLN</u>WYQQKPGKAPKLLI

Y<u>NASSLQS</u>GVPSRFSGSGSGTDFTLTISSLQPEDFATYYC<u>QQSYTSPFIT</u>

FGPGTKVEIKRTVAAPSVFIFPPSDEQLKSGTASVVCLLNNFYPREAKVQ

WKVDNALQSGNSQESVIEQDSKDSTYSLSSTLTLSKADYEKHKLYACEVT

HQGLSSPVTKSFNRGEC

SEQ ID NO. 112
EVQLLESGGGLVQPGGSLRLSCAASGFTFS<u>PYPMM</u>WVRQAPGKGLEWVS<u>Y</u>

<u>ISPSGGKTHYADSVKG</u>RFTISRDNSKNTLYLQMNSLRAEDTAVYYCAR<u>GG</u>

<u>DTYFDYFDY</u>WGQGTLVTVSSASTKGPSVFPLAPSSKSTSGGTAALGCLVK

DYFPEPVTVSWNSGALTSGVHTFPAVLQSSGLYSLSSVVIVPSSSLGTQT

YICNVNHKPSNIKVDKKVEPKSCDKTHICPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

Amino acid sequences of the light (SEQ ID NO.111) and heavy (SEQ ID NO.112) chains of TPP-1858; CDRs both of the heavy and the light chain are underlined.

Example 2: Biochemical Characteristics of the Antibodies

Determination of Binding Affinities by Biacore Analysis:

Binding affinities of anti-TWEAKR antibodies were examined using surface plasmon resonance analysis on a Biacore T100 instrument (GE Healthcare Biacore, Inc.). The antibodies were immobilized on a CM5 sensor chip using an indirect capture reagent, anti-human IgG(Fc). Reagents of the "Human Antibody Capture Kit" (BR-1008-39, GE Healthcare Biacore, Inc.) were used as described by the manufacturer. Anti-TWEAKR antibodies were injected at a concentration of 10 µg/ml at 10 µl/min for 10 sec.

TABLE AK-3

List of recombinant antigen (TWEAKR) used for affinity measurement

| Nomenclature | Description | Origin | Cat. No. (Fitzgerald Inc) | SEQ ID NO |
|---|---|---|---|---|
| TPP-2305 | hTNFRSF12 amino acids a28-80 | human | 30R-AT080 | 168 |

TABLE AK-4

List of antibodies used for the affinity measurement

| | | | SEQ ID NO | |
| Nomenclature | Description | Light chain | Heavy chain |
|---|---|---|---|
| P3G5(TPP-2195) | murine IgG2a | 121 | 122 |
| P4A8(TPP-1324) | human IgG1 | 125 | 126 |
| P2D3(TPP-2196) | murine IgG2a | 131 | 132 |
| 136.1(TPP-2194) | murine IgG2a | 123 | 124 |
| PDL-192(TPP-1104) | human IgG1 | 127 | 128 |
| 18.3.3(TPP-2193) | murine IgG2a | 129 | 130 |
| TPP-883 | human IgG1 | 71 | 72 |
| TPP-1538 | human IgG1 | 61 | 62 |
| TPP-2077 | human IgG1 | 51 | 52 |
| TPP-2084 | human IgG1 | 41 | 42 |
| TPP-2148 | human IgG1 | 31 | 32 |
| TPP-2093 | human IgG1 | 21 | 22 |
| TPP-2149 | human IgG1 | 11 | 12 |
| TPP-2090 | human IgG1 | 1 | 2 |

TABLE AK-5

List of commercially available antibodies used for the affinity measurement

| Nomenclature | Description | Cat. No. (Abcam) |
|---|---|---|
| ITEM-1 | murine IgG1 | ab21359 |
| ITEM-4 | murine IgG1 | ab21127 |

Various concentrations (200 nM, 100 nM, 50 nM, 25 nM, 12.5 nM, 6.25 nM, 3.12 nM, 1.56 nM) of purified recombinant human TWEAKR protein (TPP-2305, SEQ ID NO: 168) in HEPES-EP buffer (GE Healthcare Biacore, Inc.) were injected over immobilised anti-TWEAKR antibodies at a flow rate of 60 µl/min for 3 minutes, the dissociation time being 5 minutes. Sensorgrams were generated after in-line reference cell correction, followed by subtraction of the buffer sample. The dissociation constant ($K_D$) was calculated based on the ratio of association ($k_{on}$) and dissociation ($k_{off}$) constants, obtained by fitting sensorgrams using a 1:1 first order binding model.

TABLE AK-6

Monovalent $K_D$ values of anti-TWEAKR antibodies measured using Biacore with TWEAKR protein (TPP-2305 (SEQ ID NO: 168)).

| | ka (1/Ms) | kd (1/s) | $K_D$ (nM) |
|---|---|---|---|
| TPP-883 | 4.40E+06 | 9.10E-01 | 205.9 |
| TPP-1538 | 4.20E+06 | 1.10E-01 | 27.6 |
| TPP-2077 | 3.00E+06 | 8.60E-02 | 28.9 |
| TPP-2084 | 4.20E+06 | 1.10E-01 | 27.6 |
| TPP-2148 | 5.10E+06 | 1.30E-01 | 24.5 |
| TPP-2093 | 4.10E+06 | 9.00E-02 | 22.1 |
| TPP-2149 | 8.40E+06 | 1.00E-01 | 12.1 |
| TPP 2090 | 9.10E+06 | 1.10E-01 | 12.4 |
| PDL-192(TPP-1104) | 1.00E+07 | 3.80E-02 | 3.7 |
| 136.1(TPP-2194) | 3.84E+07 | 3.24E-02 | 0.8 |
| 18.3.3(TPP-2193) | 1.64E+07 | 2.85E-02 | 1.7 |
| P4A8(TPP-1324) | 1.20E+06 | 2.70E-03 | 2.3 |
| P3G5(TPP-2195) | 2.31E+06 | 1.22E-03 | 0.5 |
| P2D3(TPP-2196) | 1.32E+06 | 5.64E-04 | 0.4 |
| ITEM-1 | 3.80E+06 | 1.10E-02 | 2.9 |
| ITEM-4 | 2.80E+06 | 2.00E-03 | 0.7 |

It was determined that the antibodies of the invention bind TWEAKR with morate affinity ($K_D$10-200 nM), whereas some comparative antibodies (e.g. PDL-192(TPP-1104), 136.1(TPP-2194), 18.3.3(TPP-2193), P4A8(TPP-1324), P3G5(TPP-2195), P2D3(TPP-2196), ITEM-1, ITEM-4) show high-affinity binding (0.7-3.7 nM). The sequences of the variable domains of the antibodies PDL-192, 136.1, 18.3.3, P4A8, P3G5 snd P2D3 were obtained from the patent literature WO2009/020933 and WO2009/140177, and the sequences coding for the constant region of human IgG1 and murine IgG2 were added, resulting in full-length IgGs PDL-192(TPP-1104), 136.1(TPP-2194), 18.3.3(TPP-2193), P4A8(TPP-1324), P3G5(TPP-2195), P2D3(TPP-2196). The range of the affinities measured in this study agrees well with published data: for PDL-192, 18.3.3 and 136.1, KD values of 5.5, 0.2 and 0.7 nM have been published (WO2009/020933); for P4A8 2.6 nM (WO2009/140177). For comparison: the native ligand TWEAK binds TWEAKR with a $K_D$ value of 0.8-2.4 nM (Immunity. 2001 November; 15(5):837-46; Biochem J. 2006 Jul. 15; 397(2): 297-304; Arterioscler Thromb Vasc Biol. 2003 Apr. 1; 23(4):594-600).

As a result, it can be recorded that the antibodies of the invention (TPP-883, TPP-1538, TPP-2077, TPP-2084, TPP-2148, TPP-2093, TPP-2149 and TPP-2090) bind TWEAKR with morate affinity ($K_D$ 10-200 nM).

Figure 2B:
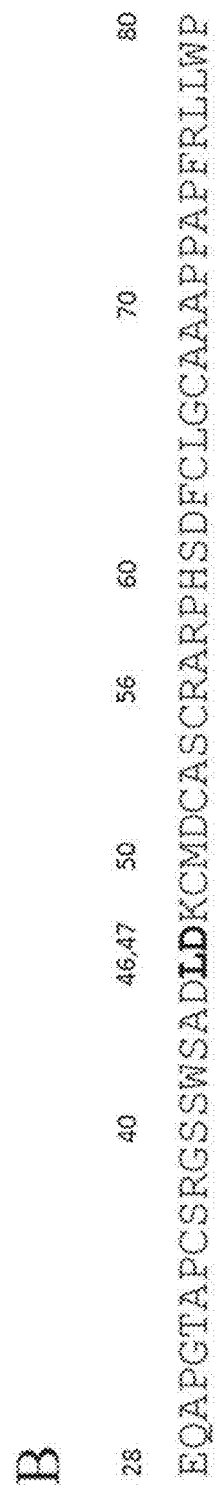
FIG. 2B shows an amino acid sequence of the extracellular domain (SEQ ID NO: 168): It has been published that the amino acid 64 is essential for TWEAK ligand binding; and the amino acid 47 is essential for binding of the antibodies according to the invention, as was determined here.

Characterization of the Binding Epitope of TPP-2090 Using N- and C-Terminally Truncated Variants of the TWEAKR Ectodomain:

The alignment of the cysteine-rich domain of TWEAKR (amino acids 34-68) of different species (FIG. 1) shows that it is well conserved in all 6 species analysed. PDL-192 binds depending on $R^{56}$ (WO2009/020933: FIG. 2B) and does therefore not bind to rat, pig and mouse TWEAKR. TPP-2090 binds depending on the conserved amino acid D47, and therefore binds to all species shown.

In a first approach to characterizing the binding epitope of the antibodies mentioned above, a N- and C-terminally truncated mutant of the TWEAKR ectodomain was generated and examined for its ability to bind the various anti-TWEAKR antibodies. Amino acids 28 to 33 were deleted N-terminally and amino acids 69 to 80 were deleted C-terminally, such that the cysteine-rich domains with disulphide bridges between Cys36-Cys49, Cys52-Cys67 and Cys55-Cys64 remained intact (compare FIG. 2). Both constructs, the full ectodomain 28-80 including N- and C-terminus and the truncated ectodomain 34-68, were expressed and purified as Fc fusion proteins TPP-2202 and TPP-2203, respectively.

Figure 3:
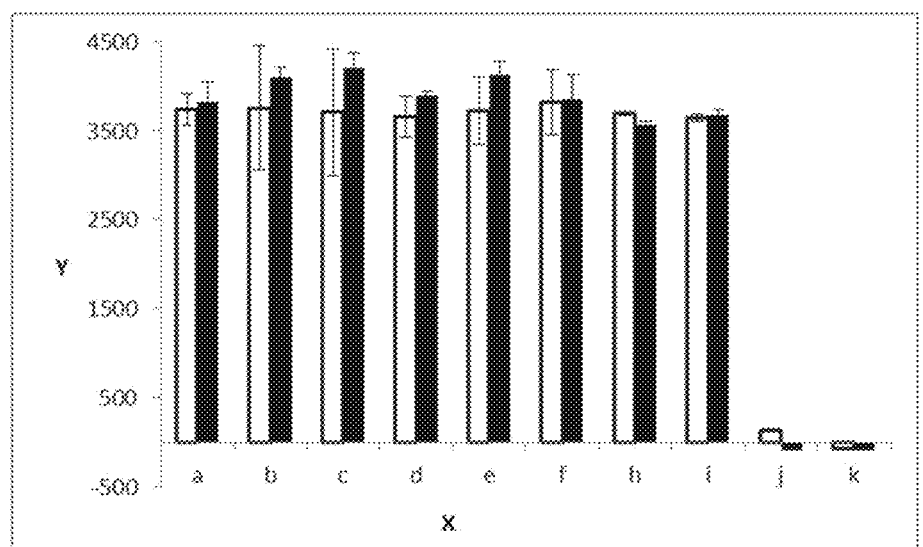
FIG. 3 shows the interaction of the TWEAKR ectodomain with antibodies and reference antibodies. What is shown is the result of an ELISA with TWEAKR-Fc fusion protein coating (TPP-2202, 1 µg/ml) and with 0.08 µg/ml (open bars) and 0.03 µ/ml (solid bars) of biotinylated IgG as soluble binding partner. Detection was carried out using streptavidin-HRP and Amplex Red substrate. Y is the "ELISA signal intensity [Rfu]"; X are the "tested antibody constructs": a is "TPP-2090"; b is "TPP-2084"; c is "PDL-192(TPP-1104)"; d is "P4A8(TPP-1324)"; e is "P3G5(TPP-2195)"; f is "136.1(TPP-2194)"; h is "ITEM1"; i is "ITEM4"; j is a mouse isotype control; k is a human isotype control. All antibodies examined show saturated binding at a concentration of 80 ng/ml.
Figure 4:
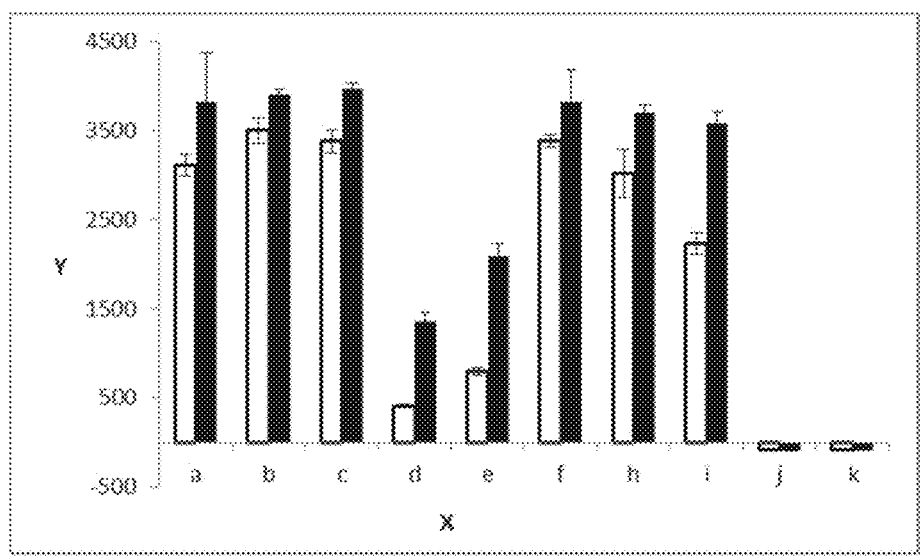
FIG. 4 shows the interaction of the cysteine-rich domain of TWEAKR with antibodies according to the invention and reference antibodies. What is shown is the result of an ELISA with TWEAKR (34-68)-Fc fusion protein coating (TPP-2203, 1 µg/ml) and 0.08 µg/ml (open bars) and 0.3 µ/ml (solid bars) of biotinylated IgG as soluble binding partner. Detection was carried out using streptavidin-HRP and Amplex Red substrate. X are the "antibody constructs tested": a is "TPP-2090"; b is "TPP-2084"; c is "PDL-192 (TPP-1104)"; d is "P4A8(TPP-1324)"; e is "P3G5(TPP-2195)"; f is "136.1(TPP-2194)"; h is "ITEM1"; i is "ITEM4"; j is a mouse isotype control; k is a human isotype control. All antibodies examined show saturated binding at a concentration of 80 ng/ml.
Figure 5:
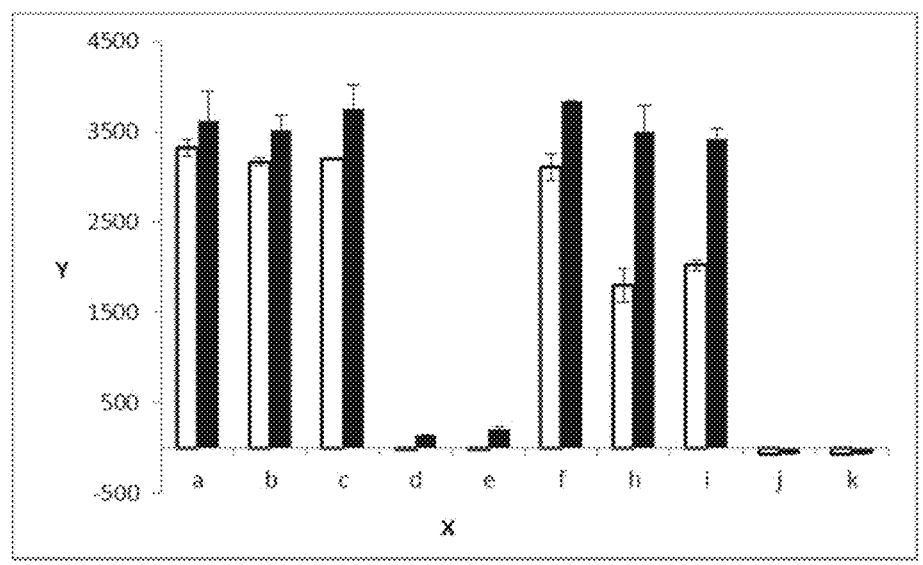
FIG. 5 shows the interaction of TWEAKR (28-68) with antibodies according to the invention and reference antibodies. What is shown is the result of an ELISA with TWEAKR (28-68)-HIS coating (TTP-1984, 1 µg/ml) and 0.08 µg/ml (open bars) and 0.3 µ/ml (solid bars) of biotinylated IgG as soluble binding partner. Detection was carried out using streptavidin-HRP and Amplex Red substrate. X are the "antibody constructs tested": a is "TPP-2090"; b is "TPP-2084"; c is "PDL-192(TPP-1104)"; d is "P4A8(TPP-1324)"; e is "P3G5(TPP-2195)"; f is "136.1(TPP-2194)"; h is "ITEM1"; i is "ITEM4"; j is a mouse isotype control; k is a human isotype control. All antibodies examined show saturated binding at a concentration of 80 ng/ml.

To analyse the binding, 1 µg/ml of the corresponding dimeric TWEAKR Fc construct was coated, and 0.3 µg/ml and 0.08 µg/ml of biotinylated IgG were used as soluble binding partner. Detection was carried out using streptavidin-HRP and Amplex Red substrate. IgGs were biotinylated using an about 2-fold molar excess of biotin-LC-NHS (Pierce; Cat. No. 21347) according to the instructions of the manufacturer and desalted using Zeba desalting columns (Pierce; Cat. No. 89889). At all concentrations used of the soluble ligand, the antibodies of the present invention displayed saturated binding to both constructs, whereas the antibodies P4A8(TPP-1324), P3G5(TPP-2195) and Item-4 showed saturated binding only to the full-length ectodomain, but worsened binding to the N- and C-terminally truncated constructs (FIG. 3 and FIG. 4). This shows that the binding epitope of the antibodies of the present invention is located in the cysteine-rich domain between amino acids 34-68. To analyse whether the N-terminus or the C-terminus of the TWEAKR ectodomain is required for P4A8(TPP-1324) and P3G5(TPP-2195) binding, a monomeric ectodomain having the C-terminal deletion of amino acids 69 to 80 was generated. Binding of P4A8(TPP-1324) and P3G5 (TPP-2195) to the C-terminally truncated TWEAKR ectodomain is likewise worsened, whereas the antibodies of the present invention show saturated binding (FIG. 5).

TABLE AK-9

List of recombinant antigens used in the ELISA analysis for epitope profiling

| Nomenclature | Description | SEQ ID NO |
|---|---|---|
| TPP-2202 | TWEAKR-ECD-28-80-hIgGFc-His | 139 |
| TPP-2203 | TWEAKR-ECD-34-68-hIgGFc-His | 140 |
| TPP-1984 | hTNFRSF12 amino acids 28-68-CT-His | 141 |

TABLE AK-10

List of antibodies used in the ELISA analysis for epitope profiling

| | | SEQ ID NO | |
|---|---|---|---|
| Nomenclature | Description | Light chain | Heavy chain |
| P3G5(TPP-2195) | murine IgG2a | 121 | 122 |
| P4A8(TPP-1324) | human IgG1 | 125 | 126 |
| 136.1(TPP-2194) | murine IgG2a | 123 | 124 |
| PDL-192(TPP-1104) | human IgG1 | 127 | 128 |
| TPP 2090 | human IgG1 | 1 | 2 |
| TPP-2084 | human IgG1 | 41 | 42 |

Thus, the binding epitope of TPP-2090, TPP-2084, PDL-192(TPP-1104) and 136.1(TPP-2194) in the cysteine-rich domain and the binding epitope of P4A8(TPP-1324) and P3G5(TPP-2195) are located at least partially outside of the cysteine-rich domain.

Effect of TWEAKR-Fc Muteins on the Antibody Affinity

To examine the binding characteristics of the antibodies of the invention in more detail, certain muteins of TWEAKR suggested to be of relevance for the activity of known agonistic antibodies (WO2009/140177) were investigated. To this end, the full-length ectodomain (amino acids 28-80) having the individual amino acid substitutions below were expressed and purified as Fc fusion proteins: T33Q; S40R; W42A; M50A; $R^{56}P$; H60K; L65Q.

TABLE AK-11

List of recombinant proteins used in the ELISA analysis for mutein binding

| Nomenclature | Description | SEQ ID NO |
|---|---|---|
| TPP-1990 | hTNFRSF12 amino acids a28-80-L65Q-hIgG1-Fc | 142 |
| TPP-1989 | hTNFRSF12 amino acids a28-80-H60K-hIgG1-Fc | 143 |
| TPP-2683 | hTNFRSF12 amino acids a28-80-R56P-hIgG1-Fc | 144 |
| TPP-1988 | hTNFRSF12 amino acids a28-80-M50A-hIgG1-Fc | 145 |
| TPP-1985 | hTNFRSF12 amino acids a28-80-W42A-hIgG1-Fc | 146 |
| TPP-1987 | hTNFRSF12 amino acids a28-80-S40R-hIgG1-Fc | 147 |
| TPP-1986 | hTNFRSF12 amino acids a28-80-T33Q-hIgG1-Fc | 148 |
| TPP-599 | hTNFRSF12 amino acids a28-80-hIgG1-Fc | 138 |

To obtain dose-reaction data, the different TWEAKR-Fc muteins were coated at a low concentration (62 ng/ml) onto a 384-well Maxisorb ELISA plate, and a serial 2-fold dilution of biotinylated IgG beginning with a concentration of 100 nM was used as a soluble binding partner. Detection was carried out using streptavidin-HRP and Amplex Red. The IgGs examined were TPP-2090 and TPP-2084 of the present invention, PDL-192, 136.1 and 18.3.3 of WO2009/020933, P4A8 and P3G5 of WO2009/140177, and ITEM-1 and ITEM-4 of Nakayama et al [Biochem Biophys Res Com 306: 819-825].

TABLE AK-12

List of antibodies used in the ELISA analysis for mutein binding

| | | SEQ ID NO | |
|---|---|---|---|
| Nomenclature | Description | Light chain | Heavy chain |
| P3G5(TPP-2195) | murine IgG2a | 121 | 122 |
| P4A8(TPP-1324) | human IgG1 | 125 | 126 |
| 136.1(TPP-2194) | murine IgG2a | 123 | 124 |
| PDL-192(TPP-1104) | human IgG1 | 127 | 128 |
| 18.3.3(TPP-2193) | murine IgG2a | 129 | 130 |
| TPP 2090 | human IgG1 | 1 | 2 |
| TPP-2084 | human IgG1 | 41 | 42 |

TABLE AK-13

List of commercially available antibodies used in the ELISA for mutein binding

| Nomenclature | Description | Cat. No. (Abcam) |
|---|---|---|
| ITEM-1 | murine IgG1 | ab21359 |
| ITEM-4 | murine IgG1 | ab21127 |

IgGs were biotinylated using an about 2-fold molar excess of biotin-LC-NHS (Pierce; Cat. No. 21347) according to the instructions of the manufacturer and desalted using Zeba desalting columns (Pierce; Cat. No. 89889). The dose-reaction data were fitted and the IC50s were determined. To illustrate the results, a table was generated; "−" marks IC50s over 50 nM, "+" marks IC50s in the range from 1 to 150 μM.

TABLE AK-14

Effect of muteins on antibody binding

| | T33Q | S40R | W42A | M50A | R56P | H60K | L65Q | WT |
|---|---|---|---|---|---|---|---|---|
| TPP-2084 | + | + | − | + | + | + | + | + |
| TPP-2090 | + | + | − | + | + | + | + | + |
| PDL-192(TPP-1104) | + | + | − | + | − | + | + | + |
| 136.1(TPP-2194) | + | + | − | + | − | + | + | + |
| 18.3.3(TPP-2193) | + | + | − | + | | + | + | + |
| P4A8(TPP-1324) | + | + | − | + | − | + | + | + |
| P3G5(TPP-2195) | + | + | − | + | + | + | + | + |
| ITEM1 | + | + | − | + | − | + | + | + |
| ITEM4 | + | + | − | + | + | − | + | + |

As already published, ITEM-4 shows worsened binding to the H60K mutein [WO2009/140177: FIG. 23F] and PDL-192 to the $R^{56}P$ mutein [WO2009/020933: FIG. 22B]. In contrast to published data, ITEM-1 shows worsened binding to $R^{56}P$, and all antibodies to W42A [WO2009/140177: FIG. 23E, FIG. 23F]. These differences can be explained by the methods chosen.

In contrast to ITEM-1, ITEM-4, PDL-192, 136.1 and 18.3.3, the antibodies of the present invention bind independently of all substitutions except for W42A.

Figure 6A:
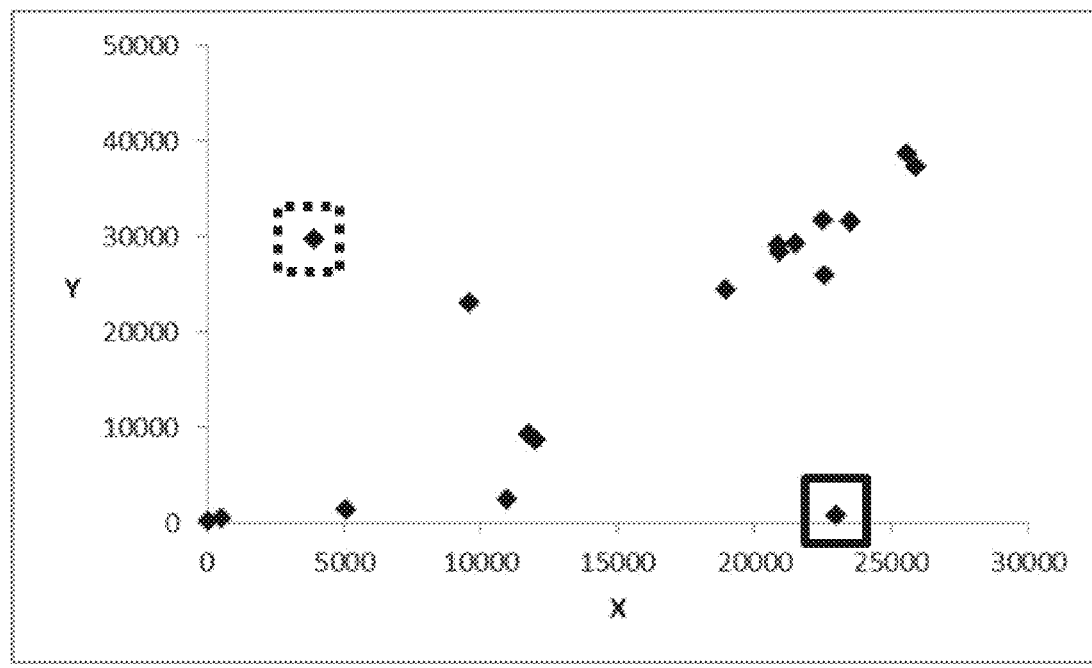
FIG. 6A shows an alanine scan of the cysteine-rich domain. Muteins of TWEAKR(34-68)-Fc were analysed for PDL-192(TPP-1104) (X)- and TPP-2090 (Y)-binding. S37A, R38A, S40A, W42A, S43A, D45A, D47A, K48A, D51A, S54A, R56A, R58A, P59A, H60A, S61A, D62A, F63A and L65A muteins were expressed in HEK293 cells (black diamonds). PFL192(TPP-1104) and TPP-2090 were coated (1 µg/ml) and an 8-fold diluted supernatant of the HEK293 fermentation broth was added for TWEAKR protein binding. X is the "ELISA intensity of the PDL-192/TTP-1104 interaction [Rfu]", Y is the "ELISA intensity of the TPP-2090 interaction [Rfu]". TPP-2090 (Y) shows reduced binding for the D74A-TWEAKR mutein (closed box), and PDL-192(TPP-1104) (X) shows reduced binding to R56A (spotted box).

Alanine Scan of the Cysteine-Rich Domain:

An alanine scan of the cysteine-rich domain (amino acids 34-68) was carried out in order to locate the binding site of the antibodies of the invention. FIG. 6A shows that N- and C-terminally truncated variants of the full-length ectodomain of TWEAKR do not worsen binding of the antibodies of the invention. Accordingly, the binding epitope is located in the cysteine-rich domain. The substitutions below were introduced into the TWEAKR(34-68) Fc construct: S37A, R³⁸A, S40A, S41A, W42A, S43A, D45A, D47A, K48A, D51A, S54A, R⁵⁶A, R⁵⁸A, P59A, H60A, S61A, D62A, F63A und L65A.

TABLE AK-15

List of TWEAKR mutein constructs for the alanine scan of the cysteine-rich domain

| Nomenclature | Description | SEQ ID NO |
|---|---|---|
| TPP-2203 | TweakR-ECD-34-68-hIgGFc-His | 140 |
| TPP-2625 | TweakR-ECD-34-68-hIgGFc-His-L65A | 149 |
| TPP-2624 | TweakR-ECD-34-68-hIgGFc-His-F63A | 150 |
| TPP-2623 | TweakR-ECD-34-68-hIgGFc-His-D62A | 151 |
| TPP-2622 | TweakR-ECD-34-68-hIgGFc-His-S61A | 152 |
| TPP-2621 | TweakR-ECD-34-68-hIgGFc-His-H60A | 153 |
| TPP-2620 | TweakR-ECD-34-68-hIgGFc-His-P59A | 154 |
| TPP-2619 | TweakR-ECD-34-68-hIgGFc-His-R58A | 155 |
| TPP-2618 | TweakR-ECD-34-68-hIgGFc-His-R56A | 156 |
| TPP-2617 | TweakR-ECD-34-68-hIgGFc-His-S54A | 157 |
| TPP-2616 | TweakR-ECD-34-68-hIgGFc-His-D51A | 158 |
| TPP-2615 | TweakR-ECD-34-68-hIgGFc-His-K48A | 159 |
| TPP-2614 | TweakR-ECD-34-68-hIgGFc-His-D47A | 160 |
| TPP-2613 | TweakR-ECD-34-68-hIgGFc-His-D45A | 161 |
| TPP-2612 | TweakR-ECD-34-68-hIgGFc-His-S43A | 162 |
| TPP-2611 | TweakR-ECD-34-68-hIgGFc-His-W42A | 163 |
| TPP-2610 | TweakR-ECD-34-68-hIgGFc-His-S41A | 164 |
| TPP-2609 | TweakR-ECD-34-68-hIgGFc-His-S40A | 165 |
| TPP-2608 | TweakR-ECD-34-68-hIgGFc-His-R38A | 166 |
| TPP-2607 | TweakR-ECD-34-68-hIgGFc-His-S37A | 167 |

These TWEAKR(34-68) Fc muteins were expressed in HEK293 cells. To obtain dose-reaction data, IgGs were coated at a concentration of 1 µg/ml onto a 384-well Maxisorp ELISA plate, and a serial 2-fold dilution of the supernatant comprising the TWEAKR mutein was used as soluble binding partner. Detection was carried out using anti-HIS-HRP and Amplex Red. The IgGs examined were TPP-2090 of the present invention, PDL-192 of WO2009/020933 and P4A8 of WO2009/140177.

TABLE AK-16

List of antibodies used for the alanine scan of the cysteine-rich domain

| | | SEQ ID NO | |
|---|---|---|---|
| Nomenclature | Description | Light chain | Heavy chain |
| P4A8(TPP-1324) | human IgG1 | 125 | 126 |
| PDL-192(TPP-1104) | human IgG1 | 127 | 128 |
| TPP 2090 | human IgG1 | 1 | 2 |

Figure 6B:
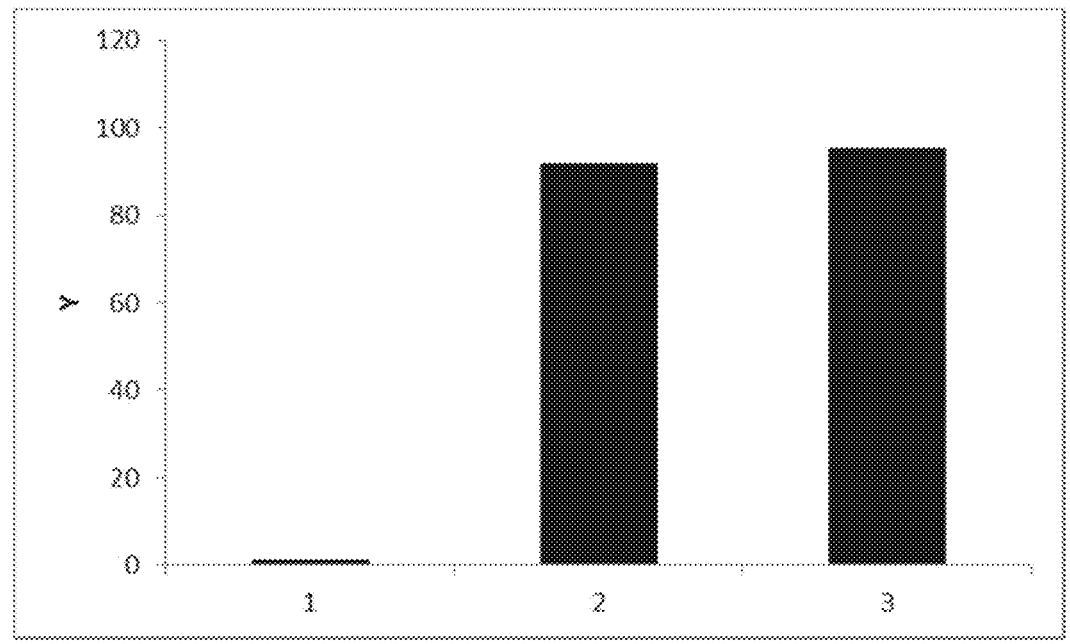
FIG. 6B shows the correlation blots for the 8-fold diluted supernatants of the TWEAKR expression broth, with PDL-192(TPP-1104) on the X axis and TPP-2090 on the Y axis. Y is the "binding in % normalized to the wild-type binding signal [%]", 1 is "TPP-2090"; 2 is "PDL-192(TPP-1104)"; 3 is "P4A8(TPP-1324)". (1 µg/ml), the TWEAKR variant was added at 250 ng/ml, detection was via anti-HIS HRP. Compared to the wild-type construct, TTP-2090 shows less than 5% binding.
Figure 7:
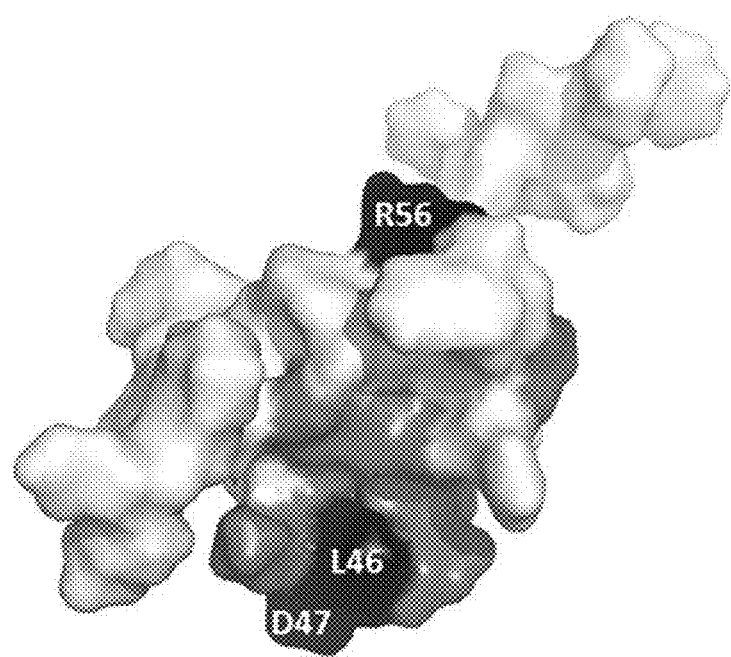
FIG. 7 shows the NMR structure of the TWEAKR ectodomain as published by Pellegrini et al. (FEBS 280:1818-1829). TWEAK binding depends on L46 (Pellegrini et al.), TTP-2090 binding depends on D47 and PDL-192 binds to R56. PDL-192 binds opposite the TWEAK ligand binding site, TPP-2090 binds directly to the TWEAK ligand site.
Figure 8:
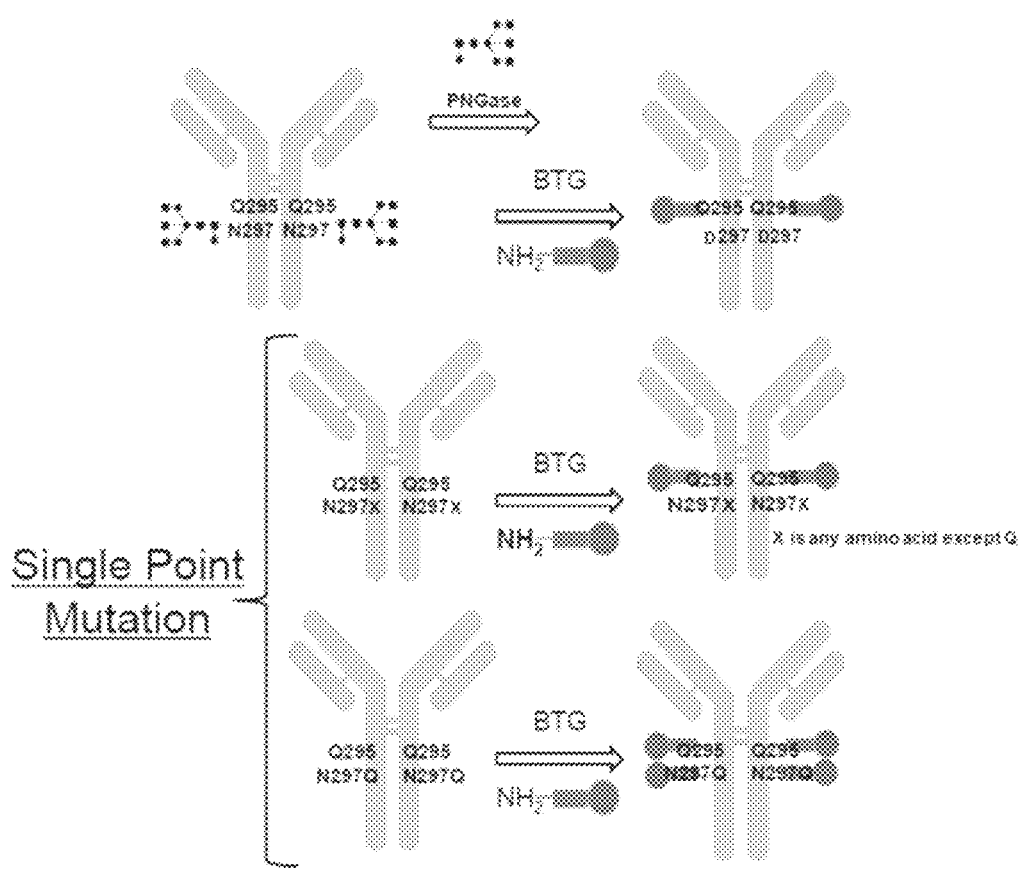
FIG. 8 depicts the strategy using transglutaminase catalyzed conjugation of aglycosylated antibodies.

To assess the relevance of the TWEAKR mutein for binding to various IgGs, a correlation blot at a certain mutein concentration was prepared. By way of example, FIG. 6B shows the correlation blots for the 8-fold diluted supernatants of the TWEAKR expression broth, with PDL-192 (TPP-1104) on the X axis and TPP-2090 on the Y axis. The blot shows that binding of TPP-2090 was worsened by substitution D47A, and binding of PDL-192(TPP-1104) was worsened by substitution R⁵⁶A. Binding to P4A8(TPP-1324) was demonstrated for none of the constructs, which agrees with the results obtained above (FIG. 6B). Thus, the P4A8 epitope is localized at least partially outside of the cysteine-rich domain. The dependencies identified for certain TWEAKR amino acids for antibody interaction correlates with the agonistic activity determined for these antibodies. The native ligand TWEAK shows an effective activation of the TWEAKR and binds depending on leucine 46 in the cysteine-rich domain of TWEAKR (Pellegrini et al, FEBS 280:1818-1829). P4A8 displays a very low agonistic activity and interacts at least partially with domains outside of the cysteine-rich domain of TWEAKR. PDL-192 displays a morate agonistic activity and binds depending on R⁵⁶ to the cysteine-rich domain, but opposite the TWEAK ligand site. TPP-2090 and TWEAK binding depends on D47 and L46, respectively, and they therefore bind to a similar binding site (FIG. 7).

It can be concluded the antibodies of the invention (e.g. TPP-2090) bind to TWEAKR in a manner depending on D47.

The dependencies identified for certain TWEAKR amino acids for antibody interaction correlates with the agonistic activity determined for these antibodies. The native ligand TWEAK shows an effective activation of the TWEAKR and binds depending on leucine 46 in the cysteine-rich domain of TWEAKR (Pellegrini et al, FEBS 280:1818-1829). P4A8 displays a very low agonistic activity and interacts at least partially with domains outside of the cysteine-rich domain of TWEAKR. PDL-192 displays a morate agonistic activity and binds depending on R⁵⁶ to the cysteine-rich domain, but opposite the TWEAK ligand site. Antibodies of the present invention (Example TPP-2090) bind in a manner depending on D47, and TWEAK binds in a manner depending on L46, and binds to a similar, but distinct, binding site (FIG. 7). Accordingly, the antibodies of the present invention displaying strong agonistic activity bind to a novel epitope (D47-dependent) for antibodies associated with very high agonistic activity. It is interesting to note that Michaelson et al. (see page 369, left column in Michaelson J S et al, MAbs. 2011 July-August; 3(4):362-75) gave an explanation for the fact that all agonistic antibodies examined by them have weaker agonistic activity than the natural ligand TWEAK. They conclude that reduced efficacy could be a function of the dimeric binding interaction of the antibodies with TWEAKR, with TWEAK probably entering into a trimeric interaction. It is therefore a surprising result that an antibody of the invention, in spite of its dimeric interaction with TWEAKR, has an even higher agonistic activity. This surprising activity is linked to the specific binding properties of the antibodies of the invention, i.e. the specific binding to D47 of TWEAKR.

The invention claimed is:
1. A conjugate of an aglycosylated anti-TWEAKR antibody or antigen-binding fragment thereof, or aglycosylated anti-HER2 antibody or antigen-binding fragment thereof, wherein the antibody or antigen-binding fragment thereof comprises a mutation N297A, with one or more active compound molecules,
wherein the active compound molecule is a kinesin spindle protein inhibitor attached to the antibody or antigen-binding fragment thereof via a linker L,
wherein the linker L is attached to a glutamine side chain of the antibody or antigen-binding fragment thereof,
wherein 1 to 5 kinesin spindle protein inhibitors are attached to the linker L, and
wherein the kinesin spindle protein inhibitor attached to the linker L has the formula (IIa) below:

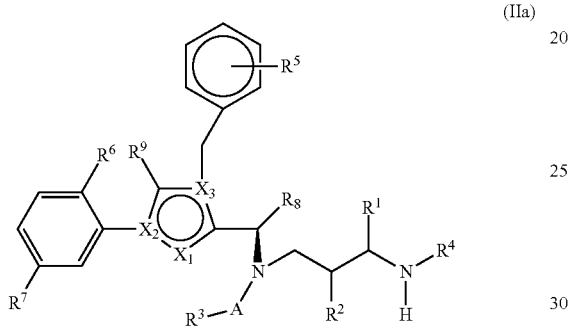

(IIa)

wherein
$X_1$ is N, $X_2$ is N and $X_3$ is C; or
$X_1$ is CH or CF, $X_2$ is C and $X_3$ is N; or
$X_1$ is NH, $X_2$ is C and $X_3$ is C; or
$X_1$ is CH or CF, $X_2$ is N and $X_3$ is C;
$R^1$ is —H, -L-#1, -MOD or —$(CH_2)_{0-3}$Z,
wherein -L-#1 is the linker and #1 represents the bond to the antibody or antigen-binding fragment thereof,
wherein -MOD is as defined infra,
wherein Z is —H, halogen, —$OY^3$, —$SY^3$, —$NHY^3$, —C(=O)—$NY^1Y^2$ or —C(=O)—$OY^3$,
wherein $Y^1$ and $Y^2$ are independently —H, —$NH_2$, —$(CH_2CH_2O)_{0-3}$—$(CH_2)_{0-3}$Z' or —CH($CH_2$W)Z',
wherein $Y^3$ is —H or —$(CH_2)_{0-3}$Z',
wherein Z' is —H, —$NH_2$, —$SO_3H$, —COOH, —NH—C(=O)—$CH_2$—$CH_2$—CH($NH_2$)COOH or —(C(=O)—NH—$CHY^4$)$_{1-3}$COOH,
wherein W is —H or —OH,
wherein $Y^4$ is linear or branched $C_{1-6}$-alkyl which is optionally substituted by —NHC(=O)—$NH_2$, or is aryl or benzyl which are optionally substituted by —$NH_2$;
$R^2$ is —H, -L-#1, -MOD, —C(=O)—$CHY^4$—$NHY^5$ or —$(CH_2)_{0-3}$Z,
wherein -L-#1 is the linker and #1 is the bond to the binder or derivative thereof, antibody or antigen-binding fragment thereof,
wherein -MOD is as defined infra,
wherein Z is —H, halogen, —$OY^3$, —$SY^3$, $NHY^3$, —C(=O)—$NY^1Y^2$ or —C(=O)—$OY^3$,
wherein $Y^1$ and $Y^2$ are independently —H, —$NH_2$ or —$(CH_2)_{0-3}$Z', and
wherein $Y^3$ is s —H or —$(CH_2)_{0-3}$Z',
wherein Z' is —H, —$SO_3H$, —$NH_2$ or —COOH;
wherein $Y^4$ is linear or branched $C_{1-6}$-alkyl which is optionally substituted by —NHC(=O)—$NH_2$, or is aryl or benzyl which are optionally substituted by —$NH_2$,
wherein $Y^5$ is —H or —C(=O)—$CHY^6$—$NH_2$,
wherein $Y^6$ is linear or branched $C_{1-6}$-alkyl;
$R^4$ is —H, -L-#1, —C(=O)—$CHY^4$—$NHY^5$ or —$(CH_2)_{0-3}$Z,
wherein -L-#1 is the linker and #1 is the bond to the binder or derivative thereof, antibody or antigen-binding fragment thereof,
wherein Z is —H, —$OY^3$, —$SY^3$, —$NHY^3$, —C(=O)—$NY^1Y^2$ or —C(=O)—$OY^3$,
wherein $Y^1$ and $Y^2$ are independently —H, —$NH_2$ or —$(CH_2)_{0-3}$Z',
wherein $Y^3$ is —H or —$(CH_2)_{0-3}$Z',
wherein Z' is —H, —$SO_3H$, —$NH_2$ or —COOH;
wherein $Y^4$ is linear or branched $C_{1-6}$-alkyl which is optionally substituted by —NHC(=O)—$NH_2$, or is aryl or benzyl which are optionally substituted by —$NH_2$, and
wherein $Y^5$ is —H or —C(=O)—$CHY^6$—$NH_2$,
wherein $Y^6$ is linear or branched $C_{1-6}$-alkyl; or
$R^4$ is the cathepsin cleavable group $R^{21}$—(C=O)$_{(0-1)}$-(P3)$_{(1-2)}$-P2-,
wherein $R^{21}$ is H, $C_{1-10}$-alkyl-, $C_{5-10}$-aryl- or $C_{6-10}$-aralkyl-, $C_{5-10}$-heteroalkyl-, $C_{1-10}$-alkyl-O—$C_{6-10}$-aryl-, $C_{5-10}$-heterocycloalkyl-, heteroaryl-, heteroaryl-alkyl-, $C_{1-10}$-alkoxy-, $C_{6-10}$-aryloxy- or $C_{6-10}$-aralkoxy-, $C_{5-10}$-heteroalkoxy-, $C_{1-10}$-alkyl-O—$C_{6-10}$-aryloxy-, $C_{5-10}$-heterocycloalkoxy group (which is optionally substituted one or more times with —$NH_2$, —NH-alkyl, —N(alkyl)$_2$, —NH—C(=O)-alkyl, N(alkyl)-C(=O)-alkyl, —$SO_3H$, —$SO_2NH_2$, —S(O)$_2$—N(alkyl)$_2$, —COOH, —C(=O)—$NH_2$, —C(=O)—N(alkyl)$_2$, or —OH), —H or a group —(O)$_x$—$(CH_2CH_2O)_y$—$R^{22}$,
wherein x is 0 or 1, and
wherein v is a number from 1 to 20,
wherein $R^{22}$ is —H, -alkyl (preferably $C_{1-12}$-alkyl), —$CH_2$—COOH, —$CH_2$—$CH_2$—COOH, or —$CH_2$—$CH_2$—$NH_2$);
wherein P2 is an amino acid selected from the group consisting of Gly, Pro, Ala, Val, Nva, Leu, Ile, Met, Phe, Tyr, Trp, Ser, Thr, Cys, Asn, Gln, Asp, Glu, Lys, Arg, citrulline and His;
wherein P3 is an amino acid independently selected from the group consisting of Gly, Pro, Ala, Val, Nva, Leu, Ile, Met, Phe, Tyr, Trp, Ser, Thr, Cys, Asn, Gln, Asp, Glu, Lys, Arg, citrulline and His or one of the corresponding N-alkyl amino acids, preferably N-methyl amino acids; in case there is more than one amino acid P3, P3 may have the same or different amino acids, as defined above; or
$R^2$ and $R^4$ together (with formation of a pyrrolidine ring) represent —$CH_2$—$CHR^{10}$— or —$CHR^{10}$—$CH_2$—,
wherein $R^{10}$ is —H, halogen, —$NH_2$, —SO3H, —COOH, —SH, C1-4-alkyl, halo-$C_{1-4}$-alkyl, $C_{1-4}$-alkoxy, hydroxy substituted $C_{1-4}$-alkyl, —C(=O)—O—($C_{1-4}$-alkyl) or OH;
wherein L-#1 is the linker and #1 represents the bond to the antibody or antigen-binding fragment thereof;

A is —C(=O)—, —S(=O)—, —S(=O)$_2$—, —S(=O)$_2$—NH— or —C(=N—NH$_2$)—;

R$^3$ is -L-#1, -MOD or an optionally substituted alkyl, cycloalkyl, aryl, heteroaryl, heteroalkyl, heterocycloalkyl group which is optionally substituted by 1-3 OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—C(=O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)$_n$-alkyl groups, 1-3 —S(=O)$_2$—NH-alkyl groups, 1-3 —NH-alkyl groups, 1-3 —N(alkyl)$_2$ groups, 1-3 —NH((CH$_2$CH$_2$O)$_{1-20}$H) groups, 1-3 —NH$_2$ groups or 1-3 —(CH$_2$)$_{0-3}$Z groups, wherein -L-#1 is the linker and #1 represents the bond to the antibody or antigen-binding fragment thereof, wherein -MOD is as defined infra, wherein n is 0, 1 or 2, wherein Z is —H, halogen, —OY$^3$, —SY$^3$, —NHY$^3$, —C(=O)—NY$^1$Y$^2$ or —C(=O)—OY$^3$, wherein Y$^1$ and Y$^2$ are independently —H, —NH$_2$ or —(CH$_2$)$_{0-3}$Z' and wherein Y$^3$ is —H, —(CH$_2$)$_{0-3}$—CH(NH—C(=O)—CH$_3$)Z', —(CH$_2$)$_{0-3}$—CH(NH$_2$)Z' or —(CH$_2$)$_{0-3}$Z', wherein wherein Z' is —H, —SO$_3$H, —NH$_2$ or —COOH;

R$^5$ is -L-#1, H, -MOD, —NH$_2$, —NO$_2$, halogen, —CN, —CF$_3$, —OCF$_3$, —CH$_2$F, —CH$_2$F, —SH or —(CH$_2$)$_{0-3}$Z, wherein Z is —H, —OY$^3$, —SY$^3$, halogen, —NHY$^3$, —C(=O)—NY$^1$Y$^2$ or —C(=O)—OY$^3$, wherein Y$^1$ and Y$^2$ are independently —H, —NH$_2$ or —(CH$_2$)$_{0-3}$Z', wherein Y$^3$ is —H or —(CH$_2$)$_{0-3}$Z', wherein Z' is —H, —SO$_3$H, —NH$_2$ or —COOH;

R$^6$ and R$^7$ are independently —H, cyano, C$_{1-10}$-alkyl, fluoro-C$_{1-10}$-alkyl, C$_{2-10}$-alkenyl, fluoro-C$_{2-10}$-alkenyl, C$_{2-10}$-alkynyl, fluoro-C$_{2-10}$-alkynyl, hydroxy, —NO$_2$, —NH$_2$, —COOH or halogen, R$^8$ is C$_{1-10}$-alkyl, fluoro-C$_{1-10}$-alkyl, C$_{2-10}$-alkenyl, fluoro-C$_{2-10}$-alkenyl, C$_{2-10}$-alkynyl, fluoro-C$_{2-10}$-alkynyl, C$_{4-10}$-cycloalkyl, fluoro-C$_{4-10}$-cycloalkyl, or —(CH$_2$)$_{0-2}$-(HZ$^2$), wherein HZ$^2$ is a 4- to 7-membered heterocycle having up to two heteroatoms selected from the group consisting of N, O and S, wherein each of these groups is optionally substituted by —OH, —COOH or —NH$_2$ or -L-#1;

wherein -L-#1 is the linker and #1 is the bond to the antibody or antigen-binding fragment thereof, wherein one of the substituents R$^1$, R$^2$, R$^3$, R$^4$, R$^5$, R$^8$ and R$^{10}$ is (or in the case of R$^8$ contains) -L-#1, R$^9$ is —H, —F, —CH$_3$, —CF$_3$, —CH$_2$F or —CHF$_2$;

-MOD as defined supra is —(NR$^{10}$)n-(G1)o-G2-G3, wherein R$^{10}$ is —H or C$_1$-C$_3$-alkyl;

wherein G1 is —NH—C(=O)—, —C(=O)—NH— or

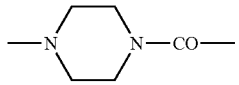

wherein n is 0 or 1;

wherein o is 0 or 1;

wherein G2 is a linear and/or branched hydrocarbon group which has 1 to 10 carbon atoms and which is optionally interrupted once or more than once by one or more of the groups —O—, —S—, —S(=O)—, —S(=O)$_2$-, —NR$^y$—, —NR$^y$C(=O)—, —C(=O)—NR$^y$—, —NR$^y$NR$^y$—, —S(=O)$_2$—NR$^y$NR$^y$—, —C(=O)—NR$^y$NR$^y$—, —C(=O)—, —CR$^x$=N—O—, and wherein the hydrocarbon chain including any side chains is optionally substituted by —NH—C(=O)—NH$_2$, —COOH, —OH, —NH$_2$, NH—CN—NH$_2$, sulphonamide, sulphone, sulphoxide or sulphonic acid, wherein R$^y$ is —H, phenyl, C$_1$-C$_{10}$-alkyl, C$_2$-C$_{10}$-alkenyl or C$_2$-C$_{10}$-alkynyl, each of which is optionally substituted by —NH—C(=O)—NH$_2$, —COOH, —OH, —NH$_2$, NH—CN—NH$_2$, sulphonamide, sulphone, sulphoxide or sulphonic acid, wherein R$^x$ is —H, C$_1$-C$_3$-alkyl or phenyl, wherein G3 is —H or —COOH, and wherein -MOD has at least one —COOH group;

or a salt, a solvate, a salt of the solvate, or an epimer thereof.

2. The conjugate according to claim 1, wherein X$_1$ is CH, X$_2$ is C and X$_3$ is N.

3. The conjugate according to claim 1, wherein the linker L is attached to a glutamine side chain of the antibody or antigen-binding fragment thereof, wherein 1 to 5 kinesin spindle protein inhibitors are attached to the linker L, wherein the active compound molecule linker is represented by general formula (II):

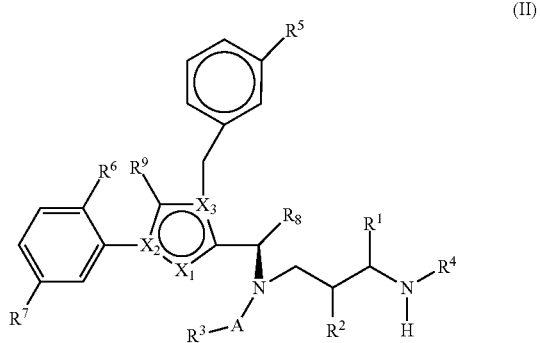

(II)

wherein

X$_1$ is N, X$_2$ is N and X$_3$ is C; or

X$_1$ is CH or CF, X$_2$ is C and X$_3$ is N; or

X$_1$ is NH, X$_2$ is C and X$_3$ is C; or

X$_1$ is CH, X$_2$ is N and X$_3$ is C

R$^1$ is —H, -MOD, -L-#1 or —(CH$_2$)$_{0-3}$Z, wherein -L-#1 is the linker and #1 is the bond to the antibody or antigen-binding fragment thereof, wherein -MOD is represented as defined infra, wherein Z is —H, halogen, —OY$^3$, —SY$^3$, —NHY$^3$, —C(=O)—NY$^1$Y$^2$ or —C(=O)—OY$^3$, wherein Y$^1$ and Y$^2$ are independently —H, —NH$_2$, —(CH$_2$CH$_2$O)$_{0-3}$—(CH$_2$)$_{0-3}$Z' or —CH(CH$_2$W)Z', wherein Y$^3$ is —H or —(CH$_2$)$_{0-3}$Z', wherein Z' is —H, —NH$_2$, —SO$_3$H, —COOH, —NH—C(=O)—CH$_2$—CH$_2$—CH(NH$_2$)COOH or —(C(=O)—NH—CHY$^4$)$_{1-3}$COOH, wherein W is —H or —OH,
wherein $Y^4$ is linear or branched $C_{1-6}$-alkyl which is optionally substituted by —NH—C(=O)—NH$_2$, or is aryl or benzyl which are optionally substituted by —NH$_2$;

$R^2$ is -L-#1, H, -MOD, —C(=O)—CHY$^4$—NHY$^5$ or —(CH$_2$)$_{0-3}$Z,
  wherein -L-#1 is the linker and #1 is the bond to the antibody or antigen-binding fragment thereof,
  wherein -MOD is as defined infra,
  wherein Z is —H, halogen, —OY$^3$, —SY$^3$, NHY$^3$, —C(=O)—NY$^1$Y$^2$ or —C(=O)—OY$^3$,
  wherein $Y^1$ and $Y^2$ are independently —H, —NH$_2$ or —(CH$_2$)$_{0-3}$Z', and
  wherein $Y^3$ is —H or —(CH$_2$)$_{0-3}$Z',
  wherein Z' is —H, —SO$_3$H, —NH$_2$ or —COOH;
  wherein $Y^4$ is linear or branched $C_{1-6}$-alkyl which is optionally substituted by —NH—C(=O)—NH$_2$, or is aryl or benzyl which are optionally substituted by —NH$_2$,
  wherein $Y^5$ is —H or —C(=O)—CHY$^6$—NH$_2$,
  wherein $Y^6$ is linear or branched $C_{1-6}$-alkyl;

$R^4$ is -L-#1, —H, —C(=O)—CHY$^4$—NHY$^5$ or —(CH$_2$)$_{0-3}$Z,
  wherein -L-#1 is the linker and #1 is the bond to the antibody or antigen-binding fragment thereof,
  wherein Z is —H, —OY$^3$, —SY$^3$, —NHY$^3$, —C(=O)—NY$^1$Y$^2$ or —C(=O)—OY$^3$,
  wherein $Y^1$ and $Y^2$ are independently —H, —NH$_2$ or —(CH$_2$)$_{0-3}$Z',
  wherein $Y^3$ is —H or —(CH$_2$)$_{0-3}$Z',
  wherein Z' is —H, —SO$_3$H, —NH$_2$ or —COOH;
  wherein $Y^4$ is linear or branched $C_{1-6}$-alkyl which is optionally substituted by —NH—C(=O)—NH$_2$, or is aryl or benzyl which are optionally substituted by —NH$_2$, and
  wherein $Y^5$ is —H or —C(=O)—CHY$^6$—NH$_2$,
  wherein $Y^6$ is linear or branched $C_{1-6}$-alkyl,
  or
$R^4$ is the cathepsin cleavable group $R^{21}$—(C=O)$_{(0-1)}$-(P3)$_{(1-2)}$-P2-,
  wherein $R^{21}$ is —H, $C_{1-10}$-alkyl-, $C_{5-10}$-aryl- or $C_{6-10}$-aralkyl-, $C_{5-10}$-heteroalkyl-, $C_{1-10}$-alkyl-O—$C_{6-10}$-aryl-, $C_{5-10}$-heterocycloalkyl-, heteroaryl-, heteroaryl-alkyl-, $C_{1-10}$-alkoxy-, $C_{6-10}$-aryloxy- or $C_{6-10}$-aralkoxy-, $C_{5-10}$-heteroalkoxy-, $C_{1-10}$-alkyl-O—$C_{6-10}$-aryloxy-, $C_{5-10}$-heterocycloalkoxy group, which is optionally substituted one or more times with —NH$_2$, —NH-alkyl, —N(alkyl)$_2$, —NH—C(=O)-alkyl, N(alkyl)-C(=O)-alkyl, —SO$_3$H, —S(=O)$_2$NH$_2$, —S(=O)$_2$—N(alkyl)$_2$, —COOH, —C(=O)—NH$_2$, —C(=O)—N(alkyl)$_2$, or —OH, or represent —H or a group —(O)$_x$—(CH$_2$CH$_2$O)$_y$—R$^{22}$,
  wherein x is 0 or 1, and
  wherein v is a number from 1 to 20,
  wherein $R^{22}$ is —H, -alkyl, —CH$_2$—COOH, —CH$_2$—CH$_2$—COOH, or —CH$_2$—CH$_2$—NH$_2$);
  wherein P2 is an amino acid selected from the group consisting of Gly, Pro, Ala, Val, Nva, Leu, Ile, Met, Phe, Tyr, Trp, Ser, Thr, Cys, Asn, Gln, Asp, Glu, Lys, Arg, citrulline and His;
  wherein P3 is an amino acid independently selected from the group consisting of Gly, Pro, Ala, Val, Nva, Leu, Ile, Met, Phe, Tyr, Trp, Ser, Thr, Cys, Asn, Gln, Asp, Glu, Lys, Arg, citrulline and His or one of the corresponding N-alkyl amino acids; in case there is more than one amino acid P3, P3 may have the same or different amino acids, as defined above;
  or $R^2$ and $R^4$ together (with formation of a pyrrolidine ring) represent —CH$_2$—CHR$^{10}$— or —CHR$^{10}$—CH$_2$—,
  wherein $R^{10}$ is —H, halogen, —NH$_2$, —SO$_3$H, —COOH, —SH or OH;
  wherein L-#1 is the linker and #1 is the bond to the antibody or antigen-binding fragment thereof;

A is —C(=O)—, —S(=O)—, —S(=O)$_2$—, —S(=O)$_2$—NH— or —C(=N—NH$_2$)—;

$R^3$ is -L-#1, -MOD or an optionally substituted alkyl, cycloalkyl, aryl, heteroaryl, heteroalkyl, heterocycloalkyl group, preferably -L-#1 or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which is optionally substituted by 1-3 —OH groups, 1-3 halogen atoms, 1-3 halogenated alkyl groups (each having 1-3 halogen atoms), 1-3 —O-alkyl groups, 1-3 —SH groups, 1-3 —S-alkyl groups, 1-3 —O—C(=O)-alkyl groups, 1-3 —O—C(=O)—NH-alkyl groups, 1-3 —NH—C(=O)-alkyl groups, 1-3 —NH—C(=O)—NH-alkyl groups, 1-3 —S(=O)$_n$-alkyl groups, 1-3 —S(=O)$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups,
  wherein -L-#1 is the linker and #1 is the bond to the binder or derivative thereof, antibody or antigen-binding fragment thereof,
  wherein -MOD is as defined infra,
  wherein n is 0, 1 or 2,
  wherein Z is —H, halogen, —OY$^3$, —SY$^3$, —NHY$^3$, —C(=O)—NY$^1$Y$^2$ or —C(=O)—OY$^3$,
  wherein $Y^1$ and $Y^2$ are independently —H, —NH$_2$ or —(CH$_2$)$_{0-3}$Z' and
  wherein $Y^3$ is —H, —(CH$_2$)$_{0-3}$—CH(NHC(=O)—CH$_3$)Z', —(CH$_2$)$_{0-3}$—CH(NH$_2$)Z' or —(CH$_2$)$_{0-3}$Z',
  wherein Z' is —H, —SO$_3$H, —NH$_2$ or —COOH;

$R^5$ is —H, —NH$_2$, —NO$_2$, halogen, —SH or —(CH$_2$)$_{0-3}$Z,
  wherein Z is —H, —OY$^3$, —SY$^3$, halogen, —NHY$^3$, —C(O)—NY$^1$Y$^2$ or —C(O)—OY$^3$,
  wherein $Y^1$ and $Y^2$ are independently —H, —NH$_2$ or —(CH$_2$)$_{0-3}$Z',
  wherein $Y^3$ is —H or —(CH$_2$)$_{0-3}$Z',
  wherein Z' is —H, —SO$_3$H, —NH$_2$ or —COOH;

$R^6$ and $R^7$ are independently —H, cyano, $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, hydroxy or halogen, $R^8$ is $C_{1-10}$-alkyl, fluoro-$C_{1-10}$-alkyl, $C_{4-10}$-cycloalkyl, fluoro-$C_{4-10}$-cycloalkyl, or optionally substituted oxetane; and $R^9$ is —H, —F, —CH$_3$, —CF$_3$, —CH$_2$F or —CHF$_2$;
or a salt, a solvate, a salt of the solvate, or an epimer thereof.

4. The conjugate according to claim 3,
$R^1$ is —H, -L-#1 or —(CH$_2$)$_{0-3}$Z,
  wherein -L-#1 is the linker and #1 is the bond to the antibody or antigen-binding fragment thereof,
  wherein Z is —H, —OY$^3$, —SY$^3$, —NHY$^3$, —C(=O)—NY$^1$Y$^2$ or —C(=O)—OY$^3$,
  wherein $Y^1$ and $Y^2$ are independently —H, —NH$_2$, —(CH$_2$CH$_2$O)$_{0-3}$—(CH$_2$)$_{0-3}$Z' or —CH(CH$_2$W)Z',
  wherein $Y^3$ is —H or —(CH$_2$)$_{0-3}$Z', wherein Z' is —H, —NH$_2$, —COOH, —NH—C(=O)—CH$_2$—CH$_2$—CH(NH$_2$)COOH or —(C(=O)—NH—CHY$^4$)$_{1-3}$COOH,
wherein W is —H or —OH,
wherein Y$^4$ is linear or branched C$_{1-6}$-alkyl which is optionally substituted by —NH—C(=O)—NH$_2$, or is aryl or benzyl which are optionally substituted by —NH$_2$;
R$^2$ and R$^4$ are independently -L-#1, —H or —C(=O)—CHY$^4$—NHY$^5$,
wherein -L-#1 is the linker and #1 is the bond to the binder or derivative thereof, antibody or antigen-binding fragment thereof,
wherein Y$^4$ is linear or branched C$_{1-6}$-alkyl which is optionally substituted by —NH—C(=O)—NH$_2$, or is aryl or benzyl which are optionally substituted by —NH$_2$,
wherein Y$^5$ is —H or —C(=O)—CHY$^6$—NH$_2$,
wherein Y$^6$ is linear or branched C$_{1-6}$-alkyl; or
R$^2$ and R$^4$ together (with formation of a pyrrolidine ring) represent —CH$_2$—CHR$^{10}$—,
wherein R$^{10}$ is -L-#1, —H, —NH$_2$, —SO$_3$H, —COOH, —SH or —OH,
wherein L-#1 is the linker and #1 is the bond to the antibody or antigen-binding fragment thereof,
A is —C(=O);
R$^3$ is —(CH$_2$)OH or -L-#1,
wherein -L-#1 is the linker and #1 is the bond to the antibody or antigen-binding fragment thereof,
R$^5$ is -L-#1 or —H,
wherein -L-#1 is the linker and #1 is the bond to the antibody or antigen-binding fragment thereof,
wherein one of the substituents R$^1$, R$^2$, R$^3$, R$^4$ and R$^5$ is -L-#1,
or a salt, a solvate, a salt of the solvate, or an epimer thereof.

5. The conjugate according to claim 3, wherein R$^6$ and R$^7$ are independently H, C$_{1-3}$-alkyl or halogen.

6. The conjugate according to claim 3, wherein R$^8$ is C$_{1-4}$-alkyl.

7. The conjugate according to claim 3, wherein R$^9$ is H.

8. The conjugate according to claim 3, wherein R$^6$ and R$^7$ are F.

9. The conjugate according to claim 1, wherein the antibody or antigen-binding fragment thereof is a binder peptide or protein or a derivative of a binder peptide or protein.

10. The conjugate according to claim 1, wherein the conjugate has 2 conjugation sites per antibody or antigen-binding fragment thereof.

11. The conjugate according to claim 9, wherein the antibody or antigen-binding fragment thereof comprises an acceptor glutamine side chain which can be recognized by transglutaminase.

12. The conjugate according to claim 9, produced by transglutaminase mediated conjugation.

13. The conjugate according to claim 9, produced using transglutaminase originated from *Streptomyces mobaraensis*.

14. The conjugate according to claim 1, wherein the antibody or antigen-binding fragment thereof binds to a cancer target molecule.

15. The conjugate according to claim 14, wherein the antibody or antigen-binding fragment thereof binds to an extracellular target molecule.

16. The conjugate according to claim 15, wherein the antibody or antigen-binding fragment thereof, after binding to the extracellular target molecule, is internalized and processed intracellularly by the cell expressing the target molecule.

17. The conjugate according to claim 9, wherein the antibody or antigen-binding fragment thereof is a human, humanized or chimeric monoclonal antibody or an antigen-binding fragment thereof.

18. The conjugate according to claim 1, wherein the antibody or antigen-binding fragment thereof is an antibody bearing acceptor glutamine residue(s) in its heavy chain, optionally within the CH2 domain.

19. The conjugate according to claim 18, wherein the antibody or antigen-binding fragment thereof is an antibody bearing acceptor glutamine residue is in its heavy chain at position 295 (KABAT numbering system).

20. The conjugate according to claim 1, wherein the antibody or antigen-binding fragment thereof is an anti-TWEAKR antibody or an antigen-binding fragment thereof.

21. The conjugate according to claim 20, wherein the anti-TWEAKR antibody binds specifically to amino acid D in position 47 (D47) of TWEAKR (SEQ ID NO:169).

22. The conjugate according to claim 20, wherein the anti-TWEAKR antibody binds specifically to amino acid D in position 47 (D47) of TWEAKR (SEQ ID NO:169) and is selected from the group consisting of anti-TWEAKR antibody TPP-2090 and aglycosylated variants thereof.

23. The conjugate according to claim 1, wherein the linker L is attached to a glutamine side chain of the antibody or antigen-binding fragment thereof, wherein 1 to 5 kinesin spindle protein inhibitors are attached to the linker L, wherein the linker L has one of the basic structures (i) to (iv) below:
(i) —(C=O)$_m$-SG1-L1-L2-
(ii) —(C=O)$_m$-L1-SG-L1-L2-
(iii) —(C=O)$_m$-L1-L2-
(iv) —(C=O)$_m$-L1-SG-L2
wherein m is 0 or 1, SG and SG1 are in vivo cleavable groups, each L1 is independently organic groups not cleavable in vivo, and L2 is a coupling group to the antibody or antigen-binding fragment thereof.

24. The conjugate according to claim 23, wherein the linker L is attached to a glutamine side chain of the antibody or antigen-binding fragment thereof, wherein 1 to 5 kinesin spindle protein inhibitors are attached to the linker L, wherein the in vivo cleavable group SG is a 2-8 oligopeptide group, or a disulphide, a hydrazone, an acetal or an aminal, and SG1 is a 2-8 oligopeptide group.

25. The conjugate according to claim 23, wherein L2 is one of the groups below:
L2 is

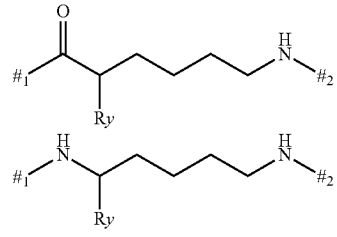

wherein Ry is —H, —C(=O)—NH-alkyl, —NH—C(=O)-alkyl, —C(=O)—NH$_2$, —NH$_2$, and wherein #$^1$ denotes the point of attachment to group L$^1$, and

² denotes the point of attachment to the glutamine residue of the antibody or antigen-binding fragment thereof.

26. The conjugate according to claim 25, wherein Ry is —H or —NH—C(=O)—CH₃.

27. The conjugate according to claim 25, wherein R¹ or R⁴ is -L-#1.

28. The conjugate according to claim 20, wherein the anti-TWEAKR antibody is an agonistic antibody.

29. The conjugate according to claim 1, wherein the antibody or antigen-binding fragment thereof is an antibody comprising:
a variable heavy chain comprising:
   a. a CDR1 of the heavy chain encoded by an amino acid sequence comprising the formula PYPMX (SEQ ID NO: 171), wherein X is I or M;
   b. a CDR2 of the heavy chain encoded by an amino acid sequence comprising the formula YISPSGGXTHY-ADSVKG (SEQ ID NO: 172), wherein X is S or K; and
   c. a CDR3 of the heavy chain encoded by an amino acid sequence comprising the formula GGDTYFDYFDY (SEQ ID NO: 173);
and a variable light chain comprising:
   d. a CDR1 of the light chain encoded by an amino acid sequence comprising the formula RASQSISXYLN (SEQ ID NO: 174), wherein X is G or S;
   e. a CDR2 of the light chain encoded by an amino acid sequence comprising the formula XASSLQS (SEQ ID NO: 175), wherein X is Q, A or N; and
   f. a CDR3 of the light chain encoded by an amino acid sequence comprising the formula QQSYXXPXIT (SEQ ID NO: 176), wherein X at position 5 is T or S, X at position 6 is T or S and X at position 8 is G or F.

30. The conjugate according to claim 1, wherein the antibody or antigen-binding fragment thereof is an antibody comprising:
   a. a variable sequence of the heavy chain, as shown in SEQ ID NO:10, and also a variable sequence of the light chain, as shown in SEQ ID NO:9, or
   b. a variable sequence of the heavy chain, as shown in SEQ ID NO:20, and also a variable sequence of the light chain, as shown in SEQ ID NO:19, or
   c. a variable sequence of the heavy chain, as shown in SEQ ID NO:30, and also a variable sequence of the light chain, as shown in SEQ ID NO:29, or
   d. a variable sequence of the heavy chain, as shown in SEQ ID NO:40, and also a variable sequence of the light chain, as shown in SEQ ID NO:39, or
   e. a variable sequence of the heavy chain, as shown in SEQ ID NO:50, and also a variable sequence of the light chain, as shown in SEQ ID NO:49, or
   f. a variable sequence of the heavy chain, as shown in SEQ ID NO:60, and also a variable sequence of the light chain, as shown in SEQ ID NO:59, or
   g. a variable sequence of the heavy chain, as shown in SEQ ID NO:70, and also a variable sequence of the light chain, as shown in SEQ ID NO:69, or
   h. a variable sequence of the heavy chain, as shown in SEQ ID NO:80, and also a variable sequence of the light chain, as shown in SEQ ID NO:79, or
   i. a variable sequence of the heavy chain, as shown in SEQ ID NO:90, and also a variable sequence of the light chain, as shown in SEQ ID NO:89, or
   j. a variable sequence of the heavy chain, as shown in SEQ ID NO:100, and also a variable sequence of the light chain, as shown in SEQ ID NO:99, or
   k. a variable sequence of the heavy chain, as shown in SEQ ID NO:110, and also a variable sequence of the light chain, as shown in SEQ ID NO:109, or
   l. a variable sequence of the heavy chain, as shown in SEQ ID NO:120, and also a variable sequence of the light chain, as shown in SEQ ID NO:119.

31. The conjugate according to claim 1, wherein the antibody is an IgG antibody.

32. A process for preparing the conjugate according to claim 1, wherein a compound of one of the formulae below, is conjugated to a residue of an antibody or antigen-binding fragment thereof using transglutaminase, wherein the compound is employed in a 2- to 100-fold molar excess with respect to the antibody or antigen-binding fragment thereof:

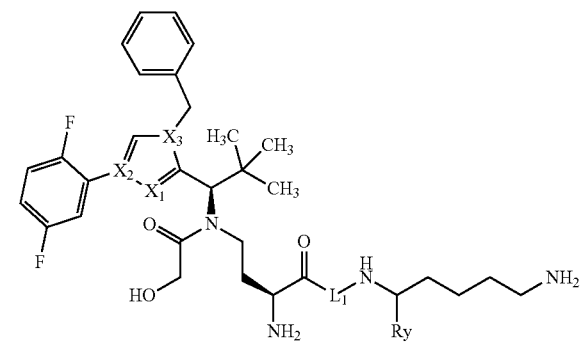

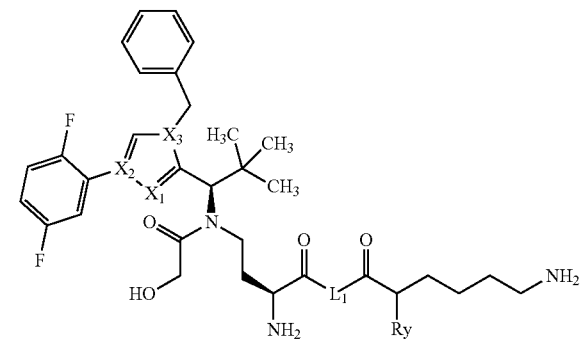

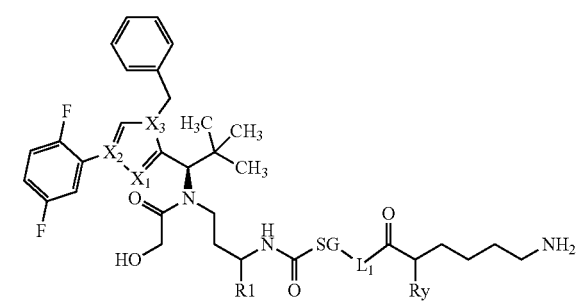

669

-continued

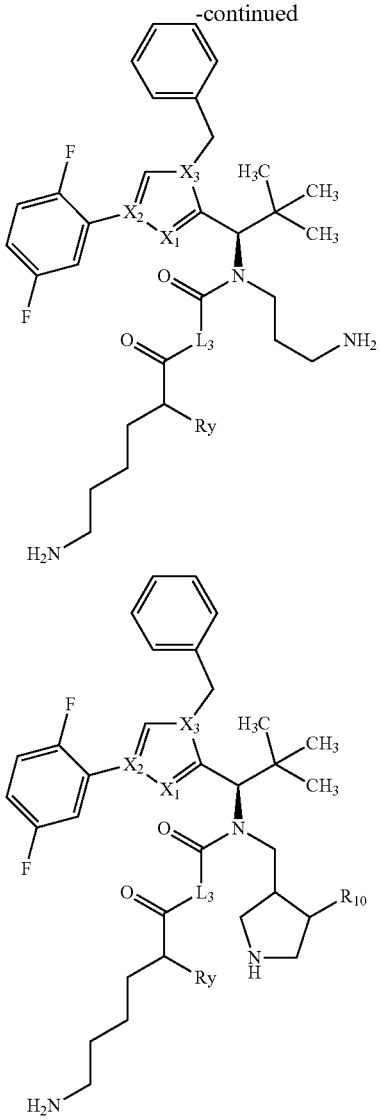

670

-continued

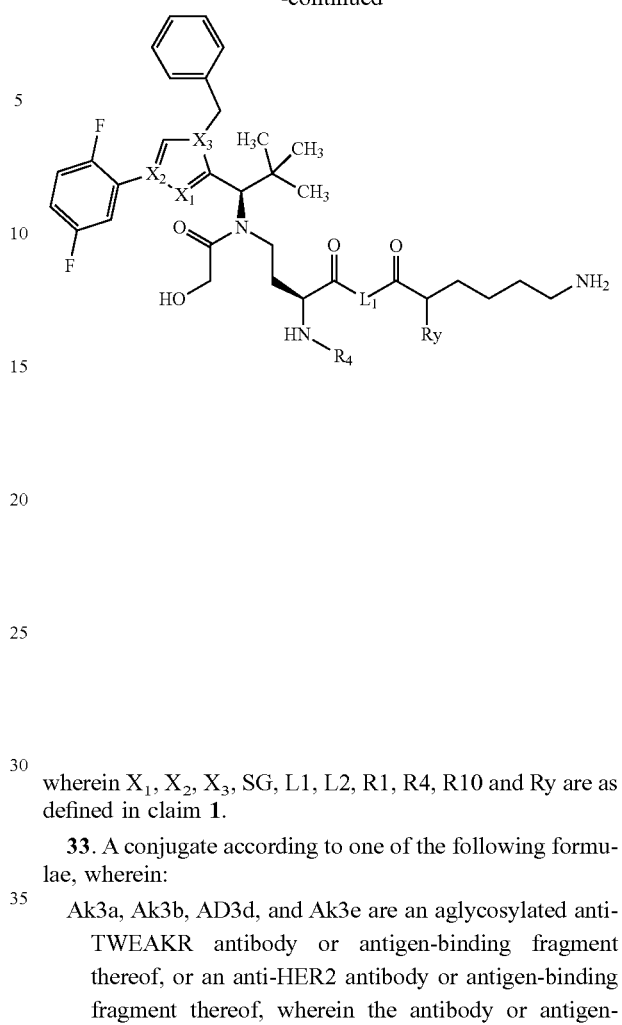

wherein $X_1$, $X_2$, $X_3$, SG, L1, L2, R1, R4, R10 and Ry are as defined in claim 1.

33. A conjugate according to one of the following formulae, wherein:

Ak3a, Ak3b, AD3d, and Ak3e are an aglycosylated anti-TWEAKR antibody or antigen-binding fragment thereof, or an anti-HER2 antibody or antigen-binding fragment thereof, wherein the antibody or antigen-binding fragment thereof comprises a mutation N297A, and n is 2 to 10:

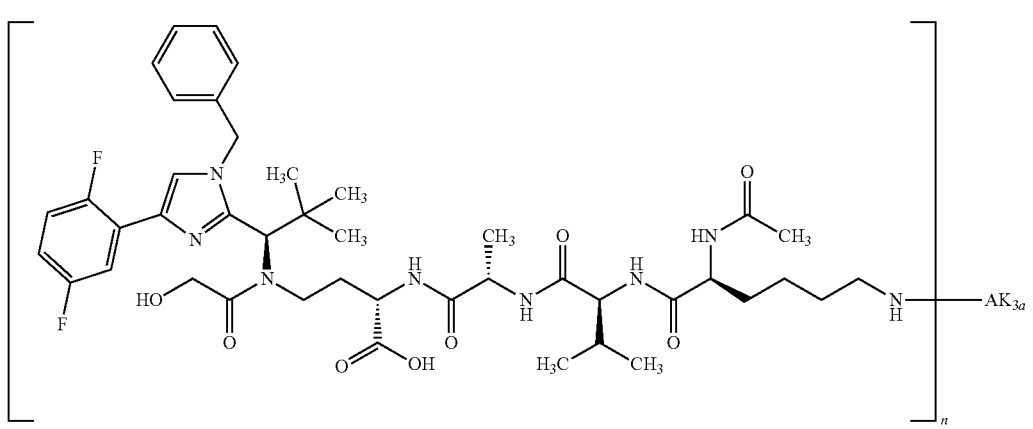

-continued
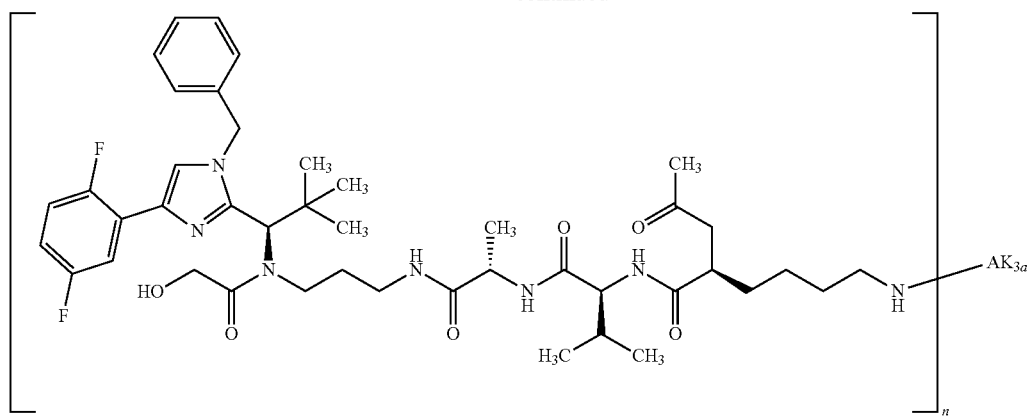
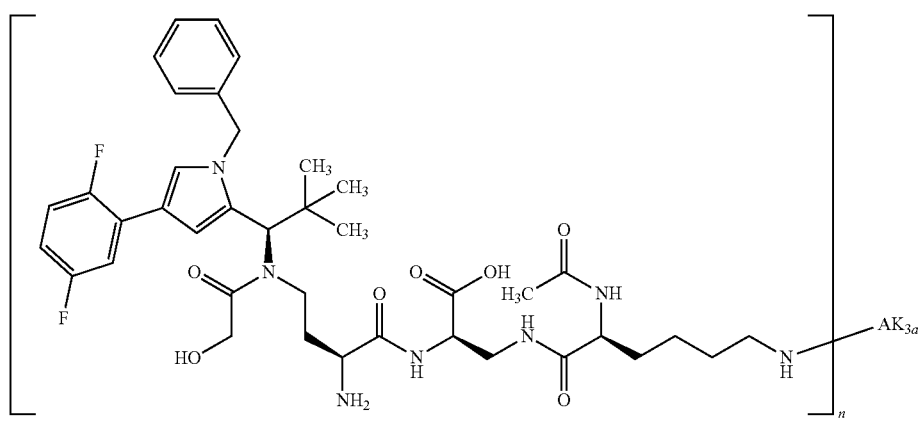
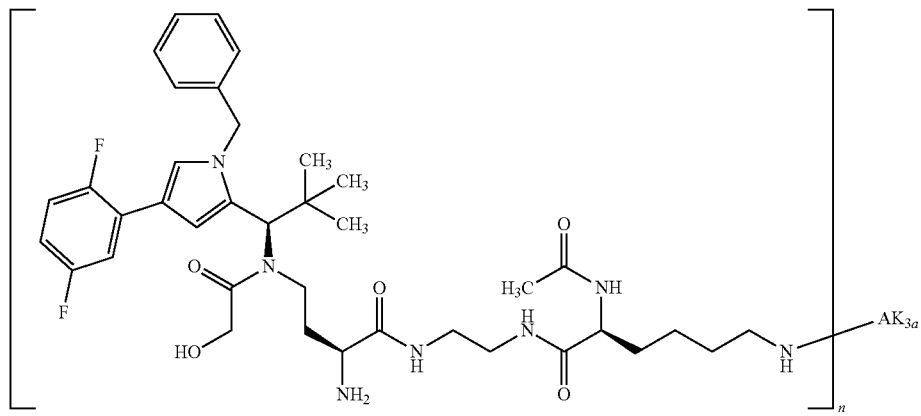
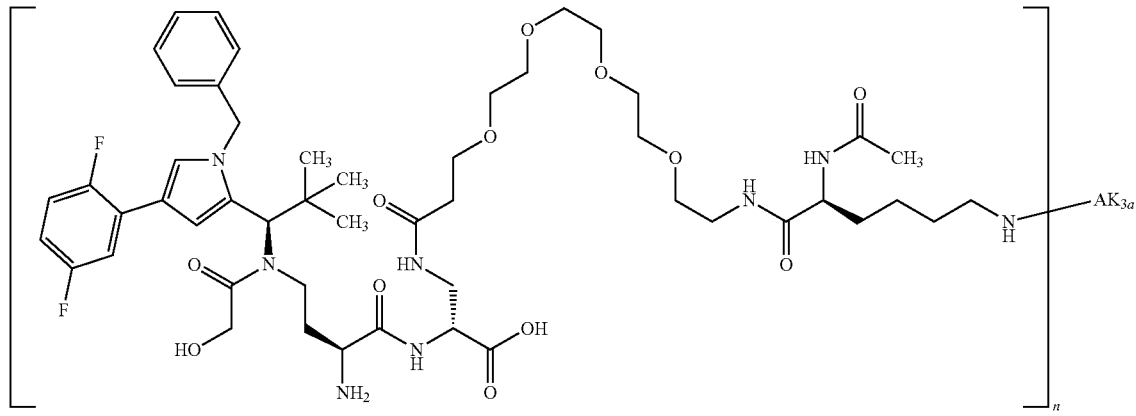

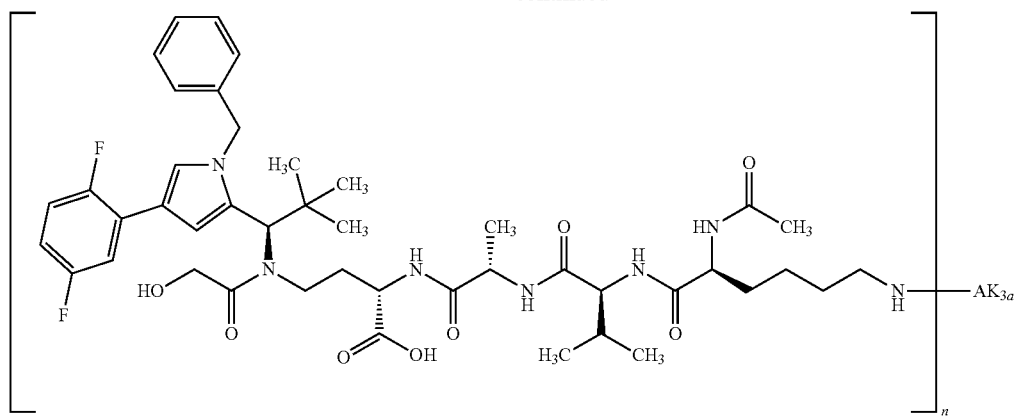
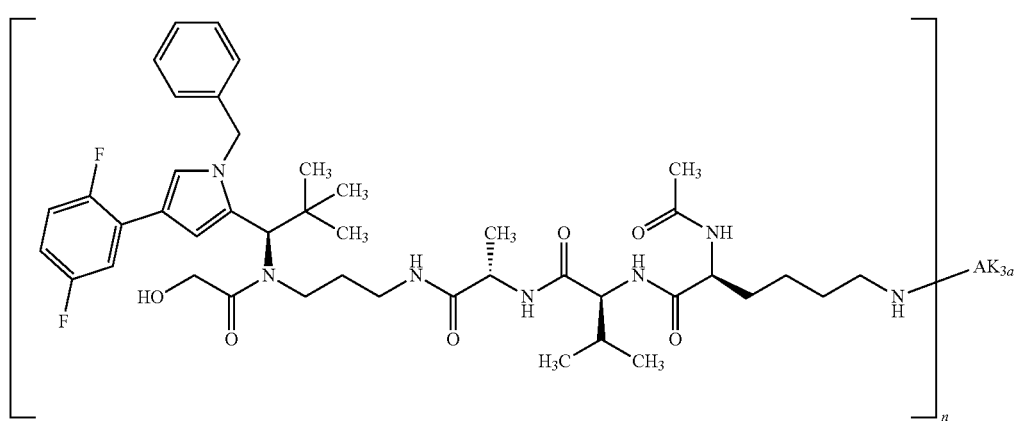
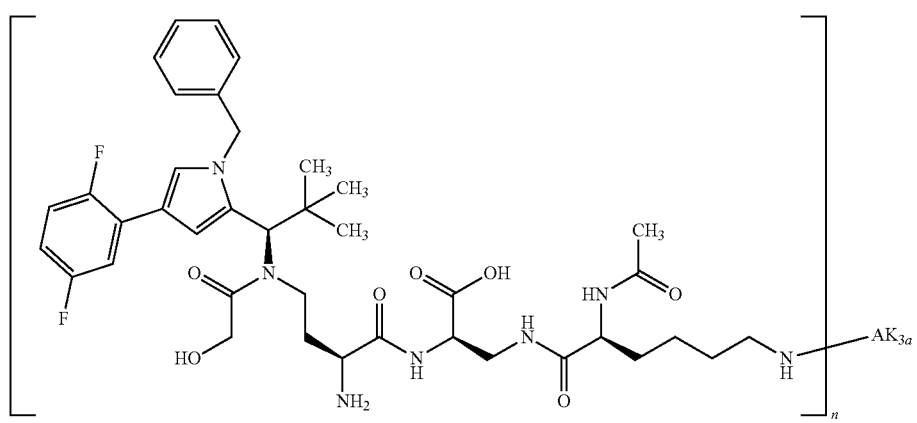
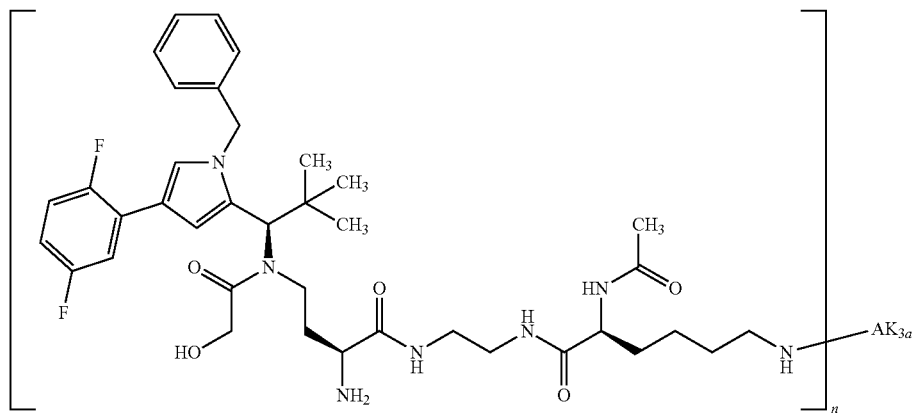

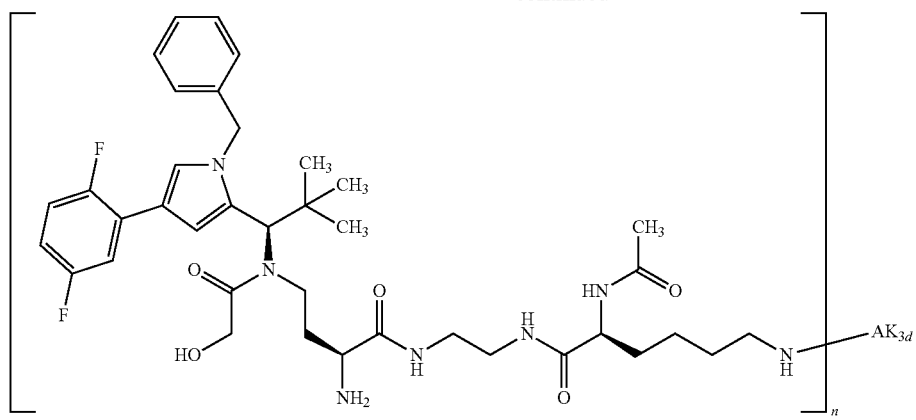
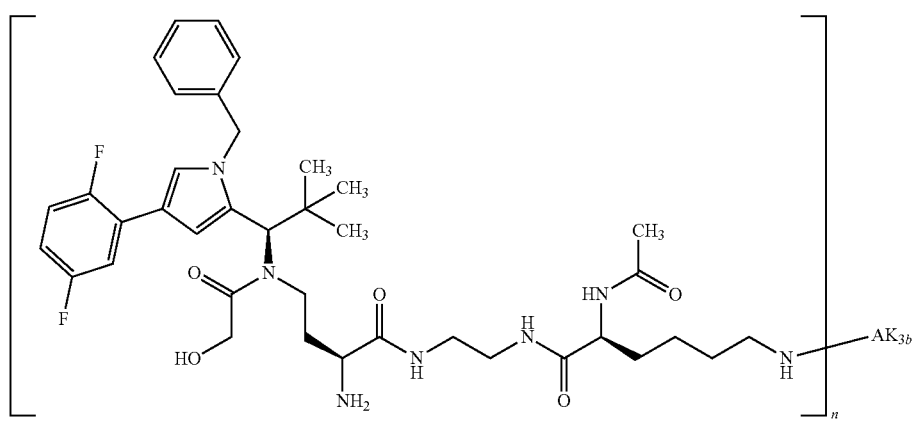
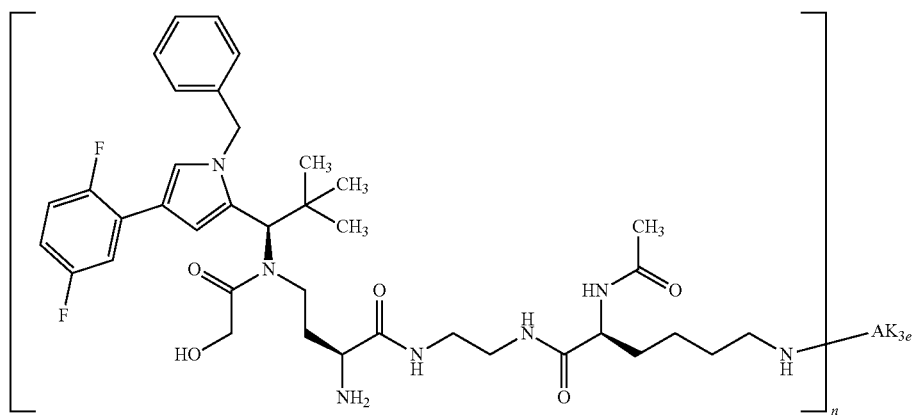
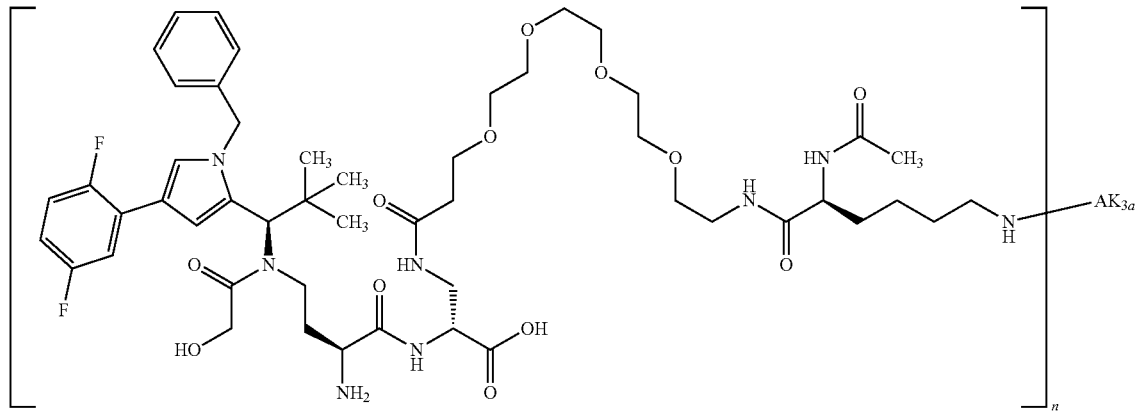

-continued
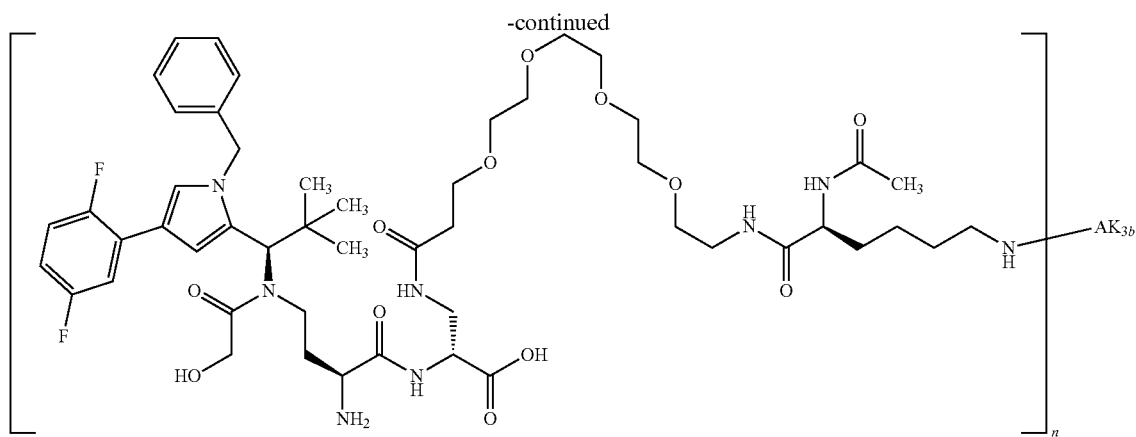
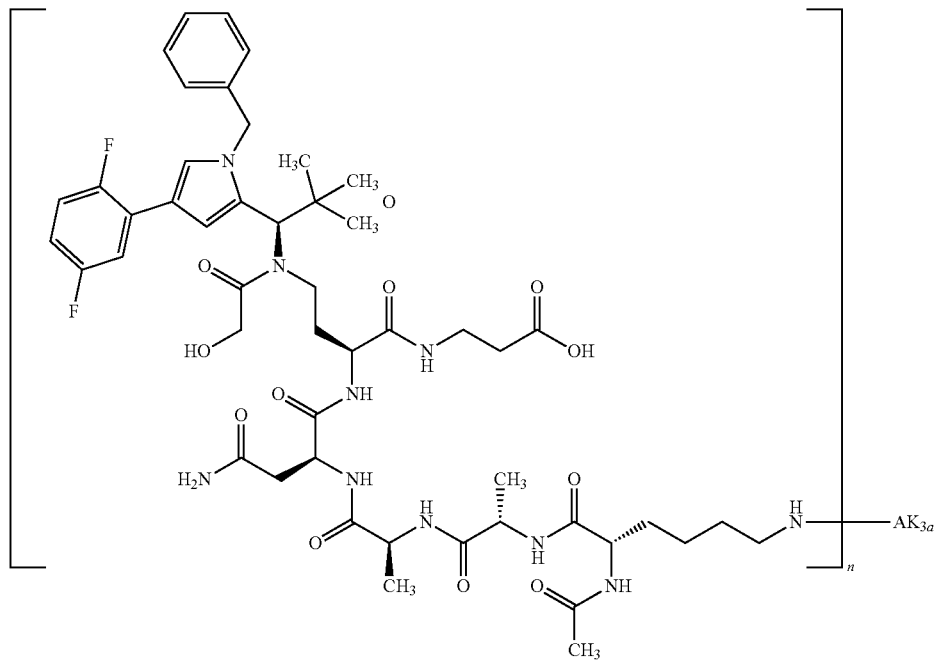
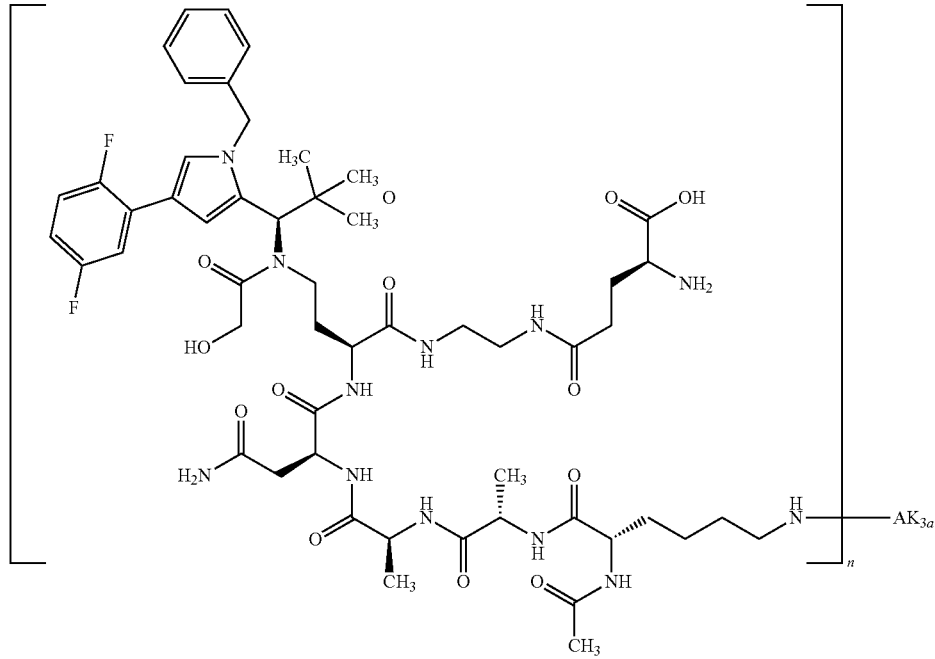

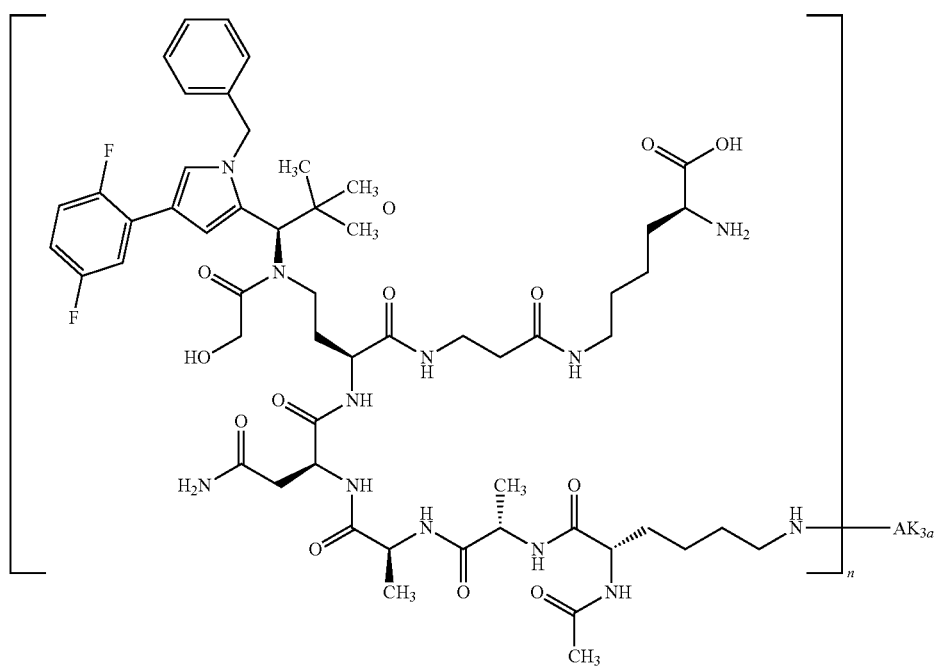
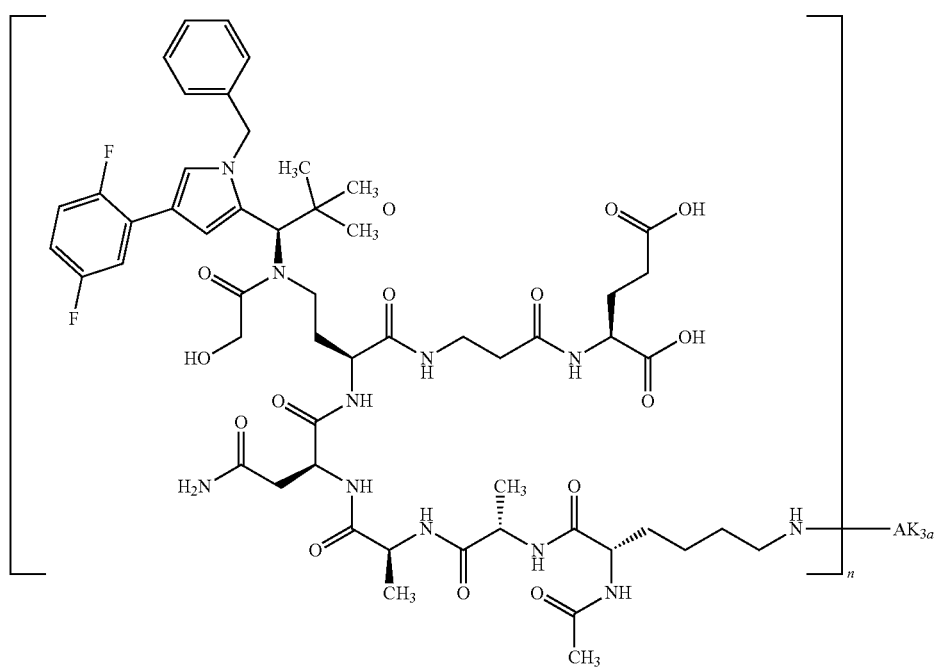

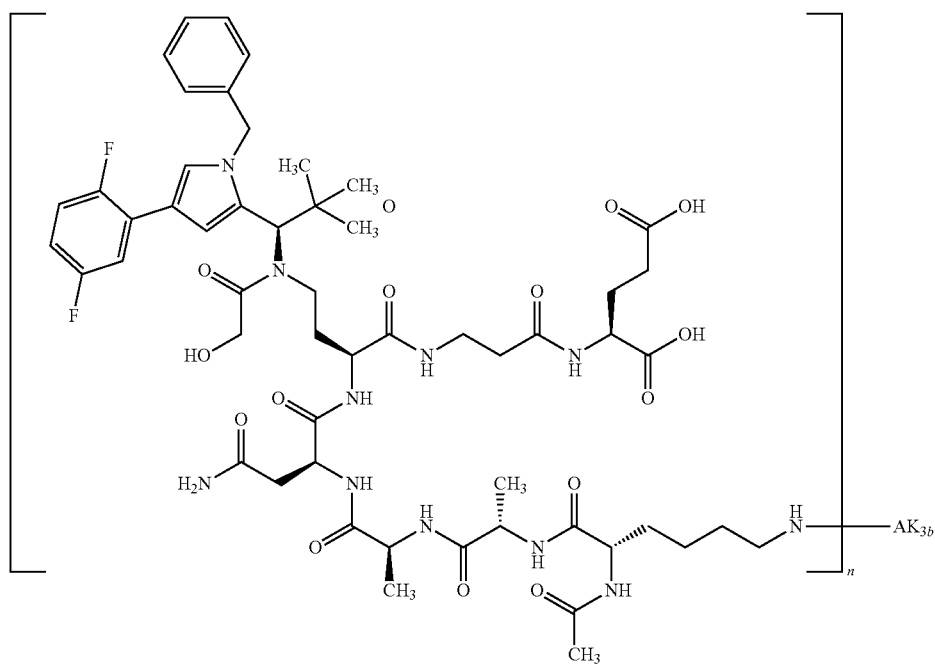
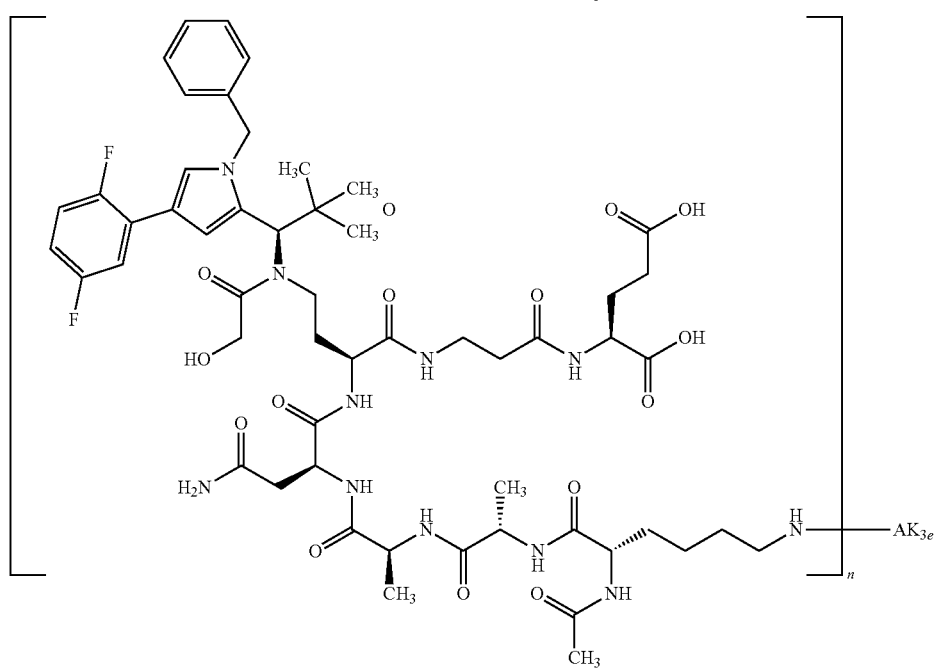
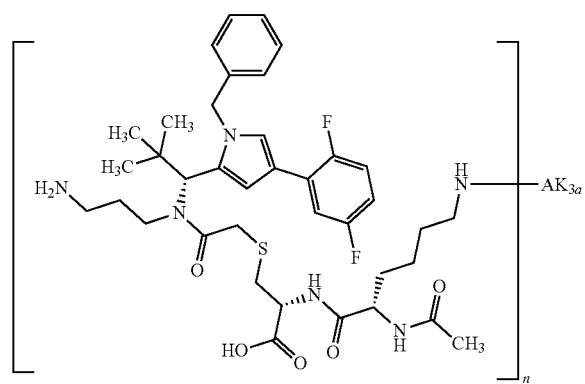

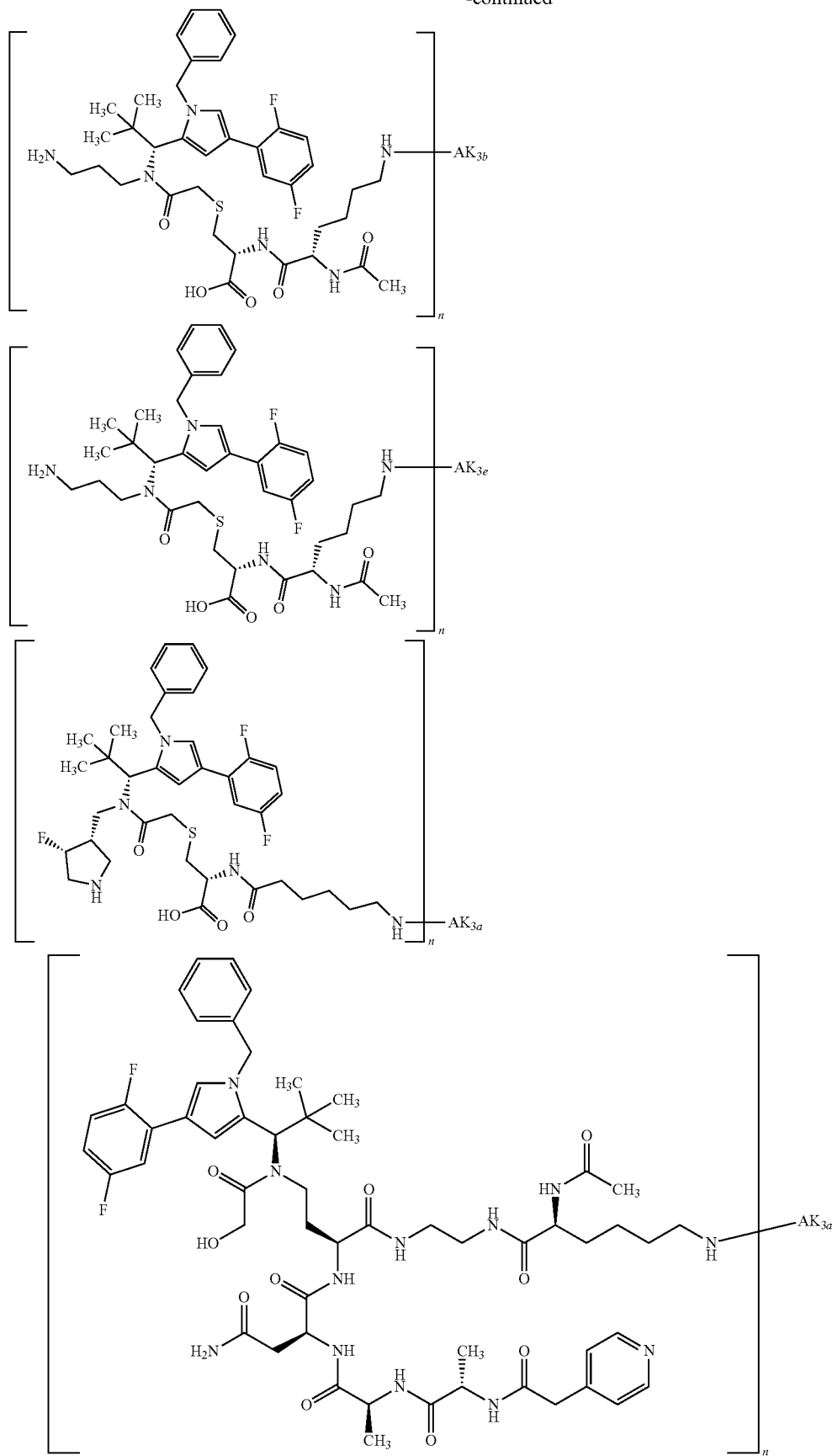

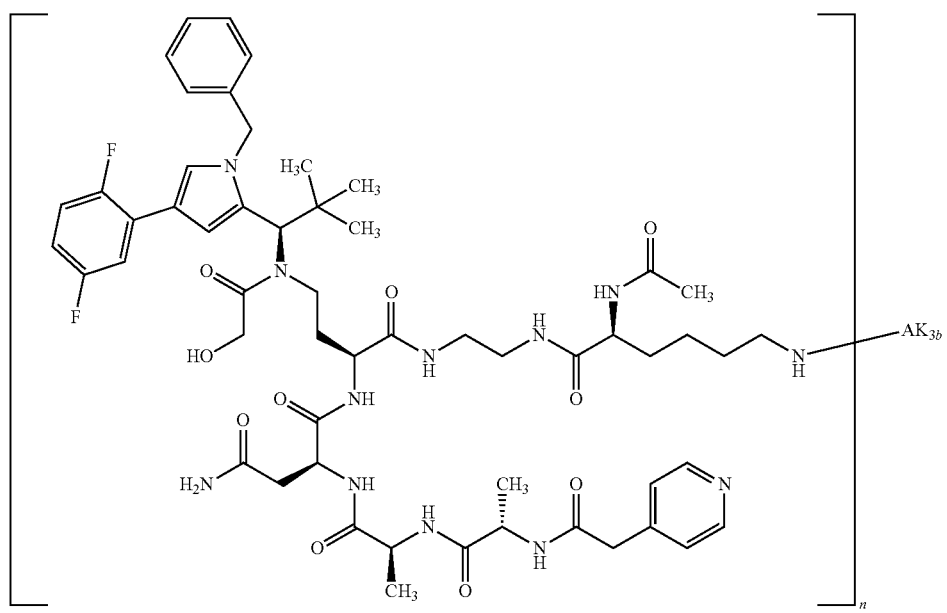
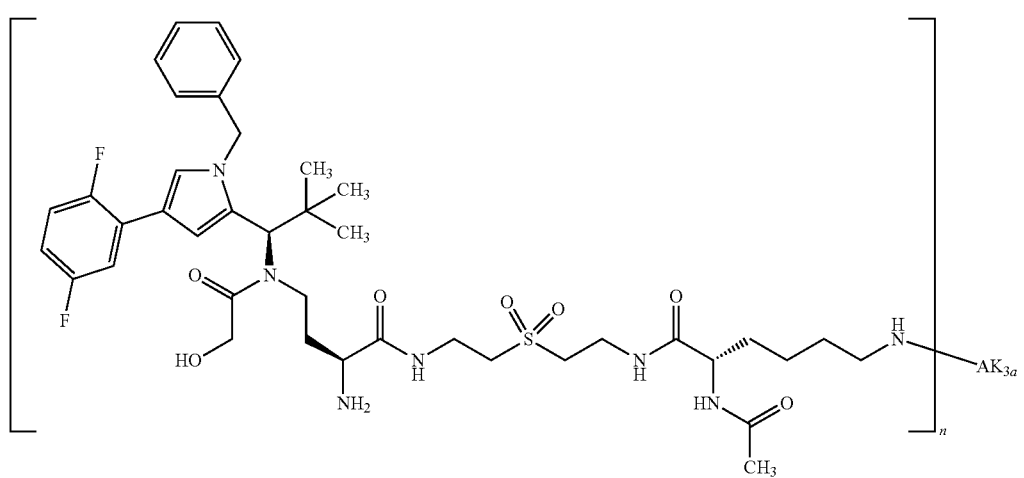
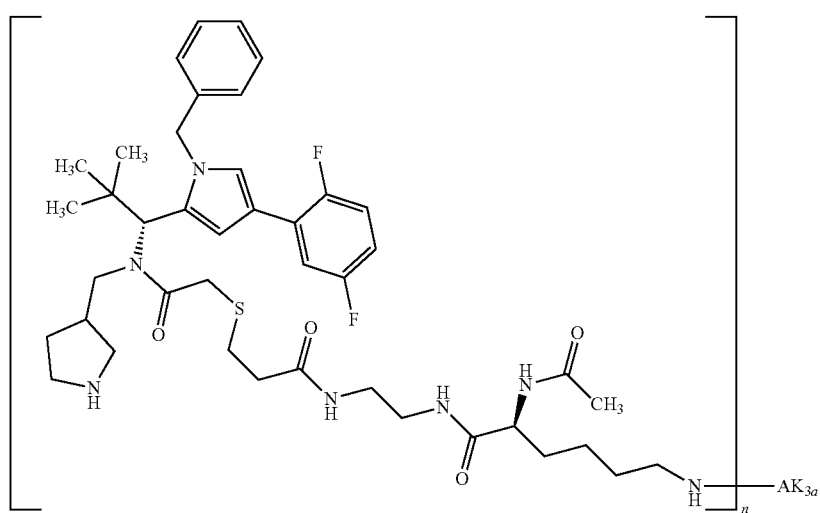

687                                  688
-continued
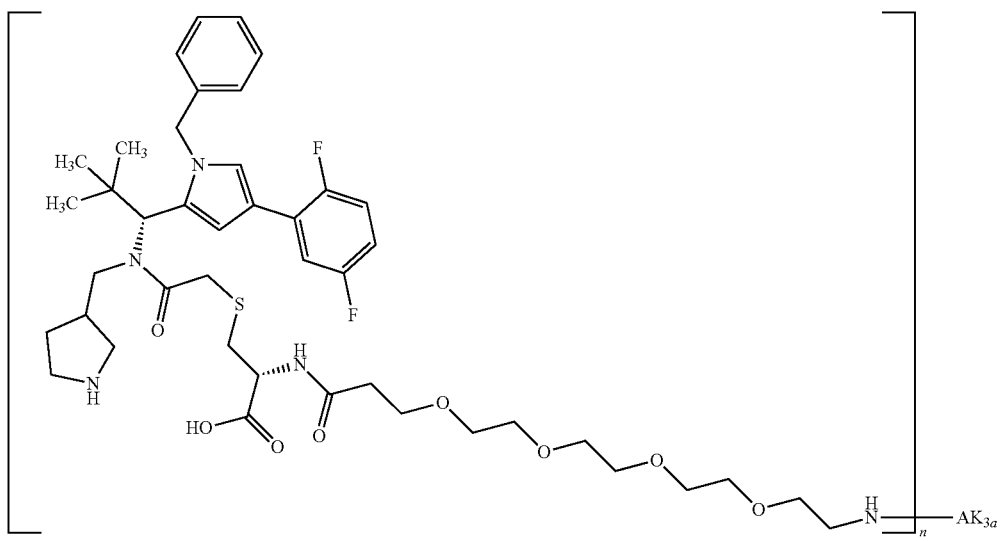
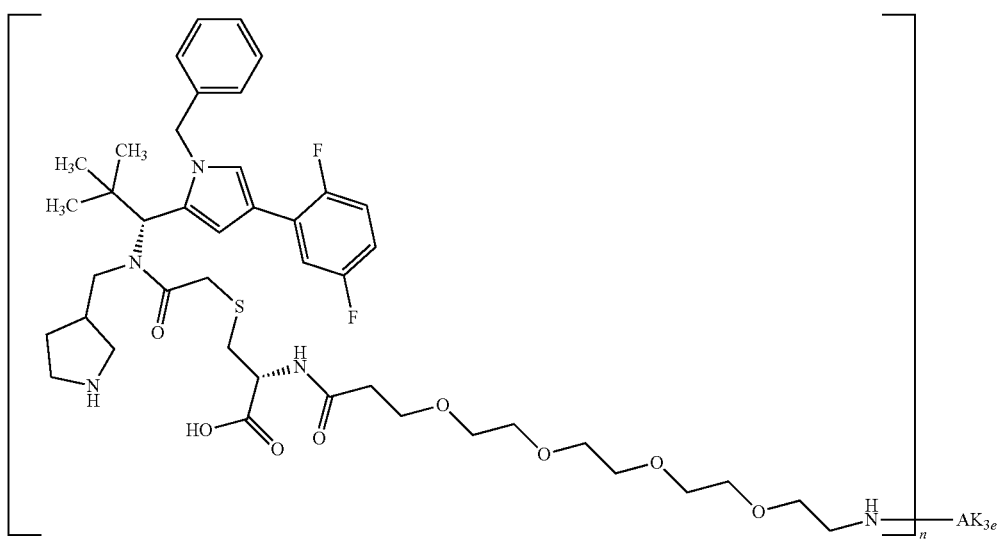
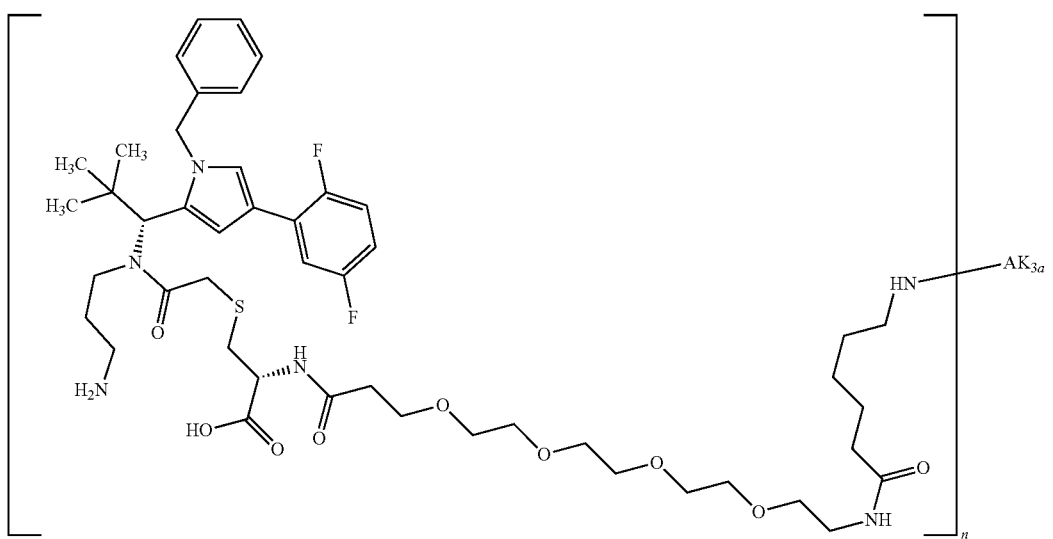

689 690
-continued
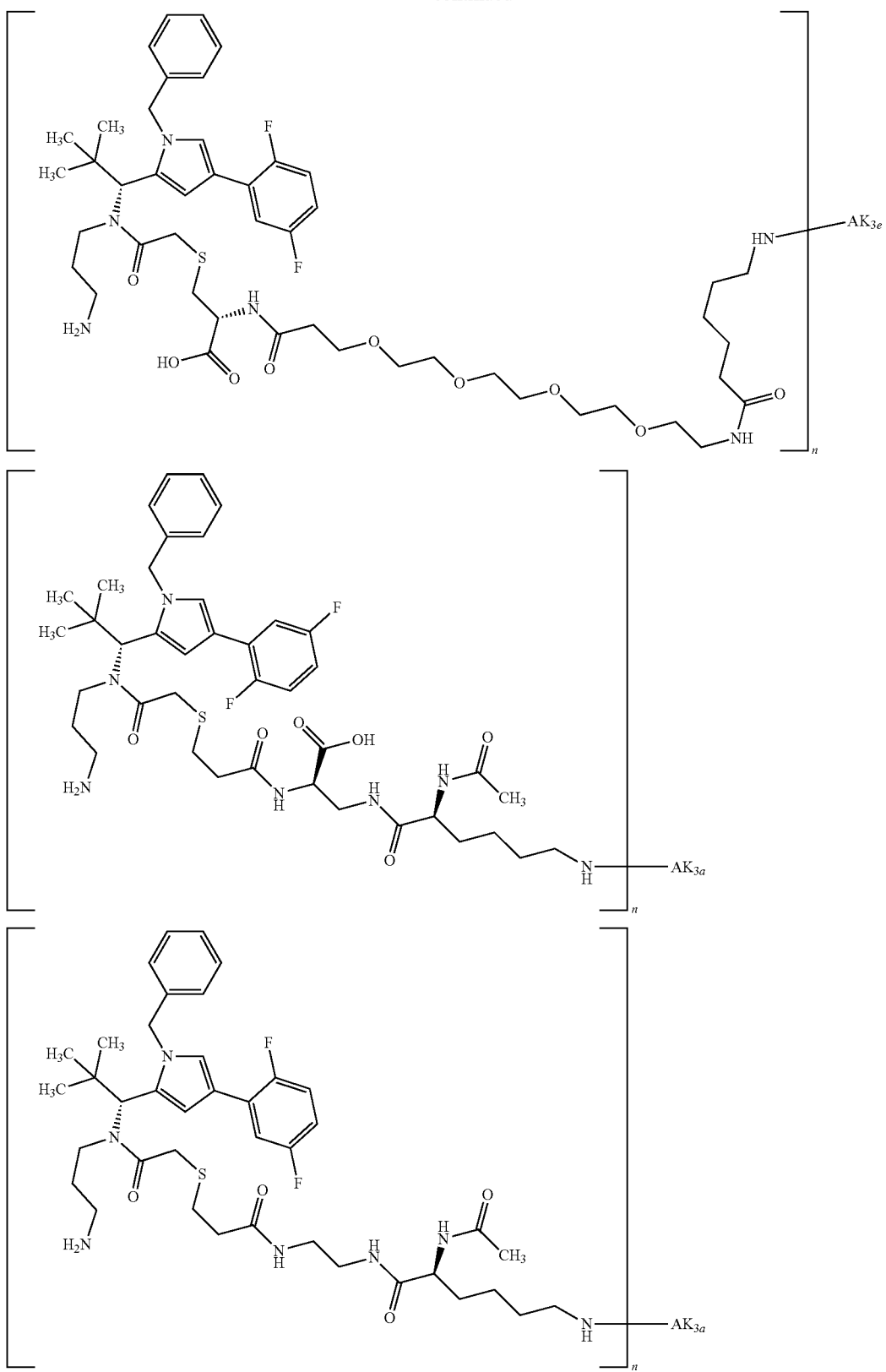

34. A pharmaceutical composition comprising a conjugate according to claim 1 in combination with an inert non-toxic pharmaceutically suitable auxiliary.

35. A method for the treatment and/or prophylaxis of diseases, comprising administering an effective amount of at least one conjugate according to claim 1 to a human or animal in need thereof.

36. A method for the treatment of hyperproliferative and/or angiogenic disorders, comprising administering an effective amount of at least one conjugate according to claim 33 to a human or animal in need thereof.

37. A method for the treatment and/or prophylaxis of hyperproliferative and/or angiogenic disorders comprising administering an effective amount of at least one conjugate according to claim 1 to a human or animal in need thereof.

* * * * *

SEQUENCE LISTING

<160> NUMBER OF SEQ ID NOS: 245

<210> SEQ ID NO 1
<211> LENGTH: 215
<212> TYPE: PRT
<213> ORGANISM: Homo Sapiens

<400> SEQUENCE: 1

```
Asp Ile Gln Met Thr Gln Ser Pro Ser Ser Leu Ser Ala Ser Val Gly
  1               5                  10                 15

Asp Arg Val Thr Ile Thr Cys Arg Ala Ser Gln Ser Ile Ser Gly Tyr
             20                  25                  30

Leu Asn Trp Tyr Gln Gln Lys Pro Gly Lys Ala Pro Lys Leu Leu Ile
         35                  40                  45

Tyr Gln Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65              70                  75                  80

Glu Asp Phe Ala Thr Tyr Tyr Cys Gln Gln Ser Tyr Thr Ser Pro Phe
                 85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210             215

<210> SEQ ID NO 2
<211> LENGTH: 449
<212> TYPE: PRT
<213> ORGANISM: Homo Sapiens

<400> SEQUENCE: 2

Glu Val Gln Leu Leu Glu Ser Gly Gly Gly Leu Val Gln Pro Gly Gly
  1               5                  10                 15

Ser Leu Arg Leu Ser Cys Ala Ala Ser Gly Phe Thr Phe Ser Pro Tyr
             20                  25                  30

Pro Met Ile Trp Val Arg Gln Ala Pro Gly Lys Gly Leu Glu Trp Val
         35                  40                  45

Ser Tyr Ile Ser Pro Ser Gly Gly Ser Thr His Tyr Ala Asp Ser Val
 50                  55                  60

Lys Gly Arg Phe Thr Ile Ser Arg Asp Asn Lys Asn Thr Leu Tyr
 65              70                  75                  80

Leu Gln Met Asn Ser Leu Arg Ala Glu Asp Thr Ala Val Tyr Tyr Cys
                 85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160
```

-continued

```
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 3
<211> LENGTH: 11
<212> TYPE: PRT
<213> ORGANISM: Homo Sapiens

<400> SEQUENCE: 3

Arg Ala Ser Gln Ser Ile Ser Gly Tyr Leu Asn
1               5                   10

<210> SEQ ID NO 4
<211> LENGTH: 7
<212> TYPE: PRT
<213> ORGANISM: Homo Sapiens

<400> SEQUENCE: 4

Gln Ala Ser Ser Leu Gln Ser
1               5
```

<210> SEQ ID NO 5
<211> LENGTH: 10
<212> TYPE: PRT
<213> ORGANISM: Homo Sapiens

<400> SEQUENCE: 5

Gln Gln Ser Tyr Thr Ser Pro Phe Ile Thr
1               5                   10

<210> SEQ ID NO 6
<211> LENGTH: 5
<212> TYPE: PRT
<213> ORGANISM: Homo Sapiens

<400> SEQUENCE: 6

Pro Tyr Pro Met Ile
1               5

<210> SEQ ID NO 7
<211> LENGTH: 17
<212> TYPE: PRT
<213> ORGANISM: Homo Sapiens

<400> SEQUENCE: 7

Tyr Ile Ser Pro Ser Gly Gly Ser Thr His Tyr Ala Asp Ser Val Lys
1               5                   10                  15

Gly

<210> SEQ ID NO 8
<211> LENGTH: 11
<212> TYPE: PRT
<213> ORGANISM: Homo Sapiens

<400> SEQUENCE: 8

Gly Gly Asp Thr Tyr Phe Asp Tyr Phe Asp Tyr
1               5                   10

<210> SEQ ID NO 9
<211> LENGTH: 108
<212> TYPE: PRT
<213> ORGANISM: Homo Sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Gln Gly Thr Lys Val Glu Ile Lys
            100                 105

<210> SEQ ID NO 10
<211> LENGTH: 121
<212> TYPE: PRT

<213> ORGANISM: Homo Sapiens

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120
```

<210> SEQ ID NO 11
<211> LENGTH: 215
<212> TYPE: PRT
<213> ORGANISM: Homo Sapiens

<400> SEQUENCE: 11

```
Asp Ile Gln Met Thr Gln Ser Pro Ala Thr Leu Ser Ala Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Pro Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

```
<210> SEQ ID NO 12
<211> LENGTH: 449
<212> TYPE: PRT
<213> ORGANISM: Homo Sapiens

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 13
<211> LENGTH: 11
<212> TYPE: PRT
<213> ORGANISM: Homo Sapiens

<400> SEQUENCE: 13

Arg Ala Ser Gln Ser Ile Ser Gly Tyr Leu Asn
1               5                   10

<210> SEQ ID NO 14
<211> LENGTH: 7
<212> TYPE: PRT
<213> ORGANISM: Homo Sapiens

<400> SEQUENCE: 14

Gln Ala Ser Ser Leu Gln Ser
1               5

<210> SEQ ID NO 15
<211> LENGTH: 10
<212> TYPE: PRT
<213> ORGANISM: Homo Sapiens

<400> SEQUENCE: 15

Gln Gln Ser Tyr Thr Ser Pro Phe Ile Thr
1               5                   10

<210> SEQ ID NO 16
<211> LENGTH: 5
<212> TYPE: PRT
<213> ORGANISM: Homo Sapiens

<400> SEQUENCE: 16

Pro Tyr Pro Met Ile
1               5

<210> SEQ ID NO 17
<211> LENGTH: 17
<212> TYPE: PRT
<213> ORGANISM: Homo Sapiens

<400> SEQUENCE: 17

Tyr Ile Ser Pro Ser Gly Gly Lys Thr His Tyr Ala Asp Ser Val Lys
1               5                   10                  15

Gly

<210> SEQ ID NO 18
<211> LENGTH: 11
<212> TYPE: PRT
<213> ORGANISM: Homo Sapiens

<400> SEQUENCE: 18
```

```
Gly Gly Asp Thr Tyr Phe Asp Tyr Phe Asp Tyr
1               5                   10
```

<210> SEQ ID NO 19
<211> LENGTH: 108
<212> TYPE: PRT
<213> ORGANISM: Homo Sapiens

<400> SEQUENCE: 19

```
Asp Ile Gln Met Thr Gln Ser Pro Ala Thr Leu Ser Ala Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Pro Gly Thr Lys Val Glu Ile Lys
            100                 105
```

<210> SEQ ID NO 20
<211> LENGTH: 121
<212> TYPE: PRT
<213> ORGANISM: Homo Sapiens

<400> SEQUENCE: 20

```
Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120
```

<210> SEQ ID NO 21
<211> LENGTH: 215
<212> TYPE: PRT
<213> ORGANISM: Homo Sapiens

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
```

-continued

```
                35                  40                  45
Tyr Gln Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Thr Ser Pro Phe
                 85                  90                  95

Ile Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 22
<211> LENGTH: 449
<212> TYPE: PRT
<213> ORGANISM: Homo Sapiens

<400> SEQUENCE: 22

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Pro Tyr
             20                  25                  30

Pro Met Met Trp Val Arg Gln Ala Pro Gly Lys Gly Leu Glu Trp Val
         35                  40                  45

Ser Tyr Ile Ser Pro Ser Gly Gly Ser Thr His Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Asp Thr Tyr Asp Tyr Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 23
<211> LENGTH: 11
<212> TYPE: PRT
<213> ORGANISM: Homo Sapiens

<400> SEQUENCE: 23

Arg Ala Ser Gln Ser Ile Ser Ser Tyr Leu Asn
1               5                   10

<210> SEQ ID NO 24
<211> LENGTH: 7
<212> TYPE: PRT
<213> ORGANISM: Homo Sapiens

<400> SEQUENCE: 24

Gln Ala Ser Ser Leu Gln Ser
1               5

<210> SEQ ID NO 25
<211> LENGTH: 10
<212> TYPE: PRT
<213> ORGANISM: Homo Sapiens

<400> SEQUENCE: 25
```

-continued

```
Gln Gln Ser Tyr Thr Ser Pro Phe Ile Thr
1               5                   10

<210> SEQ ID NO 26
<211> LENGTH: 5
<212> TYPE: PRT
<213> ORGANISM: Homo Sapiens

<400> SEQUENCE: 26

Pro Tyr Pro Met Met
1               5

<210> SEQ ID NO 27
<211> LENGTH: 17
<212> TYPE: PRT
<213> ORGANISM: Homo Sapiens

<400> SEQUENCE: 27

Tyr Ile Ser Pro Ser Gly Gly Ser Thr His Tyr Ala Asp Ser Val Lys
1               5                   10                  15

Gly

<210> SEQ ID NO 28
<211> LENGTH: 11
<212> TYPE: PRT
<213> ORGANISM: Homo Sapiens

<400> SEQUENCE: 28

Gly Gly Asp Thr Tyr Phe Asp Tyr Phe Asp Tyr
1               5                   10

<210> SEQ ID NO 29
<211> LENGTH: 108
<212> TYPE: PRT
<213> ORGANISM: Homo Sapiens

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Gln Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Gln Gly Thr Lys Val Glu Ile Lys
            100                 105

<210> SEQ ID NO 30
<211> LENGTH: 121
<212> TYPE: PRT
<213> ORGANISM: Homo Sapiens

<400> SEQUENCE: 30

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
            35                  40                  45

Ser Tyr Ile Ser Pro Ser Gly Gly Ser Thr His Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
            115                 120
```

<210> SEQ ID NO 31
<211> LENGTH: 215
<212> TYPE: PRT
<213> ORGANISM: Homo Sapiens

<400> SEQUENCE: 31

```
Asp Ile Gln Met Thr Gln Ser Pro Ala Thr Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Gln Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Thr Ser Pro Phe
                85                  90                  95

Ile Thr Phe Gly Pro Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215
```

<210> SEQ ID NO 32
<211> LENGTH: 449
<212> TYPE: PRT
<213> ORGANISM: Homo Sapiens

<400> SEQUENCE: 32

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
```

```
                    420                 425                 430
Glu Ala Leu His Asn His Tyr Thr Gln Lys Ser Leu Ser Leu Ser Pro
        435                 440                 445

Gly

<210> SEQ ID NO 33
<211> LENGTH: 11
<212> TYPE: PRT
<213> ORGANISM: Homo Sapiens

<400> SEQUENCE: 33

Arg Ala Ser Gln Ser Ile Ser Ser Tyr Leu Asn
1               5                   10

<210> SEQ ID NO 34
<211> LENGTH: 7
<212> TYPE: PRT
<213> ORGANISM: Homo Sapiens

<400> SEQUENCE: 34

Gln Ala Ser Ser Leu Gln Ser
1               5

<210> SEQ ID NO 35
<211> LENGTH: 10
<212> TYPE: PRT
<213> ORGANISM: Homo Sapiens

<400> SEQUENCE: 35

Gln Gln Ser Tyr Thr Ser Pro Phe Ile Thr
1               5                   10

<210> SEQ ID NO 36
<211> LENGTH: 5
<212> TYPE: PRT
<213> ORGANISM: Homo Sapiens

<400> SEQUENCE: 36

Pro Tyr Pro Met Met
1               5

<210> SEQ ID NO 37
<211> LENGTH: 17
<212> TYPE: PRT
<213> ORGANISM: Homo Sapiens

<400> SEQUENCE: 37

Tyr Ile Ser Pro Ser Gly Gly Lys Thr His Tyr Ala Asp Ser Val Lys
1               5                   10                  15

Gly

<210> SEQ ID NO 38
<211> LENGTH: 11
<212> TYPE: PRT
<213> ORGANISM: Homo Sapiens

<400> SEQUENCE: 38

Gly Gly Asp Thr Tyr Phe Asp Tyr Phe Asp Tyr
1               5                   10

<210> SEQ ID NO 39
<211> LENGTH: 108
<212> TYPE: PRT
```

<213> ORGANISM: Homo Sapiens

<400> SEQUENCE: 39

Asp Ile Gln Met Thr Gln Ser Pro Ala Thr Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Pro Gly Thr Lys Val Glu Ile Lys
            100                 105

<210> SEQ ID NO 40
<211> LENGTH: 121
<212> TYPE: PRT
<213> ORGANISM: Homo Sapiens

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ala
        115                 120

<210> SEQ ID NO 41
<211> LENGTH: 215
<212> TYPE: PRT
<213> ORGANISM: Homo Sapiens

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Tyr Ser Thr Pro Gly
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 42
<211> LENGTH: 449
<212> TYPE: PRT
<213> ORGANISM: Homo Sapiens

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
```

```
            225                 230                 235                 240
    Pro Ser Val Phe Leu Phe Pro Lys Pro Lys Asp Thr Leu Met Ile
                    245                 250                 255

Ser Arg Thr Pro Glu Val Thr Cys Val Val Val Asp Val Ser His Glu
                    260                 265                 270

Asp Pro Glu Val Lys Phe Asn Trp Tyr Val Asp Gly Val Glu Val His
                    275                 280                 285

Asn Ala Lys Thr Lys Pro Arg Glu Glu Gln Tyr Asn Ser Thr Tyr Arg
                    290                 295                 300

Val Val Ser Val Leu Thr Val Leu His Gln Asp Trp Leu Asn Gly Lys
    305                 310                 315                 320

Glu Tyr Lys Cys Lys Val Ser Asn Lys Ala Leu Pro Ala Pro Ile Glu
                    325                 330                 335

Lys Thr Ile Ser Lys Ala Lys Gly Gln Pro Arg Glu Pro Gln Val Tyr
                    340                 345                 350

Thr Leu Pro Pro Ser Arg Asp Glu Leu Thr Lys Asn Gln Val Ser Leu
                    355                 360                 365

Thr Cys Leu Val Lys Gly Phe Tyr Pro Ser Asp Ile Ala Val Glu Trp
                    370                 375                 380

Glu Ser Asn Gly Gln Pro Glu Asn Asn Tyr Lys Thr Thr Pro Pro Val
    385                 390                 395                 400

Leu Asp Ser Asp Gly Ser Phe Phe Leu Tyr Ser Lys Leu Thr Val Asp
                    405                 410                 415

Lys Ser Arg Trp Gln Gln Gly Asn Val Phe Ser Cys Ser Val Met His
                    420                 425                 430

Glu Ala Leu His Asn His Tyr Thr Gln Lys Ser Leu Ser Leu Ser Pro
                    435                 440                 445

Gly

<210> SEQ ID NO 43
<211> LENGTH: 11
<212> TYPE: PRT
<213> ORGANISM: Homo Sapiens

<400> SEQUENCE: 43

Arg Ala Ser Gln Ser Ile Ser Ser Tyr Leu Asn
1               5                   10

<210> SEQ ID NO 44
<211> LENGTH: 7
<212> TYPE: PRT
<213> ORGANISM: Homo Sapiens

<400> SEQUENCE: 44

Ala Ala Ser Ser Leu Gln Ser
1               5

<210> SEQ ID NO 45
<211> LENGTH: 10
<212> TYPE: PRT
<213> ORGANISM: Homo Sapiens

<400> SEQUENCE: 45

Gln Gln Ser Tyr Ser Thr Pro Gly Ile Thr
1               5                   10

<210> SEQ ID NO 46
<211> LENGTH: 5
```

```
<212> TYPE: PRT
<213> ORGANISM: Homo Sapiens

<400> SEQUENCE: 46

Pro Tyr Pro Met Met
1               5

<210> SEQ ID NO 47
<211> LENGTH: 17
<212> TYPE: PRT
<213> ORGANISM: Homo Sapiens

<400> SEQUENCE: 47

Tyr Ile Ser Pro Ser Gly Gly Ser Thr His Tyr Ala Asp Ser Val Lys
1               5                   10                  15

Gly

<210> SEQ ID NO 48
<211> LENGTH: 11
<212> TYPE: PRT
<213> ORGANISM: Homo Sapiens

<400> SEQUENCE: 48

Gly Gly Asp Thr Tyr Phe Asp Tyr Phe Asp Tyr
1               5                   10

<210> SEQ ID NO 49
<211> LENGTH: 108
<212> TYPE: PRT
<213> ORGANISM: Homo Sapiens

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gly
                85                  90                  95

Ile Thr Phe Gly Gln Gly Thr Lys Val Glu Ile Lys
            100                 105

<210> SEQ ID NO 50
<211> LENGTH: 121
<212> TYPE: PRT
<213> ORGANISM: Homo Sapiens

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
                20                  25                  30

Pro Met Met Trp Val Arg Gln Ala Pro Gly Lys Gly Leu Glu Trp Val
            35                  40                  45

Ser Tyr Ile Ser Pro Ser Gly Gly Ser Thr His Tyr Ala Asp Ser Val
```

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Asp Thr Tyr Phe Asp Tyr Phe Asp Tyr Trp Gly Gln
                100                 105                 110

Gly Thr Leu Val Thr Val Ser Ser Ala
            115                 120

<210> SEQ ID NO 51
<211> LENGTH: 215
<212> TYPE: PRT
<213> ORGANISM: Homo Sapiens

<400> SEQUENCE: 51

Asp Ile Gln Met Thr Gln Ser Pro Ala Thr Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Ser Pro Gly
                 85                  90                  95

Ile Thr Phe Gly Pro Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 52
<211> LENGTH: 449
<212> TYPE: PRT
<213> ORGANISM: Homo Sapiens

<400> SEQUENCE: 52

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Pro Tyr
                 20                  25                  30

Pro Met Met Trp Val Arg Gln Ala Pro Gly Lys Gly Leu Glu Trp Val
```

```
                 35                  40                  45
Ser Tyr Ile Ser Pro Ser Gly Gly Lys Thr His Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Asp Thr Tyr Phe Asp Tyr Phe Asp Tyr Trp Gly Gln
                100                 105                 110

Gly Thr Leu Val Thr Val Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly
```

<210> SEQ ID NO 53
<211> LENGTH: 11
<212> TYPE: PRT
<213> ORGANISM: Homo Sapiens

<400> SEQUENCE: 53

Arg Ala Ser Gln Ser Ile Ser Ser Tyr Leu Asn
1               5                   10

<210> SEQ ID NO 54
<211> LENGTH: 7
<212> TYPE: PRT
<213> ORGANISM: Homo Sapiens

<400> SEQUENCE: 54

Ala Ala Ser Ser Leu Gln Ser
1               5

<210> SEQ ID NO 55
<211> LENGTH: 10
<212> TYPE: PRT
<213> ORGANISM: Homo Sapiens

<400> SEQUENCE: 55

Gln Gln Ser Tyr Ser Ser Pro Gly Ile Thr
1               5                   10

<210> SEQ ID NO 56
<211> LENGTH: 5
<212> TYPE: PRT
<213> ORGANISM: Homo Sapiens

<400> SEQUENCE: 56

Pro Tyr Pro Met Met
1               5

<210> SEQ ID NO 57
<211> LENGTH: 17
<212> TYPE: PRT
<213> ORGANISM: Homo Sapiens

<400> SEQUENCE: 57

Tyr Ile Ser Pro Ser Gly Gly Lys Thr His Tyr Ala Asp Ser Val Lys
1               5                   10                  15

Gly

<210> SEQ ID NO 58
<211> LENGTH: 11
<212> TYPE: PRT
<213> ORGANISM: Homo Sapiens

<400> SEQUENCE: 58

Gly Gly Asp Thr Tyr Phe Asp Tyr Phe Asp Tyr
1               5                   10

<210> SEQ ID NO 59
<211> LENGTH: 108
<212> TYPE: PRT
<213> ORGANISM: Homo Sapiens

<400> SEQUENCE: 59

Asp Ile Gln Met Thr Gln Ser Pro Ala Thr Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Pro Gly
                85                  90                  95

Ile Thr Phe Gly Pro Gly Thr Lys Val Glu Ile Lys
            100                 105

<210> SEQ ID NO 60
<211> LENGTH: 121
<212> TYPE: PRT
<213> ORGANISM: Homo Sapiens

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120

<210> SEQ ID NO 61
<211> LENGTH: 217
<212> TYPE: PRT
<213> ORGANISM: Homo Sapiens

<400> SEQUENCE: 61

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Ser
                85                  90                  95

Pro Gly Ile Thr Phe Gly Pro Gly Thr Lys Val Glu Ile Lys Arg Thr
            100                 105                 110

```
Val Ala Ala Pro Ser Val Phe Ile Phe Pro Ser Asp Glu Gln Leu
            115                 120                 125
Lys Ser Gly Thr Ala Ser Val Val Cys Leu Leu Asn Asn Phe Tyr Pro
130                 135                 140
Arg Glu Ala Lys Val Gln Trp Lys Val Asp Asn Ala Leu Gln Ser Gly
145                 150                 155                 160
Asn Ser Gln Glu Ser Val Thr Glu Gln Asp Ser Lys Asp Ser Thr Tyr
                165                 170                 175
Ser Leu Ser Ser Thr Leu Thr Leu Ser Lys Ala Asp Tyr Glu Lys His
            180                 185                 190
Lys Leu Tyr Ala Cys Glu Val Thr His Gln Gly Leu Ser Ser Pro Val
        195                 200                 205
Thr Lys Ser Phe Asn Arg Gly Glu Cys
    210                 215
```

<210> SEQ ID NO 62
<211> LENGTH: 449
<212> TYPE: PRT
<213> ORGANISM: Homo Sapiens

<400> SEQUENCE: 62

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Pro Tyr
            20                  25                  30
Pro Met Met Trp Val Arg Gln Ala Pro Gly Lys Gly Leu Glu Trp Val
        35                  40                  45
Ser Tyr Ile Ser Pro Ser Gly Gly Lys Thr His Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gly Gly Asp Thr Tyr Phe Asp Tyr Phe Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 63
<211> LENGTH: 11
<212> TYPE: PRT
<213> ORGANISM: Homo Sapiens

<400> SEQUENCE: 63

Arg Ala Ser Gln Ser Ile Ser Ser Tyr Leu Asn
1               5                   10

<210> SEQ ID NO 64
<211> LENGTH: 7
<212> TYPE: PRT
<213> ORGANISM: Homo Sapiens

<400> SEQUENCE: 64

Ala Ala Ser Ser Leu Gln Ser
1               5

<210> SEQ ID NO 65
<211> LENGTH: 10
<212> TYPE: PRT
<213> ORGANISM: Homo Sapiens

<400> SEQUENCE: 65

Gln Gln Ser Tyr Ser Ser Pro Gly Ile Thr
1               5                   10

<210> SEQ ID NO 66
<211> LENGTH: 5
<212> TYPE: PRT
<213> ORGANISM: Homo Sapiens

<400> SEQUENCE: 66

Pro Tyr Pro Met Met
1               5
```

<210> SEQ ID NO 67
<211> LENGTH: 17
<212> TYPE: PRT
<213> ORGANISM: Homo Sapiens

<400> SEQUENCE: 67

Tyr Ile Ser Pro Ser Gly Gly Lys Thr His Tyr Ala Asp Ser Val Lys
1               5                   10                  15

Gly

<210> SEQ ID NO 68
<211> LENGTH: 11
<212> TYPE: PRT
<213> ORGANISM: Homo Sapiens

<400> SEQUENCE: 68

Gly Gly Asp Thr Tyr Phe Asp Tyr Phe Asp Tyr
1               5                   10

<210> SEQ ID NO 69
<211> LENGTH: 110
<212> TYPE: PRT
<213> ORGANISM: Homo Sapiens

<400> SEQUENCE: 69

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Ser
                85                  90                  95

Pro Gly Ile Thr Phe Gly Pro Gly Thr Lys Val Glu Ile Lys
            100                 105                 110

<210> SEQ ID NO 70
<211> LENGTH: 121
<212> TYPE: PRT
<213> ORGANISM: Homo Sapiens

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

-continued

Ala Arg Gly Gly Asp Thr Tyr Phe Asp Tyr Phe Asp Tyr Trp Gly Gln
            100                 105                 110

Gly Thr Leu Val Thr Val Ser Ser Ala
            115                 120

<210> SEQ ID NO 71
<211> LENGTH: 217
<212> TYPE: PRT
<213> ORGANISM: Homo Sapiens

<400> SEQUENCE: 71

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Ala Ala Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Ser
                85                  90                  95

Pro Gly Ile Thr Phe Gly Pro Gly Thr Lys Val Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 72
<211> LENGTH: 449
<212> TYPE: PRT
<213> ORGANISM: Homo Sapiens

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                 85                  90                  95

Ala Arg Gly Gly Asp Gly Tyr Phe Asp Tyr Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 73
<211> LENGTH: 11
<212> TYPE: PRT
<213> ORGANISM: Homo Sapiens

<400> SEQUENCE: 73
```

-continued

```
Arg Ala Ser Gln Ser Ile Ser Ser Tyr Leu Asn
1               5                   10

<210> SEQ ID NO 74
<211> LENGTH: 7
<212> TYPE: PRT
<213> ORGANISM: Homo Sapiens

<400> SEQUENCE: 74

Ala Ala Ser Ser Leu Gln Ser
1               5

<210> SEQ ID NO 75
<211> LENGTH: 10
<212> TYPE: PRT
<213> ORGANISM: Homo Sapiens

<400> SEQUENCE: 75

Gln Gln Ser Tyr Ser Ser Pro Gly Ile Thr
1               5                   10

<210> SEQ ID NO 76
<211> LENGTH: 5
<212> TYPE: PRT
<213> ORGANISM: Homo Sapiens

<400> SEQUENCE: 76

Pro Tyr Pro Met Met
1               5

<210> SEQ ID NO 77
<211> LENGTH: 17
<212> TYPE: PRT
<213> ORGANISM: Homo Sapiens

<400> SEQUENCE: 77

Tyr Ile Ser Pro Ser Gly Gly Lys Thr His Tyr Ala Asp Ser Val Lys
1               5                   10                  15

Gly

<210> SEQ ID NO 78
<211> LENGTH: 11
<212> TYPE: PRT
<213> ORGANISM: Homo Sapiens

<400> SEQUENCE: 78

Gly Gly Asp Gly Tyr Phe Asp Tyr Phe Asp Tyr
1               5                   10

<210> SEQ ID NO 79
<211> LENGTH: 110
<212> TYPE: PRT
<213> ORGANISM: Homo Sapiens

<400> SEQUENCE: 79

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
                20                  25                  30

Ser Tyr Leu Asn Trp Tyr Gln Gln Lys Pro Gly Lys Ala Pro Lys Leu
            35                  40                  45

Leu Ile Tyr Ala Ala Ser Ser Leu Gln Ser Gly Val Pro Ser Arg Phe
```

```
                      50                  55                  60
Ser Gly Ser Gly Ser Gly Thr Asp Phe Thr Leu Thr Ile Ser Leu
 65                  70                  75                  80

Gln Pro Glu Asp Phe Ala Thr Tyr Tyr Cys Gln Gln Ser Tyr Ser Ser
                     85                  90                  95

Pro Gly Ile Thr Phe Gly Pro Gly Thr Lys Val Glu Ile Lys
                100                 105                 110
```

<210> SEQ ID NO 80
<211> LENGTH: 121
<212> TYPE: PRT
<213> ORGANISM: Homo Sapiens

<400> SEQUENCE: 80

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Pro Tyr
                 20                  25                  30

Pro Met Met Trp Val Arg Gln Ala Pro Gly Lys Gly Leu Glu Trp Val
                 35                  40                  45

Ser Tyr Ile Ser Pro Ser Gly Gly Lys Thr His Tyr Ala Asp Ser Val
             50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Asp Gly Tyr Phe Asp Tyr Phe Asp Tyr Trp Gly Gln
                100                 105                 110

Gly Thr Leu Val Thr Val Ser Ser Ala
            115                 120
```

<210> SEQ ID NO 81
<211> LENGTH: 217
<212> TYPE: PRT
<213> ORGANISM: Homo Sapiens

<400> SEQUENCE: 81

```
Ala Gln Asp Ile Gln Met Thr Gln Ser Pro Ala Thr Leu Ser Ala Ser
  1               5                  10                  15

Val Gly Asp Arg Val Thr Ile Thr Cys Arg Ala Ser Gln Ser Ile Ser
                 20                  25                  30

Gly Tyr Leu Asn Trp Tyr Gln Gln Lys Pro Gly Lys Ala Pro Lys Leu
             35                  40                  45

Leu Ile Tyr Asn Ala Ser Ser Leu Gln Ser Gly Val Pro Ser Arg Phe
         50                  55                  60

Ser Gly Ser Gly Ser Gly Thr Asp Phe Thr Leu Thr Ile Ser Ser Leu
 65                  70                  75                  80

Gln Pro Glu Asp Phe Ala Thr Tyr Tyr Cys Gln Gln Ser Tyr Thr Ser
                 85                  90                  95

Pro Phe Ile Thr Phe Gly Pro Gly Thr Lys Val Glu Ile Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
```

```
                145                 150                 155                 160
Asn Ser Gln Glu Ser Val Thr Glu Gln Asp Ser Lys Asp Ser Thr Tyr
                    165                 170                 175

Ser Leu Ser Ser Thr Leu Thr Leu Ser Lys Ala Asp Tyr Glu Lys His
                180                 185                 190

Lys Leu Tyr Ala Cys Glu Val Thr His Gln Gly Leu Ser Ser Pro Val
                195                 200                 205

Thr Lys Ser Phe Asn Arg Gly Glu Cys
            210                 215

<210> SEQ ID NO 82
<211> LENGTH: 449
<212> TYPE: PRT
<213> ORGANISM: Homo Sapiens

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

-continued

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly

<210> SEQ ID NO 83
<211> LENGTH: 11
<212> TYPE: PRT
<213> ORGANISM: Homo Sapiens

<400> SEQUENCE: 83

Arg Ala Ser Gln Ser Ile Ser Gly Tyr Leu Asn
1               5                   10

<210> SEQ ID NO 84
<211> LENGTH: 7
<212> TYPE: PRT
<213> ORGANISM: Homo Sapiens

<400> SEQUENCE: 84

Asn Ala Ser Ser Leu Gln Ser
1               5

<210> SEQ ID NO 85
<211> LENGTH: 10
<212> TYPE: PRT
<213> ORGANISM: Homo Sapiens

<400> SEQUENCE: 85

Gln Gln Ser Tyr Thr Ser Pro Phe Ile Thr
1               5                   10

<210> SEQ ID NO 86
<211> LENGTH: 5
<212> TYPE: PRT
<213> ORGANISM: Homo Sapiens

<400> SEQUENCE: 86

Pro Tyr Pro Met Ile
1               5

<210> SEQ ID NO 87
<211> LENGTH: 17
<212> TYPE: PRT
<213> ORGANISM: Homo Sapiens
```

```
<400> SEQUENCE: 87

Tyr Ile Ser Pro Ser Gly Gly Lys Thr His Tyr Ala Asp Ser Val Lys
1               5                   10                  15

Gly

<210> SEQ ID NO 88
<211> LENGTH: 11
<212> TYPE: PRT
<213> ORGANISM: Homo Sapiens

<400> SEQUENCE: 88

Gly Gly Asp Thr Tyr Phe Asp Tyr Phe Asp Tyr
1               5                   10

<210> SEQ ID NO 89
<211> LENGTH: 110
<212> TYPE: PRT
<213> ORGANISM: Homo Sapiens

<400> SEQUENCE: 89

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Gly Tyr Leu Asn Trp Tyr Gln Gln Lys Pro Gly Lys Ala Pro Lys Leu
        35                  40                  45

Leu Ile Tyr Asn Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95

Pro Phe Ile Thr Phe Gly Pro Gly Thr Lys Val Glu Ile Lys
            100                 105                 110

<210> SEQ ID NO 90
<211> LENGTH: 121
<212> TYPE: PRT
<213> ORGANISM: Homo Sapiens

<400> SEQUENCE: 90

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120
```

<210> SEQ ID NO 91
<211> LENGTH: 217
<212> TYPE: PRT
<213> ORGANISM: Homo Sapiens

<400> SEQUENCE: 91

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Asn Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95

Pro Gly Ile Thr Phe Gly Pro Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 92
<211> LENGTH: 449
<212> TYPE: PRT
<213> ORGANISM: Homo Sapiens

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

```
Gly Thr Leu Val Thr Val Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 93
<211> LENGTH: 11
<212> TYPE: PRT
<213> ORGANISM: Homo Sapiens

<400> SEQUENCE: 93

Arg Ala Ser Gln Ser Ile Ser Ser Tyr Leu Asn
1               5                   10

<210> SEQ ID NO 94
<211> LENGTH: 7
```

```
<212> TYPE: PRT
<213> ORGANISM: Homo Sapiens

<400> SEQUENCE: 94

Asn Ala Ser Ser Leu Gln Ser
1               5

<210> SEQ ID NO 95
<211> LENGTH: 10
<212> TYPE: PRT
<213> ORGANISM: Homo Sapiens

<400> SEQUENCE: 95

Gln Gln Ser Tyr Thr Ser Pro Gly Ile Thr
1               5                   10

<210> SEQ ID NO 96
<211> LENGTH: 5
<212> TYPE: PRT
<213> ORGANISM: Homo Sapiens

<400> SEQUENCE: 96

Pro Tyr Pro Met Met
1               5

<210> SEQ ID NO 97
<211> LENGTH: 17
<212> TYPE: PRT
<213> ORGANISM: Homo Sapiens

<400> SEQUENCE: 97

Tyr Ile Ser Pro Ser Gly Gly Lys Thr His Tyr Ala Asp Ser Val Lys
1               5                   10                  15

Gly

<210> SEQ ID NO 98
<211> LENGTH: 11
<212> TYPE: PRT
<213> ORGANISM: Homo Sapiens

<400> SEQUENCE: 98

Gly Gly Asp Thr Tyr Phe Asp Tyr Phe Asp Tyr
1               5                   10

<210> SEQ ID NO 99
<211> LENGTH: 110
<212> TYPE: PRT
<213> ORGANISM: Homo Sapiens

<400> SEQUENCE: 99

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Asn Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95
```

```
Pro Gly Ile Thr Phe Gly Pro Gly Thr Lys Val Glu Ile Lys
            100                 105                 110

<210> SEQ ID NO 100
<211> LENGTH: 121
<212> TYPE: PRT
<213> ORGANISM: Homo Sapiens

<400> SEQUENCE: 100

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120

<210> SEQ ID NO 101
<211> LENGTH: 217
<212> TYPE: PRT
<213> ORGANISM: Homo Sapiens

<400> SEQUENCE: 101

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Gly Tyr Leu Asn Trp Tyr Gln Gln Lys Pro Gly Lys Ala Pro Lys Leu
        35                  40                  45

Leu Ile Tyr Asn Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95

Pro Gly Ile Thr Phe Gly Pro Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190
```

-continued

```
Lys Leu Tyr Ala Cys Glu Val Thr His Gln Gly Leu Ser Ser Pro Val
        195                 200                 205

Thr Lys Ser Phe Asn Arg Gly Glu Cys
        210                 215

<210> SEQ ID NO 102
<211> LENGTH: 449
<212> TYPE: PRT
<213> ORGANISM: Homo Sapiens

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
```

340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 103
<211> LENGTH: 11
<212> TYPE: PRT
<213> ORGANISM: Homo Sapiens

<400> SEQUENCE: 103

Arg Ala Ser Gln Ser Ile Ser Gly Tyr Leu Asn
1               5                   10

<210> SEQ ID NO 104
<211> LENGTH: 7
<212> TYPE: PRT
<213> ORGANISM: Homo Sapiens

<400> SEQUENCE: 104

Asn Ala Ser Ser Leu Gln Ser
1               5

<210> SEQ ID NO 105
<211> LENGTH: 10
<212> TYPE: PRT
<213> ORGANISM: Homo Sapiens

<400> SEQUENCE: 105

Gln Gln Ser Tyr Thr Ser Pro Gly Ile Thr
1               5                   10

<210> SEQ ID NO 106
<211> LENGTH: 5
<212> TYPE: PRT
<213> ORGANISM: Homo Sapiens

<400> SEQUENCE: 106

Pro Tyr Pro Met Met
1               5

<210> SEQ ID NO 107
<211> LENGTH: 17
<212> TYPE: PRT
<213> ORGANISM: Homo Sapiens

<400> SEQUENCE: 107

Tyr Ile Ser Pro Ser Gly Gly Lys Thr His Tyr Ala Asp Ser Val Lys
1               5                   10                  15

Gly

<210> SEQ ID NO 108
<211> LENGTH: 11
<212> TYPE: PRT
<213> ORGANISM: Homo Sapiens

<400> SEQUENCE: 108

Gly Gly Asp Thr Tyr Phe Asp Tyr Phe Asp Tyr
1               5                   10

<210> SEQ ID NO 109
<211> LENGTH: 110
<212> TYPE: PRT
<213> ORGANISM: Homo Sapiens

<400> SEQUENCE: 109

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Gly Tyr Leu Asn Trp Tyr Gln Gln Lys Pro Gly Lys Ala Pro Lys Leu
        35                  40                  45

Leu Ile Tyr Asn Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95

Pro Gly Ile Thr Phe Gly Pro Gly Thr Lys Val Glu Ile Lys
            100                 105                 110

<210> SEQ ID NO 110
<211> LENGTH: 121
<212> TYPE: PRT
<213> ORGANISM: Homo Sapiens

<400> SEQUENCE: 110

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120

<210> SEQ ID NO 111
<211> LENGTH: 217
<212> TYPE: PRT
<213> ORGANISM: Homo Sapiens

<400> SEQUENCE: 111

```
Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Asn Ala Ser Ser Leu Gln Ser Gly Val Pro Ser Arg Phe
50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
            85                  90                  95

Pro Phe Ile Thr Phe Gly Pro Gly Thr Lys Val Glu Ile Lys Arg Thr
        100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
            165                 170                 175

Ser Leu Ser Ser Thr Leu Thr Leu Ser Lys Ala Asp Tyr Glu Lys His
        180                 185                 190

Lys Leu Tyr Ala Cys Glu Val Thr His Gln Gly Leu Ser Ser Pro Val
        195                 200                 205

Thr Lys Ser Phe Asn Arg Gly Glu Cys
210                 215

<210> SEQ ID NO 112
<211> LENGTH: 449
<212> TYPE: PRT
<213> ORGANISM: Homo Sapiens

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Gly Asp Thr Tyr Phe Asp Tyr Phe Asp Tyr Trp Gly Gln
        100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
```

```
             145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly

<210> SEQ ID NO 113
<211> LENGTH: 11
<212> TYPE: PRT
<213> ORGANISM: Homo Sapiens

<400> SEQUENCE: 113

Arg Ala Ser Gln Ser Ile Ser Ser Tyr Leu Asn
1               5                   10

<210> SEQ ID NO 114
<211> LENGTH: 7
<212> TYPE: PRT
<213> ORGANISM: Homo Sapiens

<400> SEQUENCE: 114

Asn Ala Ser Ser Leu Gln Ser
1               5
```

<210> SEQ ID NO 115
<211> LENGTH: 10
<212> TYPE: PRT
<213> ORGANISM: Homo Sapiens

<400> SEQUENCE: 115

Gln Gln Ser Tyr Thr Ser Pro Phe Ile Thr
1               5                   10

<210> SEQ ID NO 116
<211> LENGTH: 5
<212> TYPE: PRT
<213> ORGANISM: Homo Sapiens

<400> SEQUENCE: 116

Pro Tyr Pro Met Met
1               5

<210> SEQ ID NO 117
<211> LENGTH: 17
<212> TYPE: PRT
<213> ORGANISM: Homo Sapiens

<400> SEQUENCE: 117

Tyr Ile Ser Pro Ser Gly Gly Lys Thr His Tyr Ala Asp Ser Val Lys
1               5                   10                  15

Gly

<210> SEQ ID NO 118
<211> LENGTH: 11
<212> TYPE: PRT
<213> ORGANISM: Homo Sapiens

<400> SEQUENCE: 118

Gly Gly Asp Thr Tyr Phe Asp Tyr Phe Asp Tyr
1               5                   10

<210> SEQ ID NO 119
<211> LENGTH: 110
<212> TYPE: PRT
<213> ORGANISM: Homo Sapiens

<400> SEQUENCE: 119

Ala Gln Asp Ile Gln Met Thr Gln Ser Pro Ala Thr Leu Ser Ala Ser
1               5                   10                  15

Val Gly Asp Arg Val Thr Ile Thr Cys Arg Ala Ser Gln Ser Ile Ser
                20                  25                  30

Ser Tyr Leu Asn Trp Tyr Gln Gln Lys Pro Gly Lys Ala Pro Lys Leu
            35                  40                  45

Leu Ile Tyr Asn Ala Ser Ser Leu Gln Ser Gly Val Pro Ser Arg Phe
        50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Thr Ser
                85                  90                  95

Pro Phe Ile Thr Phe Gly Pro Gly Thr Lys Val Glu Ile Lys
            100                 105                 110

<210> SEQ ID NO 120
<211> LENGTH: 121

```
<212> TYPE: PRT
<213> ORGANISM: Homo Sapiens

<400> SEQUENCE: 120

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Met Trp Val Arg Gln Ala Pro Gly Lys Gly Leu Glu Trp Val
        35                  40                  45

Ser Tyr Ile Ser Pro Ser Gly Gly Lys Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala
        115                 120

<210> SEQ ID NO 121
<211> LENGTH: 218
<212> TYPE: PRT
<213> ORGANISM: Mus Musculus

<400> SEQUENCE: 121

Asp Ile Val Leu Thr Gln Ser Pro Ala Ser Leu Ala Val Ser Leu Gly
1               5                   10                  15

Gln Arg Ala Thr Ile Ser Cys Arg Ala Asn Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Ile Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

<210> SEQ ID NO 122
<211> LENGTH: 450
<212> TYPE: PRT
<213> ORGANISM: Mus Musculus

<400> SEQUENCE: 122

Gln Val Gln Leu Gln Gln Ser Gly Pro Glu Val Arg Pro Gly Val
1               5                   10                  15

Ser Val Lys Ile Ser Cys Lys Gly Ser Gly Tyr Thr Phe Thr Asp Tyr
                20                  25                  30

Gly Ile His Trp Val Lys Gln Ser His Ala Lys Ser Leu Glu Trp Ile
            35                  40                  45

Gly Val Ile Ser Thr Tyr Asn Gly Tyr Thr Asn Tyr Asn Gln Lys Phe
        50                  55                  60

Lys Gly Lys Ala Thr Met Thr Val Asp Lys Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Ala Tyr Tyr Gly Asn Leu Tyr Tyr Ala Met Asp Tyr Trp Gly
            100                 105                 110

Gln Gly Thr Ser Val Thr Val Ser Ser Ala Lys Thr Thr Ala Pro Ser
        115                 120                 125

Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Asp Val Ser Glu
            260                 265                 270

Asp Asp Pro Asp Val Gln Ile Ser Trp Phe Val Asn Asn Val Glu Val
        275                 280                 285

His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
            340                 345                 350

Tyr Val Leu Pro Pro Pro Glu Glu Glu Met Thr Lys Lys Gln Val Thr
        355                 360                 365

Leu Thr Cys Met Val Thr Asp Phe Met Pro Glu Asp Ile Tyr Val Glu
    370                 375                 380

```
Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
            420                 425                 430

His Glu Gly Leu His Asn His His Thr Thr Lys Ser Phe Ser Arg Thr
        435                 440                 445

Pro Gly
    450

<210> SEQ ID NO 123
<211> LENGTH: 218
<212> TYPE: PRT
<213> ORGANISM: Mus Musculus

<400> SEQUENCE: 123

Asp Ile Val Leu Thr Gln Ser Pro Ala Ser Leu Thr Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met Gln Trp Tyr Gln Gln Arg Pro Gly Gln Pro Pro
        35                  40                  45

Lys Leu Leu Ile Lys Tyr Ala Thr Asn Leu Asp Ser Gly Val Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 124
<211> LENGTH: 448
<212> TYPE: PRT
<213> ORGANISM: Mus Musculus

<400> SEQUENCE: 124

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Asn Asn Tyr
            20                  25                  30
```

```
Trp Met Ser Trp Val Arg Gln Ser Pro Glu Lys Gly Leu Glu Trp Leu
        35                  40                  45

Ala Glu Ile Arg Leu Lys Ser Asp Asn Tyr Ala Thr His Tyr Ala Glu
 50                  55                  60

Ser Val Lys Gly Lys Phe Thr Ile Ser Arg Asp Asp Ser Lys Ser Arg
 65                  70                  75                  80

Leu Tyr Leu Gln Met Asn Asn Leu Arg Ala Glu Asn Thr Gly Ile Tyr
                 85                  90                  95

Tyr Cys Thr Gly Gly Phe Ala Asp Tyr Phe Asp Tyr Trp Gly Gln Gly
            100                 105                 110

Thr Thr Leu Thr Val Ser Ser Ala Lys Thr Thr Ala Pro Ser Val Tyr
            115                 120                 125

Pro Leu Ala Pro Val Cys Gly Asp Thr Thr Gly Ser Ser Val Thr Leu
 130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
            195                 200                 205

Ser Thr Lys Val Asp Lys Lys Ile Glu Pro Arg Gly Pro Thr Ile Lys
 210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
            275                 280                 285

Ala Gln Thr Gln Thr His Arg Glu Asp Tyr Asn Ser Thr Leu Arg Val
 290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
            355                 360                 365

Cys Met Val Thr Asp Phe Met Pro Glu Asp Ile Tyr Val Glu Trp Thr
 370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
            435                 440                 445
```

<210> SEQ ID NO 125
<211> LENGTH: 218
<212> TYPE: PRT
<213> ORGANISM: Homo Sapiens

<400> SEQUENCE: 125

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln His Ser Arg
                85                  90                  95

Glu Leu Pro Phe Thr Phe Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 126
<211> LENGTH: 450
<212> TYPE: PRT
<213> ORGANISM: Homo Sapiens

<400> SEQUENCE: 126

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Gly Met His Trp Val Arg Gln Ala Pro Gly Gln Gly Leu Glu Trp Met
        35                  40                  45

Gly Val Ile Ser Thr Tyr Asn Gly Tyr Thr Asn Tyr Asn Gln Lys Phe
    50                  55                  60

Lys Gly Arg Val Thr Met Thr Val Asp Lys Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Ala Tyr Tyr Gly Asn Leu Tyr Tyr Ala Met Asp Tyr Trp Gly
            100                 105                 110

```
Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 127
<211> LENGTH: 218
<212> TYPE: PRT
<213> ORGANISM: Homo Sapiens

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Thr Ser
            20                  25                  30
```

Ser Tyr Ser Tyr Met His Trp Tyr Gln Gln Lys Pro Gly Lys Ala Pro
    35                  40                  45

Lys Leu Leu Ile Lys Tyr Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Trp
                85                  90                  95

Glu Ile Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 128
<211> LENGTH: 449
<212> TYPE: PRT
<213> ORGANISM: Homo Sapiens

<400> SEQUENCE: 128

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Glu Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Thr Gly Tyr Tyr Ala Asp Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser

```
                180             185             190
        Ser Ser Leu Gly Thr Gln Thr Tyr Ile Cys Asn Val Asn His Lys Pro
                    195             200             205
        Ser Asn Thr Lys Val Asp Lys Lys Val Glu Pro Lys Ser Cys Asp Lys
                    210             215             220
        Thr His Thr Cys Pro Pro Cys Pro Ala Pro Glu Leu Leu Gly Gly Pro
        225             230             235             240
        Ser Val Phe Leu Phe Pro Pro Lys Pro Lys Asp Thr Leu Met Ile Ser
                        245             250             255
        Arg Thr Pro Glu Val Thr Cys Val Val Val Asp Val Ser His Glu Asp
                    260             265             270
        Pro Glu Val Lys Phe Asn Trp Tyr Val Asp Gly Val Glu Val His Asn
                    275             280             285
        Ala Lys Thr Lys Pro Arg Glu Glu Gln Tyr Asn Ser Thr Tyr Arg Val
                    290             295             300
        Val Ser Val Leu Thr Val Leu His Gln Asp Trp Leu Asn Gly Lys Glu
        305             310             315             320
        Tyr Lys Cys Lys Val Ser Asn Lys Ala Leu Pro Ala Pro Ile Glu Lys
                        325             330             335
        Thr Ile Ser Lys Ala Lys Gly Gln Pro Arg Glu Pro Gln Val Tyr Thr
                        340             345             350
        Leu Pro Pro Ser Arg Asp Glu Leu Thr Lys Asn Gln Val Ser Leu Thr
                    355             360             365
        Cys Leu Val Lys Gly Phe Tyr Pro Ser Asp Ile Ala Val Glu Trp Glu
        370             375             380
        Ser Asn Gly Gln Pro Glu Asn Asn Tyr Lys Thr Thr Pro Pro Val Leu
        385             390             395             400
        Asp Ser Asp Gly Ser Phe Phe Leu Tyr Ser Lys Leu Thr Val Asp Lys
                        405             410             415
        Ser Arg Trp Gln Gln Gly Asn Val Phe Ser Cys Ser Val Met His Glu
                    420             425             430
        Ala Leu His Asn His Tyr Thr Gln Lys Ser Leu Ser Leu Ser Pro Gly
                    435             440             445
        Lys

<210> SEQ ID NO 129
<211> LENGTH: 218
<212> TYPE: PRT
<213> ORGANISM: Mus Musculus

<400> SEQUENCE: 129

Asp Ile Val Leu Thr Gln Ser Pro Ala Ser Leu Ala Val Ser Leu Gly
        1               5                   10                  15
        Gln Arg Ala Thr Ile Ser Cys Lys Ala Ser Gln Ser Val Ser Thr Ser
                        20                  25                  30
        Thr Tyr Ser Tyr Met Gln Trp Tyr Gln Gln Arg Pro Gly Gln Ser Pro
                    35                  40                  45
        Lys Leu Leu Ile Lys Tyr Ala Ser Lys Leu Asp Ser Gly Val Pro Ala
                50                  55                  60
        Arg Phe Ser Gly Ser Gly Ser Gly Thr Asp Phe Thr Leu Asn Ile His
        65                  70                  75                  80
        Pro Val Glu Glu Glu Asp Thr Ala Thr Tyr Tyr Cys Gln His Ser Trp
                        85                  90                  95
        Glu Leu Pro Tyr Thr Phe Gly Gly Gly Thr Arg Leu Glu Ile Lys Arg
```

```
            100                 105                 110
Ala Asp Ala Ala Pro Thr Val Ser Ile Phe Pro Pro Ser Ser Glu Gln
            115                 120                 125

Leu Thr Ser Gly Gly Ala Ser Val Val Cys Phe Leu Asn Asn Phe Tyr
        130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 130
<211> LENGTH: 448
<212> TYPE: PRT
<213> ORGANISM: Mus Musculus

<400> SEQUENCE: 130

Glu Val Lys Leu Gly Glu Ser Gly Gly Gly Leu Val Gln Pro Gly Gly
1               5                   10                  15

Ser Met Lys Leu Ser Cys Val Ala Ser Gly Phe Pro Phe Thr Lys Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asp Asn Tyr Ala Thr His Tyr Ala Glu
    50                  55                  60

Ser Ala Lys Gly Arg Phe Thr Ile Ser Arg Asp Asp Ser Arg Ser Ser
65                  70                  75                  80

Val Tyr Leu Gln Met Asn Asn Leu Arg Ala Glu Asp Thr Ala Ile Tyr
                85                  90                  95

Tyr Cys Ser Pro Thr Tyr Ala Asp Thr Met Asp Tyr Trp Gly Gln Gly
            100                 105                 110

Thr Ser Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255
```

```
Leu Ser Pro Ile Val Thr Cys Val Val Asp Val Ser Asp Asp
            260                 265                 270

Pro Asp Val Gln Ile Ser Trp Phe Val Asn Asn Val Glu Val His Thr
                275                 280                 285

Ala Gln Thr Gln Thr His Arg Glu Asp Tyr Asn Ser Thr Leu Arg Val
        290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
            355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
            435                 440                 445

<210> SEQ ID NO 131
<211> LENGTH: 218
<212> TYPE: PRT
<213> ORGANISM: Mus Musculus

<400> SEQUENCE: 131

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Thr Ser Asn Leu Glu Ser Gly Val Pro Ala
    50                  55                  60

Arg Phe Ser Gly Ser Gly Ser Gly Thr Asp Phe Ile Leu Asn Ile His
65                  70                  75                  80

Pro Val Glu Glu Glu Asp Ala Ala Thr Tyr Tyr Cys Gln His Ser Arg
                85                  90                  95

Glu Leu Pro Trp Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190
```

His Asn Ser Tyr Thr Cys Glu Ala Thr His Lys Thr Ser Thr Ser Pro
        195                 200                 205

Ile Val Lys Ser Phe Asn Arg Asn Glu Cys
210                 215

<210> SEQ ID NO 132
<211> LENGTH: 451
<212> TYPE: PRT
<213> ORGANISM: Mus Musculus

<400> SEQUENCE: 132

Gln Val Ser Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Gly Pro Asp Tyr Tyr Gly Tyr Tyr Pro Met Asp Tyr
            100                 105                 110

Trp Gly Gln Gly Thr Ser Val Thr Val Ser Ala Lys Thr Thr Ala Pro
        115                 120                 125

Ser Val Tyr Pro Leu Ala Pro Val Cys Gly Asp Thr Thr Gly Ser Ser
    130                 135                 140

Val Thr Leu Gly Cys Leu Val Lys Gly Tyr Phe Pro Glu Pro Val Thr
145                 150                 155                 160

Leu Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Thr Ser Ser Thr Trp Pro Ser Gln Ser Ile Thr Cys Asn Val Ala His
        195                 200                 205

Pro Ala Ser Ser Thr Lys Val Asp Lys Lys Ile Glu Pro Arg Gly Pro
    210                 215                 220

Thr Ile Lys Pro Cys Pro Pro Cys Lys Cys Pro Ala Pro Asn Leu Leu
225                 230                 235                 240

Gly Gly Pro Ser Val Phe Ile Phe Pro Pro Lys Ile Lys Asp Val Leu
                245                 250                 255

Met Ile Ser Leu Ser Pro Ile Val Thr Cys Val Val Val Asp Val Ser
            260                 265                 270

Glu Asp Asp Pro Asp Val Gln Ile Ser Trp Phe Val Asn Asn Val Glu
        275                 280                 285

Val His Thr Ala Gln Thr Gln Thr His Arg Glu Asp Tyr Asn Ser Thr
    290                 295                 300

Leu Arg Val Val Ser Ala Leu Pro Ile Gln His Gln Asp Trp Met Ser
305                 310                 315                 320

Gly Lys Glu Phe Lys Cys Lys Val Asn Asn Lys Asp Leu Pro Ala Pro
                325                 330                 335

Ile Glu Arg Thr Ile Ser Lys Pro Lys Gly Ser Val Arg Ala Pro Gln

```
                    340                 345                 350
Val Tyr Val Leu Pro Pro Glu Glu Glu Met Thr Lys Lys Gln Val
            355                 360                 365

Thr Leu Thr Cys Met Val Thr Asp Phe Met Pro Glu Asp Ile Tyr Val
        370                 375                 380

Glu Trp Thr Asn Asn Gly Lys Thr Glu Leu Asn Tyr Lys Asn Thr Glu
385                 390                 395                 400

Pro Val Leu Asp Ser Asp Gly Ser Tyr Phe Met Tyr Ser Lys Leu Arg
                405                 410                 415

Val Glu Lys Lys Asn Trp Val Glu Arg Asn Ser Tyr Ser Cys Ser Val
            420                 425                 430

Val His Glu Gly Leu His Asn His His Thr Thr Lys Ser Phe Ser Arg
        435                 440                 445

Thr Pro Gly
        450

<210> SEQ ID NO 133
<211> LENGTH: 282
<212> TYPE: PRT
<213> ORGANISM: Macaca fascicularis

<400> SEQUENCE: 133

Glu Gln Ala Pro Gly Thr Ala Pro Cys Ser His Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ser Ala Ala Pro Pro Ala Pro Phe
        35                  40                  45

Arg Leu Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255
```

```
Val Phe Ser Cys Ser Val Met His Glu Ala Leu His Asn His Tyr Thr
            260                 265                 270

Gln Lys Ser Leu Ser Leu Ser Pro Gly Lys
        275                 280
```

<210> SEQ ID NO 134
<211> LENGTH: 282
<212> TYPE: PRT
<213> ORGANISM: Rattus norvegicus

<400> SEQUENCE: 134

```
Glu Gln Ala Pro Gly Asn Ala Pro Cys Ser Gly Ser Ser Trp Ser
1               5                   10                  15

Ala Asp Leu Asp Lys Cys Met Asp Cys Ala Ser Cys Pro Ala Arg Pro
            20                  25                  30

His Ser Asp Phe Cys Leu Gly Cys Ala Ala Pro Pro Ala His Phe
        35                  40                  45

Arg Met Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280
```

<210> SEQ ID NO 135
<211> LENGTH: 282
<212> TYPE: PRT
<213> ORGANISM: Sus scrofa

<400> SEQUENCE: 135

```
Glu Arg Val Pro Gly Thr Thr Pro Cys Ser Arg Gly Ser Ser Trp Ser
1               5                   10                  15
```

```
Ala Asp Leu Asp Lys Cys Met Asp Cys Ala Ser Cys Pro Arg Pro
            20                  25                  30

His Ser Asp Phe Cys Leu Gly Cys Ala Ala Pro Pro Ala Ser Phe
        35                  40                  45

Arg Leu Leu Trp Pro Arg Ser Asp Lys Thr His Thr Cys Pro Pro Cys
50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
                100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
        130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280

<210> SEQ ID NO 136
<211> LENGTH: 282
<212> TYPE: PRT
<213> ORGANISM: Canis lupus

<400> SEQUENCE: 136

Glu Arg Val Pro Gly Thr Thr Pro Cys Pro Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Thr Ala Pro Ala Pro Ala Pro Phe
        35                  40                  45

Arg Leu Leu Trp Pro Arg Ser Asp Lys Thr His Thr Cys Pro Pro Cys
50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
                100                 105                 110
```

```
Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
        130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
            210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280

<210> SEQ ID NO 137
<211> LENGTH: 282
<212> TYPE: PRT
<213> ORGANISM: Mus Musculus

<400> SEQUENCE: 137

Glu Gln Ala Pro Gly Thr Ser Pro Cys Ser Ser Gly Ser Ser Trp Ser
1               5                   10                  15

Ala Asp Leu Asp Lys Cys Met Asp Cys Ala Ser Cys Pro Ala Arg Pro
                20                  25                  30

His Ser Asp Phe Cys Leu Gly Cys Ala Ala Pro Pro Ala His Phe
            35                  40                  45

Arg Leu Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
        130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
```

```
              195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280

<210> SEQ ID NO 138
<211> LENGTH: 282
<212> TYPE: PRT
<213> ORGANISM: Homo Sapiens

<400> SEQUENCE: 138

Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Pro Ala Pro Ala Pro Phe
        35                  40                  45

Arg Leu Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280
```

<210> SEQ ID NO 139
<211> LENGTH: 296
<212> TYPE: PRT
<213> ORGANISM: Homo Sapiens

<400> SEQUENCE: 139

Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Pro Ala Pro Phe
        35                  40                  45

Arg Leu Leu Trp Pro Ile Glu Gly Arg Met Asp Pro Lys Ser Cys Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
            85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
        115                 120                 125

Asn Ala Lys Thr Lys Pro Arg Glu Glu Gln Tyr Asn Ser Thr Tyr Arg
    130                 135                 140

Val Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
            180                 185                 190

Thr Leu Pro Pro Ser Arg Glu Glu Met Thr Lys Asn Gln Val Ser Leu
        195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
        275                 280                 285

Gly Lys His His His His His His
    290                 295

<210> SEQ ID NO 140
<211> LENGTH: 278
<212> TYPE: PRT
<213> ORGANISM: Homo Sapiens

<400> SEQUENCE: 140

Ala Pro Cys Ser Arg Gly Ser Ser Trp Ser Ala Asp Leu Asp Lys Cys
1               5                   10                  15

Met Asp Cys Ala Ser Cys Arg Ala Arg Pro His Ser Asp Phe Cys Leu
            20                  25                  30

```
Gly Cys Ala Ile Glu Gly Arg Met Asp Pro Lys Ser Cys Asp Lys Thr
            35                  40                  45

His Thr Cys Pro Pro Cys Pro Ala Pro Glu Leu Leu Gly Gly Pro Ser
 50                  55                  60

Val Phe Leu Phe Pro Pro Lys Pro Lys Asp Thr Leu Met Ile Ser Arg
 65                  70                  75                  80

Thr Pro Glu Val Thr Cys Val Val Val Asp Val Ser His Glu Asp Pro
                 85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
            115                 120                 125

Ser Val Leu Thr Val Leu His Gln Asp Trp Leu Asn Gly Lys Glu Tyr
130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
            195                 200                 205

Asn Gly Gln Pro Glu Asn Asn Tyr Lys Thr Thr Pro Pro Val Leu Asp
210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
            275

<210> SEQ ID NO 141
<211> LENGTH: 47
<212> TYPE: PRT
<213> ORGANISM: Homo Sapiens

<400> SEQUENCE: 141

Glu Gln Ala Pro Gly Thr Ala Pro Cys Ser Arg Gly Ser Ser Trp Ser
 1               5                  10                  15

Ala Asp Leu Asp Lys Cys Met Asp Cys Ala Ser Cys Arg Ala Arg Pro
            20                  25                  30

His Ser Asp Phe Cys Leu Gly Cys Ala His His His His His His
            35                  40                  45

<210> SEQ ID NO 142
<211> LENGTH: 282
<212> TYPE: PRT
<213> ORGANISM: Homo Sapiens

<400> SEQUENCE: 142

Glu Gln Ala Pro Gly Thr Ala Pro Cys Ser Arg Gly Ser Ser Trp Ser
 1               5                  10                  15

Ala Asp Leu Asp Lys Cys Met Asp Cys Ala Ser Cys Arg Ala Arg Pro
            20                  25                  30
```

His Ser Asp Phe Cys Gln Gly Cys Ala Ala Ala Pro Pro Ala Pro Phe
        35                  40                  45

Arg Leu Leu Trp Pro Arg Ser Asp Lys Thr His Thr Cys Pro Pro Cys
 50                  55                  60

Pro Ala Pro Glu Leu Leu Gly Gly Pro Ser Val Phe Leu Phe Pro Pro
 65                  70                  75                  80

Lys Pro Lys Asp Thr Leu Met Ile Ser Arg Thr Pro Glu Val Thr Cys
                 85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
        130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280

<210> SEQ ID NO 143
<211> LENGTH: 282
<212> TYPE: PRT
<213> ORGANISM: Homo Sapiens

<400> SEQUENCE: 143

Glu Gln Ala Pro Gly Thr Ala Pro Cys Ser Arg Gly Ser Ser Trp Ser
 1               5                  10                  15

Ala Asp Leu Asp Lys Cys Met Asp Cys Ala Ser Cys Arg Ala Arg Pro
             20                  25                  30

Lys Ser Asp Phe Cys Leu Gly Cys Ala Ala Ala Pro Ala Pro Pro Phe
        35                  40                  45

Arg Leu Leu Trp Pro Arg Ser Asp Lys Thr His Thr Cys Pro Pro Cys
 50                  55                  60

Pro Ala Pro Glu Leu Leu Gly Gly Pro Ser Val Phe Leu Phe Pro Pro
 65                  70                  75                  80

Lys Pro Lys Asp Thr Leu Met Ile Ser Arg Thr Pro Glu Val Thr Cys
                 85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
            115                 120                 125

Glu Gln Tyr Asn Ser Thr Tyr Arg Val Val Ser Val Leu Thr Val Leu
             130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280

<210> SEQ ID NO 144
<211> LENGTH: 282
<212> TYPE: PRT
<213> ORGANISM: Homo Sapiens

<400> SEQUENCE: 144

Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Pro Ala Arg Pro
            20                  25                  30

His Ser Asp Phe Cys Leu Gly Cys Ala Ala Ala Pro Ala Pro Ala Phe
        35                  40                  45

Arg Leu Leu Trp Pro Arg Ser Asp Lys Thr His Thr Cys Pro Pro Cys
50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
            245                 250                 255

Val Phe Ser Cys Ser Val Met His Glu Ala Leu His Asn His Tyr Thr
                260                 265                 270

Gln Lys Ser Leu Ser Leu Ser Pro Gly Lys
        275                 280

<210> SEQ ID NO 145
<211> LENGTH: 282
<212> TYPE: PRT
<213> ORGANISM: Homo Sapiens

<400> SEQUENCE: 145

Glu Gln Ala Pro Gly Thr Ala Pro Cys Ser Arg Gly Ser Ser Trp Ser
1               5                   10                  15

Ala Asp Leu Asp Lys Cys Ala Asp Cys Ala Ser Cys Arg Ala Arg Pro
            20                  25                  30

His Ser Asp Phe Cys Leu Gly Cys Ala Ala Ala Pro Pro Ala Pro Phe
        35                  40                  45

Arg Leu Leu Trp Pro Arg Ser Asp Lys Thr His Thr Cys Pro Pro Cys
50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
            245                 250                 255

Val Phe Ser Cys Ser Val Met His Glu Ala Leu His Asn His Tyr Thr
        260                 265                 270

Gln Lys Ser Leu Ser Leu Ser Pro Gly Lys
        275                 280

<210> SEQ ID NO 146
<211> LENGTH: 282

```
<212> TYPE: PRT
<213> ORGANISM: Homo Sapiens

<400> SEQUENCE: 146

Glu Gln Ala Pro Gly Thr Ala Pro Cys Ser Arg Gly Ser Ser Ala Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Pro Ala Pro Phe
        35                  40                  45

Arg Leu Leu Trp Pro Arg Ser Asp Lys Thr His Thr Cys Pro Pro Cys
    50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280

<210> SEQ ID NO 147
<211> LENGTH: 282
<212> TYPE: PRT
<213> ORGANISM: Homo Sapiens

<400> SEQUENCE: 147

Glu Gln Ala Pro Gly Thr Ala Pro Cys Ser Arg Gly Arg Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Pro Ala Pro Phe
        35                  40                  45

Arg Leu Leu Trp Pro Arg Ser Asp Lys Thr His Thr Cys Pro Pro Cys
    50                  55                  60
```

```
Pro Ala Pro Glu Leu Leu Gly Gly Pro Ser Val Phe Leu Phe Pro Pro
 65                  70                  75                  80

Lys Pro Lys Asp Thr Leu Met Ile Ser Arg Thr Pro Glu Val Thr Cys
                 85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Glu Glu
            180                 185                 190

Met Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
    210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280

<210> SEQ ID NO 148
<211> LENGTH: 282
<212> TYPE: PRT
<213> ORGANISM: Homo Sapiens

<400> SEQUENCE: 148

Glu Gln Ala Pro Gly Gln Ala Pro Cys Ser Arg Gly Ser Ser Trp Ser
 1               5                  10                  15

Ala Asp Leu Asp Lys Cys Met Asp Cys Ala Ser Cys Arg Ala Arg Pro
                 20                  25                  30

His Ser Asp Phe Cys Leu Gly Cys Ala Ala Pro Ala Pro Ala Pro Phe
             35                  40                  45

Arg Leu Leu Trp Pro Arg Ser Asp Lys Thr His Thr Cys Pro Pro Cys
 50                  55                  60

Pro Ala Pro Glu Leu Leu Gly Gly Pro Ser Val Phe Leu Phe Pro Pro
 65                  70                  75                  80

Lys Pro Lys Asp Thr Leu Met Ile Ser Arg Thr Pro Glu Val Thr Cys
                 85                  90                  95

Val Val Val Asp Val Ser His Glu Asp Pro Glu Val Lys Phe Asn Trp
            100                 105                 110

Tyr Val Asp Gly Val Glu Val His Asn Ala Lys Thr Lys Pro Arg Glu
        115                 120                 125

Glu Gln Tyr Asn Ser Thr Tyr Arg Val Val Ser Val Leu Thr Val Leu
    130                 135                 140

His Gln Asp Trp Leu Asn Gly Lys Glu Tyr Lys Cys Lys Val Ser Asn
145                 150                 155                 160
```

```
Lys Ala Leu Pro Ala Pro Ile Glu Lys Thr Ile Ser Lys Ala Lys Gly
            165                 170                 175

Gln Pro Arg Glu Pro Gln Val Tyr Thr Leu Pro Pro Ser Arg Glu Glu
        180                 185                 190

Met Thr Lys Asn Gln Val Ser Leu Thr Cys Leu Val Lys Gly Phe Tyr
            195                 200                 205

Pro Ser Asp Ile Ala Val Glu Trp Glu Ser Asn Gly Gln Pro Glu Asn
        210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
            260                 265                 270

Gln Lys Ser Leu Ser Leu Ser Pro Gly Lys
        275                 280

<210> SEQ ID NO 149
<211> LENGTH: 278
<212> TYPE: PRT
<213> ORGANISM: Homo Sapiens

<400> SEQUENCE: 149

Ala Pro Cys Ser Arg Gly Ser Ser Trp Ser Ala Asp Leu Asp Lys Cys
1               5                   10                  15

Met Asp Cys Ala Ser Cys Arg Ala Arg Pro His Ser Asp Phe Cys Ala
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
```

```
                        245                 250                 255
Leu His Asn His Tyr Thr Gln Lys Ser Leu Ser Leu Ser Pro Gly Lys
                260                 265                 270

His His His His His His
            275

<210> SEQ ID NO 150
<211> LENGTH: 278
<212> TYPE: PRT
<213> ORGANISM: Homo Sapiens

<400> SEQUENCE: 150

Ala Pro Cys Ser Arg Gly Ser Ser Trp Ser Ala Asp Leu Asp Lys Cys
1               5                   10                  15

Met Asp Cys Ala Ser Cys Arg Ala Arg Pro His Ser Asp Ala Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 151
<211> LENGTH: 278
<212> TYPE: PRT
<213> ORGANISM: Homo Sapiens

<400> SEQUENCE: 151

Ala Pro Cys Ser Arg Gly Ser Ser Trp Ser Ala Asp Leu Asp Lys Cys
```

| | 1 | | | | 5 | | | | | 10 | | | | | 15 | |
|---|---|---|---|---|---|---|---|---|---|---|---|---|---|---|---|---|
| | Met | Asp | Cys | Ala | Ser | Cys | Arg | Ala | Arg | Pro | His | Ser | Ala | Phe | Cys | Leu |
| | | | | 20 | | | | | 25 | | | | | 30 | | |
| | Gly | Cys | Ala | Ile | Glu | Gly | Arg | Met | Asp | Pro | Lys | Ser | Cys | Asp | Lys | Thr |
| | | | | 35 | | | | | 40 | | | | | 45 | | |
| | His | Thr | Cys | Pro | Pro | Cys | Pro | Ala | Pro | Glu | Leu | Leu | Gly | Gly | Pro | Ser |
| | | | | 50 | | | | | 55 | | | | | 60 | | |
| | Val | Phe | Leu | Phe | Pro | Pro | Lys | Pro | Lys | Asp | Thr | Leu | Met | Ile | Ser | Arg |
| | 65 | | | | | 70 | | | | | 75 | | | | | 80 |
| | Thr | Pro | Glu | Val | Thr | Cys | Val | Val | Asp | Val | Ser | His | Glu | Asp | Pro |
| | | | | | 85 | | | | | 90 | | | | | 95 | |
| | Glu | Val | Lys | Phe | Asn | Trp | Tyr | Val | Asp | Gly | Val | Glu | Val | His | Asn | Ala |
| | | | | 100 | | | | | 105 | | | | | 110 | | |
| | Lys | Thr | Lys | Pro | Arg | Glu | Glu | Gln | Tyr | Asn | Ser | Thr | Tyr | Arg | Val | Val |
| | | | | 115 | | | | | 120 | | | | | 125 | | |
| | Ser | Val | Leu | Thr | Val | Leu | His | Gln | Asp | Trp | Leu | Asn | Gly | Lys | Glu | Tyr |
| | | | | 130 | | | | | 135 | | | | | 140 | | |
| | Lys | Cys | Lys | Val | Ser | Asn | Lys | Ala | Leu | Pro | Ala | Pro | Ile | Glu | Lys | Thr |
| | 145 | | | | | 150 | | | | | 155 | | | | | 160 |
| | Ile | Ser | Lys | Ala | Lys | Gly | Gln | Pro | Arg | Glu | Pro | Gln | Val | Tyr | Thr | Leu |
| | | | | 165 | | | | | 170 | | | | | 175 | | |
| | Pro | Pro | Ser | Arg | Glu | Glu | Met | Thr | Lys | Asn | Gln | Val | Ser | Leu | Thr | Cys |
| | | | | 180 | | | | | 185 | | | | | 190 | | |
| | Leu | Val | Lys | Gly | Phe | Tyr | Pro | Ser | Asp | Ile | Ala | Val | Glu | Trp | Glu | Ser |
| | | | | 195 | | | | | 200 | | | | | 205 | | |
| | Asn | Gly | Gln | Pro | Glu | Asn | Asn | Tyr | Lys | Thr | Thr | Pro | Pro | Val | Leu | Asp |
| | | | | 210 | | | | | 215 | | | | | 220 | | |
| | Ser | Asp | Gly | Ser | Phe | Phe | Leu | Tyr | Ser | Lys | Leu | Thr | Val | Asp | Lys | Ser |
| | 225 | | | | | 230 | | | | | 235 | | | | | 240 |
| | Arg | Trp | Gln | Gln | Gly | Asn | Val | Phe | Ser | Cys | Ser | Val | Met | His | Glu | Ala |
| | | | | 245 | | | | | 250 | | | | | 255 | | |
| | Leu | His | Asn | His | Tyr | Thr | Gln | Lys | Ser | Leu | Ser | Leu | Ser | Pro | Gly | Lys |
| | | | | 260 | | | | | 265 | | | | | 270 | | |
| | His | His | His | His | His | His |
| | | | | 275 | | | |

```
<210> SEQ ID NO 152
<211> LENGTH: 278
<212> TYPE: PRT
<213> ORGANISM: Homo Sapiens

<400> SEQUENCE: 152
```

| | Ala | Pro | Cys | Ser | Arg | Gly | Ser | Ser | Trp | Ser | Ala | Asp | Leu | Asp | Lys | Cys |
|---|---|---|---|---|---|---|---|---|---|---|---|---|---|---|---|---|
| 1 | | | | | 5 | | | | | 10 | | | | | 15 | |
| | Met | Asp | Cys | Ala | Ser | Cys | Arg | Ala | Arg | Pro | His | Ala | Asp | Phe | Cys | Leu |
| | | | | 20 | | | | | 25 | | | | | 30 | | |
| | Gly | Cys | Ala | Ile | Glu | Gly | Arg | Met | Asp | Pro | Lys | Ser | Cys | Asp | Lys | Thr |
| | | | | 35 | | | | | 40 | | | | | 45 | | |
| | His | Thr | Cys | Pro | Pro | Cys | Pro | Ala | Pro | Glu | Leu | Leu | Gly | Gly | Pro | Ser |
| | | | | 50 | | | | | 55 | | | | | 60 | | |
| | Val | Phe | Leu | Phe | Pro | Pro | Lys | Pro | Lys | Asp | Thr | Leu | Met | Ile | Ser | Arg |
| | 65 | | | | | 70 | | | | | 75 | | | | | 80 |
| | Thr | Pro | Glu | Val | Thr | Cys | Val | Val | Asp | Val | Ser | His | Glu | Asp | Pro |
| | | | | | 85 | | | | | 90 | | | | | 95 | |

```
Glu Val Lys Phe Asn Trp Tyr Val Asp Gly Val Glu Val His Asn Ala
            100                 105                 110
Lys Thr Lys Pro Arg Glu Glu Gln Tyr Asn Ser Thr Tyr Arg Val Val
        115                 120                 125
Ser Val Leu Thr Val Leu His Gln Asp Trp Leu Asn Gly Lys Glu Tyr
    130                 135                 140
Lys Cys Lys Val Ser Asn Lys Ala Leu Pro Ala Pro Ile Glu Lys Thr
145                 150                 155                 160
Ile Ser Lys Ala Lys Gly Gln Pro Arg Glu Pro Gln Val Tyr Thr Leu
                165                 170                 175
Pro Pro Ser Arg Glu Glu Met Thr Lys Asn Gln Val Ser Leu Thr Cys
            180                 185                 190
Leu Val Lys Gly Phe Tyr Pro Ser Asp Ile Ala Val Glu Trp Glu Ser
        195                 200                 205
Asn Gly Gln Pro Glu Asn Asn Tyr Lys Thr Thr Pro Pro Val Leu Asp
    210                 215                 220
Ser Asp Gly Ser Phe Phe Leu Tyr Ser Lys Leu Thr Val Asp Lys Ser
225                 230                 235                 240
Arg Trp Gln Gln Gly Asn Val Phe Ser Cys Ser Val Met His Glu Ala
                245                 250                 255
Leu His Asn His Tyr Thr Gln Lys Ser Leu Ser Leu Ser Pro Gly Lys
            260                 265                 270
His His His His His His
            275

<210> SEQ ID NO 153
<211> LENGTH: 278
<212> TYPE: PRT
<213> ORGANISM: Homo Sapiens

<400> SEQUENCE: 153

Ala Pro Cys Ser Arg Gly Ser Ser Trp Ser Ala Asp Leu Asp Lys Cys
1               5                   10                  15
Met Asp Cys Ala Ser Cys Arg Ala Arg Pro Ala Ser Asp Phe Cys Leu
            20                  25                  30
Gly Cys Ala Ile Glu Gly Arg Met Asp Pro Lys Ser Cys Asp Lys Thr
        35                  40                  45
His Thr Cys Pro Pro Cys Pro Ala Pro Glu Leu Leu Gly Gly Pro Ser
    50                  55                  60
Val Phe Leu Phe Pro Pro Lys Pro Lys Asp Thr Leu Met Ile Ser Arg
65                  70                  75                  80
Thr Pro Glu Val Thr Cys Val Val Asp Val Ser His Glu Asp Pro
            85                  90                  95
Glu Val Lys Phe Asn Trp Tyr Val Asp Gly Val Glu Val His Asn Ala
            100                 105                 110
Lys Thr Lys Pro Arg Glu Glu Gln Tyr Asn Ser Thr Tyr Arg Val Val
        115                 120                 125
Ser Val Leu Thr Val Leu His Gln Asp Trp Leu Asn Gly Lys Glu Tyr
    130                 135                 140
Lys Cys Lys Val Ser Asn Lys Ala Leu Pro Ala Pro Ile Glu Lys Thr
145                 150                 155                 160
Ile Ser Lys Ala Lys Gly Gln Pro Arg Glu Pro Gln Val Tyr Thr Leu
                165                 170                 175
Pro Pro Ser Arg Glu Glu Met Thr Lys Asn Gln Val Ser Leu Thr Cys
            180                 185                 190
```

```
Leu Val Lys Gly Phe Tyr Pro Ser Asp Ile Ala Val Glu Trp Glu Ser
            195                 200                 205

Asn Gly Gln Pro Glu Asn Asn Tyr Lys Thr Thr Pro Pro Val Leu Asp
        210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 154
<211> LENGTH: 278
<212> TYPE: PRT
<213> ORGANISM: Homo Sapiens

<400> SEQUENCE: 154

Ala Pro Cys Ser Arg Gly Ser Ser Trp Ser Ala Asp Leu Asp Lys Cys
1               5                   10                  15

Met Asp Cys Ala Ser Cys Arg Ala Arg Ala His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
```

<210> SEQ ID NO 155
<211> LENGTH: 278
<212> TYPE: PRT
<213> ORGANISM: Homo Sapiens

<400> SEQUENCE: 155

```
Ala Pro Cys Ser Arg Gly Ser Ser Trp Ser Ala Asp Leu Asp Lys Cys
1               5                   10                  15
Met Asp Cys Ala Ser Cys Arg Ala Ala Pro His Ser Asp Phe Cys Leu
            20                  25                  30
Gly Cys Ala Ile Glu Gly Arg Met Asp Pro Lys Ser Cys Asp Lys Thr
        35                  40                  45
His Thr Cys Pro Pro Cys Pro Ala Pro Glu Leu Leu Gly Gly Pro Ser
    50                  55                  60
Val Phe Leu Phe Pro Pro Lys Pro Lys Asp Thr Leu Met Ile Ser Arg
65                  70                  75                  80
Thr Pro Glu Val Thr Cys Val Val Val Asp Val Ser His Glu Asp Pro
                85                  90                  95
Glu Val Lys Phe Asn Trp Tyr Val Asp Gly Val Glu Val His Asn Ala
            100                 105                 110
Lys Thr Lys Pro Arg Glu Glu Gln Tyr Asn Ser Thr Tyr Arg Val Val
        115                 120                 125
Ser Val Leu Thr Val Leu His Gln Asp Trp Leu Asn Gly Lys Glu Tyr
    130                 135                 140
Lys Cys Lys Val Ser Asn Lys Ala Leu Pro Ala Pro Ile Glu Lys Thr
145                 150                 155                 160
Ile Ser Lys Ala Lys Gly Gln Pro Arg Glu Pro Gln Val Tyr Thr Leu
                165                 170                 175
Pro Pro Ser Arg Glu Glu Met Thr Lys Asn Gln Val Ser Leu Thr Cys
            180                 185                 190
Leu Val Lys Gly Phe Tyr Pro Ser Asp Ile Ala Val Glu Trp Glu Ser
        195                 200                 205
Asn Gly Gln Pro Glu Asn Asn Tyr Lys Thr Thr Pro Pro Val Leu Asp
    210                 215                 220
Ser Asp Gly Ser Phe Phe Leu Tyr Ser Lys Leu Thr Val Asp Lys Ser
225                 230                 235                 240
Arg Trp Gln Gln Gly Asn Val Phe Ser Cys Ser Val Met His Glu Ala
                245                 250                 255
Leu His Asn His Tyr Thr Gln Lys Ser Leu Ser Leu Ser Pro Gly Lys
            260                 265                 270
His His His His His His
        275
```

<210> SEQ ID NO 156
<211> LENGTH: 240
<212> TYPE: PRT
<213> ORGANISM: Homo Sapiens

<400> SEQUENCE: 156

```
Ala Pro Cys Ser Arg Gly Ser Ser Trp Ser Ala Asp Leu Asp Lys Cys
1               5                   10                  15
Met Asp Cys Ala Ser Cys Ala Ala Arg Pro His Ser Asp Phe Cys Leu
            20                  25                  30
Gly Cys Ala Ile Glu Gly Arg Met Asp Pro Lys Ser Cys Asp Lys Thr
```

```
            35                  40                  45
His Thr Cys Pro Pro Cys Pro Ala Pro Glu Leu Leu Gly Gly Pro Ser
 50                  55                  60

Val Phe Leu Phe Pro Pro Lys Pro Lys Asp Thr Leu Met Ile Ser Arg
 65                  70                  75                  80

Thr Pro Glu Val Thr Cys Val Val Val Asp Val Ser His Glu Asp Pro
                 85                  90                  95

Glu Val Lys Phe Asn Trp Tyr Val Asp Gly Val Glu Val His Asn Ala
                100                 105                 110

Lys Thr Lys Pro Arg Glu Glu Gln Tyr Asn Ser Thr Tyr Arg Val Val
            115                 120                 125

Ser Val Leu Thr Val Leu His Gln Asp Trp Leu Asn Gly Lys Glu Tyr
        130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240
```

<210> SEQ ID NO 157
<211> LENGTH: 278
<212> TYPE: PRT
<213> ORGANISM: Homo Sapiens

<400> SEQUENCE: 157

```
Ala Pro Cys Ser Arg Gly Ser Ser Trp Ser Ala Asp Leu Asp Lys Cys
 1                   5                  10                  15

Met Asp Cys Ala Ala Cys Arg Ala Arg Pro His Ser Asp Phe Cys Leu
                 20                  25                  30

Gly Cys Ala Ile Glu Gly Arg Met Asp Pro Lys Ser Cys Asp Lys Thr
            35                  40                  45

His Thr Cys Pro Pro Cys Pro Ala Pro Glu Leu Leu Gly Gly Pro Ser
 50                  55                  60

Val Phe Leu Phe Pro Pro Lys Pro Lys Asp Thr Leu Met Ile Ser Arg
 65                  70                  75                  80

Thr Pro Glu Val Thr Cys Val Val Val Asp Val Ser His Glu Asp Pro
                 85                  90                  95

Glu Val Lys Phe Asn Trp Tyr Val Asp Gly Val Glu Val His Asn Ala
                100                 105                 110

Lys Thr Lys Pro Arg Glu Glu Gln Tyr Asn Ser Thr Tyr Arg Val Val
            115                 120                 125

Ser Val Leu Thr Val Leu His Gln Asp Trp Leu Asn Gly Lys Glu Tyr
        130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175
```

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
        210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
            275

<210> SEQ ID NO 158
<211> LENGTH: 278
<212> TYPE: PRT
<213> ORGANISM: Homo Sapiens

<400> SEQUENCE: 158

Ala Pro Cys Ser Arg Gly Ser Ser Trp Ser Ala Asp Leu Asp Lys Cys
1               5                   10                  15

Met Ala Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
        210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 159
<211> LENGTH: 278
<212> TYPE: PRT
<213> ORGANISM: Homo Sapiens

<400> SEQUENCE: 159

Ala Pro Cys Ser Arg Gly Ser Ser Trp Ser Ala Asp Leu Asp Ala Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 160
<211> LENGTH: 278
<212> TYPE: PRT
<213> ORGANISM: Homo Sapiens

<400> SEQUENCE: 160

Ala Pro Cys Ser Arg Gly Ser Ser Trp Ser Ala Asp Leu Ala Lys Cys
1               5                   10                  15

Met Asp Cys Ala Ser Cys Arg Ala Arg Pro His Ser Asp Phe Cys Leu
            20                  25                  30

```
Gly Cys Ala Ile Glu Gly Arg Met Asp Pro Lys Ser Cys Asp Lys Thr
            35                  40                  45

His Thr Cys Pro Pro Cys Pro Ala Pro Glu Leu Leu Gly Gly Pro Ser
        50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 161
<211> LENGTH: 278
<212> TYPE: PRT
<213> ORGANISM: Homo Sapiens

<400> SEQUENCE: 161

Ala Pro Cys Ser Arg Gly Ser Ser Trp Ser Ala Leu Asp Lys Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
            35                  40                  45

His Thr Cys Pro Pro Cys Pro Ala Pro Glu Leu Leu Gly Gly Pro Ser
        50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
```

```
            115                 120                 125
Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
            275

<210> SEQ ID NO 162
<211> LENGTH: 278
<212> TYPE: PRT
<213> ORGANISM: Homo Sapiens

<400> SEQUENCE: 162

Ala Pro Cys Ser Arg Gly Ser Ser Trp Ala Ala Asp Leu Asp Lys Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205
```

```
Asn Gly Gln Pro Glu Asn Asn Tyr Lys Thr Thr Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
                260                 265                 270

His His His His His His
            275
```

<210> SEQ ID NO 163
<211> LENGTH: 278
<212> TYPE: PRT
<213> ORGANISM: Homo Sapiens

<400> SEQUENCE: 163

```
Ala Pro Cys Ser Arg Gly Ser Ser Ala Ser Ala Asp Leu Asp Lys Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
            35                  40                  45

His Thr Cys Pro Pro Cys Pro Ala Pro Glu Leu Leu Gly Gly Pro Ser
        50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
                260                 265                 270

His His His His His His
            275
```

<210> SEQ ID NO 164

```
<211> LENGTH: 278
<212> TYPE: PRT
<213> ORGANISM: Homo Sapiens

<400> SEQUENCE: 164

Ala Pro Cys Ser Arg Gly Ser Ala Trp Ser Ala Asp Leu Asp Lys Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 165
<211> LENGTH: 278
<212> TYPE: PRT
<213> ORGANISM: Homo Sapiens

<400> SEQUENCE: 165

Ala Pro Cys Ser Arg Gly Ala Ser Trp Ser Ala Asp Leu Asp Lys Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
        35                  40                  45

His Thr Cys Pro Pro Cys Pro Ala Pro Glu Leu Leu Gly Gly Pro Ser
    50                  55                  60
```

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
            85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
            115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
            165                 170                 175

Pro Pro Ser Arg Glu Glu Met Thr Lys Asn Gln Val Ser Leu Thr Cys
            180                 185                 190

Leu Val Lys Gly Phe Tyr Pro Ser Asp Ile Ala Val Glu Trp Glu Ser
    195                 200                 205

Asn Gly Gln Pro Glu Asn Asn Tyr Lys Thr Thr Pro Pro Val Leu Asp
210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
            245                 250                 255

Leu His Asn His Tyr Thr Gln Lys Ser Leu Ser Leu Ser Pro Gly Lys
            260                 265                 270

His His His His His His
        275

<210> SEQ ID NO 166
<211> LENGTH: 278
<212> TYPE: PRT
<213> ORGANISM: Homo Sapiens

<400> SEQUENCE: 166

Ala Pro Cys Ser Ala Gly Ser Ser Trp Ser Ala Asp Leu Asp Lys Cys
1               5                   10                  15

Met Asp Cys Ala Ser Cys Arg Ala Arg Pro His Ser Asp Phe Cys Leu
            20                  25                  30

Gly Cys Ala Ile Glu Gly Arg Met Asp Pro Lys Ser Cys Asp Lys Thr
            35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
            85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
            115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr

```
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
                180                 185                 190

Leu Val Lys Gly Phe Tyr Pro Ser Asp Ile Ala Val Glu Trp Glu Ser
                195                 200                 205

Asn Gly Gln Pro Glu Asn Asn Tyr Lys Thr Thr Pro Pro Val Leu Asp
                210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
                260                 265                 270

His His His His His His
                275

<210> SEQ ID NO 167
<211> LENGTH: 278
<212> TYPE: PRT
<213> ORGANISM: Homo Sapiens

<400> SEQUENCE: 167

Ala Pro Cys Ala Arg Gly Ser Ser Trp Ser Ala Asp Leu Asp Lys Cys
1               5                   10                  15

Met Asp Cys Ala Ser Cys Arg Ala Arg Pro His Ser Asp Phe Cys Leu
                20                  25                  30

Gly Cys Ala Ile Glu Gly Arg Met Asp Pro Lys Ser Cys Asp Lys Thr
                35                  40                  45

His Thr Cys Pro Pro Cys Pro Ala Pro Glu Leu Leu Gly Gly Pro Ser
                50                  55                  60

Val Phe Leu Phe Pro Pro Lys Pro Lys Asp Thr Leu Met Ile Ser Arg
65              70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
                100                 105                 110

Lys Thr Lys Pro Arg Glu Glu Gln Tyr Asn Ser Thr Tyr Arg Val Val
                115                 120                 125

Ser Val Leu Thr Val Leu His Gln Asp Trp Leu Asn Gly Lys Glu Tyr
                130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Glu Glu Met Thr Lys Asn Gln Val Ser Leu Thr Cys
                180                 185                 190

Leu Val Lys Gly Phe Tyr Pro Ser Asp Ile Ala Val Glu Trp Glu Ser
                195                 200                 205

Asn Gly Gln Pro Glu Asn Asn Tyr Lys Thr Thr Pro Pro Val Leu Asp
                210                 215                 220

Ser Asp Gly Ser Phe Phe Leu Tyr Ser Lys Leu Thr Val Asp Lys Ser
225                 230                 235                 240
```

```
Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

His His His His His His
        275

<210> SEQ ID NO 168
<211> LENGTH: 53
<212> TYPE: PRT
<213> ORGANISM: Homo Sapiens

<400> SEQUENCE: 168

Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Pro Pro Ala Pro Phe
        35                  40                  45

Arg Leu Leu Trp Pro
    50

<210> SEQ ID NO 169
<211> LENGTH: 129
<212> TYPE: PRT
<213> ORGANISM: Homo Sapiens

<400> SEQUENCE: 169

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
    50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Arg Glu Lys Phe Thr Thr
            100                 105                 110

Pro Ile Glu Glu Thr Gly Gly Glu Gly Cys Pro Ala Val Ala Leu Ile
        115                 120                 125

Gln

<210> SEQ ID NO 170
<211> LENGTH: 959
<212> TYPE: DNA
<213> ORGANISM: Homo Sapiens

<400> SEQUENCE: 170
atggctcggg gctcgctgcg ccggttgctg cggctcctcg tgctggggct ctggctggcg    60
ttgctgcgct ccgtggccgg ggagcaagcg ccaggcaccg cccctgctc  ccgcggcagc   120 tcctggagcg cggacctgga caagtgcatg gactgcgcgt cttgcagggc gcgaccgcac   180
agcgacttct gcctgggctg cgctgcagca cctcctgccc ccttccggct gctttggccc   240
```

-continued

```
atccttgggg gcgctctgag cctgaccttc gtgctggggc tgctttctgg cttttttggtc      300 tggagacgat gccgcaggag agagaagttc accaccccca tagaggagac cggcggagag      360
ggctgcccag ctgtggcgct gatccagtga caatgtgccc cctgccagcc ggggctcgcc      420
cactcatcat tcattcatcc attctagagc cagtctctgc ctcccagacg cggcgggagc      480
caagctcctc caaccacaag gggggtgggg ggcggtgaat cacctctgag gcctgggccc      540
agggttcagg ggaaccttcc aaggtgtctg gttgccctgc ctctggctcc agaacagaaa      600
gggagcctca cgctggctca cacaaaacag ctgacactga ctaaggaact gcagcatttg      660
cacaggggag gggggtgccc tccttcctta ggacctgggg gccaggctga cttgggggc       720 agacttgaca ctaggcccca ctcactcaga tgtcctgaaa ttccaccacg ggggtcaccc      780 tgggggggtta gggacctatt tttaacacta ggggctggcc cactaggagg gctgccccta     840
agatacagac ccccccaact ccccaaagcg gggaggagat atttattttg gggagagttt      900
ggaggggagg gagaatttat taataaaaga atctttaact ttaaaaaaaa aaaaaaaa       959
```

<210> SEQ ID NO 171
<211> LENGTH: 5
<212> TYPE: PRT
<213> ORGANISM: Homo Sapiens
<220> FEATURE:
<221> NAME/KEY: VARIANT
<222> LOCATION: 5..5
<223> OTHER INFORMATION: Xaa = Ile or Met

<400> SEQUENCE: 171

Pro Tyr Pro Met Xaa
1               5

<210> SEQ ID NO 172
<211> LENGTH: 17
<212> TYPE: PRT
<213> ORGANISM: Homo Sapiens
<220> FEATURE:
<221> NAME/KEY: VARIANT
<222> LOCATION: 8..8
<223> OTHER INFORMATION: Xaa = ser or Lys

<400> SEQUENCE: 172

Tyr Ile Ser Pro Ser Gly Gly Xaa Thr His Tyr Ala Asp Ser Val Lys
1               5                   10                  15
Gly

<210> SEQ ID NO 173
<211> LENGTH: 11
<212> TYPE: PRT
<213> ORGANISM: Homo Sapiens

<400> SEQUENCE: 173

Gly Gly Asp Thr Tyr Phe Asp Tyr Phe Asp Tyr
1               5                   10

<210> SEQ ID NO 174
<211> LENGTH: 11
<212> TYPE: PRT
<213> ORGANISM: Homo Sapiens
<220> FEATURE:
<221> NAME/KEY: VARIANT
<222> LOCATION: 8..8
<223> OTHER INFORMATION: Xaa = Gly or Ser

<400> SEQUENCE: 174

-continued

Arg Ala Ser Gln Ser Ile Ser Xaa Tyr Leu Asn
1               5                   10

<210> SEQ ID NO 175
<211> LENGTH: 7
<212> TYPE: PRT
<213> ORGANISM: Homo Sapiens
<220> FEATURE:
<221> NAME/KEY: VARIANT
<222> LOCATION: 1..1
<223> OTHER INFORMATION: Xaa = Gln, Ala or Asn

<400> SEQUENCE: 175

Xaa Ala Ser Ser Leu Gln Ser
1               5

<210> SEQ ID NO 176
<211> LENGTH: 10
<212> TYPE: PRT
<213> ORGANISM: Homo Sapiens
<220> FEATURE:
<221> NAME/KEY: VARIANT
<222> LOCATION: 5..6
<223> OTHER INFORMATION: Xaa = Thr or Ser
<220> FEATURE:
<221> NAME/KEY: VARIANT
<222> LOCATION: 8..8
<223> OTHER INFORMATION: Xaa = Gly or Phe

<400> SEQUENCE: 176

Gln Gln Ser Tyr Xaa Xaa Pro Xaa Ile Thr
1               5                   10

<210> SEQ ID NO 177
<211> LENGTH: 645
<212> TYPE: DNA
<213> ORGANISM: Homo Sapiens

<400> SEQUENCE: 177
gacatccaga tgacccagag ccccagcagc ctgagcgcct ccgtgggcga cagagtgacc        60
atcacctgtc gggccagcca gagcatcagc ggctacctga actggtatca gcagaagccc       120
ggcaaggccc ccaagctgct gatctaccag gccagctccc tgcagagcgg cgtgccaagc       180
agattcagcg gcagcggctc cggcaccgac ttcaccctga ccatcagcag cctgcagccc       240
gaggacttcg ccacctacta ctgccagcag agctacacca cccccttcat cacccttcggc      300 cagggcacca aggtggaaat caagcggacc gtggccgctc ccagcgtgtt catcttccca       360
cccagcgacg agcagctgaa gtccggcaca gccagcgtgg tctgcctgct gaacaacttc       420 taccccgcg aggccaaggt gcagtggaag gtggacaacg ccctgcagtc cggcaactcc        480
caggaaagcg tgaccgagca ggacagcaag gactccacct acagcctgag cagcaccctg       540
accctgagca aggccgacta cgagaagcac aaggtgtacg cctgcgaagt gacccaccag       600
ggcctgtcca gccccgtgac caagagcttc aaccggggcg agtgc                       645

<210> SEQ ID NO 178
<211> LENGTH: 1347
<212> TYPE: DNA
<213> ORGANISM: Homo Sapiens

<400> SEQUENCE: 178
gaagttcaat tgttagagtc cggcggaggc ctggtgcagc ctggcggcag cctgagactg        60
tcttgcgccg ccagcggctt cacattcagc ccctaccccca tgatctgggt ccgccaggct      120

| | |
|---|---|
| ccaggcaagg gcctggaatg ggtgtcctac atcagcccca gcggcggcag cacccactac | 180 |
| gccgatagcg tgaagggccg gttcaccatc agccgggaca cagcaagaa cccctgtac | 240 |
| ctgcagatga acagcctgcg ggccgaggac accgccgtgt actattgcgc cagaggcggc | 300 |
| gacacctact tcgattactt cgactactgg ggccagggca ccctggtgac agtgtccagc | 360 |
| gcctccacca agggcccatc ggtcttcccg ctagcaccca gcagcaagag caccagcggc | 420 |
| ggaacagccg ccctgggctg cctggtgaaa gactacttcc ccgagcccgt gaccgtgtcc | 480 |
| tggaactctg gcgccctgac cagcggagtg cataccttcc ccgccgtgct gcagagcagc | 540 |
| ggcctgtaca gcctgagcag cgtggtgaca gtgcccagca gcagcctggg aacccagacc | 600 |
| tacatctgca acgtgaacca caagcccagc aacaccaagg tggacaagaa ggtggaaccc | 660 |
| aagagctgcg acaagaccca cacctgtccc cctgccctg ccctgaact gctgggcgga | 720 |
| cccagcgtgt tcctgttccc cccaaagccc aaggacaccc tgatgatcag ccggacccc | 780 |
| gaagtgacct gcgtggtggt ggacgtgtcc cacgaggacc cagaagtgaa gtttaattgg | 840 |
| tacgtggacg gcgtggaagt gcataacgcc aagaccaagc ccgagagga acagtacaac | 900 |
| agcaccctacc gggtggtgtc cgtgctgacc gtgctgcacc aggactggct gaacggcaaa | 960 |
| gagtacaagt gcaaggtctc caacaaggcc ctgcctgccc ccatcgagaa aaccatcagc | 1020 |
| aaggccaagg gccagccccg cgagcctcag gtgtacacac tgcccccag ccgggatgag | 1080 |
| ctgaccaaga accaggtgtc cctgacctgt ctggtgaaag gcttctaccc cagcgatatc | 1140 |
| gccgtggaat gggagagcaa cggccagccc gagaacaatt acaagaccac cccccctgtg | 1200 |
| ctggacagcg acggctcatt cttcctgtac tccaagctga ccgtggacaa gagccggtgg | 1260 |
| cagcagggca acgtgttcag ctgcagcgtg atgcacgagg ccctgcacaa tcactacacc | 1320 |
| cagaagtccc tgagcctgag ccccggc | 1347 |

<210> SEQ ID NO 179
<211> LENGTH: 645
<212> TYPE: DNA
<213> ORGANISM: Homo Sapiens

<400> SEQUENCE: 179

| | |
|---|---|
| gacatccaga tgacccagtc tccagccacc ctgtctgcat ctgtaggaga cagagtcacc | 60 |
| atcacttgcc gggcaagtca gagcattagc ggctatttaa attggtatca gcagaaacca | 120 |
| gggaaagccc ctaagctcct gatctatcag gcatccagtt tgcaaagtgg ggtcccatca | 180 |
| aggttcagtg gcagtggatc tgggacagat ttcactctca ccatcagcag tctgcaacct | 240 |
| gaagattttg caacttacta ctgtcaacag agctacacta gtccattcat cactttcggc | 300 |
| cctgggacca aggtggagat caaacgaact gtggctgcac catctgtctt catcttcccg | 360 |
| ccatctgatg agcagttgaa atctggaact gcctctgttg tgtgcctgct gaataacttc | 420 |
| tatcccagag aggccaaagt acagtggaag gtggataacg ccctccaatc gggtaactcc | 480 |
| caggagagtg tcacagagca ggacagcaag gacagcacct acagcctcag cagcaccctg | 540 |
| acgctgagca aagcagacta cgagaaacac aaactctacg cctgcgaagt cacccatcag | 600 |
| ggcctgagct cgcccgtcac aaagagcttc aacaggggag agtgt | 645 |

<210> SEQ ID NO 180
<211> LENGTH: 1347
<212> TYPE: DNA
<213> ORGANISM: Homo Sapiens

<400> SEQUENCE: 180

```
gaagttcaat tgttagagtc tggtggcggt cttgttcagc ctggtggttc tttacgtctt      60
tcttgcgctg cttccggatt cactttctct ccttaccgta tgatctgggt tcgccaagct     120
cctggtaaag gtttggagtg ggtttcttat atctctcctt ctggtggcaa gactcattat     180
gctgactccg ttaaaggtcg cttcactatc tctagagaca actctaagaa tactctctac     240
ttgcagatga acagcttaag ggctgaggac acggccgtgt attactgtgc gagagggggt     300
gatacttatt tcgactactt tgactactgg ggccagggaa ccctggtcac cgtctcaagc     360
gcctccacca agggcccatc ggtcttcccg ctagcaccca gcagcaagag caccagcggc     420
ggaacagccg ccctgggctg cctggtgaaa gactacttcc ccgagcccgt gaccgtgtcc     480
tggaactctg gcgccctgac cagcggagtg catacctccc ccgccgtgct gcagagcagc     540
ggcctgtaca gcctgagcag cgtggtgaca gtgcccagca gcagcctggg aacccagacc     600
tacatctgca acgtgaacca caagcccagc aacaccaagg tggacaagaa ggtggaaccc     660
aagagctgcg acaagaccca cacctgtccc cctgccctg ccctgaact gctgggcgga     720 cccagcgtgt tcctgttccc cccaaagccc aaggacaccc tgatgatcag ccggaccccc     780
gaagtgacct gcgtggtggt ggacgtgtcc cacgaggacc cagaagtgaa gtttaattgg     840
tacgtggacg gcgtggaagt gcataacgcc aagaccaagc cagagaggga acagtacaac     900
agcacctacc gggtggtgtc cgtgctgacc gtgctgcacc aggactggct gaacggcaaa     960
gagtacaagt gcaaggtctc caacaaggcc ctgcctgccc catcgagaa aaccatcagc    1020 aaggccaagg gccagccccg cgagcctcag gtgtacacac tgcccccag ccgggatgag    1080 ctgaccaaga accaggtgtc cctgacctgt ctggtgaaag gcttctaccc cagcgatatc    1140
gccgtggaat gggagagcaa cggccagccc gagaacaatt acaagaccac cccccctgtg    1200
ctggacagcg acggctcatt cttcctgtac tccaagctga ccgtggacaa gagccggtgg    1260
cagcagggca acgtgttcag ctgcagcgtg atgcacgagg ccctgcacaa tcactacacc    1320
cagaagtccc tgagcctgag ccccggc                                         1347

<210> SEQ ID NO 181
<211> LENGTH: 645
<212> TYPE: DNA
<213> ORGANISM: Homo Sapiens

<400> SEQUENCE: 181
gacatccaga tgacccagag ccccagcagc ctgagcgcct ccgtgggcga cagagtgacc      60
atcacctgtc gggccagcca gagcatcagc agctacctga actggtatca gcagaagccc     120
ggcaaggccc ccaagctgct gatctaccag gccagctccc tgcagagcgg cgtgccaagc     180
agattcagcg gcagcggctc cggcaccgac ttcaccctga ccatcagcag cctgcagccc     240
gaggacttcg ccacctacta ctgccagcag agctacacca gccccttcat caccttcggc     300
cagggcacca aggtggaaat caagcggacc gtggccgctc ccagcgtgtt catcttccca     360
cccagcgacg agcagctgaa gtccggcaca gccagcgtgg tctgcctgct gaacaacttc     420 taccccgcg aggccaaggt gcagtggaag gtggacaacg ccctgcagtc cggcaactcc     480
caggaaagcg tgaccgagca ggacagcaag gactccacct acagcctgag cagcaccctg     540
accctgagca aggccgacta cgagaagcac aaggtgtacg cctgcgaagt gacccaccag     600
ggcctgtcca gccccgtgac caagagcttc aaccggggcg agtgc                    645

<210> SEQ ID NO 182
```

```
<211> LENGTH: 1347
<212> TYPE: DNA
<213> ORGANISM: Homo Sapiens

<400> SEQUENCE: 182
gaagttcaat tgttagagtc cggcggaggc ctggtgcagc ctggcggcag cctgagactg        60
tcttgcgccg ccagcggctt cacattcagc ccctacccca tgatgtgggt ccgccaggct       120
ccaggcaagg gcctggaatg ggtgtcctac atcagcccca gcggcggcag cacccactac       180
gccgatagcg tgaagggccg gttcaccatc agccgggaca acagcaagaa cacactgtac       240
ctgcagatga acagcctgcg ggccgaggac accgccgtgt actattgcgc cagaggcggc       300
gacacctact cgattactt cgactactgg ggccagggca ccctggtgac agtgtccagc        360
gcctccacca agggcccatc ggtcttcccg ctagcaccca gcagcaagag caccagcggc       420
ggaacagccg ccctgggctg cctggtgaaa gactacttcc ccgagcccgt gaccgtgtcc       480
tggaactctg gcgccctgac cagcggagtg catacctttcc ccgccgtgct gcagagcagc      540
ggcctgtaca gcctgagcag cgtggtgaca gtgcccagca gcctgggg aacccagacc        600 tacatctgca acgtgaacca caagcccagc aacaccaagg tggacaagaa ggtggaaccc       660
aagagctgcg acaagaccca cacctgtccc cctgccctg ccctgaact gctgggcgga         720 cccagcgtgt tcctgttccc cccaaagccc aaggacaccc tgatgatcag ccggaccccc       780
gaagtgacct gcgtggtggt ggacgtgtcc cacgaggacc cagaagtgaa gtttaattgg       840
tacgtggacg gcgtggaagt gcataacgcc aagaccaagc cagagagga acagtacaac       900 agcacctacc gggtggtgtc cgtgctgacc gtgctgcacc aggactggct gaacggcaaa       960
gagtacaagt gcaaggtctc caacaaggcc ctgcctgccc ccatcgagaa aaccatcagc      1020
aaggccaagg gccagcccg cgagcctcag gtgtacacac tgccccccag ccgggatgag      1080
ctgaccaaga accaggtgtc cctgacctgt ctggtgaaag gcttctaccc cagcgatatc     1140
gccgtggaat gggagagcaa cggccagccc gagaacaatt acaagaccac ccccctgtg      1200 ctggacagcg acggctcatt cttcctgtac tccaagctga ccgtggacaa gagccggtgg      1260
cagcagggca acgtgttcag ctgcagcgtg atgcacgagg ccctgcacaa tcactacacc      1320
cagaagtccc tgagcctgag ccccggc                                          1347

<210> SEQ ID NO 183
<211> LENGTH: 645
<212> TYPE: DNA
<213> ORGANISM: Homo Sapiens

<400> SEQUENCE: 183
gacatccaga tgacccagtc tccagccacc ctgtctgcat ctgtaggaga cagagtcacc        60
atcacttgcc gggcaagtca gagcattagc agctatttaa attggtatca gcagaaacca       120
gggaaagccc ctaagctcct gatctatcag gcatccagtt tgcaaagtgg ggtcccatca       180
aggttcagtg gcagtggatc tgggacagat ttcactctca ccatcagcag tctgcaacct       240
gaagattttg caacttacta ctgtcaacag agctacacta gtccattcat cactttcggc       300
cctgggacca aggtggagat caaacgaact gtggctgcac catctgtctt catcttcccg       360
ccatctgatg agcagttgaa atctggaact gcctctgttg tgtgcctgct gaataacttc       420
tatcccagag aggccaaagt acagtggaag gtggataacg cctccaatc gggtaactcc       480 caggagagtg tcacagagca ggacagcaag gacagcacct acagcctcag cagcaccctg       540
acgctgagca aagcagacta cgagaaacac aaactctacg cctgcgaagt cacccatcag       600
```

```
ggcctgagct cgcccgtcac aaagagcttc aacaggggag agtgt           645
```

<210> SEQ ID NO 184
<211> LENGTH: 1347
<212> TYPE: DNA
<213> ORGANISM: Homo Sapiens

<400> SEQUENCE: 184

```
gaagttcaat tgttagagtc tggtggcggt cttgttcagc ctggtggttc tttacgtctt    60
tcttgcgctg cttccggatt cactttctct ccttacccta tgatgtgggt tcgccaagct   120
cctggtaaag gtttggagtg ggtttcttat atctctcctt ctggtggcaa gactcattat   180
gctgactccg ttaaaggtcg cttcactatc tctagagaca actctaagaa tactctctac   240
ttgcagatga acagcttaag ggctgaggac acggccgtgt attactgtgc gagaggggt    300
gatacttatt tcgactactt tgactactgg ggccagggaa ccctggtcac cgtctcaagc   360
gcctccacca agggcccatc ggtcttcccg ctagcaccca gcagcaagag caccagcggc   420
ggaacagccg ccctgggctg cctggtgaaa gactacttcc ccgagccgt gaccgtgtcc    480
tggaactctg gcgccctgac cagcggagtg cataccttcc ccgccgtgct gcagagcagc   540
ggcctgtaca gcctgagcag cgtggtgaca gtgcccagca gcagcctggg aacccagacc   600
tacatctgca acgtgaacca caagcccagc aacaccaagg tggacaagaa ggtggaaccc   660
aagagctgcg acaagaccca cacctgtccc cctgccctg cccctgaact gctgggcgga   720
cccagcgtgt tcctgttccc cccaaagccc aaggacaccc tgatgatcag ccggaccccc   780
gaagtgacct gcgtggtggt ggacgtgtcc cacgaggacc cagaagtgaa gtttaattgg   840
tacgtggacg gcgtggaagt gcataacgcc aagaccaagc ccagagagga acagtacaac   900
agcacctacc gggtggtgtc cgtgctgacc gtgctgcacc aggactggct gaacggcaaa   960
gagtacaagt gcaaggtctc caacaaggcc ctgcctgccc catcgagaa aaccatcagc    1020
aaggccaagg gccagccccg cgagcctcag gtgtacacac tgcccccag ccgggatgag   1080
ctgaccaaga accaggtgtc cctgacctgt ctggtgaaag gcttctaccc cagcgatatc   1140
gccgtggaat gggagagcaa cggccagccc gagaacaatt acaagaccac ccccctgtg    1200
ctggacagcg acggctcatt cttcctgtac tccaagctga ccgtggacaa gagccggtgg   1260
cagcagggca acgtgttcag ctgcagcgtg atgcacgagg ccctgcacaa tcactacacc   1320
cagaagtccc tgagcctgag ccccggc                                       1347
```

<210> SEQ ID NO 185
<211> LENGTH: 645
<212> TYPE: DNA
<213> ORGANISM: Homo Sapiens

<400> SEQUENCE: 185

```
gacatccaga tgacccagag ccccagcagc ctgtctgcca gcgtgggcga cagagtgacc    60
atcacctgta gagccagcca gagcatcagc agctacctga actggtatca gcagaagccc   120
ggcaaggccc ccaagctgct gatctatgcc gccagctctc tgcagagcgg agtgcccagc   180
agattttctg gcagcggcag cggcaccgac ttcaccctga caatcagcag cctgcagccc   240
gaggacttcg ccacctacta ctgccagcag agctacagca ccccggcat cacatttggc   300
cagggcacca aggtggaaat caagcggaca gtggccgctc ccagcgtgtt catcttccca   360
cctagcgacg agcagctgaa gtccggcaca gccagcgtcg tgtgcctgct gaacaacttc   420
```

```
taccccgcg aggccaaggt gcagtggaag gtggacaatg ccctgcagtc cggcaactcc    480
caggaaagcg tcaccgagca ggacagcaag gactccacct acagcctgag cagcaccctg    540
accctgagca aggccgacta cgagaagcac aaggtgtacg cctgcgaagt gacccaccag    600
ggcctgtcta gccccgtgac caagagcttc aaccggggcg agtgt                    645
```

<210> SEQ ID NO 186
<211> LENGTH: 1347
<212> TYPE: DNA
<213> ORGANISM: Homo Sapiens

<400> SEQUENCE: 186

```
gaagttcaat tgttagagtc cggcggaggc ctggtgcagc ctggcggatc tctgagactg     60
agctgtgccg ccagcggctt caccttcagc ccctacccta tgatgtgggt ccgacaggcc    120
cctggcaagg gactggaatg ggtgtcctac atctctccca gcggcggcag cacccactac    180
gccgattctg tgaagggccg gttcaccatc agccgggaca cagcaagaa caccctgtac    240 ctgcagatga acagcctgcg ggccgaggac accgccgtgt actattgtgc cagaggcggc    300
gacacctact cgattactt cgactactgg ggccagggca ccctggtcac cgtgtcatct    360
gcctccacca agggcccatc ggtcttcccg ctagcaccca gcagcaagag caccagcggc    420
ggaacagccg ccctgggctg cctggtgaaa gactacttcc ccgagcccgt gaccgtgtcc    480
tggaactctg gcgccctgac cagcggagtg cataccttcc ccgccgtgct gcagagcagc    540
ggcctgtaca gcctgagcag cgtggtgaca gtgcccagca gcagcctggg aacccagacc    600
tacatctgca acgtgaacca caagcccagc aacaccaagg tggacaagaa ggtggaaccc    660
aagagctgcg acaagaccca cacctgtccc ccctgccctg ccctgaact gctgggcgga    720 cccagcgtgt tcctgttccc cccaaagccc aaggacaccc tgatgatcag ccggaccccc    780
gaagtgacct gcgtggtggt ggacgtgtcc cacgaggacc cagaagtgaa gtttaattgg    840
tacgtggacg gcgtggaagt gcataacgcc aagaccaagc ccagagagga acagtacaac    900
agcacctacc gggtggtgtc cgtgctgacc gtgctgcacc aggactggct gaacggcaaa    960
gagtacaagt gcaaggtctc caacaaggcc ctgcctgccc catcgagaa aaccatcagc   1020 aaggccaagg gccagccccg cgagcctcag gtgtacacac tgcccccag ccgggatgag   1080 ctgaccaaga accaggtgtc cctgacctgt ctggtgaaag gcttctaccc cagcgatatc   1140
gccgtggaat gggagagcaa cggccagccc gagaacaatt acaagaccac cccccctgtg   1200
ctggacagcg acggctcatt cttcctgtac tccaagctga ccgtggacaa gagccggtgg   1260
cagcagggca acgtgttcag ctgcagcgtg atgcacgagg ccctgcacaa tcactacacc   1320
cagaagtccc tgagcctgag ccccggc                                       1347
```

<210> SEQ ID NO 187
<211> LENGTH: 645
<212> TYPE: DNA
<213> ORGANISM: Homo Sapiens

<400> SEQUENCE: 187

```
gacatccaga tgacccagtc tccagccacc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agctactcta gtccagggat cactttcggc    300
```

```
cctgggacca aggtggagat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag acagcacct acagcctcag cagcaccctg    540
acgctgagca agcagactac gagaaacac aaactctacg cctgcgaagt cacccatcag    600
ggcctgagct cgcccgtcac aaagagcttc aacaggggag agtgt              645

<210> SEQ ID NO 188
<211> LENGTH: 1347
<212> TYPE: DNA
<213> ORGANISM: Homo Sapiens

<400> SEQUENCE: 188
gaagttcaat tgttagagtc tggtggcggt cttgttcagc ctggtggttc tttacgtctt    60
tcttgcgctg cttccggatt cactttctct ccttacccta tgatgtgggt tcgccaagct    120
cctggtaaag gtttggagtg ggtttcttat atctctcctt ctggtggcaa gactcattat    180
gctgactccg ttaaaggtcg cttcactatc tctagagaca actctaagaa tactctctac    240
ttgcagatga acagcttaag ggctgaggac acggccgtgt attactgtgc gagagggggt    300
gatacgtatt tcgactactt tgactactgg ggccagggaa ccctggtcac cgtctcaagc    360
gcctccacca agggcccatc ggtcttcccg ctagcaccca gcagcaagag caccagcggc    420
ggaacagccg ccctgggctg cctggtgaaa gactacttcc ccgagcccgt gaccgtgtcc    480
tggaactctg gcgccctgac cagcggagtg catacctcc ccgccgtgct gcagagcagc    540
ggcctgtaca gcctgagcag cgtggtgaca gtgcccagca gcagcctggg aacccagacc    600
tacatctgca acgtgaacca caagcccagc aacaccaagg tggacaagaa ggtggaaccc    660
aagagctgcg acaagaccca cacctgtccc cctgccctg ccctgaact gctgggcgga    720 cccagcgtgt tcctgttccc cccaaagccc aaggacaccc tgatgatcag ccggaccccc    780
gaagtgacct gcgtggtggt ggacgtgtcc cacgaggacc cagaagtgaa gtttaattgg    840
tacgtggacg gcgtggaagt gcataacgcc aagaccaagc ccagagagga acagtacaac    900
agcacctacc gggtggtgtc cgtgctgacc gtgctgcacc aggactggct gaacggcaaa    960
gagtacaagt gcaaggtctc caacaaggcc ctgcctgccc ccatcgagaa aaccatcagc    1020
aaggccaagg gccagccccg cgagcctcag gtgtacacac tgcccccag ccgggatgag    1080 ctgaccaaga accaggtgtc cctgacctgt ctggtgaaag gcttctaccc cagcgatatc    1140
gccgtggaat gggagagcaa cggccagccc gagaacaatt acaagaccac cccccctgtg    1200
ctggacagcg acggctcatt cttcctgtac tccaagctga ccgtggacaa gagccggtgg    1260
cagcagggca acgtgttcag ctgcagcgtg atgcacgagg ccctgcacaa tcactacacc    1320
cagaagtccc tgagcctgag ccccggc                                      1347

<210> SEQ ID NO 189
<211> LENGTH: 651
<212> TYPE: DNA
<213> ORGANISM: Homo Sapiens

<400> SEQUENCE: 189
gcacaagaca tccagatgac ccagtctcca gccaccctgt ctgcatctgt aggagacaga    60
gtcaccatca cttgccgggc aagtcagagc attagcagct atttaaattg gtatcagcag    120
```

```
aaaccaggga aagcccctaa gctcctgatc tatgctgcat ccagtttgca aagtggggtc      180
ccatcaaggt tcagtggcag tggatctggg acagatttca ctctcaccat cagcagtctg      240
caacctgaag attttgcaac ttactactgt caacagagct actctagtcc agggatcact      300
ttcggccctg ggaccaaggt ggagatcaaa cgaactgtgg ctgcaccatc tgtcttcatc      360
ttcccgccat ctgatgagca gttgaaatct ggaactgcct ctgttgtgtg cctgctgaat      420
aacttctatc ccagagaggc caaagtacag tggaaggtgg ataacgccct ccaatcgggt      480
aactcccagg agagtgtcac agagcaggac agcaaggaca gcacctacag cctcagcagc      540
accctgacgc tgagcaaagc agactacgag aaacacaaac tctacgcctg cgaagtcacc      600
catcagggcc tgagctcgcc cgtcacaaag agcttcaaca ggggagagtg t              651
```

<210> SEQ ID NO 190
<211> LENGTH: 1347
<212> TYPE: DNA
<213> ORGANISM: Homo Sapiens

<400> SEQUENCE: 190

```
gaagttcaat tgttagagtc tggtggcggt cttgttcagc ctggtggttc tttacgtctt      60
tcttgcgctg cttccggatt cactttctct ccttacccta tgatgtgggt tcgccaagct      120
cctggtaaag gttggagtg gtttcttat atctctcctt ctggtggcaa gactcattat      180
gctgactccg ttaaaggtcg cttcactatc tctagagaca actctaagaa tactctctac      240
ttgcagatga acagcttaag ggctgaggac acggccgtgt attactgtgc gagaggggt      300 gatacgtatt tcgactactt tgactactgg ggccagggaa ccctggtcac cgtctcaagc      360
gcctccacca agggcccatc ggtcttcccg ctagcaccca gcagcaagag caccagcggc      420
ggaacagccg ccctgggctg cctggtgaaa gactacttcc ccgagccgt gaccgtgtcc      480 tggaactctg gcgccctgac cagcggagtg cataccttcc ccgccgtgct gcagagcagc      540
ggcctgtaca gcctgagcag cgtggtgaca gtgcccagca gcagcctggg aacccagacc      600
tacatctgca acgtgaacca caagcccagc aacaccaagg tggacaagcg ggtggaaccc      660
aagagctgcg acaagaccca cacctgtccc ccctgccctg ccctgaact gctgggcgga      720 cccagcgtgt tcctgttccc cccaaagccc aaggacaccc tgatgatcag ccggacccc      780 gaagtgacct gcgtggtggt ggacgtgtcc cacgaggacc cagaagtgaa gtttaattgg     840
tacgtggacg gcgtggaagt gcataacgcc aagaccaagc ccagagagga acagtacaac      900
agcacctacc gggtggtgtc cgtgctgacc gtgctgcacc aggactggct gaacggcaaa      960
gagtacaagt gcaaggtctc caacaaggcc ctgcctgccc ccatcgagaa aaccatcagc     1020
aaggccaagg gccagccccg cgagcctcag gtgtacacac tgcccccag ccgggaagag     1080 atgaccaaga accaggtgtc cctgacctgt ctggtgaaag gcttctaccc cagcgatatc     1140
gccgtggaat gggagagcaa cggccagccc gagaacaatt acaagaccac cccccctgtg     1200
ctggacagcg acggctcatt cttcctgtac tccaagctga ccgtggacaa gagccggtgg     1260
cagcagggca acgtgttcag ctgcagcgtg atgcacgagg ccctgcacaa tcactacacc     1320
cagaagtccc tgagcctgag ccccggc                                         1347
```

<210> SEQ ID NO 191
<211> LENGTH: 651
<212> TYPE: DNA
<213> ORGANISM: Homo Sapiens

<400> SEQUENCE: 191

```
gcacaagaca tccagatgac ccagtctcca gccaccctgt ctgcatctgt aggagacaga      60
gtcaccatca cttgccgggc aagtcagagc attagcagct atttaaattg gtatcagcag     120
aaaccaggga aagcccctaa gctcctgatc tatgctgcat ccagtttgca aagtggggtc     180
ccatcaaggt tcagtggcag tggatctggg acagatttca ctctcaccat cagcagtctg     240
caacctgaag attttgcaac ttactactgt caacagagct actctagtcc agggatcact     300
ttcggccctg ggaccaaggt ggagatcaaa cgaactgtgg ctgcaccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaac tctacgcctg cgaagtcacc     600
catcagggcc tgagctcgcc cgtcacaaag agcttcaaca ggggagagtg t              651
```

```
<210> SEQ ID NO 192
<211> LENGTH: 1347
<212> TYPE: DNA
<213> ORGANISM: Homo Sapiens

<400> SEQUENCE: 192
gaagttcaat tgttagagtc tggtggcggt cttgttcagc ctggtggttc tttacgtctt      60
tcttgcgctg cttccggatt cactttctct ccttacccta tgatgtgggt tcgccaagct     120
cctggtaaag gtttggagtg gtttctttat atctctcctt ctggtggcaa gactcattat     180
gctgactccg ttaaaggtcg cttcactatc tctagagaca actctaagaa tactctctac     240
ttgcagatga acagcttaag ggctgaggac acggccgtgt attactgtgc gagaggggt      300 gatggttatt tcgactactt tgactactgg ggccagggaa ccctggtcac cgtctcaagc     360
gcctccacca agggcccatc ggtcttcccg ctagcaccca gcagcaagag caccagcggc     420
ggaacagccg ccctgggctg cctggtgaaa gactacttcc ccgagcccgt gaccgtgtcc     480
tggaactctg gcgccctgac cagcggagtg cataccttcc ccgccgtgct gcagagcagc     540
ggcctgtaca gcctgagcag cgtggtgaca gtgcccagca gcagcctggg aacccagacc     600
tacatctgca acgtgaacca caagcccagc aacaccaagg tggacaagcg ggtggaaccc     660
aagagctgcg acaagaccca cacctgtccc cctgccctg ccctgaact gctgggcgga     720 cccagcgtgt tcctgttccc cccaaagccc aaggacaccc tgatgatcag ccggacccc     780 gaagtgacct gcgtggtggt ggacgtgtcc cacgaggacc cagaagtgaa gtttaattgg     840
tacgtggacg gcgtggaagt gcataacgcc aagaccaagc ccagagagga acagtacaac     900
agcacctacc gggtggtgtc cgtgctgacc gtgctgcacc aggactggct gaacggcaaa     960
gagtacaagt gcaaggtctc caacaaggcc ctgcctgccc ccatcgagaa aaccatcagc    1020
aaggccaagg gccagccccg cgagcctcag gtgtacacac tgcccccag ccgggaagag    1080 atgaccaaga accaggtgtc cctgacctgt ctggtgaaag gcttctaccc cagcgatatc    1140
gccgtggaat gggagagcaa cggccagccc gagaacaatt acaagaccac cccccctgtg    1200
ctggacagcg acggctcatt cttcctgtac tccaagctga ccgtggacaa gagccggtgg    1260
cagcagggca acgtgttcag ctgcagcgtg atgcacgagg ccctgcacaa tcactacacc    1320
cagaagtccc tgagcctgag ccccggc                                       1347
```

```
<210> SEQ ID NO 193
```

<211> LENGTH: 651
<212> TYPE: DNA
<213> ORGANISM: Homo Sapiens

<400> SEQUENCE: 193

```
gcacaagaca tccagatgac ccagtctcca gccaccctgt ctgcatctgt aggagacaga    60
gtcaccatca cttgccgggc aagtcagagc attagcggct atttaaattg gtatcagcag   120
aaaccaggga aagcccctaa gctcctgatc tataacgcat ccagtttgca aagtggggtc   180
ccatcaaggt tcagtggcag tggatctggg acagatttca ctctcaccat cagcagtctg   240
caacctgaag attttgcaac ttactactgt caacagagct acactagtcc attcatcact   300
ttcggccctg ggaccaaggt ggagatcaaa cgaactgtgg ctgcaccatc tgtcttcatc   360
ttcccgccat ctgatgagca gttgaaatct ggaactgcct ctgttgtgtg cctgctgaat   420
aacttctatc ccagagaggc caaagtacag tggaaggtgg ataacgccct ccaatcgggt   480
aactcccagg agagtgtcac agagcaggac agcaaggaca gcacctacag cctcagcagc   540
accctgacgc tgagcaaagc agactacgag aaacacaaac tctacgcctg cgaagtcacc   600
catcagggcc tgagctcgcc cgtcacaaag agcttcaaca ggggagagtg t            651
```

<210> SEQ ID NO 194
<211> LENGTH: 1347
<212> TYPE: DNA
<213> ORGANISM: Homo Sapiens

<400> SEQUENCE: 194

```
gaagttcaat tgttagagtc tggtggcggt cttgttcagc ctggtggttc tttacgtctt    60
tcttgcgctg cttccggatt cactttctct ccttacccta tgatctgggt tcgccaagct   120
cctggtaaag gtttggagtg gtttcttat atctctcctt ctggtggcaa gactcattat   180
gctgactccg ttaaaggtcg cttcactatc tctagagaca actctaagaa tactctctac   240
ttgcagatga acagcttaag ggctgaggac acggccgtgt attactgtgc gagagggggt   300
gatacttatt tcgactactt tgactactgg ggccagggaa ccctggtcac cgtctcaagc   360
gcctccacca agggcccatc ggtcttcccg ctagcaccca gcagcaagag caccagcggc   420
ggaacagccg ccctgggctg cctggtgaaa gactacttcc ccgagcccgt gaccgtgtcc   480
tggaactctg gcgccctgac cagcggagtg catacctcc ccgccgtgct gcagagcagc   540
ggcctgtaca gcctgagcag cgtggtgaca gtgcccagca gcagcctggg aacccagacc   600
tacatctgca acgtgaacca caagcccagc aacaccaagg tggacaagaa ggtgaaccc   660
aagagctgcg acaagaccca cacctgtccc cctgccctg cccctgaact gctgggcgga   720
cccagcgtgt tcctgttccc cccaaagccc aaggacaccc tgatgatcag ccggacccc   780
gaagtgacct gcgtggtggt ggacgtgtcc cacgaggacc cagaagtgaa gtttaattgg   840
tacgtggacg gcgtggaagt gcataacgcc aagaccaagc cagagagga cagtacaac   900
agcacctacc gggtggtgtc cgtgctgacc gtgctgcacc aggactggct gaacggcaaa   960
gagtacaagt gcaaggtctc caacaaggcc ctgcctgccc ccatcgagaa aaccatcagc  1020
aaggccaagg gccagccccg cgagcctcag gtgtacacac tgcccccag ccgggatgag  1080
ctgaccaaga accaggtgtc cctgacctgt ctggtgaaag gcttctaccc cagcgatatc  1140
gccgtggaat gggagagcaa cggccagccc gagaacaatt acaagaccac ccccctgtg  1200
ctggacagcg acggctcatt cttcctgtac tccaagctga ccgtggacaa gagccggtgg  1260
cagcagggca acgtgttcag ctgcagcgtg atgcacgagg ccctgcacaa tcactacacc  1320
```
cagaagtccc tgagcctgag ccccggc    1347

<210> SEQ ID NO 195
<211> LENGTH: 651
<212> TYPE: DNA
<213> ORGANISM: Homo Sapiens

<400> SEQUENCE: 195
gcacaagaca tccagatgac ccagtctcca gccaccctgt ctgcatctgt aggagacaga    60
gtcaccatca cttgccgggc aagtcagagc attagcagct atttaaattg gtatcagcag   120
aaaccaggga aagcccctaa gctcctgatc tataacgcat ccagtttgca aagtggggtc   180
ccatcaaggt tcagtggcag tggatctggg acagatttca ctctcaccat cagcagtctg   240
caacctgaag attttgcaac ttactactgt caacagagct acactagtcc agggatcact   300
ttcggccctg ggaccaaggt ggagatcaaa cgaactgtgg ctgcaccatc tgtcttcatc   360
ttcccgccat ctgatgagca gttgaaatct ggaactgcct ctgttgtgtg cctgctgaat   420
aacttctatc ccagagaggc caaagtacag tggaaggtgg ataacgccct ccaatcgggt   480
aactcccagg agagtgtcac agagcaggac agcaaggaca gcacctacag cctcagcagc   540
accctgacgc tgagcaaagc agactacgag aaacacaaac tctacgcctg cgaagtcacc   600
catcagggcc tgagctcgcc cgtcacaaag agcttcaaca ggggagagtg t              651

<210> SEQ ID NO 196
<211> LENGTH: 1347
<212> TYPE: DNA
<213> ORGANISM: Homo Sapiens

<400> SEQUENCE: 196
gaagttcaat tgttagagtc tggtggcggt cttgttcagc ctggtggttc tttacgtctt    60
tcttgcgctg cttccggatt cactttctct ccttaccctn tgatgtgggt tcgccaagct   120
cctggtaaag gtttggagtg gtttcttat atctctcctt ctggtggcaa gactcattat    180
gctgactccg ttaaaggtcg cttcactatc tctagagaca actctaagaa tactctctac   240
ttgcagatga acagcttaag ggctgaggac acggccgtgt attactgtgc gagaggggt   300
gatacttatt tcgactactt tgactactgg ggccagggaa ccctggtcac cgtctcaagc   360
gcctccacca agggcccatc ggtcttcccg ctagcaccca gcagcaagag caccagcggc   420
ggaacagccg ccctgggctg cctggtgaaa gactacttcc ccgagcccgt gaccgtgtcc   480
tggaactctg gcgccctgac cagcggagtg cataccttcc ccgccgtgct gcagagcagc   540
ggcctgtaca gcctgagcag cgtggtgaca gtgcccagca gcagcctggg aacccagacc   600
tacatctgca acgtgaacca caagcccagc aacaccaagg tggacaagaa ggtggaaccc   660
aagagctgcg acaagaccca cacctgtccc cctgccctg cccctgaact gctgggcgga   720
cccagcgtgt tcctgttccc cccaaagccc aaggacaccc tgatgatcag ccggaccccc   780
gaagtgacct gcgtggtggt ggacgtgtcc cacgaggacc cagaagtgaa gtttaattgg   840
tacgtggacg gcgtggaagt gcataacgcc aagaccaagc ccagagagga acagtacaac   900
agcacctacc gggtggtgtc cgtgctgacc gtgctgcacc aggactggct gaacggcaaa   960
gagtacaagt gcaaggtctc caacaaggcc ctgcctgccc ccatcgagaa aaccatcagc  1020
aaggccaagg gccagccccg cgagcctcag gtgtacacac tgcccccag ccgggatgag  1080
ctgaccaaga accaggtgtc cctgacctgt ctggtgaaag gcttctaccc cagcgatatc  1140

```
gccgtggaat gggagagcaa cggccagccc gagaacaatt acaagaccac cccccctgtg    1200
ctggacagcg acggctcatt cttcctgtac tccaagctga ccgtggacaa gagccggtgg    1260
cagcagggca acgtgttcag ctgcagcgtg atgcacgagg ccctgcacaa tcactacacc    1320
cagaagtccc tgagcctgag ccccggc                                        1347

<210> SEQ ID NO 197
<211> LENGTH: 651
<212> TYPE: DNA
<213> ORGANISM: Homo Sapiens

<400> SEQUENCE: 197
gcacaagaca tccagatgac ccagtctcca gccaccctgt ctgcatctgt aggagacaga      60
gtcaccatca cttgccgggc aagtcagagc attagcggct atttaaattg gtatcagcag     120
aaaccaggga aagcccctaa gctcctgatc tataacgcat ccagtttgca aagtggggtc     180
ccatcaaggt tcagtggcag tggatctggg acagatttca ctctcaccat cagcagtctg     240
caacctgaag attttgcaac ttactactgt caacagagct acactagtcc agggatcact     300
ttcggccctg ggaccaaggt ggagatcaaa cgaactgtgg ctgcaccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaac tctacgcctg cgaagtcacc     600
catcagggcc tgagctcgcc cgtcacaaag agcttcaaca ggggagagtg t             651

<210> SEQ ID NO 198
<211> LENGTH: 1347
<212> TYPE: DNA
<213> ORGANISM: Homo Sapiens

<400> SEQUENCE: 198
gaagttcaat tgttagagtc tggtggcggt cttgttcagc ctggtggttc tttacgtctt      60
tcttgcgctg cttccggatt cactttctct ccttaccctg atgtgtgggt tcgccaagct     120
cctggtaaag gtttggagtg ggtttcttat atctctcctt ctggtggcaa gactcattat     180
gctgactccg ttaaaggtcg cttcactatc tctagagaca actctaagaa tactctctac     240
ttgcagatga acagcttaag ggctgaggac acggccgtgt attactgtgc gagaggggt     300 gatacttatt tcgactactt tgactactgg ggccagggaa ccctggtcac cgtctcaagc     360
gcctccacca agggcccatc ggtcttcccg ctagcaccca gcagcaagag caccagcggc     420
ggaacagccg ccctgggctg cctggtgaaa gactacttcc ccgagcccgt gaccgtgtcc     480
tggaactctg gcgccctgac cagcggagtg cataccttcc ccgccgtgct gcagagcagc     540
ggcctgtaca gcctgagcag cgtggtgaca gtgcccagca gcagcctggg aacccagacc     600
tacatctgca acgtgaacca caagcccagc aacaccaagg tggacaagaa ggtggaaccc     660
aagagctgcg acaagaccca cacctgtccc cctgccctg ccctgaact gctgggcgga     720 cccagcgtgt tcctgttccc cccaaagccc aaggacaccc tgatgatcag ccggacccc     780 gaagtgacct gcgtggtggt ggacgtgtcc cacgaggacc cagaagtgaa gtttaattgg     840
tacgtggacg gcgtggaagt gcataacgcc aagaccaagc ccagagagga acagtacaac     900
agcacctacc gggtggtgtc cgtgctgacc gtgctgcacc aggactggct gaacggcaaa     960
gagtacaagt gcaaggtctc caacaaggcc ctgcctgccc ccatcgagaa aaccatcagc    1020
```

```
aaggccaagg gccagcccg cgagcctcag gtgtacacac tgcccccag ccgggatgag    1080 ctgaccaaga accaggtgtc cctgacctgt ctggtgaaag gcttctaccc cagcgatatc    1140
gccgtggaat gggagagcaa cggccagccc gagaacaatt acaagaccac ccccctgtg    1200 ctggacagcg acggctcatt cttcctgtac tccaagctga ccgtggacaa gagccggtgg    1260
cagcagggca acgtgttcag ctgcagcgtg atgcacgagg ccctgcacaa tcactacacc    1320
cagaagtccc tgagcctgag ccccggc                                         1347
```

<210> SEQ ID NO 199
<211> LENGTH: 651
<212> TYPE: DNA
<213> ORGANISM: Homo Sapiens

<400> SEQUENCE: 199

```
gcacaagaca tccagatgac ccagtctcca gccaccctgt ctgcatctgt aggagacaga     60
gtcaccatca cttgccgggc aagtcagagc attagcagct atttaaattg gtatcagcag    120
aaaccaggga aagcccctaa gctcctgatc tataacgcat ccagtttgca aagtggggtc    180
ccatcaaggt tcagtggcag tggatctggg acagatttca ctctcaccat cagcagtctg    240
caacctgaag attttgcaac ttactactgt caacagagct acactagtcc attcatcact    300
ttcggccctg ggaccaaggt ggagatcaaa cgaactgtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaac tctacgcctg cgaagtcacc    600
catcagggcc tgagctcgcc cgtcacaaag agcttcaaca ggggagagtg t              651
```

<210> SEQ ID NO 200
<211> LENGTH: 1347
<212> TYPE: DNA
<213> ORGANISM: Homo Sapiens

<400> SEQUENCE: 200

```
gaagttcaat tgttagagtc tggtggcggt cttgttcagc ctggtggttc tttacgtctt     60
tcttgcgctg cttccggatt cactttctct ccttacccta tgatgtgggt tcgccaagct    120
cctggtaaag gtttggagtg ggtttcttat atctctcctt ctggtggcaa gactcattat    180
gctgactccg ttaaaggtcg cttcactatc tctagagaca actctaagaa tactctctac    240
ttgcagatga acagcttaag ggctgaggac acggccgtgt attactgtgc gagagggggt    300
gatacttatt tcgactactt tgactactgg ggccagggaa ccctggtcac cgtctcaagc    360
gcctccacca agggcccatc ggtcttcccg ctagcaccca gcagcaagag caccagcggc    420
ggaacagccg ccctgggctg cctggtgaaa gactacttcc ccgagcccgt gaccgtgtcc    480
tggaactctg gcgccctgac cagcggagtg cataccttcc ccgccgtgct gcagagcagc    540
ggcctgtaca gcctgagcag cgtggtgaca gtgcccagca gcagcctggg aacccagacc    600
tacatctgca acgtgaacca caagcccagc aacaccaagg tggacaagaa ggtggaaccc    660
aagagctgcg acaagaccca cacctgtccc ccctgccctg cccctgaact gctgggcgga    720
cccagcgtgt tcctgttccc cccaaagccc aaggacaccc tgatgatcag ccggaccccc    780
gaagtgacct gcgtggtggt ggacgtgtcc cacgaggacc cagaagtgaa gtttaattgg    840
```

| | |
|---|---|
| tacgtggacg gcgtggaagt gcataacgcc aagaccaagc ccagagagga acagtacaac | 900 |
| agcacctacc gggtggtgtc cgtgctgacc gtgctgcacc aggactggct gaacggcaaa | 960 |
| gagtacaagt gcaaggtctc caacaaggcc ctgcctgccc ccatcgagaa aaccatcagc | 1020 |
| aaggccaagg gccagccccg cgagcctcag gtgtacacac tgcccccag ccgggatgag | 1080 |
| ctgaccaaga accaggtgtc cctgacctgt ctggtgaaag gcttctaccc cagcgatatc | 1140 |
| gccgtggaat gggagagcaa cggccagccc gagaacaatt acaagaccac ccccctgtg | 1200 |
| ctggacagcg acggctcatt cttcctgtac tccaagctga ccgtggacaa gagccggtgg | 1260 |
| cagcagggca acgtgttcag ctgcagcgtg atgcacgagg ccctgcacaa tcactacacc | 1320 |
| cagaagtccc tgagcctgag ccccggc | 1347 |

<210> SEQ ID NO 201
<211> LENGTH: 654
<212> TYPE: DNA
<213> ORGANISM: Mus Musculus

<400> SEQUENCE: 201

| | |
|---|---|
| gatatcgtgc tgacacagtc tcccgccagc ctggccgtgt ctctcggcca gagagccacc | 60 |
| atcagctgcc gggccaacaa gagcgtgtcc accagcagct acagctacat gcactggtat | 120 |
| cagcagaagc ccggccagcc ccccaagctg ctgattaagt acgccagcaa cctggaaagc | 180 |
| ggcgtgcccg ccagattcag cggcagcggc tctggcaccg acttcatcct gaacatccac | 240 |
| cccgtggaag aagaggacgc cgccacctac tactgccagc acagcagaga gctgcccttc | 300 |
| accttcggca gcggcaccaa gctggaaatc aagcgggccg atgccgcccc taccgtgtcc | 360 |
| atcttcccac ccagcagcga gcagctgacc agcggcggag ccagcgtcgt gtgcttcctg | 420 |
| aacaacttct accccaagga catcaacgtg aagtggaaga tcgacggcag cgagcggcag | 480 |
| aacggcgtgc tgaacagctg gaccgaccag gacagcaagg actccaccta cagcatgagc | 540 |
| agcaccctga ccctgaccaa ggacgagtac gagcggcaca cagctacac atgcgaggcc | 600 |
| acccacaaga ccagcaccag ccccatcgtg aagtccttca ccggaacga gtgc | 654 |

<210> SEQ ID NO 202
<211> LENGTH: 1350
<212> TYPE: DNA
<213> ORGANISM: Mus Musculus

<400> SEQUENCE: 202

| | |
|---|---|
| caggtgcagc tgcagcagtc tggccctgaa gtcgtgcggc ctggcgtgtc cgtgaagatc | 60 |
| agctgcaagg gcagcggcta caccttcacc gactacggca tccactgggt caagcagagc | 120 |
| cacgccaaga gcctggaatg gatcggcgtg atcagcacct acaacggcta caccaactac | 180 |
| aaccagaagt tcaagggcaa ggccaccatg accgtggaca gagcagcag caccgcctac | 240 |
| atggaactgg cccggctgac cagcgaggac agcgccatct actactgcgc cagagcctac | 300 |
| tacggcaacc tgtactacgc catggactac tggggccagg caccagcgt gaccgtgtcc | 360 |
| tctgccaaga ccaccgcccc tagcgtgtac cctctggccc ctgtgtgtgg cgacaccacc | 420 |
| ggcagctctg tgactctggg ctgcctggtc aagggctact cccccgagcc cgtgacactg | 480 |
| acctggaaca gcggcagcct gagcagcggc gtgcacacct ttccagccgt gctgcagagc | 540 |
| gacctgtaca ccctgagcag ctcgtgacc gtgacaagca gcacctggcc cagcagagc | 600 |
| atcacctgta acgtgcccca ccccgccagc agcaccaagg tggacaagaa gatcgagccc | 660 |
| agaggcccca ccatcaagcc ctgcccccct tgcaagtgcc cagcccccaa tctgctgggc | 720 |

```
ggacccagcg tgttcatctt cccacccaag atcaaggacg tgctgatgat cagcctgagc      780
cccatcgtga cctgcgtggt ggtggacgtg tccgaggacg accccgacgt gcagatcagt      840
tggttcgtga acaacgtgga agtgcacacc gcccagaccc agacccacag agaggactac      900
aacagcaccc tgcgggtggt gtccgccctg cccatccagc accaggactg gatgagcggc      960
aaagaattca gtgcaaagt gaacaacaag gacctgcctg ccccatcga gcggaccatc       1020 agcaagccca gggcagcgt gcgggctccc caggtgtacg tgctgccccc acccgaggaa       1080
gagatgacca agaagcaggt cacactgacc tgcatggtca ccgacttcat gcccgaggac      1140
atctacgtgg aatggaccaa aacggcaag accgagctga actacaagaa caccgagcct      1200
gtgctggaca gcgacggcag ctacttcatg tacagcaagc tgcgggtgga aaagaaaaac      1260
tgggtggaac ggaacagcta cagctgcagc gtggtgcacg agggcctgca caaccaccac      1320
accaccaaga gcttcagccg dacccccggc                                       1350
```

<210> SEQ ID NO 203
<211> LENGTH: 654
<212> TYPE: DNA
<213> ORGANISM: Mus Musculus

<400> SEQUENCE: 203

```
gatatcgtgc tgacacagag ccccgccagc ctgaccgtgt ctctcggcca gagagccacc       60
atcagctgcc gggccagcca gagcgtgtcc accagcagct acagctacat gcagtggtat      120
cagcagcggc ctggccagcc ccccaagctg ctgattaagt acgccaccaa cctggacagc      180
ggcgtgcccg ccagattttc tggcagcggc agcggcacag acttcaccct gaacatccac      240
cccgtggaag aagaggacgc cgccacctac tactgccagc acagctggga gatcccttac      300
accttcggcg gaggcaccaa gctggaaatc aagcgggccg atgccgcccc taccgtgtcc      360
atcttcccac ccagcagcga gcagctgacc agcggcggag ccagcgtcgt gtgcttcctg      420
aacaacttct accccaagga catcaacgtg aagtggaaga tcgacggcag cgagcggcag      480
aacggcgtgc tgaacagctg gaccgaccag gacagcaagg actccaccta cagcatgagc      540
agcaccctga ccctgaccaa ggacgagtac gagcggcaca acagctacac atgcgaggcc      600
acccacaaga ccagcaccag ccccatcgtg aagtccttca ccggaacga gtgc            654
```

<210> SEQ ID NO 204
<211> LENGTH: 1344
<212> TYPE: DNA
<213> ORGANISM: Mus Musculus

<400> SEQUENCE: 204

```
gaagtgaagc tggaagagtc tggcggcgga ctggtccagc ctggcggcag catgaagctg       60
agctgcgtgg ccagcggctt caccttcaac aactactgga tgagctgggt ccgacagagc      120
cccgagaagg gcctggaatg gctggccgag atccggctga gtccgacaa ctacgccacc      180 cactacgccg agagcgtgaa gggcaagttc accatcagcc gggacgacag caagagccgg      240
ctgtacctgc agatgaacaa cctgcgggcc gagaacaccg gcatctacta ctgcaccggc      300
ggcttcgccg actacttcga ctactgggc cagggcacca ccctgaccgt gtcctctgcc       360
aagaccaccg cccctagcgt gtaccctctg gcccctgtgt gtggcgacac caccggcagc      420
tctgtgactc tgggctgcct ggtcaagggc tacttcccg agcccgtgac actgacctgg      480
aacagcggca gcctgagcag cggcgtgcac accttccag ccgtgctgca gagcgacctg      540
```

```
tacaccctga gcagctccgt gaccgtgaca agcagcacct ggcccagcca gagcatcacc       600
tgtaacgtgg cccaccccgc cagcagcacc aaggtggaca agaagatcga gcccagaggc       660
cccaccatca agccctgccc cccttgcaag tgcccagccc caatctgctg ggcggacccc       720
agcgtgttca tcttcccacc caagatcaag gacgtgctga tgatcagcct gagccccatc       780
gtgacctgcg tggtggtgga cgtgtccgag gacgaccccg acgtgcagat cagttggttc       840
gtgaacaacg tggaagtgca caccgcccag acccagaccc acagagagga ctacaacagc       900
accctgcggg tggtgtccgc cctgcccatc cagcaccagg actggatgag cggcaaagaa       960
ttcaagtgca aagtgaacaa caaggacctg cctgccccca tcgagcggac catcagcaag      1020
cccaagggca gcgtgcgggc tccccaggtg tacgtgctgc ccccacccga ggaagagatg      1080
accaagaagc aggtcacact gacctgcatg gtcaccgact tcatgcccga ggacatctac      1140
gtggaatgga ccaacaacgg caagaccgag ctgaactaca gaacaccgga gcctgtgctg      1200
gacagcgacg gcagctactt catgtacagc aagctgcggg tggaaaagaa aaactgggtg      1260
gaacggaaca gctacagctg cagcgtggtg cacgagggcc tgcacaacca ccacaccacc      1320
aagagcttca gccggacccc cggc                                             1344
```

<210> SEQ ID NO 205
<211> LENGTH: 654
<212> TYPE: DNA
<213> ORGANISM: Homo Sapiens

<400> SEQUENCE: 205

```
gacattgtgc tgacacagtc tcctgcttcc ctggctgtat ctctgggggca gagggccacc       60 atctcatgca gggccagcaa agtgtcagt acatctagct atagttatat gcactggtac        120
caacagaaac caggacagcc acccaaactc ctcatcaaat atgcatccaa cctagaatct       180
ggggtccctg ccaggttcag tggcagtggg tctgggacag acttctccct caacatccat       240
cccatggagg aggacgatac cgcaatgtat ttctgtcagc acagtaggga gcttccattc       300
acgttcggcg agggacaaa gttggaaata aaacgtacgg tggccgctcc cagcgtgttc        360
atcttcccac ccagcgacga gcagctgaag tccggcaccg ccagcgtcgt gtgcctgctg       420
aacaacttct accccgcga ggccaaggtg cagtggaagg tggacaacgc cctgcagagc        480
ggcaacagcc aggaaagcgt caccgagcag gacagcaagg actccaccta cagcctgtcc       540
agcaccctga ccctgagcaa ggccgactac gagaagcaca aggtgtacgc ctgcgaagtg       600
acccaccagg gcctgagcag ccccgtgacc aagagcttca accggggcga gtgc             654
```

<210> SEQ ID NO 206
<211> LENGTH: 1350
<212> TYPE: DNA
<213> ORGANISM: Homo Sapiens

<400> SEQUENCE: 206

```
caggtccagc tggtgcagtc tggggctgag gtgaagaagc ctggggcctc agtgaaggtt       60
tcctgcaagg gttccggcta cacattcact gattatggca tgcactgggt gcggcaggcc       120
cctggacaag gctagagtg gatgggagtt attagtactt acaatggtta tacaaactac        180
aaccagaagt ttaagggcag agtcacaatg actgtagaca atccacgag cacagcctat       240 atggaacttc ggagcttgag atctgacgat acggccgtgt attactgtgc aagagcctac       300
tatggcaacc tttactatgc tatggactac tggggtcaag gaaccctggt caccgtctcc       360
tcagctagca ccaaaggccc gagcgtgttt ccgctggccc cgagcagcaa gagcaccagc       420
```

```
ggcggaacag ccgccctggg ctgcctggtg aaagactact tccccgaacc ggtgaccgtg     480
tcctggaact ctggcgccct gaccagcgga gtgcatacct tccccgccgt gctgcagagc     540
agcggcctgt acagcctgag cagcgtggtg acagtgccca gcagcagcct gggaacccag     600
acctacatct gcaacgtgaa ccacaagccc agcaacacca aggtggacaa gaaggtggaa     660
cccaagagct gcgacaagac ccacacctgt ccccctgcc ctgcccctga actgctgggc     720
ggacccagcg tgttcctgtt cccccccaaag cccaaggaca ccctgatgat cagccggacc     780
cccgaagtga cctgcgtggt ggtggacgtg tcccacgagg acccagaagt gaagtttaat     840
tggtacgtgg acggcgtgga agtgcataac gccaagacca gcccagaga ggaacagtac     900 aacagcacct accgggtggt gtccgtgctg accgtgctgc accaggactg gctgaacggc     960
aaagagtaca gtgcaaggt ctccaacaag gccctgcctg cccccatcga gaaaaccatc    1020
agcaaggcca agggccagcc ccgcgagcct caggtgtaca cactgccccc cagccgggat    1080
gagctgacca gaaccaggt gtccctgacc tgtctggtga aaggcttcta ccccagcgat    1140
atcgccgtgg aatgggagag caacggccag cccgagaaca attacaagac caccccccct    1200
gtgctggaca gcgacggctc attcttcctg tactccaagc tgaccgtgga caagagccgg    1260
tggcagcagg gcaacgtgtt cagctgcagc gtgatgcacg aggccctgca caatcactac    1320
acccagaagt ccctgagcct gagccccggc                                     1350

<210> SEQ ID NO 207
<211> LENGTH: 654
<212> TYPE: DNA
<213> ORGANISM: Homo Sapiens

<400> SEQUENCE: 207
gatatccaga tgacccagag ccccagcagc ctgagcgcca gcgtgggcga cagagtgacc      60
atcacctgtc gggccagcca gagcgtgtcc accagcagct acagctacat gcactggtat     120 cagcagaaagc ccggcaaggc ccccaagctg ctgattaagt acgccagcaa cctggaaagc     180
ggcgtgccca gccggtttag cggctctggc agcggcaccg acttcaccct gaccatcagc     240
agtctgcagc ccgaggactt cgccacctac tactgccagc acagctggga gatcccttac     300
accttcggcg gaggcaccaa ggtggaaatc aagcgtacgg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagga cagcaccta gagcctcagc     540 agcacccga cgctgtctaa agcagactac gagaaacaca agtctacgc ctgcgaagtc     600 acccatcagg gcctgagctc gcccgtcaca aagagcttca caggggagag tgt           654

<210> SEQ ID NO 208
<211> LENGTH: 1347
<212> TYPE: DNA
<213> ORGANISM: Homo Sapiens

<400> SEQUENCE: 208
caggtggaat tggtggaaag cggcggaggc ctggtgcagc ctggcggaag cctgagactg      60
agctgtgccg ccagcggctt caccttcagc agctactgga tgagctgggt ccgacaggct     120
ccaggcaagg gcctggaatg ggtggccgag atccggctga gtccgacaa ctacgccacc     180 cactacgccg agagcgtgaa gggccggttc accatcagcc gggacgacag caagaacagc     240
```

```
ctgtacctgc agatgaacag cctgcgggcc gaggacaccg ccgtgtacta ctgcaccggc      300
tactacgccg acgccatgga ctactggggc cagggcaccc tggtcaccgt cagctcagcc      360
tccaccaagg gtccatcggt cttccccctg gcaccctcct ccaagagcac ctctgggggc      420
acagcggccc tgggctgcct ggtcaaggac tacttccccg aaccggtgac ggtgtcgtgg      480
aactcaggcg ccctgaccag cggcgtgcac accttcccgg ctgtcctaca gtcctcagga      540
ctctactccc tcagcagcgt ggtgaccgtg ccctccagca gcttgggcac ccagacctac      600
atctgcaacg tgaatcacaa gcccagcaac accaaggtgg acaagcgggt tgagcccaaa      660
tcttgtgaca aaactcacac atgcccaccg tgcccagcac ctgaactcct ggggggaccg      720
tcagtcttcc tcttccccCC aaaacccaag gacaccctca tgatctcccg gacccctgag      780
gtcacatgcg tggtggtgga cgtgagccac gaagaccctg aggtcaagtt caactggtac      840
gtggacggcg tggaggtgca taatgccaag acaaagccgc gggaggagca gtacaacagc      900
acgtaccggg tggtcagcgt cctcaccgtc ctgcaccagg actggctgaa tggcaaggag      960
tacaagtgca aggtctccaa caaagccctc ccagccccca tcgagaaaac catctccaaa     1020 gccaagggc agccccgaga accacaggtg tacaccctgc ccccatcccg ggaagagatg     1080
accaagaacc aggtcagcct gacctgcctg gtcaaaggct tctatcccag cgacatcgcc     1140
gtggagtggg agagcaatgg gcagccggag aacaactaca agaccacgcc tcccgtgctg     1200
gactccgacg gctccttctt cctctacagc aagctcaccg tggacaagag caggtggcag     1260
caggggaacg tcttctcatg ctccgtgatg catgaggctc tgcacaacca ctacacgcag     1320
aagagcctct ccctgtctcc gggtaaa                                          1347
```

<210> SEQ ID NO 209
<211> LENGTH: 654
<212> TYPE: DNA
<213> ORGANISM: Mus Musculus

<400> SEQUENCE: 209

```
gatatcgtgc tgacacagtc tcccgccagc ctggccgtgt ctctcggcca gagagccacc       60
atcagctgca aggccagcca gagcgtgtcc accagcacct acagctacat gcagtggtat      120
cagcagcggc ctggacagag ccccaagctg ctgattaagt acgccagcaa gctggacagc      180
ggcgtgcccg ccagatttc tggcagcggg agcggcaccg acttcaccct gaacatccac      240
cccgtggaag aagaggacac cgccacctac tactgccagc acagctggga gctgccctac      300
accttcggcg gaggcacccg gctggaaatc aagagggccg atgccgcccc taccgtgtcc      360
atcttcccac ccagcagcga gcagctgacc agcggcggag ccagcgtcgt gtgcttcctg      420
aacaacttct accccaagga catcaacgtg aagtggaaga tcgacggcag cgagcggcag      480
aacggcgtgc tgaacagctg gaccgaccag gacagcaagg actccaccta cagcatgagc      540
agcaccctga cctgaccaa ggacgagtac gagcggcaca acagctacac atgcgaggcc      600
acccacaaga ccagcaccag ccccatcgtg aagtccttca accggaacga gtgc            654
```

<210> SEQ ID NO 210
<211> LENGTH: 1344
<212> TYPE: DNA
<213> ORGANISM: Mus Musculus

<400> SEQUENCE: 210

```
gaagtgaagc tgggagagtc tggcggcgga ctggtccagc ctggcggcag catgaagctg       60
agctgcgtgg ccagcggctt cccattcacc aaatactgga tgaactgggt ccgacagagc      120
```

-continued

```
cccgagaagg gcctggaatg ggtggccgag atccggctga agtccgacaa ctacgccacc      180
cactacgccg agagcgccaa gggccggttc accatcagcc gggacgacag ccggtccagc      240
gtgtacctgc agatgaacaa cctgcgggcc gaggacaccg ccatctacta ctgcagcccc      300
acctatgccg acaccatgga ctactgggc caggggcacca gcgtgacagt gtccagcgcc      360
aagaccaccg cccctagcgt gtaccctctg gcccctgtgt gtggcgacac caccggcagc      420
tctgtgactc tgggctgcct ggtcaagggc tacttccccg agcccgtgac actgacctgg      480
aacagcggca gcctgagcag cggcgtgcac acctttccag ccgtgctgca gagcgacctg      540
tacaccctga gcagctccgt gaccgtgaca agcagcacct ggcccagcca gagcatcacc      600
tgtaacgtgg cccaccccgc cagcagcacc aaggtggaca gaagatcga gcccagaggc      660 cccaccatca gccctgccc ccttgcaag tgcccagccc ccaatctgct gggcggaccc      720
agcgtgttca tcttcccacc caagatcaag gacgtgctga tgatcagcct gagccccatc      780
gtgacctgcg tggtggtgga cgtgtccgag gacgaccccg acgtgcagat cagttggttc      840
gtgaacaacg tggaagtgca caccgcccag acccagaccc acagagagga ctacaacagc      900
accctgcggg tggtgtccgc cctgcccatc cagcaccagg actggatgag cggcaaagaa      960
ttcaagtgca aagtgaacaa caaggacctg cctgccccca tcgagcggac catcagcaag     1020
cccaagggca gcgtgcgggc tccccaggtg tacgtgctgc ccccacccga ggaagagatg     1080
accaagaagc aggtcacact gacctgcatg gtcaccgact tcatgcccga ggacatctac     1140
gtggaatgga ccaacaacgg caagaccgag ctgaactaca gaacaccga gcctgtgctg     1200 gacagcgacg gcagctactt catgtacagc aagctgcggg tggaaaagaa aaactgggtg     1260
gaacggaaca gctacagctg cagcgtggtg cacgagggcc tgcacaacca ccacaccacc     1320
aagagcttca gccggacccc cggc                                           1344
```

<210> SEQ ID NO 211
<211> LENGTH: 654
<212> TYPE: DNA
<213> ORGANISM: Mus Musculus

<400> SEQUENCE: 211

```
gatatcgtgc tgacacagtc tcccgccagc ctggccgtgt ctctcggcca gagagccacc       60
atcagctgcc gggccagcaa gagcgtgtcc accagcagct acagctacat gcactggtat      120
cagcagaagc ccggccagcc ccccaagctg ctgatcaagt acaccagcaa cctggaaagc      180
ggcgtgcccg ccagattcag cggaagcggc tccggcaccg acttcatcct gaacatccac      240
cccgtggaag aagaggacgc cgccacctac tactgccagc acagcagaga gctgcccctgg      300 accttcggcg gaggcaccaa gctggaaatc aagcggccc atgccgcccc taccgtgtcc      360
atcttcccac ccagcagcga gcagctgacc agcggcggag ccagcgtcgt gtgcttcctg      420
aacaacttct accccaagga catcaacgtg aagtggaaga tcgacggcag cgagcggcag      480
aacggcgtgc tgaacagctg gaccgaccag gacagcaagg actccaccta cagcatgagc      540
agcaccctga cctgaccaa ggacgagtac gagcggcaca acagctacac atgcgaggcc      600
acccacaaga ccagcaccag ccccatcgtg aagtccttca ccggaacga gtgc             654
```

<210> SEQ ID NO 212
<211> LENGTH: 1353
<212> TYPE: DNA
<213> ORGANISM: Mus Musculus

<400> SEQUENCE: 212

```
caggtgtccc tgaaagagag cggccctggc atcctgcagc ctagccagac cctgagcctg      60
acctgcagct tcagcggctt cagcctgagc accagcggca tgggcgtgtc ctggatcaga     120
cagcccagcg gcaagggcct ggaatggctg gcccacatct actgggacga cgacaagcgg     180
tacaacccca gcctgaagtc ccggctgacc atctccaagg acaccagccg gaatcaggtg     240
ttcctgaaga tcaccagcgt ggacaccgcc gataccgcca cctactactg cgccagaaga     300
ggccccgact actacggcta ctaccccatg gactattggg gccagggcac cagcgtgacc     360
gtgtctgcca agaccaccgc ccctagcgtg taccctctgg cccctgtgtg tggcgacacc     420
accggcagct ctgtgactct gggctgcctg gtcaagggct acttcccga gcccgtgaca      480
ctgacctgga cagcggcag cctgagcagc ggcgtgcaca cctttccagc cgtgctgcag     540
agcgacctgt acaccctgag cagctccgtg accgtgacaa gcagcacctg gcccagccag     600
agcatcacct gtaacgtggc ccaccccgcc agcagcacca aggtggacaa gaagatcgag     660
cccagaggcc ccaccatcaa gccctgcccc ccttgcaagt gccagccccc caatctgctg     720
ggcggaccca gcgtgttcat cttcccaccc aagatcaagg acgtgctgat gatcagcctg     780
agccccatcg tgacctgcgt ggtggtggac gtgtccgagg acgaccccga cgtgcagatc     840
agttggttcg tgaacaacgt ggaagtgcac accgcccaga cccagaccca cagagaggac     900
tacaacagca ccctgcgggt ggtgtccgcc ctgcccatcc agcaccagga ctggatgagc     960
ggcaaagaat tcaagtgcaa agtgaacaac aaggacctgc ctgcccccat cgagcggacc    1020
atcagcaagc caagggcag cgtgcgggct ccccaggtgt acgtgctgcc ccacccgag     1080
gaagagatga ccaagaagca ggtcacactg acctgcatgg tcaccgactt catgcccgag    1140
gacatctacg tggaatggac caacaacggc aagaccgagc tgaactacaa gaacaccgag    1200
cctgtgctgg acagcgacgg cagctacttc atgtacagca agctgcgggt ggaaaagaaa    1260
aactgggtgg aacggaacag ctacagctgc agcgtggtgc acgagggcct gcacaaccac    1320
cacaccacca gagcttcag ccggaccccc ggc                                  1353
```

<210> SEQ ID NO 213
<211> LENGTH: 1210
<212> TYPE: PRT
<213> ORGANISM: Homo sapiens

<400> SEQUENCE: 213

```
Met Arg Pro Ser Gly Thr Ala Gly Ala Ala Leu Leu Ala Leu Leu Ala
  1               5                  10                  15

Ala Leu Cys Pro Ala Ser Arg Ala Leu Glu Glu Lys Lys Val Cys Gln
             20                  25                  30

Gly Thr Ser Asn Lys Leu Thr Gln Leu Gly Thr Phe Glu Asp His Phe
         35                  40                  45

Leu Ser Leu Gln Arg Met Phe Asn Asn Cys Glu Val Val Leu Gly Asn
     50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125
```

-continued

```
Lys Thr Gly Leu Lys Glu Leu Pro Met Arg Asn Leu Gln Glu Ile Leu
        130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
530                 535                 540
```

-continued

```
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
            660                 665                 670
Ile Val Arg Lys Arg Thr Leu Arg Arg Leu Leu Gln Glu Arg Glu Leu
        675                 680                 685
Val Glu Pro Leu Thr Pro Ser Gly Glu Ala Pro Asn Gln Ala Leu Leu
    690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
        755                 760                 765
Val Asp Asn Pro His Val Cys Arg Leu Leu Gly Ile Cys Leu Thr Ser
    770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
            820                 825                 830
Leu Val His Arg Asp Leu Ala Ala Arg Asn Val Leu Val Lys Thr Pro
        835                 840                 845
Gln His Val Lys Ile Thr Asp Phe Gly Leu Ala Lys Leu Leu Gly Ala
    850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
            900                 905                 910
Lys Pro Tyr Asp Gly Ile Pro Ala Ser Glu Ile Ser Ser Ile Leu Glu
        915                 920                 925
Lys Gly Glu Arg Leu Pro Gln Pro Pro Ile Cys Thr Ile Asp Val Tyr
    930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
```

965                 970                 975
Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe Phe
    1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
                1045                1050                1055

Ser Cys Pro Ile Lys Glu Asp Ser Phe Leu Gln Arg Tyr Ser Ser Asp
            1060                1065                1070

Pro Thr Gly Ala Leu Thr Glu Asp Ser Ile Asp Asp Thr Phe Leu Pro
        1075                1080                1085

Val Pro Glu Tyr Ile Asn Gln Ser Val Pro Lys Arg Pro Ala Gly Ser
    1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
                1125                1130                1135

Glu Tyr Leu Asn Thr Val Gln Pro Thr Cys Val Asn Ser Thr Phe Asp
            1140                1145                1150

Ser Pro Ala His Trp Ala Gln Lys Gly Ser His Gln Ile Ser Leu Asp
        1155                1160                1165

Asn Pro Asp Tyr Gln Gln Asp Phe Phe Pro Lys Glu Ala Lys Pro Asn
    1170                1175                1180

Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
                1205                1210

<210> SEQ ID NO 214
<211> LENGTH: 622
<212> TYPE: PRT
<213> ORGANISM: Homo sapiens

<400> SEQUENCE: 214

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

```
Asp Ala Phe Ser Gly Pro Gln Ala Cys Thr Arg Phe Phe Ser Arg Ile
130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
                180                 185                 190

Pro Gly Arg Phe Val Ala Glu Ser Ala Glu Val Leu Leu Pro Arg Leu
                195                 200                 205

Val Ser Cys Pro Gly Pro Leu Asp Gln Asp Gln Gln Glu Ala Ala Arg
210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
                260                 265                 270

Gln Arg Ser Ser Arg Asp Pro Ser Trp Arg Gln Pro Glu Arg Thr Ile
                275                 280                 285

Leu Arg Pro Arg Phe Arg Arg Glu Val Glu Lys Thr Ala Cys Pro Ser
290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
                340                 345                 350

Lys His Lys Leu Asp Glu Leu Tyr Pro Gln Gly Tyr Pro Glu Ser Val
                355                 360                 365

Ile Gln His Leu Gly Tyr Leu Phe Leu Lys Met Ser Pro Glu Asp Ile
                370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
                420                 425                 430

Leu Thr Ala Phe Tyr Pro Gly Tyr Leu Cys Ser Leu Ser Pro Glu Glu
                435                 440                 445

Leu Ser Ser Val Pro Pro Ser Ser Ile Trp Ala Val Arg Pro Gln Asp
450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
                500                 505                 510

Gln Gln Asn Val Ser Met Asp Leu Ala Thr Phe Met Lys Leu Arg Thr
                515                 520                 525

Asp Ala Val Leu Pro Leu Thr Val Ala Glu Val Gln Lys Leu Leu Gly
530                 535                 540

Pro His Val Glu Gly Leu Lys Ala Glu Glu Arg His Arg Pro Val Arg
```

```
            545                 550                 555                 560
Asp Trp Ile Leu Arg Gln Arg Gln Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Met Gln Glu Ala Leu Ser Gly Thr Pro Cys Leu Leu Gly Pro Gly Pro
            595                 600                 605

Val Leu Thr Val Leu Ala Leu Leu Leu Ala Ser Thr Leu Ala
            610                 615                 620

<210> SEQ ID NO 215
<211> LENGTH: 459
<212> TYPE: PRT
<213> ORGANISM: Homo sapiens

<400> SEQUENCE: 215

Met Ala Pro Leu Cys Pro Ser Pro Trp Leu Pro Leu Leu Ile Pro Ala
1               5                   10                  15

Pro Ala Pro Gly Leu Thr Val Gln Leu Leu Ser Leu Leu Leu Leu
            20                  25                  30

Val Pro Val His Pro Gln Arg Leu Pro Arg Met Gln Glu Asp Ser Pro
            35                  40                  45

Leu Gly Gly Gly Ser Ser Gly Glu Asp Asp Pro Leu Gly Glu Glu Asp
        50                  55                  60

Leu Pro Ser Glu Glu Asp Ser Pro Arg Glu Glu Asp Pro Pro Gly Glu
65                  70                  75                  80

Glu Asp Leu Pro Gly Glu Glu Asp Leu Pro Gly Glu Glu Asp Leu Pro
                85                  90                  95

Glu Val Lys Pro Lys Ser Glu Glu Gly Ser Leu Lys Leu Glu Asp
            100                 105                 110

Leu Pro Thr Val Glu Ala Pro Gly Asp Pro Gln Glu Pro Gln Asn Asn
            115                 120                 125

Ala His Arg Asp Lys Glu Gly Asp Asp Gln Ser His Trp Arg Tyr Gly
        130                 135                 140

Gly Asp Pro Pro Trp Pro Arg Val Ser Pro Ala Cys Ala Gly Arg Phe
145                 150                 155                 160

Gln Ser Pro Val Asp Ile Arg Pro Gln Leu Ala Ala Phe Cys Pro Ala
                165                 170                 175

Leu Arg Pro Leu Glu Leu Leu Gly Phe Gln Leu Pro Pro Leu Pro Glu
            180                 185                 190

Leu Arg Leu Arg Asn Asn Gly His Ser Val Gln Leu Thr Leu Pro Pro
            195                 200                 205

Gly Leu Glu Met Ala Leu Gly Pro Gly Arg Glu Tyr Arg Ala Leu Gln
        210                 215                 220

Leu His Leu His Trp Gly Ala Ala Gly Arg Pro Gly Ser Glu His Thr
225                 230                 235                 240

Val Glu Gly His Arg Phe Pro Ala Glu Ile His Val Val His Leu Ser
                245                 250                 255

Thr Ala Phe Ala Arg Val Asp Glu Ala Leu Gly Arg Pro Gly Gly Leu
            260                 265                 270

Ala Val Leu Ala Ala Phe Leu Glu Glu Gly Pro Glu Glu Asn Ser Ala
        275                 280                 285

Tyr Glu Gln Leu Leu Ser Arg Leu Glu Glu Ile Ala Glu Glu Gly Ser
        290                 295                 300
```

Glu Thr Gln Val Pro Gly Leu Asp Ile Ser Ala Leu Leu Pro Ser Asp
305                 310                 315                 320

Phe Ser Arg Tyr Phe Gln Tyr Glu Gly Ser Leu Thr Thr Pro Pro Cys
                325                 330                 335

Ala Gln Gly Val Ile Trp Thr Val Phe Asn Gln Thr Val Met Leu Ser
            340                 345                 350

Ala Lys Gln Leu His Thr Leu Ser Asp Thr Leu Trp Gly Pro Gly Asp
        355                 360                 365

Ser Arg Leu Gln Leu Asn Phe Arg Ala Thr Gln Pro Leu Asn Gly Arg
    370                 375                 380

Val Ile Glu Ala Ser Phe Pro Ala Gly Val Asp Ser Ser Pro Arg Ala
385                 390                 395                 400

Ala Glu Pro Val Gln Leu Asn Ser Cys Leu Ala Ala Gly Asp Ile Leu
                405                 410                 415

Ala Leu Val Phe Gly Leu Leu Phe Ala Val Thr Ser Val Ala Phe Leu
            420                 425                 430

Val Gln Met Arg Arg Gln His Arg Arg Gly Thr Lys Gly Gly Val Ser
        435                 440                 445

Tyr Arg Pro Ala Glu Val Ala Glu Thr Gly Ala
    450                 455

<210> SEQ ID NO 216
<211> LENGTH: 346
<212> TYPE: PRT
<213> ORGANISM: Homo sapiens

<400> SEQUENCE: 216

Met Asp Pro Ala Arg Lys Ala Gly Ala Gln Ala Met Ile Trp Thr Ala
1               5                   10                  15

Gly Trp Leu Leu Leu Leu Leu Leu Arg Gly Gly Ala Gln Ala Leu Glu
            20                  25                  30

Cys Tyr Ser Cys Val Gln Lys Ala Asp Asp Gly Cys Ser Pro Asn Lys
        35                  40                  45

Met Lys Thr Val Lys Cys Ala Pro Gly Val Asp Val Cys Thr Glu Ala
    50                  55                  60

Val Gly Ala Val Glu Thr Ile His Gly Gln Phe Ser Leu Ala Val Arg
65                  70                  75                  80

Gly Cys Gly Ser Gly Leu Pro Gly Lys Asn Asp Arg Gly Leu Asp Leu
                85                  90                  95

His Gly Leu Leu Ala Phe Ile Gln Leu Gln Gln Cys Ala Gln Asp Arg
            100                 105                 110

Cys Asn Ala Lys Leu Asn Leu Thr Ser Arg Ala Leu Asp Pro Ala Gly
        115                 120                 125

Asn Glu Ser Ala Tyr Pro Pro Asn Gly Val Glu Cys Tyr Ser Cys Val
    130                 135                 140

Gly Leu Ser Arg Glu Ala Cys Gln Gly Thr Ser Pro Pro Val Val Ser
145                 150                 155                 160

Cys Tyr Asn Ala Ser Asp His Val Tyr Lys Gly Cys Phe Asp Gly Asn
                165                 170                 175

Val Thr Leu Thr Ala Ala Asn Val Thr Val Ser Leu Pro Val Arg Gly
            180                 185                 190

Cys Val Gln Asp Glu Phe Cys Thr Arg Asp Gly Val Thr Gly Pro Gly
        195                 200                 205

Phe Thr Leu Ser Gly Ser Cys Cys Gln Gly Ser Arg Cys Asn Ser Asp
    210                 215                 220

Leu Arg Asn Lys Thr Tyr Phe Ser Pro Arg Ile Pro Pro Leu Val Arg
225                 230                 235                 240

Leu Pro Pro Pro Glu Pro Thr Thr Val Ala Ser Thr Thr Ser Val Thr
            245                 250                 255

Thr Ser Thr Ser Ala Pro Val Arg Pro Thr Ser Thr Thr Lys Pro Met
        260                 265                 270

Pro Ala Pro Thr Ser Gln Thr Pro Arg Gln Gly Val Glu His Glu Ala
        275                 280                 285

Ser Arg Asp Glu Glu Pro Arg Leu Thr Gly Gly Ala Ala Gly His Gln
    290                 295                 300

Asp Arg Ser Asn Ser Gly Gln Tyr Pro Ala Lys Gly Gly Pro Gln Gln
305                 310                 315                 320

Pro His Asn Lys Gly Cys Val Ala Pro Thr Ala Gly Leu Ala Ala Leu
                325                 330                 335

Leu Leu Ala Val Ala Ala Gly Val Leu Leu
            340                 345

<210> SEQ ID NO 217
<211> LENGTH: 61
<212> TYPE: PRT
<213> ORGANISM: Homo sapiens

<400> SEQUENCE: 217

Met Lys Arg Phe Leu Phe Leu Leu Leu Thr Ile Ser Leu Leu Val Met
1               5                   10                  15

Val Gln Ile Gln Thr Gly Leu Ser Gly Gln Asn Asp Thr Ser Gln Thr
            20                  25                  30

Ser Ser Pro Ser Ala Ser Ser Asn Ile Ser Gly Gly Ile Phe Leu Phe
        35                  40                  45

Phe Val Ala Asn Ala Ile Ile His Leu Phe Cys Phe Ser
    50                  55                  60

<210> SEQ ID NO 218
<211> LENGTH: 1255
<212> TYPE: PRT
<213> ORGANISM: Homo sapiens

<400> SEQUENCE: 218

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

```
Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
            405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
            530                 535                 540

Arg Val Leu Gln Gly Leu Pro Arg Glu Tyr Val Asn Ala Arg His Cys
545                 550                 555                 560
```

```
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
        595                 600                 605
Ser Tyr Met Pro Ile Trp Lys Phe Pro Asp Glu Gly Ala Cys Gln
    610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
                645                 650                 655
Ala Val Val Gly Ile Leu Leu Val Val Val Leu Gly Val Val Phe Gly
                660                 665                 670
Ile Leu Ile Lys Arg Arg Gln Gln Lys Ile Arg Lys Tyr Thr Met Arg
                675                 680                 685
Arg Leu Leu Gln Glu Thr Glu Leu Val Glu Pro Leu Thr Pro Ser Gly
            690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
                740                 745                 750
Lys Val Leu Arg Glu Asn Thr Ser Pro Lys Ala Asn Lys Glu Ile Leu
                755                 760                 765
Asp Glu Ala Tyr Val Met Ala Gly Val Gly Ser Pro Tyr Val Ser Arg
                770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
Leu Gly Ser Gln Asp Leu Leu Asn Trp Cys Met Gln Ile Ala Lys Gly
                820                 825                 830
Met Ser Tyr Leu Glu Asp Val Arg Leu Val His Arg Asp Leu Ala Ala
            835                 840                 845
Arg Asn Val Leu Val Lys Ser Pro Asn His Val Lys Ile Thr Asp Phe
            850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                885                 890                 895
Arg Arg Phe Thr His Gln Ser Asp Val Trp Ser Tyr Gly Val Thr Val
            900                 905                 910
Trp Glu Leu Met Thr Phe Gly Ala Lys Pro Tyr Asp Gly Ile Pro Ala
            915                 920                 925
Arg Glu Ile Pro Asp Leu Leu Glu Lys Gly Glu Arg Leu Pro Gln Pro
            930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                965                 970                 975
Ser Arg Met Ala Arg Asp Pro Gln Arg Phe Val Val Ile Gln Asn Glu
```

```
                980              985              990
Asp Leu Gly Pro Ala Ser Pro Leu Asp Ser Thr Phe Tyr Arg Ser Leu
            995              1000             1005

Leu Glu Asp Asp Met Gly Asp Leu Val Asp Ala Glu Glu Tyr Leu
    1010             1015             1020

Val Pro Gln Gln Gly Phe Phe Cys Pro Asp Pro Ala Pro Gly Ala Gly
1025             1030             1035             1040

Gly Met Val His His Arg His Arg Ser Ser Thr Arg Ser Gly Gly
            1045             1050             1055

Gly Asp Leu Thr Leu Gly Leu Glu Pro Ser Glu Glu Glu Ala Pro Arg
            1060             1065             1070

Ser Pro Leu Ala Pro Ser Glu Gly Ala Gly Ser Asp Val Phe Asp Gly
            1075             1080             1085

Asp Leu Gly Met Gly Ala Ala Lys Gly Leu Gln Ser Leu Pro Thr His
            1090             1095             1100

Asp Pro Ser Pro Leu Gln Arg Tyr Ser Glu Asp Pro Thr Val Pro Leu
1105             1110             1115             1120

Pro Ser Glu Thr Asp Gly Tyr Val Ala Pro Leu Thr Cys Ser Pro Gln
            1125             1130             1135

Pro Glu Tyr Val Asn Gln Pro Asp Val Arg Pro Gln Pro Pro Ser Pro
            1140             1145             1150

Arg Glu Gly Pro Leu Pro Ala Ala Arg Pro Ala Gly Ala Thr Leu Glu
            1155             1160             1165

Arg Pro Lys Thr Leu Ser Pro Gly Lys Asn Gly Val Val Lys Asp Val
            1170             1175             1180

Phe Ala Phe Gly Gly Ala Val Glu Asn Pro Glu Tyr Leu Thr Pro Gln
1185             1190             1195             1200

Gly Gly Ala Ala Pro Gln Pro His Pro Pro Ala Phe Ser Pro Ala
            1205             1210             1215

Phe Asp Asn Leu Tyr Tyr Trp Asp Gln Asp Pro Pro Glu Arg Gly Ala
            1220             1225             1230

Pro Pro Ser Thr Phe Lys Gly Thr Pro Thr Ala Glu Asn Pro Glu Tyr
            1235             1240             1245

Leu Gly Leu Asp Val Pro Val
            1250             1255

<210> SEQ ID NO 219
<211> LENGTH: 297
<212> TYPE: PRT
<213> ORGANISM: Homo sapiens

<400> SEQUENCE: 219

Met Thr Thr Pro Arg Asn Ser Val Asn Gly Thr Phe Pro Ala Glu Pro
1               5               10              15

Met Lys Gly Pro Ile Ala Met Gln Ser Gly Pro Lys Pro Leu Phe Arg
            20              25              30

Arg Met Ser Ser Leu Val Gly Pro Thr Gln Ser Phe Phe Met Arg Glu
        35              40              45

Ser Lys Thr Leu Gly Ala Val Gln Ile Met Asn Gly Leu Phe His Ile
    50              55              60

Ala Leu Gly Gly Leu Leu Met Ile Pro Ala Gly Ile Tyr Ala Pro Ile
65              70              75              80

Cys Val Thr Val Trp Tyr Pro Leu Trp Gly Gly Ile Met Tyr Ile Ile
            85              90              95
```

```
Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
            115                 120                 125

Ser Gly Met Ile Leu Ser Ile Met Asp Ile Leu Asn Ile Lys Ile Ser
            130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
            195                 200                 205

Ala Gly Ile Val Glu Asn Glu Trp Lys Arg Thr Cys Ser Arg Pro Lys
            210                 215                 220

Ser Asn Ile Val Leu Leu Ser Ala Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Pro Ile Gln Glu Glu Glu Glu
            260                 265                 270

Glu Glu Thr Glu Thr Asn Phe Pro Glu Pro Gln Asp Gln Glu Ser
            275                 280                 285

Ser Pro Ile Glu Asn Asp Ser Ser Pro
290                 295

<210> SEQ ID NO 220
<211> LENGTH: 595
<212> TYPE: PRT
<213> ORGANISM: Homo sapiens

<400> SEQUENCE: 220

Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
            20                  25                  30

Pro Ser His Tyr Tyr Asp Lys Ala Val Arg Arg Cys Cys Tyr Arg Cys
        35                  40                  45

Pro Met Gly Leu Phe Pro Thr Gln Gln Cys Pro Gln Arg Pro Thr Asp
    50                  55                  60

Cys Arg Lys Gln Cys Glu Pro Asp Tyr Tyr Leu Asp Glu Ala Asp Arg
65                  70                  75                  80

Cys Thr Ala Cys Val Thr Cys Ser Arg Asp Asp Leu Val Glu Lys Thr
                85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe Phe His
            115                 120                 125

Ser Val Cys Pro Ala Gly Met Ile Val Lys Phe Pro Gly Thr Ala Gln
            130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175
```

```
Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
        195                 200                 205

Thr Arg Ala Pro Asp Ser Pro Ser Ser Val Gly Arg Pro Ser Ser Asp
    210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Ala Gly Arg Cys
                245                 250                 255

Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
        275                 280                 285

Cys Ala Thr Ser Ala Thr Asn Ser Arg Ala Arg Cys Val Pro Tyr Pro
    290                 295                 300

Ile Cys Ala Ala Glu Thr Val Thr Lys Pro Gln Asp Met Ala Glu Lys
305                 310                 315                 320

Asp Thr Thr Phe Glu Ala Pro Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
        355                 360                 365

Ser Ala Pro Val Ala Leu Ser Ser Thr Gly Lys Pro Val Leu Asp Ala
    370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
                405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
        435                 440                 445

Ser Gly Ala Ser Val Thr Glu Pro Val Ala Glu Glu Arg Gly Leu Met
    450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495

Pro Arg Asp Leu Pro Glu Pro Arg Val Ser Thr Glu His Thr Asn Asn
            500                 505                 510

Lys Ile Glu Lys Ile Tyr Ile Met Lys Ala Asp Thr Val Ile Val Gly
        515                 520                 525

Thr Val Lys Ala Glu Leu Pro Glu Gly Arg Gly Leu Ala Gly Pro Ala
    530                 535                 540

Glu Pro Glu Leu Glu Glu Glu Leu Glu Ala Asp His Thr Pro His Tyr
545                 550                 555                 560

Pro Glu Gln Glu Thr Glu Pro Pro Leu Gly Ser Cys Ser Asp Val Met
                565                 570                 575

Leu Ser Val Glu Glu Glu Gly Lys Glu Asp Pro Leu Pro Thr Ala Ala
            580                 585                 590
```

```
Ser Gly Lys
        595

<210> SEQ ID NO 221
<211> LENGTH: 847
<212> TYPE: PRT
<213> ORGANISM: Homo sapiens

<400> SEQUENCE: 221

Met His Leu Leu Gly Pro Trp Leu Leu Leu Val Leu Glu Tyr Leu
1               5                   10                  15

Ala Phe Ser Asp Ser Ser Lys Trp Val Phe Glu His Pro Glu Thr Leu
            20                  25                  30

Tyr Ala Trp Glu Gly Ala Cys Val Trp Ile Pro Cys Thr Tyr Arg Ala
            35                  40                  45

Leu Asp Gly Asp Leu Glu Ser Phe Ile Leu Phe His Asn Pro Glu Tyr
        50                  55                  60

Asn Lys Asn Thr Ser Lys Phe Asp Gly Thr Arg Leu Tyr Glu Ser Thr
65                  70                  75                  80

Lys Asp Gly Lys Val Pro Ser Glu Gln Lys Arg Val Gln Phe Leu Gly
                85                  90                  95

Asp Lys Asn Lys Asn Cys Thr Leu Ser Ile His Pro Val His Leu Asn
            100                 105                 110

Asp Ser Gly Gln Leu Gly Leu Arg Met Glu Ser Lys Thr Glu Lys Trp
        115                 120                 125

Met Glu Arg Ile His Leu Asn Val Ser Glu Arg Pro Phe Pro Pro His
    130                 135                 140

Ile Gln Leu Pro Pro Glu Ile Gln Glu Ser Gln Glu Val Thr Leu Thr
145                 150                 155                 160

Cys Leu Leu Asn Phe Ser Cys Tyr Gly Tyr Pro Ile Gln Leu Gln Trp
                165                 170                 175

Leu Leu Glu Gly Val Pro Met Arg Gln Ala Ala Val Thr Ser Thr Ser
            180                 185                 190

Leu Thr Ile Lys Ser Val Phe Thr Arg Ser Glu Leu Lys Phe Ser Pro
        195                 200                 205

Gln Trp Ser His His Gly Lys Ile Val Thr Cys Gln Leu Gln Asp Ala
    210                 215                 220

Asp Gly Lys Phe Leu Ser Asn Asp Thr Val Gln Leu Asn Val Lys His
225                 230                 235                 240

Thr Pro Lys Leu Glu Ile Lys Val Thr Pro Ser Asp Ala Ile Val Arg
                245                 250                 255

Glu Gly Asp Ser Val Thr Met Thr Cys Glu Val Ser Ser Ser Asn Pro
            260                 265                 270

Glu Tyr Thr Thr Val Ser Trp Leu Lys Asp Gly Thr Ser Leu Lys Lys
        275                 280                 285

Gln Asn Thr Phe Thr Leu Asn Leu Arg Glu Val Thr Lys Asp Gln Ser
    290                 295                 300

Gly Lys Tyr Cys Cys Gln Val Ser Asn Asp Val Gly Pro Gly Arg Ser
305                 310                 315                 320

Glu Glu Val Phe Leu Gln Val Gln Tyr Ala Pro Glu Pro Ser Thr Val
                325                 330                 335

Gln Ile Leu His Ser Pro Ala Val Glu Gly Ser Gln Val Glu Phe Leu
            340                 345                 350

Cys Met Ser Leu Ala Asn Pro Leu Pro Thr Asn Tyr Thr Trp Tyr His
        355                 360                 365
```

```
Asn Gly Lys Glu Met Gln Gly Arg Thr Glu Lys Val His Ile Pro
    370                 375                 380

Lys Ile Leu Pro Trp His Ala Gly Thr Tyr Ser Cys Val Ala Glu Asn
385                 390                 395                 400

Ile Leu Gly Thr Gly Gln Arg Gly Pro Gly Ala Glu Leu Asp Val Gln
                405                 410                 415

Tyr Pro Pro Lys Lys Val Thr Thr Val Ile Gln Asn Pro Met Pro Ile
            420                 425                 430

Arg Glu Gly Asp Thr Val Thr Leu Ser Cys Asn Tyr Asn Ser Ser Asn
            435                 440                 445

Pro Ser Val Thr Arg Tyr Glu Trp Lys Pro His Gly Ala Trp Glu Glu
    450                 455                 460

Pro Ser Leu Gly Val Leu Lys Ile Gln Asn Val Gly Trp Asp Asn Thr
465                 470                 475                 480

Thr Ile Ala Cys Ala Ala Cys Asn Ser Trp Cys Ser Trp Ala Ser Pro
                485                 490                 495

Val Ala Leu Asn Val Gln Tyr Ala Pro Arg Asp Val Arg Val Arg Lys
                500                 505                 510

Ile Lys Pro Leu Ser Glu Ile His Ser Gly Asn Ser Val Ser Leu Gln
    515                 520                 525

Cys Asp Phe Ser Ser Ser His Pro Lys Glu Val Gln Phe Phe Trp Glu
530                 535                 540

Lys Asn Gly Arg Leu Leu Gly Lys Glu Ser Gln Leu Asn Phe Asp Ser
545                 550                 555                 560

Ile Ser Pro Glu Asp Ala Gly Ser Tyr Ser Cys Trp Val Asn Asn Ser
                565                 570                 575

Ile Gly Gln Thr Ala Ser Lys Ala Trp Thr Leu Glu Val Leu Tyr Ala
                580                 585                 590

Pro Arg Arg Leu Arg Val Ser Met Ser Pro Gly Asp Gln Val Met Glu
    595                 600                 605

Gly Lys Ser Ala Thr Leu Thr Cys Glu Ser Asp Ala Asn Pro Pro Val
    610                 615                 620

Ser His Tyr Thr Trp Phe Asp Trp Asn Asn Gln Ser Leu Pro Tyr His
625                 630                 635                 640

Ser Gln Lys Leu Arg Leu Glu Pro Val Lys Val Gln His Ser Gly Ala
                645                 650                 655

Tyr Trp Cys Gln Gly Thr Asn Ser Val Gly Lys Gly Arg Ser Pro Leu
                660                 665                 670

Ser Thr Leu Thr Val Tyr Tyr Ser Pro Glu Thr Ile Gly Arg Arg Val
    675                 680                 685

Ala Val Gly Leu Gly Ser Cys Leu Ala Ile Leu Ile Leu Ala Ile Cys
    690                 695                 700

Gly Leu Lys Leu Gln Arg Arg Trp Lys Arg Thr Gln Ser Gln Gln Gly
705                 710                 715                 720

Leu Gln Glu Asn Ser Ser Gly Gln Ser Phe Phe Val Arg Asn Lys Lys
                725                 730                 735

Val Arg Arg Ala Pro Leu Ser Glu Gly Pro His Ser Leu Gly Cys Tyr
            740                 745                 750

Asn Pro Met Met Glu Asp Gly Ile Ser Tyr Thr Thr Leu Arg Phe Pro
            755                 760                 765

Glu Met Asn Ile Pro Arg Thr Gly Asp Ala Glu Ser Ser Glu Met Gln
770                 775                 780
```

Arg Pro Pro Asp Cys Asp Asp Thr Val Thr Tyr Ser Ala Leu His
785                 790                 795                 800

Lys Arg Gln Val Gly Asp Tyr Glu Asn Val Ile Pro Asp Phe Pro Glu
            805                 810                 815

Asp Glu Gly Ile His Tyr Ser Glu Leu Ile Gln Phe Gly Val Gly Glu
            820                 825                 830

Arg Pro Gln Ala Gln Glu Asn Val Asp Tyr Val Ile Leu Lys His
        835                 840                 845

<210> SEQ ID NO 222
<211> LENGTH: 364
<212> TYPE: PRT
<213> ORGANISM: Homo sapiens

<400> SEQUENCE: 222

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
                20                  25                  30

Glu Gly Leu Cys Val Leu Val Pro Cys Thr Phe Phe His Pro Ile Pro
            35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

```
Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360

<210> SEQ ID NO 223
<211> LENGTH: 572
<212> TYPE: PRT
<213> ORGANISM: Homo sapiens

<400> SEQUENCE: 223

Met Glu Cys Leu Tyr Tyr Phe Leu Gly Phe Leu Leu Leu Ala Ala Arg
1               5                   10                  15

Leu Pro Leu Asp Ala Ala Lys Arg Phe His Asp Val Leu Gly Asn Glu
            20                  25                  30

Arg Pro Ser Ala Tyr Met Arg Glu His Asn Gln Leu Asn Gly Trp Ser
        35                  40                  45

Ser Asp Glu Asn Asp Trp Asn Glu Lys Leu Tyr Pro Val Trp Lys Arg
50                  55                  60

Gly Asp Met Arg Trp Lys Asn Ser Trp Lys Gly Gly Arg Val Gln Ala
65                  70                  75                  80

Val Leu Thr Ser Asp Ser Pro Ala Leu Val Gly Ser Asn Ile Thr Phe
                85                  90                  95

Ala Val Asn Leu Ile Phe Pro Arg Cys Gln Lys Glu Asp Ala Asn Gly
            100                 105                 110

Asn Ile Val Tyr Glu Lys Asn Cys Arg Asn Glu Ala Gly Leu Ser Ala
        115                 120                 125

Asp Pro Tyr Val Tyr Asn Trp Thr Ala Trp Ser Glu Asp Ser Asp Gly
130                 135                 140

Glu Asn Gly Thr Gly Gln Ser His His Asn Val Phe Pro Asp Gly Lys
145                 150                 155                 160

Pro Phe Pro His His Pro Gly Trp Arg Arg Trp Asn Phe Ile Tyr Val
                165                 170                 175

Phe His Thr Leu Gly Gln Tyr Phe Gln Lys Leu Gly Arg Cys Ser Val
            180                 185                 190

Arg Val Ser Val Asn Thr Ala Asn Val Thr Leu Gly Pro Gln Leu Met
        195                 200                 205

Glu Val Thr Val Tyr Arg Arg His Gly Arg Ala Tyr Val Pro Ile Ala
210                 215                 220

Gln Val Lys Asp Val Tyr Val Val Thr Asp Gln Ile Pro Val Phe Val
225                 230                 235                 240

Thr Met Phe Gln Lys Asn Asp Arg Asn Ser Ser Asp Glu Thr Phe Leu
                245                 250                 255

Lys Asp Leu Pro Ile Met Phe Asp Val Leu Ile His Asp Pro Ser His
            260                 265                 270

Phe Leu Asn Tyr Ser Thr Ile Asn Tyr Lys Trp Ser Phe Gly Asp Asn
        275                 280                 285

Thr Gly Leu Phe Val Ser Thr Asn His Thr Val Asn His Thr Tyr Val
290                 295                 300

Leu Asn Gly Thr Phe Ser Leu Asn Leu Thr Val Lys Ala Ala Ala Pro
305                 310                 315                 320

Gly Pro Cys Pro Pro Pro Pro Pro Pro Pro Arg Pro Ser Lys Pro Thr
```

325                 330                 335
Pro Ser Leu Ala Thr Thr Leu Lys Ser Tyr Asp Ser Asn Thr Pro Gly
            340                 345                 350

Pro Ala Gly Asp Asn Pro Leu Glu Leu Ser Arg Ile Pro Asp Glu Asn
        355                 360                 365

Cys Gln Ile Asn Arg Tyr Gly His Phe Gln Ala Thr Ile Thr Ile Val
    370                 375                 380

Glu Gly Ile Leu Glu Val Asn Ile Ile Gln Met Thr Asp Val Leu Met
385                 390                 395                 400

Pro Val Pro Trp Pro Glu Ser Ser Leu Ile Asp Phe Val Val Thr Cys
            405                 410                 415

Gln Gly Ser Ile Pro Thr Glu Val Cys Thr Ile Ile Ser Asp Pro Thr
        420                 425                 430

Cys Glu Ile Thr Gln Asn Thr Val Cys Ser Pro Val Asp Val Asp Glu
    435                 440                 445

Met Cys Leu Leu Thr Val Arg Arg Thr Phe Asn Gly Ser Gly Thr Tyr
450                 455                 460

Cys Val Asn Leu Thr Leu Gly Asp Asp Thr Ser Leu Ala Leu Thr Ser
465                 470                 475                 480

Thr Leu Ile Ser Val Pro Asp Arg Asp Pro Ala Ser Pro Leu Arg Met
            485                 490                 495

Ala Asn Ser Ala Leu Ile Ser Val Gly Cys Leu Ala Ile Phe Val Thr
        500                 505                 510

Val Ile Ser Leu Leu Val Tyr Lys Lys His Lys Glu Tyr Asn Pro Ile
    515                 520                 525

Glu Asn Ser Pro Gly Asn Val Val Arg Ser Lys Gly Leu Ser Val Phe
530                 535                 540

Leu Asn Arg Ala Lys Ala Val Phe Phe Pro Gly Asn Gln Glu Lys Asp
545                 550                 555                 560

Pro Leu Leu Lys Asn Gln Glu Phe Lys Gly Val Ser
            565                 570

<210> SEQ ID NO 224
<211> LENGTH: 848
<212> TYPE: PRT
<213> ORGANISM: Homo sapiens

<400> SEQUENCE: 224

Met Leu Gln Thr Lys Asp Leu Ile Trp Thr Leu Phe Phe Leu Gly Thr
1               5                   10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
    50                  55                  60

Asn Gln Gln Arg Ile Ser Val Val Trp Asn Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

```
Phe Arg Glu Gly Glu Asp Ala Val Ile Val Cys Asp Val Val Ser Ser
130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205

Asn Val Pro Pro Thr Ile Gln Ala Arg Gln Asn Ile Val Asn Ala Thr
210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
                245                 250                 255

Glu Glu Asp Asp Glu Lys Tyr Ile Phe Ser Asp Ser Ser Gln Leu
            260                 265                 270

Thr Ile Lys Lys Val Asp Lys Asn Asp Glu Ala Glu Tyr Ile Cys Ile
        275                 280                 285

Ala Glu Asn Lys Ala Gly Glu Gln Asp Ala Thr Ile His Leu Lys Val
290                 295                 300

Phe Ala Lys Pro Lys Ile Thr Tyr Val Glu Asn Gln Thr Ala Met Glu
305                 310                 315                 320

Leu Glu Glu Gln Val Thr Leu Thr Cys Glu Ala Ser Gly Asp Pro Ile
                325                 330                 335

Pro Ser Ile Thr Trp Arg Thr Ser Thr Arg Asn Ile Ser Ser Glu Glu
            340                 345                 350

Lys Thr Leu Asp Gly His Met Val Val Arg Ser His Ala Arg Val Ser
        355                 360                 365

Ser Leu Thr Leu Lys Ser Ile Gln Tyr Thr Asp Ala Gly Glu Tyr Ile
370                 375                 380

Cys Thr Ala Ser Asn Thr Ile Gly Gln Asp Ser Gln Ser Met Tyr Leu
385                 390                 395                 400

Glu Val Gln Tyr Ala Pro Lys Leu Gln Gly Pro Val Ala Val Tyr Thr
                405                 410                 415

Trp Glu Gly Asn Gln Val Asn Ile Thr Cys Glu Val Phe Ala Tyr Pro
            420                 425                 430

Ser Ala Thr Ile Ser Trp Phe Arg Asp Gly Gln Leu Leu Pro Ser Ser
        435                 440                 445

Asn Tyr Ser Asn Ile Lys Ile Tyr Asn Thr Pro Ser Ala Ser Tyr Leu
450                 455                 460

Glu Val Thr Pro Asp Ser Glu Asn Asp Phe Gly Asn Tyr Asn Cys Thr
465                 470                 475                 480

Ala Val Asn Arg Ile Gly Gln Glu Ser Leu Glu Phe Ile Leu Val Gln
                485                 490                 495

Ala Asp Thr Pro Ser Ser Pro Ser Ile Asp Gln Val Glu Pro Tyr Ser
            500                 505                 510

Ser Thr Ala Gln Val Gln Phe Asp Glu Pro Glu Ala Thr Gly Gly Val
        515                 520                 525

Pro Ile Leu Lys Tyr Lys Ala Glu Trp Arg Ala Val Gly Glu Glu Val
530                 535                 540

Trp His Ser Lys Trp Tyr Asp Ala Lys Glu Ala Ser Met Glu Gly Ile
```

```
            545                 550                 555                 560
Val Thr Ile Val Gly Leu Lys Pro Glu Thr Thr Tyr Ala Val Arg Leu
                565                 570                 575

Ala Ala Leu Asn Gly Lys Gly Leu Gly Glu Ile Ser Ala Ala Ser Glu
                580                 585                 590

Phe Lys Thr Gln Pro Val Gln Gly Glu Pro Ser Ala Pro Lys Leu Glu
                595                 600                 605

Gly Gln Met Gly Glu Asp Gly Asn Ser Ile Lys Val Asn Leu Ile Lys
                610                 615                 620

Gln Asp Asp Gly Gly Ser Pro Ile Arg His Tyr Leu Val Arg Tyr Arg
625                 630                 635                 640

Ala Leu Ser Ser Glu Trp Lys Pro Glu Ile Arg Leu Pro Ser Gly Ser
                645                 650                 655

Asp His Val Met Leu Lys Ser Leu Asp Trp Asn Ala Glu Tyr Glu Val
                660                 665                 670

Tyr Val Val Ala Glu Asn Gln Gln Gly Lys Ser Lys Ala Ala His Phe
                675                 680                 685

Val Phe Arg Thr Ser Ala Gln Pro Thr Ala Ile Pro Ala Asn Gly Ser
                690                 695                 700

Pro Thr Ser Gly Leu Ser Thr Gly Ala Ile Val Gly Ile Leu Ile Val
705                 710                 715                 720

Ile Phe Val Leu Leu Leu Val Val Val Asp Ile Thr Cys Tyr Phe Leu
                725                 730                 735

Asn Lys Cys Gly Leu Phe Met Cys Ile Ala Val Asn Leu Cys Gly Lys
                740                 745                 750

Ala Gly Pro Gly Ala Lys Gly Lys Asp Met Glu Glu Gly Lys Ala Ala
                755                 760                 765

Phe Ser Lys Asp Glu Ser Lys Glu Pro Ile Val Glu Val Arg Thr Glu
                770                 775                 780

Glu Glu Arg Thr Pro Asn His Asp Gly Gly Lys His Thr Glu Pro Asn
785                 790                 795                 800

Glu Thr Thr Pro Leu Thr Glu Pro Glu Lys Gly Pro Val Glu Ala Lys
                805                 810                 815

Pro Glu Cys Gln Glu Thr Glu Thr Lys Pro Ala Pro Ala Glu Val Lys
                820                 825                 830

Thr Val Pro Asn Asp Ala Thr Gln Thr Lys Glu Asn Glu Ser Lys Ala
                835                 840                 845

<210> SEQ ID NO 225
<211> LENGTH: 193
<212> TYPE: PRT
<213> ORGANISM: Homo sapiens

<400> SEQUENCE: 225

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
                35                  40                  45

Pro Leu Glu Ser Leu Gly Trp Asp Val Ala Glu Leu Gln Leu Asn His
                50                  55                  60

Thr Gly Pro Gln Gln Asp Pro Arg Leu Tyr Trp Gln Gly Gly Pro Ala
65                  70                  75                  80
```

```
Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
            115                 120                 125

Ala Val Gly Ile Cys Ser Pro Ala Ser Arg Ser Ile Ser Leu Leu Arg
            130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
                180                 185                 190

Pro

<210> SEQ ID NO 226
<211> LENGTH: 232
<212> TYPE: PRT
<213> ORGANISM: Homo sapiens

<400> SEQUENCE: 226

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
            115                 120                 125

Gln Asn Ala Thr Lys Tyr Gly Asn Met Thr Glu Asp His Val Met His
130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
            195                 200                 205

Glu Ser Leu Glu Leu Glu Asp Pro Ser Ser Gly Leu Gly Val Thr Lys
        210                 215                 220

Gln Asp Leu Gly Pro Val Pro Met
225                 230

<210> SEQ ID NO 227
<211> LENGTH: 557
```

<212> TYPE: PRT
<213> ORGANISM: Homo sapiens

<400> SEQUENCE: 227

```
Met Pro Pro Pro Arg Leu Leu Phe Phe Leu Leu Phe Leu Thr Pro Met
1               5                   10                  15

Glu Val Arg Pro Glu Glu Pro Leu Val Lys Val Glu Glu Gly Asp
            20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
                100                 105                 110

Val Asn Val Glu Gly Ser Gly Glu Leu Phe Arg Trp Asn Val Ser Asp
            115                 120                 125

Leu Gly Gly Leu Gly Cys Gly Leu Lys Asn Arg Ser Ser Glu Gly Pro
            130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
        210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
        290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
        370                 375                 380

Val Gln Ala Asp Gly Ala Leu Gly Ser Arg Ser Pro Pro Gly Val Gly
385                 390                 395                 400
```

```
Pro Glu Glu Glu Gly Gly Tyr Glu Pro Asp Ser Glu
            405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Ala
            485                 490                 495

Gly Ser Gln Ser Tyr Glu Asp Met Arg Gly Ile Leu Tyr Ala Ala Pro
            500                 505                 510

Gln Leu Arg Ser Ile Arg Gly Gln Pro Gly Pro Asn His Glu Glu Asp
            515                 520                 525

Ala Asp Ser Tyr Glu Asn Met Asp Asn Pro Asp Gly Pro Asp Pro Ala
            530                 535                 540

Trp Gly Gly Gly Gly Arg Met Gly Thr Trp Ser Thr Arg
545                 550                 555

<210> SEQ ID NO 228
<211> LENGTH: 273
<212> TYPE: PRT
<213> ORGANISM: Homo sapiens

<400> SEQUENCE: 228

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Leu Ser Thr Gly Val Ser Phe Phe Phe Leu Ser
50                  55                  60

Phe His Ile Ser Asn Leu Gln Phe Asn Ser Ser Leu Glu Asp Pro Ser
65                  70                  75                  80

Thr Asp Tyr Tyr Gln Glu Leu Gln Arg Asp Ile Ser Glu Met Phe Leu
            85                  90                  95

Gln Ile Tyr Lys Gln Gly Gly Phe Leu Gly Leu Ser Asn Ile Lys Phe
            100                 105                 110

Arg Pro Gly Ser Val Val Val Gln Leu Thr Leu Ala Phe Arg Glu Gly
            115                 120                 125

Thr Ile Asn Val His Asp Val Glu Thr Gln Phe Asn Gln Tyr Lys Thr
130                 135                 140

Glu Ala Ala Ser Arg Tyr Asn Leu Thr Ile Ser Asp Val Ser Val Ser
145                 150                 155                 160

Asp Val Pro Phe Pro Phe Ser Ala Gln Ser Gly Ala Gly Val Pro Gly
            165                 170                 175

Trp Gly Ile Ala Leu Leu Val Leu Val Cys Val Leu Val Ala Leu Ala
            180                 185                 190

Ile Val Tyr Leu Ile Ala Leu Ala Val Cys Gln Cys Arg Arg Lys Asn
            195                 200                 205

Tyr Gly Gln Leu Asp Ile Phe Pro Ala Arg Asp Thr Tyr His Pro Met
```

```
            210                 215                 220
Ser Glu Tyr Pro Thr Tyr His Thr His Gly Arg Tyr Val Pro Ser
225                 230                 235                 240

Ser Thr Asp Arg Ser Pro Tyr Glu Lys Val Ser Ala Gly Asn Gly Gly
                245                 250                 255

Ser Ser Leu Ser Tyr Thr Asn Pro Ala Val Ala Ala Thr Ser Ala Asn
                260                 265                 270

Leu

<210> SEQ ID NO 229
<211> LENGTH: 310
<212> TYPE: PRT
<213> ORGANISM: Homo sapiens

<400> SEQUENCE: 229

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
                20                  25                  30

Asp Gln Asp Gly Ser Gly Asp Asp Ser Asp Asn Phe Ser Gly Ser Gly
            35                  40                  45

Ala Gly Ala Leu Gln Asp Ile Thr Leu Ser Gln Gln Thr Pro Ser Thr
        50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Gln Ala Ser Thr Thr Thr Ala Thr Thr
130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
```

```
305                 310
```

<210> SEQ ID NO 230
<211> LENGTH: 1048
<212> TYPE: PRT
<213> ORGANISM: Homo sapiens

<400> SEQUENCE: 230

| | | | | | | | | | | | | | | |
|---|---|---|---|---|---|---|---|---|---|---|---|---|---|---|
| Met | Ala | Phe | Pro | Pro | Arg | Arg | Leu | Arg | Leu | Gly | Pro | Arg | Gly | Leu |
| 1 | | | | 5 | | | | | 10 | | | | | 15 |
| Pro | Leu | Leu | Leu | Ser | Gly | Leu | Leu | Pro | Leu | Cys | Arg | Ala | Phe | Asn |
| | | | | 20 | | | | | 25 | | | | | 30 |
| Leu | Asp | Val | Asp | Ser | Pro | Ala | Glu | Tyr | Ser | Gly | Pro | Glu | Gly | Ser | Tyr |
| | | | 35 | | | | | 40 | | | | | 45 | | |
| Phe | Gly | Phe | Ala | Val | Asp | Phe | Phe | Val | Pro | Ser | Ala | Ser | Ser | Arg | Met |
| | 50 | | | | | 55 | | | | | 60 | | | | |
| Phe | Leu | Leu | Val | Gly | Ala | Pro | Lys | Ala | Asn | Thr | Thr | Gln | Pro | Gly | Ile |
| 65 | | | | | 70 | | | | | 75 | | | | | 80 |
| Val | Glu | Gly | Gly | Gln | Val | Leu | Lys | Cys | Asp | Trp | Ser | Ser | Thr | Arg | Arg |
| | | | | 85 | | | | | 90 | | | | | 95 | |
| Cys | Gln | Pro | Ile | Glu | Phe | Asp | Ala | Thr | Gly | Asn | Arg | Asp | Tyr | Ala | Lys |
| | | | 100 | | | | | 105 | | | | | 110 | | |
| Asp | Asp | Pro | Leu | Glu | Phe | Lys | Ser | His | Gln | Trp | Phe | Gly | Ala | Ser | Val |
| | | 115 | | | | | 120 | | | | | 125 | | | |
| Arg | Ser | Lys | Gln | Asp | Lys | Ile | Leu | Ala | Cys | Ala | Pro | Leu | Tyr | His | Trp |
| | 130 | | | | | 135 | | | | | 140 | | | | |
| Arg | Thr | Glu | Met | Lys | Gln | Arg | Glu | Pro | Val | Gly | Thr | Cys | Phe | Leu |
| 145 | | | | | 150 | | | | | 155 | | | | | 160 |
| Gln | Asp | Gly | Thr | Lys | Thr | Val | Glu | Tyr | Ala | Pro | Cys | Arg | Ser | Gln | Asp |
| | | | | 165 | | | | | 170 | | | | | 175 | |
| Ile | Asp | Ala | Asp | Gly | Gln | Gly | Phe | Cys | Gln | Gly | Gly | Phe | Ser | Ile | Asp |
| | | | 180 | | | | | 185 | | | | | 190 | | |
| Phe | Thr | Lys | Ala | Asp | Arg | Val | Leu | Leu | Gly | Gly | Pro | Gly | Ser | Phe | Tyr |
| | | 195 | | | | | 200 | | | | | 205 | | | |
| Trp | Gln | Gly | Gln | Leu | Ile | Ser | Asp | Gln | Val | Ala | Glu | Ile | Val | Ser | Lys |
| | 210 | | | | | 215 | | | | | 220 | | | | |
| Tyr | Asp | Pro | Asn | Val | Tyr | Ser | Ile | Lys | Tyr | Asn | Asn | Gln | Leu | Ala | Thr |
| 225 | | | | | 230 | | | | | 235 | | | | | 240 |
| Arg | Thr | Ala | Gln | Ala | Ile | Phe | Asp | Asp | Ser | Tyr | Leu | Gly | Tyr | Ser | Val |
| | | | | 245 | | | | | 250 | | | | | 255 | |
| Ala | Val | Gly | Asp | Phe | Asn | Gly | Asp | Gly | Ile | Asp | Asp | Phe | Val | Ser | Gly |
| | | | 260 | | | | | 265 | | | | | 270 | | |
| Val | Pro | Arg | Ala | Ala | Arg | Thr | Leu | Gly | Met | Val | Tyr | Ile | Tyr | Asp | Gly |
| | | 275 | | | | | 280 | | | | | 285 | | | |
| Lys | Asn | Met | Ser | Ser | Leu | Tyr | Asn | Phe | Thr | Gly | Glu | Gln | Met | Ala | Ala |
| | 290 | | | | | 295 | | | | | 300 | | | | |
| Tyr | Phe | Gly | Phe | Ser | Val | Ala | Ala | Thr | Asp | Ile | Asn | Gly | Asp | Asp | Tyr |
| 305 | | | | | 310 | | | | | 315 | | | | | 320 |
| Ala | Asp | Val | Phe | Ile | Gly | Ala | Pro | Leu | Phe | Met | Asp | Arg | Gly | Ser | Asp |
| | | | | 325 | | | | | 330 | | | | | 335 | |
| Gly | Lys | Leu | Gln | Glu | Val | Gly | Gln | Val | Ser | Val | Ser | Leu | Gln | Arg | Ala |
| | | | 340 | | | | | 345 | | | | | 350 | | |
| Ser | Gly | Asp | Phe | Gln | Thr | Thr | Lys | Leu | Asn | Gly | Phe | Glu | Val | Phe | Ala |
| | | 355 | | | | | 360 | | | | | 365 | | | |

-continued

```
Arg Phe Gly Ser Ala Ile Ala Pro Leu Gly Asp Leu Asp Gln Asp Gly
    370                 375                 380

Phe Asn Asp Ile Ala Ile Ala Ala Pro Tyr Gly Gly Glu Asp Lys Lys
385                 390                 395                 400

Gly Ile Val Tyr Ile Phe Asn Gly Arg Ser Thr Gly Leu Asn Ala Val
                405                 410                 415

Pro Ser Gln Ile Leu Glu Gly Gln Trp Ala Ala Arg Ser Met Pro Pro
            420                 425                 430

Ser Phe Gly Tyr Ser Met Lys Gly Ala Thr Asp Ile Asp Lys Asn Gly
        435                 440                 445

Tyr Pro Asp Leu Ile Val Gly Ala Phe Gly Val Asp Arg Ala Ile Leu
    450                 455                 460

Tyr Arg Ala Arg Pro Val Ile Thr Val Asn Ala Gly Leu Glu Val Tyr
465                 470                 475                 480

Pro Ser Ile Leu Asn Gln Asp Asn Lys Thr Cys Ser Leu Pro Gly Thr
                485                 490                 495

Ala Leu Lys Val Ser Cys Phe Asn Val Arg Phe Cys Leu Lys Ala Asp
            500                 505                 510

Gly Lys Gly Val Leu Pro Arg Lys Leu Asn Phe Gln Val Glu Leu Leu
        515                 520                 525

Leu Asp Lys Leu Lys Gln Lys Gly Ala Ile Arg Arg Ala Leu Phe Leu
    530                 535                 540

Tyr Ser Arg Ser Pro Ser His Ser Lys Asn Met Thr Ile Ser Arg Gly
545                 550                 555                 560

Gly Leu Met Gln Cys Glu Glu Leu Ile Ala Tyr Leu Arg Asp Glu Ser
                565                 570                 575

Glu Phe Arg Asp Lys Leu Thr Pro Ile Thr Ile Phe Met Glu Tyr Arg
            580                 585                 590

Leu Asp Tyr Arg Thr Ala Ala Asp Thr Thr Gly Leu Gln Pro Ile Leu
        595                 600                 605

Asn Gln Phe Thr Pro Ala Asn Ile Ser Arg Gln Ala His Ile Leu Leu
    610                 615                 620

Asp Cys Gly Glu Asp Asn Val Cys Lys Pro Lys Leu Glu Val Ser Val
625                 630                 635                 640

Asp Ser Asp Gln Lys Lys Ile Tyr Ile Gly Asp Asp Asn Pro Leu Thr
                645                 650                 655

Leu Ile Val Lys Ala Gln Asn Gln Gly Glu Gly Ala Tyr Glu Ala Glu
            660                 665                 670

Leu Ile Val Ser Ile Pro Leu Gln Ala Asp Phe Ile Gly Val Val Arg
        675                 680                 685

Asn Asn Glu Ala Leu Ala Arg Leu Ser Cys Ala Phe Lys Thr Glu Asn
    690                 695                 700

Gln Thr Arg Gln Val Val Cys Asp Leu Gly Asn Pro Met Lys Ala Gly
705                 710                 715                 720

Thr Gln Leu Leu Ala Gly Leu Arg Phe Ser Val His Gln Gln Ser Glu
                725                 730                 735

Met Asp Thr Ser Val Lys Phe Asp Leu Gln Ile Gln Ser Ser Asn Leu
            740                 745                 750

Phe Asp Lys Val Ser Pro Val Val Ser His Lys Val Asp Leu Ala Val
        755                 760                 765

Leu Ala Ala Val Glu Ile Arg Gly Val Ser Ser Pro Asp His Ile Phe
    770                 775                 780

Leu Pro Ile Pro Asn Trp Glu His Lys Glu Asn Pro Glu Thr Glu Glu
```

```
                785                 790                 795                 800
Asp Val Gly Pro Val Gln His Ile Tyr Glu Leu Arg Asn Asn Gly
                805                 810                 815
Pro Ser Ser Phe Ser Lys Ala Met Leu His Leu Gln Trp Pro Tyr Lys
                820                 825                 830
Tyr Asn Asn Thr Leu Leu Tyr Ile Leu His Tyr Asp Ile Asp Gly
                835                 840                 845
Pro Met Asn Cys Thr Ser Asp Met Glu Ile Asn Pro Leu Arg Ile Lys
    850                 855                 860
Ile Ser Ser Leu Gln Thr Thr Glu Lys Asn Asp Thr Val Ala Gly Gln
865                 870                 875                 880
Gly Glu Arg Asp His Leu Ile Thr Lys Arg Asp Leu Ala Leu Ser Glu
                885                 890                 895
Gly Asp Ile His Thr Leu Gly Cys Gly Val Ala Gln Cys Leu Lys Ile
                900                 905                 910
Val Cys Gln Val Gly Arg Leu Asp Arg Gly Lys Ser Ala Ile Leu Tyr
            915                 920                 925
Val Lys Ser Leu Leu Trp Thr Glu Thr Phe Met Asn Lys Glu Asn Gln
    930                 935                 940
Asn His Ser Tyr Ser Leu Lys Ser Ser Ala Ser Phe Asn Val Ile Glu
945                 950                 955                 960
Phe Pro Tyr Lys Asn Leu Pro Ile Glu Asp Ile Thr Asn Ser Thr Leu
                965                 970                 975
Val Thr Thr Asn Val Thr Trp Gly Ile Gln Pro Ala Pro Met Pro Val
                980                 985                 990
Pro Val Trp Val Ile Ile Leu Ala Val Leu Ala Gly Leu Leu Leu
            995                 1000                1005
Ala Val Leu Val Phe Val Met Tyr Arg Met Gly Phe Phe Lys Arg Val
        1010                1015                1020
Arg Pro Pro Gln Glu Glu Gln Glu Arg Glu Gln Leu Gln Pro His Glu
1025                1030                1035                1040
Asn Gly Glu Gly Asn Ser Glu Thr
                1045

<210> SEQ ID NO 231
<211> LENGTH: 188
<212> TYPE: PRT
<213> ORGANISM: Homo sapiens

<400> SEQUENCE: 231

Met Asp Cys Arg Lys Met Ala Arg Phe Ser Tyr Ser Val Ile Trp Ile
1               5                   10                  15
Met Ala Ile Ser Lys Val Phe Glu Leu Gly Leu Val Ala Gly Leu Gly
                20                  25                  30
His Gln Glu Phe Ala Arg Pro Ser Arg Gly Tyr Leu Ala Phe Arg Asp
            35                  40                  45
Asp Ser Ile Trp Pro Gln Glu Glu Pro Ala Ile Arg Pro Arg Ser Ser
        50                  55                  60
Gln Arg Val Pro Pro Met Gly Ile Gln His Ser Lys Glu Leu Asn Arg
65                  70                  75                  80
Thr Cys Cys Leu Asn Gly Gly Thr Cys Met Leu Gly Ser Phe Cys Ala
                85                  90                  95
Cys Pro Pro Ser Phe Tyr Gly Arg Asn Cys Glu His Asp Val Arg Lys
                100                 105                 110
```

Glu Asn Cys Gly Ser Val Pro His Asp Thr Trp Leu Pro Lys Lys Cys
            115                 120                 125

Ser Leu Cys Lys Cys Trp His Gly Gln Leu Arg Cys Phe Pro Gln Ala
130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
            165                 170                 175

Leu Val Gly Ile Cys Leu Ser Ile Gln Ser Tyr Tyr
            180                 185

<210> SEQ ID NO 232
<211> LENGTH: 750
<212> TYPE: PRT
<213> ORGANISM: Homo sapiens

<400> SEQUENCE: 232

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
            35                  40                  45

Ala Thr Asn Ile Thr Pro Lys His Asn Met Lys Ala Phe Leu Asp Glu
50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
            85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
            115                 120                 125

Ser Ile Ile Asn Glu Asp Gly Asn Glu Ile Phe Asn Thr Ser Leu Phe
130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
            165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
            195                 200                 205

Phe Arg Gly Asn Lys Val Lys Asn Ala Gln Leu Ala Gly Ala Lys Gly
            210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
            245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
            275                 280                 285

Leu Pro Ser Ile Pro Val His Pro Ile Gly Tyr Tyr Asp Ala Gln Lys
            290                 295                 300

```
Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
            325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
            355                 360                 365

Asp Arg Tyr Val Ile Leu Gly His Arg Asp Ser Trp Val Phe Gly
370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
            405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
            485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
            565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
            610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
            645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720
```

```
Pro Ser Lys Ala Trp Gly Glu Val Lys Arg Gln Ile Tyr Val Ala Ala
                725                 730                 735

Phe Thr Val Gln Ala Ala Glu Thr Leu Ser Glu Val Ala
            740                 745                 750

<210> SEQ ID NO 233
<211> LENGTH: 976
<212> TYPE: PRT
<213> ORGANISM: Homo sapiens

<400> SEQUENCE: 233

Met Glu Leu Gln Ala Ala Arg Ala Cys Phe Ala Leu Leu Trp Gly Cys
1               5                   10                  15

Ala Leu Ala Ala Ala Ala Ala Gln Gly Lys Glu Val Val Leu Leu
            20                  25                  30

Asp Phe Ala Ala Ala Gly Gly Glu Leu Gly Trp Leu Thr His Pro Tyr
        35                  40                  45

Gly Lys Gly Trp Asp Leu Met Gln Asn Ile Met Asn Asp Met Pro Ile
50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Ile Phe Ile
                85                  90                  95

Glu Leu Lys Phe Thr Val Arg Asp Cys Asn Ser Phe Pro Gly Gly Ala
            100                 105                 110

Ser Ser Cys Lys Glu Thr Phe Asn Leu Tyr Tyr Ala Glu Ser Asp Leu
        115                 120                 125

Asp Tyr Gly Thr Asn Phe Gln Lys Arg Leu Phe Thr Lys Ile Asp Thr
130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175

Gly Phe Tyr Leu Ala Phe Gln Asp Ile Gly Ala Cys Val Ala Leu Leu
            180                 185                 190

Ser Val Arg Val Tyr Tyr Lys Lys Cys Pro Glu Leu Leu Gln Gly Leu
        195                 200                 205

Ala His Phe Pro Glu Thr Ile Ala Gly Ser Asp Ala Pro Ser Leu Ala
210                 215                 220

Thr Val Ala Gly Thr Cys Val Asp His Ala Val Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285

Pro Cys Leu Glu Cys Pro Glu His Thr Leu Pro Ser Pro Glu Gly Ala
290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
            340                 345                 350
```

```
Asp Ser Gly Gly Arg Glu Asp Ile Val Tyr Ser Val Thr Cys Glu Gln
            355                 360                 365

Cys Trp Pro Glu Ser Gly Glu Cys Gly Pro Cys Glu Ala Ser Val Arg
370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
                420                 425                 430

Ser Ile Asn Gln Thr Glu Pro Pro Lys Val Arg Leu Glu Gly Arg Ser
            435                 440                 445

Thr Thr Ser Leu Ser Val Ser Trp Ser Ile Pro Pro Pro Gln Gln Ser
450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
                500                 505                 510

Glu Gly Gln Gly Ala Gly Ser Lys Val His Glu Phe Gln Thr Leu Ser
            515                 520                 525

Pro Glu Gly Ser Gly Asn Leu Ala Val Ile Gly Gly Val Ala Val Gly
530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
                580                 585                 590

Thr Tyr Glu Asp Pro Asn Gln Ala Val Leu Lys Phe Thr Thr Glu Ile
            595                 600                 605

His Pro Ser Cys Val Thr Arg Gln Lys Val Ile Gly Ala Gly Glu Phe
610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                645                 650                 655

Arg Val Asp Phe Leu Gly Glu Ala Gly Ile Met Gly Gln Phe Ser His
                660                 665                 670

His Asn Ile Ile Arg Leu Glu Gly Val Ile Ser Lys Tyr Lys Pro Met
            675                 680                 685

Met Ile Ile Thr Glu Tyr Met Glu Asn Gly Ala Leu Asp Lys Phe Leu
690                 695                 700

Arg Glu Lys Asp Gly Glu Phe Ser Val Leu Gln Leu Val Gly Met Leu
705                 710                 715                 720

Arg Gly Ile Ala Ala Gly Met Lys Tyr Leu Ala Asn Met Asn Tyr Val
                725                 730                 735

His Arg Asp Leu Ala Ala Arg Asn Ile Leu Val Asn Ser Asn Leu Val
                740                 745                 750

Cys Lys Val Ser Asp Phe Gly Leu Ser Arg Val Leu Glu Asp Asp Pro
            755                 760                 765
```

```
Glu Ala Thr Tyr Thr Thr Ser Gly Gly Lys Ile Pro Ile Arg Trp Thr
770                 775                 780

Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
            805                 810                 815

Pro Tyr Trp Glu Leu Ser Asn His Glu Val Met Lys Ala Ile Asn Asp
            820                 825                 830

Gly Phe Arg Leu Pro Thr Pro Met Asp Cys Pro Ser Ala Ile Tyr Gln
        835                 840                 845

Leu Met Met Gln Cys Trp Gln Gln Glu Arg Ala Arg Arg Pro Lys Phe
850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
                885                 890                 895

Ser Thr Ser Gly Ser Glu Gly Val Pro Phe Arg Thr Val Ser Glu Trp
            900                 905                 910

Leu Glu Ser Ile Lys Met Gln Gln Tyr Thr Glu His Phe Met Ala Ala
            915                 920                 925

Gly Tyr Thr Ala Ile Glu Lys Val Val Gln Met Thr Asn Asp Asp Ile
930                 935                 940

Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
                965                 970                 975

<210> SEQ ID NO 234
<211> LENGTH: 668
<212> TYPE: PRT
<213> ORGANISM: Homo sapiens

<400> SEQUENCE: 234

Met Gly Gly Lys Gln Arg Asp Glu Asp Asp Glu Ala Tyr Gly Lys Pro
1               5                   10                  15

Val Lys Tyr Asp Pro Ser Phe Arg Gly Pro Ile Lys Asn Arg Ser Cys
                20                  25                  30

Thr Asp Val Ile Cys Cys Val Leu Phe Leu Leu Phe Ile Leu Gly Tyr
            35                  40                  45

Ile Val Val Gly Ile Val Ala Trp Leu Tyr Gly Asp Pro Arg Gln Val
50                  55                  60

Leu Tyr Pro Arg Asn Ser Thr Gly Ala Tyr Cys Gly Met Gly Glu Asn
65                  70                  75                  80

Lys Asp Lys Pro Tyr Leu Leu Tyr Phe Asn Ile Phe Ser Cys Ile Leu
                85                  90                  95

Ser Ser Asn Ile Ile Ser Val Ala Glu Asn Gly Leu Gln Cys Pro Thr
            100                 105                 110

Pro Gln Thr Val Ile Thr Ser Leu Gln Gln Glu Leu Cys Pro Ser Phe
        115                 120                 125

Leu Leu Pro Ser Ala Pro Ala Leu Gly Arg Cys Phe Pro Trp Thr Asn
130                 135                 140

Val Thr Pro Pro Ala Leu Pro Gly Ile Thr Asn Asp Thr Thr Ile Gln
145                 150                 155                 160

Gln Gly Ile Ser Gly Leu Ile Asp Ser Leu Asn Ala Arg Asp Ile Ser
                165                 170                 175
```

-continued

```
Val Lys Ile Phe Glu Asp Phe Ala Gln Ser Trp Tyr Trp Ile Leu Val
            180                 185                 190
Ala Leu Gly Val Ala Leu Val Leu Ser Leu Leu Phe Ile Leu Leu Leu
        195                 200                 205
Arg Leu Val Ala Gly Pro Leu Val Leu Val Leu Ile Leu Gly Val Leu
    210                 215                 220
Gly Val Leu Ala Tyr Gly Ile Tyr Tyr Cys Trp Glu Glu Tyr Arg Val
225                 230                 235                 240
Leu Arg Asp Lys Gly Ala Ser Ile Ser Gln Leu Gly Phe Thr Thr Asn
                245                 250                 255
Leu Ser Ala Tyr Gln Ser Val Gln Glu Thr Trp Leu Ala Ala Leu Ile
            260                 265                 270
Val Leu Ala Val Leu Glu Ala Ile Leu Leu Met Leu Ile Phe Leu
        275                 280                 285
Arg Gln Arg Ile Arg Ile Ala Ile Ala Leu Leu Lys Glu Ala Ser Lys
    290                 295                 300
Ala Val Gly Gln Met Met Ser Thr Met Phe Tyr Pro Leu Val Thr Phe
305                 310                 315                 320
Val Leu Leu Leu Ile Cys Ile Ala Tyr Trp Ala Met Thr Ala Leu Tyr
                325                 330                 335
Leu Ala Thr Ser Gly Gln Pro Gln Tyr Val Leu Trp Ala Ser Asn Ile
            340                 345                 350
Ser Ser Pro Gly Cys Glu Lys Val Pro Ile Asn Thr Ser Cys Asn Pro
        355                 360                 365
Thr Ala His Leu Val Asn Ser Cys Pro Gly Leu Met Cys Val Phe
    370                 375                 380
Gln Gly Tyr Ser Ser Lys Gly Leu Ile Gln Arg Ser Val Phe Asn Leu
385                 390                 395                 400
Gln Ile Tyr Gly Val Leu Gly Leu Phe Trp Thr Leu Asn Trp Val Leu
                405                 410                 415
Ala Leu Gly Gln Cys Val Leu Ala Gly Ala Phe Ala Ser Phe Tyr Trp
            420                 425                 430
Ala Phe His Lys Pro Gln Asp Ile Pro Thr Phe Pro Leu Ile Ser Ala
        435                 440                 445
Phe Ile Arg Thr Leu Arg Tyr His Thr Gly Ser Leu Ala Phe Gly Ala
    450                 455                 460
Leu Ile Leu Thr Leu Val Gln Ile Ala Arg Val Ile Leu Glu Tyr Ile
465                 470                 475                 480
Asp His Lys Leu Arg Gly Val Gln Asn Pro Val Ala Arg Cys Ile Met
                485                 490                 495
Cys Cys Phe Lys Cys Cys Leu Trp Cys Leu Glu Lys Phe Ile Lys Phe
            500                 505                 510
Leu Asn Arg Asn Ala Tyr Ile Met Ile Ala Ile Tyr Gly Lys Asn Phe
        515                 520                 525
Cys Val Ser Ala Lys Asn Ala Phe Met Leu Leu Met Arg Asn Ile Val
    530                 535                 540
Arg Val Val Val Leu Asp Lys Val Thr Asp Leu Leu Leu Phe Phe Gly
545                 550                 555                 560
Lys Leu Leu Val Val Gly Val Gly Val Leu Ser Phe Phe Phe
                565                 570                 575
Ser Gly Arg Ile Pro Gly Leu Gly Lys Asp Phe Lys Ser Pro His Leu
            580                 585                 590
```

```
Asn Tyr Tyr Trp Leu Pro Ile Met Thr Ser Ile Leu Gly Ala Tyr Val
            595                 600                 605

Ile Ala Ser Gly Phe Phe Ser Val Phe Gly Met Cys Val Asp Thr Leu
    610                 615                 620

Phe Leu Cys Phe Leu Glu Asp Leu Glu Arg Asn Asn Gly Ser Leu Asp
625                 630                 635                 640

Arg Pro Tyr Tyr Met Ser Lys Ser Leu Leu Lys Ile Leu Gly Lys Lys
                645                 650                 655

Asn Glu Ala Pro Pro Asp Asn Lys Lys Arg Lys Lys
            660                 665
```

<210> SEQ ID NO 235
<211> LENGTH: 214
<212> TYPE: PRT
<213> ORGANISM: Artificial Sequence
<220> FEATURE:
<223> OTHER INFORMATION: antibody constituent

<400> SEQUENCE: 235

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 236
<211> LENGTH: 449
<212> TYPE: PRT
<213> ORGANISM: Artificial Sequence
<220> FEATURE:
<223> OTHER INFORMATION: antibody consituent

<400> SEQUENCE: 236

```
Gln Val Gln Leu Lys Gln Ser Gly Pro Gly Leu Val Gln Pro Ser Gln
1               5                   10                  15
```

```
Ser Leu Ser Ile Thr Cys Thr Val Ser Gly Phe Ser Leu Thr Asn Tyr
             20                  25                  30

Gly Val His Trp Val Arg Gln Ser Pro Gly Lys Gly Leu Glu Trp Leu
         35                  40                  45

Gly Val Ile Trp Ser Gly Gly Asn Thr Asp Tyr Asn Thr Pro Phe Thr
 50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
             115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

```
Ala Leu His Asn His Tyr Thr Gln Lys Ser Leu Ser Leu Ser Pro Gly
        435                 440                 445

Lys

<210> SEQ ID NO 237
<211> LENGTH: 214
<212> TYPE: PRT
<213> ORGANISM: Artificial Sequence
<220> FEATURE:
<223> OTHER INFORMATION: antibody constituent

<400> SEQUENCE: 237

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 238
<211> LENGTH: 444
<212> TYPE: PRT
<213> ORGANISM: Artificial Sequence
<220> FEATURE:
<223> OTHER INFORMATION: antibody constituent

<400> SEQUENCE: 238

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Asp Tyr Tyr Trp Thr Trp Ile Arg Gln Ser Pro Gly Lys Gly Leu Glu
        35                  40                  45

Trp Ile Gly His Ile Tyr Tyr Ser Gly Asn Thr Asn Tyr Asn Pro Ser
    50                  55                  60
```

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
            85                  90                  95

Cys Val Arg Asp Arg Val Thr Gly Ala Phe Asp Ile Trp Gly Gln Gly
        100                 105                 110

Thr Met Val Thr Val Ser Ser Ala Ser Thr Lys Gly Pro Ser Val Phe
    115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 239
<211> LENGTH: 219
<212> TYPE: PRT
<213> ORGANISM: Artificial Sequence
<220> FEATURE:
<223> OTHER INFORMATION: antibody constituent

<400> SEQUENCE: 239

Asp Ile Gln Met Thr Gln Ser Pro Ser Ser Leu Ser Ala Ser Val Gly
1               5                   10                  15

Asp Arg Val Thr Ile Thr Cys Arg Ser Gln Asn Ile Val His Ser
            20                  25                  30

Asn Gly Asn Thr Tyr Leu Asp Trp Tyr Gln Gln Thr Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Phe Gln Tyr
                85                  90                  95

Ser His Val Pro Trp Thr Phe Gly Gln Gly Thr Lys Leu Gln Ile Thr
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 240
<211> LENGTH: 453
<212> TYPE: PRT
<213> ORGANISM: Artificial Sequence
<220> FEATURE:
<223> OTHER INFORMATION: antibody constituent

<400> SEQUENCE: 240

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Ala Asp Glu Ser Thr Thr Ala Tyr
65                  70                  75                  80

Met Glu Leu Ser Ser Leu Arg Ser Glu Asp Thr Ala Phe Tyr Phe Cys
                85                  90                  95

Thr Arg Gln Gly Leu Trp Phe Asp Ser Asp Gly Arg Gly Phe Asp Phe
            100                 105                 110

Trp Gly Gln Gly Thr Thr Val Thr Val Ser Ser Ala Ser Thr Lys Gly
        115                 120                 125

```
Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 241
<211> LENGTH: 449
<212> TYPE: PRT
<213> ORGANISM: Artificial Sequence
<220> FEATURE:
<223> OTHER INFORMATION: antibody constituent

<400> SEQUENCE: 241

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30
```

```
Pro Met Ile Trp Val Arg Gln Ala Pro Gly Lys Gly Leu Glu Trp Val
        35                  40                  45
Ser Tyr Ile Ser Pro Ser Gly Ser Thr His Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
             85                  90                  95
Ala Arg Gly Gly Asp Thr Tyr Phe Asp Tyr Phe Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
            210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Ala Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly
```

<210> SEQ ID NO 242
<211> LENGTH: 449
<212> TYPE: PRT
<213> ORGANISM: Artificial Sequence
<220> FEATURE:
<223> OTHER INFORMATION: antibody constituent

<400> SEQUENCE: 242

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 243
<211> LENGTH: 449
<212> TYPE: PRT
<213> ORGANISM: Artificial Sequence
<220> FEATURE:
<223> OTHER INFORMATION: antibody constituent

<400> SEQUENCE: 243

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
            35                  40                  45

Ser Tyr Ile Ser Pro Ser Gly Ser Thr His Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
            275                 280                 285

Asn Ala Lys Thr Lys Pro Arg Glu Glu Asn Tyr Gln Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 244
<211> LENGTH: 449
<212> TYPE: PRT
<213> ORGANISM: Artificial Sequence
<220> FEATURE:
<223> OTHER INFORMATION: antibody constituent

<400> SEQUENCE: 244

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
                180                 185                 190
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 245
<211> LENGTH: 449
<212> TYPE: PRT
<213> ORGANISM: Artificial Sequence
<220> FEATURE:
<223> OTHER INFORMATION: antibody constituent

<400> SEQUENCE: 245

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```